US008105574B2

(12) United States Patent
Wilson et al.

(10) Patent No.: US 8,105,574 B2
(45) Date of Patent: *Jan. 31, 2012

(54) SIMIAN ADENOVIRUS NUCLEIC ACID AND AMINO ACID SEQUENCES, VECTORS CONTAINING SAME, AND METHODS OF USE

(75) Inventors: James M Wilson, Gladwyne, PA (US); Guangping Gao, Rosemont, PA (US); Soumitra Roy, Wayne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 918 days.

This patent is subject to a terminal disclaimer.

(21) Appl. No.: 11/820,439

(22) Filed: Jun. 19, 2007

(65) Prior Publication Data

US 2008/0090281 A1 Apr. 17, 2008

Related U.S. Application Data

(63) Continuation of application No. 10/494,364, filed as application No. PCT/US02/33645 on Nov. 20, 2002, now Pat. No. 7,247,472.

(60) Provisional application No. 60/366,798, filed on Mar. 22, 2002, provisional application No. 60/331,951, filed on Nov. 21, 2001.

(51) Int. Cl.
*C12N 15/00* (2006.01)
*C12N 15/34* (2006.01)
*C12N 15/11* (2006.01)
*C12N 15/63* (2006.01)

(52) U.S. Cl. ............... 424/93.2; 435/69.1; 435/320.1; 435/456; 514/44; 536/23.5

(58) Field of Classification Search ................ None
See application file for complete search history.

(56) References Cited

U.S. PATENT DOCUMENTS

| | | | |
|---|---|---|---|
| 5,698,202 | A | 12/1997 | Ertl et al. |
| 5,770,442 | A | 6/1998 | Wickham |
| 5,922,315 | A * | 7/1999 | Roy ................. 424/93.2 |
| 5,972,596 | A | 10/1999 | Pavlakis et al. |
| 6,001,557 | A | 12/1999 | Wilson et al. |
| 6,019,978 | A | 2/2000 | Ertl et al. |
| 6,083,716 | A | 7/2000 | Wilson et al. |
| 6,127,525 | A | 10/2000 | Crystal et al. |
| 6,203,975 | B1 | 3/2001 | Wilson et al. |
| 6,210,663 | B1 | 4/2001 | Ertl et al. |
| 6,287,571 | B1 | 9/2001 | Ertl et al. |

(Continued)

FOREIGN PATENT DOCUMENTS

EP 0 787 200 B1 4/2005

(Continued)

OTHER PUBLICATIONS

Guo et al, Protein tolerance to random amino acid change, PNAS, 2004, vol. 101 (25), pp. 9205-9210.*

(Continued)

*Primary Examiner* — Maria B Marvich
(74) *Attorney, Agent, or Firm* — Howson & Howson LLP

(57) ABSTRACT

A recombinant vector comprises simian adenovirus sequences and a heterologous gene under the control of regulatory sequences. A cell line which expresses simian adenovirus gene(s) is also disclosed. Methods of using the vectors and cell lines are provided.

17 Claims, 2 Drawing Sheets

```
Hu5    APKGAPNPCEWDEAATALEINLEEEDDDNEDEVDEQAEQQKTHVFGQAPYSGINITKEGIQIGVEGQT--
Pan-6  APKGAPNSSQWEQAKTG----------------NGGTMETHTYGVAPMGGENITKDGLQIGTDVTANQ
Pan-5  APKGAPNTCQWTYKADG----------------DTGTEKTYTYGNAPVQGISITKDGIQLGTDTDD--
Pan-7  APKGAPNTCQWTYKAG-----------------DTDTEKTYTYGNAPVQGISITKDGIQLGTDSDG--
Pan-9  APKGAPNTCQWTYKADG----------------ETATEKTYTYGNAPVQGINITKDGIQLGTDTDD--

Hu5    --PKYADKTFQPEPQIGESQWYETEIN--HAAGRVLKKTTPMKPCYGSYAKPTNENGGQGILVKQQN--G
Pan-6  NKPIYADKTFQPEPQVGEENWQETEN---FYGGRALKKDTNMKPCYGSYARPTNEKGGQAKLKVGDDGVP
Pan-5  -QPIYADKTYQPEPQVGDAEWHDITGTDEKYGGRALKPDTKMKPCYGSFAKPTNKEGGQANVKTETG--G
Pan-7  -QAIYADETYQPEPQVGDAEWHDITGTDEKYGGRALKPDTKMKPCYGSFAKPTNKEGGQANVKTETG--G
Pan-9  -QPIYADKTYQPEPQVGDAEWHDITGTDEKYGGRALKPDTKMKPCYGSFAKPTNKEGGQANVKTGTG--T

Hu5    KLESQVEMQFFSTTEATAGNGDNLTPKVVLYSEDVDIETPDTHISYMPTIKEGNSRELMGQQSMPNRPNY
Pan-6  TKEFDIDLAFFDTPGGTVNGQDEYKADIVMYTENTYLETPDTHVVYKPGKDDASSEINLVQQSMPNRPNY
Pan-5  TKEYDIDMAFFDNRSAAAAG---LAPEIVLYTENVDLETPDTHIVYKAGTDDSSSSINLGQQSMPNRPNY
Pan-7  TKEYDIDMAFFDNRSAAAAG---LAPEIVLYTENVDLETPDTHIVYKAGTDDSSSSINLGQQSMPNRPNY
Pan-9  TKEYDIDMAFFDNRSAAAAG---LAPEIVLYTENVDLETPDTHIVYKAGTDDSSSSINLGQQAMPNRPNY

Hu5    IAFRDNFIGLMYYNSTGNMGVLAGQASQLNAVVDLQDRNTELSYQLLLDSIGDRTRYFSMWNQAVDSYDP
Pan-6  IGFRDNFIGLMYYNSTGNMGVLAGQASQLNAVVDLQDRNTELSYQLLLDSLGDRTRYFSMWNQAVDSYDP
Pan-5  IGFRDNFIGLMYYNSTGNMGVLAGQASQLNAVVDLQDRNTELSYQLLLDSLGDRTRYFSMWNQAVDSYDP
Pan-7  IGFRDNFIGLMYYNSTGNMGVLAGQASQLNAVVDLQDRNTELSYQLLLDSLGDRTRYFSMWNQAVDSYDP
Pan-9  IGFRDNFIGLMYYNSTGNMGVLAGQASQLNAVVDLQDRNTELSYQLLLDSLGDRTRYFSMWNQAVDSYDP

Hu5    DVRIIENHGTEDELPNYCFPLGGVINTETLTKVKPKTG----QENGWEKDATEFSDKNEIRVGNNFAMEI
Pan-6  DVRIIENHGVEDELPNYCFPLDGSGTNAAYQGVKVKDGQDGDVESEWENDDTVA-ARNQLCKGNIFAMEI
Pan-5  DVRIIENHGVEDELPNYCFPLDAVGRTDTYQGIKAN----GADQTTWTKDDTVN-DANELGKGNPFAMEI
Pan-7  DVRIIENHGVEDELPNYCFPLDAVGRTDTYQGIKAN----GDNQTTWTKDDTVN-DANELGKGNPFAMEI
Pan-9  DVRIIENHGVEDELPNYCFPLDAVGRTDTYQGIKAN----GTDQTTWTKDDSVN-DANEIGKGNPFAMEI
```

U.S. PATENT DOCUMENTS

| | | | |
|---|---|---|---|
| 7,247,472 | B2 | 7/2007 | Wilson |
| 2004/0136963 | A1 | 7/2004 | Wilson et al. |
| 2004/0171807 | A1 | 9/2004 | Gao et al. |
| 2004/0241181 | A1 | 12/2004 | Ertl |
| 2006/0211115 | A1 | 9/2006 | Roy |
| 2007/0218536 | A1 | 9/2007 | Gao |
| 2007/0231347 | A1 | 10/2007 | Wilson |
| 2008/0241189 | A1 | 10/2008 | Wilson |

FOREIGN PATENT DOCUMENTS

| | | |
|---|---|---|
| WO | WO 96/13597 A3 | 5/1996 |
| WO | WO 99/16884 A1 | 4/1999 |
| WO | WO 00/03029 | 1/2000 |
| WO | WO 00/11140 A1 | 3/2000 |
| WO | WO 01/02607 A1 | 1/2001 |
| WO | WO 01/54719 A3 | 8/2001 |
| WO | WO 03/000283 | 1/2003 |
| WO | WO 03/000851 A2 | 1/2003 |

OTHER PUBLICATIONS

Lesk et al, Prediction of Protein Function from Protein Sequence and Structure, p. 27 and 28, downloaded Sep. 16, 2007.*

Gall, et al., "Construction and characterization of hexon-chimeric adenoviruses: Specification of adenovirus serotype", J. Virology, 72(12):10260-10264 (Dec. 1998).

Wu, Hongju, et al., "Construction and characterization of adenovirus serotype 5 packaged by serotype 3 hexon", J. Virology, 76(24):12775-12782 (Dec. 2002).

Siemens, et al., "Cutting edge: Restoration of the ability to generate CTL in mice immune to adenovirus by delivery of virus in a collagen-based matrix", J. Immunol., 166(2):731-735 (Jan. 15, 2001).

Youil et al, Hexon Gene Switch Strategy for the Generation of Chimeric Recombinant Adenovirus, Human Gene Therapy, 13:311-320, (Jan. 20, 2002).

Office Action dated Jun. 2, 2009 and issued in Japanese Patent Application No. 547559/03.

Office Action dated Feb. 6, 2007 and issued in European Patent Application No. 02803963.4.

Response to Office Action dated Feb. 6, 2007 and issued in European Patent Application No. 02803963.4.

Office Action dated May 27, 2008 and issued in European Patent Application No. 02803963.4.

Response to Office Action dated May 27, 2008 and issued in European Patent Application No. 02803963.4.

Office Action dated Sep. 28, 2009 and issued in Singapore Patent Application No. 200605559-4.

Office Action dated Apr. 10, 2007 and issued in Australian Patent Application No. 2006204656.

Response to Office Action dated Apr. 10, 2007 and issued in Australian Patent Application No. 2006204656.

Office Action dated Aug. 4, 2005 and issued in Australian Patent Application No. 2002365366.

Response to Office Action dated Aug. 4, 2005 and issued in Australian Patent Application No. 2002365366.

Office Action dated Sep. 26, 2006 and issued in Australian Patent Application No. 2002365366.

Response to Office Action dated Sep. 26, 2006 and issued in Australian Patent Application No. 2002365366.

Office Action dated Jun. 8, 2005 and issued in New Zealand Patent Application No. 532383.

Response to Office Action dated Jun. 8, 2005 and issued in New Zealand Patent Application No. 532383.

Correspondence dated Jan. 5, 2009 from agent including informal translation of Office Action issued in Mexican Patent Application No. PA/A/2004/004876.

Office Action dated Oct. 31, 2006 and issued in U.S. Appl. No. 10/494,364.

Response to Office Action dated Oct. 31, 2006 and issued in U.S. Appl. No. 10/494,364.

Office Action dated Dec. 28, 2006 and issued in U.S. Appl. No. 10/739,096.

Response to Office Action dated Dec. 28, 2006 and issued in U.S. Appl. No. 10/739,096.

Office Action dated Jun. 11, 2007 and issued in U.S. Appl. No. 10/739,096.

Response to Office Action dated Jun. 11, 2007 and issued in U.S. Appl. No. 10/739,096.

Office Action dated Oct. 3, 2007 and issued in U.S. Appl. No. 10/739,096.

Wilson et al, U.S. Appl. No. 13/084,596, "Simian Adenovirus Vectors and Methods of Use", filed Apr. 12, 2011.

Communication pursuant to Article 94(2) EPC issued in EP Application No. 08003966.2-2405 Jan. 11, 2011 and Applicant's Response.

Crawford-Miksza et al, "Strain Variation in Adenovirus Serotypes 4 and 7A Causing Acute Respiratory Disease", Journal of Clinical Microbiology, 37(4): 1107-1112, XP000957717, (Apr. 1, 1999).

Eiz et al, "Immunological Adenovirus Variant Strains of Subgenus D: Comparison of the Hexon and Fiber Sequences", Virology, 213(2): 313-320, XP004828620, (Nov. 1, 1995).

Roy et al, "Circumvention of Immunity to the Adenovirus Major Coat Protein Hexon", Journal of Virology, 72(8): 6875-6879, (Aug. 1, 1998).

De Jong et al, "Detection, Typing and Subtyping of Enteric Adenoviruses 40 and 41 from Fecal Samples and Observation of Changing Incidences of Infection with These Types and Subtypes", J. Clinical Microbiology vol. 31, No. 6, pp. 1562-1569, (Jun. 1993).

Roy et al, Characterization of a Family of Chimpanzee Adenoviruses and Development of Molecular Clones for Gene Transfer Vectors, Human Gene Therapy, 15:519-530 (May 2004).

Fitzgerald et al, A Simian Replication-Defective Adenoviral Recombinant Vaccine to HIV-1 Gag[I], The Journal of Immunology, 170(3):1416-1422, (Feb. 1, 2003).

Russell et al, Update on Adenovirus and its Vectors, Journal of General Virology, 81, pp. 2573-2604, (Nov. 2000).

Farina et al, Replication-Defective Vector Based on a Chimpanzee Adenovirus, Journal of Virology, vol. 75, No. 23, pp. 11603-11613, (Dec. 2001).

Crawford-Miksza et al, Analysis of 15 Adenovirus Hexon Proteins Reveals the Location and Structure of Seven Hypervariable Regions Containing Serotype-Specific Residues, Journal of Virology, vol. 70, No. 3, pp. 1836-1844, (Mar. 1996).

Hashimoto et al, Induction of Protective Immunity to Anthrax Lethal Toxin with a Chimpanzee Adenovirus-Based Vaccine Carrier in the Presence of Pre-Existing Anti-Human Adenovirus Immunity, Abstract 1015, 7th Annual Meeting of the American Society of Gene Therapy [Jun. 2-6, 2004] Minneapolis, Minnesota, (e-published-May 2, 2004).

Zhi et al, Comparison of Antigen-Specific Immune Responses Elicited by Recombinant Simian Adenoviral Vectors with Deletions in Either E1, or E1/E3, or E1/E4 Regions, Abstract 568, 7th Annual Meeting of the American Society of Gene Therapy [Jun. 2-6, 2004] Minneapolis, Minnesota, (e-published-May 2, 2004).

Gao et al, Autoimmune Anemia in Macaques Following Erythropoietin Gene Therapy, Abstract 341, 7th Annual Meeting of the American Society of Gene Therapy [Jun. 2-6, 2004] Minneapolis, Minnesota, (e-published-May 2, 2004).

Kobinger et al, Pseudotyping HIV Vector with the Spike Envelope Protein of SARS-CoV for Studying Viral Tropism, Immunology and Gene Therapy Applications, Abstract 368, 7th Annual Meeting of the American Society of Gene Therapy [Jun. 2-6, 2004] Minneapolis, Minnesota, (e-published-May 2, 2004).

Kobinger et al, Simian Adenoviral Vector Based-Vaccine Fully Protect Against Ebola Virus Even in the Presence of Pre-Existing Immunity to Human Adenovirus, Abstract 373, 7th Annual Meeting of the American Society of Gene Therapy [Jun. 2-6, 2004] Minneapolis, Minnesota, (e-published-May 2, 2004).

Kobinger et al, Pharmacologically Regulated Regeneration of Functional Human Pancreatic Islets, Abstract 1053, 7th Annual Meeting of the American Society of Gene Therapy [Jun. 2-6, 2004] Minneapolis, Minnesota, (e-published-May 2, 2004).

Roy et al, Use of Chimeric Adenoviral Vectors to Assess Capsid Neutralization Determinants, Abstract 128, 7th Annual Meeting of the American Society of Gene Therapy [Jun. 2-6, 2004] Minneapolis, Minnesota, (e-published-May 2, 2004).

Lebherz et al, Nonhuman Primate Models for Retinal and Choroidal Neovascularization using AAV2-Mediated Overexpression of Vascular Endothelial Growth Factor, Abstract 218, 7th Annual Meeting of the American Society of Gene Therapy [Jun. 2-6, 2004] Minneapolis, Minnesota, (e-published-May 2, 2004).

Lubeck etal, Immunogenicity of Recombinant Adenovirus-human Immunodeficiency Virus Vaccines in Chimpanzees following Inrranasal Administration, AIDS Res Hum Retroviruses, 10(11):1443-9, (Nov. 1994).

Amara et al, Control of a Mucosal Challenge and Prevention of AIDS by a Multiprotein DNA/MVA Vaccine, Science, vol. 292, pp. 69-74 (Apr. 6, 2001).

Babiuk et al, Adenoviruses as Vectors for Delivering Vaccines to Mucosal Surfaces, Journal of Biotechnology, 83, pp. 105-113, (Sep. 29, 2000).

Cohen et al, Chimpanzee Adenovirus CV-68 Adapted as a Gene Delivery Vector Interacts with the Coxsackievirus and Adenovirus Receptor, Journal of General Virology, 83, pp. 151-155, (Jan. 2002).

Ertl et al, Mucosal Vaccine to HIV-1 Gag, (Apr. 15, 2001) Abstract.

Holmgren et al, Mucosal Immunity: Implications for Vaccine Development, Immunobiol, vol. 184, pp. 157-179, (Feb. 1992).

Qiu et al, Evaluation of Novel Human Immunodeficiency Virus Type 1 Gag DNA Vaccines for Protein Expression in Mammalian Cells and Induction of Immune Responses, Journal of Virology, vol. 73, No. 11, pp. 9145-9152, (Nov. 1999).

Santra et al, Recombinant canarypox Vaccine-Elicited CTL Specific for dominant and Subdominant Simian Immunodeficiency Virus Epitopes in Rhesus Monkeys, The Journal of Immunology, 168:pp. 1847-1853 (Feb. 15, 2002).

Schneider et al, Inactibation of the Human Immunodeficiency Virus Type 1 Inhibitory Elements Allows Rev-Independent Expression of Gag and Gag/Protease and Particle Formation, Journal of Virology, vol. 71, No. 7, pp. 4892-4903, (Jul. 1997).

Toes et al, Protective Anti-tumor Immunity Induced by Vaccination with Recombinant Adenoviruses Encoding Multiple Tumor-Associated Cytotoxic T Lymphocyte Epitopes in a String-of-Beads Fashion, Proc Natl. Acad. Sci. vol. 94, pp. 14660-14665, (Dec. 1997).

Van Olphen et al, Development and Characterization of bovine X Human Hybrid Cell Lines that Efficiently Support the Replication of Both Wild-type Bovine and Human Adenoviruses and Those with E1 Deleted, Journal of Virology, vol. 76, No. 12, pp. 5882-5892, (Jun. 2002).

Xiang et al, Novel Chimpanzee Serotype 68-Based Adenoviral Vaccine Carrier for Induction of Antibodies to a Transgene Product, Journal of Virology, vol. 76, No. 6, pp. 2667-2675 (Mar. 2002).

Zolla-Pazner et al, Induction of Neutralizing Antibodies to T-Cell Line Adapted and Primary Human Immunodeficiency Virus Type 1 Isolates with a Prime-Boost Vaccine Regimen in Chimpanzees, Journal of Virology, vol. 72, No. 2, pp. 1052-1059 (Feb. 1998).

Roy et al, Complete Nucleotide Sequences and Genome Organization of Four Chimpanzee Adenoviruses, Virology, 324, pp. 361-372, (May 2004).

Stevens, D, American Type Culture Collection Catalogue of Strains II 4th Edition, Viruses and Antisera, p. 226, (1983), XP002392467.

Bruce et al, Replication-deficient Recombinant Adenoviruses Expressing the Human Immunodeficiency Virus Env Antigen can Induce both Humoral and CTL Immune Responses in Mice, Journal of General Virology, 80, pp. 2621-2628, (Oct. 1999).

Wigand et al, Chimpanzee Adenoviruses are Related to Four Subgenera of Human Adenoviruses, Intervirology, 30:1-9, (Jan. 1989) XP002052837.

* cited by examiner

FIGURE 1

```
Hu5    APKGAPNPCEWDEAATALEINLEEEDDNEDEVDEQAEQQKTHVFGQAPYSGINITKEGIQIGVEGQT--
Pan-6  APKGAPNSSQWEQAKTG----------------NGGTMETHTYGVAPMGGENITKDGLQIGTDVTANQ
Pan-5  APKGAPNTCQWTYKADG----------------DTGTEKTYTYGNAPVQGISITKDGIQLGTDTDD--
Pan-7  APKGAPNTCQWTYKAG-----------------DTDTEKTYTYGNAPVQGISITKDGIQLGTDSDG--
Pan-9  APKGAPNTCQWTYKADG----------------ETATEKTYTYGNAPVQGINITKDGIQLGTDTDD--

Hu5    --PKYADKTFQPEPQIGESQWYETEIN--HAAGRVLKKTTPMKPCYGSYAKPTNENGGQGILVKQQN--G
Pan-6  NKPIYADKTFQPEPQVGEENWQETEN---FYGGRALKKDTNMKPCYGSYARPTNEKGGQAKLKVGDDGVP
Pan-5  -QPIYADKTYQPEPQVGDAEWHDITGTDEKYGGRALKPDTKMKPCYGSEAKPTNKEGGQANVKTETG--G
Pan-7  -QAIYADETYQPEPQVGDAEWHDITGTDEKYGGRALKPDTKQMKPCYGSEAKPTNKEGGQANVKTETG--G
Pan-9  -QPIYADKTYQPEPQVGDAEWHDITGTDEKYGGRALKPDTKMKPCYGSFAKPTNKEGGQANVKTGTG---T

Hu5    KLESQVEMQFFSTTEATAGNGDNLTPKVVLYSEDVDIETPDTHISYMPTIKEGNSRELMGQQSMPNRPNY
Pan-6  TKEFDIDLAFFDTPGGTVNGQODEYKADIVMYTENTYLETPDTHVVYKPGKDDASSEINLVQQSMPNRPNY
Pan-5  TKEYDIDMAFFDNRSAAAAG----LAPEIVLYTENVDLETPDTHIVYKAGTDDSSSSINLGQQSMPNRPNY
Pan-7  TKEYDIDMAFFDNRSAAAAG----LAPEIVLYTENVDLETPDTHIVYKAGTDDSSSSINLGQQSMPNRPNY
Pan-9  TKEYDIDMAFFDNRSAAAAG----LAPEIVLYTENVDLETPDTHIVYKAGTDDSSSSINLGQQAMPNRPNY

Hu5    IAFRDNFIGLMYYNSTGNMGVLAGQASQLNAVVDLQDRNTELSYQLLLDSIGDRTRYFSMWNQAVDSYDP
Pan-6  IGFRDNFIGLMYYNSTGNMGVLAGQASQLNAVVDLQDRNTELSYQLLLDSLGDRTRYFSMWNQAVDSYDP
Pan-5  IGFRDNFIGLMYYNSTGNMGVLAGQASQLNAVVDLQDRNTELSYQLLLDSLGDRTRYFSMWNQAVDSYDP
Pan-7  IGFRDNFIGLMYYNSTGNMGVLAGQASQLNAVVDLQDRNTELSYQLLLDSLGDRTRYFSMWNQAVDSYDP
Pan-9  IGFRDNFIGLMYYNSTGNMGVLAGQASQLNAVVDLQDRNTELSYQLLLDSLGDRTRYFSMWNQAVDSYDP

Hu5    DVRIIENHGTEDELPNYCFPLGGVINTETLTKVPKTG----QENGWEKDATEFSDKNEIRVGNNFAMEI
Pan-6  DVRIIENHGVEDELPNYCFPLDGSGTNAAYQGVKVKDGQDGDVESEWENDDTVA-ARNQLCKGNIFAMEI
Pan-5  DVRIIENHGVEDELPNYCFPLDAVGRTDTYQGIKAN----GADQTTWTKDDTVN-DANELGKGNPFAMEI
Pan-7  DVRIIENHGVEDELPNYCFPLDAVGRTDTYQGIKAN----GDNQTTWTKDDTVN-DANELGKGNPFAMEI
Pan-9  DVRIIENHGVEDELPNYCFPLDAVGRTDTYQGIKAN----GTDQTTWTKDDSVN-DANEIGKGNPFAMEI
```

Fig. 2

```
Pan-9 fiber knob   (1)  TLWTTPDPSPNCQILAENDAKLTLCLTTCGSQILATVSVLVYGSG-NTNP
Pan-6 fiber knob   (1)  TLNTTPDPSPNCQLLSDRDAKFTLCLTTCGSQILGTVAVAATTVGSALNP
Ad 2 fiber knob    (1)  TLWTTPDPSPNCRIHSDNDCKFTLVLIKGSQVIAHVAALAVSG--DTSS
Ad 5 fiber knob    (1)  TLWTTPAPSPNCRLNAEKDAKLTLVLTKCGSQILATVSVLAVKG--STAP
Pan-7 fiber knob   (1)  TLNTTADESNCKIYSEKDAKLTLCLTKCGSQILGTVTVLAVNNG-STNP
Pan-5 fiber knob   (1)  TLWTADESNGHIYSEKDAKLTLCLTKCGSQILGTVSLIANDTG-STNP Pan-9 fiber knob   (50) ITGTVSSAQVELRFDANGVLTEHSTLKKYTGYRQGDSIDGTPTTTEVGT
Pan-6 fiber knob   (51) INDVKSAIVFLRFTSDCTIMSNSSMVGDITMNFFESQTTQSVATTNAVGT
Ad 2 fiber knob    (49) MTGTVASVSIEFLRFDQNGVLMENSSLKKHTNFRNGNSTNANPTTTEVGT
Ad 5 fiber knob    (49) ISGTVQSAHLIIRFDENGVLINNSFLDPETNFRNGDLTEGTATTNAVGT
Pan-7 fiber knob   (50) ITNPVSTALVSLKFDASGTLLSSTLDKEYTNFRKGDVTPAEPTTNAIGT
Pan-5 fiber knob   (50) ITGTVTTALVSLKFDANGVLQSSSTLDSDTNFRQGDVTPAEALTTLIGT Pan-9 fiber knob   (100) MFNLKAYLFSQSSTTFNNLVGQVTMNGDVSKPMLTTTLNGTDDS-----
Pan-6 fiber knob   (101) MFNIGAYLFSTQSKTPFNSLVSQVLTGETTMPMTTTLFPNGIDEK-DTTP
Ad 2 fiber knob    (99)  MFNLLAYPFTQSQTAKNNLVSQVVLHGDKTKPMILTTTLNGTSESTETSE
Ad 5 fiber knob    (99)  MFNLSAYPFSHGKTALSNLVSQVTLNGDKTKPVTTTTLNGTQET-GDTT
Pan-7 fiber knob   (100) MFNIKAYLPRNTSAASKSHTVSQVLNGDEAKPLMITTFNFTEDAT-----
Pan-5 fiber knob   (100) MFNLKAYLFKNTSGAAFSHHGKVLHGDTGKFLDFIITFNFHSDES-----

Pan-9 fiber knob   (145) NSTYSMSFSYTFT-NGSYVGATFGANSYTTFSYTTAQE
Pan-6 fiber knob   (150) VSTFSMTFTWQFTGDYKDKNITEATNSFSFSYTTAQE
Ad 2 fiber knob    (149) VSTYSMSFTWSFE-SGKYTTETEATNSYTTSYAQEN
Ad 5 fiber knob    (148) PSAFSMSFSMSFS-GHNYINEIFATSFYTTSYTAQE
Pan-7 fiber knob   (146) -CTFSITFQWKFD-STKYTGETLATSFFTFSYTTAQE
Pan-5 fiber knob   (146) -CTFCINFQWQFG-ADQYKNETLAVSSFTFSLTAKE
```

US 8,105,574 B2

SIMIAN ADENOVIRUS NUCLEIC ACID AND AMINO ACID SEQUENCES, VECTORS CONTAINING SAME, AND METHODS OF USE

CROSS-REFERENCE TO RELATED APPLICATION

This is a continuation of U.S. patent application Ser. No. 10/494,364, filed May 12, 2004, now U.S. Pat. No. 7,247,472, which is a 371 of PCT/US02/33645, filed Nov. 20, 2002, which claims the benefit under 35 USC 119(e) of U.S. Provisional Patent Application No. 60/366,798, filed Mar. 22, 2002, now expired, and U.S. Provisional Patent Application No. 60/331,951, filed Nov. 21, 2001, now expired.

BACKGROUND OF THE INVENTION

Adenovirus is a double-stranded DNA virus with a genome size of about 36 kilobases (kb), which has been widely used for gene transfer applications due to its ability to achieve highly efficient gene transfer in a variety of target tissues and large transgene capacity. Conventionally, E1 genes of adenovirus are deleted and replaced with a transgene cassette consisting of the promoter of choice, cDNA sequence of the gene of interest and a poly A signal, resulting in a replication defective recombinant virus.

Adenoviruses have a characteristic morphology with an icosahedral capsid consisting of three major proteins, hexon (II), penton base (III) and a knobbed fibre (IV), along with a number of other minor proteins, VI, VIII, IX, IIIa and IVa2 [W. C. Russell, *J. Gen Virol.*, 81:2573-2604 (November 2000)]. The virus genome is a linear, double-stranded DNA with a terminal protein attached covalently to the 5' termini, which have inverted terminal repeats (ITRs). The virus DNA is intimately associated with the highly basic protein VII and a small peptide termed mu. Another protein, V, is packaged with this DNA-protein complex and provides a structural link to the capsid via protein VI. The virus also contains a virus-encoded protease, which is necessary for processing of some of the structural proteins to produce mature infectious virus.

Recombinant adenoviruses have been described for delivery of molecules to host cells. See, U.S. Pat. No. 6,083,716, which describes the genome of two chimpanzee adenoviruses.

What is needed in the art are more effective vectors which avoid the effect of pre-existing immunity to selected adenovirus serotypes in the population and/or which are useful for repeat administration and for titer boosting by second vaccination, if required.

SUMMARY OF THE INVENTION

The present invention provides the isolated nucleic acid sequences and amino acid sequences of six simian adenoviruses, vectors containing these sequences, and cell lines expressing simian adenovirus genes. Also provided are a number of methods for using the vectors and cells of the invention.

The methods of the invention involve delivering one or more selected heterologous gene(s) to a mammalian patient by administering a vector of the invention. Because the various vector constructs are derived from simian rather than from human adenoviruses, the immune system of the non-simian human or veterinary patient is not primed to respond immediately to the vector as a foreign antigen. Use of the compositions of this invention thus permits a more stable expression of the selected transgene when administered to a non-simian patient. Use of the compositions of this invention for vaccination permits presentation of a selected antigen for the elicitation of protective immune responses. Without wishing to be bound by theory, the ability of the adenoviruses of the invention to transduce human dendritic cells is at least partially responsible for the ability of the recombinant constructs of the invention to induce an immune response. The recombinant simian adenoviruses of this invention may also be used for producing heterologous gene products in vitro. Such gene products are themselves useful in a variety for a variety of purposes such as are described herein.

These and other embodiments and advantages of the invention are described in more detail below.

BRIEF DESCRIPTION OF THE DRAWINGS

FIG. 1 provides an alignment of the amino acid sequences of the L1 and a portion of the L2 loops of the capsid protein hexon of the chimpanzee adenovirus C1 [SEQ ID NO:13], chimpanzee adenovirus C68 (Pan-9) [SEQ ID NO:14], and the novel Pan5 [SEQ ID NO:15], Pan6 [SEQ ID NO:16] and Pan7 [SEQ ID NO:17] chimpanzee adenovirus sequences of the invention. The intervening conserved region is part of the pedestal domain conserved between adenovirus serotypes.

FIG. 2 provides an alignment of the amino acid sequences of the fiber knob domains of chimpanzee C68 (Pan-9) [SEQ ID NO:18], Pan-6 [SEQ ID NO:19], Pan-7 [SEQ ID NO:20], and Pan-5 [SEQ ID NO:21] and the human adenoviruses serotypes 2 [SEQ ID NO:22] and 5 [SEQ ID NO:23].

DETAILED DESCRIPTION OF THE INVENTION

The invention provides novel nucleic acid and amino acid sequences from Ad Pan5 [SEQ ID NO:1-4, 15 and 21], Ad Pan6 [SEQ ID NO: 5-8, 16, 19], and Ad serotype Pan7 [SEQ ID NO: 9-12, 17, 20], which were originally isolated from chimpanzee lymph nodes. In several instances throughout the specification, these adenoviruses are alternatively termed herein C5, C6 and C7, respectively. Also provided are sequences from adenovirus SV1 [SEQ ID NO: 24-28], which was originally isolated from the kidney cells of cynomolgus monkey. The invention also provides sequences of adenoviruses SV-25 [SEQ ID NO:29-33] and SV-39 [SEQ ID NO: 34-37], which were originally isolated from rhesus monkey kidney cells.

The present invention provides novel adenovirus vectors and packaging cell lines to produce those vectors for use in the in vitro production of recombinant proteins or fragments or other reagents. The invention further provides compositions for use in delivering a heterologous molecule for therapeutic or vaccine purposes. Such therapeutic or vaccine compositions contain the adenoviral vectors carrying an inserted heterologous molecule. In addition, novel sequences of the invention are useful in providing the essential helper functions required for production of recombinant adeno-associated viral (AAV) vectors. Thus, the invention provides helper constructs, methods and cell lines which use these sequences in such production methods.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 95 to 99% of the aligned sequences.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, or a fragment thereof which is at least 8 amino acids, or more desirably, at least 15 amino acids in length. Examples of suitable fragments are described herein.

The term "percent sequence identity" or "identical" in the context of nucleic acid sequences refers to the residues in the two sequences that are the same when aligned for maximum correspondence. The length of sequence identity comparison may be over the full-length of the genome (e.g., about 36 kbp), the full-length of an open reading frame of a gene, protein, subunit, or enzyme [see, e.g., the tables providing the adenoviral coding regions], or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

Identity is readily determined using such algorithms and computer programs as are defined herein at default settings. Preferably, such identity is over the full length of the protein, enzyme, subunit, or over a fragment of at least about 8 amino acids in length. However, identity may be based upon shorter regions, where suited to the use to which the identical gene product is being put.

As described herein, alignments are performed using any of a variety of publicly or commercially available Multiple Sequence Alignment Programs, such as "Clustal W", accessible through Web Servers on the internet. Alternatively, Vector NTI utilities are also used. There are also a number of algorithms known in the art that can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similarly programs are available for performing amino acid alignments. Generally, these programs are used at default settings, although one of skill in the art can alter these settings as needed. Alternatively, one of skill in the art can utilize another algorithm or computer program that provides at least the level of identity or alignment as that provided by the referenced algorithms and programs.

As used throughout this specification and the claims, the term "comprise" and its variants including, "comprises", "comprising", among other variants, is inclusive of other components, elements, integers, steps and the like. The term "consists of" or "consisting of" are exclusive of other components, elements, integers, steps and the like.

I. The Simian Adenovirus Sequences

The invention provides nucleic acid sequences and amino acid sequences of Pan5, Pan6, Pan7, SV1, SV25 and SV39, which are isolated from the other viral material with which they are associated in nature.

A. Nucleic Acid Sequences

The Pan5 nucleic acid sequences of the invention include nucleotides 1 to 36462 of SEQ ID NO:1. The Pan6 nucleic acid sequences of the invention include nucleotides 1 to 36604 of SEQ ID NO: 5. The Pan7 nucleic acid sequences of the invention include nucleotides 1 to 36535 of SEQ ID NO: 9. The SV1 nucleic acid sequences of the invention include nucleotides 1 to 34264 of SEQ ID NO: 24. The SV25 nucleic acid sequences of the invention include nucleotides 1 to 31044 of SEQ ID NO: 29. The SV39 nucleic acid sequences of the invention include nucleotides 1 to 34115 of SEQ ID NO: 34. See, Sequence Listing, which is incorporated by reference herein.

The nucleic acid sequences of the invention further encompass the strand which is complementary to the sequences of SEQ ID NO: 5, 9, 24, 29 and 34, as well as the RNA and cDNA sequences corresponding to the sequences of these sequences figures and their complementary strands. Further included in this invention are nucleic acid sequences which are greater than 95 to 98%, and more preferably about 99 to 99.9% homologous or identical to the Sequence Listing. Also included in the nucleic acid sequences of the invention are natural variants and engineered modifications of the sequences provided in SEQ ID NO: 5, 9, 24, 29 and 34 and their complementary strands. Such modifications include, for example, labels that are known in the art, methylation, and substitution of one or more of the naturally occurring nucleotides with a degenerate nucleotide.

The invention further encompasses fragments of the sequences of Pan5, Pan6, Pan7, SV1, SV25 and SV39, their complementary strand, cDNA and RNA complementary thereto. Suitable fragments are at least 15 nucleotides in length, and encompass functional fragments, i.e., fragments which are of biological interest. For example, a functional fragment can express a desired adenoviral product or may be useful in production of recombinant viral vectors. Such fragments include the gene sequences and fragments listed in the tables below.

The following tables provide the transcript regions and open reading frames in the simian adenovirus sequences of the invention. For certain genes, the transcripts and open reading frames (ORFs) are located on the strand complementary to that presented in SEQ ID NO: 5, 9, 24, 29 and 34. See, e.g., E2b, E4 and E2a. The calculated molecular weights of the encoded proteins are also shown. Note that the E1a open reading frame Pan5 [nt 576-1436 of SEQ ID NO:1], Pan6 [nt 576 to 1437 of SEQ ID NO: 5] and Pan7 [nt 576 to 1437 of SEQ ID NO: 9] contain internal splice sites. These splice sites are noted in the following tables.

| | Ad Pan-5 [SEQ ID NO: 1] | | | |
|---|---|---|---|---|
| | Regions | Start (nt) | End (nt) | M.W. (Daltons) |
| ITR | | 1 | 120 | — |
| E1a | Transcript | 478 | | — |
| | 13S | 576-664, 1233-1436 | | 28120 |
| | 12S | 576-1046, 1233-1436 | | 24389 |
| | 9S | 576-644, 1233-1436 | | 9962 |
| | Transcript | | 1516 | — |
| E1b | Transcript | 1552 | | — |
| | Small T | 1599 | 2171 | 22317 |
| | Large T | 1904 | 3412 | 55595 |

Ad Pan-5 [SEQ ID NO: 1] -continued

| Regions | | Start (nt) | End (nt) | M.W. (Daltons) |
|---|---|---|---|---|
| | IX | 3492 | 3920 | 14427 |
| | Transcript | | 3959 | — |
| E2b | Transcript | 10349 | | — |
| | PTP | 10349 | 8451 | 72930 |
| | Polymerase | 8448 | 5083 | 127237 |
| | IVa2 | 5604 | 3980 | 50466 |
| | Transcript | | 3960 | — |
| 28.1 kD | | 5155 | 5979 | 28141 |
| Agnoprotein | | 7864 | 8580 | 25755 |
| L1 | Transcript | 10849 | | — |
| | 52/55D | 10851 | 12025 | — |
| | IIIa | 12050 | 13819 | 65669 |
| | Transcript | | 13832 | — |
| | Transcript | 13894 | | — |
| L2 | Penton | 13898 | 15490 | 59292 |
| | VII | 15494 | 16078 | 21478 |
| | V | 16123 | 17166 | 39568 |
| | Mu | 17189 | 17422 | 8524 |
| | transcript | | 17442 | — |
| | Transcript | 17488 | | — |
| L3 | VI | 17491 | 18222 | 26192 |
| | Hexon | 18315 | 21116 | 104874 |
| | Endoprotease | 20989 | 21783 | 28304 |
| | transcript | | 21811 | — |
| E2a | Transcript | 26782 | | — |
| | DBP | 23386 | 21845 | 57358 |
| | transcript | | 21788 | — |
| L4 | Transcript | 23406 | | — |
| | 100 kD | 23412 | 25805 | 88223 |
| | 33 kD homolog | 25525 | 26356 | 24538 |
| | VIII | 26428 | 27111 | 24768 |
| | transcript | | 27421 | — |
| E3 | Transcript | 26788 | | — |
| | Orf #1 | 27112 | 27432 | 12098 |
| | Orf #2 | 27386 | 28012 | 23040 |
| | Orf #3 | 27994 | 28527 | 19525 |
| | Orf #4 | 28557 | 29156 | 22567 |
| | Orf #5 | 29169 | 29783 | 22267 |
| | Orf #6 | 29798 | 30673 | 31458 |
| | Orf #7 | 30681 | 30956 | 10477 |
| | Orf #8 | 30962 | 31396 | 16523 |
| | Orf #9 | 31389 | 31796 | 15236 |
| | transcript | | 31837 | — |
| L5 | Transcript | 32032 | | — |
| | Fiber | 32035 | 33372 | 47670 |
| | transcript | | 33443 | — |
| E4 | Transcript | 36135 | | — |
| | Orf 7 | 33710 | 33462 | 9191 |
| | Orf 6 | 34615 | 33710 | 35005 |
| | Orf 4 | 34886 | 34521 | 13878 |
| | Orf 3 | 35249 | 34896 | 13641 |
| | Orf 2 | 35635 | 35246 | 14584 |
| | Orf 1 | 36050 | 35676 | 13772 |
| | Transcript | | 33437 | — |
| ITR | | 36343 | 36462 | — |

Ad Pan-6 [SEQ ID NO: 5]

| Regions | | Start (nt) | End (nt) | M.W. (Daltons) |
|---|---|---|---|---|
| ITR | | 1 | 123 | — |
| E1a | transcript | 478 | | — |
| | 13S | 576-1143, 1229-1437 | | 28291 |
| | 12S | 576-1050, 1229-1437 | | 24634 |
| | 9S | 576-645, 1229-1437 | | 10102 |
| | transcript | | 1516 | — |

Ad Pan-6 [SEQ ID NO: 5] -continued

| Regions | | Start (nt) | End (nt) | M.W. (Daltons) |
|---|---|---|---|---|
| E1b | transcript | 1553 | | — |
| | Small T | 1600 | 2172 | 22315 |
| | LargeT | 1905 | 3413 | 55594 |
| | IX | 3498 | 3926 | 14427 |
| | transcript | | 3965 | — |
| E2b | transcript | 10341 | | — |
| | PTP | 10340 | 8451 | 72570 |
| | Polymerase | 8445 | 5089 | 126907 |
| | IVa2 | 5610 | 3986 | 50452 |
| | transcript | | 3966 | — |
| L1 | transcript | 10838 | | — |
| | 52/55 kD | 10840 | 12012 | 44205 |
| | IIIa | 12036 | 13799 | 65460 |
| | Transcript | | 13812 | — |
| 28.1 kd | | 5161 | 5985 | 28012 |
| Agnoprotein | | 7870 | 8580 | 25382 |
| L2 | transcript | 13874 | | — |
| | Penton | 13878 | 15467 | 59314 |
| | VII | 15471 | 16055 | 21508 |
| | V | 16100 | 17137 | 39388 |
| | Mu | 17160 | 17393 | 8506 |
| | transcript | | 17415 | — |
| L3 | transcript | 17466 | | — |
| | VI | 17469 | 18188 | 25860 |
| | Hexon | 18284 | 21112 | 106132 |
| | Endoprotease | 21134 | 21754 | 23445 |
| | transcript | | 21803 | — |
| E2a | transcript | 26780 | | — |
| | DBP | 23375 | 21837 | 57299 |
| | transcript | | 21780 | — |
| L4 | Transcript | 23398 | | — |
| | 100 kD | 23404 | 25806 | 88577 |
| | 33 kD homolog | 25523 | 26357 | 24609 |
| | VIII | 26426 | 27109 | 24749 |
| | transcript | | 27419 | — |
| E3 | transcript | 26786 | | — |
| | Orf #1 | 27110 | 27430 | 12098 |
| | Orf #2 | 27384 | 28007 | 22880 |
| | Orf #3 | 27989 | 28519 | 19460 |
| | Orf #4 | 28553 | 29236 | 25403 |
| | Orf #5 | 29249 | 29860 | 22350 |
| | Orf #6 | 29875 | 30741 | 31028 |
| | Orf #7 | 30749 | 31024 | 10469 |
| | Orf #8 | 31030 | 31464 | 16540 |
| | Orf #9 | 31457 | 31864 | 15264 |
| | transcript | | 31907 | — |
| L5 | transcript | 32159 | | — |
| | Fiber | 32162 | 33493 | 47364 |
| | transcript | | 33574 | — |
| E4 | transcript | 36276 | | — |
| | Orf 7 | 33841 | 33593 | 9177 |
| | Orf 6 | 34746 | 33841 | 35094 |
| | Orf 4 | 35017 | 34652 | 13937 |
| | Orf 3 | 35380 | 35027 | 13627 |
| | Orf 2 | 35766 | 35377 | 14727 |
| | Orf 1 | 36181 | 35807 | 13739 |
| | transcript | | 33558 | — |
| ITR | | 36482 | 36604 | — |

Ad Pan-7 [SEQ ID NO: 9]

| Regions | | Start (nt) | End (nt) | M.W. (Daltons) |
|---|---|---|---|---|
| ITR | | 1 | 132 | — |
| E1a | transcript | 478 | | — |
| | 13S | 576-1143, 1229-1437 | | 28218 |
| | 12S | 576-1050, 1229-1437 | | 24561 |

Ad Pan-7 [SEQ ID NO: 9]

| Regions | | Start (nt) | End (nt) | M.W. (Daltons) |
|---|---|---|---|---|
| | 9S | 576-645, 1229-1437 | | 10102 |
| | transcript | | 1516 | — |
| E1b | transcript | 1553 | | — |
| | Small T | 1600 | 2178 | 22559 |
| | LargeT | 1905 | 3419 | 55698 |
| | IVa2 | 3992 | 5616 | 50210 |
| | transcript | | 3971 | — |
| E2b | transcript | 10341 | | — |
| | PTP | 10340 | 8457 | 72297 |
| | Polymerase | 8451 | 5095 | 126994 |
| | IX | 3504 | 3932 | 14441 |
| | transcript | | 3972 | — |
| | 28.1 kD | 5167 | 5991 | 28028 |
| | Agnoprotein | 7876 | 8586 | 25424 |
| L1 | transcript | 10834 | | — |
| | 52/55 kD | 10836 | 12011 | 44302 |
| | IIIa | 12035 | 13795 | 65339 |
| | transcript | | 13808 | — |
| L2 | transcript | 13870 | | — |
| | Penton | 13874 | 15469 | 59494 |
| | VII | 15473 | 16057 | 21339 |
| | V | 16102 | 17139 | 39414 |
| | Mu | 17167 | 17400 | 8506 |
| | transcript | | 17420 | — |
| L3 | transcript | 17467 | | — |
| | VI | 17470 | 18198 | 26105 |
| | Hexon | 18288 | 21086 | 104763 |
| | Endoprotease | 21106 | 21732 | 23620 |
| | transcript | | 21781 | — |
| E2a | transcript | 26764 | | — |
| | DBP | 23353 | 21815 | 57199 |
| | transcript | | 21755 | — |
| L4 | transcript | 23370 | | — |
| | 100 kD | 23376 | 25781 | 88520 |
| | 33 kD homolog | 25489 | 26338 | 25155 |
| | VIII | 26410 | 27093 | 24749 |
| | transcript | | 27403 | — |
| E3 | transcript | 26770 | | — |
| | Orf #1 | 27094 | 27414 | 12056 |
| | Orf #2 | 27368 | 27988 | 22667 |
| | Orf #3 | 27970 | 28500 | 19462 |
| | Orf #4 | 28530 | 29150 | 22999 |
| | Orf #5 | 29163 | 29777 | 22224 |
| | Orf #6 | 29792 | 30679 | 32153 |
| | Orf #7 | 30687 | 30962 | 10511 |
| | Orf #8 | 30968 | 31399 | 16388 |
| | Orf #9 | 31392 | 31799 | 15205 |
| | transcript | | 31842 | — |
| L5 | transcript | 32091 | | — |
| | Fiber | 32094 | 33425 | 47344 |
| | transcript | | 33517 | — |
| E4 | transcript | 36208 | | — |
| | Orf 7 | 33784 | 33536 | 9191 |
| | Orf 6 | 34689 | 33784 | 35063 |
| | Orf 4 | 34960 | 34595 | 13879 |
| | Orf 3 | 35323 | 34970 | 13641 |
| | Orf 2 | 35709 | 35320 | 14644 |
| | Orf 1 | 36123 | 35749 | 13746 |
| | transcript | | 33501 | — |
| ITR | | 36404 | 36535 | — |

| | Ad SV-1 [SEQ ID NO: 24] | | Ad SV-25 [SEQ ID NO: 29] | | Ad SV-39 [SEQ ID NO: 34] | |
|---|---|---|---|---|---|---|
| Region | Start | End | Start | End | Start | End |
| ITR | 1 | 106 | 1 | 133 | 1 | 150 |
| E1a | 352 | 1120 | — | — | 404 | 1409 |
| E1b | 1301 | 2891 | 359 | 2273 | 1518 | 3877 |
| E2b | 9257 | 2882 | 9087 | 2754 | 10143 | 3868 |
| E2a | 24415 | 20281 | 24034 | 20086 | 25381 | 21228 |
| E3 | 24974 | 27886 | 24791 | 25792 | 25790 | 29335 |
| E4 | 33498 | 30881 | 30696 | 28163 | 33896 | 31157 |
| ITR | 34145 | 34264 | 30912 | 31044 | 33966 | 34115 |
| ITR | 1 | 106 | 1 | 133 | 1 | 150 |
| L1 | 9513 | 12376 | 9343 | 12206 | 10416 | 13383 |
| L2 | 12453 | 15858 | 12283 | 15696 | 13444 | 16877 |
| L3 | 15910 | 20270 | 15748 | 20080 | 17783 | 21192 |
| L4 | 21715 | 25603 | 21526 | 25420 | 22659 | 26427 |
| L5 | 28059 | 30899 | 25320 | 28172 | 29513 | 31170 |
| ITR | 34145 | 34264 | 30912 | 31044 | 33966 | 34115 |

| | Ad SV-1, SEQ ID NO: 24 | | | |
|---|---|---|---|---|
| | protein | Start | End | M.W. |
| ITR | | 1 | 106 | — |
| E1a | 13S | 459 | 953 | 18039 |
| | 12S | | | |
| E1b | Small T | | | |
| | LargeT | 1301 | 2413 | 42293 |
| | IX | 2391 | 2885 | 16882 |
| E2b | IVa2 | 4354 | 2924 | 54087 |
| | Polymerase | 6750 | 4027 | 102883 |
| | PTP | 9257 | 7371 | 72413 |
| | Agno-protein | 6850 | 7455 | 20984 |
| L1 | 52/55 kD | 9515 | 10642 | 42675 |
| | IIIa | 10663 | 12372 | 636568 |
| L2 | Penton | 12454 | 13965 | 56725 |
| | VII | 13968 | 14531 | 20397 |
| | V | 14588 | 15625 | 39374 |
| | Mu | 15645 | 15857 | 7568 |
| L3 | VI | 15911 | 16753 | 30418 |
| | Hexon | 16841 | 19636 | 104494 |
| | Endoprotease | 19645 | 20262 | 23407 |
| 2a | DBP | 21700 | 20312 | 52107 |
| L4 | 100 kD | 21721 | 24009 | 85508 |
| | VIII | 24591 | 25292 | 25390 |
| E3 | Orf #1 | 25292 | 25609 | 11950 |
| | Orf #2 | 25563 | 26081 | 18940 |
| | Orf #3 | 26084 | 26893 | 30452 |
| | Orf #4 | 26908 | 27180 | 10232 |
| | Orf #5 | 27177 | 17512 | 12640 |
| | Orf #6 | 27505 | 27873 | 13639 |
| L5 | Fiber #2 | 28059 | 29150 | 39472 |
| | Fiber #1 | 29183 | 30867 | 61128 |
| E4 | Orf 7 | 31098 | 30892 | 7837 |
| | Orf 6 | 31982 | 31122 | 33921 |
| | Orf 4 | 32277 | 31915 | 14338 |
| | Orf 3 | 32629 | 32279 | 13386 |
| | Orf 2 | 33018 | 32626 | 14753 |
| | Orf 1 | 33423 | 33043 | 14301 |
| ITR | | 34145 | 34264 | |

| | | Ad SV-25, SEQ ID NO: 29 | | | Ad SV-39, SEQ ID NO: 34 | | |
|---|---|---|---|---|---|---|---|
| | protein | Start | End | M.W. | Start | End | M.W. |
| ITR | | 1 | 133 | — | 1 | 150 | — |
| E1a | 13S | | | | 492 | 1355 | 28585 |
| | 12S | | | | 492 | 1355 | 25003 |
| E1b | Small T | 478 | 1030 | 20274 | 1518 | 2075 | 21652 |
| | Large T | 829 | 2244 | 52310 | 1823 | 3349 | 55534 |
| | IX | 2306 | 2716 | 13854 | 3434 | 3844 | 14075 |

-continued

| | | Ad SV-25, SEQ ID NO: 29 | | | Ad SV-39, SEQ ID NO: 34 | | |
|---|---|---|---|---|---|---|---|
| | protein | Start | End | M.W. | Start | End | M.W. |
| E2b | IVa2 | 4208 | 2755 | 54675 | 3912 | 5141 | 46164 |
| | Polymerase | 6581 | 3858 | 102839 | 7753 | 5033 | 103988 |
| | PTP | 9087 | 7207 | 71326 | 10143 | 8335 | 69274 |
| | Agnoprotein | 6681 | 7139 | 16025 | — | — | — |
| L1 | 52/55 kD | 9345 | 10472 | 42703 | 10418 | 11608 | 44232 |
| | IIIa | 10493 | 12202 | 63598 | 11574 | 13364 | 66078 |
| L2 | Penton | 12284 | 13801 | 56949 | 13448 | 14959 | 56292 |
| | VII | 13806 | 14369 | 20369 | 14960 | 15517 | 20374 |
| | V | 14426 | 15463 | 39289 | 15567 | 16628 | 39676 |
| | Mu | 15483 | 15695 | 7598 | 16650 | 16871 | 7497 |
| L3 | VI | 15749 | 16591 | 30347 | 16925 | 17695 | 28043 |
| | Hexon | 16681 | 19446 | 104035 | 17785 | 20538 | 102579 |
| | Endoprotease | 19455 | 20072 | 23338 | 20573 | 21181 | 22716 |
| 2a | DBP | 21511 | 20123 | 52189 | 22631 | 21231 | 53160 |
| L4 | 100 kD | 21532 | 23829 | 85970 | 22659 | 25355 | 100362 |
| | VIII | 24408 | 25109 | 25347 | 25410 | 26108 | 25229 |
| E3 | Orf #1 | 25109 | 25426 | 11890 | 26375 | 27484 | 42257 |
| | Orf #2 | | | | 27580 | 28357 | 29755 |
| | Orf #3 | | | | 28370 | 28645 | 10514 |
| | Orf #4 | | | | 28863 | 29333 | 18835 |
| | Orf #5 | | | | | | |
| | Orf #6 | | | | | | |
| L5 | Fiber #2 | 25380 | 26423 | 37529 | | | |
| | Fiber #1 | 26457 | 28136 | 60707 | 29515 | 31116 | 56382 |
| E4 | Orf 7 | | | | 31441 | 31118 | 11856 |
| | Orf 6 | 29255 | 28395 | 33905 | 32292 | 31438 | 33437 |
| | Orf 4 | 29550 | 29188 | 14399 | 32587 | 32222 | 13997 |
| | Orf 3 | 29902 | 29552 | 13284 | 32954 | 32607 | 13353 |
| | Orf 2 | 30291 | 29899 | 14853 | 33348 | 32959 | 14821 |
| | Orf 1 | 30316 | 30696 | 14301 | 33764 | 33378 | 14235 |
| ITR | | 30912 | 31044 | | 33966 | 34115 | |

The Pan5, Pan6, Pan7, SV1, SV25 and SV39 adenoviral nucleic acid sequences are useful as therapeutic agents and in construction of a variety of vector systems and host cells. As used herein, a vector includes any suitable nucleic acid molecule including, naked DNA, a plasmid, a virus, a cosmid, or an episome. These sequences and products may be used alone or in combination with other adenoviral sequences or fragments, or in combination with elements from other adenoviral or non-adenoviral sequences. The adenoviral sequences of the invention are also useful as antisense delivery vectors, gene therapy vectors, or vaccine vectors. Thus, the invention further provides nucleic acid molecules, gene delivery vectors, and host cells which contain the Ad sequences of the invention.

For example, the invention encompasses a nucleic acid molecule containing simian Ad ITR sequences of the invention. In another example, the invention provides a nucleic acid molecule containing simian Ad sequences of the invention encoding a desired Ad gene product. Still other nucleic acid molecule constructed using the sequences of the invention will be readily apparent to one of skill in the art, in view of the information provided herein.

In one embodiment, the simian Ad gene regions identified herein may be used in a variety of vectors for delivery of a heterologous molecule to a cell. For example, vectors are generated for expression of an adenoviral capsid protein (or fragment thereof) for purposes of generating a viral vector in a packaging host cell. Such vectors may be designed for expression in trans. Alternatively, such vectors are designed to provide cells which stably contain sequences which express desired adenoviral functions, e.g., one or more of E1a, E1b, the terminal repeat sequences, E2a, E2b, E4, E4ORF6 region.

In addition, the adenoviral gene sequences and fragments thereof are useful for providing the helper functions necessary for production of helper-dependent viruses (e.g., adenoviral vectors deleted of essential functions or adeno-associated viruses (AAV)). For such production methods, the simian adenoviral sequences of the invention are utilized in such a method in a manner similar to those described for the human Ad. However, due to the differences in sequences between the simian adenoviral sequences of the invention and those of human Ad, the use of the sequences of the invention essentially eliminate the possibility of homologous recombination with helper functions in a host cell carrying human Ad E1 functions, e.g., 293 cells, which may produce infectious adenoviral contaminants during rAAV production.

Methods of producing rAAV using adenoviral helper functions have been described at length in the literature with human adenoviral serotypes. See, e.g., U.S. Pat. No. 6,258, 595 and the references cited therein. See, also, U.S. Pat. No. 5,871,982; WO 99/14354; WO 99/15685; WO 99/47691. These methods may also be used in production of non-human serotype AAV, including non-human primate AAV serotypes. The simian adenoviral gene sequences of the invention which provide the necessary helper functions (e.g., E1a, E1b, E2a and/or E4 ORF6) can be particularly useful in providing the necessary adenoviral function while minimizing or eliminating the possibility of recombination with any other adenoviruses present in the rAAV-packaging cell which are typically of human origin. Thus, selected genes or open reading frames of the adenoviral sequences of the invention may be utilized in these rAAV production methods.

Alternatively, recombinant adenoviral simian vectors of the invention may be utilized in these methods. Such recombinant adenoviral simian vectors may include, e.g., a hybrid chimp Ad/AAV in which chimp Ad sequences flank a rAAV expression cassette composed of, e.g., AAV 3' and/or 5' ITRs and a transgene under the control of regulatory sequences which control its expression. One of skill in the art will recognize that still other simian adenoviral vectors and/or gene sequences of the invention will be useful for production of rAAV and other viruses dependent upon adenoviral helper.

In still another embodiment, nucleic acid molecules are designed for delivery and expression of selected adenoviral gene products in a host cell to achieve a desired physiologic effect. For example, a nucleic acid molecule containing sequences encoding an adenovirus E1a protein of the invention may be delivered to a subject for use as a cancer therapeutic. Optionally, such a molecule is formulated in a lipid-based carrier and preferentially targets cancer cells. Such a formulation may be combined with other cancer therapeutics (e.g., cisplatin, taxol, or the like). Still other uses for the adenoviral sequences provided herein will be readily apparent to one of skill in the art.

In addition, one of skill in the art will readily understand that the Ad sequences of the invention can be readily adapted for use for a variety of viral and non-viral vector systems for in vitro, ex vivo or in vivo delivery of therapeutic and immunogenic molecules. For example, the Pan5, Pan6, Pan7, SV1, SV25 and/or SV39 simian Ad genomes of the invention can be utilized in a variety of rAd and non-rAd vector systems. Such vectors systems may include, e.g., plasmids, lentiviruses, retroviruses, poxviruses, vaccinia viruses, and adeno-associated viral systems, among others. Selection of these vector systems is not a limitation of the present invention.

The invention further provides molecules useful for production of the simian and simian-derived proteins of the invention. Such molecules which carry polynucleotides including the simian Ad DNA sequences of the invention can be in the form of naked DNA, a plasmid, a virus or any other genetic element.

B. Simian Adenoviral Proteins of the Invention

The invention further provides gene products of the above adenoviruses, such as proteins, enzymes, and fragments thereof, which are encoded by the adenoviral nucleic acids of the invention. The invention further encompasses Pan5, Pan6 and Pan7, SV1, SV25 and SV39 proteins, enzymes, and fragments thereof, having the amino acid sequences encoded by these nucleic acid sequences which are generated by other methods. Such proteins include those encoded by the open reading frames identified in the tables above, in FIGS. 1 and 2, and fragments thereof.

Thus, in one aspect, the invention provides unique simian adenoviral proteins which are substantially pure, i.e., are free of other viral and proteinaceous proteins. Preferably, these proteins are at least 10% homogeneous, more preferably 60% homogeneous, and most preferably 95% homogeneous.

In one embodiment, the invention provides unique simian-derived capsid proteins. As used herein, a simian-derived capsid protein includes any adenoviral capsid protein that contains a Pan5, Pan6, Pan7, SV1, SV25 or SV39 capsid protein or a fragment thereof, as defined above, including, without limitation, chimeric capsid proteins, fusion proteins, artificial capsid proteins, synthetic capsid proteins, and recombinantly capsid proteins, without limitation to means of generating these proteins.

Suitably, these simian-derived capsid proteins contain one or more Pan5, Pan6, Pan7, SV1, SV25 or SV39 regions or fragments thereof (e.g., a hexon, penton, fiber or fragment thereof) in combination with capsid regions or fragments thereof of different adenoviral serotypes, or modified simian capsid proteins or fragments, as described herein. A "modification of a capsid protein associated with altered tropism" as used herein includes an altered capsid protein, i.e., a penton, hexon or fiber protein region, or fragment thereof, such as the knob domain of the fiber region, or a polynucleotide encoding same, such that specificity is altered. The simian-derived capsid may be constructed with one or more of the simian Ad of the invention or another Ad serotypes which may be of human or non-human origin. Such Ad may be obtained from a variety of sources including the ATCC, commercial and academic sources, or the sequences of the Ad may be obtained from GenBank or other suitable sources.

The amino acid sequences of the simian adenoviruses penton proteins of the invention are provided herein. The AdPan5 penton protein is provided in SEQ ID NO:2. The AdPan7 penton is provided in SEQ ID NO:6. The AdPan6 penton is provided in SEQ ID NO:10. The SV1 penton is provided in SEQ ID NO:25. The SV25 penton protein is provided in SEQ ID NO:30. The SV39 penton is provided in SEQ ID NO:35. Suitably, any of these penton proteins, or unique fragments thereof, may be utilized for a variety of purposes. Examples of suitable fragments include the penton having N-terminal and/or C-terminal truncations of about 50, 100, 150, or 200 amino acids, based upon the amino acid numbering provided above and in SEQ ID NO:2; SEQ ID NO:6; SEQ ID NO:25; SEQ ID NO:30, or SEQ ID NO:35. Other suitable fragments include shorter internal, C-terminal, or N-terminal fragments. Further, the penton protein may be modified for a variety of purposes known to those of skill in the art.

The invention further provides the amino acid sequences of the hexon protein of Pan5 [SEQ ID NO:3], Pan6 [SEQ ID NO:7], Pan 7 [SEQ ID NO:11], SV1 [SEQ ID NO:26], SV25 [SEQ ID NO:31], and/or SV39 [SEQ ID NO:36]. Suitably, this hexon protein, or unique fragments thereof, may be utilized for a variety of purposes. Examples of suitable fragments include the hexon having N-terminal and/or C-terminal truncations of about 50, 100, 150, 200, 300, 400, or 500 amino acids, based upon the amino acid numbering provided above and in SEQ ID NO: 3, 7, 11, 26, 31 and 36. Other suitable fragments include shorter internal, C-terminal, or N-terminal fragments. For example, one suitable fragment the loop region (domain) of the hexon protein, designated DE1 and FG1, or a hypervariable region thereof. Such fragments include the regions spanning amino acid residues about 125 to 443; about 138 to 441, or smaller fragments, such as those spanning about residue 138 to residue 163; about 170 to about 176; about 195 to about 203; about 233 to about 246; about 253 to about 264; about 287 to about 297; and about 404 to about 430 of the simian hexon proteins, with reference to SEQ ID NO: 3, 7, 11, 26, 31 or 36. Other suitable fragments may be readily identified by one of skill in the art. Further, the hexon protein may be modified for a variety of purposes known to those of skill in the art. Because the hexon protein is the determinant for serotype of an adenovirus, such artificial hexon proteins would result in adenoviruses having artificial serotypes. Other artificial capsid proteins can also be constructed using the chimp Ad penton sequences and/or fiber sequences of the invention and/or fragments thereof.

In one example, it may be desirable to generate an adenovirus having an altered hexon protein utilizing the sequences of a hexon protein of the invention. One suitable method for altering hexon proteins is described in U.S. Pat. No. 5,922,315, which is incorporated by reference. In this method, at least one loop region of the adenovirus hexon is changed with at least one loop region of another adenovirus serotype. Thus, at least one loop region of such an altered adenovirus hexon protein is a simian Ad hexon loop region of the invention (e.g. Pan7). In one embodiment, a loop region of the Pan7 hexon protein is replaced by a loop region from another adenovirus serotype. In another embodiment, the loop region of the Pan7 hexon is used to replace a loop region from another adenovirus serotype. Suitable adenovirus serotypes may be readily selected from among human and non-human serotypes, as described herein. Pan7 is selected for purposes of illustration only; the other simian Ad hexon proteins of the invention may be similarly altered, or used to alter another Ad hexon. The selection of a suitable serotype is not a limitation of the present invention. Still other uses for the hexon protein sequences of the invention will be readily apparent to those of skill in the art.

The invention further encompasses the fiber proteins of the simian adenoviruses of the invention. The fiber protein of AdPan 5 has the amino acid sequence of SEQ ID NO:4. The fiber protein AdPan6 has the amino acid sequence of SEQ ID NO: 8. The fiber protein of AdPan7 has the amino acid sequence of SEQ ID NO: 12. SV-1 has two fiber proteins; fiber 2 has the amino acid sequence of SEQ ID NO:27 and fiber 1 has the amino acid sequence of SEQ ID NO:28. SV-25 also has two fiber proteins; fiber 2 has the amino acid sequence of SEQ ID NO:32 and fiber 1 has the amino acid sequence of SEQ ID NO:33. The fiber protein of SV-39 has the amino acid sequence of SEQ ID NO:37.

Suitably, this fiber protein, or unique fragments thereof, may be utilized for a variety of purposes. One suitable fragment is the fiber knob, which spans about amino acids 247 to 425 of SEQ ID NO: 4, 8, 12, 28, 32, 33 and 37. See FIG. 2. Examples of other suitable fragments include the fiber having N-terminal and/or C-terminal truncations of about 50, 100, 150, or 200 amino acids, based upon the amino acid numbering provided above and in SEQ ID NO: 4, 8, 12, 28, 32, 33 and 37. Still other suitable fragments include internal fragments.

Further, the fiber protein may be modified using a variety of techniques known to those of skill in the art.

The invention further encompasses unique fragments of the proteins of the invention which are at least 8 amino acids in length. However, fragments of other desired lengths can be readily utilized. In addition, the invention encompasses such modifications as may be introduced to enhance yield and/or expression of a Pan5, Pan6, Pan7, SV1, SV25 or SV39 gene product, e.g., construction of a fusion molecule in which all or a fragment of the Pan5, Pan6, Pan7, SV1, SV25 or SV39 gene product is fused (either directly or via a linker) with a fusion partner to enhance. Other suitable modifications include, without limitation, truncation of a coding region (e.g., a protein or enzyme) to eliminate a pre- or pro-protein ordinarily cleaved and to provide the mature protein or enzyme and/or mutation of a coding region to provide a secretable gene product. Still other modifications will be readily apparent to one of skill in the art. The invention further encompasses proteins having at least about 95% to 99% identity to the Pan5, Pan6, Pan7, SV1, SV25 or SV39 proteins provided herein.

As described herein, vectors of the invention containing the adenoviral capsid proteins of the invention are particularly well suited for use in applications in which the neutralizing antibodies diminish the effectiveness of other Ad serotype based vectors, as well as other viral vectors. The rAd vectors of the invention are particularly advantageous in readministration for repeat gene therapy or for boosting immune response (vaccine titers).

Under certain circumstances, it may be desirable to use one or more of the Pan5, Pan6, Pan7, SV1, SV25 and/or SV39 gene products (e.g., a capsid protein or a fragment thereof) to generate an antibody. The term "an antibody," as used herein, refers to an immunoglobulin molecule which is able to specifically bind to an epitope. Thus, the antibodies of the invention bind, preferably specifically and without cross-reactivity, to a Pan5, Pan6, Pan7, SV1, SV25 or SV39 epitope. The antibodies in the present invention exist in a variety of forms including, for example, high affinity polyclonal antibodies, monoclonal antibodies, synthetic antibodies, chimeric antibodies, recombinant antibodies and humanized antibodies. Such antibodies originate from immunoglobulin classes IgG, IgM, IgA, IgD and IgE.

Such antibodies may be generated using any of a number of methods know in the art. Suitable antibodies may be generated by well-known conventional techniques, e.g. Kohler and Milstein and the many known modifications thereof. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., 1986 *Science*, 233:747-753; Queen et al., 1989 *Proc. Nat'l. Acad. Sci. USA*, 86:10029-10033; PCT Patent Application No. PCT/WO9007861; and Riechmann et al., *Nature*, 332:323-327 (1988); Huse et al, 1988a *Science*, 246:1275-1281]. Alternatively, antibodies can be produced by manipulating the complementarity determining regions of animal or human antibodies to the antigen of this invention. See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994); Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, *Proc. Natl. Acad. Sci. USA* 85:5879-5883; and Bird et al., 1988, *Science* 242:423-426. Further provided by the present invention are anti-idiotype antibodies (Ab2) and anti-anti-idiotype antibodies (Ab3). See, e.g., M. Wettendorff et al., "Modulation of anti-tumor immunity by anti-idiotypic antibodies." In Idiotypic Network and Diseases, ed. by J. Cerny and J. Hiernaux, 1990 *J. Am. Soc. Microbiol.*, Washington D.C.: pp. 203-229]. These anti-idiotype and anti-anti-idiotype antibodies are produced using techniques well known to those of skill in the art. These antibodies may be used for a variety of purposes, including diagnostic and clinical methods and kits.

Under certain circumstances, it may be desirable to introduce a detectable label or a tag onto a Pan5, Pan6, Pan7, SV1, SV25 or SV39 gene product, antibody or other construct of the invention. As used herein, a detectable label is a molecule which is capable, alone or upon interaction with another molecule, of providing a detectable signal. Most desirably, the label is detectable visually, e.g. by fluorescence, for ready use in immunohistochemical analyses or immunofluorescent microscopy. For example, suitable labels include fluorescein isothiocyanate (FITC), phycoerythrin (PE), allophycocyanin (APC), coriphosphine-O(CPO) or tandem dyes, PE-cyanin-5 (PC5), and PE-Texas Red (ECD). All of these fluorescent dyes are commercially available, and their uses known to the art. Other useful labels include a colloidal gold label. Still other useful labels include radioactive compounds or elements. Additionally, labels include a variety of enzyme systems that operate to reveal a colorimetric signal in an assay, e.g., glucose oxidase (which uses glucose as a substrate) releases peroxide as a product which in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength.

Other label systems that are utilized in the methods of this invention are detectable by other means, e.g., colored latex microparticles [Bangs Laboratories, Indiana] in which a dye is embedded are used in place of enzymes to form conjugates with the target sequences provide a visual signal indicative of the presence of the resulting complex in applicable assays.

Methods for coupling or associating the label with a desired molecule are similarly conventional and known to those of skill in the art. Known methods of label attachment are described [see, for example, Handbook of Fluorescent probes and Research Chemicals, 6th Ed., R. P. M. Haugland, Molecular Probes, Inc., Eugene, Oreg., 1996; Pierce Catalog and Handbook, Life Science and Analytical Research Products, Pierce Chemical Company, Rockford, Ill., 1994/1995]. Thus, selection of the label and coupling methods do not limit this invention.

The sequences, proteins, and fragments of the invention may be produced by any suitable means, including recombinant production, chemical synthesis, or other synthetic means. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, *J. Am. Chem. Soc.*, 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

In addition, one of skill in the art will readily understand that the Ad sequences of the invention can be readily adapted for use for a variety of viral and non-viral vector systems for in vitro, ex vivo or in vivo delivery of therapeutic and immunogenic molecules. For example, in one embodiment, the simian Ad capsid proteins and other simian adenovirus proteins described herein are used for non-viral, protein-based delivery of genes, proteins, and other desirable diagnostic, therapeutic and immunogenic molecules. In one such embodiment, a protein of the invention is linked, directly or indirectly, to a molecule for targeting to cells with a receptor for adenoviruses. Preferably, a capsid protein such as a hexon, penton, fiber or a fragment thereof having a ligand for a cell surface receptor is selected for such targeting. Suitable molecules for delivery are selected from among the therapeutic molecules described herein and their gene products. A variety of linkers including, lipids, polyLys, and the like may be utilized as linkers. For example, the simian penton protein may be readily utilized for such a purpose by production of a fusion protein using the simian penton sequences in a manner analogous to that described in Medina-Kauwe L K, et al, *Gene Ther.* 2001 May; 8(10):795-803 and Medina-Kauwe L K, et al, *Gene Ther.* 2001 December; 8(23): 1753-1761. Alternatively, the amino acid sequences of simian Ad protein IX may be utilized for targeting vectors to a cell surface receptor, as described in US Patent Appln 20010047081. Suitable ligands include a CD40 antigen, an RGD-containing or polylysine-containing sequence, and the like. Still other simian Ad proteins, including, e.g., the hexon protein and/or the fiber protein, may be used for used for these and similar purposes.

Still other adenoviral proteins of the invention may be used as alone, or in combination with other adenoviral protein, for a variety of purposes which will be readily apparent to one of skill in the art. In addition, still other uses for the adenoviral proteins of the invention will be readily apparent to one of skill in the art.

II. Recombinant Adenoviral Vectors

The compositions of this invention include vectors that deliver a heterologous molecule to cells, either for therapeutic or vaccine purposes. As used herein, a vector may include any genetic element including, without limitation, naked DNA, a phage, transposon, cosmid, episome, plasmid, or a virus. Such vectors contain simian adenovirus DNA of Pan5, Pan6, Pan7, SV1, SV25 and/or SV39 and a minigene. By "minigene" is meant the combination of a selected heterologous gene and the other regulatory elements necessary to drive translation, transcription and/or expression of the gene product in a host cell.

Typically, an adenoviral vector of the invention is designed such that the minigene is located in a nucleic acid molecule which contains other adenoviral sequences in the region native to a selected adenoviral gene. The minigene may be inserted into an existing gene region to disrupt the function of that region, if desired. Alternatively, the minigene may be inserted into the site of a partially or fully deleted adenoviral gene. For example, the minigene may be located in the site of such as the site of a functional E1 deletion or functional E3 deletion, among others that may be selected. The term "functionally deleted" or "functional deletion" means that a sufficient amount of the gene region is removed or otherwise damaged, e.g., by mutation or modification, so that the gene region is no longer capable of producing functional products of gene expression. If desired, the entire gene region may be removed. Other suitable sites for gene disruption or deletion are discussed elsewhere in the application.

For example, for a production vector useful for generation of a recombinant virus, the vector may contain the minigene and either the 5' end of the adenoviral genome or the 3' end of the adenoviral genome, or both the 5' and 3' ends of the adenoviral genome. The 5' end of the adenoviral genome contains the 5' cis-elements necessary for packaging and replication; i.e., the 5' inverted terminal repeat (ITR) sequences (which functions as origins of replication) and the native 5' packaging enhancer domains (that contain sequences necessary for packaging linear Ad genomes and enhancer elements for the E1 promoter). The 3' end of the adenoviral genome includes the 3' cis-elements (including the ITRs) necessary for packaging and encapsidation. Suitably, a recombinant adenovirus contains both 5' and 3' adenoviral cis-elements and the minigene is located between the 5' and 3' adenoviral sequences. Any adenoviral vector of the invention may also contain additional adenoviral sequences.

Suitably, these adenoviral vectors of the invention contain one or more adenoviral elements derived from an adenoviral genome of the invention. In one embodiment, the vectors contain adenoviral ITRs from Pan5, Pan6, Pan7, SV1, SV25 or SV39 and additional adenoviral sequences from the same adenoviral serotype. In another embodiment, the vectors contain adenoviral sequences that are derived from a different adenoviral serotype than that which provides the ITRs. As defined herein, a pseudotyped adenovirus refers to an adenovirus in which the capsid protein of the adenovirus is from a different serotype than the serotype which provides the ITRs. The selection of the serotype of the ITRs and the serotype of any other adenoviral sequences present in vector is not a limitation of the present invention. A variety of adenovirus strains are available from the American Type Culture Collection, Manassas, Va., or available by request from a variety of commercial and institutional sources. Further, the sequences of many such strains are available from a variety of databases including, e.g., PubMed and GenBank. Homologous adenovirus vectors prepared from other simian or from human adenoviruses are described in the published literature [see, for example, U.S. Pat. No. 5,240,846]. The DNA sequences of a number of adenovirus types are available from GenBank, including type Ad5 [GenBank Accession No. M73260]. The adenovirus sequences may be obtained from any known adenovirus serotype, such as serotypes 2, 3, 4, 7, 12 and 40, and further including any of the presently identified human types. Similarly adenoviruses known to infect non-human animals (e.g., simians) may also be employed in the vector constructs of this invention. See, e.g., U.S. Pat. No. 6,083,716.

The viral sequences, helper viruses, if needed, and recombinant viral particles, and other vector components and sequences employed in the construction of the vectors described herein are obtained as described above. The DNA sequences of the Pan5, Pan6, Pan7, SV1, SV25 and/or SV39 simian adenovirus sequences of the invention are employed to construct vectors and cell lines useful in the preparation of such vectors.

Modifications of the nucleic acid sequences forming the vectors of this invention, including sequence deletions, insertions, and other mutations may be generated using standard molecular biological techniques and are within the scope of this invention.

A. The "Minigene"

The methods employed for the selection of the transgene, the cloning and construction of the "minigene" and its insertion into the viral vector are within the skill in the art given the teachings provided herein.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is GFP or luciferase, the vector carrying the signal may be measured visually by color or light production in a luminometer.

However, desirably, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used for treatment, e.g., of genetic deficiencies, as a cancer therapeutic or vaccine, for induction of an immune response, and/or for prophylactic vaccine purposes. As used herein, induction of an immune response refers to the ability of a molecule (e.g., a gene product) to induce a T cell and/or a humoral immune response to the molecule. The invention further includes using multiple transgenes, e.g., to correct or ameliorate a condition caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Virol.*, 78(Pt 1):13-21 (January 1997); Furler, S., et al, *Gene Ther.*, 8(11):864-873 (June 2001); Klump H., et al., *Gene Ther.*, 8(10):811-817 (May 2001). This 2A peptide is significantly smaller than an IRES, making it well suited for use when space is a limiting factor. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements necessary which are operably linked to the transgene in a manner that permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system [WO 98/10088]; the ecdysone insect promoter [No et al, *Proc. Natl. Acad. Sci. USA*, 93:3346-3351 (1996)], the tetracycline-repressible system [Gossen et al, *Proc. Natl. Acad. Sci. USA*, 89:5547-5551 (1992)], the tetracycline-inducible system [Gossen et al, *Science*, 268:1766-1769 (1995), see also Harvey et al, *Curr. Opin. Chem. Biol.*, 2:512-518 (1998)]. Other systems include the FK506 dimer, VP16 or p65 using castradiol, diphenol murislerone, the RU486-inducible system [Wang et al, *Nat. Biotech.*, 15:239-243 (1997) and Wang et al, *Gene Ther.*, 4:432-441 (1997)] and the rapamycin-inducible system [Magari et al, *J. Clin. Invest.*, 100:2865-2872 (1997)]. The effectiveness of some inducible promoters increases over time. In such cases one can enhance the effectiveness of such systems by inserting multiple repressors in tandem, e.g., TetR linked to a TetR by an IRES. Alternatively, one can wait at least 3 days before screening for the desired function. One can enhance expression of desired proteins by known means to enhance the effectiveness of this system. For example, using the Woodchuck Hepatitis Virus Posttranscriptional Regulatory Element (WPRE).

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal ∃-actin, myosin light chain 2A, dystrophin, muscle creatine kinase, as well as synthetic muscle promoters with activities higher than naturally occurring promoters (see Li et al., *Nat. Biotech.*, 17:241-245 (1999)). Examples of promoters that are tissue-specific are known for liver (albumin, Miyatake et al., *J. Virol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)), bone osteocalcin (Stein et al., *Mol. Biol. Rep.*, 24:185-96 (1997)); bone sialoprotein (Chen et al., *J. Bone Miner. Res.*, 11:654-64 (1996)), lymphocytes (CD2, Hansal et al., *J. Immunol.*, 161:1063-8 (1998); immunoglobulin heavy chain; T cell receptor chain), neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA*, 88:5611-5 (1991)), and the neuron-specific vgf gene (Piccioli et al., *Neuron*, 15:373-84 (1995)), among others.

Optionally, vectors carrying transgenes encoding therapeutically useful or immunogenic products may also include selectable markers or reporter genes may include sequences encoding geneticin, hygromicin or purimycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication. Selection of these and other promoters and vector elements are conventional and many such sequences are available [see, e.g., Sambrook et al, and references cited therein].

These vectors are generated using the techniques and sequences provided herein, in conjunction with techniques known to those of skill in the art. Such techniques include conventional cloning techniques of cDNA such as those described in texts [Sambrook et al, Molecular Cloning: A Laboratory Manual, Cold Spring Harbor Press, Cold Spring Harbor, N.Y.], use of overlapping oligonucleotide sequences of the adenovirus genomes, polymerase chain reaction, and any suitable method which provides the desired nucleotide sequence.

III. Production of the Recombinant Viral Particle

In one embodiment, the simian adenoviral plasmids (or other vectors) are used to produce recombinant adenoviral particles. In one embodiment, the recombinant adenoviruses are functionally deleted in the E1a or E1b genes, and optionally bearing other mutations, e.g., temperature-sensitive mutations or deletions in other genes. In other embodiments, it is desirable to retain an intact E1a and/or E1b region in the recombinant adenoviruses. Such an intact E1 region may be located in its native location in the adenoviral genome or placed in the site of a deletion in the native adenoviral genome (e.g., in the E3 region).

In the construction of useful simian adenovirus vectors for delivery of a gene to the human (or other mammalian) cell, a range of adenovirus nucleic acid sequences can be employed in the vectors. For example, all or a portion of the adenovirus delayed early gene E3 may be eliminated from the simian adenovirus sequence which forms a part of the recombinant virus. The function of simian E3 is believed to be irrelevant to the function and production of the recombinant virus particle. Simian adenovirus vectors may also be constructed having a deletion of at least the ORF6 region of the E4 gene, and more desirably because of the redundancy in the function of this region, the entire E4 region. Still another vector of this invention contains a deletion in the delayed early gene E2a. Deletions may also be made in any of the late genes L1 through L5 of the simian adenovirus genome. Similarly, deletions in the intermediate genes IX and IVa$_2$ may be useful for some purposes. Other deletions may be made in the other structural or non-structural adenovirus genes. The above discussed deletions may be used individually, i.e., an adenovirus sequence for use in the present invention may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2a and E3 genes, or of the E1 and E3 genes, or of E1, E2a and E4 genes, with or without deletion of E3, and so on. As discussed above, such deletions may be used in combination with other mutations, such as temperature-sensitive mutations, to achieve a desired result.

An adenoviral vector lacking any essential adenoviral sequences (e.g., E1a, E1b, E2a, E2b, E4 ORF6, L1, L2, L3, L4 and L5) may be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell. See, for example, the techniques described for preparation of a "minimal" human Ad vector in International Patent Application WO96/13597, published May 9, 1996, and incorporated herein by reference.

1. Helper Viruses

Thus, depending upon the simian adenovirus gene content of the viral vectors employed to carry the minigene, a helper adenovirus or non-replicating virus fragment may be necessary to provide sufficient simian adenovirus gene sequences necessary to produce an infective recombinant viral particle containing the minigene. Useful helper viruses contain selected adenovirus gene sequences not present in the adenovirus vector construct and/or not expressed by the packaging cell line in which the vector is transfected. In one embodiment, the helper virus is replication-defective and contains a variety of adenovirus genes in addition to the sequences described above. Such a helper virus is desirably used in combination with an E1-expressing cell line.

Helper viruses may also be formed into poly-cation conjugates as described in Wu et al, *J. Biol. Chem.*, 264:16985-16987 (1989); K. J. Fisher and J. M. Wilson, *Biochem. J*, 299:49 (Apr. 1, 1994). Helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter is used to enable separation between the resulting recombinant virus and the helper virus upon purification.

2. Complementation Cell Lines

To generate recombinant simian adenoviruses (Ad) deleted in any of the genes described above, the function of the deleted gene region, if essential to the replication and infectivity of the virus, must be supplied to the recombinant virus by a helper virus or cell line, i.e., a complementation or packaging cell line. In many circumstances, a cell line expressing the human E1 can be used to transcomplement the chimp Ad vector. This is particularly advantageous because, due to the diversity between the chimp Ad sequences of the invention and the human AdE1 sequences found in currently available packaging cells, the use of the current human E1-containing cells prevents the generation of replication-competent adenoviruses during the replication and production process. However, in certain circumstances, it will be desirable to utilize a cell line which expresses the E1 gene products can be utilized for production of an E1-deleted simian adenovirus. Such cell lines have been described. See, e.g., U.S. Pat. No. 6,083,716.

If desired, one may utilize the sequences provided herein to generate a packaging cell or cell line that expresses, at a minimum, the adenovirus E1 gene from Pan5, Pan6, Pan7, SV1, SV25 or SV39 under the transcriptional control of a promoter for expression in a selected parent cell line. Inducible or constitutive promoters may be employed for this purpose. Examples of such promoters are described in detail elsewhere in this specification. A parent cell is selected for the generation of a novel cell line expressing any desired AdPan5, Pan6, Pan7, SV1, SV25 or SV39 gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources.

Such E1-expressing cell lines are useful in the generation of recombinant simian adenovirus E1 deleted vectors. Additionally, or alternatively, the invention provides cell lines that express one or more simian adenoviral gene products, e.g., E1a, E1b, E2a, and/or E4 ORF6, can be constructed using essentially the same procedures for use in the generation of recombinant simian viral vectors. Such cell lines can be utilized to transcomplement adenovirus vectors deleted in the essential genes that encode those products, or to provide helper functions necessary for packaging of a helper-dependent virus (e.g., adeno-associated virus). The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus genomes, combined with polymerase chain reaction, synthetic methods, and any other suitable methods which provide the desired nucleotide sequence.

In still another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, HEK 293 cells or PERC6 (both of which express functional adenoviral E1) [Fallaux, F J et al, (1998), Hum Gene Ther, 9:1909-1917], Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

3. Assembly of Viral Particle and Transfection of a Cell Line

Generally, when delivering the vector comprising the minigene by transfection, the vector is delivered in an amount from about 5 µg to about 100 µg DNA, and preferably about 10 to about 50 µg DNA to about $1 \times 10^4$ cells to about $1 \times 10^{13}$ cells, and preferably about $10^5$ cells. However, the relative amounts of vector DNA to host cells may be adjusted, taking into consideration such factors as the selected vector, the delivery method and the host cells selected.

The vector may be any vector known in the art or disclosed above, including naked DNA, a plasmid, phage, transposon, cosmids, episomes, viruses, etc. Introduction into the host cell of the vector may be achieved by any means known in the art or as disclosed above, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation.

Assembly of the selected DNA sequences of the adenovirus (as well as the transgene and other vector elements into various intermediate plasmids, and the use of the plasmids and vectors to produce a recombinant viral particle are all achieved using conventional techniques. Such techniques include conventional cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like.

For example, following the construction and assembly of the desired minigene-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. The current method for producing such virus particles is transfection-based. However, the invention is not limited to such methods.

The resulting recombinant simian adenoviruses are useful in transferring a selected transgene to a selected cell. In in vivo experiments with the recombinant virus grown in the packaging cell lines, the E1-deleted recombinant simian adenoviral vectors of the invention demonstrate utility in transferring a transgene to a non-simian, preferably a human, cell.

IV. Use of the Recombinant Adenovirus Vectors

The recombinant simian adenovirus vectors of the invention are useful for gene transfer to a human or non-simian veterinary patient in vitro, ex vivo, and in vivo.

The recombinant adenovirus vectors described herein can be used as expression vectors for the production of the products encoded by the heterologous genes in vitro. For example, the recombinant adenoviruses containing a gene inserted into the location of an E1 deletion may be transfected into an E1-expressing cell line as described above. Alternatively, replication-competent adenoviruses may be used in another selected cell line. The transfected cells are then cultured in the conventional manner, allowing the recombinant adenovirus to express the gene product from the promoter. The gene product may then be recovered from the culture medium by known conventional methods of protein isolation and recovery from culture.

A Pan5, Pan6, Pan7, SV1, SV25 or SV39-derived recombinant simian adenoviral vector of the invention provides an efficient gene transfer vehicle that can deliver a selected transgene to a selected host cell in vivo or ex vivo even where the organism has neutralizing antibodies to one or more AAV serotypes. In one embodiment, the rAAV and the cells are mixed ex vivo; the infected cells are cultured using conventional methodologies; and the transduced cells are re-infused into the patient. These compositions are particularly well suited to gene delivery for therapeutic purposes and for immunization, including inducing protective immunity.

More commonly, the Pan 5, Pan6, Pan7, SV1, SV25, or SV39 recombinant adenoviral vectors of the invention will be utilized for delivery of therapeutic or immunogenic molecules, as described below. It will be readily understood for both applications, that the recombinant adenoviral vectors of the invention are particularly well suited for use in regimens involving repeat delivery of recombinant adenoviral vectors. Such regimens typically involve delivery of a series of viral vectors in which the viral capsids are alternated. The viral capsids may be changed for each subsequent administration, or after a pre-selected number of administrations of a particular serotype capsid (e.g., one, two, three, four or more). Thus, a regimen may involve delivery of a rAd with a first simian capsid, delivery with a rAd with a second simian capsid, and delivery with a third simian capsid. A variety of other regimens which use the Ad capsids of the invention alone, in combination with one another, or in combination with other Ad serotypes will be apparent to those of skill in the art. Optionally, such a regimen may involve administration of rAd with capsids of other non-human primate adenoviruses, human adenoviruses, or artificial serotypes such as are described herein. Each phase of the regimen may involve administration of a series of injections (or other delivery routes) with a single Ad serotype capsid followed by a series with another Ad serotype capsid. Alternatively, the recombinant Ad vectors of the invention may be utilized in regimens involving other non-adenoviral-mediated delivery systems, including other viral systems, non-viral delivery systems, protein, peptides, and other biologically active molecules.

The following sections will focus on exemplary molecules which may be delivered via the adenoviral vectors of the invention.

A. Ad-Mediated Delivery of Therapeutic Molecules

In one embodiment, the above-described recombinant vectors are administered to humans according to published methods for gene therapy. A simian viral vector bearing the selected transgene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The simian adenoviral vectors are administered in sufficient amounts to transduce the target cells and to provide sufficient levels of gene transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the retina and other intraocular delivery methods, direct delivery to the liver, inhalation, intranasal, intravenous, intramuscular, intratracheal, subcutaneous, intradermal, rectal, oral and other parenteral routes of administration. Routes of administration may be combined, if desired, or adjusted depending upon the transgene or the condition. The route of administration primarily will depend on the nature of the condition being treated.

Dosages of the viral vector will depend primarily on factors such as the condition being treated, the age, weight and health of the patient, and may thus vary among patients. For example, a therapeutically effective adult human or veterinary dosage of the viral vector is generally in the range of from about 100 µL to about 100 mL of a carrier containing concentrations of from about $1 \times 10^6$ to about $1 \times 10^{15}$ particles, about $1 \times 10^{11}$ to $1 \times 10^{13}$ particles, or about $1 \times 10^9$ to $1 \times 10^{12}$ particles virus. Dosages will range depending upon the size of the animal and the route of administration. For example, a suitable human or veterinary dosage (for about an 80 kg animal) for intramuscular injection is in the range of about $1 \times 10^9$ to about $5 \times 10^{12}$ particles per mL, for a single site. Optionally, multiple sites of administration may be delivered. In another example, a suitable human or veterinary dosage may be in the range of about $1 \times 10^{11}$ to about $1 \times 10^{15}$ particles for an oral formulation. One of skill in the art may adjust these doses, depending the route of administration, and the therapeutic or vaccinal application for which the recombinant vector is employed. The levels of expression of the transgene, or for an immunogen, the level of circulating antibody, can be monitored to determine the frequency of dosage administration. Yet other methods for determining the timing of frequency of administration will be readily apparent to one of skill in the art.

An optional method step involves the co-administration to the patient, either concurrently with, or before or after administration of the viral vector, of a suitable amount of a short acting immune modulator. The selected immune modulator is defined herein as an agent capable of inhibiting the formation of neutralizing antibodies directed against the recombinant vector of this invention or capable of inhibiting cytolytic T lymphocyte (CTL) elimination of the vector. The immune modulator may interfere with the interactions between the T helper subsets ($T_{H1}$ or $T_{H2}$) and B cells to inhibit neutralizing antibody formation. Alternatively, the immune modulator may inhibit the interaction between $T_{H1}$ cells and CTLs to reduce the occurrence of CTL elimination of the vector. A variety of useful immune modulators and dosages for use of same are disclosed, for example, in Yang et al., *J. Virol.*, 70(9) (September, 1996); International Patent Application No. WO96/12406, published May 2, 1996; and International Patent Application No. PCT/US96/03035, all incorporated herein by reference.

1. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor (TGF), platelet-derived growth factor (PDGF), insulin growth factors I and II (IGF-I and IGF-II), any one of the transforming growth factor superfamily, including TGF, activins, inhibins, or any one of the bone morphogenic proteins (BMP) BMPs 1-15, any one of the heregluin/neuregulin/AR1A/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, e.g., IL-2, IL-4, IL-12 and IL-18), monocyte chemoattractant protein, leukemia inhibitory factor, granulocyte-macrophage colony stimulating factor, Fas ligand, tumor necrosis factors and, interferons, and, stem cell factor, flk-2/flt3 ligand. Gene products produced by the immune system are also useful in the invention. These include, without limitation, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase 1, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence.

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene are particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce self-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

The simian adenoviral vectors of the invention are particularly well suited for therapeutic regimens in which multiple adenoviral-mediated deliveries of transgenes is desired, e.g., in regimens involving redelivery of the same transgene or in combination regimens involving delivery of other transgenes. Such regimens may involve administration of a Pan5, Pan6, Pan7, SV1, SV25 or SV39 simian adenoviral vector, followed by re-administration with a vector from the same serotype adenovirus. Particularly desirable regimens involve administration of a Pan5, Pan6, Pan7, SV1, SV25 or SV39 simian adenoviral vector of the invention, in which the serotype of the viral vector delivered in the first administration differs from the serotype of the viral vector utilized in one or more of the subsequent administrations. For example, a therapeutic regimen involves administration of a Pan5, Pan6, Pan7, SV1, SV25 or SV39 vector and repeat administration with one or more adenoviral vectors of the same or different serotypes. In another example, a therapeutic regimen involves administration of an adenoviral vector followed by repeat administration with a Pan5, Pan6, Pan7, SV1, SV25 or SV39 vector of the invention which differs from the serotype of the first delivered adenoviral vector, and optionally further administration with another vector which is the same or, preferably, differs from the serotype of the vector in the prior administration steps. These regimens are not limited to delivery of adenoviral vectors constructed using the Pan5, Pan6, Pan7, SV1, SV25 or SV39 simian serotypes of the invention. Rather, these regimens can readily utilize vectors other adenoviral serotypes, including, without limitation, other simian adenoviral serotypes (e.g., Pan9 or C68, C1, etc), other non-human primate adenoviral serotypes, or human adenoviral serotypes, in combination with one or more of the Pan5, Pan6, Pan7, SV1, SV25 or SV39 vectors of the invention. Examples of such simian, other non-human primate and human adenoviral serotypes are discussed elsewhere in this document. Further, these therapeutic regimens may involve either simultaneous or sequential delivery of Pan 5, Pan6, Pan7, SV1, SV25, and/or SV39 adenoviral vectors of the invention in combination with non-adenoviral vectors, non-viral vectors, and/or a variety of other therapeutically useful compounds or molecules. The present invention is not limited to these therapeutic regimens, a variety of which will be readily apparent to one of skill in the art.

B. Ad-Mediated Delivery of Immunogenic Transgenes

The recombinant simian adenoviruses may also be employed as immunogenic compositions. As used herein, an immunogenic composition is a composition to which a humoral (e.g., antibody) or cellular (e.g., a cytotoxic T cell) response is mounted to a transgene product delivered by the immunogenic composition following delivery to a mammal, and preferably a primate. The present invention provides a recombinant simian Ad that can contain in any of its adenovirus sequence deletions a gene encoding a desired immunogen. The simian adenovirus is likely to be better suited for use as a live recombinant virus vaccine in different animal species compared to an adenovirus of human origin, but is not limited to such a use. The recombinant adenoviruses can be used as prophylactic or therapeutic vaccines against any pathogen for which the antigen(s) crucial for induction of an immune response and able to limit the spread of the pathogen has been identified and for which the cDNA is available.

Such vaccinal (or other immunogenic) compositions are formulated in a suitable delivery vehicle, as described above. Generally, doses for the immunogenic compositions are in the range defined above for therapeutic compositions. The levels of immunity of the selected gene can be monitored to determine the need, if any, for boosters. Following an assessment of antibody titers in the serum, optional booster immunizations may be desired.

Optionally, a vaccinal composition of the invention may be formulated to contain other components, including, e.g. adjuvants, stabilizers, pH adjusters, preservatives and the like. Such components are well known to those of skill in the vaccine art. Examples of suitable adjuvants include, without limitation, liposomes, alum, monophosphoryl lipid A, and any biologically active factor, such as cytokine, an interleukin, a chemokine, a ligands, and optimally combinations thereof. Certain of these biologically active factors can be expressed in vivo, e.g., via a plasmid or viral vector. For example, such an adjuvant can be administered with a priming DNA vaccine encoding an antigen to enhance the antigen-specific immune response compared with the immune response generated upon priming with a DNA vaccine encoding the antigen only.

The recombinant adenoviruses are administered in a "an immunogenic amount", that is, an amount of recombinant adenovirus that is effective in a route of administration to transfect the desired cells and provide sufficient levels of expression of the selected gene to induce an immune response. Where protective immunity is provided, the recombinant adenoviruses are considered to be vaccine compositions useful in preventing infection and/or recurrent disease.

Alternatively, or in addition, the vectors of the invention may contain a transgene encoding a peptide, polypeptide or protein which induces an immune response to a selected immunogen. The recombinant adenoviruses of this invention are expected to be highly efficacious at inducing cytolytic T cells and antibodies to the inserted heterologous antigenic protein expressed by the vector.

For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirtis, rotavirus (which causes acute gastroenteritis in children), orbiviruses, and cultivirus (Colorado Tick fever, Lebombo (humans), equine encephalosis, blue tongue).

The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. No. 5,891,994 and U.S. Pat. No. 6,193,981.] See, also, the HIV and SIV proteins described in D. H. Barouch et al, J. Virol., 75(5): 2462-2467 (March 2001), and R. R. Amara, et al, *Science*, 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins have been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. Optionally, another combination may involve delivery of one or more expressed immunogens with delivery of one or more of the immunogens in protein form. Such combinations are discussed in more detail below.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek's disease virus, and rhadinovirus. The poxvirus family includes the sub-family chordopoxyirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxyirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include *meningococcus; gonococcus*. Pathogenic enteric gram-negative bacilli include enterobacteriaceae; *pseudomonas, acinetobacteria* and *eikenella*; melioidosis; *salmonella; shigella; haemophilus; moraxella; H. ducreyi* (which causes chancroid); *brucella; Franisella tularensis* (which causes tularemia); *yersinia* (pasteurella); *streptobacillus moniliformis* and *spirillum*; Gram-positive bacilli include listeria monocytogenes; *erysipelothrix rhusiopathiae; Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of *mycoplasma* and *chlamydial* infections include: *mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii*; Trichans; *Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); *Brucella* species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In RA, several specific variable regions of TCRs which are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In MS, several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a recombinant simian adenovirus that encodes at least one of these polypeptides will elicit an immune response that will target T cells involved in scleroderma.

C. Ad-Mediated Delivery Methods

The therapeutic levels, or levels of immunity, of the selected gene can be monitored to determine the need, if any, for boosters. Following an assessment of CD8+ T cell response, or optionally, antibody titers, in the serum, optional booster immunizations may be desired. Optionally, the recombinant simian adenoviral vectors of the invention may be delivered in a single administration or in various combination regimens, e.g., in combination with a regimen or course of treatment involving other active ingredients or in a prime-boost regimen. A variety of such regimens have been described in the art and may be readily selected.

For example, prime-boost regimens may involve the administration of a DNA (e.g., plasmid) based vector to prime the immune system to second, booster, administration with a traditional antigen, such as a protein or a recombinant virus carrying the sequences encoding such an antigen. See, e.g., WO 00/11140, published Mar. 2, 2000, incorporated by reference. Alternatively, an immunization regimen may involve the administration of a recombinant simian adenoviral vector of the invention to boost the immune response to a vector (either viral or DNA-based) carrying an antigen, or a protein. In still another alternative, an immunization regimen involves administration of a protein followed by booster with a vector encoding the antigen.

In one embodiment, the invention provides a method of priming and boosting an immune response to a selected antigen by delivering a plasmid DNA vector carrying said antigen, followed by boosting with a recombinant simian adenoviral vector of the invention. In one embodiment, the prime-boost regimen involves the expression of multiproteins from the prime and/or the boost vehicle. See, e.g., R. R. Amara, *Science,* 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered in a recombinant adenovirus construct of the invention. Still other regimens are described in WO 99/16884 and WO 01/54719.

However, the prime-boost regimens are not limited to immunization for HIV or to delivery of these antigens. For example, priming may involve delivering with a first chimp vector of the invention followed by boosting with a second chimp vector, or with a composition containing the antigen itself in protein form. In one example, the prime-boost regimen can provide a protective immune response to the virus, bacteria or other organism from which the antigen is derived. In another desired embodiment, the prime-boost regimen provides a therapeutic effect that can be measured using convention assays for detection of the presence of the condition for which therapy is being administered.

The priming composition may be administered at various sites in the body in a dose dependent manner, which depends on the antigen to which the desired immune response is being targeted. The invention is not limited to the amount or situs of injection(s) or to the pharmaceutical carrier. Rather, the regimen may involve a priming and/or boosting step, each of which may include a single dose or dosage that is administered hourly, daily, weekly or monthly, or yearly. As an example, the mammals may receive one or two doses containing between about 10 μg to about 50 μg of plasmid in carrier. A desirable amount of a DNA composition ranges between about 1 μg to about 10,000 μg of the DNA vector. Dosages may vary from about 1 μg to 1000 μg DNA per kg of subject body weight. The amount or site of delivery is desirably selected based upon the identity and condition of the mammal.

The dosage unit of the vector suitable for delivery of the antigen to the mammal is described herein. The vector is prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes. Optionally, the priming step of this invention also includes administering with the priming composition, a suitable amount of an adjuvant, such as are defined herein.

Preferably, a boosting composition is administered about 2 to about 27 weeks after administering the priming composition to the mammalian subject. The administration of the boosting composition is accomplished using an effective amount of a boosting composition containing or capable of delivering the same antigen as administered by the priming DNA vaccine. The boosting composition may be composed of a recombinant viral vector derived from the same viral source (e.g., adenoviral sequences of the invention) or from another source. Alternatively, the "boosting composition" can be a composition, containing the same antigen as encoded in the priming DNA vaccine, but in the form of a protein or peptide, which composition induces an immune response in the host. In another embodiment, the boosting composition contains a DNA sequence encoding the antigen under the control of a regulatory sequence directing its expression in a mammalian cell, e.g., vectors such as well-known bacterial or viral vectors. The primary requirements of the boosting composition are that the antigen of the composition is the same antigen, or a cross-reactive antigen, as that encoded by the priming composition.

In another embodiment, the simian adenoviral vectors of the invention are also well suited for use in a variety of other immunization and therapeutic regimens. Such regimens may involve delivery of simian adenoviral vectors of the invention simultaneously or sequentially with Ad vectors of different serotype capsids, regimens in which adenoviral vectors of the invention are delivered simultaneously or sequentially with non-Ad vectors, regimens in which the adenoviral vectors of the invention are delivered simultaneously or sequentially with proteins, peptides, and/or other biologically useful therapeutic or immunogenic compounds. Such uses will be readily apparent to one of skill in the art.

The following examples illustrate the cloning of the simian adenoviruses and the construction of exemplary recombinant adenovirus vectors of the present invention. These examples are illustrative only, and do not limit the scope of the present invention.

Example 1

Viral Propagation

The Pan5 [ATCC Accession No. VR-591], Pan6 [ATCC Accession No. VR-592], and Pan7 [ATCC Accession No. VR-593] viruses, originally isolated from lymph nodes from chimpanzees, were propagated in 293 cells [ATCC CRL1573]. Typically, these cells are cultured in Dulbecco's Modified Eagles Medium (DMEM; Sigma, St. Louis, Mo.) supplemented with 10% fetal calf serum (FCS) [Sigma or Hyclone, Logan, Utah] and 1% Penicillin-Streptomycin (Sigma). Infection of 293 cells is carried out in DMEM supplemented with 2% FCS for the first 24 hours, after which FCS is added to bring the final concentration to 10%. Infected cells are harvested when 100% of the cells exhibit virus-induced cytopathic effect (CPE), and are then collected, and concentrated by centrifugation. Cell pellets are resuspended in 10 mM Tris (pH 8.0), and lysed by 3 cycles of freezing and thawing. Virus preparations are obtained following two ultra centrifugation steps on cesium chloride density gradients and stocks of virus are diluted to 1 to $5 \times 10^{12}$ particles/ml in 10 mM Tris/100 mM NaCl/50% glycerol and stored at −70° C.

The ability of 293 cells to propagate these adenoviruses exceeded expectations which were based on knowledge of other non-human adenovirus serotypes.

| Virus | Yield (virus particles produced in $8 \times 10^8$ cells) |
|---|---|
| Pan5 | $8.8 \times 10^{13}$ |
| Pan6 | $1.6 \times 10^{14}$ |
| Pan7 | $8.8 \times 10^{13}$ |

Example 2

Characterization of Viral Genomic DNA

Genomic DNA was isolated from the purified virus preparations of Example 1 and digested with HindIII or BamHI restriction enzymes following the manufacturers' recommendations. The results (not shown) revealed that that the Pan5, Pan6, Pan7 genomes of the invention and the published Pan 9 (C68) genome show different restriction patterns, and thus, are distinct from each other.

The nucleotide sequences of Pan5, Pan6 and Pan7 were determined. The nucleotide sequence of the top strand of Pan5 DNA is reported in SEQ ID NO: 1. The nucleotide sequence of the top strand of Pan6 DNA is reported in SEQ ID NO: 5. The nucleotide sequence of the top strand of Pan7 DNA is reported in SEQ ID NO: 9.

Regulatory and coding regions in the viral DNA sequences were identified by homology to known adenoviral sequences using the "Clustal W" program described above at conventional settings. See the tables above providing the adenoviral sequences. Open reading frames were translated and the predicted amino acid sequences examined for homology to previously described adenoviral protein sequences, Ad4, Ad5, Ad7, Ad12, and Ad40.

Analysis of the sequence revealed a genome organization that is similar to that present in human adenoviruses, with the greatest similarity to human Ad4. However, substantial differences in the hexon hypervariable regions were noted between the chimpanzee adenoviruses and other known adenoviruses, including AdHu4. These differences fit well with the serological cross-reactivity data that has been obtained (see below).

An alignment of a portion of the hexon sequences is shown in FIG. 1. The portion shown is from the region of the hexon that corresponds to the outwardly disposed extended loops DE1 and FG1 where the most variability between serotypes is observed. An intervening portion that contributes to the base of the hexon (corresponding to residues 308-368 of the published AdC68 sequence; U.S. Pat. No. 6,083,716), and is highly conserved between serotypes, is also present. The following table summarizes the pair-wise comparisons of the amino acids in the hexon proteins.

| Comparison | | Hexon amino-acid |
|---|---|---|
| #1 | #2 | Similarity (%) |
| AdC5 | AdC7 | 99.0 |
| AdC5 | AdC68 | 98.3 |
| AdC5 | AdC6 | 88.0 |
| AdC5 | AdC1 | 84.9 |
| AdC6 | AdC7 | 87.7 |
| AdC6 | AdC68 | 87.3 |
| AdC6 | AdC1 | 84.9 |
| AdC7 | AdC68 | 97.5 |
| AdC7 | AdC1 | 84.8 |
| AdC68 | AdC1 | 84.9 |

Analysis of the fiber knob domain (which is responsible for receptor binding) of the chimpanzee adenoviruses shows an overall similarity in structure (FIG. 2).

The degree of sequence similarity between the E1 proteins of huAd5 and C68 (see Tables below) is similar to that between huAd5 and Pan-5, Pan-6, and Pan-7.

| Comparison | | E1a (13S) amino-acid |
|---|---|---|
| #1 | #2 | identity (%) |
| AdHu5 | AdC5 | 36.6 |
| AdHu5 | AdC6 | 28.5 |

-continued

| Comparison | | E1a (13S) amino-acid |
| --- | --- | --- |
| #1 | #2 | identity (%) |
| AdHu5 | AdC7 | 34.9 |
| AdHu5 | AdC68 | 35.6 |
| AdHu5 | AdC1 | 35.6 |
| AdC5 | AdC6 | 68.3 |
| AdC5 | AdC7 | 96.9 |
| AdC5 | AdC68 | 80.4 |
| AdC5 | AdC1 | 51.3 |
| AdC6 | AdC7 | 69.3 |
| AdC6 | AdC68 | 59.4 |
| AdC6 | AdC1 | 37.7 |
| AdC7 | AdC68 | 81.5 |
| AdC7 | AdC1 | 51.0 |
| AdC68 | AdC1 | 54.9 |

| | Sequence Identity with human Ad5 | |
| --- | --- | --- |
| | E1b Small T Protein | E1b Large T Protein |
| C68 | 47.3% | 55.8% |
| Pan-5 | 43.2% | 54.5% |
| Pan-6 | 45.3% | 54.5% |
| Pan-7 | 46.4% | 53.8% |

Replication-defective versions of AdC5, AdC6 and AdC7 were created by molecular cloning methods described in the following examples in which minigene cassettes were inserted into the place of the E1a and E1b genes. The molecular clones of the recombinant viruses were rescued and grown up in 293 cells for large-scale purification using the published CsCl sedimentation method [K. Fisher et al., J. Virol., 70:520 (1996)]. Vector yields were based on 50 plate (150 mm) preps in which approximately $1\times10^9$ 293 cells were infected with the corresponding viruses. Yields were determined by measuring viral particle concentrations spectrophotometrically. After having constructed E1-deleted vectors, it was determined that HEK 293 cells (which express human adenovirus serotype 5 E1 functions) trans-complement the E1 deletions of the novel viral vectors and allow for the production of high titer stocks. Examples of virus yields for a few of these recombinant viruses are shown in the table below.

The transgenes for these vectors, β-galactosidase (LacZ), green fluorescent protein (GFP), alpha-1-anti-trypsin (A1AT), ebola glycoprotein (ebo), a soluble ebola glycoprotein variant lacking the transmembrane and cytoplasmic domains (sEbo), and three deletion mutants of the ebola glycoprotein (EboΔ2, EboΔ3, and EboΔ4), were expressed by the cytomegalovirus promoter (CMV). In the following table, ND indicates that the study has not yet been done.

| | Viral backbone/Vector yield (Viral particles × $10^{13}$) | | | |
| --- | --- | --- | --- | --- |
| Transgene | AdHu5 | AdC7 | AdC68 | AdC6 |
| CMVLacZ | 1.5 | 1.4 | 3.3 | 6.1 |
| CMVGFP | 2.5 | 3.6 | 8 | 10 |
| CMVA1AT | 3.7 | 6 | 10 | ND |
| CMVEbo | 1.1 | 4.3 | ND | ND |
| CMVsEbo | 4.9 | 5.4 | ND | ND |
| CMVEboΔ2 | 1 | 9.3 | ND | ND |
| CMVEboΔ3 | 0.8 | 9.5 | ND | ND |
| CMVEboΔ4 | 1.4 | 6.2 | ND | ND |

The ability of human adenovirus E1 to trans-complement the E1-deleted chimpanzee viruses of the invention is highly advantageous, as it permits the production of E1-deleted chimpanzee adenoviral vectors of the invention, while reducing or eliminating the risk of homologous recombination due to the differences in sequences between human Ad and the chimpanzee adenoviruses described herein.

Example 3

Serological Studies of Pan 5, 6, and 7 Viruses

Because of the differences in the hexon hypervariable region, it was anticipated that the C5, C6, and C7 viruses would be serologically distinct from human adenoviruses, including AdHu4.

1. Cross-Reactivity of Wild-Type Viruses

For screening of wild-type viruses in order to make a determination of antibody cross-reactivity, the replication competent viruses were used and inhibition of cytopathic effects (CPE) was measured. Briefly, preparations of adenoviruses (Adhu5, Pan-5, Pan-6, Pan-7 and AdC68) stored at $5\times10^{12}$ particles/ml were diluted 1/600 for the assays. This concentration of virus was selected since it results in 100% CPE within 48 hours in the absence of neutralization. Prior to adding the virus to 293 cells ($4\times10^4$ cells/well in a 96 well dish), 1:20 dilutions of sera were added. The assay is read as the presence or absence of CPE; full neutralization would read as no cytopathic effect. The results are summarized in the Table below. The fact that 9/36 human sera neutralized Adhu5 induced CPE is consistent with previous estimates of neutralizing antibodies in the human population. The numbers indicate the total individuals who showed neutralization (numerator) versus the total number screened (denominator). ND=not determined.

| | Neutralization by 1/20 diln of serum | | |
| --- | --- | --- | --- |
| | Human (N = 36) | Rhesus (N = 52) | Chimpanzee (N = 20) |
| Adhu5 | 9/36 | ND | ND |
| AdC68 | 1/36 | 0/52 | 12/20 |
| Pan 5 | 0/36 | 0/52 | 10/20 |
| Pan 6 | 0/36 | 0/52 | 9/20 |
| Pan 7 | 0/36 | 0/52 | 12/20 |

Of all human sera screened, 35/36 were negative for neutralization to AdC68 while 36/36 were negative for neutralization to Pan-S, Pan-6 and Pan-7. Of 52 rhesus monkeys screened, none showed neutralization to any chimpanzee adenovirus; rhesus monkey is the preferred pre-clinical model for evaluating HIV vaccines. Between 9 to 12 out of 20 chimpanzees had substantial neutralization to one or another of the chimpanzee adenoviruses consistent with the fact these are indeed endemic chimpanzee-specific pathogens. Interestingly, there are chimpanzees with neutralizing antibodies only to Pan-5, Pan-6 or AdC68 supporting the hypothesis that several of these chimpanzee adenoviral vectors will not cross neutralize each other and are distinct serotypes.

The same assay was carried out for 20 chimpanzee serum samples. Fifty percent (50%) of the samples reacted serologically, in different degrees to Pan5; 40% to Pan6; 55% to Pan7 and 60% to C68. Among the positive serum samples, one of them had strong neutralizing activity to all four chimp viruses.

2. Cross-Neutralization with Recombinant Viruses

High-titer polyclonal antibodies were obtained to each of the simian adenoviruses in order to more precisely gauge the degree of cross-neutralization among the different serotypes. This was done by intramuscular immunization of rabbits using a recombinant virus containing GFP based on previously the described C68 chimpanzee adenovirus as an adjuvant. The serum was then used to assay for neutralizing activity against each of the three chimpanzee adenoviruses of the invention, AdC5, AdC6 and AdC7. A rabbit was injected with $5 \times 10^{12}$ viral particle per kg of C68CMVGFP vector intramuscularly and boosted 5 weeks later using the same dose. A bleed collected at the 9 week time point revealed extremely potent neutralizing activity against C68 as well as Pan-5 and Pan-7 but not against Pan-6 (see Table below), indicating that the administration of a C68 (or Pan-5 and Pan-7) based vaccine could be effectively followed by a boost using a vector based on Pan-6. However, it has been found that this level of inter-relatedness does not necessarily prevent with re-administration in a setting where antiviral antibody titers were not as high as was achieved in this rabbit. In the following table, + indicates 33% CPE; ++ indicates 66% CPE; +++ indicates 100% CPE.

| Infection on 293 cells with virus: | | | | | |
|---|---|---|---|---|---|
| Pan5 | Pan6 | Pan7 | Pan9 (C68) | C68 GFP | Serum Dilution |
| − | +++ | − | − | − | 1/20 |
| − | +++ | − | − | − | 1/40 |
| − | +++ | − | − | − | 1/80 |
| − | +++ | − | − | − | 1/160 |
| − | +++ | − | − | − | 1/320 |
| − | +++ | − | − | − | 1/640 |
| − | +++ | − | − | − | 1/1,280 |
| − | +++ | − | − | − | 1/2,560 |
| − | +++ | − | − | − | 1/5,120 |
| + | +++ | − | − | − | 1/10,240 |
| + | +++ | ++ | − | − | 1/20,480 |
| ++ | +++ | +++ | − | − | 1/40,960 |
| ++ | +++ | +++ | + | + | 1/81,920 |
| +++ | +++ | +++ | ++ | ++ | 1/163,840 |
| +++ | +++ | +++ | +++ | +++ | 1/327,680 |
| +++ | +++ | +++ | +++ | +++ | 1/665,360 |
| +++ | +++ | +++ | +++ | +++ | 1/1,310,720 |
| +++ | +++ | +++ | +++ | +++ | 1/2,621,440 |

3. Quantitative Assay for Detection of Neutralizing Antibody

The result was validated by a more quantitative-based assay for detecting neutralizing antibody, which is based on transduction of a GFP vector. Briefly, groups of C57BL/6 mice were immunized intramuscularly or intravenously with $5.0 \times 10^{10}$ particles/ml Pan5, Pan6, Pan7 or C68. Sera from day 28 bleeds were tested for cross-neutralizing activity against C68CMVEGFP at dilutions of 1/20 and 1/80. In summary, when a pharmaceutical preparation of human immunoglobulin was tested for serological reactions to Pan 5, 6, and 7, and C68, some low levels of neutralizing activities against Pan 7 and C68 were detected. No neutralizing activity against Pan5 or Pan6 was detected. Serum samples from 36 human subjects were run for the same assay. Serum samples were tested at a 1/20 dilution. The results indicated that only one individual has clear neutralizing activity to C68. No neutralizing activity to Pan5, Pan6 or Pan7 was detected.

4. In Vitro Cross-Neutralization

Cross-neutralization of the simian adenoviruses by high-titer rabbit polyclonal antibodies raised against each of the adenoviruses Pan-5, Pan-6, Pan-7, and C68 was tested.

Rabbits were immunized with intra-muscular injections of $10^{13}$ particles of each of the chimpanzee adenoviruses and boosted 40 days later with the same dose with incomplete Freund's adjuvant. Sera were analyzed or the presence of neutralizing antibodies by incubating serial two-fold dilutions with $10^9$ genome copies of each of the appropriate chimpanzee adenovirus vector expressing GFP and testing for the attenuation of GFP expression when applied to 293 cells. The serum dilution which produced a 50% reduction of GFP expression was scored as the neutralizing antibody titer against that particular virus.

The results are shown in the Table. The data are consistent with the expectation from sequence analysis of the hexon amino-acid sequences, which indicated that Ad Pan-6 was likely to be the most serologically distinct compared to the other chimpanzee adenoviruses.

| Serum from rabbit immunized with: | Infection of 293 cells with $10^9$ genome copies of | | | |
|---|---|---|---|---|
| | Ad Pan-5 | Ad Pan-6 | Ad Pan-7 | Ad C68 |
| Ad Pan-5 | 1/5120 | <1/20 | 1/2560 | 1/2560 |
| Ad Pan-6 | No neutralization | 1/20,480 | <1/20 | <1/20 |
| Ad Pan-7 | 1/2560 | 1/160 | 1/163,840 | 1/2560 |
| Ad C68 | No neutralization | <1/20 | <1/20 | 1/5120 |

In order to determine whether antibodies cross-reacting with the simian adenoviruses were likely to be of low prevalence in humans, simian adenoviruses SV1, SV39, and SV25 were tested for their ability to withstand neutralization when incubated with commercially available pooled human immunoglobulins (Ig). The same assay was also performed with Adhu5 and the chimpanzee adenoviruses Pan-5, Pan-6, Pan-7, and C68. In a further study, sera from mice has been immunized with one of the chimpanzee adenoviruses C5, C6, C7, and C68 and their ability to cross-neutralize the simian adenoviruses SV-15, SV-23, SA-17, and Baboon Adenovirus has been tested. No cross-reactivity was observed in any case.

Example 4

Generation of Recombinant E1-Deleted Pan5 Vector

A modified pX plasmid was prepared by destroying the Fspi site in the bla gene region of pX (Clontech) by site-directed mutagenesis. The resulting modified plasmid, termed pX', is a circular plasmid of 3000 bp which contains an f1 ori and an ampicillin resistance gene (AmpR-cds).

A. Production of Pan-5 Adenovirus Plasmid

A polylinker for sequential cloning of the Pan5 DNA fragments into pX' is created. The polylinker is substituted for the existing pX' polylinker following digestion with MluI and EcoRI. The blunt-FseI fragment of the Pan 5 is inserted into the SmaI and FseI sites of the polylinker. This fragment contains the 5' end of the adenoviral genome (bp 1 to 3606, SEQ ID NO:1). The SnaBI-FspI fragment of Pan 5 (bp 455 to 3484, SEQ ID NO:1) is replaced with a short sequence flanked by I-Ceu and PI-Sce sites from pShuttle (Clontech), to eliminate the E1 region of the adenoviral genome. The EcoRI-blunt fragment of Pan5 (bp 28658 to 36462, SEQ ID NO:1) is inserted into the EcoRI and EcoRV sites of the polylinker (to provide the 3' end of the adenoviral genome); the FseI-MluI fragment (bp 3606 to 15135, SEQ ID NO:1) is inserted into the polylinker; and the MluI-EcoRI fragment is inserted into the polylinker (bp 15135 to 28658, SEQ ID NO:1). Optionally, a desired transgene is inserted into I-CeuI and PI-SceI sites of the newly created pX'Pan5)E1 vector.

B. Alternative Method of Generating pX'Pan5)E1.

The initial plasmid pX is derived from pAdX adenovirus plasmid available from Clontech, as described above. Thereafter, a PacI-XhoI region of pX' was deleted and the blunt-ended Pan5 polylinker was inserted into the FspI site to generate pX'PLNK (2994 bp). The 5' end-FseI region of Pan 5 (bp 1-3607, SEQ ID NO:1) was inserted into SmaI and FseI sites of pX'LNK to generate the pX'Pan5-5' plasmid (6591 bp). The SnaBi-NdeI region of pX'Pan5-5' was excised and replaced with the Ceu/Sce cassette, which had been PCR amplified from pRCS to create pX'Pan5-5')E1 (4374 bp). Briefly, a sequence containing I-CeuI and PI-SceI rare cutter sites was PCR amplified from pRCS (3113 bp). The 3' PCR primer was introduced an NdeI site into the PCR product.

To extend the Pan5 DNA in pX'Pan5-5')E1 (4374 bp), the FseI-MluI region of Pan 5 (bp 3607-15135, SEQ ID NO:1) is added, to create pX'Pan5-5'Mlu (15900 bp). The remaining MluI-3' end of the Pan5 sequence (bp 15135-36462, SEQ ID NO:1) is added to the vector between the MluI and EcoRV sites of the vector polylinker to form pX'Pan5)E1 which contains the full-length Pan5 sequence containing a deletion in the E1 region.

C. Generation of Recombinant Viruses

To generate the recombinant adenoviruses from pX'Pan5)E1, the plasmid is co-transfected with a helper expressing E1, or from an E1-expressing packaging cell line, such as 293 cell line or a cell line prepared as described herein. The expression of E1 in the packaging cell permits the replication and packaging of the Pan5)E1 into a virion capsid. In another embodiment, the packaging cell transfected with pX'Pan5)E1 is transfected with an adenovirus vector as described above bearing the transgene of interest. Homologous recombination occurs between the helper and the plasmid, which permits the adenovirus-transgene sequences in the vector to be replicated and packaged into virion capsids, resulting in the recombinant adenovirus.

Transfection is followed by an agar overlay for 2 weeks, after which the viruses are plaqued, expanded and screened for expression of the transgene. Several additional rounds of plaque purification are followed by another expansion of the cultures. Finally the cells are harvested, a virus extract prepared and the recombinant chimpanzee adenovirus containing the desired transgene is purified by buoyant density ultracentrifugation in a CsCl gradient or by alternative means known to those of skill in the art.

Example 5

Generation of Recombinant E1-Deleted Pan6 Vector

A. Strategy for Construction of Pan-6 Adenoviral Plasmid
1. Cloning of Terminal Fragments
Pan 6 virus is deproteinated by pronase and proteanase K treatment and phenol extraction. Synthetic 12 bp Pme I linkers are ligated onto the viral DNA as described by Berkner and Sharp, *Nucleic Acids Research,* 11: 6003 (1983). The viral DNA is then digested with Xba I to isolate a 5' terminal fragment (6043 bp). The Ad6 XbaI 5' fragment is then ligated into pX link at Sma I and Xba I sites to form pX-AdPan6-0-16.5. The viral DNA with Pme I linkers is also digested with Pac I to isolate the 6475 bp 3' terminal fragment and cloned into pX link at Pac I and Sma I sites, resulting in pXAdPan 6-82-100.

2. Deletion of E1 from the 5' clone

To delete E1 (m.u.1.2-9), the BsiWi-Xba I fragment in pX-AdPan6-0-16.5 is replaced with a PCR fragment spanning m.u.9-16.7 fragment treated with BsiWi and Xba I, leading to pX-Ad-Pan6 m.u.0-1, 9-16.5.

3. Fusion of 5' and 3' Clones and to Create an Anchor Site to Accept the Middle Hind III Fragment First, the 5' clone, pX-Ad-Pan6 m.u.0-1, 9-16.5, is further expanded by inserting the $2^{nd}$ Xba I fragment (4350 bp, m.u.16.5-28) from Pan 6 genome into the Xba I site in the pX-Ad-Pan6 m.u.0-1, 9-16.5. This construct is named pXAd-Pan6-mu 0-1, 9-28.

Second, the 3' clone is also expanded by inserting the 15026 bp Mlu I/Pac I fragment covering m.u.41-82 from Pan 6 genome into the Mlu I/Pac I sites of pXAdPan6-82-100, generating pXAdPan6-m.u.41-100.

Then a 8167 bp Hind III/Eco 47III Pan 6 fragment is isolated from pXAd-Pan6-mu 0-1, 9-28 and subcloned into pXAdPan6-m.u.41-100 at Hind III and Xba I blunt sites. This 5' and 3' fusion clone is called pXAdPan6mu0-1, 9-19.5, 64-100.

4. Drop of the Middle Fragment of the Genome into the Fusion Clone

A 16335 bp Hind III fragment (m.u.19.5-64) from Pan 6 is inserted into Hind III site of pXAdPan6mu0-1, 9-19.5, 64-100 to form pXAdPan6-0-1, 9-100.

5. Introduction of a PKGFP Selective Marker into the Final Construct for Direct Cloning the Gene of Interest and Green/White Selection of Recombinant Transformants.

A minigene cassette that expresses GFP under a lac promoter and is flanked with recognition sites of rare intron encoding restriction enzymes, PI-Sce I and I-Ceu I, was isolated from pShuttle-pkGFP (bare) by Sap I and Dra III digestions followed by filling-in reaction. The pShuttle-pkGFP (bare) plasmid is 4126 bp in length, and contains a ColE1-Ori, a kanamycin resistance gene, plac, a LacZ promoter-GFP-mut3-1 cds (Clontech), and a GFPmut3-1 cds (Clontech). This cassette is subcloned into Srf I cut and blunted pXAd-Pan6-0-1, 9-100. This final construct is called pX-Pan6-pkGFP mu.0-1, 9-100, which is useful for generating recombinant E1-deleted Pan 6 molecular clones carrying genes of interest by direct ligation and green/white selection in combination with the generic pShuttlepkGFP vectors.

B. Alternative Strategy for Generation of Pan-6 Plasmid
1. Cloning of 5' Terminal Fragment
The Pan 6 virus is deproteinated by pronase and proteanase K treatment and phenol extraction as described above and synthetic 12 bp Pme I linkers are ligated onto the viral DNA as described. The AdPan6 5' XbaI fragment is isolated and ligated into pX to form pX-AdPan6-0-16.5 (9022 bp) as described in Part A above.

2. Deletion of E1 from the 5' Clone
To delete E1 (m.u. 1.2-9), pX-AdPan6-0-16.5 is digested with SnaBI and NdeI to remove the regions encoding the E1a and E1b proteins (3442-6310 bp). This vector is subsequently digested with BsiWI in preparation for blunting with the minigene cassette carrying a selective marker.

3. Introduction of a Selective Marker

A minigene cassette that expressed GFP under a lac promoter and which is flanked with recognition sites of rare intron encoding restriction enzymes, PI-XceI and I-CeuI, was isolated from pShuttle-pkGFP as described above. The DraIII-SapI fragment is then ligated with the digested pX-AdPan6-0-16.5 to form pX-AdPan6 MU 0-16.5)E1 (7749 bp).

4. Extension of Pan-6 Adenoviral Sequences pX-AdPan6 MU 0-16.5)E1 was subjected to XbaI digestion to permit insertion of an XbaI-RsrII linker. An XbaI/RsrII digestion fragment from the AdPan6 genome was isolated (mu 28-100, 26240 bp) and ligated into the Xba/RsrII-digested pX-AdPan6 MU 0-16.5)E1 to provide pX-AdPan6 MU 0-1, 9-16.5, 28-100. A second XbaI fragment from the Pan6 genome (mu 16.5-28, 4350 bp) is then ligated into this plasmid to form pX-AdPan6 MU 0-1, 9-100 (38551 bp).

C. Generation of Recombinant Adenoviruses

To generate the recombinant adenoviruses from a E1-deleted Pan6 plasmid prepared as described in Parts A or b, the plasmid is co-transfected with a helper expressing E1, or from an E1-expressing packaging cell line, such as 293 cell line or a cell line prepared as described herein. The expression of E1 in the packaging cell permits the replication and packaging of the Pan6-pkGFP mu.0-1, 9-100 into a virion capsid. Alternatively, the packaging cell transfected with pX-Pan6-pkGFP mu.0-1, 9-100 is transfected with an adenovirus vector as described above bearing another transgene of interest.

Example 6

Generation of Recombinant E1-Deleted Pan7 Vector

A. Generation of Pan 7 Plasmids

A synthetic linker containing the restriction sites PacI-SmaI-FseI-MluI-EcoRV-PacI was cloned into pBR322 that was cut with EcoRI and NdeI. The left end (bp1 to 3618) of Ad Pan7 was cloned into the linker between the SmaI and FseI sites. The adenovirus E1 was then excised from the cloned left end by cutting with SnaBI and NdeI and inserting an I-CeuI-GFP-PI-ScelI cassette from pShuttle (Clontech) in its place. The resulting plasmid was cut with FseI and MluI and Ad Pan7 fragment FseI (bp 3618) to MluI (bp 155114 was inserted to extend the left end. The construct (pPan7pGFP) was completed by inserting the 21421 bp Ad Pan7 right end fragment from the MluI site (bp 15114) into the above plasmid between MluI and EcoRV to generate a complete molecular clone of E1 deleted adenovirus Pan7 suitable for the generation of recombinant adenoviruses. Optionally, a desired transgene is inserted into the I-CeuI and PI-ScelI sites of the newly created pPan7 vector plasmid.

B. Construction of E1-Deleted Pan7 Viral Vectors

To generate the recombinant adenoviruses from pPan7)E1, the plasmid is co-transfected with a helper expressing E1, or from an E1-expressing packaging cell line, such as 293 cell line or a cell line prepared as described herein. The expression of E1 in the packaging cell permits the replication and packaging of the Pan7)E1 into a virion capsid. In another embodiment, the packaging cell transfected with pX'Pan7)E1 is transfected with an adenovirus vector as described above bearing the transgene of interest. Homologous recombination occurs between the helper and the plasmid, which permits the adenovirus-transgene sequences in the vector to be replicated and packaged into virion capsids, resulting in the recombinant adenovirus. Transfection and purification is as described above.

Example 7

Generation of Plasmid Vectors Expressing the E1 Genes

Plasmid vectors are constructed which encode the Pan5 E1 region gene, and these plasmids are used to generate stable cell lines expressing viral E1 proteins.

The E1 region of Pan5 is cloned into pX', essentially as described in Example 4 above, prior to replacement of this region with the fragment from pShuttle (Clontech). The expression plasmid contains the Pan5 adenoviral genome sequence spanning at least bp 1 to 3959 in the Pan5 genomic sequence. Thus, the expression plasmid contains the sequence encoding E1a and E1b of chimpanzee Ad Pan5 under the control of a heterologous promoter. Similar expression plasmids can be generated using the Ad Pan6 and AdPan 7 E1 regions, identified in the tables above.

Example 8

Generation of Cell Lines Expressing Chimpanzee Adenovirus E1 Proteins

Cell lines expressing viral E1 proteins are generated by transfecting HeLa (ATCC Acc. No. CCL2) with the plasmid of Example 6. These cell lines are useful for the production of E1-deleted recombinant chimpanzee adenoviruses by co-transfection of genomic viral DNA and the expression plasmids described above. Transfection of these cell lines, as well as isolation and purification of recombinant chimpanzee adenoviruses therefrom are performed by methods conventional for other adenoviruses, i.e., human adenoviruses [see, e.g., Horwitz, cited above and other standard texts].

A. Cell Lines Expressing Pan5 E1 Proteins

HeLa cells in 10 cm dishes are transfected with 10 μg of pX-Pan51-E1 DNA using a Cellphect™ kit (Pharmacia, Uppsala, Sweden) and following the manufacturer's protocol. 22 hours post-transfection, the cells are subjected to a three minute glycerol shock (15% glycerol in Hepes Buffered Saline, pH 7.5) washed once in DMEM (HeLa) or F12K (A549; Life Technologies, Inc., Grand Island, N.Y.) media supplemented with 10% FCS, 1% Pen-Strep, then incubated for six hours at 37° C. in the above described media. The transfected cells are then split into duplicate 15 cm plates at ratios of 1:20, 1:40, 1:80, 1:160, and 1:320. Following incubation at 37° C. overnight, the media is supplemented with G418 (Life Technologies, Inc.) at a concentration of 1 μg/ml. The media is replaced every 5 days and clones are isolated 20 days post-transfection.

HeLa E1 cell clones are isolated and assayed for their ability to augment adeno-associated virus (AAV) infection and expression of recombinant LacZ protein as described below.

B. AAV Augmentation Assay for Screening E1 Expressing Cell Lines

AAV requires adenovirus-encoded proteins in order to complete its life cycle. The adenoviral E1 proteins as well as the E4 region-encoded ORF6 protein are necessary for the augmentation of AAV infection. An assay for E1 expression based on AAV augmentation is used. Briefly, the method for identifying adenoviral E1-expressing cells comprises the steps of infecting in separate cultures a putative adenovirus E1-expressing cell and a cell containing no adenovirus sequence, with both an adeno-associated virus (AAV) expressing a marker gene and an AAV expressing the ORF6 of the E4 gene of human adenovirus, for a suitable time. The marker gene activity in the resulting cells is measured and those cells with significantly greater measurable marker activity than the control cells are selected as confirmed E1-expressing cells. In the following experiment, the marker gene is a lacZ gene and the marker activity is the appearance of blue stain.

For example, the cell lines described above, as well as untransfected control cells (HeLa) are infected with 100 genomes per cell of an AAV vector bearing a marker gene, e.g., AV.LacZ [K. Fisher et al., J. Virol., 70:520 (1996)] and an AAV vector expressing the ORF6 region of human 5 (AV.orf6). The DNA sequence of the plasmid generates a novel recombinant adeno-associated virus (rAAV) containing the LacZ transgene and the Ad E4 ORF 6, which is an open reading frame whose expression product facilitates single-stranded (ss) to double-stranded (ds) conversion of rAAV genomic DNA. These vectors are incubated in medium containing 2% FCS and 1% Pen-Strep at 37° C. for 4 hours, at which point an equal volume of medium containing 10% FCS is added. It should be understood by one of skill in the art that any marker gene (or reporter gene) may be employed in the first AAV vector of this assay, e.g., alkaline phosphatase, luciferase, and others. An antibody-enzyme assay can also be used to quantitate levels of antigen, where the marker expresses an antigen. The assay is not limited by the identity of the marker gene. Twenty to twenty-four hours post-infection, the cells are stained for LacZ activity using standard methods. After 4 hours the cells are observed microscopically and cell lines with significantly more blue cells than the A549 or HeLa cell controls are scored as positive.

Example 9

Delivery of Transgene to Host Cell

The resulting recombinant chimpanzee adenovirus described in Example 4, 5 or 6 above is then employed to deliver the transgene to a mammalian, preferably human, cell. For example, following purification of the recombinant virus, human embryonic kidney 293 cells are infected at an MOI of 50 particles per cell. GFP expression was documented 24 hours post-infection.

A. Gene Transfer in Mouse Models via Pan-6, Pan-7, and Pan-9 Vectors

Gene transfer efficiencies and toxicological profile of recombinant chimpanzee adenoviruses were compared in mouse liver directed gene transfer, mouse lung directed gene transfer, and mouse muscle directed gene transfer.

E1-deleted adenoviral vectors containing LacZ under the control of the CMV promoter were constructed using the techniques herein for human Ad5, chimpanzee Pan 6, chimpanzee Pan 7 and chimpanzee Pan 9 (C68). The vectors were delivered to immune-deficient NCR nude mice (80 for each study) as follows. For the liver study, 100 µl (1×10$^{11}$ particles) were injected into the tail vein. For the lung study, 50 µl (5×10$^{10}$ particles) were delivered intratracheally. For the muscle study, 25 µl (5×10$^{10}$ particles) were injected into tibialis anterior. The mice were sacrificed on days 3, 7, 14 and 28 post-vector injection (5 animals per group at each time point). At each necropsy, the liver/lung/muscle tissue was harvested and prepared for cryoblocks and paraffin embedding. The cryoblocks were sectioned for X-gal staining and the paraffin sections are H&E stained for histopathic analysis. At each time point, terminal bleeding was performed. Serum samples were subjected to liver function tests.

It was observed in this experiment the chimpanzee adenoviruses Pan-6, Pan-7, and Pan-9 were less efficient than huAd5 in gene transfer to the liver and to the lung. However, this may be desirable in certain circumstances, to reduce liver toxicity observed for huAds. The gene transfer efficiency in muscle varied less between serotypes.

B. Mouse Study to Feasibility of Re-Administration of Adenovirus Vectors by Serotype Switching Between Adhu5, Pan-6, Pan-7, and Pan-9 Vectors Mice were administered (C57/B16; 4/group) LacZ vectors based on huAdS, Pan-6, Pan-7, and Pan-9 (H5.040CMVLacZ, Pan6.000CMVLacZ, Pan7.000C MV LacZ, Pan9.000CMVLacZ; 10$^{11}$ particles/injection) by tail vein. Thirty days later the mice were re-administered adenovirus vectors expressing α1-antitrypsin (H5.040 CMVhA1AT, Pan6.000CMVhA1AT, 1×10$^{11}$ particles, Pan7.000CMVhA1AT, Pan9.000CMVhA1AT, 10$^{11}$ particles/injection). Successful transduction by the re-administered vector is monitored by measuring serum α1-antitrypsin on days 3 and 7, following re-administration.

The ability of adenovirus vectors based on huAd5, Pan-6, Pan-7, and Pan-9 respectively to transduce the livers of mice in the presence of neutralizing antibodies to the other serotypes was determined. The results are tabulated here.

| 1$^{st}$ injection | 2$^{nd}$ injection | Cross-neutralization |
|---|---|---|
| Adhu5 | Adhu5 | Yes (+ve control) |
| | Pan-6 | No |
| | Pan-7 | No |
| | Pan-9 (C68) | No |
| Pan-6 | Adhu5 | No |
| | Pan-6 | Yes (+ve control) |
| | Pan-7 | Yes |
| | Pan-9 (C68) | No |
| Pan-7 | Adhu5 | No |
| | Pan-6 | Yes |
| | Pan-7 | Yes (+ve control) |
| | Pan-9 (C68) | Yes |
| Pan-9 (C68) | Adhu5 | No |
| | Pan-6 | No |
| | Pan-7 | Yes |
| | Pan-9 (C68) | Yes (+ve control) |

Ability of vectors to transduce murine liver in the presence of neutralizing antibodies to other serotypes.

Thus, immunization with huAd5 does not prevent re-administration with either of the chimpanzee adenovirus vectors Pan-6, Pan-7, or Pan-9 (C68). This experiment also appears to indicate that Pan-7 is between Pan-6 and Pan-9 in the spectrum of antigenic relatedness and cross-reacts with both; however Pan-6 and Pan-9 do not neutralize each other. This is a surprising result based on homology comparisons, which indicates that Pan-6 is quite distinct from Pan-7 and Pan-9. Evaluation of antisera generated against Pan-9 indicated no cross-neutralization against Pan-6 but some neutralization against Pan-7, arguing that Pan-6 is distinct from the others.

Example 10

Generation of Recombinant E1-Deleted SV-25 Vector

A plasmid was constructed containing the complete SV-25 genome except for an engineered E1 deletion. At the site of the E1 deletion recognition sites for the restriction enzymes I-CeuI and PI-SceI which would allow insertion of transgene from a shuttle plasmid where the transgene expression cassette is flanked by these two enzyme recognition sites were inserted.

A synthetic linker containing the restriction sites SwaI-SnaBI-SpeI-AflIII-EcoRV-SwaI was cloned into pBR322 that was cut with EcoRI and NdeI. This was done by annealing together two synthetic oligomers SV25T (5'-AAT TTA AAT ACG TAG CGC ACT AGT CGC GCT AAG CGC GGA TAT CAT TTA AA-3', SEQ ID NO: 38) and SV25B (5'-TAT TTA AAT GAT ATC CGC GCT TAA GCG CGA CTA GTG CGC TAC GTA TTT A-3', SEQ ID NO:39) and inserting it into pBR322 digested with EcoRI and NdeI. The left end (bp1 to 1057, SEQ ID NO:29) of Ad SV25 was cloned into the above linker between the SnaBI and SpeI sites. The right end (bp28059 to 31042, SEQ ID NO: 29) of Ad SV25 was cloned into the linker between the AflIII and EcoRV sites. The adenovirus E1 was then excised between the EcoRI site (bp 547) to XhoI (bp 2031) from the cloned left end as follows. A PCR generated I-CeuI-PI-SceI cassette from pShuttle (Clontech) was inserted between the EcoRI and SpeI sites. The 10154 bp XhoI fragment of Ad SV-25 (bp2031 to 12185, SEQ ID NO:29) was then inserted into the SpeI site. The resulting plasmid was digested with HindIII and the construct (pSV25) was completed by inserting the 18344 bp Ad SV-25 HindIII fragment (bp11984 to 30328, SEQ ID NO:29) to generate a complete molecular clone of E1 deleted adenovirus SV25 suitable for the generation of recombinant adenoviruses. Optionally, a desired transgene is inserted into the I-CeuI and PI-SceI sites of the newly created pSV25 vector plasmid.

To generate an AdSV25 carrying a marker gene, a GFP (green fluorescent protein) expression cassette previously cloned in the plasmid pShuttle (Clontech) was excised with the restriction enzymes I-CeuI and PI-SceI and ligated into pSV25 (or another of the Ad chimp plasmids described herein) digested with the same enzymes. The resulting plasmid (pSV25GFP) was digested with SwaI to separate the bacterial plasmid backbone and transfected into the E1 complementing cell line HEK 293. About 10 days later, a cytopathic effect was observed indicating the presence of replicative virus. The successful generation of an Ad SV25 based adenoviral vector expressing GFP was confirmed by applying the supernatant from the transfected culture on to fresh cell cultures. The presence of secondarily infected cells was determined by observation of green fluorescence in a population of the cells.

Example 11

Construction of E3 Deleted Pan-5, Pan-6, Pan-7 and C68 Vectors

In order to enhance the cloning capacity of the adenoviral vectors, the E3 region can be deleted because this region encodes genes that are not required for the propagation of the virus in culture. Towards this end, E3-deleted versions of Pan-5, Pan-6, Pan-7, and C68 have been made (a 3.5 kb Nru-AvrII fragment containing E31-9 is deleted).

A. E3 Deleted Pan5 Based Vector

E1-deleted pPan5-pkGFP plasmid was treated with Avr II endonuclease to isolate a 5.8 kb fragment containing the E3 region and re-circulate pPan5-pkGFP with Avr II deletion to form construct pPan5-pkGFP-E3-Avr II. Subsequently, the 5.8 kb Avr II fragment was subcloned into pSL-Pan5-E3-Avr II for a further deletion of E3 region by Nru I digestion. This led to a plasmid pSL-Pan5-E3-deletion. The final construct pPan5-E3-pkGFP was produced by removing a 4.3 kb Avr II/Spe I fragment from pSL-Pan5-E3-deletion plasmid and inserting into pPan5-pkGFP-E3-Avr II at Avr II site. In this final construct, a 3.1 kb deletion in E3 region was accomplished.

B. E3 Deletion in Pan6 Based Vector

E1-deleted pPan6-pkGFP molecular clone was digested with Sbf I and Not I to isolate 19.3 kb fragment and ligated back at Sbf I site. The resulting construct pPan6-SbfI-E3 was treated with Eco 47 III and Swa I, generating pPan6-E3. Finally, 21 kb Sbf I fragment from Sbf I digestion of pPan6-pkGFP was subcloned into pPan6-E3 to create pPan6-E3-pkGFP with a 4 kb deletion in E3.

C. E3 Deleted Pan7 and Pan9 Vectors

The same strategy was used to achieve E3 deletions in both vectors. First, a 5.8 kb Avr II fragment spanning the E3 region was subcloned pSL-1180, followed by deletion of E3 by Nru I digestion. The resulting plasmids were treated with Spe I and Avr II to obtain 4.4 kb fragments and clone into pPan7-pkGFP and pPan9-pkGFP at Avr II sites to replace the original E3 containing Avr II fragments, respectively. The final pPan7-E3-pkGFP and pPan9-E3-pkGFP constructs have 3.5 kb E3-deletions.

Example 12

Construction of E3- and E4-Deleted Pan-7 Vector

Although the deletion of the E1 region of adenoviruses (first generation adenovirus vectors) renders them replication-incompetent, expression of the adenoviral vector backbone genes is not fully abolished. Deletion of the E4 region considerably attenuates this residual gene expression and may confer a safety advantage. An E4-deleted Pan-7 vector containing a 2.5 kb deletion (a PvuII-AgeI fragment containing E40RF 1-ORF7 is deleted) has been constructed. High titer stocks of this virus were generated using a HEK 293-based cell line, which in addition to E1, expresses an essential E4 gene (orf 6).

1. E4 Deletion in the Molecular Clone of Pan7

A 19 kb Xba I fragment was deleted from pPan7-pkGFP to create pPan7-Xba I from which a 2.5 kb E4 fragment was deleted by Age I and Pvu II partial digestion, resulting in pPan7-Xba I-E4. pPan7-E4-pkGFP plasmid was generated from pPan7-Xba I-E4 in two sequential cloning steps, adding 19 kb Xba I and 15 kb I-Ceu I/Mlu I fragments, both of which came from pPan7-pkGFP construct.

2. Introduction of E3 and E4 Deletions in Pan9 Vector

A 11 kb plasmid, pPan9-EcoRI, containing E4 region was created by retrieving 11 kb EcoRI fragment from pPan9 pkGFP after EcoRI digestion and self-ligation. E4 region was deleted from this construct by Age I digestion/filled in and Pvu II partial digestion and slef-ligation to generate pPan9-EcoR I-E4. A 23 kb EcoR I fragment was isolated from pPan9-pkGFP and inserted into pPan9-EcoR I-E4 at EcoR I site, followed by adding 5.8 kb Avr II fragment from pPan9-pkGFP, to form the final product pPan9-E3-E4-pkGF. Compared to the genome size of wild type Pan9, this E1-E3-E4-deleted vector could have a transgene capacity up to 8 kb.

3. Introduction of Minigene Cassettes with Genes of Interest Including Reporter Genes, Glyco- and Nuclear Proteins of Ebo into Molecular Clones of Pan Vectors A highly efficient direct cloning and green/white selection procedure was employed for creating molecular clones of recombinant viruses. Briefly, genes of interest were cloned into pShuttlepkGFP by screening white colonies for recombinants. Subsequently, the minigene cassettes were transferred into chimpanzee adenovirus backbone plasmids, pPanX-pkGFP with various deletions, easily by swapping with pkGFP cassette at I-Ceu I and PI-Sce I sites and screening a few white colonies for correct recombinants.

4. Rescue of Molecular Clones of Pan Vectors with Multiple Deletions in Early Regions and Virus Propagation For rescue of E1-E3-deleted molecular clones of chimpanzee adenovirus vectors, the clones were linearized with appropriate restriction enzymes and transfected into regular 293 cells. Once a full cytopathic effect (CPE) observed in the transfected cells, crude lysate was harvested and expanded in 293 cells to large-scale infections. The viruses were purified by CsCl sedimentation method.

For E1-E4 and E1-E3-E4-deleted Pan vectors, 10-3 cells, a 293-based E1-E4-complementing cell line, were used for rescue and propagation of vectors. E4 ORF6 gene expression in 10-3 cells was induced by addition of 150 μM $ZnSO^4$ to the culture medium.

Example 13

Vaccination with Adenovirus Vectors Expressing Wild Type and Variant EboZ GP

AdHu5 or AdC7 vectors expressing Ebola envelope chimeras were produced for in vivo immunization experiments in C57BL/6 mice. Recombinant viruses with different viral backbones were created by molecular cloning method in which the minigene cassettes were inserted into the place of E1-deletions. The molecular clones of all recombinant viruses were rescued and grown up in 293 cells for large-scale purification using CsCl sedimentation method. Five EboZ variants encoded by AdHu5 or AdPan7 (C7) were selected and produced to evaluate their relative immunogenicity following an intramuscular Ad injection. The wt Ebo, a soluble Ebo variant, EboΔ1, EboΔ2, EboΔ3, EboΔ4, EboΔ5S, EboΔ6S, EboΔ7S and EboΔ8S were evaluated in the initial vaccine studies. For the data summarized in the following table, the number of viral particles (per ml or total) produced and amplified from infected 293 cells was established by spectrophotometry reading.

TABLE

Production of Adhu5 or AdC7 Adenoviral vector encoding EboZ variant.

| | HuAd5 | | AdC7 | |
|---|---|---|---|---|
| Gene | Titer (VP × $10^{12}$/ml) | Total yield (VP × $10^{12}$) | Titer (VP × $10^{12}$/ml) | Total yield (VP × $10^{12}$) |
| Ebo wt | 2.6 | 12 | 4.3 | 43 |
| EboS | 4.9 | 49 | 4.6 | 55 |
| EboΔ2 | 2.1 | 9 | 5.8 | 93 |
| EboΔ3 | 1.7 | 8 | 5.3 | 95 |
| EboΔ4 | 3 | 12 | 4.1 | 62 |

Vector was administered intramuscularly ($10^{11}$ genome copies/cell) in C57BL/6 mice and the presence of virus neutralizing antibody (VNA0 was evaluated 28 days later as a first measure of an immune response generated against the Ebola envelope glycoprotein. VNA is defined here as serum antibody able to inhibit transduction of HeLa cells mediated by HIV-based vector pseudotyped with the wild-type Ebola envelope.

VNA to the EboZ pseudotypes was detected with AdPan7 (C7) yielding higher titers than AdHu5. The EboZΔ3 elicited the highest VNA in terms of the transgene targets. For the data summarized in the following table, neutralizing antibody titers to HIV-EboZ-GFP pseudotypes (reciprocal dilution) are provided (N=5 animals/group).

| | VNA Titers | | |
|---|---|---|---|
| | EboZ wildtype | EboZs | EboZΔ3 |
| AdHu5 | 12 | 16 | 12 |
| AdC7 | 44 | 12 | 140 |

Example 14

Pan7-Mediated Expression of Ebola Proteins

Mouse studies to evaluate. Pan-7 vectors expressing Ebola envelope proteins and the Ebola nuclear antigen have been initiated. These are directed towards evaluation of neutralizing antibodies in C57Bl/6 mice injected intramuscularly (IM) with Adhu5 or Pan-7 expressing each of 4 Ebola env constructs.

A. Evaluation of CTL from C57Bl/6 Mice Injected IM with Adhu5 or Pan-7 Expressing the Ebola Env Constructs.

1. Challenge Experiment in Mice with Ebola Virus.

Neutralizing antibody (NAB) responses to the Ebola envelope were analyzed by looking at immunized mouse sera mediated neutralization of a lentiviral (HIV) vector pseudotyped with the several constructs (eEbo, NTD2, NTD3, NTD4) of the Ebola envelope glycoprotein. C57BL/6 or BALB/c mice received a single intramuscular injection of $5 \times 10^{10}$ particles per mouse of C7 (Ad Pan-7) encoding Ebola envelope variant. Neutralizing antibody was evaluated 30 days post-vaccination. Briefly, Ebola Zaire pseudotyped HIV vector encoding for β-galactosidase (EboZ-HIV-LacZ) was incubated for 2 hr at 37° C. with different dilution of heat inactivated mouse serum. Following the incubation with serum, EboZ-HIV-LacZ was then used to infect HeLa cells for 16 hr at 37° C. Infectivity was revealed by X-gal staining of transduced HeLa cells positive for β-galactosidase. Neutralizing titer represent the serum reciprocal dilution where a 50% decrease in the number of β-galactosidase positive blue cells was observed. Sera were collected 30 days post-immunization, which consisted in a single intramuscular (I.M.) administration of $5 \times 10^{10}$ particles/animal. Neutralizing antibody to Ebola pseudotyped HIV could be detected from all groups with antibody titers ranging from 20 for Ad-EboZ (Adhu5 expressing EboZ), Ad-NTD3 (Adhu5 expressing NTD3) and C7-sEbo (Ad Pan-7 expressing soluble EboZ) to over 130 for C7-NTD3 (Ad Pan-7 expressing soluble NTD3) and C7-NTD4 (Ad Pan-7 expressing soluble NTD3). The same immunization strategy in BALB/c mice resulted in lower neutralizing antibody titers for Ad- and C7-NTD2, and NTD4.

B. Cellular Immune Response

The cellular immune response to the Ebola envelope in C57BL/6 mice was evaluated 8 days after a single I.M. administration of $5 \times 10^{10}$ particles of C7-LacZ or C7-Ebola envelope variant per animal. Mice were vaccinated I.M. with $5 \times 10^{10}$ particles of C7 encoding LacZ or Ebola envelope variant. Splenic lymphocytes from immunized mice were collected 8 days post vaccination and stimulated in vitro with feeder cells (splenic lymphocytes from untreated mice infected with human Adenovirus serotype 5 encoding for the wild-type Ebola envelope and irradiated). Standard 5-hr CTL assays were performed using $^{51}$Cr-labeled syngenic C57 cells transfected with an expressor of EboZ.

A positive MHC-restricted cytotoxic T lymphocyte (CTL) response was observed from all AdPan-7 encoding for Ebola envelope variants with a higher response from NTD2, NTD3 or NTD4 immunized mice. Indeed, effector cells from C7 encoding Ebola envelope variant immunized mice recognized EboZ transfected target cells and gave recall CTL responses up to 30% specific lysis. Less than 5% lysis was seen with effector cells from naïve or LacZ immunized control mice confirming that lysis was specific for Ebola envelope antigens.

C. Protection Studies

The most direct means of evaluating C7 (Ad Pan-7) encoding for the EboZ variants as a successful vaccine in mice was to assess protection against weight loss and death following lethal challenge with mouse adapted Ebola Zaire virus. BALB/c mice were immunized with a single dose of $5 \times 10^{10}$ particles per animal as performed previously and vaccinated animals were challenged with 200 $LD_{50}$ of mouse adapted Ebola Zaire 21 days later. All control mice (vehicle and C7-LacZ) died between day 5 to day 9 post-challenge. In contrast, all vaccinated mice but one, (from the C7-sEbo group), survived the challenge with Ebola Zaire.

Weight loss was observed from mice vaccinated with C7-sEbo from day 4 to day 7. Signs of illness such as piloerection and from light to severe lethargy were also noted from mice vaccinated with C7-sEbo, NTD2 and NTD3 between day 4 to day 7. Mice immunized with C7-EboZ and C7-NTD4 did not show sign of illness. Overall, a single dose of C7-EboZ and C7-NTD4 completely protected immunized mice from illness and death possibly due to a significant T cell mediated immunity.

All documents recited above are incorporated herein by reference. Numerous modifications and variations of the present invention are included in the scope of the above-identified specification and are expected to be obvious to one of skill in the art. Such modifications and alterations to the compositions and processes of the present invention, such as selections of different minigenes or selection or dosage of the vectors or immune modulators are believed to be within the scope of the claims appended hereto.

The invention claimed is:

1. A recombinant adenovirus having a capsid comprising an AdPan6 hexon protein having the amino acid sequence of SEQ ID NO:7, said adenovirus further comprising a nucleic acid sequence heterologous to AdPan6.

2. The adenovirus according to claim 1, wherein the capsid further comprises an AdPan6 fiber protein.

3. The adenovirus according to claim 2, wherein the capsid further comprises an AdPan6 penton protein.

4. The adenovirus according to claim 1, wherein said adenovirus is a pseudotyped adenovirus-comprising an AdPan6 capsid and an expression cassette comprising an adenovirus 5' inverted terminal repeat, the heterologous nucleic acid sequence, and an adenovirus 3' inverted terminal repeat which are heterologous to AdPan6.

5. The adenovirus according to claim 1, wherein the adenovirus further comprises a second heterologous nucleic acid sequence encoding a product, said product-encoding sequence being operatively linked to sequences which direct expression of said product in a host cell.

6. The adenovirus according to claim 1 which comprises one or more adenovirus genes.

7. The adenovirus according to claim 6, wherein the adenovirus comprises a deletion in the E1 region of the adenovirus genes.

8. A composition comprising the adenovirus according to claim 1 and a pharmaceutically acceptable carrier.

9. A recombinant adenovirus having a capsid comprising a chimeric adenovirus hexon protein containing a fragment of the AdPan6 hexon protein the adenovirus further comprising a nucleic acid sequence heterologous to the AdPan6, wherein the fragment of the AdPan6 hexon protein is the AdPan6 hexon protein of SEQ ID NO:7 with an N-terminal or a C-terminal truncation of about 50 amino acids in length or is selected from the group consisting of: the amino acid residues 125 to 443 of SEQ ID NO:7; the amino acid residues 138 to 441 of SEQ ID NO:7; the amino acid residues 138 to 163 of SEQ ID NO:7; the amino acid residues 170 to 176 of SEQ ID NO:7; and the amino acid residues 404 to 430 of to SEQ ID NO: 7.

10. A composition comprising the adenovirus according to claim 9 and a pharmaceutically acceptable carrier.

11. A recombinant adenovirus having a capsid comprising an AdPan6 hexon protein having the amino acid sequence of SEQ ID NO: 7, said capsid encapsidating a heterologous nucleic acid sequence operably linked to expression control sequences which direct transcription, translation, and/or expression thereof in a host cell.

12. The adenovirus according to claim 11, wherein the capsid further comprises an AdPan6 fiber protein.

13. The adenovirus according to claim 12 wherein the capsid further comprises an AdPan6 penton protein.

14. A composition comprising the adenovirus according to claim 11 and a pharmaceutically acceptable carrier.

15. A recombinant adenovirus having a chimeric adenovirus capsid comprising a hexon protein of Pan6 having the sequence of SEQ ID NO:7 and a heterologous adenovirus capsid protein sequence.

16. The adenovirus according to claim 15, wherein the heterologous adenovirus capsid protein sequence is selected from Pan7 (SEQ ID NO:20) and Pan5 (SEQ ID NO:21).

17. A composition comprising the adenovirus according to claim 15 and a pharmaceutically acceptable carrier.

* * * * *

SEQUENCE LISTING

```
<160> NUMBER OF SEQ ID NOS: 40

<210> SEQ ID NO 1
<211> LENGTH: 36462
<212> TYPE: DNA
<213> ORGANISM: chimpanzee adenovirus serotype Pan5
<220> FEATURE:
<221> NAME/KEY: CDS
<222> LOCATION: (13898)..(15490)
<223> OTHER INFORMATION: L2 Penton
<220> FEATURE:
<221> NAME/KEY: CDS
<222> LOCATION: (18315)..(21116)
<223> OTHER INFORMATION: L3 Hexon
<220> FEATURE:
<221> NAME/KEY: CDS
<222> LOCATION: (32035)..(33372)
<223> OTHER INFORMATION: L5 Fiber

<400> SEQUENCE: 1
catcatcaat aatatacctc aaactttgg tgcgcgttaa tatgcaaatg aggtatttga      60
atttggggat gcgggcggt gattggctgc gggagcggcg accgttaggg gcggggcggg     120
tgacgttttg atgacgtggc cgtgaggcgg agccggtttg caagttctcg tgggaaaagt    180
gacgtcaaac gaggtgtggt ttgaacacgg aaatactcaa ttttcccgcg ctctctgaca    240
ggaaatgagg tgtttctggg cggatgcaag tgaaaacggg ccattttcgc gcgaaaactg    300
aatgaggaag tgaaaatctg agtaattccg cgtttatggc agggaggagt atttgccgag    360
ggccgagtag actttgaccg attacgtggg ggtttcgatt accgtatttt tcacctaaat    420
ttccgcgtac ggtgtcaaag tccggtgttt ttacgtaggt gtcagctgat cgccagggta    480
tttaaacctg cgctctctag tcaagaggcc actcttgagt gccagcgagt agagtttct     540 cctccgcgcc gcgagtcaga tctacacttt gaaagatgag gcacctgaga gacctgcccg    600
gtaatgtttt cctggctact gggaacgaga ttctggaact ggtggtggac gccatgatgg    660
gtgacgaccc tccggagccc cctaccccat ttgaagcgcc ttcgctgtac gatttgtatg    720
atctggaggt ggatgtgccc gagaacgacc ccaacgagga ggcggtgaat gatttgtta     780 gcgatgccgc gctgctggct gccgagcagg ctaatacgga ctctggctca gacagcgatt    840
cctctctcca taccccgaga cccggcagag gtgagaaaaa gatccccgag cttaaagggg    900
```

```
aagagctcga cctgcgctgc tatgaggaat gcttgcctcc gagcgatgat gaggaggacg    960
aggaggcgat tcgagctgca gcgaaccagg gagtgaaaac agcgagcgag ggctttagcc   1020
tggactgtcc tactctgccc ggacacggct gtaagtcttg tgaatttcat cgcatgaata   1080
ctggagataa gaatgtgatg tgtgccctgt gctatatgag agcttacaac cattgtgttt   1140
acagtaagtg tgattaactt tagctgggga ggcagagggt gactgggtgc tgactggttt   1200
atttatgtat atgttttta tgtgtaggtc ccgtctctga cgtagatgag accccccacta  1260
cagagtgcat ttcatcaccc ccagaaattg gcgaggaacc gcccgaagat attattcata   1320
gaccagttgc agtgagagtc accgggcgta gagcagctgt ggagagtttg gatgacttgc   1380
tacagggtgg ggatgaacct ttggacttgt gtacccggaa acgccccagg cactaagtgc   1440
cacacatgtg tgtttactta aggtgatgtc agtatttata gggtgtggag tgcaataaaa   1500
tccgtgttga ctttaagtgc gtggtttatg actcaggggt ggggactgtg ggtatataag   1560
caggtgcaga cctgtgtggt cagttcagag caggactcat ggagatctgg acagtcttgg   1620
aagactttca ccagactaga cagctgctag agaactcatc ggagggagtc tcttacctgt   1680
ggagattctg cttcggtggg cctctagcta agctagtcta tagggccaag caggattata   1740
aggatcaatt tgaggatatt ttgagagagt gtcctggtat ttttgactct ctcaacttgg   1800
gccatcagtc tcactttaac cagagtattc tgagagccct tgactttct actcctggca    1860
gaactaccgc cgcggtagcc tttttttgcct ttatccttga caaatggagt caagaaaccc  1920
atttcagcag ggattaccgt ctggactgct tagcagtagc tttgtggaga acatggaggt   1980
gccagcgcct gaatgcaatc tccggctact tgccagtaca gccggtagac acgctgagga   2040
tcctgagtct ccagtcaccc caggaacacc aacgccgcca gcagccgcag caggagcagc   2100
agcaagagga ggaccgagaa gagaacctga gagccggtct ggaccctccg gtggcggagg   2160
aggaggagta gctgacttgt ttcccgagct gcgccgggtg ctgactaggt cttccagtgg   2220
acgggagagg gggattaagc gggagaggca tgaggagact agccacagaa ctgaactgac   2280
tgtcagtctg atgagtcgca ggcgcccaga atcggtgtgg tggcatgagg tgcagtcgca   2340
ggggatagat gaggtctcag tgatgcatga gaaatattcc ctagaacaag tcaagacttg   2400
ttggttggag cccgaggatg attgggaggt agccatcagg aattatgcca agctggctct   2460
gaggccagac aagaagtaca agattaccaa actgattaat atcagaaatt cctgctacat   2520
ttcagggaat ggggccgagg tggagatcag tacccaggag agggtggcct tcagatgctg   2580
catgatgaat atgtacccgg gggtggtggg catggaggga gtcacccttta tgaacgcgag  2640
gttcaggggt gatgggtata atggggtggt ctttatggcc aacaccaagc tgacagtgca   2700
cggatgctcc ttctttggct tcaataacat gtgcattgag gcctgggca gtgtttcagt    2760
gaggggatgc agttttttcag ccaactggat gggggtcgtg gcagaaccca agagcatggt  2820
gtcagtgaag aaatgcctgt tcgagaggtg ccacctgggg gtgatgagcg agggcgaagc   2880
caaagtcaaa cactgcgcct ctaccgagac gggctgcttt gtactgatca agggcaatgc   2940
caaagtcaag cataatatga tctgtggggc ctcggatgag cgcggctacc agatgctgac   3000
ctgcgccggt gggaacagcc atatgctagc caccgtgcat gtggcctcgc accccgcaa    3060
gacatggccc gagttcgagc acaacgtcat gacccgctgc aatgtgcacc tggggtcccg   3120
ccgaggcatg ttcatgccct accagtgcaa catgcaattt gtgaaggtgc tgctggagcc   3180
cgatgccatg tccagagtga gcctgacggg ggtgtttgac atgaatgtgg agctgtggaa   3240
aattctgaga tatgatgaat ccaagaccag gtgccgggcc tgcgaatgcg gaggcaagca   3300
```

```
cgccaggctt cagcccgtgt gtgtggaggt gacggaggac ctgcgacccg atcatttggt    3360
gttgtcctgc aacgggacgg agttcggctc cagcgggaaa gaatctgact agagtgagta    3420
gtgtttggga ctgggtggga gcctgcatga tgggcagaat gactaaaatc tgtgtttttc    3480
tgcgcagcag catgagcgga agcgcctcct ttgaggaggg gtattcagc ccttatctga     3540 cggggcgtct cccctcctgg gcgggagtgc gtcagaatgt gatgggatcc acggtggacg    3600 gccgcccgt gcagcccgcg aactcttcaa ccctgaccta cgcgaccctg agctcctcgt     3660
ccgtggacgc agctgccgcc gcagctgctg cttccgccgc cagcgccgtg cgcggaatgg    3720
ccctgggcgc cggctactac agctctctgg tggccaactc gagttccacc aataatcccg    3780
ccagcctgaa cgaggagaag ctgctgctgc tgatggccca gctcgaggcc ctgacccagc    3840
gcctgggcga gctgacccag caggtggctc agctgcaggc ggagacgcgg gccgcggttg    3900
ccacggtgaa aaccaaataa aaaatgaatc aataaataaa cggagacggt tgttgatttt    3960
aacacagagt cttgaatctt tatttgattt ttcgcgcgcg gtaggccctg gaccaccggt    4020
ctcgatcatt gagcacccgg tggatctttt ccaggacccg gtagaggtgg gcttggatgt    4080
tgaggtacat gggcatgagc ccgtcccggg ggtggaggta gctccattgc agggcctcgt    4140 gctcggggggt ggtgttgtaa atcacccagt catagcaggg gcgcagggcg tggtgctgca   4200
cgatgtcctt gaggaggaga ctgatggcca cgggcagccc cttggtgtag gtgttgacga    4260
acctgttgag ctgggaggga tgcatgcggg gggagatgag atgcatcttg gcctggatct    4320
tgagattggc gatgttcccg cccagatccc gccgggggtt catgttgtgc aggaccacca    4380
gcacggtgta tccggtgcac ttggggaatt tgtcatgcaa cttggaaggg aaggcgtgaa    4440
agaatttgga gacgcccttg tgaccgccca ggttttccat gcactcatcc atgatgatgg    4500
cgatgggccc gtgggcggcg gcttgggcaa agacgtttcg ggggtcggac acatcgtagt    4560
tgtggtcctg ggtgagctcg tcataggcca ttttaatgaa tttggggcgg agggtgcccg    4620 actggggggac gaaggtgccc tcgatcccgg gggcgtagtt gccctcgcag atctgcatct    4680
cccaggcctt gagctcggag gggggatca tgtccacctg cggggcgatg aaaaaaacgg     4740
tttccggggc gggggagatg agctgggccg aaagcaggtt ccggagcagc tgggacttgc    4800
cgcagccggt ggggccgtag atgaccccga tgaccggctg caggtggtag ttgagggaga    4860
gacagctgcc gtcctcgcgg aggaggggg ccacctcgtt catcatctcg cgcacatgca     4920
tgttctcgcg cacgagttcc gccaggaggc gctcgccccc aagcgagagg agctcttgca    4980
gcgaggcgaa gttttcagc ggcttgagcc cgtcggccat gggcattttg gagagggtct     5040
gttgcaagag ttccagacgg tcccagagct cggtgatgtg ctctagggca tctcgatcca    5100
gcagacctcc tcgtttcgcg ggttgggcg actgcgggag tagggcacca ggcgatgggc     5160
gtccagcgag gccagggtcc ggtccttcca ggggcgcagg gtccgcgtca gcgtggtctc    5220
cgtcacggta aagggtgcg cgccgggctg ggcgcttgcg agggtgcgct tcaggctcat     5280
ccggctggtc gagaaccgct cccggtcggc gccctgcgcg tcgccaggt agcaattgag     5340 catgagttcg tagttgagcg cctcggccgc gtggcccttg gcgcggagct tacctttgga    5400
agtgtgtccg cagacgggac agaggaggga cttgagggcg tagagcttgg gggcgaggaa    5460
gacggactcg ggggcgtagg cgtccgcgcc gcagctggcg cagacggtct cgcactccac    5520
gagccaggtg aggtctggcc ggtcgggtc aaaaacgagg tttcctccgt gcttttttgat    5580 gcgtttctta cctctggtct ccatgagctc gtgtccccgc tgggtgacaa agaggctgtc    5640
cgtgtccccg tagaccgact ttatgggccg gtcctcgagc ggggtgccgc ggtcctcgtc    5700
```

```
gtagaggaac cccgcccact ccgagacgaa ggcccgggtc caggccagca cgaaggaggc    5760
cacgtgggag gggtagcggt cgttgtccac cagcgggtcc accttctcca gggtatgcaa    5820
gcacatgtcc ccctcgtcca catccaggaa ggtgattggc ttgtaagtgt aggccacgtg    5880
accgggggtc ccgccggggg gggtataaaa ggggcgggc ccctgctcgt cctcactgtc     5940
ttccggatcg ctgtccagga gcgccagctg ttggggtagg tattccctct cgaaggcggg    6000
catgacctcg gcactcaggt tgtcagtttc tagaaacgag gaggatttga tattgacggt    6060
gccgttggag acgcctttca tgagcccctc gtccatctgg tcagaaaaga cgatctttt     6120 gttgtcgagc ttggtggcga aggagccgta gagggcgttg gagagcagct tggcgatgga    6180
gcgcatggtc tggttctttt ccttgtcggc gcgctccttg gcggcgatgt tgagctgcac    6240
gtactcgcgc gccacgcact tccattcggg gaagacggtg gtgagcttgt cgggcacgat    6300
tctgacccgc cagccgcggt tgtgcagggt gatgaggtcc acgctggtgg ccacctcgcc    6360
gcgcaggggc tcgttggtcc agcagaggcg cccgcccttg cgcgagcaga aggggggcag    6420
cgggtccagc atgagctcgt cggggggggtc ggcgtccacg gtgaagatgc cgggcaggag   6480
ctcggggtcg aagtagctga tgcaggtgcc cagatcgtcc agcgccgctt gccagtcgcg    6540
cacggccagc gcgcgctcgt aggggctgag gggcgtgccc cagggcatgg ggtgcgtgag    6600
cgcggaggcg tacatgccgc agatgtcgta gacgtagagg ggctcctcga ggacgccgat    6660
gtaggtgggg tagcagcgcc ccccgcggat gctggcgcgc acgtagtcgt acagctcgtg    6720
cgagggcgcg aggagcccgg tgccgaggtt ggagcgctgc ggcttttcgg cgcggtagac    6780
gatctggcgg aagatggcgt gggagttgga ggagatggtg ggcctctgga agatgttgaa    6840
gtgggcgtgg ggcagtccga ccgagtccct gatgaagtgg gcgtaggagt cctgcagctt    6900
ggcgacgagc tcggcggtga cgaggacgtc cagggcgcag tagtcgaggg tctcttggat    6960
gatgtcgtac ttgagctggc ccttctgctt ccacagctcg cggttgagaa ggaactcttc    7020
gcggtccttc cagtactctt cgaggggaa cccgtcctga tcggcacggt aagagcccac     7080
catgtagaac tggttgacgg ccttgtaggc gcagcagccc ttctccacgg ggagggcgta    7140
agcttgcgcg gccttgcgca gggaggtgtg ggtgagggcg aaggtgtcgc gcaccatgac    7200
cttgaggaac tggtgcttga agtcgaggtc gtcgcagccg ccctgctccc agagctggaa    7260
gtccgtgcgc ttcttgtagg cggggttggg caaagcgaaa gtaacatcgt tgaagaggat    7320
cttgcccgcg cggggcatga agttgcgagt gatgcggaaa ggctggggca cctcggcccg    7380
gttgttgatg acctgggcgg cgaggacgat ctcgtcgaag ccgttgatgt tgtgcccgac    7440
gatgtagagt tccacgaatc gcgggcggcc cttgacgtgg ggcagcttct tgagctcgtc    7500
gtaggtgagc tcggcgggt cgctgaggcc gtgctgctcg agggcccagt cggcgaggtg     7560
ggggttggcg ccgaggaagg aagtccagag atccacggcc agggcggtct gcaagcggtc    7620
ccggtactga cggaactgct ggcccacggc catttttttcg ggggtgacgc agtagaaggt   7680
gcgggggtcg ccgtgccagc ggtcccactt gagctggagg gcgaggtcgt gggcgagctc    7740
gacgagcggc gggtccccgg agagtttcat gaccagcatg aagggacga gctgcttgcc     7800 gaaggacccc atccaggtgt aggtttccac gtcgtaggtg aggaagagcc tttcggtgcg    7860
aggatgcgag ccgatgggga agaactggat ctcctgccac cagttggagg aatggctgtt    7920
gatgtgatgg aagtagaaat gccgacggcg cgccgagcac tcgtgcttgt gtttatacaa    7980
gcgtccgcag tgctcgcaac gctgcacggg atgcacgtgc tgcacgagct gtacctgggt    8040
tcctttgacg aggaatttca gtgggcagtg gagcgctggc ggctgcatct ggtgctgtac    8100
```

-continued

```
tacgtcctgg ccatcggcgt ggccatcgtc tgcctcgatg gtggtcatgc tgacgaggcc    8160
gcgcgggagg caggtccaga cctcggctcg gacgggtcgg agagcgagga cgagggcgcg    8220
caggccggag ctgtccaggg tcctgagacg ctgcggagtc aggtcagtgg gcagcggcgg    8280
cgcgcggttg acttgcagga gcttttccag ggcgcgcggg aggtccagat ggtacttgat    8340
ctccacggcg ccgttggtgg cgacgtccac ggcttgcagg gtcccgtgcc cctggggcgc    8400
caccaccgtg ccccgtttct tcttgggtgc tggcggcggc ggctccatgc ttagaagcgg    8460
cggcgaggac gcgcgccggg cggcaggggc ggctcggggc ccggaggcag gggcggcagg    8520
ggcacgtcgg cgccgcgcgc gggcaggttc tggtactgcg cccggagaag actggcgtga    8580
gcgacgacgc gacggttgac gtcctggatc tgacgcctct gggtgaaggc cacgggaccc    8640
gtgagtttga acctgaaaga gagttcgaca gaatcaatct cggtatcgtt gacgcggcc    8700 tgccgcagga tctcttgcac gtcgcccgag ttgtcctggt aggcgatctc ggtcatgaac    8760
tgctcgatct cctcctcctg aaggtctccg cgaccggcgc gctcgacggt ggccgcgagg    8820
tcgttggaga tgcggcccat gagctgcgag aaggcgttca tgccggcctc gttccagacg    8880
cggctgtaga ccacggctcc gtcggggtcg cgcgcgcgca tgaccacctg ggcgaggttg    8940
agctcgacgt ggcgcgtgaa gaccgcgtag ttgcagaggc gctggtagag gtagttgagc    9000
gtggtggcga tgtgctcggt gacgaagaag tacatgatcc agcggcggag cggcatctcg    9060
ctgacgtcgc ccagggcttc caagcgctcc atggcctcgt agaagtccac ggcgaagttg    9120
aaaaactggg agttgcgcgc cgagacggtc aactcctcct ccagaagacg gatgagctcg    9180
gcgatggtgg cgcgcacctc gcgctcgaag gccccggggg gctcctcttc ttccatctcc    9240
tcctcctctt ccatctcctc cactaacatc tcttctactt cctcctcagg aggcggcggc    9300
gggggagggg ccctgcgtcg ccggcggcgc acgggcagac ggtcgatgaa gcgctcgatg    9360
gtctccccgc gccggcgacg catggtctcg gtgacggcgc gcccgtcctc gcggggccgc    9420
agcgtgaaga cgccgccgcg catctccagg tggccgccgg ggggtctcc gttgggcagg     9480 gagagggcgc tgacgatgca tcttatcaat tggcccgtag ggactccgcg caaggacctg    9540
agcgtctcga gatccacggg atccgaaaac cgctgaacga aggcttcgag ccagtcgcag    9600
tcgcaaggta ggctgagccc ggtttcttgt tcttcgggta tttggtcggg aggcgggcgg    9660
gcgatgctgc tggtgatgaa gttgaagtag gcggtcctga gacggcggat ggtggcgagg    9720
agcaccaggt ccttgggccc ggcttgctgg atgcgcagac ggtcggccat gccccaggcg    9780
tggtcctgac acctggcgag gtccttgtag tagtcctgca tgagccgctc cacgggcacc    9840
tcctcctcgc ccgcgcggcc gtgcatgcgc gtgagcccga acccgcgctg cggctggacg    9900
agcgccaggt cggcgacgac gcgctcggcg aggatggcct gctggatctg ggtgagggtg    9960
gtctggaagt cgtcgaagtc gacgaagcgg tggtaggctc cggtgttgat ggtgtaggag    10020
cagttggcca tgacggacca gttgacggtc tggtggccgg ggcgcacgag ctcgtggtac    10080
ttgaggcgcg agtaggcgcg cgtgtcgaag atgtagtcgt tgcaggtgcg cacgaggtac    10140
tggtatccga cgaggaagtg cggcggcggc tggcggtaga gcggccatcg ctcggtggcg    10200
ggggcgccgg gcgcgaggtc ctcgagcatg aggcggtggt agccgtagat gtacctggac    10260
atccaggtga tgccggcggc ggtggtggag gcgcgcggga actcgcggac gcggttccag    10320
atgttgcgca gcggcaggaa gtagttcatg gtggccgcgg tctggcccgt gaggcgcgcg    10380
cagtcgtgga tgctctagac atacgggcaa aaacgaaagc ggtcagcggc tcgactccgt    10440
ggcctggagg ctaagcgaac gggttgggct gcgcgtgtac cccggttcga gtccctgctc    10500
```

```
gaatcaggct ggagccgcag ctaacgtggt actggcactc ccgtctcgac ccaagcctgc   10560
taacgaaacc tccaggatac ggaggcgggt cgttttggcc attttcgtca ggccggaaat   10620
gaaactagta agcgcggaaa gcggccgtcc gcgatggctc gctgccgtag tctggagaaa   10680
gaatcgccag ggttgcgttg cggtgtgccc cggttcgagc ctcagcgctc ggcgccggcc   10740
ggattccgcg gctaacgtgg gcgtggctgc cccgtcgttt ccaagacccc ttagccagcc   10800
gacttctcca gttacggagc gagccctct ttttcttgtg tttttgccag atgcatcccg   10860
tactgcggca gatgcgcccc caccctccac cacaaccgcc cctaccgcag cagcagcaac   10920
agccggcgct tctgccccg ccccagcagc agcagccagc cactaccgcg gcggccgccg   10980
tgagcggagc cggcgttcag tatgacctgg ccttggaaga gggcgagggg ctggcgcggc   11040
tgggggcgtc gtcgcggag cggcaccgc gcgtgcagat gaaaagggac gctcgcgagg   11100
cctacgtgcc caagcagaac ctgttcagag acaggagcgg cgaggagccc gaggagatgc   11160
gcgcctcccg cttccacgcg gggcgggagc tgcggcgcgg cctggaccga aagcgggtgc   11220
tgagggacga ggatttcgag gcggacgagc tgacggggat cagccccgcg cgcgcgcacg   11280
tggccgcggc caacctggtc acggcgtacg agcagaccgt gaaggaggag agcaacttcc   11340
aaaaatcctt caacaaccac gtgcgcacgc tgatcgcgcg cgaggaggtg accctgggcc   11400
tgatgcacct gtgggacctg ctggaggcca tcgtgcagaa ccccacgagc aagccgctga   11460
cggcgcagct gtttctggtg gtgcagcaca gtcgggacaa cgagacgttc agggaggcgc   11520
tgctgaatat caccgagccc gagggccgct ggctcctgga cctggtgaac attctgcaga   11580
gcatcgtggt gcaggagcgc gggctgccgc tgtccgagaa gctggcggcc atcaacttct   11640
cggtgctgag cctgggcaag tactacgcta ggaagatcta caagacccg tacgtgccca   11700 tagacaagga ggtgaagatc gacgggtttt acatgcgcat gaccctgaaa gtgctgaccc   11760
tgagcgacga tctgggggtg taccgcaacg acaggatgca ccgcgcggtg agcgccagcc   11820
gccggcgcga gctgagcgac caggagctga tgcacagcct gcagcgggcc ctgaccgggg   11880
ccgggaccga ggggagagc tactttgaca tgggcgcgga cctgcgctgg cagcctagcc   11940
gccgggcctt ggaagctgcc ggcggttccc cctacgtgga ggaggtggac gatgaggagg   12000
aggagggcga gtacctggaa gactgatggc gcgaccgtat ttttgctaga tgcagcaaca   12060
gccaccgccg cctcctgatc ccgcgatgcg ggcggcgctg cagagccagc cgtccggcat   12120
taactcctcg gacgattgga cccaggccat gcaacgcatc atggcgctga cgacccgcaa   12180
tcccgaagcc tttagacagc agcctcaggc caaccgactc tcggccatcc tggaggccgt   12240
ggtgccctcg cgctcgaacc ccacgcacga aaggtgctg gccatcgtga acgcgctggt   12300
ggagaacaag gccatccgcg gcgacgaggc cgggctggtg tacaacgcgc tgctggagcg   12360
cgtggcccgc tacaacagca ccaacgtgca gacgaacctg accgcatgg tgaccgacgt   12420 gcgcgaggcg tgtcgcagc gcgagcggtt ccaccgcgag tcgaacctgg gctccatggt   12480
ggcgctgaac gccttcctga gcacgcagcc cgccaacgtg cccgggggcc aggaggacta   12540
caccaacttc atcagcgcgc tgcggctgat ggtggccgag gtgccccaga gcgaggtgta   12600
ccagtcgggg ccggactact tcttccagac cagtcgccag ggcttgcaga ccgtgaacct   12660
gagccaggct ttcaagaact tgcagggact gtggggcgtg caggcccgg tcggggaccg   12720 ccgcgacggt tcgagcctgc tgacgccgaa ctcgcgcctg ctgctgctgc tggtggcgcc   12780
cttcacggac agcggcagcg tgagccgcga ctcgtacctg ggctacctgc ttaacctgta   12840
ccgcgaggcc atcgggcagg cgcacgtgga cgagcagacc taccaggaga tcacccacgt   12900
```

-continued

```
gagccgcgcg ctgggccagg aggacccggg caacctggag gccaccctga acttcctgct   12960
gaccaaccgg tcgcagaaga tcccgcccca gtacgcgctg agcaccgagg aggagcgcat   13020
cctgcgctac gtgcagcaga gcgtggggct gttcctgatg caggagggg ccacgcccag    13080 cgccgcgctc gacatgaccg cgcgcaacat ggagcccagc atgtacgccc gcaaccgccc   13140
gttcatcaat aagctgatgg actacttgca tcgggcggcc gccatgaact cggactactt   13200
taccaacgcc atcttgaacc cgcactggct cccgccgccc gggttctaca cgggcgagta   13260
cgacatgccc gaccccaacg acgggttcct gtgggacgac gtggacagca gcgtgttctc   13320
gccgcgcccc accaccacca ccgtgtggaa gaaagagggc ggggaccggc ggccgtcctc   13380
ggcgctgtcc ggtcgcgcgg gtgctgccgc ggcggtgccc gaggccgcca gccccttccc   13440
gagcctgccc ttttcgctga acagcgtgcg cagcagcgag ctgggtcggc tgacgcggcc   13500
gcgcctgctg ggcgaggagg agtacctgaa cgactccttg cttcggcccg agcgcgagaa   13560
gaacttcccc aataacggga tagagagcct ggtggacaag atgagccgct ggaagacgta   13620
cgcgcacgag cacagggacg agccccgagc tagcagcagc accggcgcca cccgtagacg   13680
ccagcggcac gacaggcagc ggggtctggt gtgggacgat gaggattccg ccgacgcacg   13740
cagcgtgttg gacttgggtg ggagtggtgg tggtaacccg ttcgctcacc tgcgcccccg   13800
tatcgggcgc ctgatgtaag aatctgaaaa aataaaagac ggtactcacc aaggccatgg   13860
cgaccagcgt gcgttcttct ctgttgtttg tagtagt atg atg agg cgc gtg tac    13915
                                    Met Met Arg Arg Val Tyr
                                      1               5 ccg gag ggt cct cct ccc tcg tac gag agc gtg atg cag cag gcg gtg    13963
Pro Glu Gly Pro Pro Pro Ser Tyr Glu Ser Val Met Gln Gln Ala Val
             10                  15                  20 gcg gcg gcg atg cag ccc ccg ctg gag gcg cct tac gtg ccc ccg cgg    14011
Ala Ala Ala Met Gln Pro Pro Leu Glu Ala Pro Tyr Val Pro Pro Arg
         25                  30                  35 tac ctg gcg cct acg gag ggg cgg aac agc att cgt tac tcg gag ctg    14059
Tyr Leu Ala Pro Thr Glu Gly Arg Asn Ser Ile Arg Tyr Ser Glu Leu
     40                  45                  50 gca ccc ttg tac gat acc acc cgg ttg tac ctg gtg gac aac aag tcg    14107
Ala Pro Leu Tyr Asp Thr Thr Arg Leu Tyr Leu Val Asp Asn Lys Ser
55                  60                  65                  70 gcg gac atc gcc tcg ctg aac tac cag aac gac cac agc aac ttc ctg    14155
Ala Asp Ile Ala Ser Leu Asn Tyr Gln Asn Asp His Ser Asn Phe Leu
                 75                  80                  85 acc acc gtg gtg cag aac aac gat ttc acc ccc acg gag gcc agc acc    14203
Thr Thr Val Val Gln Asn Asn Asp Phe Thr Pro Thr Glu Ala Ser Thr
             90                  95                 100 cag acc atc aac ttt gac gag cgc tcg cgg tgg ggc ggc cag ctg aaa    14251
Gln Thr Ile Asn Phe Asp Glu Arg Ser Arg Trp Gly Gly Gln Leu Lys
        105                 110                 115 acc atc atg cac acc aac atg ccc aac gtg aac gag ttc atg tac agc    14299
Thr Ile Met His Thr Asn Met Pro Asn Val Asn Glu Phe Met Tyr Ser
    120                 125                 130 aac aag ttc aag gcg cgg gtg atg gtc tcg cgc aag acc ccc aac ggg    14347
Asn Lys Phe Lys Ala Arg Val Met Val Ser Arg Lys Thr Pro Asn Gly
135                 140                 145                 150 gtc aca gta aca gat ggt agt cag gac gag ctg acc tac gag tgg gtg    14395
Val Thr Val Thr Asp Gly Ser Gln Asp Glu Leu Thr Tyr Glu Trp Val
                155                 160                 165 gag ttt gag ctg ccc gag ggc aac ttc tcg gtg acc atg acc atc gat    14443
Glu Phe Glu Leu Pro Glu Gly Asn Phe Ser Val Thr Met Thr Ile Asp
            170                 175                 180
```

```
ctg atg aac aac gcc atc atc gac aac tac ttg gcg gtg ggg cgg cag    14491
Leu Met Asn Asn Ala Ile Ile Asp Asn Tyr Leu Ala Val Gly Arg Gln
    185                 190                 195 aac ggg gtg ctg gag agc gac atc ggc gtg aag ttc gac acg cgc aac    14539
Asn Gly Val Leu Glu Ser Asp Ile Gly Val Lys Phe Asp Thr Arg Asn
200                 205                 210 ttc cgg ctg ggc tgg gac ccc gtg acc gag ctg gtg atg ccg ggc gtg    14587
Phe Arg Leu Gly Trp Asp Pro Val Thr Glu Leu Val Met Pro Gly Val
215                 220                 225                 230 tac acc aac gag gcc ttc cac ccc gac atc gtc ctg ctg ccc ggc tgc    14635
Tyr Thr Asn Glu Ala Phe His Pro Asp Ile Val Leu Leu Pro Gly Cys
                235                 240                 245 ggc gtg gac ttc acc gag agc cgc ctc agc aac ctg ctg ggc atc cgc    14683
Gly Val Asp Phe Thr Glu Ser Arg Leu Ser Asn Leu Leu Gly Ile Arg
            250                 255                 260 aag cgg cag ccc ttc cag gag ggc ttc cag atc ctg tac gag gac ctg    14731
Lys Arg Gln Pro Phe Gln Glu Gly Phe Gln Ile Leu Tyr Glu Asp Leu
        265                 270                 275 gag ggg ggc aac atc ccc gcg ctg ctg gac gtg gac gcc tac gag aaa    14779
Glu Gly Gly Asn Ile Pro Ala Leu Leu Asp Val Asp Ala Tyr Glu Lys
    280                 285                 290 agc aag gag gat agc gcc gcc gcg acc gca gcc gtg gcc acc gcc        14827
Ser Lys Glu Asp Ser Ala Ala Ala Thr Ala Ala Val Ala Thr Ala
295                 300                 305                 310 tct acc gag gtg cgg ggc gat aat ttt gct agc gcc gcg aca ctg gca    14875
Ser Thr Glu Val Arg Gly Asp Asn Phe Ala Ser Ala Ala Thr Leu Ala
            315                 320                 325 gcg gcc gag gcg gct gaa acc gaa agt aag ata gtg atc cag ccg gtg    14923
Ala Ala Glu Ala Ala Glu Thr Glu Ser Lys Ile Val Ile Gln Pro Val
        330                 335                 340 gag aag gac agc aag gag agg agc tac aac gtg ctc gcg gac aag aaa    14971
Glu Lys Asp Ser Lys Glu Arg Ser Tyr Asn Val Leu Ala Asp Lys Lys
    345                 350                 355 aac acc gcc tac cgc agc tgg tac ctg gcc tac aac tac ggc gac ccc    15019
Asn Thr Ala Tyr Arg Ser Trp Tyr Leu Ala Tyr Asn Tyr Gly Asp Pro
360                 365                 370 gag aag ggc gtg cgc tcc tgg acg ctg ctc acc acc tcg gac gtc acc    15067
Glu Lys Gly Val Arg Ser Trp Thr Leu Leu Thr Thr Ser Asp Val Thr
375                 380                 385                 390 tgc ggc gtg gag caa gtc tac tgg tcg ctg ccc gac atg atg caa gac    15115
Cys Gly Val Glu Gln Val Tyr Trp Ser Leu Pro Asp Met Met Gln Asp
            395                 400                 405 ccg gtc acc ttc cgc tcc acg cgt caa gtt agc aac tac ccg gtg gtg    15163
Pro Val Thr Phe Arg Ser Thr Arg Gln Val Ser Asn Tyr Pro Val Val
        410                 415                 420 ggc gcc gag ctc ctg ccc gtc tac tcc aag agc ttc ttc aac gag cag    15211
Gly Ala Glu Leu Leu Pro Val Tyr Ser Lys Ser Phe Phe Asn Glu Gln
    425                 430                 435 gcc gtc tac tcg cag cag ctg cgc gcc ttc acc tcg ctc acg cac gtc    15259
Ala Val Tyr Ser Gln Gln Leu Arg Ala Phe Thr Ser Leu Thr His Val
440                 445                 450 ttc aac cgc ttc ccc gag aac cag atc ctc gtt cgc ccg ccc gcg ccc    15307
Phe Asn Arg Phe Pro Glu Asn Gln Ile Leu Val Arg Pro Pro Ala Pro
455                 460                 465                 470 acc att acc acc gtc agt gaa aac gtt cct gct ctc aca gat cac ggg    15355
Thr Ile Thr Thr Val Ser Glu Asn Val Pro Ala Leu Thr Asp His Gly
            475                 480                 485 acc ctg ccg ctg cgc agc agt atc cgg gga gtc cag cgc gtg acc gtc    15403
Thr Leu Pro Leu Arg Ser Ser Ile Arg Gly Val Gln Arg Val Thr Val
        490                 495                 500
```

```
act gac gcc aga cgc cgc acc tgc ccc tac gtc tac aag gcc ctg ggc      15451
Thr Asp Ala Arg Arg Arg Thr Cys Pro Tyr Val Tyr Lys Ala Leu Gly
        505                 510                 515 gta gtc gcg ccg cgc gtc ctc tcg agc cgc acc ttc taa aaaatgtcca       15500
Val Val Ala Pro Arg Val Leu Ser Ser Arg Thr Phe
520                 525                 530 ttctcatctc gcccagtaat aacaccggtt ggggcctgcg cgcgcccagc aagatgtacg    15560
gaggcgctcg ccaacgctcc acgcaacacc ccgtgcgcgt gcgcgggcac ttccgcgctc    15620
cctggggcgc cctcaagggc gcgtgcgct cgcgcaccac cgtcgacgac gtgatcgacc     15680
aggtggtggc cgacgcgcgc aactacacgc ccgccgccgc gcccgtctcc accgtggacg    15740
ccgtcatcga cagcgtggtg gccgacgcgc gccggtacgc ccgcgccaag agccggcggc    15800
ggcgcatcgc ccggcggcac cggagcaccc ccgccatgcg cgcggcgcga gccttgctgc    15860
gcagggccag gcgcacggga cgcagggcca tgctcagggc ggccagacgc gcggcctccg    15920
gcagcagcag cgccggcagg acccgcagac gcgcggccac ggcggcggcg gcggccatcg    15980
ccagcatgtc ccgcccgcgg cgcggcaacg tgtactgggt gcgcgacgcc gccaccggtg    16040
tgcgcgtgcc cgtgcgcacc cgccccccctc gcacttgaag atgctgactt cgcgatgttg   16100
atgtgtccca gcggcgagga ggatgtccaa gcgcaaattc aaggaagaga tgctccaggt    16160
catcgcgcct gagatctacg gcccggcggc ggtgaaggag gaaagaaagc cccgcaaact    16220
gaagcgggtc aaaaaggaca aaaaggagga ggaagatgtg gacggactgg tggagtttgt    16280
gcgcgagttc gcccccccggc ggcgcgtgca gtggcgcggg cggaaagtga accggtgct    16340 gcgacccggc accacggtgg tcttcacgcc cggcgagcgt tccggctccg cctccaagcg    16400
ctcctacgac gaggtgtacg gggacgagga catcctcgag caggcggccg aacgtctggg    16460
cgagtttgct tacggcaagc gcagccgccc cgcgcccttg aaagaggagg cggtgtccat    16520
cccgctggac cacggcaacc ccacgccgag cctgaagccg gtgaccctgc agcaggtgct    16580
gcctggtgcg gcgccgcgcc ggggcttcaa gcgcgagggc ggcgaggatc tgtacccgac    16640
catgcagctg atggtgccca agcgccagaa gctggaggac gtgctggagc acatgaaggt    16700
ggaccccgag gtgcagcccg aggtcaaggt gcggcccatc aagcaggtgg ccccgggcct    16760
gggcgtgcag accgtggaca tcaagatccc cacggagccc atggaaacgc agaccgagcc    16820
cgtgaagccc agcaccagca ccatggaggt gcagacggat ccctggatgc cggcaccggc    16880
ttccaccacc cgccgaagac gcaagtacgg cgcggccagc ctgctgatgc ccaactacgc    16940
gctgcatcct tccatcatcc ccacgccggg ctaccgcggc acgcgcttct accgcggcta    17000
caccagcagc cgccgccgca agaccaccac ccgccgccgc cgtcgtcgca cccgccgcag    17060
cagcaccgcg acttccgccg ccgccctggt gcggagagtg taccgcagcg ggcgcgagcc    17120
tctgaccctg ccgcgcgcgc gctaccaccc gagcatcgcc atttaactac cgcctcctac    17180
ttgcagatat ggccctcaca tgccgcctcc gcgtccccat tacgggctac cgaggaagaa    17240
agccgcgccg tagaaggctg acggggaacg ggctgcgtcg ccatcaccac cggcggcggc    17300
gcgccatcag caagcggttg gggggaggct tcctgcccgc gctgatgccc atcatcgccg    17360
cggcgatcgg ggcgatcccc ggcatagctt ccgtggcggt gcaggcctct cagcgccact    17420
gagacacagc ttgaaaaatt tgtaataaaa aatggactga cgctcctggt cctgtgatgt    17480
gtgtttttag atggaagaca tcaatttttc gtccctggca ccgcgacacg gcacgcggcc    17540 gtttatggc acctggagcg acatcggcaa cagccaactg aacggggcg ccttcaattg      17600 gagcagtctc tggagcgggc ttaagaattt cgggtccacg ctcaaaacct atggcaacaa    17660
```

| | | |
|---|---|---|
| ggcgtggaac agcagcacag ggcaggcgct gagggaaaag ctgaaagagc agaacttcca | | 17720 |
| gcagaaggtg gtcgatggcc tggcctcggg catcaacggg gtggtggacc tggccaacca | | 17780 |
| ggccgtgcag aaacagatca acagccgcct ggacgcggtc ccgcccgcgg ggtccgtgga | | 17840 |
| gatgccccag gtgaggagg agctgcctcc cctggacaag cgcggcgaca gcgaccgcg | | 17900 |
| tcccgacgcg gaggagacgc tgctgacgca cacggacgag ccgcccccgt acgaggaggc | | 17960 |
| ggtgaaactg ggtctgccca ccacgcggcc cgtggcgcct ctggccaccg gggtgctgaa | | 18020 |
| acccagcagc agcagcagcc agcccgcgac cctggacttg cctccgcctg cttcccgccc | | 18080 |
| ctccacagtg gctaagcccc tgccgccggt ggccgtcgcg tcgcgcgccc ccgaggccg | | 18140 |
| cccccaggcg aactggcaga gcactctgaa cagcatcgtg ggtctgggag tgcagagtgt | | 18200 |
| gaagcgccgc cgctgctatt aaaagacact gtagcgctta acttgcttgt ctgtgtgtat | | 18260 |
| atgtatgtcc gccgaccaga aggaggagga agaggcgcgt cgccgagttg caag atg | | 18317 |
| | Met | |
| gcc acc cca tcg atg ctg ccc cag tgg gcg tac atg cac atc gcc gga | | 18365 |
| Ala Thr Pro Ser Met Leu Pro Gln Trp Ala Tyr Met His Ile Ala Gly | | |
| 535 540 545 | | |
| cag gac gct tcg gag tac ctg agt ccg ggt ctg gtg cag ttc gcc cgc | | 18413 |
| Gln Asp Ala Ser Glu Tyr Leu Ser Pro Gly Leu Val Gln Phe Ala Arg | | |
| 550 555 560 | | |
| gcc aca gac acc tac ttc agt ctg ggg aac aag ttt agg aac ccc acg | | 18461 |
| Ala Thr Asp Thr Tyr Phe Ser Leu Gly Asn Lys Phe Arg Asn Pro Thr | | |
| 565 570 575 | | |
| gtg gcg ccc acg cac gat gtg acc acc gac cgc agc cag cgg ctg acg | | 18509 |
| Val Ala Pro Thr His Asp Val Thr Thr Asp Arg Ser Gln Arg Leu Thr | | |
| 580 585 590 595 | | |
| ctg cgc ttc gtg ccc gtg gac cgc gag gac aac acc tac tcg tac aaa | | 18557 |
| Leu Arg Phe Val Pro Val Asp Arg Glu Asp Asn Thr Tyr Ser Tyr Lys | | |
| 600 605 610 | | |
| gtg cgc tac acg ctg gcc gtg ggc gac aac cgc gtg ctg gac atg gcc | | 18605 |
| Val Arg Tyr Thr Leu Ala Val Gly Asp Asn Arg Val Leu Asp Met Ala | | |
| 615 620 625 | | |
| agc acc tac ttt gac atc cgc ggc gtg ctg gat cgg ggc cct agc ttc | | 18653 |
| Ser Thr Tyr Phe Asp Ile Arg Gly Val Leu Asp Arg Gly Pro Ser Phe | | |
| 630 635 640 | | |
| aaa ccc tac tcc ggc acc gct tac aac agc ctg gct ccc aag gga gcg | | 18701 |
| Lys Pro Tyr Ser Gly Thr Ala Tyr Asn Ser Leu Ala Pro Lys Gly Ala | | |
| 645 650 655 | | |
| ccc aac act tgc cag tgg aca tat aaa gct gat ggt gat act ggt aca | | 18749 |
| Pro Asn Thr Cys Gln Trp Thr Tyr Lys Ala Asp Gly Asp Thr Gly Thr | | |
| 660 665 670 675 | | |
| gaa aaa acc tat aca tat gga aat gcg cct gtg caa ggc att agt att | | 18797 |
| Glu Lys Thr Tyr Thr Tyr Gly Asn Ala Pro Val Gln Gly Ile Ser Ile | | |
| 680 685 690 | | |
| aca aaa gat ggt att caa ctt gga act gac act gat gat cag ccc att | | 18845 |
| Thr Lys Asp Gly Ile Gln Leu Gly Thr Asp Thr Asp Asp Gln Pro Ile | | |
| 695 700 705 | | |
| tat gca gat aaa act tat caa cca gag cct caa gtg ggt gat gct gaa | | 18893 |
| Tyr Ala Asp Lys Thr Tyr Gln Pro Glu Pro Gln Val Gly Asp Ala Glu | | |
| 710 715 720 | | |
| tgg cat gac atc act ggt act gat gaa aaa tat gga ggc aga gct ctc | | 18941 |
| Trp His Asp Ile Thr Gly Thr Asp Glu Lys Tyr Gly Gly Arg Ala Leu | | |
| 725 730 735 | | |
| aag cct gac acc aaa atg aag ccc tgc tat ggt tct ttt gcc aag cct | | 18989 |
| Lys Pro Asp Thr Lys Met Lys Pro Cys Tyr Gly Ser Phe Ala Lys Pro | | |
| 740 745 750 755 | | |
| acc aat aaa gaa gga ggt cag gca aat gtg aaa acc gaa aca ggc ggt | | 19037 |

```
                Thr Asn Lys Glu Gly Gly Gln Ala Asn Val Lys Thr Glu Thr Gly Gly
                            760                 765                 770 acc aaa gaa tat gac att gac atg gca ttc ttc gat aat cga agt gca    19085
Thr Lys Glu Tyr Asp Ile Asp Met Ala Phe Phe Asp Asn Arg Ser Ala
            775                 780                 785 gct gcg gct ggc ctg gcc cca gaa att gtt ttg tat act gag aat gtg    19133
Ala Ala Ala Gly Leu Ala Pro Glu Ile Val Leu Tyr Thr Glu Asn Val
            790                 795                 800 gat ctg gaa act cca gat act cat att gta tac aag gcg ggc aca gat    19181
Asp Leu Glu Thr Pro Asp Thr His Ile Val Tyr Lys Ala Gly Thr Asp
    805                 810                 815 gac agc agc tct tct atc aat ttg ggt cag cag tcc atg ccc aac aga    19229
Asp Ser Ser Ser Ser Ile Asn Leu Gly Gln Gln Ser Met Pro Asn Arg
820                 825                 830                 835 ccc aac tac att ggc ttt aga gac aac ttt atc ggg ctc atg tac tac    19277
Pro Asn Tyr Ile Gly Phe Arg Asp Asn Phe Ile Gly Leu Met Tyr Tyr
                840                 845                 850 aac agc act ggc aac atg ggc gtg ctg gct ggt cag gcc tcc cag ctg    19325
Asn Ser Thr Gly Asn Met Gly Val Leu Ala Gly Gln Ala Ser Gln Leu
            855                 860                 865 aat gct gtg gtg gac ttg cag gac aga aac act gaa ctg tcc tac cag    19373
Asn Ala Val Val Asp Leu Gln Asp Arg Asn Thr Glu Leu Ser Tyr Gln
            870                 875                 880 ctc ttg ctt gac tct ctg ggc gac aga acc agg tat ttc agt atg tgg    19421
Leu Leu Leu Asp Ser Leu Gly Asp Arg Thr Arg Tyr Phe Ser Met Trp
    885                 890                 895 aat cag gcg gtg gac agc tat gac ccc gat gtg cgc att att gaa aat    19469
Asn Gln Ala Val Asp Ser Tyr Asp Pro Asp Val Arg Ile Ile Glu Asn
900                 905                 910                 915 cac ggt gtg gag gat gaa ctc cct aac tat tgc ttc ccc ctg gat gct    19517
His Gly Val Glu Asp Glu Leu Pro Asn Tyr Cys Phe Pro Leu Asp Ala
                920                 925                 930 gtg ggt aga act gat act tac cag gga att aag gcc aat ggt gct gat    19565
Val Gly Arg Thr Asp Thr Tyr Gln Gly Ile Lys Ala Asn Gly Ala Asp
            935                 940                 945 caa acc acc tgg acc aaa gat gat act gtt aat gat gct aat gaa ttg    19613
Gln Thr Thr Trp Thr Lys Asp Asp Thr Val Asn Asp Ala Asn Glu Leu
            950                 955                 960 ggc aag ggc aat cct ttc gcc atg gag atc aac atc cag gcc aac ctg    19661
Gly Lys Gly Asn Pro Phe Ala Met Glu Ile Asn Ile Gln Ala Asn Leu
    965                 970                 975 tgg cgg aac ttc ctc tac gcg aac gtg gcg ctg tac ctg ccc gac tcc    19709
Trp Arg Asn Phe Leu Tyr Ala Asn Val Ala Leu Tyr Leu Pro Asp Ser
980                 985                 990                 995 tac aag tac acg ccg gcc aac atc acg ctg ccg acc aac acc aac        19754
Tyr Lys Tyr Thr Pro Ala Asn Ile Thr Leu Pro Thr Asn Thr Asn
                1000                1005                1010 acc tac gat tac atg aac ggc cgc gtg gtg gcg ccc tcg ctg gtg        19799
Thr Tyr Asp Tyr Met Asn Gly Arg Val Val Ala Pro Ser Leu Val
            1015                1020                1025 gac gcc tac atc aac atc ggg gcg cgc tgg tcg ctg gac ccc atg        19844
Asp Ala Tyr Ile Asn Ile Gly Ala Arg Trp Ser Leu Asp Pro Met
            1030                1035                1040 gac aac gtc aac ccc ttc aac cac cac cgc aac gcg ggc ctg cgc        19889
Asp Asn Val Asn Pro Phe Asn His His Arg Asn Ala Gly Leu Arg
            1045                1050                1055 tac cgc tcc atg ctc ctg ggc aac ggg cgc tac gtg ccc ttc cac        19934
Tyr Arg Ser Met Leu Leu Gly Asn Gly Arg Tyr Val Pro Phe His
            1060                1065                1070 atc cag gtg ccc caa aag ttc ttc gcc atc aag agc ctc ctg ctc        19979
```

```
Ile Gln Val Pro Gln Lys Phe Phe Ala Ile Lys Ser Leu Leu Leu
            1075                1080                1085 ctg ccc ggg tcc tac acc tac gag tgg aac ttc cgc aag gac gtc      20024
Leu Pro Gly Ser Tyr Thr Tyr Glu Trp Asn Phe Arg Lys Asp Val
            1090                1095                1100 aac atg atc ctg cag agc tcc ctc ggc aac gac ctg cgc acg gac      20069
Asn Met Ile Leu Gln Ser Ser Leu Gly Asn Asp Leu Arg Thr Asp
            1105                1110                1115 ggg gcc tcc atc gcc ttc acc agc atc aac ctc tac gcc acc ttc      20114
Gly Ala Ser Ile Ala Phe Thr Ser Ile Asn Leu Tyr Ala Thr Phe
            1120                1125                1130 ttc ccc atg gcg cac aac acc gcc tcc acg ctc gag gcc atg ctg      20159
Phe Pro Met Ala His Asn Thr Ala Ser Thr Leu Glu Ala Met Leu
            1135                1140                1145 cgc aac gac acc aac gac cag tcc ttc aac gac tac ctc tcg gcg      20204
Arg Asn Asp Thr Asn Asp Gln Ser Phe Asn Asp Tyr Leu Ser Ala
            1150                1155                1160 gcc aac atg ctc tac ccc atc ccg gcc aac gcc acc aac gtg ccc      20249
Ala Asn Met Leu Tyr Pro Ile Pro Ala Asn Ala Thr Asn Val Pro
            1165                1170                1175 atc tcc atc ccc tcg cgc aac tgg gcc gcc ttc cgc gga tgg tcc      20294
Ile Ser Ile Pro Ser Arg Asn Trp Ala Ala Phe Arg Gly Trp Ser
            1180                1185                1190 ttc acg cgc ctc aag acc cgc gag acg ccc tcg ctc ggc tcc ggg      20339
Phe Thr Arg Leu Lys Thr Arg Glu Thr Pro Ser Leu Gly Ser Gly
            1195                1200                1205 ttc gac ccc tac ttc gtc tac tcg ggc tcc atc ccc tac ctc gac      20384
Phe Asp Pro Tyr Phe Val Tyr Ser Gly Ser Ile Pro Tyr Leu Asp
            1210                1215                1220 ggc acc ttc tac ctc aac cac acc ttc aag aag gtc tcc atc acc      20429
Gly Thr Phe Tyr Leu Asn His Thr Phe Lys Lys Val Ser Ile Thr
            1225                1230                1235 ttc gac tcc tcc gtc agc tgg ccc ggc aac gac cgc ctc ctg acg      20474
Phe Asp Ser Ser Val Ser Trp Pro Gly Asn Asp Arg Leu Leu Thr
            1240                1245                1250 ccc aac gag ttc gaa atc aag cgc acc gtc gac gga gag ggg tac      20519
Pro Asn Glu Phe Glu Ile Lys Arg Thr Val Asp Gly Glu Gly Tyr
            1255                1260                1265 aac gtg gcc cag tgc aac atg acc aag gac tgg ttc ctg gtc cag      20564
Asn Val Ala Gln Cys Asn Met Thr Lys Asp Trp Phe Leu Val Gln
            1270                1275                1280 atg ctg gcc cac tac aac atc ggc tac cag ggc ttc tac gtg ccc      20609
Met Leu Ala His Tyr Asn Ile Gly Tyr Gln Gly Phe Tyr Val Pro
            1285                1290                1295 gag ggc tac aag gac cgc atg tac tcc ttc ttc cgc aac ttc cag      20654
Glu Gly Tyr Lys Asp Arg Met Tyr Ser Phe Phe Arg Asn Phe Gln
            1300                1305                1310 ccc atg agc cgc cag gtc gtg gac gag gtc aac tac aag gac tac      20699
Pro Met Ser Arg Gln Val Val Asp Glu Val Asn Tyr Lys Asp Tyr
            1315                1320                1325 cag gcc gtc acc ctg gcc tac cag cac aac aac tcg ggc ttc gtc      20744
Gln Ala Val Thr Leu Ala Tyr Gln His Asn Asn Ser Gly Phe Val
            1330                1335                1340 ggc tac ctc gcg ccc acc atg cgc cag gga cag ccc tac ccc gcc      20789
Gly Tyr Leu Ala Pro Thr Met Arg Gln Gly Gln Pro Tyr Pro Ala
            1345                1350                1355 aac tac ccc tac ccg ctc atc ggc aag agc gcc gtc gcc agc gtc      20834
Asn Tyr Pro Tyr Pro Leu Ile Gly Lys Ser Ala Val Ala Ser Val
            1360                1365                1370 acc cag aaa aag ttc ctc tgc gac cgg gtc atg tgg cgc atc ccc      20879
```

```
                Thr Gln Lys Lys Phe Leu Cys Asp Arg Val Met Trp Arg Ile Pro
                            1375                1380                1385 ttc tcc agc aac ttc atg tcc atg ggc gcg ctc acc gac ctc ggc         20924
Phe Ser Ser Asn Phe Met Ser Met Gly Ala Leu Thr Asp Leu Gly
            1390                1395                1400 cag aac atg ctc tac gcc aac tcc gcc cac gcg cta gac atg aat         20969
Gln Asn Met Leu Tyr Ala Asn Ser Ala His Ala Leu Asp Met Asn
            1405                1410                1415 ttc gaa gtc gac ccc atg gat gag tcc acc ctt ctc tat gtt gtc         21014
Phe Glu Val Asp Pro Met Asp Glu Ser Thr Leu Leu Tyr Val Val
            1420                1425                1430 ttc gaa gtc ttc gac gtc gtc cga gtg cac cag ccc cac cgc ggc         21059
Phe Glu Val Phe Asp Val Val Arg Val His Gln Pro His Arg Gly
            1435                1440                1445 gtc atc gag gcc gtc tac ctg cgc acg ccc ttc tcg gcc ggc aac         21104
Val Ile Glu Ala Val Tyr Leu Arg Thr Pro Phe Ser Ala Gly Asn
            1450                1455                1460 gcc acc acc taa gccccgctct tgcttcttgc aagatgacgg cctgtgcggg         21156
Ala Thr Thr ctccggcgag caggagctca ggccatcct ccgcgacctg gctgcgggc cctgcttcct    21216 gggcaccttc gacaagcgct tcccgggatt catggccccg cacaagctgg cctgcgccat   21276
cgtcaacacg gccggccgcg agaccggggg cgagcactgg ctggccttcg cctggaaccc   21336
gcgctcccac acctgctacc tcttcgaccc cttcgggttc tcggacgagc gcctcaagca   21396
gatctaccag ttcgagtacg agggcctgct gcgccgcagc gccctggcca ccgaggaccg   21456
ctgcgtcacc ctggaaaagt ccacccagac cgtgcagggt ccgcgctcgg ccgcctgcgg   21516
gctcttctgc tgcatgttcc tgcacgcctt cgtgcactgg cccgaccgcc ccatggacaa   21576
gaaccccacc atgaacttgc tgacgggggt gcccaacggc atgctccagt cgccccaggt   21636
ggaacccacc ctgcgccgca accaggaggc gctctaccgc ttcctcaacg cccactccgc   21696
ctactttcgc tcccaccgcg cgcgcatcga gaaggccacc gccttcgacc gcatgaatca   21756
agacatgtaa accgtgtgtg tatgtgaatg ctttattcat aataaacagc acatgtttat   21816 gccaccttt ctgaggctct gactttattt agaaatcgaa ggggttctgc cggctctcgg   21876
cgtgccccgc gggcagggat acgttgcgga actggtactt gggcagccac ttgaactcgg   21936
ggatcagcag cttcggcacg gggaggtcgg ggaacgagtc gctccacagc ttgcgcgtga   21996
gttgcagggc gcccagcagg tcgggcgcgg agatcttgaa atcgcagttg gacccgcgt   22056 tctgcgcgcg ggagttgcgg tacacggggt tgcagcactg gaacaccatc agggccgggt   22116
gcttcacgct cgccagcacc gtcgcgtcgg tgatgccctc cacgtccaga tcctcggcgt   22176
tggccatccc gaaggggtc atcttgcagg tctgccgcc catgctgggc acgcagccgg   22236
gcttgtggtt gcaatcgcag tgcaggggga tcagcatcat ctgggcctgc tcggagctca   22296
tgcccgggta catggccttc atgaaagcct ccagctggcg gaaggcctgc tgcgccttgc   22356
cgccctcggt gaagaagacc ccgcaggact tgctagagaa ctggttggtg gcgcagccgg   22416
cgtcgtgcac gcagcagcgc gcgtcgttgt tggccagctg caccacgctg cgccccagc   22476 ggttctgggt gatcttggcc cggtcggggt tctccttcag cgcgcgctgc ccgttctcgc   22536
tcgccacatc catctcgatc gtgtgctcct tctggatcat cacggtcccg tgcaggcatc   22596
gcagcttgcc ctcggcctcg gtcacccgt gcagccacag cgcgcagccg gtgcactccc   22656
agttcttgtg ggcgatctgg gagtgcgagt gcacgaagcc ctgcaggaag cggcccatca   22716
tcgtggtcag ggtcttgttg ctggtgaagg tcagcgggat gccgcggtgc tcctcgttca   22776
```

```
catacaggtg gcagatgcgg cggtacacct cgccctgctc gggcatcagc tggaaggcgg   22836
acttcaggtc gctctccacg cggtaccggt ccatcagcag cgtcatgact tccatgccct   22896
tctcccaggc cgagacgatc ggcaggctca gggggttctt caccgccgtt gtcatcttag   22956
tcgccgccgc tgaggtcagg gggtcgttct cgtccaggt  ctcaaacact cgcttgccgt   23016
ccttctcggt gatgcgcacg gggggaaagc tgaagcccac ggccgccagc tcctcctcgg   23076
cctgcctttc gtcctcgctg tcctggctga tgtcttgcaa aggcacatgc ttggtcttgc   23136
ggggtttctt tttgggcggc agaggcggcg gcggagacgt gctgggcgag cgcgagttct   23196
cgctcaccac gactatttct tcttcttggc cgtcgtccga gaccacgcgg cggtaggcat   23256
gcctcttctg gggcagaggc ggaggcgacg ggctctcgcg gttcggcggg cggctggcag   23316
agccccttcc gcgttcgggg gtgcgctcct ggcggcgctg ctctgactga cttcctccgc   23376
ggccggccat tgtgttctcc tagggagcaa caagcatgga gactcagcca tcgtcgccaa   23436
catcgccatc tgcccccgcc gccgccgacg agaaccagca gcagaatgaa agcttaaccg   23496
ccccgccgcc cagccccacc tccgacgccg ccgcggcccc agacatgcaa gagatggagg   23556
aatccatcga gattgacctg ggctacgtga cgcccgcgga gcacgaggag gagctggcag   23616
cgcgcttttc agccccggaa gagaaccacc aagagcagcc agagcaggaa gcagagagcg   23676
agcagcagca ggctgggctc gagcatggcg actacctgag cggggcagag gacgtgctca   23736
tcaagcatct ggcccgccaa tgcatcatcg tcaaggacgc gctgctcgac cgcgccgagg   23796
tgcccctcag cgtggcggag ctcagccgcg cctacgagcg caacctcttc tcgccgcgcg   23856
tgccccccaa gcgccagccc aacggcacct gcgagcccaa cccgcgcctc aacttctacc   23916
cggtcttcgc ggtgcccgag gccctggcca cctaccacct ctttttcaag aaccaaagga   23976
tccccgtctc ctgccgcgcc aaccgcaccc gcgccgacgc cctgctcaac ctgggtcccg   24036
gcgcccgcct acctgatatc gcctccttgg aagaggttcc caagatcttc gagggtctgg   24096
gcagcgacga gactcgggcc gcgaacgctc tgcaaggaag cggagaggag catgagcacc   24156
acagcgccct ggtggagttg gaaggcgaca acgcgcgcct ggcggtgctc aagcgcacgg   24216
tcgagctgac ccacttcgcc tacccggcgc tcaacctgcc ccccaaggtc atgagcgccg   24276
tcatggacca ggtgctcatc aagcgcgcct cgcccctctc ggatgaggac atgcaggacc   24336
ccgagagctc ggacgagggc aagcccgtgg tcagcgacga gcagctggcg cgctggctgg   24396
gagcgagtag cacccccag  agcttggaag agcggcgcaa gctcatgatg gccgtggtcc   24456
tggtgaccgt ggagctggag tgtctgcgcc gcttcttcgc cgacgcagag accctgcgca   24516
aggtcgagga gaacctgcac tacctcttca ggcacgggtt tgtgcgccag gcctgcaaga   24576
tctccaacgt ggagctgacc aacctggtct cctacatggg catcctgcac gagaaccgcc   24636
tggggcagaa cgtgctgcac accaccctgc gcggggaggc ccgccgcgac tacatccgcg   24696
actgcgtcta cctgtacctc tgccacacct ggcagacggg catgggcgtg tggcagcagt   24756
gcctggagga gcagaacctg aaagagctct gcaagctcct gcagaagaac ctgaaggccc   24816
tgtggaccgg gttcgacgag cgcaccaccg cctcggacct ggccgacctc atcttccccg   24876
agcgcctgcg gctgacgctg cgcaacggac tgcccgactt tatgagtcaa agcatgttgc   24936
aaaactttcg ctctttcatc ctcgaacgct ccgggatcct gcccgccacc tgctccgcgc   24996
tgccctcgga cttcgtgccg ctgaccttcc gcgagtgccc ccgccgctc  tggagccact   25056
gctacctgct gcgcctggcc aactacctgg cctaccactc ggacgtgatc gaggacgtca   25116
gcggcgaggg tctgctcgag tgccactgcc gctgcaacct ctgcacgccg caccgctccc   25176
```

```
tggcctgcaa ccccccagctg ctgagcgaga cccagatcat cggcaccttc gagttgcaag   25236
gccccggcga gggcaagggg ggtctgaaac tcaccccggg gctgtggacc tcggcctact   25296
tgcgcaagtt cgtgcccgag gactaccatc ccttcgagat caggttctac gaggaccaat   25356
cccagccgcc caaggccgaa ctgtcggcct gcgtcatcac ccagggggcc atcctggccc   25416
aattgcaagc catccagaaa tcccgccaag aatttctgct gaaaaagggc cacggggtct   25476
acctggaccc ccagaccgga gaggagctca accccagctt cccccaggat gccccgagga   25536
agcagcaaga agctgaaagt ggagctgccg ccgccggagg atttggagga agactgggag   25596
agcagtcagg cagaggagga ggagatggaa gactgggaca gcactcaggc agaggaggac   25656
agcctgcaag acagtctgga gacgaggtg gaggaggagg cagaggaaga agcagccgcc   25716
gccagaccgt cgtcctcggc ggagaaagca agcagcacgg ataccatctc cgctccgggt   25776
cggggtcgcg gcgaccgggc ccacagtagg tgggacgaga ccgggcgctt cccgaacccc   25836
accacccaga ccggtaagaa ggagcggcag ggatacaagt cctggcgggg gcacaaaaac   25896
gccatcgtct cctgcttgca agcctgcggg ggcaacatct ccttcacccg ccgctacctg   25956
ctcttccacc gcggggtgaa cttccccgc aacatcttgc attactaccg tcacctccac   26016
agcccctact actgtttcca agaagaggca gaaacccagc agcagcagaa aaccagcggc   26076
agcagcagct agaaaatcca cagcggcggc aggtggactg aggatcgcag cgaacgagcc   26136
ggcgcagacc cgggagctga ggaaccggat cttttccacc ctctatgcca tcttccagca   26196
gagtcggggg caggagcagg aactgaaagt caagaaccgt tctctgcgct cgctcacccg   26256
cagttgtctg tatcacaaga gcgaagacca acttcagcgc actctcgagg acgccgaggc   26316
tctcttcaac aagtactgcg cgctcactct taaagagtag cccgcgcccg cccacacacg   26376
gaaaaaggcg ggaattacgt caccacctgc gcccttcgcc cgaccatcat catgagcaaa   26436
gagattccca cgccttacat gtggagctac cagccccaga tgggcctggc cgccggcgcc   26496
gcccaggact actccacccg catgaactgg ctcagcgccg ggcccgcgat gatctcacgg   26556
gtgaatgaca tccgcgcccg ccgaaaccag atactcctag aacagtcagc gatcaccgcc   26616
acgccccgcc atcaccttaa tccgcgtaat tggcccgccg ccctggtgta ccaggaaatt   26676
ccccagccca cgaccgtact acttccgcga gacgcccagg ccgaagtcca gctgactaac   26736
tcaggtgtcc agctggccgg cggcgccgcc ctgtgtcgtc accgccccgc tcagggtata   26796
aagcggctgg tgatccgagg cagaggcaca cagctcaacg acgaggtggt gagctcttcg   26856
ctgggtctgc gacctgacgg agtcttccaa ctcgccggat cggggagatc ttccttcacg   26916
cctcgtcagg ccgtcctgac tttggagagt tcgtcctcgc agcccgctc gggtggcatc   26976
ggcactctcc agttcgtgga ggagttcact ccctcggtct acttcaaccc cttctccggc   27036
tcccccggcc actacccgga cgagttcatc ccgaacttcg acgccatcag cgagtcggtg   27096
gacggctacg attgaatgtc ccatggtggc gcagctgacc tagctcggct tcgacacctg   27156
gaccactgcc gccgcttccg ctgcttcgct cgggatctcg ccgagtttgc ctactttgag   27216
ctgcccgagg agcaccctca gggcccggcc cacggagtgc ggatcatcgt cgaagggggc   27276
ctcgactccc acctgcttcg gatcttcagc cagcgaccga tcctggtcga gcgcgagcaa   27336
ggacagaccc ttctgacccct gtactgcatc tgcaaccacc ccggcctgca tgaaagtctt   27396
tgttgtctgc tgtgtactga gtataataaa agctgagatc agcgactact ccggactcga   27456
ttgtggtgtt cctgctatca accggtccct gttcttcacc gggaacgaga ccgagctcca   27516
gcttcagtgt aagccccaca agaagtacct cacctggctg ttccagggct ccccgatcgc   27576
```

```
cgttgtcaac cactgcgaca acgacggagt cctgctgagc ggccccgcca accttacttt   27636
ttccacccgc agaagcaagc tccagctctt ccaacccttc ctccccggga cctatcagtg   27696
cgtctcggga ccctgccatc acaccttcca cctgatcccg aataccacag cgccgctccc   27756
cgctactaac aaccaaacta cccaccatcg ccaccgtcgc gacctttctg aatctaacac   27816
taccacccac accggaggtg agctccgagg tcgaccaacc tctgggattt actacggccc   27876
ctgggaggtg gtggggttaa tagcgctagg cctagttgtg ggtgggcttt ggctctctg    27936 ctacctatac ctcccttgct gttcgtactt agtggtgctg tgttgctggt ttaagaaatg   27996
gggaagatca ccctagtgag ctgcggtgcg ctggtggcgg tggtggtgtt ttcgattgtg   28056
ggactgggcg gcgcggctgt agtgaaggag aaggccgatc cctgcttgca tttcaatccc   28116
gacaattgcc agctgagttt tcagcccgat ggcaatcggt gcgcggtgct gatcaagtgc   28176
ggatgggaat gcgagaacgt gagaatcgag tacaataaca agactcggaa caatactctc   28236
gcgtccgtgt ggcagcccgg ggaccccgag tggtacaccg tctctgtccc cggtgctgac   28296
ggctccccgc gcaccgtgaa caatactttc attttgcgc acatgtgcga cacggtcatg   28356
tggatgagca agcagtacga tatgtggccc cccacgaagg agaacatcgt ggtcttctcc   28416
atcgcttaca gcgcgtgcac ggcgctaatc accgctatcg tgtgcctgag cattcacatg   28476
ctcatcgcta ttcgccccag aaataatgcc gaaaagagag aacagccata acacgttttt   28536
tcacacacct ttttcagacc atggcctctg ttaaattttt gcttttattt gccagtctca   28596
ttactgttat aagtaatgag aaactcacta tttacattgg cactaaccac acttagacg    28656 gaattccaaa atcctcatgg tattgctatt ttgatcaaga tccagactta actatagaac   28716
tgtgtggtaa caagggaaaa aatacaagca ttcatttaat taactttaat tgcggagaca   28776
atttgaaatt aattaatatc actaaagagt atggaggtat gtattactat gttgcagaaa   28836
ataacaacat gcagttttat gaagttactg taactaatcc caccacacct agaacaacaa   28896
caaccaccac cacaaaaact acacctgtta ccactatgca gctcactacc aataacattt   28956
ttgccatgcg tcaaatggtc aacaatagca ctcaacccac cccacccagt gaggaaattc   29016
ccaaatccat gattggcatt attgttgctg tagtggtgtg catgttgatc atcgccttgt   29076
gcatggtgta ctatgccttc tgctacagaa agcacagact gaacgacaag ctggaacact   29136
tactaagtgt tgaattttaa ttttttagaa ccatgaagat cctaggcctt ttaattttt   29196 ctatcattac ctctgctcta tgcaattctg acaatgagga cgttactgtc gttgtcggaa   29256
ccaattatac actgaaaggt ccagcgaagg gtatgctttc gtggtattgc tggtttggaa   29316
ctgacgagca acagacagag ctctgcaatg ctcaaaaagg caaaacctca aattctaaaa   29376
tctctaatta tcaatgcaat ggcactgact tagtactgct caatgtcacg aaagcatatg   29436
ctggcagcta cacctgccct ggagatgata ctgagaacat gatttttac aaagtggaag   29496 tggttgatcc cactactcca cctccaccca ccacaactac tcacaccaca cacagaac    29556 aaaccacagc agaggaggca gcaaagttag ccttgcaggt ccaagacagt tcatttgttg   29616
gcattacccc tacacctgat cagcggtgtc cggggctgct cgtcagcggc attgtcggtg   29676
tgctttcggg attagcagtc ataatcatct gcatgttcat ttttgcttgc tgctatagaa   29736
ggctttaccg acaaaaatca gacccactgc tgaacctcta tgtttaattt tttccagagc   29796
catgaaggca gttagcactc tagtttttg ttctttgatt ggcactgttt ttagtgttag   29856
ctttttgaaa caaatcaatg ttactgaggg ggaaaatgtg acactggtag gcgtagaggg   29916
tgctcaaaat accacctgga caaaattcca tctagatggg tggaaagaaa tttgcacctg   29976
```

```
gaatgtcagt acttatacat gtgaaggagt taatcttacc attgtcaatg tcagccaaat    30036
tcaaaagggt tggattaaag ggcaatctgt tagtgttagc aatagtgggt actataccca    30096
gcatactctt atctatgaca ttatagttat accactgcct acacctagcc cacctagcac    30156
taccacacag acaacccaca ctacacaaac aaccacatac agtacatcaa atcagcctac    30216
caccactaca acagcagagg ttgccagctc gtctggggtc cgagtggcat ttttgatgtt    30276
ggccccatct agcagtccca ctgctagtac caatgagcag actactgaat ttttgtccac    30336
tgtcgagagc cacaccacag ctacctcgag tgccttctct agcaccgcca atctatcctc    30396
gctttcctct acaccaatca gtcccgctac tactcctacc cccgctattc tccccactcc    30456
cctgaagcaa acagacggcg acatgcaatg gcagatcacc ctgctcattg tgatcgggtt    30516
ggtcatcctg gccgtgttgc tctactacat cttctgccgc cgcattccca acgcgcaccg    30576
caagccggcc tacaagccca tcgttgtcgg gcagccggag ccgcttcagg tggaagggg    30636 tctaaggaat cttctcttct cttttacagt atggtgattg aattatgatt cctagacaaa    30696
tcttgatcac tattcttatc tgcctcctcc aagtctgtgc caccctcgct ctggtggcca    30756
acgccagtcc agactgtatt gggcccttcg cctcctacgt gctctttgcc ttcatcacct    30816
gcatctgctg ctgtagcata gtctgcctgc ttatcacctt cttccagttc attgactgga    30876
tctttgtgcg catcgcctac ctgcgccacc accccagta ccgcgaccag cgagtggcgc     30936
ggctgctcag gatcctctga taagcatgcg ggctctgcta cttctcgcgc ttctgctgtt    30996
agtgctcccc cgtcccgtcg accccggac ccccacccag tccccgagg aggtccgcaa     31056 atgcaaattc caagaaccct ggaaattcct caaatgctac cgccaaaaat cagacatgca    31116
tcccagctgg atcatgatca ttgggatcgt gaacattctg gcctgcaccc tcatctcctt    31176
tgtgatttac ccctgctttg actttggttg gaactcgcca gaggcgctct atctcccgcc    31236
tgaacctgac acaccaccac agcaacctca ggcacacgca ctaccaccac caccacagcc    31296
taggccacaa tacatgccca tattagacta tgaggccgag ccacagcgac ccatgctccc    31356
cgctattagt tacttcaatc taaccggcgg agatgactga cccactggcc aacaacaacg    31416
tcaacgacct tctcctggac atggacggcc gcgcctcgga gcagcgactc gcccaacttc    31476
gcattcgcca gcagcaggag agagccgtca aggagctgca ggacggcata gccatccacc    31536
agtgcaagaa aggcatcttc tgcctggtga acaggccaa gatctcctac gaggtcaccc     31596
agaccgacca tcgcctctcc tacgagctcc tgcagcagcg ccagaagttc acctgcctgg    31656
tcggagtcaa ccccatcgtc atcacccagc agtcgggcga taccaagggg tgcatccact    31716
gctcctgcga ctcccccgac tgcgtccaca ctctgatcaa gaccctctgc ggcctccgcg    31776
acctcctccc catgaactaa tcaccccctt atccagtgaa ataaagatca tattgatgat    31836
ttgagtttaa taaaataaa gaatcactta cttgaaatct gataccaggt ctctgtccat     31896
gttttctgcc aacaccactt cactcccctc ttcccagctc tggtactgca ggccccggcg    31956
ggctgcaaac ttcctccaca ccctgaaggg gatgtcaaat tcctcctgtc cctcaatctt    32016
cattttatct tctatcag atg tcc  aaa aag cgc gtc cgg  gtg gat gat gac    32067
                     Met Ser  Lys Lys Arg Val Arg  Val Asp Asp Asp
                         1465             1470 ttc  gac ccc gtc  tac ccc  tac gat gca gac  aac  gca ccg acc gtg    32112
Phe  Asp Pro Val  Tyr Pro  Tyr Asp Ala Asp  Asn  Ala Pro Thr Val
1475           1480               1485 ccc  ttc atc aac  ccc ccc  ttc gtc tct tca gat  gga ttc caa gag      32157
Pro  Phe Ile Asn  Pro Pro  Phe Val Ser Ser Asp  Gly Phe Gln Glu
1490           1495              1500
```

| | | | | | | | | | | | |
|---|---|---|---|---|---|---|---|---|---|---|---|
| aag | ccc | ctg | ggg | gtg | ctg | tcc | ctg | cgt | ctg | gcc | gat | ccc | gtc | acc | 32202 |
| Lys | Pro | Leu | Gly | Val | Leu | Ser | Leu | Arg | Leu | Ala | Asp | Pro | Val | Thr | |
| 1505 | | | | 1510 | | | | | 1515 | | | | | | | acc aag aac ggg gaa atc acc ctc aag ctg gga gat ggg gtg gac    32247
Thr Lys Asn Gly Glu Ile Thr Leu Lys Leu Gly Asp Gly Val Asp
1520                1525                1530 ctc gac tcc tcg gga aaa ctc atc tcc aac acg gcc acc aag gcc    32292
Leu Asp Ser Ser Gly Lys Leu Ile Ser Asn Thr Ala Thr Lys Ala
1535                1540                1545 gcc gcc cct ctc agt ttt tcc aac aac acc att tcc ctt aac atg    32337
Ala Ala Pro Leu Ser Phe Ser Asn Asn Thr Ile Ser Leu Asn Met
1550                1555                1560 gat acc cct ttt tac aac aac aat gga aag tta ggc atg aaa gtc    32382
Asp Thr Pro Phe Tyr Asn Asn Asn Gly Lys Leu Gly Met Lys Val
1565                1570                1575 act gct cca ctg aag ata cta gac aca gac ttg cta aaa aca ctt    32427
Thr Ala Pro Leu Lys Ile Leu Asp Thr Asp Leu Leu Lys Thr Leu
1580                1585                1590 gtt gta gct tat gga caa ggt tta gga aca aac acc act ggt gcc    32472
Val Val Ala Tyr Gly Gln Gly Leu Gly Thr Asn Thr Thr Gly Ala
1595                1600                1605 ctt gtt gcc caa cta gca tcc cca ctt gct ttt gat agc aat agc    32517
Leu Val Ala Gln Leu Ala Ser Pro Leu Ala Phe Asp Ser Asn Ser
1610                1615                1620 aaa att gcc ctt aat tta ggc aat gga cca ttg aaa gtg gat gca    32562
Lys Ile Ala Leu Asn Leu Gly Asn Gly Pro Leu Lys Val Asp Ala
1625                1630                1635 aat aga ctg aac atc aat tgc aat aga gga ctc tat gtt act acc    32607
Asn Arg Leu Asn Ile Asn Cys Asn Arg Gly Leu Tyr Val Thr Thr
1640                1645                1650 aca aaa gat gca ctg gaa gcc aat ata agt tgg gct aat gct atg    32652
Thr Lys Asp Ala Leu Glu Ala Asn Ile Ser Trp Ala Asn Ala Met
1655                1660                1665 aca ttt ata gga aat gcc atg ggt gtc aat att gat aca caa aaa    32697
Thr Phe Ile Gly Asn Ala Met Gly Val Asn Ile Asp Thr Gln Lys
1670                1675                1680 ggc ttg caa ttt ggc acc act agt acc gtc gca gat gtt aaa aac    32742
Gly Leu Gln Phe Gly Thr Thr Ser Thr Val Ala Asp Val Lys Asn
1685                1690                1695 gct tac ccc ata caa atc aaa ctt gga gct ggt ctc aca ttt gac    32787
Ala Tyr Pro Ile Gln Ile Lys Leu Gly Ala Gly Leu Thr Phe Asp
1700                1705                1710 agc aca ggt gca att gtt gca tgg aac aaa gat gat gac aag ctt    32832
Ser Thr Gly Ala Ile Val Ala Trp Asn Lys Asp Asp Asp Lys Leu
1715                1720                1725 aca cta tgg acc aca gcc gac ccc tct cca aat tgt cac ata tat    32877
Thr Leu Trp Thr Thr Ala Asp Pro Ser Pro Asn Cys His Ile Tyr
1730                1735                1740 tct gaa aag gat gct aag ctt aca ctt tgc ttg aca aag tgt ggc    32922
Ser Glu Lys Asp Ala Lys Leu Thr Leu Cys Leu Thr Lys Cys Gly
1745                1750                1755 agt cag att ctg ggc act gtt tcc ctc ata gct gtt gat act ggc    32967
Ser Gln Ile Leu Gly Thr Val Ser Leu Ile Ala Val Asp Thr Gly
1760                1765                1770 agt tta aat ccc ata aca gga aca gta acc act gct ctt gtc tca    33012
Ser Leu Asn Pro Ile Thr Gly Thr Val Thr Thr Ala Leu Val Ser
1775                1780                1785 ctt aaa ttc gat gca aat gga gtt ttg caa agc agc tca aca cta    33057
Leu Lys Phe Asp Ala Asn Gly Val Leu Gln Ser Ser Ser Thr Leu
1790                1795                1800

| | | | | | | | | | | | | | |
|---|---|---|---|---|---|---|---|---|---|---|---|---|---|
| gac | tca | gac | tat | tgg | aat | ttc | aga | cag | gga | gat | gtt | aca | cct | gct | 33102 |
| Asp | Ser | Asp | Tyr | Trp | Asn | Phe | Arg | Gln | Gly | Asp | Val | Thr | Pro | Ala |
| 1805 | | | | 1810 | | | | | 1815 | | | | | |

| | | | | | | | | | | | | | | |
|---|---|---|---|---|---|---|---|---|---|---|---|---|---|---|---|
| gaa | gcc | tat | act | aat | gct | ata | ggt | ttc | atg | ccc | aat | cta | aaa | gca | 33147 |
| Glu | Ala | Tyr | Thr | Asn | Ala | Ile | Gly | Phe | Met | Pro | Asn | Leu | Lys | Ala | |
| 1820 | | | | | 1825 | | | | | 1830 | | | | | |

| | | | | | | | | | | | | | | | |
|---|---|---|---|---|---|---|---|---|---|---|---|---|---|---|---|
| tac | cct | aaa | aac | aca | agt | gga | gct | gca | aaa | agt | cac | att | gtt | ggg | 33192 |
| Tyr | Pro | Lys | Asn | Thr | Ser | Gly | Ala | Ala | Lys | Ser | His | Ile | Val | Gly | |
| 1835 | | | | | 1840 | | | | | 1845 | | | | | |

| | | | | | | | | | | | | | | | |
|---|---|---|---|---|---|---|---|---|---|---|---|---|---|---|---|
| aaa | gtg | tac | cta | cat | ggg | gat | aca | ggc | aaa | cca | ctg | gac | ctc | att | 33237 |
| Lys | Val | Tyr | Leu | His | Gly | Asp | Thr | Gly | Lys | Pro | Leu | Asp | Leu | Ile | |
| 1850 | | | | | 1855 | | | | | 1860 | | | | | |

| | | | | | | | | | | | | | | | |
|---|---|---|---|---|---|---|---|---|---|---|---|---|---|---|---|
| att | act | ttc | aat | gaa | aca | agt | gat | gaa | tct | tgc | act | tac | tgt | att | 33282 |
| Ile | Thr | Phe | Asn | Glu | Thr | Ser | Asp | Glu | Ser | Cys | Thr | Tyr | Cys | Ile | |
| 1865 | | | | | 1870 | | | | | 1875 | | | | | |

| | | | | | | | | | | | | | | | |
|---|---|---|---|---|---|---|---|---|---|---|---|---|---|---|---|
| aac | ttt | caa | tgg | cag | tgg | ggg | gct | gat | caa | tat | aaa | aat | gaa | aca | 33327 |
| Asn | Phe | Gln | Trp | Gln | Trp | Gly | Ala | Asp | Gln | Tyr | Lys | Asn | Glu | Thr | |
| 1880 | | | | | 1885 | | | | | 1890 | | | | | |

| | | | | | | | | | | | | | |
|---|---|---|---|---|---|---|---|---|---|---|---|---|---|---|
| ctt | gcc | gtc | agt | tca | ttc | acc | ttt | tcc | tat | att | gct | aaa | gaa | taa | 33372 |
| Leu | Ala | Val | Ser | Ser | Phe | Thr | Phe | Ser | Tyr | Ile | Ala | Lys | Glu | |
| 1895 | | | | | 1900 | | | | | 1905 | | | | |

```
accccactct gtaccccatc tctgtctatg gaaaaaactc tgaaacacaa aataaaataa    33432
agttcaagtg ttttattgat tcaacagttt tacaggattc gagcagttat ttttcctcca    33492
ccctcccagg acatggaata caccaccctc tcccccgca cagccttgaa catctgaatg     33552
ccattggtga tggacatgct tttggtctcc acgttccaca cagtttcaga gcgagccagt    33612
ctcgggtcgg tcaggagat gaaaccctcc gggcactccc gcatctgcac ctcacagctc     33672
aacagctgag gattgtcctc ggtggtcggg atcacggtta tctggaagaa gcagaagagc    33732
ggcggtggga atcatagtcc gcgaacggga tcggccggtg gtgtcgcatc aggccccgca    33792
gcagtcgctg tcgccgccgc tccgtcaagc tgctgctcag ggggtccggg tccagggact    33852
ccctcagcat gatgcccacg gccctcagca tcagtcgtct ggtgcggcgg gcgcagcagc    33912
gcatgcggat ctcgctcagg tcgctgcagt acgtgcaaca caggaccacc aggttgttca    33972
acagtccata gttcaacacg ctccagccga aactcatcgc gggaaggatg ctacccacgt    34032
ggccgtcgta ccagatcctc aggtaaatca agtggcgccc cctccagaac acgctgccca    34092
tgtacatgat ctccttgggc atgtggcggt tcaccacctc ccggtaccac atcaccctct    34152
ggttgaacat gcagccccgg atgatcctgc ggaaccacag ggccagcacc gccccgcccg    34212
ccatgcagcg aagagacccc gggtcccgac aatggcaatg gaggacccac cgctcgtacc    34272
cgtggatcat ctgggagctg aacaagtcta tgttggcaca gcacaggcat atgctcatgc    34332
atctcttcag cactctcagc tcctcggggg tcaaaaccat atcccagggc acggggaact    34392
cttgcaggac agcgaacccc gcagaacagg gcaatcctcg cacataactt acattgtgca    34452
tggacagggt atcgcaatca ggcagcaccg ggtgatcctc caccagagaa gcgcgggtct    34512
cggtctcctc acagcgtggt aaggggccg gccgatacgg gtgatggcgg gacgcggctg    34572
atcgtgttcg cgaccgtgtt atgatgcagt tgctttcgga cattttcgta cttgctgtag    34632
cagaacctgg tccgggcgct gcacaccgat cgccggcggc ggtcccggcg cttggaacgc    34692
tcggtgttga agttgtaaaa cagccactct ctcagaccgt gcagcagatc tagggcctca    34752
ggagtgatga agatcccatc atgcctgatg gctctaatca catcgaccac cgtggaatgg    34812
gccagaccca gccagatgat gcaattttgt tgggtttcgg tgacggcggg ggagggaaga    34872
acaggaagaa ccatgattaa cttttaatcc aaacggtctc ggagcacttc aaaatgaaga    34932
```

-continued

```
tcgcggagat ggcacctctc gccccgctg tgttggtgga aaataacagc caggtcaaag    34992
gtgatacggt tctcgagatg ttccacggtg gcttccagca aagcctccac gcgcacatcc    35052
agaaacaaga caatagcgaa agcgggaggg ttctctaatt cctcaatcat catgttacac    35112
tcctgcacca tccccagata attttcattt ttccagcctt gaatgattcg aactagttcc    35172
tgaggtaaat ccaagccagc catgataaag agctcgcgca gagcgccctc caccggcatt    35232
cttaagcaca ccctcataat tccaagatat tctgctcctg gttcacctgc agcagattga    35292
caagcggaat atcaaaatct ctgccgcgat ccctaagctc ctccctcagc aataactgta    35352
agtactcttt catatcctct ccgaaatttt tagccatagg accaccagga ataagattag    35412
ggcaagccac agtacagata aaccgaagtc ctccccagtg agcattgcca aatgcaagac    35472
tgctataagc atgctggcta gacccggtga tatcttccag ataactggac agaaaatcgc    35532
ccaggcaatt tttaagaaaa tcaacaaaag aaaaatcctc caggtgcacg tttagagcct    35592
cgggaacaac gatggagtaa atgcaagcgg tgcgttccag catggttagt tagctgatct    35652
gtagaaaaaa acaaaaatga acattaaacc atgctagcct ggcgaacagg tgggtaaatc    35712
gttctctcca gcaccaggca ggccacgggg tctccggcac gaccctcgta aaaattgtcg    35772
ctatgattga aaaccatcac agagagacgt tcccggtggc cggcgtgaat gattcgacaa    35832
gatgaataca cccccggaac attggcgtcc gcgagtgaaa aaaagcgccc aaggaagcaa    35892
taaggcacta caatgctcag tctcaagtcc agcaaagcga tgccatgcgg atgaagcaca    35952
aaattctcag gtgcgtacaa aatgtaatta ctcccctcct gcacaggcag caaagccccc    36012
gatccctcca ggtacacata caaagcctca gcgtccatag cttaccgagc agcagcacac    36072
aacaggcgca agagtcagag aaaggctgag ctctaacctg tccacccgct ctctgctcaa    36132
tatatagccc agatctacac tgacgtaaag gccaagtct aaaaatacc gccaaataat    36192
cacacacgcc cagcacacgc ccagaaaccg gtgacacact caaaaaaata cgcgcacttc    36252
ctcaaacgcc caaactgccg tcatttccgg gttcccacgc tacgtcatca aaattcgact    36312
ttcaaattcc gtcgaccgtt aaaaacgtcg cccgccccgc ccctaacggt cgccgctccc    36372
gcagccaatc accgccccgc atccccaaat tcaaataccct catttgcata ttaacgcgca    36432
ccaaaagttt gaggtatatt attgatgatg                                     36462
```

<210> SEQ ID NO 2
<211> LENGTH: 530
<212> TYPE: PRT
<213> ORGANISM: chimpanzee adenovirus serotype Pan5

<400> SEQUENCE: 2

```
Met Met Arg Arg Val Tyr Pro Glu Gly Pro Pro Ser Tyr Glu Ser
1               5                   10                  15

Val Met Gln Gln Ala Val Ala Ala Met Gln Pro Leu Glu Ala
                20                  25                  30

Pro Tyr Val Pro Pro Arg Tyr Leu Ala Pro Thr Glu Gly Arg Asn Ser
                35                  40                  45

Ile Arg Tyr Ser Glu Leu Ala Pro Leu Tyr Asp Thr Thr Arg Leu Tyr
        50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
                100                 105                 110
```

```
Trp Gly Gly Gln Leu Lys Thr Ile Met His Thr Asn Met Pro Asn Val
            115                 120                 125

Asn Glu Phe Met Tyr Ser Asn Lys Phe Lys Ala Arg Val Met Val Ser
130                 135                 140

Arg Lys Thr Pro Asn Gly Val Thr Val Thr Asp Gly Ser Gln Asp Glu
145                 150                 155                 160

Leu Thr Tyr Glu Trp Val Glu Phe Glu Leu Pro Glu Gly Asn Phe Ser
                165                 170                 175

Val Thr Met Thr Ile Asp Leu Met Asn Asn Ala Ile Ile Asp Asn Tyr
                180                 185                 190

Leu Ala Val Gly Arg Gln Asn Gly Val Leu Glu Ser Asp Ile Gly Val
            195                 200                 205

Lys Phe Asp Thr Arg Asn Phe Arg Leu Gly Trp Asp Pro Val Thr Glu
            210                 215                 220

Leu Val Met Pro Gly Val Tyr Thr Asn Glu Ala Phe His Pro Asp Ile
225                 230                 235                 240

Val Leu Leu Pro Gly Cys Gly Val Asp Phe Thr Glu Ser Arg Leu Ser
                245                 250                 255

Asn Leu Leu Gly Ile Arg Lys Arg Gln Pro Phe Gln Glu Gly Phe Gln
                260                 265                 270

Ile Leu Tyr Glu Asp Leu Glu Gly Gly Asn Ile Pro Ala Leu Leu Asp
                275                 280                 285

Val Asp Ala Tyr Glu Lys Ser Lys Glu Asp Ser Ala Ala Ala Ala Thr
            290                 295                 300

Ala Ala Val Ala Thr Ala Ser Thr Glu Val Arg Gly Asp Asn Phe Ala
305                 310                 315                 320

Ser Ala Ala Thr Leu Ala Ala Ala Glu Ala Glu Thr Glu Ser Lys
                325                 330                 335

Ile Val Ile Gln Pro Val Glu Lys Asp Ser Lys Glu Arg Ser Tyr Asn
                340                 345                 350

Val Leu Ala Asp Lys Lys Asn Thr Ala Tyr Arg Ser Trp Tyr Leu Ala
            355                 360                 365

Tyr Asn Tyr Gly Asp Pro Glu Lys Gly Val Arg Ser Trp Thr Leu Leu
            370                 375                 380

Thr Thr Ser Asp Val Thr Cys Gly Val Glu Gln Val Tyr Trp Ser Leu
385                 390                 395                 400

Pro Asp Met Met Gln Asp Pro Val Thr Phe Arg Ser Thr Arg Gln Val
                405                 410                 415

Ser Asn Tyr Pro Val Val Gly Ala Glu Leu Leu Pro Val Tyr Ser Lys
                420                 425                 430

Ser Phe Phe Asn Glu Gln Ala Val Tyr Ser Gln Gln Leu Arg Ala Phe
                435                 440                 445

Thr Ser Leu Thr His Val Phe Asn Arg Phe Pro Glu Asn Gln Ile Leu
            450                 455                 460

Val Arg Pro Pro Ala Pro Thr Ile Thr Thr Val Ser Glu Asn Val Pro
465                 470                 475                 480

Ala Leu Thr Asp His Gly Thr Leu Pro Leu Arg Ser Ser Ile Arg Gly
                485                 490                 495

Val Gln Arg Val Thr Val Thr Asp Ala Arg Arg Thr Cys Pro Tyr
            500                 505                 510

Val Tyr Lys Ala Leu Gly Val Val Ala Pro Arg Val Leu Ser Ser Arg
            515                 520                 525

Thr Phe
```

<210> SEQ ID NO 3
<211> LENGTH: 933
<212> TYPE: PRT
<213> ORGANISM: chimpanzee adenovirus serotype Pan5

<400> SEQUENCE: 3

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Cys Gln Trp Thr Tyr Lys Ala Asp Gly Asp Thr Gly
    130                 135                 140

Thr Glu Lys Thr Tyr Thr Tyr Gly Asn Ala Pro Val Gln Gly Ile Ser
145                 150                 155                 160

Ile Thr Lys Asp Gly Ile Gln Leu Gly Thr Asp Thr Asp Gln Pro
                165                 170                 175

Ile Tyr Ala Asp Lys Thr Tyr Gln Pro Glu Pro Gln Val Gly Asp Ala
            180                 185                 190

Glu Trp His Asp Ile Thr Gly Thr Asp Glu Lys Tyr Gly Gly Arg Ala
        195                 200                 205

Leu Lys Pro Asp Thr Lys Met Lys Pro Cys Tyr Gly Ser Phe Ala Lys
    210                 215                 220

Pro Thr Asn Lys Glu Gly Gly Gln Ala Asn Val Lys Thr Glu Thr Gly
225                 230                 235                 240

Gly Thr Lys Glu Tyr Asp Ile Asp Met Ala Phe Phe Asp Asn Arg Ser
                245                 250                 255

Ala Ala Ala Ala Gly Leu Ala Pro Glu Ile Val Leu Tyr Thr Glu Asn
            260                 265                 270

Val Asp Leu Glu Thr Pro Asp Thr His Ile Val Tyr Lys Ala Gly Thr
        275                 280                 285

Asp Asp Ser Ser Ser Ser Ile Asn Leu Gly Gln Gln Ser Met Pro Asn
    290                 295                 300

Arg Pro Asn Tyr Ile Gly Phe Arg Asp Asn Phe Ile Gly Leu Met Tyr
305                 310                 315                 320

Tyr Asn Ser Thr Gly Asn Met Gly Val Leu Ala Gly Gln Ala Ser Gln
                325                 330                 335

Leu Asn Ala Val Val Asp Leu Gln Asp Arg Asn Thr Glu Leu Ser Tyr
            340                 345                 350

Gln Leu Leu Leu Asp Ser Leu Gly Asp Arg Thr Arg Tyr Phe Ser Met
        355                 360                 365

Trp Asn Gln Ala Val Asp Ser Tyr Asp Pro Asp Val Arg Ile Ile Glu

```
                370             375             380
Asn His Gly Val Glu Asp Glu Leu Pro Asn Tyr Cys Phe Pro Leu Asp
385                 390                 395                 400

Ala Val Gly Arg Thr Asp Thr Tyr Gln Gly Ile Lys Ala Asn Gly Ala
                405                 410                 415

Asp Gln Thr Thr Trp Thr Lys Asp Asp Thr Val Asn Asp Ala Asn Glu
                420                 425                 430

Leu Gly Lys Gly Asn Pro Phe Ala Met Glu Ile Asn Ile Gln Ala Asn
                435                 440                 445

Leu Trp Arg Asn Phe Leu Tyr Ala Asn Val Ala Leu Tyr Leu Pro Asp
450                 455                 460

Ser Tyr Lys Tyr Thr Pro Ala Asn Ile Thr Leu Pro Thr Asn Thr Asn
465                 470                 475                 480

Thr Tyr Asp Tyr Met Asn Gly Arg Val Val Ala Pro Ser Leu Val Asp
                485                 490                 495

Ala Tyr Ile Asn Ile Gly Ala Arg Trp Ser Leu Asp Pro Met Asp Asn
                500                 505                 510

Val Asn Pro Phe Asn His His Arg Asn Ala Gly Leu Arg Tyr Arg Ser
                515                 520                 525

Met Leu Leu Gly Asn Gly Arg Tyr Val Pro Phe His Ile Gln Val Pro
530                 535                 540

Gln Lys Phe Phe Ala Ile Lys Ser Leu Leu Leu Pro Gly Ser Tyr
545                 550                 555                 560

Thr Tyr Glu Trp Asn Phe Arg Lys Asp Val Asn Met Ile Leu Gln Ser
                565                 570                 575

Ser Leu Gly Asn Asp Leu Arg Thr Asp Gly Ala Ser Ile Ala Phe Thr
                580                 585                 590

Ser Ile Asn Leu Tyr Ala Thr Phe Phe Pro Met Ala His Asn Thr Ala
                595                 600                 605

Ser Thr Leu Glu Ala Met Leu Arg Asn Asp Thr Asn Asp Gln Ser Phe
610                 615                 620

Asn Asp Tyr Leu Ser Ala Ala Asn Met Leu Tyr Pro Ile Pro Ala Asn
625                 630                 635                 640

Ala Thr Asn Val Pro Ile Ser Ile Pro Ser Arg Asn Trp Ala Ala Phe
                645                 650                 655

Arg Gly Trp Ser Phe Thr Arg Leu Lys Thr Arg Glu Thr Pro Ser Leu
                660                 665                 670

Gly Ser Gly Phe Asp Pro Tyr Phe Val Tyr Ser Gly Ser Ile Pro Tyr
                675                 680                 685

Leu Asp Gly Thr Phe Tyr Leu Asn His Thr Phe Lys Lys Val Ser Ile
                690                 695                 700

Thr Phe Asp Ser Ser Val Ser Trp Pro Gly Asn Asp Arg Leu Leu Thr
705                 710                 715                 720

Pro Asn Glu Phe Glu Ile Lys Arg Thr Val Asp Gly Glu Gly Tyr Asn
                725                 730                 735

Val Ala Gln Cys Asn Met Thr Lys Asp Trp Phe Leu Val Gln Met Leu
                740                 745                 750

Ala His Tyr Asn Ile Gly Tyr Gln Gly Phe Tyr Val Pro Glu Gly Tyr
                755                 760                 765

Lys Asp Arg Met Tyr Ser Phe Phe Arg Asn Phe Gln Pro Met Ser Arg
                770                 775                 780

Gln Val Val Asp Glu Val Asn Tyr Lys Asp Tyr Gln Ala Val Thr Leu
785                 790                 795                 800
```

```
Ala Tyr Gln His Asn Asn Ser Gly Phe Val Gly Tyr Leu Ala Pro Thr
                805                 810                 815
Met Arg Gln Gly Gln Pro Tyr Pro Ala Asn Tyr Pro Tyr Leu Ile
            820                 825                 830
Gly Lys Ser Ala Val Ala Ser Val Thr Gln Lys Lys Phe Leu Cys Asp
            835                 840                 845
Arg Val Met Trp Arg Ile Pro Phe Ser Ser Asn Phe Met Ser Met Gly
        850                 855                 860
Ala Leu Thr Asp Leu Gly Gln Asn Met Leu Tyr Ala Asn Ser Ala His
865                 870                 875                 880
Ala Leu Asp Met Asn Phe Glu Val Asp Pro Met Asp Glu Ser Thr Leu
                885                 890                 895
Leu Tyr Val Val Phe Glu Val Phe Asp Val Val Arg Val His Gln Pro
                900                 905                 910
His Arg Gly Val Ile Glu Ala Val Tyr Leu Arg Thr Pro Phe Ser Ala
            915                 920                 925
Gly Asn Ala Thr Thr
            930

<210> SEQ ID NO 4
<211> LENGTH: 445
<212> TYPE: PRT
<213> ORGANISM: chimpanzee adenovirus serotype Pan5

<400> SEQUENCE: 4

Met Ser Lys Lys Arg Val Arg Val Asp Asp Phe Asp Pro Val Tyr
1               5                   10                  15
Pro Tyr Asp Ala Asp Asn Ala Pro Thr Val Pro Phe Ile Asn Pro Pro
            20                  25                  30
Phe Val Ser Ser Asp Gly Phe Gln Glu Lys Pro Leu Gly Val Leu Ser
        35                  40                  45
Leu Arg Leu Ala Asp Pro Val Thr Thr Lys Asn Gly Glu Ile Thr Leu
    50                  55                  60
Lys Leu Gly Asp Gly Val Asp Leu Asp Ser Ser Gly Lys Leu Ile Ser
65                  70                  75                  80
Asn Thr Ala Thr Lys Ala Ala Ala Pro Leu Ser Phe Ser Asn Asn Thr
                85                  90                  95
Ile Ser Leu Asn Met Asp Thr Pro Phe Tyr Asn Asn Asn Gly Lys Leu
            100                 105                 110
Gly Met Lys Val Thr Ala Pro Leu Lys Ile Leu Asp Thr Asp Leu Leu
        115                 120                 125
Lys Thr Leu Val Val Ala Tyr Gly Gln Gly Leu Gly Thr Asn Thr Thr
    130                 135                 140
Gly Ala Leu Val Ala Gln Leu Ala Ser Pro Leu Ala Phe Asp Ser Asn
145                 150                 155                 160
Ser Lys Ile Ala Leu Asn Leu Gly Asn Gly Pro Leu Lys Val Asp Ala
                165                 170                 175
Asn Arg Leu Asn Ile Asn Cys Asn Arg Gly Leu Tyr Val Thr Thr Thr
            180                 185                 190
Lys Asp Ala Leu Glu Ala Asn Ile Ser Trp Ala Asn Ala Met Thr Phe
        195                 200                 205
Ile Gly Asn Ala Met Gly Val Asn Ile Asp Thr Gln Lys Gly Leu Gln
    210                 215                 220
Phe Gly Thr Thr Ser Thr Val Ala Asp Val Lys Asn Ala Tyr Pro Ile
225                 230                 235                 240
```

-continued

```
Gln Ile Lys Leu Gly Ala Gly Leu Thr Phe Asp Ser Thr Gly Ala Ile
            245                 250                 255
Val Ala Trp Asn Lys Asp Asp Lys Leu Thr Leu Trp Thr Thr Ala
        260                 265                 270
Asp Pro Ser Pro Asn Cys His Ile Tyr Ser Glu Lys Asp Ala Lys Leu
    275                 280                 285
Thr Leu Cys Leu Thr Lys Cys Gly Ser Gln Ile Leu Gly Thr Val Ser
290                 295                 300
Leu Ile Ala Val Asp Thr Gly Ser Leu Asn Pro Ile Thr Gly Thr Val
305                 310                 315                 320
Thr Thr Ala Leu Val Ser Leu Lys Phe Asp Ala Asn Gly Val Leu Gln
                325                 330                 335
Ser Ser Ser Thr Leu Asp Ser Asp Tyr Trp Asn Phe Arg Gln Gly Asp
            340                 345                 350
Val Thr Pro Ala Glu Ala Tyr Thr Asn Ala Ile Gly Phe Met Pro Asn
        355                 360                 365
Leu Lys Ala Tyr Pro Lys Asn Thr Ser Gly Ala Ala Lys Ser His Ile
    370                 375                 380
Val Gly Lys Val Tyr Leu His Gly Asp Thr Gly Lys Pro Leu Asp Leu
385                 390                 395                 400
Ile Ile Thr Phe Asn Glu Thr Ser Asp Glu Ser Cys Thr Tyr Cys Ile
                405                 410                 415
Asn Phe Gln Trp Gln Trp Gly Ala Asp Gln Tyr Lys Asn Glu Thr Leu
            420                 425                 430
Ala Val Ser Ser Phe Thr Phe Ser Tyr Ile Ala Lys Glu
        435                 440                 445

<210> SEQ ID NO 5
<211> LENGTH: 36604
<212> TYPE: DNA
<213> ORGANISM: chimpanzee adenovirus serotype Pan6
<220> FEATURE:
<221> NAME/KEY: CDS
<222> LOCATION: (13878)..(15467)
<223> OTHER INFORMATION: L2 Penton
<220> FEATURE:
<221> NAME/KEY: CDS
<222> LOCATION: (18284)..(21112)
<223> OTHER INFORMATION: L3 Hexon
<220> FEATURE:
<221> NAME/KEY: CDS
<222> LOCATION: (32162)..(33493)
<223> OTHER INFORMATION: L5 Fiber

<400> SEQUENCE: 5
catcatcaat aatatacctc aaacttttgg tgcgcgttaa tatgcaaatg agctgtttga     60
atttggggag ggaggaaggt gattggctgc gggagcggcg accgttaggg gcggggcggg    120
tgacgttttg atgacgtggc tatgaggcgg agccggtttg caagttctcg tgggaaaagt    180
gacgtcaaac gaggtgtggt ttgaacacgg aaatactcaa ttttcccgcg ctctctgaca    240
ggaaatgagg tgtttctggg cggatgcaag tgaaaacggg ccattttcgc gcgaaaactg    300
aatgaggaag tgaaaatctg agtaatttcg cgtttatggc aggaggagt atttgccgag    360
ggccgagtag actttgaccg attacgtggg ggtttcgatt accgtatttt tcacctaaat    420
ttccgcgtac ggtgtcaaag tccggtgttt ttacgtaggc gtcagctgat cgccagggta    480
tttaaacctg cgctctctag tcaagaggcc actcttgagt gccagcgagt agagttttct    540
cctccgcgcc gcgagtcaga tctacacttt gaaagatgag gcacctgaga gacctgcccg    600
gtaatgtttt cctggctact gggaacgaga ttctggaatt ggtggtggac gccatgatgg    660
```

```
gtgacgaccc tccagagccc cctaccccat ttgaggcgcc ttcgctgtac gatttgtatg     720
atctggaggt ggatgtgccc gagagcgacc ctaacgagga ggcggtgaat gatttgttta     780
gcgatgccgc gctgctggct gccgagcagg ctaatacgga ctctggctca gacagcgatt     840
cctctctcca taccccgaga cccggcagag gtgagaaaaa gatccccgag cttaaagggg     900
aagagctcga cctgcgctgc tatgaggaat gcttgcctcc gagcgatgat gaggaggacg     960
aggaggcgat tcgagctgcg gtgaaccagg gagtgaaaac tgcgggcgag agctttagcc    1020
tggactgtcc tactctgccc ggacacggct gtaagtcttg tgaatttcat cgcatgaata    1080
ctggagataa gaatgtgatg tgtgccctgt gctatatgag agcttacaac cattgtgttt    1140
acagtaagtg tgattaactt tagttgggaa ggcagagggt gactgggtgc tgactggttt    1200
atttatgtat atgtttttt atgtgtaggt cccgtctctg acgtagatga gacccccact     1260
tcagagtgca tttcatcacc cccagaaatt ggcgaggaac cgcccgaaga tattattcat    1320
agaccagttg cagtgagagt caccgggcgg agagcagctg tggagagttt ggatgacttg    1380
ctacagggtg gggatgaacc tttggacttg tgtacccgga aacgcccag gcactaagtg     1440 ccacacatgt gtgtttactt aaggtgatgt cagtatttat agggtgtgga gtgcaataaa    1500
atccgtgttg actttaagtg cgtgttttat gactcagggg tggggactgt gggtatataa    1560
gcaggtgcag acctgtgtgg tcagttcaga gcaggactca tggagatctg gactgtcttg    1620
gaagactttc accagactag acagttgcta gagaactcat cggagggagt ctcttacctg    1680
tggagattct gcttcggtgg gcctctagct aagctagtct ataggccaa acaggattat     1740 aaggaacaat ttgaggatat tttgagagag tgtcctggta ttttttgactc tctcaacttg    1800 ggccatcagt ctcactttaa ccagagtatt ctgagagccc ttgactttc tactcctggc     1860 agaactaccg ccgcggtagc cttttttgcc tttattcttg acaaatggag tcaagaaacc    1920
catttcagca gggattaccg tctgactgc ttagcagtag cttgtgtggag aacatggagg    1980 tgccagcgcc tgaatgcaat ctccggctac ttgccagtac agccggtaga cacgctgagg    2040
atcctgagtc tccagtcacc ccaggaacac caacgccgcc agcagccgca gcaggagcag    2100
cagcaagagg aggaccgaga agagaacccg agagccggtc tggacccctcc ggtggcggag   2160 gaggaggagt agctgacttg tttcccgagc tgcgccgggt gctgactagg tcttccagtg    2220
gacgggagag ggggattaag cgggagaggc atgaggagac tagccacaga actgaactga    2280
ctgtcagtct gatgagccgc aggcgcccag aatcggtgtg gtggcatgag gtgcagtcgc    2340
aggggataga tgaggtctcg gtgatgcatg agaaatattc cctagaacaa gtcaagactt    2400
gttggttgga gcccgaggat gattgggagg tagccatcag gaattatgcc aagctggctc    2460
tgaagccaga caagaagtac aagattacca aactgattaa tatcagaaat tcctgctaca    2520
tttcagggaa tggggccgag gtggagatca gtacccagga gagggtggcc ttcagatgtt    2580
gtatgatgaa tatgtacccg ggggtggtgg gcatggaggg agtcaccttt atgaacacga    2640
ggttcagggg tgatgggtat aatggggtgg tctttatggc caacaccaag ctgacagtgc    2700
acggatgctc cttctttggc ttcaataaca tgtgcatcga ggcctggggc agtgtttcag    2760 tgagggatg cagcttttca gccaactgga tggggtcgt gggcagaacc aagagcaagg     2820
tgtcagtgaa gaaatgcctg ttcgagaggt gccacctggg ggtgatgagc gagggcgaag    2880
ccaaagtcaa acactgcgcc tctaccgaga cgggctgctt tgtgctgatc aagggcaatg    2940
cccaagtcaa gcataacatg atctgtgggg cctcggatga gcgcggctac cagatgctga    3000
cctgcgccgg tgggaacagc catatgctgg ccaccgtgca tgtggcctcg cacccccgca    3060
```

```
agacatggcc cgagttcgag cacaacgtca tgacccgctg caatgtgcac ctgggctccc    3120
gccgaggcat gttcatgccc taccagtgca acatgcaatt tgtgaaggtg ctgctggagc    3180
ccgatgccat gtccagagtg agcctgacgg gggtgtttga catgaatgtg gagctgtgga    3240
aaattctgag atatgatgaa tccaagacca ggtgccgggc ctgcgaatgc ggaggcaagc    3300
acgccaggct tcagcccgtg tgtgtggagg tgacggagga cctgcgaccc gatcatttgg    3360
tgttgtcctg caacgggacg gagttcggct ccagcgggga agaatctgac tagagtgagt    3420
agtgtttggg gctgggtgtg agcctgcatg aggggcagaa tgactaaaat ctgtggtttt    3480
ctgtgtgttg cagcagcatg agcggaagcg cctcctttga gggaggggta ttcagcccct    3540
atctgacggg gcgtctcccc tcctgggcgg gagtgcgtca gaatgtgatg gatccacgg    3600 tggacggccg gcccgtgcag cccgcgaact cttcaaccct gacctacgcg accctgagct    3660
cctcgtccgt ggacgcagct gccgccgcag ctgctgcttc cgccgccagc gccgtgcgcg    3720
gaatggccct gggcgccggc tactacagct ctctggtggc caactcgagt tccaccaata    3780
atcccgccag cctgaacgag agaagctgc tgctgctgat ggcccagctc gaggccctga    3840
cccagcgcct gggcgagctg acccagcagg tggctcagct gcaggcggag acgcgggccg    3900
cggttgccac ggtgaaaacc aaataaaaaa tgaatcaata aataaacgga gacggttgtt    3960
gattttaaca cagagtcttg aatctttatt tgattttcg cgcgcggtag gccctggacc    4020
accggtctcg atcattgagc accggtgga tcttttccag gacccggtag aggtgggctt    4080
ggatgttgag gtacatgggc atgagcccgt cccggggggtg gaggtagctc cattgcaggg    4140
cctcgtgctc ggggatggtg ttgtaaatca cccagtcata gcaggggcgc agggcgtggt    4200
gctgcacgat gtccttgagg aggagactga tggccacggg cagccccttg gtgtaggtgt    4260
tgacgaacct gttgagctgg gagggatgca tgcgggggga gatgagatgc atcttggcct    4320
ggatcttgag attggcgatg ttcccgccca gatcccgccg ggggttcatg ttgtgcagga    4380
ccaccagcac ggtgtatccg gtgcacttgg ggaatttgtc atgcaacttg aagggaagg    4440 cgtgaaagaa tttggagacg cccttgtgac cgcccaggtt ttccatgcac tcatccatga    4500
tgatggcgat gggcccgtgg gcggcggcct gggcaaagac gtttcggggg tcggacacat    4560
cgtagttgtg gtcctgggtg agctcgtcat aggccatttt aatgaatttg ggcggaggg    4620 tgcccgactg ggggacgaag gtgccctcga tcccggggc gtagttgccc tcgcagatct    4680
gcatctccca ggccttgagc tcggaggggg ggatcatgtc cacctgcggg gcgatgaaaa    4740
aaacggtttc cggggcgggg gagatgagct gggccgaaag caggttccgg agcagctggg    4800
acttgccgca accggtgggg ccgtagatga ccccgatgac cggctgcagg tggtagttga    4860
gggagagaca gctgccgtcc tcgcggagga gggggggccac ctcgttcatc atctcgcgca    4920
catgcatgtt ctcgcgcacg agttccgcca ggaggcgctc gcccccagc gagaggagct    4980 cttgcagcga ggcgaagttt ttcagcggct tgagtccgtc ggccatgggc attttggaga    5040
gggtctgttg caagagttcc agacggtccc agagctcggt gatgtgctct agggcatctc    5100
gatccagcag acctcctcgt ttcgcgggtt ggggcgactg cgggagtagg gcaccaggcg    5160
atgggcgtcc agcgaggcca gggtccggtc cttccagggc cgcagggtcc gcgtcagcgt    5220
ggtctccgtc acggtgaagg ggtgcgcgcc gggctgggcg cttgcgaggg tgcgcttcag    5280
gctcatccgg ctggtcgaga accgctcccg gtcggcgccc tgcgcgtcgg ccaggtagca    5340
attgagcatg agttcgtagt tgagcgcctc ggccgcgtgg cccttggcgc ggagcttacc    5400
tttggaagtg tgtccgcaga cgggacagag gagggacttg agggcgtaga gcttgggggc    5460
```

```
gaggaagacg gactcggggg cgtaggcgtc cgcgccgcag ctggcgcaga cggtctcgca   5520
ctccacgagc caggtgaggt cggggcggtt ggggtcaaaa acgaggtttc ctccgtgctt   5580
tttgatgcgt ttcttacctc tggtctccat gagctcgtgt ccccgctggg tgacaaagag   5640
gctgtccgtg tccccgtaga ccgactttat gggccggtcc tcgagcgggg tgccgcggtc   5700
ctcgtcgtag aggaaccccg cccactccga gacgaaggcc cgggtccagg ccagcacgaa   5760
ggaggccacg tgggaggggt agcggtcgtt gtccaccagc gggtccacct tctccagggt   5820
atgcaagcac atgtcccccct cgtccacatc caggaaggtg attggcttgt aagtgtaggc   5880
cacgtgaccg ggggtcccgg ccggggggt ataaaagggg gcgggcccct gctcgtcctc     5940
actgtcttcc ggatcgctgt ccaggagcgc cagctgttgg ggtaggtatt ccctctcgaa   6000
ggcgggcatg acctcggcac tcaggttgtc agtttctaga aacgaggagg atttgatatt   6060
gacggtgccg ttggagacgc ctttcatgag cccctcgtcc atttggtcag aaaagacgat   6120 cttttttgttg tcgagcttgg tggcgaagga gccgtagagg gcgttggaga gcagcttggc   6180
gatggagcgc atggtctggt tcttttcctt gtcggcgcgc tccttggcgg cgatgttgag   6240
ctgcacgtac tcgcgcgcca cgcacttcca ttcggggaag acggtggtga gctcgtcggg   6300
cacgattctg acccgccagc cgcggttgtg caggggtgatg aggtccacgc tggtggccac   6360
ctcgccgcgc aggggctcgt tggtccagca gaggcgcccg cccttgcgcg agcagaaggg   6420
gggcagcggg tccagcatga gctcgtcggg ggggtcggcg tccacggtga agatgccggg   6480
caggagctcg gggtcgaagt agctgatgca ggtgccagat tgtccagcg ccgcttgcca    6540 gtcgcgcacg gccagcgcgc gctcgtaggg gctgaggggc gtgccccagg gcatggggtg   6600
cgtgagcgcg gaggcgtaca tgccgcagat gtcgtagacg tagaggggct cctcgaggac   6660
gccgatgtag gtggggtagc agcgcccccc gcggatgctg gcgcgcacgt agtcgtacag   6720
ctcgtgcgag ggcgcgagga gccccgtgcc gaggttggag cgttgcggct tttcggcgcg   6780
gtagacgatc tggcggaaga tggcgtggga gttggaggag atggtgggcc tttggaagat   6840
gttgaagtgg gcgtggggca ggccgaccga gtccctgatg aagtgggcgt aggagtcctg   6900
cagcttggcg acgagctcgg cggtgacgag gacgtccagg gcgcagtagt cgagggtctc   6960
ttggatgatg tcatacttga gctggcccctt ctgcttccac agctcgcggt tgagaaggaa  7020
ctcttcgcgg tccttccagt actcttcgag ggggaacccg tcctgatcgg cacggtaaga   7080
gcccaccatg tagaactggt tgacggcctt gtaggcgcag cagcccttct ccacggggag   7140
ggcgtaagct tgcgcggcct tgcgcaggga ggtgtgggtg agggcgaagg tgtcgcgcac   7200
catgaccttg aggaactggt gcttgaagtc gaggtcgtcg cagccgccct gctcccagag   7260
ttggaagtcc gtgcgcttct tgtaggcggg gttaggcaaa gcgaaagtaa catcgttgaa   7320
gaggatcttg cccgcgcggg gcatgaagtt gcgagtgatg cggaaaggct ggggcacctc   7380
ggcccggttg ttgatgacct gggcggcgag gacgatctcg tcgaagccgt tgatgttgtg   7440
cccgacgatg tagagttcca cgaatcgcgc gcggcccttg acgtgggcga gcttcttgag   7500
ctcgtcgtag gtgagctcgg cggggtcgct gagcccgtgc tgctcgaggg cccagtcggc   7560
gacgtggggg ttggcgctga ggaaggaagt ccagagatcc acggccaggg cggtctgcaa   7620
gcggtcccgg tactgacgga actgttggcc cacggccatt ttttcggggg tgacgcagta   7680
gaaggtgcgg gggtcgccgt gccagcggtc ccacttgagc tggagggcga ggtcgtgggc   7740
gagctcgacg agcggcgggt ccccggagag tttcatgacc agcatgaagg ggacgagctg   7800
cttgccgaag gaccccatcc aggtgtaggt ttccacatcg taggtgagga agagcctttc   7860
```

```
ggtgcgagga tgcgagccga tggggaagaa ctggatctcc tgccaccagt tggaggaatg   7920
gctgttgatg tgatggaagt agaaatgccg acggcgcgcc gagcactcgt gcttgtgttt   7980
atacaagcgt ccgcagtgct cgcaacgctg cacgggatgc acgtgctgca cgagctgtac   8040
ctgggttcct ttggcgagga atttcagtgg gcagtggagc gctggcggct gcatctcgtg   8100
ctgtactacg tcttggccat cggcgtggcc atcgtctgcc tcgatggtgg tcatgctgac   8160
gagcccgcgc gggaggcagg tccagacctc ggctcggacg ggtcggagag cgaggacgag   8220
ggcgcgcagg ccggagctgt ccagggtcct gagacgctgc ggagtcaggt cagtgggcag   8280
cggcggcgcg cggttgactt gcaggagctt ttccagggcg cgcgggaggt ccagatggta   8340
cttgatctcc acggcgccgt tggtggctac gtccacggct gcagggtgc cgtgcccctg    8400 gggcgccacc accgtgcccc gtttcttctt gggcgctgct ccatgtcgg tcagaagcgg    8460 cggcgaggac gcgcgccggg cggcaggggc ggctcggggc ccggaggcag gggcggcagg   8520
ggcacgtcgg cgccgcgcgc gggcaggttc tggtactgcg cccggagaag actggcgtga   8580
gcgacgacgc gacggttgac gtcctggatc tgacgcctct gggtgaaggc cacgggaccc   8640
gtgagtttga acctgaaaga gagttcgaca gaatcaatct cggtatcgtt gacggcggcc   8700
tgccgcagga tctcttgcac gtcgcccgag ttgtcctggt aggcgatctc ggtcatgaac   8760
tgctcgatct cctcctcctg aaggtctccg cggccgcgc gctcgacggt ggccgcgagg   8820
tcgttggaga tgcggcccat gagctgcgag aaggcgttca tgccggcctc gttccagacg   8880
cggctgtaga ccacggctcc gtcggggtcg cgcgcgcgca tgaccacctg ggcgaggttg   8940
agctcgacgt ggcgcgtgaa gaccgcgtag ttgcagaggc gctggtagag gtagttgagc   9000
gtggtggcga tgtgctcggt gacgaagaag tacatgatcc agcggcggag cggcatctcg   9060
ctgacgtcgc ccagggcttc caagcgttcc atggcctcgt agaagtccac ggcgaagttg   9120
aaaaactggg agttgcgcgc cgagacggtc aactcctcct ccagaagacg gatgagctcg   9180
gcgatggtgg cgcgcacctc gcgctcgaag gccccggggg gctcctcttc catctcctcc   9240
tcttcctcct ccactaacat ctcttctact tcctcctcag gaggcggtgg cggggaggg    9300 gccctgcgtc gccggcggcg cacgggcaga cggtcgatga agcgctcgat ggtctccccg   9360
cgccggcgac gcatggtctc ggtgacggcg cgccgtcct cgcggggccg cagcatgaag    9420
acgccgccgc gcatctccag gtggccgccg gggggtctc cgttgggcag ggagagggcg    9480
ctgacgatga tcttatcaa ttgacccgta gggactccgc gcaaggacct gagcgtctcg    9540
agatccacgg gatccgaaaa ccgctgaacg aaggcttcga gccagtcgca gtcgcaaggt   9600
aggctgagcc cggtttcttg ttcttcgggt atttggtcgg gaggcgggcg ggcgatgctg   9660
ctggtgatga agttgaagta ggcggtcctg agacggcgga tggtggcgag gagcaccagg   9720
tccttgggcc cggcttgctg gatgcgcaga cggtcggcca tgcccaggc gtggtcctga    9780 cacctggcga ggtccttgta gtagtcctgc atgagccgct ccacgggcac ctcctcctcg   9840
cccgcgcggc cgtgcatgcg cgtgagcccg aacccgcgct gcggctggac gagcgccagg   9900
tcggcgacga cgcgctcggt gaggatggcc tgctggatct gggtgagggt ggtctggaag   9960
tcgtcgaagt cgacgaagcg gtggtaggct ccggtgttga tggtgtagga gcagttggcc  10020
atgacggacc agttgacggt ctggtggccg ggtcgcacga gctcgtggta cttgaggcgc  10080
gagtaggcgc gcgtgtcgaa gatgtagtcg ttgcaggcgc gcacgaggta ctggtatccg  10140
acgaggaagt gcggcggcgg ctggcggtag agcggccatc gctcggtggc gggggcgccg  10200
ggcgcgaggt cctcgagcat gaggcggtgg tagccgtaga tgtacctgga catccaggtg  10260
```

```
atgccggcgg cggtggtgga ggcgcgcggg aactcgcgga cgcggttcca gatgttgcgc   10320
agcggcagga agtagttcat ggtggccgcg gtctggcccg tgaggcgcgc gcagtcgtgg   10380
atgctctaga catacgggca aaaacgaaag cggtcagcgg ctcgactccg tggcctggag   10440
gctaagcgaa cgggttgggc tgcgcgtgta ccccggttcg aatctcgaat caggctggag   10500
ccgcagctaa cgtggtactg gcactcccgt ctcgacccaa gcctgctaac gaaacctcca   10560
ggatacggag gcgggtcgtt ttttggcctt ggtcgctggt catgaaaaac tagtaagcgc   10620
ggaaagcggc cgcccgcgat ggctcgctgc cgtagtctgg agaaagaatc gccagggttg   10680
cgttgcggtg tgccccggtt cgagcctcag cgctcggcgc cggccggatt ccgcggctaa   10740
cgtgggcgtg gctgccccgt cgtttccaag accccttagc cagccgactt ctccagttac   10800
ggagcgagcc cctcttttt tttcttgtgt ttttgccaga tgcatcccgt actgcggcag   10860
atgcgccccc accctccacc acaaccgccc ctaccgcagc agcagcaaca gccggcgctt   10920
ctgccccgc cccagcagca gccagccact accgcggcgg ccgccgtgag cggagccggc   10980
gttcagtatg acctggcctt ggaagagggc gaggggctgg cgcggctggg ggcgtcgtcg   11040
ccggagcgg acccgcgcgt gcagatgaaa agggacgctc gcgaggccta cgtgcccaag   11100
cagaacctgt tcagagacag gagcggcgag gagcccgagg agatgcgcgc ctcccgcttc   11160
cacgcggggc gggagctgcg gcgcggcctg gaccgaaagc gggtgctgag ggacgaggat   11220
ttcgaggcgg acgagctgac ggggatcagc cccgcgcgcg cgcacgtggc cgcggccaac   11280
ctggtcacgg cgtacgagca gaccgtgaag gaggagagca acttccaaaa atccttcaac   11340
aaccacgtgc gcacgctgat cgcgcgcgag gaggtgaccc tgggcctgat gcacctgtgg   11400
gacctgctgg aggccatcgt gcagaacccc acgagcaagc cgctgacggc gcagctgttt   11460
ctggtggtgc agcacagtcg ggacaacgag acgttcaggg aggcgctgct gaatatcacc   11520
gagcccgagg gccgctggct cctggacctg gtgaacattt gcagagcat cgtggtgcag   11580
gagcgcgggc tgccgctgtc cgagaagctg gcggccatca acttctcggt gctgagtctg   11640
ggcaagtact acgctaggaa gatctacaag accccgtacg tgcccataga caaggaggtg   11700
aagatcgacg ggttttacat gcgcatgacc ctgaaagtgc tgaccctgag cgacgatctg   11760
ggggtgtacc gcaacgacag gatgcaccgc gcggtgagcg ccagccgccg gcgcgagctg   11820
agcgaccagg agctgatgca cagcctgcag cgggccctga ccggggccgg gaccgagggg   11880
gagagctact ttgacatggg cgcggacctg cgctggcagc ccagccgccg ggccttggaa   11940
gctgccggcg gttcccccta cgtggaggag gtggacgatg aggaggagga gggcgagtac   12000
ctggaagact gatggcgcga ccgtattttt gctagatgca gcaacagcca ccgccgccgc   12060
ctcctgatcc cgcgatgcgg gcggcgctgc agagccagcc gtccggcatt aactcctcgg   12120
acgattggac ccaggccatg caacgcatca tggcgctgac gacccgcaat cccgaagcct   12180
ttagacagca gcctcaggcc aaccggctct cggccatcct ggaggccgtg gtgccctcgc   12240
gctcgaaccc cacgcacgag aaggtgctgg ccatcgtgaa cgcgctggtg gagaacaagg   12300
ccatccgcgg tgacgaggcc gggctggtgt acaacgcgct gctggagcgc gtggcccgct   12360
acaacagcac caacgtgcag acgaacctgg accgcatggt gaccgacgtg cgcgaggcgg   12420
tgtcgcagcg cgagcggttc cacggcgagt cgaacctggg ctccatggtg gcgctgaacg   12480
ccttcctgag cacgcagccc gccaacgtgc ccgggggcca ggaggactac accaacttca   12540
tcagcgcgct gcggctgatg gtggccgagg tgccccagag cgaggtgtac cagtcggggc   12600
cggactactt cttccagacc agtcgccagg gcttgcagac cgtgaacctg agccaggctt   12660
```

```
tcaagaactt gcagggactg tggggcgtgc aggccccggt cggggaccgc gcgacggtgt   12720
cgagcctgct gacgccgaac tcgcgcctgc tgctgctgct ggtggcgccc ttcacggaca   12780
gcggcagcgt gagccgcgac tcgtacctgg gctacctgct taacctgtac cgcgaggcca   12840
tcggacaggc gcacgtggac gagcagacct accaggagat cacccacgtg agccgcgcgc   12900
tgggccagga ggacccgggc aacctggagg ccaccctgaa cttcctgctg accaaccggt   12960
cgcagaagat cccgcccag tacgcgctga gcaccgagga ggagcgcatc ctgcgctacg   13020
tgcagcagag cgtggggctg ttcctgatgc aggaggggc cacgcccagc gcggcgctcg   13080
acatgaccgc gcgcaacatg gagcccagca tgtacgcccg caaccgcccg ttcatcaata   13140
agctgatgga ctacttgcat cgggcggccg ccatgaactc ggactacttt accaacgcca   13200
tcttgaaccc gcactggctc ccgccgcccg ggttctacac gggcgagtac gacatgcccg   13260
accccaacga cgggttcctg tgggacgacg tggacagcag cgtgttctcg ccgcgtccag   13320
gaaccaatgc cgtgtggaag aaagagggcg gggaccggcg gccgtcctcg gcgctgtccg   13380
gtcgcgcggg tgctgccgcg gcggtgcccg aggccgccag ccccttcccg agcctgccct   13440
tttcgctgaa cagcgtgcgc agcagcgagc tgggtcggct gacgcgaccg cgcctgctgg   13500
gcgaggagga gtacctgaac gactccttgt tgaggcccga gcgcgagaag aacttcccca   13560
ataacgggat agagagcctg gtggacaaga tgagccgctg gaagacgtac gcgcacgagc   13620
acagggacga gccccgagct agcagcgcag gcacccgtag acgccagcgg cacgacaggc   13680
agcggggact ggtgtgggac gatgaggatt ccgccgacga cagcagcgtg ttggacttgg   13740
gtgggagtgg tggtaacccg ttcgctcacc tgcgcccccg tatcgggcgc ctgatgtaag   13800
aatctgaaaa aataaaagac ggtactcacc aaggccatgg cgaccagcgt gcgttcttct   13860
ctgttgtttg tagtagt atg atg agg cgc gtg tac ccg gag ggt cct cct      13910
                   Met Met Arg Arg Val Tyr Pro Glu Gly Pro Pro
                    1               5                  10 ccc tcg tac gag agc gtg atg cag cag gcg gtg gcg gcg gcg atg cag     13958
Pro Ser Tyr Glu Ser Val Met Gln Gln Ala Val Ala Ala Ala Met Gln
         15                  20                  25 ccc ccg ctg gag gcg cct tac gtg ccc ccg cgg tac ctg gcg cct acg     14006
Pro Pro Leu Glu Ala Pro Tyr Val Pro Pro Arg Tyr Leu Ala Pro Thr
    30                  35                  40 gag ggg cgg aac agc att cgt tac tcg gag ctg gca ccc ttg tac gat     14054
Glu Gly Arg Asn Ser Ile Arg Tyr Ser Glu Leu Ala Pro Leu Tyr Asp
45                  50                  55 acc acc cgg ttg tac ctg gtg gac aac aag tcg gca gac atc gcc tcg     14102
Thr Thr Arg Leu Tyr Leu Val Asp Asn Lys Ser Ala Asp Ile Ala Ser
60                  65                  70                  75 ctg aac tac cag aac gac cac agc aac ttc ctg acc acc gtg gtg cag     14150
Leu Asn Tyr Gln Asn Asp His Ser Asn Phe Leu Thr Thr Val Val Gln
         80                  85                  90 aac aac gat ttc acc ccc acg gag gcc agc acc cag acc atc aac ttt     14198
Asn Asn Asp Phe Thr Pro Thr Glu Ala Ser Thr Gln Thr Ile Asn Phe
             95                 100                 105 gac gag cgc tcg cgg tgg ggc ggc cag ctg aaa acc atc atg cac acc     14246
Asp Glu Arg Ser Arg Trp Gly Gly Gln Leu Lys Thr Ile Met His Thr
       110                 115                 120 aac atg ccc aac gtg aac gag ttc atg tac agc aac aag ttc aag gcg    14294
Asn Met Pro Asn Val Asn Glu Phe Met Tyr Ser Asn Lys Phe Lys Ala
   125                 130                 135 cgg gtg atg gtc tcg cgc aag acc ccc aac ggg gtg gat gat gat tat    14342
Arg Val Met Val Ser Arg Lys Thr Pro Asn Gly Val Asp Asp Asp Tyr
140                 145                 150                 155
```

| | |
|---|---|
| gat ggt agt cag gac gag ctg acc tac gag tgg gtg gag ttt gag ctg<br>Asp Gly Ser Gln Asp Glu Leu Thr Tyr Glu Trp Val Glu Phe Glu Leu<br>160                          165                    170 | 14390 |
| ccc gag ggc aac ttc tcg gtg acc atg acc atc gat ctg atg aac aac<br>Pro Glu Gly Asn Phe Ser Val Thr Met Thr Ile Asp Leu Met Asn Asn<br>          175                        180                    185 | 14438 |
| gcc atc atc gac aac tac ttg gcg gtg ggg cgg cag aac ggg gtg ctg<br>Ala Ile Ile Asp Asn Tyr Leu Ala Val Gly Arg Gln Asn Gly Val Leu<br>               190                    195                    200 | 14486 |
| gag agc gac atc ggc gtg aag ttc gac acg cgc aac ttc cgg ctg ggc<br>Glu Ser Asp Ile Gly Val Lys Phe Asp Thr Arg Asn Phe Arg Leu Gly<br>205                          210                    215 | 14534 |
| tgg gac ccc gtg acc gag ctg gtg atg ccg ggc gtg tac acc aac gag<br>Trp Asp Pro Val Thr Glu Leu Val Met Pro Gly Val Tyr Thr Asn Glu<br>220                          225                    230                    235 | 14582 |
| gcc ttc cac ccc gac atc gtg ctg ctg ccc ggc tgc ggc gtg gac ttc<br>Ala Phe His Pro Asp Ile Val Leu Leu Pro Gly Cys Gly Val Asp Phe<br>                     240                    245                    250 | 14630 |
| acc gag agc cgc ctc agc aac ctg ctg ggc atc cgc aag cgg cag ccc<br>Thr Glu Ser Arg Leu Ser Asn Leu Leu Gly Ile Arg Lys Arg Gln Pro<br>          255                        260                    265 | 14678 |
| ttc cag gag ggc ttc cag atc ctg tac gag gac ctg gag ggg ggc aac<br>Phe Gln Glu Gly Phe Gln Ile Leu Tyr Glu Asp Leu Glu Gly Gly Asn<br>               270                    275                    280 | 14726 |
| atc ccc gcg ctc ttg gat gtc gaa gcc tac gag aaa agc aag gag gat<br>Ile Pro Ala Leu Leu Asp Val Glu Ala Tyr Glu Lys Ser Lys Glu Asp<br>285                          290                    295 | 14774 |
| agc acc gcc gcg gcg acc gca gcc gtg gcc acc gcc tct acc gag gtg<br>Ser Thr Ala Ala Ala Thr Ala Ala Val Ala Thr Ala Ser Thr Glu Val<br>300                          305                    310                    315 | 14822 |
| cgg ggc gat aat ttt gct agc gct gcg gca gcg gcc gag gcg gct gaa<br>Arg Gly Asp Asn Phe Ala Ser Ala Ala Ala Ala Glu Ala Ala Glu<br>               320                    325                    330 | 14870 |
| acc gaa agt aag ata gtc atc cag ccg gtg gag aag gac agc aag gac<br>Thr Glu Ser Lys Ile Val Ile Gln Pro Val Glu Lys Asp Ser Lys Asp<br>          335                        340                    345 | 14918 |
| agg agc tac aac gtg ctc gcg gac aag aaa aac acc gcc tac cgc agc<br>Arg Ser Tyr Asn Val Leu Ala Asp Lys Lys Asn Thr Ala Tyr Arg Ser<br>               350                    355                    360 | 14966 |
| tgg tac ctg gcc tac aac tac ggc gac ccc gag aag ggc gtg cgc tcc<br>Trp Tyr Leu Ala Tyr Asn Tyr Gly Asp Pro Glu Lys Gly Val Arg Ser<br>365                          370                    375 | 15014 |
| tgg acg ctg ctc acc acc tcg gac gtc acc tgc ggc gtg gag caa gtc<br>Trp Thr Leu Leu Thr Thr Ser Asp Val Thr Cys Gly Val Glu Gln Val<br>380                          385                    390                    395 | 15062 |
| tac tgg tcg ctg ccc gac atg atg caa gac ccg gtc acc ttc cgc tcc<br>Tyr Trp Ser Leu Pro Asp Met Met Gln Asp Pro Val Thr Phe Arg Ser<br>               400                    405                    410 | 15110 |
| acg cgt caa gtt agc aac tac ccg gtg gtg ggc gcc gag ctc ctg ccc<br>Thr Arg Gln Val Ser Asn Tyr Pro Val Val Gly Ala Glu Leu Leu Pro<br>               415                    420                    425 | 15158 |
| gtc tac tcc aag agc ttc ttc aac gag cag gcc gtc tac tcg cag cag<br>Val Tyr Ser Lys Ser Phe Phe Asn Glu Gln Ala Val Tyr Ser Gln Gln<br>          430                        435                    440 | 15206 |
| ctg cgc gcc ttc acc tcg ctc acg cac gtc ttc aac cgc ttc ccc gag<br>Leu Arg Ala Phe Thr Ser Leu Thr His Val Phe Asn Arg Phe Pro Glu<br>445                          450                    455 | 15254 |
| aac cag atc ctc gtc cgc ccg ccc gcg ccc acc att acc acc gtc agt<br>Asn Gln Ile Leu Val Arg Pro Pro Ala Pro Thr Ile Thr Thr Val Ser<br>460                          465                    470                    475 | 15302 |

```
gaa aac gtt cct gct ctc aca gat cac ggg acc ctg ccg ctg cgc agc     15350
Glu Asn Val Pro Ala Leu Thr Asp His Gly Thr Leu Pro Leu Arg Ser
            480                 485                 490 agt atc cgg gga gtc cag cgc gtg acc gtc act gac gcc aga cgc cgc     15398
Ser Ile Arg Gly Val Gln Arg Val Thr Val Thr Asp Ala Arg Arg Arg
        495                 500                 505 acc tgc ccc tac gtc tac aag gcc ctg ggc gta gtc gcg ccg cgc gtc     15446
Thr Cys Pro Tyr Val Tyr Lys Ala Leu Gly Val Val Ala Pro Arg Val
        510                 515                 520 ctc tcg agc cgc acc ttc taa aaaatgtcca ttctcatctc gcccagtaat        15497
Leu Ser Ser Arg Thr Phe
    525 aacaccggtt ggggcctgcg cgcgcccagc aagatgtacg gaggcgctcg ccaacgctcc   15557
acgcaacacc ccgtgcgcgt gcgcgggcac ttccgcgctc cctggggcgc cctcaagggc   15617
cgcgtgcgct cgcgcaccac cgtcgacgac gtgatcgacc aggtggtggc cgacgcgcgc   15677
aactacacgc ccgccgccgc gcccgtctcc accgtggacg ccgtcatcga cagcgtggtg   15737
gccgacgcgc gccggtacgc ccgcaccaag agccggcggc ggcgcatcgc ccggcggcac   15797
cggagcaccc ccgccatgcg cgcggcgcga gccttgctgc gcagggccag cgcacgggga   15857
cgcagggcca tgctcagggc ggccagacgc gcggcctccg gcagcagcag cgccggcagg   15917
acccgcagac gcgcggccac ggccgcggcg cggccatcg ccagcatgtc ccgcccgcgg    15977
cgcggcaacg tgtactgggt gcgcgacgcc gccaccggtg tgcgcgtgcc cgtgcgcacc   16037
cgccccctc gcacttgaag atgctgactt cgcgatgttg atgtgtccca gcggcgagga    16097
ggatgtccaa gcgcaaatac aaggaagaga tgctccaggt catcgcgcct gagatctacg   16157
gccccgcggc ggcggtgaag gaggaaagaa agccccgcaa actgaagcgg gtcaaaaagg   16217
acaaaaagga ggaggaagat gacggactgg tggagtttgt gcgcgagttc gcccccccgc   16277
ggcgcgtgca gtggcgcggg cggaaagtga accggtgct gcggcccggc accacggtgg    16337
tcttcacgcc cggcgagcgt tccggctccg cctccaagcg ctcctacgac gaggtgtacg   16397
gggacgagga catcctcgag caggcggtcg agcgtctggg cgagtttgcg tacgcaagc    16457
gcagccgccc cgcgcccttg aaagaggagg cggtgtccat cccgctggac cacggcaacc   16517
ccacgccgag cctgaagccg gtgaccctgc agcaggtgct accgagcgcg gcgccgcgcc   16577
ggggcttcaa gcgcgagggc ggcgaggatc tgtacccgac catgcagctg atggtgccca   16637
agcgccagaa gctggaggac gtgctggagc acatgaaggt ggaccccgag gtgcagcccg   16697
aggtcaaggt gcggcccatc aagcaggtgg ccccgggcct gggcgtgcag accgtggaca   16757
tcaagatccc cacggagccc atggaaacgc agaccgagcc cgtgaagccc agcaccagca   16817
ccatggaggt gcagacggat ccctggatgc cagcaccagc ttccaccagc actcgccgaa   16877
gacgcaagta cggcgcggcc agcctgctga tgcccaacta cgcgctgcat ccttccatca   16937
tccccacgcc gggctaccgc ggcacgcgct tctaccgcgg ctacaccagc agccgccgcc   16997
gcaagaccac cacccgccgc cgtcgtcgca gccgccgcag cagcaccgcg acttccgcct   17057
tggtgcggag agtgtatcgc agcgggcgcg agcctctgac cctgccgcgc gcgcgctacc   17117
acccgagcat cgccatttaa ctaccgcctc ctacttgcag atatggccct cacatgccgc   17177
ctccgcgtcc ccattacggg ctaccgagga agaaagccgc gccgtagaag gctgacgggg   17237
aacgggctgc gtcgccatca ccaccggcg cggcgcgcca tcagcaagcg gttgggggga   17297
ggcttcctgc ccgcgctgat ccccatcatc gccgcggcga tcggggcgat ccccggcata   17357
gcttccgtgg cggtgcaggc ctctcagcgc cactgagaca caaaaaagca tggatttgta   17417
```

```
ataaaaaaaa aaatggactg acgctcctgg tcctgtgatg tgtgttttta gatggaagac    17477
atcaattttt cgtccctggc accgcgacac ggcacgcggc cgtttatggg cacctggagc    17537
gacatcggca acagccaact gaacgggggc gccttcaatt ggagcagtct ctggagcggg    17597
cttaagaatt tcgggtccac gctcaaaacc tatggcaaca aggcgtggaa cagcagcaca    17657
gggcaggcgc tgagggaaaa gctgaaagaa cagaacttcc agcagaaggt ggttgatggc    17717
ctggcctcag gcatcaacgg ggtggttgac ctggccaacc aggccgtgca gaaacagatc    17777
aacagccgcc tggacgcggt cccgcccgcg gggtccgtgg agatgcccca ggtggaggag    17837
gagctgcctc ccctggacaa gcgcgcgac aagcgaccgc gtcccgacgc ggaggagacg    17897
ctgctgacgc acacggacga gccgcccccg tacgaggagg cggtgaaact gggcctgccc    17957
accacgcggc ccgtggcgcc tctggccacc ggagtgctga aacccagcag cagccagccc    18017
gcgaccctgg acttgcctcc gcctcgcccc tccacagtgg ctaagcccct gccgccggtg    18077
gccgtcgcgt cgcgcgcccc ccgaggccgc ccccaggcga actggcagag cactctgaac    18137
agcatcgtgg gtctgggagt gcagagtgtg aagcgccgcc gctgctatta aaagacactg    18197
tagcgcttaa cttgcttgtc tgtgtgtata tgtatgtccg ccgaccagaa ggaggagtgt    18257
gaagaggcgc gtcgccgagt tgcaag atg gcc acc cca tcg atg ctg ccc cag    18310
                              Met Ala Thr Pro Ser Met Leu Pro Gln
                                  530             535 tgg gcg tac atg cac atc gcc gga cag gac gct tcg gag tac ctg agt    18358
Trp Ala Tyr Met His Ile Ala Gly Gln Asp Ala Ser Glu Tyr Leu Ser
    540             545                 550 ccg ggt ctg gtg cag ttc gcc cgc gcc aca gac acc tac ttc agt ctg    18406
Pro Gly Leu Val Gln Phe Ala Arg Ala Thr Asp Thr Tyr Phe Ser Leu
555             560                 565                 570 ggg aac aag ttt agg aac ccc acg gtg gcg ccc acg cac gat gtg acc    18454
Gly Asn Lys Phe Arg Asn Pro Thr Val Ala Pro Thr His Asp Val Thr
                575                 580                 585 acc gac cgc agc cag cgg ctg acg ctg cgc ttc gtg ccc gtg gac cgc    18502
Thr Asp Arg Ser Gln Arg Leu Thr Leu Arg Phe Val Pro Val Asp Arg
            590                 595                 600 gag gac aac acc tac tcg tac aaa gtg cgc tac acg ctg gcc gtg ggc    18550
Glu Asp Asn Thr Tyr Ser Tyr Lys Val Arg Tyr Thr Leu Ala Val Gly
        605                 610                 615 gac aac cgc gtg ctg gac atg gcc agc acc tac ttt gac atc cgc ggc    18598
Asp Asn Arg Val Leu Asp Met Ala Ser Thr Tyr Phe Asp Ile Arg Gly
    620                 625                 630 gtg ctg gac cgg ggc cct agc ttc aaa ccc tac tct ggc acc gcc tac    18646
Val Leu Asp Arg Gly Pro Ser Phe Lys Pro Tyr Ser Gly Thr Ala Tyr
635             640                 645                 650 aac agc cta gct ccc aag gga gct ccc aat tcc agc cag tgg gag caa    18694
Asn Ser Leu Ala Pro Lys Gly Ala Pro Asn Ser Ser Gln Trp Glu Gln
                655                 660                 665 gca aaa aca ggc aat ggg gga act atg gaa aca cac aca tat ggt gtg    18742
Ala Lys Thr Gly Asn Gly Gly Thr Met Glu Thr His Thr Tyr Gly Val
            670                 675                 680 gcc cca atg ggc gga gag aat att aca aaa gat ggt ctt caa att gga    18790
Ala Pro Met Gly Gly Glu Asn Ile Thr Lys Asp Gly Leu Gln Ile Gly
        685                 690                 695 act gac gtt aca gcg aat cag aat aaa cca att tat gcc gac aaa aca    18838
Thr Asp Val Thr Ala Asn Gln Asn Lys Pro Ile Tyr Ala Asp Lys Thr
    700                 705                 710 ttt caa cca gaa ccg caa gta gga gaa gaa aat tgg caa gaa act gaa    18886
Phe Gln Pro Glu Pro Gln Val Gly Glu Glu Asn Trp Gln Glu Thr Glu
715                 720                 725                 730
```

-continued

| | | |
|---|---|---|
| aac ttt tat ggc ggt aga gct ctt aaa aaa gac aca aac atg aaa cct<br>Asn Phe Tyr Gly Gly Arg Ala Leu Lys Lys Asp Thr Asn Met Lys Pro<br>               735                    740                 745 | 18934 |
| tgc tat ggc tcc tat gct aga ccc acc aat gaa aaa gga ggt caa gct<br>Cys Tyr Gly Ser Tyr Ala Arg Pro Thr Asn Glu Lys Gly Gly Gln Ala<br>            750                    755               760 | 18982 |
| aaa ctt aaa gtt gga gat gat gga gtt cca acc aaa gaa ttc gac ata<br>Lys Leu Lys Val Gly Asp Asp Gly Val Pro Thr Lys Glu Phe Asp Ile<br>            765                    770               775 | 19030 |
| gac ctg gct ttc ttt gat act ccc ggt ggc acc gtg aac ggt caa gac<br>Asp Leu Ala Phe Phe Asp Thr Pro Gly Gly Thr Val Asn Gly Gln Asp<br>780                    785                    790 | 19078 |
| gag tat aaa gca gac att gtc atg tat acc gaa aac acg tat ttg gaa<br>Glu Tyr Lys Ala Asp Ile Val Met Tyr Thr Glu Asn Thr Tyr Leu Glu<br>795                    800                    805               810 | 19126 |
| act cca gac acg cat gtg gta tac aaa cca ggc aag gat gat gca agt<br>Thr Pro Asp Thr His Val Val Tyr Lys Pro Gly Lys Asp Asp Ala Ser<br>                  815                    820               825 | 19174 |
| tct gaa att aac ctg gtt cag cag tct atg ccc aac aga ccc aac tac<br>Ser Glu Ile Asn Leu Val Gln Gln Ser Met Pro Asn Arg Pro Asn Tyr<br>            830                    835               840 | 19222 |
| att ggg ttc agg gac aac ttt atc ggt ctt atg tac tac aac agc act<br>Ile Gly Phe Arg Asp Asn Phe Ile Gly Leu Met Tyr Tyr Asn Ser Thr<br>                  845                    850               855 | 19270 |
| ggc aat atg ggt gtg ctt gct ggt cag gcc tcc cag ctg aat gct gtg<br>Gly Asn Met Gly Val Leu Ala Gly Gln Ala Ser Gln Leu Asn Ala Val<br>            860                    865               870 | 19318 |
| gtt gat ttg caa gac aga aac acc gag ctg tcc tac cag ctc ttg ctt<br>Val Asp Leu Gln Asp Arg Asn Thr Glu Leu Ser Tyr Gln Leu Leu Leu<br>875                    880                    885               890 | 19366 |
| gac tct ttg ggt gac aga acc cgg tat ttc agt atg tgg aac cag gcg<br>Asp Ser Leu Gly Asp Arg Thr Arg Tyr Phe Ser Met Trp Asn Gln Ala<br>                  895                    900               905 | 19414 |
| gtg gac agt tat gac ccc gat gtg cgc atc atc gaa aac cat ggt gtg<br>Val Asp Ser Tyr Asp Pro Asp Val Arg Ile Ile Glu Asn His Gly Val<br>            910                    915               920 | 19462 |
| gag gat gaa ttg cca aac tat tgc ttc ccc ttg gac ggc tct ggc act<br>Glu Asp Glu Leu Pro Asn Tyr Cys Phe Pro Leu Asp Gly Ser Gly Thr<br>                925                    930               935 | 19510 |
| aac gcc gca tac caa ggt gtg aaa gta aaa gat ggt caa gat ggt gat<br>Asn Ala Ala Tyr Gln Gly Val Lys Val Lys Asp Gly Gln Asp Gly Asp<br>            940                    945               950 | 19558 |
| gtt gag agt gaa tgg gaa aat gac gat act gtt gca gct cga aat caa<br>Val Glu Ser Glu Trp Glu Asn Asp Asp Thr Val Ala Ala Arg Asn Gln<br>955                    960                    965               970 | 19606 |
| tta tgt aaa ggt aac att ttc gcc atg gag att aat ctc cag gct aac<br>Leu Cys Lys Gly Asn Ile Phe Ala Met Glu Ile Asn Leu Gln Ala Asn<br>                  975                    980               985 | 19654 |
| ctg tgg aga agt ttc ctc tac tcg aac gtg gcc ctg tac ctg ccc gac<br>Leu Trp Arg Ser Phe Leu Tyr Ser Asn Val Ala Leu Tyr Leu Pro Asp<br>            990                    995              1000 | 19702 |
| tcc tac aag tac acg ccg acc aac gtc acg ctg ccg acc aac acc<br>Ser Tyr Lys Tyr Thr Pro Thr Asn Val Thr Leu Pro Thr Asn Thr<br>              1005                  1010               1015 | 19747 |
| aac acc tac gat tac atg aat ggc aga gtg aca cct ccc tcg ctg<br>Asn Thr Tyr Asp Tyr Met Asn Gly Arg Val Thr Pro Pro Ser Leu<br>              1020                  1025               1030 | 19792 |
| gta gac gcc tac ctc aac atc ggg gcg cgc tgg tcg ctg gac ccc<br>Val Asp Ala Tyr Leu Asn Ile Gly Ala Arg Trp Ser Leu Asp Pro<br>              1035                  1040               1045 | 19837 |

-continued

| | | |
|---|---|---|
| atg gac aac gtc aac ccc ttc aac cac cac cgc aac gcg ggc ctg<br>Met Asp Asn Val Asn Pro Phe Asn His His Arg Asn Ala Gly Leu<br>1050                            1055                           1060 | 19882 |
| cgc tac cgc tcc atg ctc ctg ggc aac ggg cgc tac gtg ccc ttc<br>Arg Tyr Arg Ser Met Leu Leu Gly Asn Gly Arg Tyr Val Pro Phe<br>1065                            1070                           1075 | 19927 |
| cac atc cag gtg ccc caa aag ttt ttc gcc atc aag agc ctc ctg<br>His Ile Gln Val Pro Gln Lys Phe Phe Ala Ile Lys Ser Leu Leu<br>1080                            1085                           1090 | 19972 |
| ctc ctg ccc ggg tcc tac acc tac gag tgg aac ttc cgc aag gac<br>Leu Leu Pro Gly Ser Tyr Thr Tyr Glu Trp Asn Phe Arg Lys Asp<br>1095                            1100                           1105 | 20017 |
| gtc aac atg atc ctg cag agc tcc cta ggc aac gac ctg cgc acg<br>Val Asn Met Ile Leu Gln Ser Ser Leu Gly Asn Asp Leu Arg Thr<br>1110                            1115                           1120 | 20062 |
| gac ggg gcc tcc atc gcc ttc acc agc atc aac ctc tac gcc acc<br>Asp Gly Ala Ser Ile Ala Phe Thr Ser Ile Asn Leu Tyr Ala Thr<br>1125                            1130                           1135 | 20107 |
| ttc ttc ccc atg gcg cac aac acc gcc tcc acg ctc gag gcc atg<br>Phe Phe Pro Met Ala His Asn Thr Ala Ser Thr Leu Glu Ala Met<br>1140                            1145                           1150 | 20152 |
| ctg cgc aac gac acc aac gac cag tcc ttc aac gac tac ctc tcg<br>Leu Arg Asn Asp Thr Asn Asp Gln Ser Phe Asn Asp Tyr Leu Ser<br>1155                            1160                           1165 | 20197 |
| gcg gcc aac atg ctc tac ccc atc ccg gcc aac gcc acc aac gtg<br>Ala Ala Asn Met Leu Tyr Pro Ile Pro Ala Asn Ala Thr Asn Val<br>1170                            1175                           1180 | 20242 |
| ccc atc tcc atc ccc tcg cgc aac tgg gcc gcc ttc cgc gga tgg<br>Pro Ile Ser Ile Pro Ser Arg Asn Trp Ala Ala Phe Arg Gly Trp<br>1185                            1190                           1195 | 20287 |
| tcc ttc acg cgc ctg aag acc cgc gag acg ccc tcg ctc ggc tcc<br>Ser Phe Thr Arg Leu Lys Thr Arg Glu Thr Pro Ser Leu Gly Ser<br>1200                            1205                           1210 | 20332 |
| ggg ttc gac ccc tac ttc gtc tac tcg ggc tcc atc ccc tac cta<br>Gly Phe Asp Pro Tyr Phe Val Tyr Ser Gly Ser Ile Pro Tyr Leu<br>1215                            1220                           1225 | 20377 |
| gac ggc acc ttc tac ctc aac cac acc ttc aag aag gtc tcc atc<br>Asp Gly Thr Phe Tyr Leu Asn His Thr Phe Lys Lys Val Ser Ile<br>1230                            1235                           1240 | 20422 |
| acc ttc gac tcc tcc gtc agc tgg ccc ggc aac gac cgc ctc ctg<br>Thr Phe Asp Ser Ser Val Ser Trp Pro Gly Asn Asp Arg Leu Leu<br>1245                            1250                           1255 | 20467 |
| acg ccc aac gag ttc gaa atc aag cgc acc gtc gac gga gag gga<br>Thr Pro Asn Glu Phe Glu Ile Lys Arg Thr Val Asp Gly Glu Gly<br>1260                            1265                           1270 | 20512 |
| tac aac gtg gcc cag tgc aac atg acc aag gac tgg ttc ctg gtc<br>Tyr Asn Val Ala Gln Cys Asn Met Thr Lys Asp Trp Phe Leu Val<br>1275                            1280                           1285 | 20557 |
| cag atg ctg gcc cac tac aac atc ggc tac cag ggc ttc tac gtg<br>Gln Met Leu Ala His Tyr Asn Ile Gly Tyr Gln Gly Phe Tyr Val<br>1290                            1295                           1300 | 20602 |
| ccc gag ggc tac aag gac cgc atg tac tcc ttc ttc cgc aac ttc<br>Pro Glu Gly Tyr Lys Asp Arg Met Tyr Ser Phe Phe Arg Asn Phe<br>1305                            1310                           1315 | 20647 |
| cag ccc atg agc cgc cag gtc gtg gac gag gtc aac tac aag gac<br>Gln Pro Met Ser Arg Gln Val Val Asp Glu Val Asn Tyr Lys Asp<br>1320                            1325                           1330 | 20692 |
| tac cag gcc gtc acc ctg gcc tac cag cac aac aac tcg ggc ttc<br>Tyr Gln Ala Val Thr Leu Ala Tyr Gln His Asn Asn Ser Gly Phe<br>1335                            1340                           1345 | 20737 |

```
gtc ggc tac ctc gcg ccc acc atg cgc cag ggc cag ccc tac ccc      20782
Val Gly Tyr Leu Ala Pro Thr Met Arg Gln Gly Gln Pro Tyr Pro
        1350                1355                1360 gcc aac tac ccc tac ccg ctc atc ggc aag agc gcc gtc gcc agc      20827
Ala Asn Tyr Pro Tyr Pro Leu Ile Gly Lys Ser Ala Val Ala Ser
    1365                1370                1375 gtc acc cag aaa aag ttc ctc tgc gac cgg gtc atg tgg cgc atc      20872
Val Thr Gln Lys Lys Phe Leu Cys Asp Arg Val Met Trp Arg Ile
1380                1385                1390 ccc ttc tcc agc aac ttc atg tcc atg ggc gcg ctc acc gac ctc      20917
Pro Phe Ser Ser Asn Phe Met Ser Met Gly Ala Leu Thr Asp Leu
        1395                1400                1405 ggc cag aac atg ctc tac gcc aac tcc gcc cac gcg cta gac atg      20962
Gly Gln Asn Met Leu Tyr Ala Asn Ser Ala His Ala Leu Asp Met
    1410                1415                1420 aat ttc gaa gtc gac ccc atg gat gag tcc acc ctt ctc tat gtt      21007
Asn Phe Glu Val Asp Pro Met Asp Glu Ser Thr Leu Leu Tyr Val
1425                1430                1435 gtc ttc gaa gtc ttc gac gtc gtc cga gtg cac cag ccc cac cgc      21052
Val Phe Glu Val Phe Asp Val Val Arg Val His Gln Pro His Arg
        1440                1445                1450 ggc gtc atc gaa gcc gtc tac ctg cgc acg ccc ttc tcg gcc ggc      21097
Gly Val Ile Glu Ala Val Tyr Leu Arg Thr Pro Phe Ser Ala Gly
    1455                1460                1465 aac gcc acc acc taa gccgctcttg cttcttgcaa gatgacggcg ggctccggcg   21152
Asn Ala Thr Thr
1470 agcaggagct cagggccatc ctccgcgacc tgggctgcgg gccctgcttc ctgggcacct   21212 tcgacaagcg cttccctgga ttcatggccc cgcacaagct ggcctgcgcc atcgtgaaca   21272 cggccggccg cgagaccggg ggcgagcact ggctggcctt cgcctggaac ccgcgctccc   21332 acacatgcta cctcttcgac cccttcgggt tctcggacga cgcgcctcaag cagatctacc   21392 agttcgagta cgagggcctg ctgcgtcgca gcgccctggc caccgaggac cgctgcgtca   21452 ccctggaaaa gtccaccag accgtgcagg gtccgcgctc ggccgcctgc gggctcttct   21512 gctgcatgtt cctgcacgcc ttcgtgcact ggcccgaccg ccccatggac aagaacccca   21572 ccatgaactt actgacgggg gtgcccaacg gcatgctcca gtcgcccag gtggaaccca   21632 ccctgcgccg caaccaggaa gcgctctacc gcttcctcaa tgcccactcc gcctactttc   21692 gctcccaccg cgcgcgcatc gagaaggcca ccgccttcga ccgcatgaat caagacatgt   21752 aaaaaaccgg tgtgtgtatg tgaatgcttt attcataata aacagcacat gtttatgcca   21812 ccttctctga ggctctgact ttatttagaa atcgaagggg ttctgccggc tctcggcatg   21872 gcccgcgggc agggatacgt tgcggaactg gtacttgggc agccacttga actcgggaat   21932 cagcagcttg gcacggggaa ggtcggggaa cgagtcgctc cacagcttgc gcgtgagttg   21992 cagggcgccc agcaggtcgg gcgcgagat cttgaaatcg cagttgggac ccgcgttctg   22052 cgcgcgagag ttgcggtaca cgggttgca gcactggaac accatcaggg ccgggtgctt   22112 cacgcttgcc agcaccgtcg cgtcggtgat gccctccacg tccagatcct cggcgttggc   22172 catcccgaag ggggtcatct tgcaggtctg ccgccccatg ctgggcacgc agccgggctt   22232 gtggttgcaa tcgcagtgca ggggcgatcag catcatctgg gcctgctcgg agctcatgcc   22292 cgggtacatg gccttcatga aagccctccag ctggcggaag gcctgctgcg ccttgccgcc   22352 ctcggtgaag aagaccccgc aggacttgct agagaactgg ttggtggcgc agccggcgtc   22412 gtgcacgcag cagcgcgcgt cgttgttggc cagctgcacc acgctgcgcc cccagcggtt   22472
```

```
ctgggtgatc ttggcccggt tggggttctc cttcagcgcg cgctgcccgt tctcgctcgc    22532
cacatccatc tcgatagtgt gctccttctg gatcatcacg gtcccgtgca ggcaccgcag    22592
cttgccctcg gcttcggtgc agccgtgcag ccacagcgcg cagccggtgc actcccagtt    22652
cttgtgggcg atctgggagt gcgagtgcac gaagccctgc aggaagcggc ccatcatcgc    22712
ggtcagggtc ttgttgctgg tgaaggtcag cgggatgccg cggtgctcct cgttcacata    22772
caggtggcag atgcggcggt acacctcgcc ctgctcgggc atcagctgga aggcggactt    22832
caggtcgctc tccacgcggt accggtccat cagcagcgtc atcacttcca tgcccttctc    22892
ccaggccgaa acgatcggca ggctcagggg gttcttcacc gccattgtca tcttagtcgc    22952
cgccgccgag gtcaggggt cgttctcgtc cagggtctca aacactcgct tgccgtcctt    23012
ctcgatgatg cgcacggggg gaaagctgaa gcccacggcc gccagctcct cctcggcctg    23072
cctttcgtcc tcgctgtcct ggctgatgtc ttgcaaaggc acatgcttgg tcttgcgggg    23132
tttcttttg ggcggcagag gcggcggcga tgtgctggga gagcgcgagt tctcgttcac    23192
cacgactatt tcttcttctt ggccgtcgtc cgagaccacg cggcggtagg catgcctctt    23252
ctggggcaga ggcggaggcg acgggctctc gcggttcggc gggcggctgg cagagcccct    23312
tccgcgttcg ggggtgcgct cctggcggcg ctgctctgac tgacttcctc cgcggccggc    23372
cattgtgttc tcctagggag caacaacaag catggagact cagccatcgt cgccaacatc    23432
gccatctgcc cccgccgcca ccgccgacga gaaccagcag cagaatgaaa gcttaaccgc    23492
cccgccgccc agccccacct ccgacgccgc ggccccagac atgcaagaga tggaggaatc    23552
catcgagatt gacctgggct acgtgacgcc cgcggagcac gaggaggagc tggcagcgcg    23612
cttttcagcc ccggaagaga accaccaaga gcagccagag caggaagcag agaacgagca    23672
gaaccaggct gggcacgagc atggcgacta cctgagcggg gcagaggacg tgctcatcaa    23732
gcatctggcc cgccaatgca tcatcgtcaa ggacgcgctg ctcgaccgcg ccgaggtgcc    23792
cctcagcgtg gcggagctca gccgcgccta cgagcgcaac ctcttctcgc cgcgcgtgcc    23852
ccccaagcgc cagcccaacg gcacctgtga gcccaacccg cgcctcaact tctaccggt    23912
cttcgcggtg cccgaggccc tggccaccta ccacctcttt ttcaagaacc aaaggatccc    23972
cgtctcctgc cgcgccaacc gcacccgcgc cgacgccctg ctcaacctgg ccccggcgc    24032
ccgcctacct gatatcacct ccttggaaga ggttcccaag atcttcgagg gtctgggcag    24092
cgacgagact cgggccgcga acgctctgca aggaagcgga gaggagcatg agcaccacag    24152
cgccctggtg gagttggaag gcgacaacgc gcgcctggcg gtcctcaagc gcacggtcga    24212
gctgacccac ttcgcctacc cggcgctcaa cctgcccccc aaggtcatga gcgccgtcat    24272
ggaccaggtg ctcatcaagc gcgcctcgcc cctctcggag gaggagatgc aggaccccga    24332
gagttcggac gagggcaagc ccgtggtcag cgacgagcag ctggcgcgct ggctgggagc    24392
gagtagcacc ccccagagcc tggaagagcg gcgcaagctc atgatggccg tggtcctggt    24452
gaccgtggag ctggagtgtc tgcgccgctt ctttgccgac gcggagaccc tgcgcaaggt    24512
cgaggagaac ctgcactacc tcttcaggca cgggttcgtg cgccaggcct gcaagatctc    24572
caacgtggag ctgaccaacc tggtctccta catgggcatc ctgcacgaga accgcctggg    24632
gcaaaacgtg ctgcacacca ccctgcgcgg ggaggcccgc cgcgactaca tccgcgactg    24692
cgtctacctg tacctctgcc acaccctggca gacgggcatg ggcgtgtggc agcagtgcct    24752
ggaggagcag aacctgaaag agctctgcaa gctcctgcaa aagaacctca aggccctgtg    24812
gaccggggttc gacgagcgta ccaccgcctc ggacctggcc gacctcatct tccccgagcg    24872
```

```
cctgcggctg acgctgcgca acgggctgcc cgactttatg agccaaagca tgttgcaaaa  24932
ctttcgctct ttcatcctcg aacgctccgg gatcctgccc gccacctgct ccgcgctgcc  24992
ctcggacttc gtgccgctga ccttccgcga gtgcccccg ccgctctgga gccactgcta   25052
cttgctgcgc ctggccaact acctggccta ccactcggac gtgatcgagg acgtcagcgg  25112
cgagggtctg ctggagtgcc actgccgctg caacctctgc acgccgcacc gctccctggc  25172
ctgcaacccc cagctgctga gcgagaccca gatcatcggc accttcgagt tgcaaggccc  25232
cggcgacggc gagggcaagg ggggtctgaa actcaccccg gggctgtgga cctcggccta   25292
cttgcgcaag ttcgtgcccg aggactacca tcccttcgag atcaggttct acgaggacca  25352
atcccagccg cccaaggccg agctgtcggc ctgcgtcatc acccagggg ccatcctggc   25412
ccaattgcaa gccatccaga atcccgcca agaatttctg ctgaaaaagg ccacgggg t   25472
ctacttggac ccccagaccg agaggagct caacccagc ttcccccagg atgccccgag   25532
gaagcagcaa gaagctgaaa gtggagctgc cgccgccgga ggatttggag aagactggga  25592
agagcagtca ggcagaggag gaggagatgg aagactggga cagcactcag gcagaggagg  25652
acagcctgca agacagtctg gaggaggaag acgaggtgga ggaggcagag gaagaagcag  25712
ccgccgccag accgtcgtcc tcggcggaga aagcaagcag cacggatacc atctccgctc  25772
cgggtcgggg tcgcggcggc cgggcccaca gtaggtggga cgagaccggg cgcttcccga  25832
accccaccac ccagaccggt aagaaggagc ggcagggata caagtcctgg cgggggcaca  25892
aaaacgccat cgtctcctgc ttgcaagcct gcggggcaa catctccttc acccggcgct    25952
acctgctctt ccaccgcggg gtgaacttcc cccgcaacat cttgcattac taccgtcacc  26012
tccacagccc ctactactgt ttccaagaag aggcagaaac ccagcagcag cagaaaacca  26072
gcggcagcag cagctagaaa atccacagcg gcggcaggtg gactgaggat cgcggcgaac  26132
gagccggcgc agaccgggga gctgaggaac cggatctttc ccaccctcta tgccatcttc  26192
cagcagagtc gggggcagga gcaggaactg aaagtcaaga accgttctct gcgctcgctc  26252
acccgcagtt gtctgtatca caagagcgaa gaccaacttc agcgcactct cgaggacgcc  26312
gaggctctct tcaacaagta ctgcgcgctc actcttaaag agtagcccgc gcccgcccac  26372
acacggaaaa aggcgggaat tacgtcacca cctgcgccct tcgcccgacc atcatgagca  26432
aagagattcc cacgccttac atgtggagct accagcccca gatgggcctg gccgccggcg  26492
ccgcccagga ctactccacc cgcatgaact ggctcagtgc cgggcccgcg atgatctcac  26552
gggtgaatga catccgcgcc caccgaaacc agatactcct agaacagtca gcgatcaccg  26612
ccacgccccg ccatcacctt aatccgcgta attggcccgc cgccctggtg taccaggaaa  26672
ttccccagcc cacgaccgta ctacttccgc gagacgccca ggccgaagtc cagctgacta  26732
actcaggtgt ccagctggcc ggcggcgccg ccctgtgtcg tcaccgcccc gctcagggta  26792
taaagcggct ggtgatccga ggcagaggca cacagctcaa cgacgaggtg gtgagctctt  26852
cgctgggtct gcgacctgac ggagtcttcc aactcgccgg atcggggaga tcttccttca  26912
cgcctcgtca ggccgtcctg actttggaga gttcgtcctc gcagcccgc tcgggcggca   26972
tcggcactct ccagttcgtg gaggagttca ctccctcggt ctacttcaac cccttctccg  27032
gctcccccgg ccactacccg gacgagttca tcccgaactt cgacgccatc agcgagtcgg  27092
tggacggcta cgattgaatg tcccatggtg gcgcagctga cctagctcgg cttcgacacc  27152
tggaccactg ccgccgcttc cgctgcttcg ctcgggatct cgccgagttt gcctactttg  27212
agctgcccga ggagcaccct cagggcccag cccacggagt gcggatcatc gtcgaagggg  27272
```

```
gcctcgactc ccacctgctt cggatcttca gccagcgacc gatcctggtc gagcgcgaac    27332
aaggacagac ccttcttact ttgtactgca tctgcaacca ccccggcctg catgaaagtc    27392
tttgttgtct gctgtgtact gagtataata aaagctgaga tcagcgacta ctccggactc    27452
gattgtggtg ttcctgctat caaccggtcc ctgttcttca ccgggaacga gaccgagctc    27512
cagctccagt gtaagcccca caagaagtac ctcacctggc tgttccaggg ctccccgatc    27572
gccgttgtca accactgcga caacgacgga gtcctgctga gcggccctgc caaccttact    27632
ttttccaccc gcagaagcaa gctccagctc ttccaaccct tcctcccggg gacctatcag    27692
tgcgtctcag gaccctgcca tcacaccttc cacctgatcc gaataccac agcgccgctc     27752 cccgctacta caaccaaac tacccaccaa cgccaccgtc gcgacctttc ctctgaatct     27812
aataccacta ccggaggtga gctccgaggt cgaccaacct ctgggattta ctacggcccc    27872
tgggaggtgg tggggttaat agcgctaggc ctagttgcgg gtgggctttt ggttctctgc    27932
tacctatacc tcccttgctg ttcgtactta gtggtgctgt gttgctggtt taagaaatgg    27992
ggaagatcac cctagtgagc tgcggtgcgc tggtggcggt gttgctttcg attgtgggac    28052
tgggcggcgc ggctgtagtg aaggagaagg ccgatccctg cttgcatttc aatcccaaca    28112
aatgccagct gagttttcag cccgatggca atcggtgcgc ggtactgatc aagtgcggat    28172
gggaatgcga gaacgtgaga atcgagtaca ataacaagac tcggaacaat actctcgcgt    28232
ccgtgtggca gcccggggac cccgagtggt acaccgtctc tgtccccggt gctgacggct    28292
ccccgcgcac cgtgaataat actttcattt ttgcgcacat gtgcaacacg gtcatgtgga    28352
tgagcaagca gtacgatatg tggccccca cgaaggagaa catcgtggtc ttctccatcg     28412
cttacagcct gtgcacggcg ctaatcaccg ctatcgtgtg cctgagcatt cacatgctca    28472
tcgctattcg ccccagaaat aatgccgaga agagaaaca gccataacac gttttttcac     28532
acaccttgtt tttacagaca atgcgtctgt taaattttt aaacattgtg ctcagtattg     28592
cttatgcctc tggttatgca acatacaga aaacccttta tgtaggatct gatggtacac     28652
tagagggtac ccaatcacaa gccaaggttg catggtattt ttatagaacc aacactgatc    28712
cagttaaact ttgtaagggt gaattgccgc gtacacataa aactccactt acatttagtt    28772
gcagcaataa taatcttaca cttttttcaa ttacaaaaca atatactggt acttattaca    28832
gtacaaactt tcatacagga caagataaat attatactgt taaggtagaa atcctacca    28892 ctcctagaac taccaccacc accactactg caaagcccac tgtgaaaact acaactagga    28952
ccaccacaac tacagaaacc accaccagca caacacttgc tgcaactaca cacacacaca    29012
ctaagctaac cttacagacc actaatgatt tgatcgccct gctgcaaaag ggggataaca    29072
gcaccacttc caatgaggag atacccaaat ccatgattgg cattattgtt gctgtagtgg    29132
tgtgcatgtt gatcatcgcc ttgtgcatgg tgtactatgc cttctgctac agaaagcaca    29192
gactgaacga caagctggaa cacttactaa gtgttgaatt taattttttt agaaccatga    29252
agatcctagg cctttttagt ttttctatca ttacctctgc tctttgtgaa tcagtggata    29312
gagatgttac tattaccact ggttctaatt atacactgaa agggcaccc tcaggtatgc     29372 tttcgtggta ttgctatttt ggaactgaca ctgatcaaac tgaattatgc aattttcaaa    29432
aaggcaaaac ctcaaactct aaaatctcta attatcaatg caatggcact gatctgatac    29492
tactcaatgt cacgaaagca tatggtggca gttattattg ccctggacaa aacactgaag    29552
aaatgatttt ttacaaagtg gaagtggttg atcccactac accacccacc accacaacta    29612
ttcataccac acacacagaa caaacaccag aggcaacaga agcagagttg gccttccagg    29672
```

```
ttcacggaga ttcctttgct gtcaataccc ctacacccga tcagcggtgt ccggggccgc   29732
tagtcagcgg cattgtcggt gtgctttcgg gattagcagt cataatcatc tgcatgttca   29792
tttttgcttg ctgctataga aggctttacc gacaaaaatc agacccactg ctgaacctct   29852
atgtttaatt tttccagag ccatgaaggc agttagcgct ctagttttt gttctttgat     29912 tggcattgtt tttaatagta aaattaccag agttagcttt attaaacatg ttaatgtaac   29972
tgaaggagat aacatcacac tagcaggtgt agaaggtgct caaaacacca cctggacaaa   30032
ataccatcta ggatggagag atatttgcac ctggaatgta acttattatt gcataggagt   30092
taatcttacc attgttaacg ctaaccaatc tcagaatggg ttaattaaag gacagagtgt   30152
tagtgtgacc agtgatgggt actataccca gcatagtttt aactacaaca ttactgtcat   30212
accactgcct acgcctagcc cacctagcac taccacacag acaaccacat acagtacatc   30272
aaatcagcct accaccacta cagcagcaga ggttgccagc tcgtctgggg tccgagtggc   30332 attttgatg ttggccccat ctagcagtcc cactgctagt accaatgagc agactactga    30392 attttgtcc actgtcgaga gccacaccac agctacctcc agtgccttct ctagcaccgc    30452
caatctctcc tcgcttcct ctacaccaat cagccccgct actactccta gccccgctcc    30512
tcttcccact cccctgaagc aaacagacgg cggcatgcaa tggcagatca ccctgctcat   30572
tgtgatcggg ttggtcatcc tggccgtgtt gctctactac atcttctgcc gccgcattcc   30632
caacgcgcac cgcaagccgg cctacaagcc catcgttatc gggcagccgg agccgcttca   30692
ggtggaaggg ggtctaagga atcttctctt ctcttttaca gtatggtgat tgaactatga   30752
ttcctagaca attcttgatc actattctta tctgcctcct ccaagtctgt gccaccctcg   30812
ctctggtggc caacgccagt ccagactgta ttgggccctt cgcctcctac gtgctctttg   30872
ccttcgtcac ctgcatctgc tgctgtagca tagtctgcct gcttatcacc ttcttccagt   30932
tcattgactg gatctttgtg cgcatcgcct acctgcgcca ccaccccag taccgcgacc     30992 agcgagtggc gcagctgctc aggctcctct gataagcatg cgggctctgc tacttctcgc   31052
gcttctgctg ttagtgctcc cccgtcccgt cgacccccgg tccccactc agtccccga     31112 ggaggttcgc aaatgcaaat tccaagaacc ctggaaattc tcaaatgct accgccaaaa    31172 atcagacatg catcccagct ggatcatgat cattgggatc gtgaacattc tggcctgcac   31232
cctcatctcc tttgtgattt acccctgctt tgactttggt tggaactcgc cagaggcgct   31292
ctatctcccg cctgaacctg acacaccacc acagcagcaa cctcaggcac acgcactacc   31352
accaccacag cctaggccac aatacatgcc catattagac tatgaggccg agccacagcg   31412
acccatgctc cccgctatta gttacttcaa tctaaccggc ggagatgact gacccactgg   31472
ccaataacaa cgtcaacgac cttctcctgg acatggacgg ccgcgcctcg gagcagcgac   31532
tcgcccaact tcgcattcgt cagcagcagg agagagccgt caaggagctg caggacggca   31592
tagccatcca ccagtgcaag agaggcatct tctgcctggt gaaacaggcc aagatctcct   31652
acgaggtcac ccagaccgac catcgcctct cctacgagct cctgcagcag cgccagaagt   31712
tcacctgcct ggtcggagtc aaccccatcg tcatcaccca gcagtcgggc gataccaagg   31772
ggtgcatcca ctgctcctgc gactcccccg actgcgtcca cactctgatc aagaccctct   31832
gcggcctccg cgacctcctc cccatgaact aatcacccc ttatccagtg aaataaagat     31892
catattgatg atgatttaaa taaaaaaat aatcatttga tttgaaataa agatacaatc     31952
atattgatga tttgagttta acaaaaataa agaatcactt acttgaaatc tgataccagg    32012
tctctgtcca tgtttctgc caacaccacc tcactcccct cttcccagct ctggtactgc    32072
```

```
aggcccggc gggctgcaaa cttcctccac acgctgaagg ggatgtcaaa ttcctcctgt    32132
ccctcaatct tcattttatc ttctatcag atg tcc aaa aag cgc gtc cgg gtg    32185
                                Met Ser Lys Lys Arg Val Arg Val
                                                1475 gat gat gac ttc gac ccc gtc tac ccc tac gat gca gac aac gca        32230
Asp Asp Asp Phe Asp Pro Val Tyr Pro Tyr Asp Ala Asp Asn Ala
1480                1485                1490 ccg acc gtg ccc ttc atc aac ccc ccc ttc gtc tct tca gat gga        32275
Pro Thr Val Pro Phe Ile Asn Pro Pro Phe Val Ser Ser Asp Gly
1495                1500                1505 ttc caa gag aag ccc ctg ggg gtg ttg tcc ctg cga ctg gct gac        32320
Phe Gln Glu Lys Pro Leu Gly Val Leu Ser Leu Arg Leu Ala Asp
1510                1515                1520 ccc gtc acc acc aag aac ggg gaa atc acc ctc aag ctg gga gag        32365
Pro Val Thr Thr Lys Asn Gly Glu Ile Thr Leu Lys Leu Gly Glu
1525                1530                1535 ggg gtg gac ctc gac tcg tcg gga aaa ctc atc tcc aac acg gcc        32410
Gly Val Asp Leu Asp Ser Ser Gly Lys Leu Ile Ser Asn Thr Ala
1540                1545                1550 acc aag gcc gcc gcc cct ctc agt att tca aac aac acc att tcc        32455
Thr Lys Ala Ala Ala Pro Leu Ser Ile Ser Asn Asn Thr Ile Ser
1555                1560                1565 ctt aaa act gct gcc cct ttc tac aac aac aat gga act tta agc        32500
Leu Lys Thr Ala Ala Pro Phe Tyr Asn Asn Asn Gly Thr Leu Ser
1570                1575                1580 ctc aat gtc tcc aca cca tta gca gta ttt ccc aca ttt aac act        32545
Leu Asn Val Ser Thr Pro Leu Ala Val Phe Pro Thr Phe Asn Thr
1585                1590                1595 tta ggc ata agt ctt gga aac ggt ctt cag act tca aat aag ttg        32590
Leu Gly Ile Ser Leu Gly Asn Gly Leu Gln Thr Ser Asn Lys Leu
1600                1605                1610 ttg act gta caa cta act cat cct ctt aca ttc agc tca aat agc        32635
Leu Thr Val Gln Leu Thr His Pro Leu Thr Phe Ser Ser Asn Ser
1615                1620                1625 atc aca gta aaa aca gac aaa ggg cta tat att aac tcc agt gga        32680
Ile Thr Val Lys Thr Asp Lys Gly Leu Tyr Ile Asn Ser Ser Gly
1630                1635                1640 aac aga gga ctt gag gct aat ata agc cta aaa aga gga cta gtt        32725
Asn Arg Gly Leu Glu Ala Asn Ile Ser Leu Lys Arg Gly Leu Val
1645                1650                1655 ttt gac ggt aat gct att gca aca tat att gga aat ggc tta gac        32770
Phe Asp Gly Asn Ala Ile Ala Thr Tyr Ile Gly Asn Gly Leu Asp
1660                1665                1670 tat gga tct tat gat agt gat gga aaa aca aga ccc gta att acc        32815
Tyr Gly Ser Tyr Asp Ser Asp Gly Lys Thr Arg Pro Val Ile Thr
1675                1680                1685 aaa att gga gca gga tta aat ttt gat gct aac aaa gca ata gct        32860
Lys Ile Gly Ala Gly Leu Asn Phe Asp Ala Asn Lys Ala Ile Ala
1690                1695                1700 gtc aaa cta ggc aca ggt tta agt ttt gac tcc gct ggt gcc ttg        32905
Val Lys Leu Gly Thr Gly Leu Ser Phe Asp Ser Ala Gly Ala Leu
1705                1710                1715 aca gct gga aac aaa cag gat gac aag cta aca ctt tgg act acc        32950
Thr Ala Gly Asn Lys Gln Asp Asp Lys Leu Thr Leu Trp Thr Thr
1720                1725                1730 cct gac cca agc cct aat tgt caa tta ctt tca gac aga gat gcc        32995
Pro Asp Pro Ser Pro Asn Cys Gln Leu Leu Ser Asp Arg Asp Ala
1735                1740                1745 aaa ttt act ctc tgt ctt  aca aaa tgc ggt agt caa ata cta ggc       33040
```

| | | | | | | | | | | | | |
|---|---|---|---|---|---|---|---|---|---|---|---|---|
| Lys | Phe | Thr | Leu | Cys | Leu | Thr | Lys | Cys | Gly | Ser | Gln | Ile | Leu | Gly |
| 1750 | | | | 1755 | | | | | 1760 | | | | | |

| act | gtg | gca | gtg | gcg | gct | gtt | act | gta | gga | tca | gca | cta | aat | cca | 33085 |
| Thr | Val | Ala | Val | Ala | Ala | Val | Thr | Val | Gly | Ser | Ala | Leu | Asn | Pro | |
| 1765 | | | | 1770 | | | | | 1775 | | | | | | |

| att | aat | gac | aca | gtc | aaa | agc | gcc | ata | gtt | ttc | ctt | aga | ttt | gat | 33130 |
| Ile | Asn | Asp | Thr | Val | Lys | Ser | Ala | Ile | Val | Phe | Leu | Arg | Phe | Asp | |
| 1780 | | | | 1785 | | | | | 1790 | | | | | | |

| tcc | gat | ggt | gta | ctc | atg | tca | aac | tca | tca | atg | gta | ggt | gat | tac | 33175 |
| Ser | Asp | Gly | Val | Leu | Met | Ser | Asn | Ser | Ser | Met | Val | Gly | Asp | Tyr | |
| 1795 | | | | 1800 | | | | | 1805 | | | | | | |

| tgg | aac | ttt | agg | gag | gga | cag | acc | act | caa | agt | gta | gcc | tat | aca | 33220 |
| Trp | Asn | Phe | Arg | Glu | Gly | Gln | Thr | Thr | Gln | Ser | Val | Ala | Tyr | Thr | |
| 1810 | | | | 1815 | | | | | 1820 | | | | | | |

| aat | gct | gtg | gga | ttc | atg | cca | aat | ata | ggt | gca | tat | cca | aaa | acc | 33265 |
| Asn | Ala | Val | Gly | Phe | Met | Pro | Asn | Ile | Gly | Ala | Tyr | Pro | Lys | Thr | |
| 1825 | | | | 1830 | | | | | 1835 | | | | | | |

| caa | agt | aaa | aca | cct | aaa | aat | agc | ata | gtc | agt | cag | gta | tat | tta | 33310 |
| Gln | Ser | Lys | Thr | Pro | Lys | Asn | Ser | Ile | Val | Ser | Gln | Val | Tyr | Leu | |
| 1840 | | | | 1845 | | | | | 1850 | | | | | | |

| act | gga | gaa | act | act | atg | cca | atg | aca | cta | acc | ata | act | ttc | aat | 33355 |
| Thr | Gly | Glu | Thr | Thr | Met | Pro | Met | Thr | Leu | Thr | Ile | Thr | Phe | Asn | |
| 1855 | | | | 1860 | | | | | 1865 | | | | | | |

| ggc | act | gat | gaa | aaa | gac | aca | acc | cca | gtt | agc | acc | tac | tct | atg | 33400 |
| Gly | Thr | Asp | Glu | Lys | Asp | Thr | Thr | Pro | Val | Ser | Thr | Tyr | Ser | Met | |
| 1870 | | | | 1875 | | | | | 1880 | | | | | | |

| act | ttt | aca | tgg | cag | tgg | act | gga | gac | tat | aag | gac | aaa | aat | att | 33445 |
| Thr | Phe | Thr | Trp | Gln | Trp | Thr | Gly | Asp | Tyr | Lys | Asp | Lys | Asn | Ile | |
| 1885 | | | | 1890 | | | | | 1895 | | | | | | |

| acc | ttt | gct | acc | aac | tca | ttc | tct | ttt | tcc | tac | atc | gcc | cag | gaa | 33490 |
| Thr | Phe | Ala | Thr | Asn | Ser | Phe | Ser | Phe | Ser | Tyr | Ile | Ala | Gln | Glu | |
| 1900 | | | | 1905 | | | | | 1910 | | | | | | |

```
taa tcccacccag caagccaacc ccttttccca ccacctttgt ctatatggaa      33543
actctgaaac agaaaaataa agttcaagtg ttttattgaa tcaacagttt tacaggactc   33603
gagcagttat ttttcctcca ccctcccagg acatggaata caccaccctc tcccccgca   33663 cagccttgaa catctgaatg ccattggtga tggacatgct tttggtctcc acgttccaca   33723
cagtttcaga gcgagccagt ctcggatcgg tcagggagat gaaaccctcc gggcactccc   33783
gcatctgcac ctcacagctc aacagctgag gattgtcctc ggtggtcggg atcacggtta   33843
tctggaagaa gcagaagagc ggcggtggga atcatagtcc gcgaacggga tcggccggtg   33903
gtgtcgcatc aggccccgca gcagtcgctg ccgccgccgc tccgtcaagc tgctgctcag   33963
ggggttcggg tccagggact ccctcagcat gatgcccacg gccctcagca tcagtcgtct   34023
ggtgcggcgg gcgcagcagc gcatgcgaat ctcgctcagg tcactgcagt acgtgcaaca   34083
caggaccacc aggttgttca acagtccata gttcaacacg ctccagccga aactcatcgc   34143
gggaaggatg ctacccacgt ggccgtcgta ccagatcctc aggtaaatca agtggcgctc   34203
cctccagaag acgctgccca tgtacatgat ctccttgggc atgtggcggt tcaccacctc   34263
ccggtaccac atcaccctct ggttgaacat gcagccccgg atgatcctgc ggaaccacag   34323
ggccagcacc gccccgcccg ccatgcagcg aagagacccc ggatcccggc aatgacaatg   34383
gaggaccacc cgctcgtacc cgtggatcat ctgggagctg aacaagtcta tgttggcaca   34443
gcacaggcat atgctcatgc atctcttcag cactctcagc tcctcggggg tcaaaaccat   34503
atcccagggc acgggggaact cttgcaggac agcgaacccc gcagaacagg gcaatcctcg   34563
cacataactt acattgtgca tggacagggt atcgcaatca ggcagcaccg ggtgatcctc   34623
```

```
caccagagaa gcgcgggtct cggtctcctc acagcgtggt aagggggccg gccgatacgg    34683
gtgatggcgg gacgcggctg atcgtgttct cgaccgtgtc atgatgcagt tgctttcgga    34743
cattttcgta cttgctgtag cagaacctgg tccgggcgct gcacaccgat cgccggcggc    34803
ggtctcggcg cttggaacgc tcggtgttaa agttgtaaaa cagccactct ctcagaccgt    34863
gcagcagatc tagggcctca ggagtgatga agatcccatc atgcctgata gctctgatca    34923
catcgaccac cgtggaatgg ccaggcccag ccagatgatg caattttgt tgggtttcgg     34983 tgacggcggg ggagggaaga acaggaagaa ccatgattaa cttttaatcc aaacggtctc    35043
ggagcacttc aaaatgaagg tcacggagat ggcacctctc gcccccgctg tgttggtgga    35103
aaataacagc caggtcaaag gtgatacggt tctcgagatg ttccacggtg gcttccagca    35163
aagcctccac gcgcacatcc agaaacaaga caatagcgaa agcgggaggg ttctctaatt    35223
cctcaaccat catgttacac tcctgcacca tccccagata atttcatttt ttccagcctt    35283
gaatgattcg aactagttcc tgaggtaaat ccaagccagc catgataaaa agctcgcgca    35343
gagcaccctc caccggcatt cttaagcaca ccctcataat tccaagatat tctgctcctg    35403
gttcacctgc agcagattga caagcggaat atcaaaatct ctgccgcgat ccctgagctc    35463
ctccctcagc aataactgta agtactcttt catatcgtct ccgaaatttt tagccatagg    35523 accccccagga ataagagaag ggcaagccac attacgata aaccgaagtc cccccagtg    35583 agcattgcca aatgtaagat tgaaataagc atgctggcta gacccggtga tatcttccag    35643
ataactggac agaaaatcgg gtaagcaatt tttaagaaaa tcaacaaaag aaaaatcttc    35703
caggtgcacg tttagggcct cgggaacaac gatggagtaa gtgcaagggg tgcgttccag    35763
catggttagt tagctgatct gtaaaaaaac aaaaaataaa acattaaacc atgctagcct    35823
ggcgaacagg tgggtaaatc gttctctcca gcaccaggca ggccacgggg tctccggcgc    35883
gaccctcgta aaaattgtcg ctatgattga aaaccatcac agagagacgt tcccggtggc    35943
cggcgtgaat gattcgagaa gaagcataca ccccccggaac attggagtcc gtgagtgaaa    36003
aaaagcggcc gaggaagcaa tgaggcacta caacgctcac tctcaagtcc agcaaagcga    36063
tgccatgcgg atgaagcaca aaattttcag gtgcgtaaaa aatgtaatta ctccccctcct    36123 gcacaggcag cgaagctccc gatccctcca gatacacata caaagcctca gcgtccatag    36183
cttaccgagc ggcagcagca gcggcacaca acaggcgcaa gagtcagaga aaagactgag    36243
ctctaacctg tccgcccgct ctctgctcaa tatatagccc cagatctaca ctgacgtaaa    36303
ggccaaagtc taaaaatacc cgccaaataa tcacacacgc ccagcacacg cccagaaacc    36363
ggtgacacac tcagaaaaat acgcgcactt cctcaaacgg ccaaactgcc gtcatttccg    36423
ggttcccacg ctacgtcatc aaaacacgac tttcaaattc cgtcgaccgt taaaaacatc    36483
acccgccccg cccctaacgg tcgccgctcc cgcagccaat caccttcctc cctccccaaa    36543
ttcaaacagc tcatttgcat attaacgcgc accaaaagtt tgaggtatat tattgatgat    36603
g                                                                   36604
```

<210> SEQ ID NO 6
<211> LENGTH: 529
<212> TYPE: PRT
<213> ORGANISM: chimpanzee adenovirus serotype Pan6

<400> SEQUENCE: 6

Met Met Arg Arg Val Tyr Pro Glu Gly Pro Pro Pro Ser Tyr Glu Ser
1               5                   10                  15

Val Met Gln Gln Ala Val Ala Ala Met Gln Pro Pro Leu Glu Ala
            20                  25                  30

Pro Tyr Val Pro Pro Arg Tyr Leu Ala Pro Thr Glu Gly Arg Asn Ser
        35                  40                  45

Ile Arg Tyr Ser Glu Leu Ala Pro Leu Tyr Asp Thr Thr Arg Leu Tyr
50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Gly Arg Ser Arg
            100                 105                 110

Trp Gly Gly Gln Leu Lys Thr Ile Met His Thr Asn Met Pro Asn Val
        115                 120                 125

Asn Glu Phe Met Tyr Ser Asn Lys Phe Lys Ala Arg Val Met Val Ser
130                 135                 140

Arg Lys Thr Pro Asn Gly Val Asp Asp Asp Tyr Asp Gly Ser Gln Asp
145                 150                 155                 160

Glu Leu Thr Tyr Glu Trp Val Glu Phe Glu Leu Pro Glu Gly Asn Phe
                165                 170                 175

Ser Val Thr Met Thr Ile Asp Leu Met Asn Asn Ala Ile Ile Asp Asn
            180                 185                 190

Tyr Leu Ala Val Gly Arg Gln Asn Gly Val Leu Glu Ser Asp Ile Gly
        195                 200                 205

Val Lys Phe Asp Thr Arg Asn Phe Arg Leu Gly Trp Asp Pro Val Thr
210                 215                 220

Glu Leu Val Met Pro Gly Val Tyr Thr Asn Glu Ala Phe His Pro Asp
225                 230                 235                 240

Ile Val Leu Leu Pro Gly Cys Gly Val Asp Phe Thr Glu Ser Arg Leu
                245                 250                 255

Ser Asn Leu Leu Gly Ile Arg Lys Arg Gln Pro Phe Gln Glu Gly Phe
            260                 265                 270

Gln Ile Leu Tyr Glu Asp Leu Glu Gly Gly Asn Ile Pro Ala Leu Leu
        275                 280                 285

Asp Val Glu Ala Tyr Glu Lys Ser Lys Glu Asp Ser Thr Ala Ala Ala
290                 295                 300

Thr Ala Ala Val Ala Thr Ala Ser Thr Glu Val Arg Gly Asp Asn Phe
305                 310                 315                 320

Ala Ser Ala Ala Ala Ala Glu Ala Ala Glu Thr Glu Ser Lys Ile
                325                 330                 335

Val Ile Gln Pro Val Glu Lys Asp Ser Lys Asp Arg Ser Tyr Asn Val
            340                 345                 350

Leu Ala Asp Lys Lys Asn Thr Ala Tyr Arg Ser Trp Tyr Leu Ala Tyr
        355                 360                 365

Asn Tyr Gly Asp Pro Glu Lys Gly Val Arg Ser Trp Thr Leu Leu Thr
370                 375                 380

Thr Ser Asp Val Thr Cys Gly Val Glu Gln Val Tyr Trp Ser Leu Pro
385                 390                 395                 400

Asp Met Met Gln Asp Pro Val Thr Phe Arg Ser Thr Arg Gln Val Ser
                405                 410                 415

Asn Tyr Pro Val Val Gly Ala Glu Leu Leu Pro Val Tyr Ser Lys Ser
            420                 425                 430

Phe Phe Asn Glu Gln Ala Val Tyr Ser Gln Gln Leu Arg Ala Phe Thr
        435                 440                 445

```
Ser Leu Thr His Val Phe Asn Arg Phe Pro Glu Asn Gln Ile Leu Val
    450                 455                 460

Arg Pro Pro Ala Pro Thr Ile Thr Thr Val Ser Glu Asn Val Pro Ala
465                 470                 475                 480

Leu Thr Asp His Gly Thr Leu Pro Leu Arg Ser Ser Ile Arg Gly Val
                485                 490                 495

Gln Arg Val Thr Val Thr Asp Ala Arg Arg Arg Thr Cys Pro Tyr Val
            500                 505                 510

Tyr Lys Ala Leu Gly Val Val Ala Pro Arg Val Leu Ser Ser Arg Thr
        515                 520                 525

Phe

<210> SEQ ID NO 7
<211> LENGTH: 942
<212> TYPE: PRT
<213> ORGANISM: chimpanzee adenovirus serotype Pan6

<400> SEQUENCE: 7

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Ser Ser Gln Trp Glu Gln Ala Lys Thr Gly Asn Gly Gly
    130                 135                 140

Thr Met Glu Thr His Thr Tyr Gly Val Ala Pro Met Gly Gly Glu Asn
145                 150                 155                 160

Ile Thr Lys Asp Gly Leu Gln Ile Gly Thr Asp Val Thr Ala Asn Gln
                165                 170                 175

Asn Lys Pro Ile Tyr Ala Asp Lys Thr Phe Gln Pro Glu Pro Gln Val
            180                 185                 190

Gly Glu Glu Asn Trp Gln Glu Thr Glu Asn Phe Tyr Gly Gly Arg Ala
        195                 200                 205

Leu Lys Lys Asp Thr Asn Met Lys Pro Cys Tyr Gly Ser Tyr Ala Arg
    210                 215                 220

Pro Thr Asn Glu Lys Gly Gly Gln Ala Lys Leu Lys Val Gly Asp Asp
225                 230                 235                 240

Gly Val Pro Thr Lys Glu Phe Asp Ile Asp Leu Ala Phe Phe Asp Thr
                245                 250                 255

Pro Gly Gly Thr Val Asn Gly Gln Asp Glu Tyr Lys Ala Asp Ile Val
            260                 265                 270

Met Tyr Thr Glu Asn Thr Tyr Leu Glu Thr Pro Asp Thr His Val Val
        275                 280                 285
```

-continued

Tyr Lys Pro Gly Lys Asp Asp Ala Ser Ser Glu Ile Asn Leu Val Gln
            290                 295                 300

Gln Ser Met Pro Asn Arg Pro Asn Tyr Ile Gly Phe Arg Asp Asn Phe
305                 310                 315                 320

Ile Gly Leu Met Tyr Tyr Asn Ser Thr Gly Asn Met Gly Val Leu Ala
                    325                 330                 335

Gly Gln Ala Ser Gln Leu Asn Ala Val Val Asp Leu Gln Asp Arg Asn
                340                 345                 350

Thr Glu Leu Ser Tyr Gln Leu Leu Leu Asp Ser Leu Gly Asp Arg Thr
            355                 360                 365

Arg Tyr Phe Ser Met Trp Asn Gln Ala Val Asp Ser Tyr Asp Pro Asp
370                 375                 380

Val Arg Ile Ile Glu Asn His Gly Val Glu Asp Glu Leu Pro Asn Tyr
385                 390                 395                 400

Cys Phe Pro Leu Asp Gly Ser Gly Thr Asn Ala Ala Tyr Gln Gly Val
                405                 410                 415

Lys Val Lys Asp Gly Gln Asp Gly Asp Val Glu Ser Glu Trp Glu Asn
                420                 425                 430

Asp Asp Thr Val Ala Ala Arg Asn Gln Leu Cys Lys Gly Asn Ile Phe
            435                 440                 445

Ala Met Glu Ile Asn Leu Gln Ala Asn Leu Trp Arg Ser Phe Leu Tyr
450                 455                 460

Ser Asn Val Ala Leu Tyr Leu Pro Asp Ser Tyr Lys Tyr Thr Pro Thr
465                 470                 475                 480

Asn Val Thr Leu Pro Thr Asn Thr Asn Thr Tyr Asp Tyr Met Asn Gly
                    485                 490                 495

Arg Val Thr Pro Pro Ser Leu Val Asp Ala Tyr Leu Asn Ile Gly Ala
                500                 505                 510

Arg Trp Ser Leu Asp Pro Met Asp Asn Val Asn Pro Phe Asn His His
            515                 520                 525

Arg Asn Ala Gly Leu Arg Tyr Arg Ser Met Leu Leu Gly Asn Gly Arg
            530                 535                 540

Tyr Val Pro Phe His Ile Gln Val Pro Gln Lys Phe Ala Ile Lys
545                 550                 555                 560

Ser Leu Leu Leu Leu Pro Gly Ser Tyr Thr Tyr Glu Trp Asn Phe Arg
                    565                 570                 575

Lys Asp Val Asn Met Ile Leu Gln Ser Ser Leu Gly Asn Asp Leu Arg
                580                 585                 590

Thr Asp Gly Ala Ser Ile Ala Phe Thr Ser Ile Asn Leu Tyr Ala Thr
            595                 600                 605

Phe Phe Pro Met Ala His Asn Thr Ala Ser Thr Leu Glu Ala Met Leu
610                 615                 620

Arg Asn Asp Thr Asn Asp Gln Ser Phe Asn Asp Tyr Leu Ser Ala Ala
625                 630                 635                 640

Asn Met Leu Tyr Pro Ile Pro Ala Asn Ala Thr Asn Val Pro Ile Ser
                    645                 650                 655

Ile Pro Ser Arg Asn Trp Ala Ala Phe Arg Gly Trp Ser Phe Thr Arg
                660                 665                 670

Leu Lys Thr Arg Glu Thr Pro Ser Leu Gly Ser Gly Phe Asp Pro Tyr
            675                 680                 685

Phe Val Tyr Ser Gly Ser Ile Pro Tyr Leu Asp Gly Thr Phe Tyr Leu
            690                 695                 700

Asn His Thr Phe Lys Lys Val Ser Ile Thr Phe Asp Ser Ser Val Ser
705                 710                 715                 720

```
Trp Pro Gly Asn Asp Arg Leu Leu Thr Pro Asn Glu Phe Glu Ile Lys
                725                 730                 735
Arg Thr Val Asp Gly Glu Gly Tyr Asn Val Ala Gln Cys Asn Met Thr
            740                 745                 750
Lys Asp Trp Phe Leu Val Gln Met Leu Ala His Tyr Asn Ile Gly Tyr
        755                 760                 765
Gln Gly Phe Tyr Val Pro Glu Gly Tyr Lys Asp Arg Met Tyr Ser Phe
    770                 775                 780
Phe Arg Asn Phe Gln Pro Met Ser Arg Gln Val Val Asp Glu Val Asn
785                 790                 795                 800
Tyr Lys Asp Tyr Gln Ala Val Thr Leu Ala Tyr Gln His Asn Asn Ser
                805                 810                 815
Gly Phe Val Gly Tyr Leu Ala Pro Thr Met Arg Gln Gly Gln Pro Tyr
            820                 825                 830
Pro Ala Asn Tyr Pro Tyr Pro Leu Ile Gly Lys Ser Ala Val Ala Ser
        835                 840                 845
Val Thr Gln Lys Lys Phe Leu Cys Asp Arg Val Met Trp Arg Ile Pro
    850                 855                 860
Phe Ser Ser Asn Phe Met Ser Met Gly Ala Leu Thr Asp Leu Gly Gln
865                 870                 875                 880
Asn Met Leu Tyr Ala Asn Ser Ala His Ala Leu Asp Met Asn Phe Glu
                885                 890                 895
Val Asp Pro Met Asp Glu Ser Thr Leu Leu Tyr Val Val Phe Glu Val
            900                 905                 910
Phe Asp Val Val Arg Val His Gln Pro His Arg Gly Val Ile Glu Ala
        915                 920                 925
Val Tyr Leu Arg Thr Pro Phe Ser Ala Gly Asn Ala Thr Thr
    930                 935                 940

<210> SEQ ID NO 8
<211> LENGTH: 443
<212> TYPE: PRT
<213> ORGANISM: chimpanzee adenovirus serotype Pan6

<400> SEQUENCE: 8

Met Ser Lys Lys Arg Val Arg Val Asp Asp Phe Asp Pro Val Tyr
1               5                   10                  15
Pro Tyr Asp Ala Asp Asn Ala Pro Thr Val Pro Phe Ile Asn Pro Pro
                20                  25                  30
Phe Val Ser Ser Asp Gly Phe Gln Glu Lys Pro Leu Gly Val Leu Ser
            35                  40                  45
Leu Arg Leu Ala Asp Pro Val Thr Thr Lys Asn Gly Glu Ile Thr Leu
        50                  55                  60
Lys Leu Gly Glu Gly Val Asp Leu Asp Ser Ser Gly Lys Leu Ile Ser
65                  70                  75                  80
Asn Thr Ala Thr Lys Ala Ala Ala Pro Leu Ser Ile Ser Asn Asn Thr
                85                  90                  95
Ile Ser Leu Lys Thr Ala Ala Pro Phe Tyr Asn Asn Asn Gly Thr Leu
            100                 105                 110
Ser Leu Asn Val Ser Thr Pro Leu Ala Val Phe Pro Thr Phe Asn Thr
        115                 120                 125
Leu Gly Ile Ser Leu Gly Asn Gly Leu Gln Thr Ser Asn Lys Leu Leu
    130                 135                 140
Thr Val Gln Leu Thr His Pro Leu Thr Phe Ser Ser Asn Ser Ile Thr
145                 150                 155                 160
```

```
Val Lys Thr Asp Lys Gly Leu Tyr Ile Asn Ser Ser Gly Asn Arg Gly
            165                 170                 175
Leu Glu Ala Asn Ile Ser Leu Lys Arg Gly Leu Val Phe Asp Gly Asn
        180                 185                 190
Ala Ile Ala Thr Tyr Ile Gly Asn Gly Leu Asp Tyr Gly Ser Tyr Asp
    195                 200                 205
Ser Asp Gly Lys Thr Arg Pro Val Ile Thr Lys Ile Gly Ala Gly Leu
210                 215                 220
Asn Phe Asp Ala Asn Lys Ala Ile Ala Val Lys Leu Gly Thr Gly Leu
225                 230                 235                 240
Ser Phe Asp Ser Ala Gly Ala Leu Thr Ala Gly Asn Lys Gln Asp Asp
            245                 250                 255
Lys Leu Thr Leu Trp Thr Thr Pro Asp Pro Ser Pro Asn Cys Gln Leu
        260                 265                 270
Leu Ser Asp Arg Asp Ala Lys Phe Thr Leu Cys Leu Thr Lys Cys Gly
    275                 280                 285
Ser Gln Ile Leu Gly Thr Val Ala Val Ala Ala Val Thr Val Gly Ser
290                 295                 300
Ala Leu Asn Pro Ile Asn Asp Thr Val Lys Ser Ala Ile Val Phe Leu
305                 310                 315                 320
Arg Phe Asp Ser Asp Gly Val Leu Met Ser Asn Ser Ser Met Val Gly
            325                 330                 335
Asp Tyr Trp Asn Phe Arg Glu Gly Gln Thr Thr Gln Ser Val Ala Tyr
        340                 345                 350
Thr Asn Ala Val Gly Phe Met Pro Asn Ile Gly Ala Tyr Pro Lys Thr
    355                 360                 365
Gln Ser Lys Thr Pro Lys Asn Ser Ile Val Ser Gln Val Tyr Leu Thr
370                 375                 380
Gly Glu Thr Thr Met Pro Met Thr Leu Thr Ile Thr Phe Asn Gly Thr
385                 390                 395                 400
Asp Glu Lys Asp Thr Thr Pro Val Ser Thr Tyr Ser Met Thr Phe Thr
            405                 410                 415
Trp Gln Trp Thr Gly Asp Tyr Lys Asp Lys Asn Ile Thr Phe Ala Thr
        420                 425                 430
Asn Ser Phe Ser Phe Ser Tyr Ile Ala Gln Glu
    435                 440

<210> SEQ ID NO 9
<211> LENGTH: 36535
<212> TYPE: DNA
<213> ORGANISM: chimpanzee adenovirus serotype Pan7
<220> FEATURE:
<221> NAME/KEY: CDS
<222> LOCATION: (13874)..(15469)
<223> OTHER INFORMATION: L2 Penton
<220> FEATURE:
<221> NAME/KEY: CDS
<222> LOCATION: (18288)..(21086)
<223> OTHER INFORMATION: L3 Hexon
<220> FEATURE:
<221> NAME/KEY: CDS
<222> LOCATION: (32094)..(33425)
<223> OTHER INFORMATION: L5 Fiber

<400> SEQUENCE: 9
catcatcaat aatataccte aaacttttgg tgcgcgttaa tatgcaaatg agctgtttga      60
atttggggag ggaggaaggt gattggccga gagacgggcg accgttaggg gcggggcggg     120
tgacgttttt aatacgtggc cgtgaggcgg agccggtttg caagttctcg tgggaaaagt     180
```

```
gacgtcaaac gaggtgtggt ttgaacacgg aaatactcaa ttttcccgcg ctctctgaca    240
ggaaatgagg tgtttctggg cggatgcaag tgaaaacggg ccattttcgc gcgaaaactg    300
aatgaggaag tgaaaatctg agtaatttcg cgtttatggc agggaggagt atttgccgag    360
ggccgagtag actttgaccg attacgtggg ggtttcgatt accgtatttt tcacctaaat    420
ttccgcgtac ggtgtcaaag tccggtgttt ttacgtaggc gtcagctgat cgccagggta    480
tttaaacctg cgctctctag tcaagaggcc actcttgagt gccagcgagt agagttttct    540
cctccgcgcc gcgagtcaga tctacacttt gaaagatgag gcacctgaga gacctgcccg    600
gtaatgtttt cctggctact gggaacgaga ttctggaatt ggtggtggac gccatgatgg    660
gtggcgaccc tcctgagccc cctacccccat ttgaggcgcc ttcgctgtac gatttgtatg    720
atctggaggt ggatgtgccc gagaacgacc ccaacgagga ggcggtgaat gatttgttta    780
gcgatgccgc gctgctggct gccgagcagg ctaatacgga ctctggctca gacagcgatt    840
cctctctcca taccccgaga cccggcagag gtgagaaaaa gatccccgag cttaaagggg    900
aagagctcga cctgcgctgc tatgaggaat gcttgcctcc gagcgatgat gaggaggacg    960
aggaggcgat tcgagctgca tcgaaccagg gagtgaaagc tgcgggcgaa agctttagcc   1020
tggactgtcc tactctgccc ggacacggct gtaagtcttg tgaatttcat cgcatgaata   1080
ctggagataa gaatgtgatg tgtgccctgt gctatatgag agcttacaac cattgtgttt   1140
acagtaagtg tgattaactt tagttgggaa ggcagagggt gactgggtgc tgactggttt   1200
atttatgtat atgttttttt atgtgtaggt cccgtctctg acgtagatga acccccccact   1260
tcagagtgca tttcatcacc cccagaaatt ggcgaggaac cgcccgaaga tattattcat   1320
agaccagttg cagtgagagt caccgggcgg agagcagctg tggagagttt ggatgacttg   1380
ctacagggtg gggatgaacc tttggacttg tgtacccgga aacgccccag gcactaagtg   1440
ccacacatgt gtgtttactt aaggtgatgt cagtatttat agggtgtgga gtgcaataaa   1500
atccgtgttg acttttaagtg cgtggtttat gactcagggg tggggactgt gggtatataa   1560
gcaggtgcag acctgtgtgg tcagttcaga gcaggactca tggagatctg gacggtcttg   1620
gaagactttc accagactag acagctgcta gagaactcat cggagggggt ctcttacctg   1680
tggagattct gcttcggtgg gcctctagct aagctagtct ataggggccaa acaggattat   1740
aaggatcaat ttgaggatat tttgagagag tgtcctggta ttttttgactc tctcaacttg   1800
ggccatcagt ctcactttaa ccagagtatt ctgagagccc ttgacttttc tactcctggc   1860
agaactaccg ccgcggtagc ctttttttgcc tttatccttg acaaatggag tcaagaaacc   1920
catttcagca gggattaccg tctggactgc ttagcagtag cttttgtggag aacatggagg   1980
tgccagcgcc tgaatgcaat ctccggctac ttgccagtac agccggtaga cacgctgagg   2040
atcctgagtc tccagtcacc ccaggaacac caacgccgcc agcagccgca gcaggagcag   2100
cagcaagagg aggaggagga tcgagaagag aacccgagag ccggtctgga ccctccggtg   2160
gcggaggagg aggagtagct gacttgtttc ccgagctgcg ccgggtgctg actaggtctt   2220
ccagtggacg ggagagggggg attaagcggg agaggcatga ggagactagc cacagaactg   2280
aactgactgt cagtctgatg agccgcaggc gcccagaatc ggtgtggtgg catgaggttc   2340
agtcgcaggg gatagatgag gtctcggtga tgcatgaaaa atattccctg gaacaagtca   2400
agacttgttg gttggagcct gaggatgatt gggaggtagc catcaggaat tatgccaagc   2460
tggctctgaa gccagacaag aagtacaaga ttaccaaaact gattaatatc agaaaattcct   2520
gctacatttc agggaatggg gccgaggtgg agatcagtac ccaggagagg gtggccttca   2580
```

```
gatgttgtat gatgaatatg tacccggggg tggtgggcat ggagggagtc acctttatga    2640
acgcgaggtt cagggggtgat gggtataatg gggtggtctt tatggccaac accaagctga   2700
cagtgcacgg atgctccttc tttgggttca ataacatgtg catcgaggcc tggggcagtg    2760
tttcagtgag gggatgcagc ttttcagcca actggatggg ggtcgtgggc agaaccaaga   2820
gcaaggtgtc agtgaagaaa tgcctgttcg agaggtgcca cctgggggtg atgagcgagg   2880
gcgaagccaa agtcaaacac tgcgcctcta ctgagacggg ctgctttgtg ctgatcaagg   2940
gcaatgccca agtcaagcat aacatgatct gtgggcctc ggatgagcgc ggctaccaga   3000
tgctgacctg cgccggtggg aacagccata tgctggccac cgtgcatgtg acctcgcacc   3060
cccgcaagac atggcccgag ttcgagcaca acgtcatgac ccgatgcaat gtgcacctgg   3120
ggtcccgccg aggcatgttc atgccctacc agtgcaacat gcaatttgtg aaggtgctgc   3180
tggagcccga tgccatgtcc agagtgagcc tgacggggggt gtttgacatg aatgtggagc   3240
tgtggaaaat tctgagatat gatgaatcca agaccaggtg ccgggcctgc gaatgcggag   3300
gcaagcacgc caggcttcag cccgtgtgtg tggaggtgac ggaggacctg cgacccgatc   3360
atttggtgtt gtcctgcaac gggacggagt tcggctccag cggggaagaa tctgactaga   3420
gtgagtagtg tttggggggag gtggaggggct tgtatgaggg gcagaatgac taaaatctgt   3480
gtttttctgt gtgttgcagc agcatgagcg gaagcgcctc cttttgaggga ggggtattca   3540 gcccttatct gacggggcgt ctcccctcct gggcgggagt gcgtcagaat gtgatgggat   3600
ccacggtgga cggccggccc gtgcagcccg cgaactcttc aaccctgacc tacgcgaccc   3660
tgagctcctc gtccgtggac gcagctgccg ccgcagctgc tgcttccgcc gccagcgccg   3720
tgcgcggaat ggccctgggc gccggctact acagctctct ggtggccaac tcgacttcca   3780
ccaataatcc cgccagcctg aacgaggaga agctgctgct gctgatggcc cagctcgagg   3840
ccctgaccca gcgcctgggc gagctgaccc agcaggtggc tcagctgcag gcggagacgc   3900
gggccgcggt tgccacggtg aaaaccaaat aaaaaatgaa tcaataaata aacggagacg   3960
gttgttgatt ttaacacaga gtcttgaatc tttatttgat ttttcgcgcg cggtaggccc   4020
tggaccaccg gtctcgatca ttgagcaccc ggtggatttt ttccaggacc cggtagaggt   4080
gggcttggat gttgaggtac atgggcatga gcccgtcccg ggggtggagg tagctccatt   4140
gcagggcctc gtgctcgggg gtggtgttgt aaatcaccca gtcatagcag gggcgcaggg   4200
cgtggtgctg cacgatgtcc ttgaggagga gactgatggc cacgggcagc cccttggtgt   4260
aggtgttgac gaacctgttg agctgggagg gatgcatgcg gggggagatg agatgcatct   4320
tggcctggat cttgagattg gcgatgttcc cgcccagatc ccgccggggg ttcatgttgt   4380
gcaggaccac cagcacggtg tatccggtgc acttggggaa tttgtcatgc aacttggaag   4440
ggaaggcgtg aaagaatttg gagacgcccct tgtgaccgcc caggttttcc atgcactcat   4500
ccatgatgat ggcgatgggc cgtgggcgg cggcctgggc aaagacgttt cggggggtcgg   4560 acacatcgta gttgtggtcc tgggtgagct cgtcataggc cattttaatg aatttggggc   4620
ggagggtgcc cgactggggg acgaaggtgc cctcgatccc gggggcgtag ttgccctcgc   4680
agatctgcat ctcccaggcc ttgagctcgg aggggggat catgtccacc tgcggggcga   4740
tgaaaaaaac ggtttccggg gcgggggaga tgagctgggc cgaaagcagg ttccggagca   4800
gctgggactt gccgcagccg gtgggggccgt agatgacccc gatgaccggc tgcaggtggt   4860
agttgaggga gagacagctg ccgtcctcgc ggaggagggg ggccacctcg ttcatcatct   4920
cgcgcacatg catgttctcg cgcacgagtt ccgccaggag gcgctcgccc cccagcgaga   4980
```

```
ggagctcttg cagcgaggcg aagttttca gcggcttgag yccgtcggcc atgggcattt    5040
tggagagggt ctgttgcaag agttccagac ggtcccagag ctcggtgatg tgctctaggg    5100
catctcgatc cagcagacct cctcgtttcg cgggttgggg cgactgcggg agtagggcac    5160
caggcgatgg gcgtccagcg aggccagggt ccggtccttc cagggtcgca gggtccgcgt    5220
cagcgtggtc tccgtcacgg tgaaggggtg cgcgccgggc tgggcgcttg cgagggtgcg    5280
cttcaggctc atccggctgg tcgagaaccg ctcccggtcg gcgccctgcg cgtcggccag    5340
gtagcaattg agcatgagtt cgtagttgag cgcctcggcc gcgtggccct tggcgcggag    5400
cttacctttg gaagtgtgtc cgcagacggg acagaggagg gacttgaggg cgtagagctt    5460
gggggcgagg aagacggact cggggcgta ggcgtccgcg ccgcagctgg cgcagacggt      5520
ctcgcactcc acgagccagg tgaggtcggg ccggttgggg tcaaaaacga ggtttcctcc    5580 gtgcttttg atgcgtttct tacctctggt ctccatgagc tcgtgtcccc gctgggtgac      5640
aaagaggctg tccgtgtccc cgtagaccga ctttatgggc cggtcctcga gcggggtgcc    5700
gcggtcctcg tcgtagagga accccgccca ctccgagacg aaggcccggg tccaggccag    5760
cacgaaggag gccacgtggg aggggtagcg gtcgttgtcc accagcgggt ccaccttctc    5820
cagggtatgc aagcacatgt ccccctcgtc cacatccagg aaggtgattg gcttgtaagt    5880
gtaggccacg tgaccggggg tcccggccgg ggggtataa aagggggcgg gcccctgctc     5940
gtcctcactg tcttccggat cgctgtccag gagcgccagc tgttggggta ggtattccct     6000
ctcgaaggct ggcataacct cggcactcag gttgtcagtt tctagaaacg aggaggattt     6060
gatattgacg gtgccgttgg agacgccttt catgagcccc tcgtccatct ggtcagaaaa     6120
gacgatcttt ttgttgtcga gcttggtggc gaaggagccg tagagggcgt tggagaggag    6180
cttggcgatg gagcgcatgg tctggttctt ttccttgtcg gcgcgctcct tggcggcgat     6240
gttgagctgc acgtactcgc gcgccacgca cttccattcg gggaagacgg tggtgagctc    6300
gtcgggcacg attctgaccc gccagccgcg gttgtgcagg gtgatgaggt ccacgctggt    6360
ggccacctcg ccgcgcaggg gctcgttggt ccagcagagg cgcccgccct tgcgcgagca    6420
gaaggggggc agcgggtcca gcatgagctc gtcgggggg tcggcgtcca cggtgaagat     6480
gccgggcaga agctcggggt cgaagtagct gatgcaggtg tccagatcgt ccagcgccgc    6540
ttgccagtcg cgcacggcca gcgcgcgctc gtaggggctg aggggcgtgc cccagggcat    6600
ggggtgcgtg agcgcggagg cgtacatgcc gcagatgtcg tagacgtaga ggggctcctc    6660
gaggacgccg atgtaggtgg ggtagcagcg ccccccgcgg atgctggcgc gcacgtagtc    6720
gtacagctcg tgcgagggcg cgaggagccc cgtgccgagg ttggagcgtt gcggcttttc    6780
ggcgcggtag acgatctggc ggaagatggc gtgggagttg gaggagatgg tgggcctctg    6840
gaagatgttg aagtgggcgt ggggcaggcc gaccgagtcc ctgatgaagt gggcgtagga    6900
gtcctgcagc ttggcgacga gctcggcggt gacgaggacg tccagggcgc agtagtcgag    6960
ggtctcttgg atgatgtcgt acttgagctg gcccttctgc ttccacagct cgcggttgag    7020
aaggaactct tcgcggtcct tccagtactc ttcgagggg aacccgtcct gatcggcacg     7080
gtaagagccc accatgtaga actggttgac ggccttgtag gcgcagcagc ccttctccac    7140
ggggagggcg taagcttgtg cggccttgcg caggaggtg tgggtgaggg cgaaggtgtc      7200
gcgcaccatg accttgagga actggtgctt gaagtcgagg tcgtcgcagc cgccctgctc    7260
ccagagctgg aagtccgtgc gcttcttgta ggcggggttg gcaaagcga aagtaacatc      7320 gttgaagagg atcttgcccg cgcggggcat gaagttgcga gtgatgcgga aaggctgggg    7380
```

```
cacctcggcc cggttgttga tgacctgggc ggcgaggacg atctcgtcga agccgttgat   7440
gttgtgcccg acgatgtaga gttccacgaa tcgcgggcgg cccttaacgt ggggcagctt   7500
cttgagctcg tcgtaggtga gctcggcggg gtcgctgagc ccgtgctgct cgagggccca   7560
gtcggcgacg tgggggttgg cgctgaggaa ggaagtccag agatccacgg ccagggcggt   7620
ctgcaagcgg tcccggtact gacggaactg ctggcccacg gccatttttt cggggggtgac  7680 gcagtagaag gtgcgggggt cgccgtgcca gcggtcccac ttgagctgga gggcgaggtc   7740
gtgggcgagc tcgacgagcg gcgggtcccc ggagagtttc atgaccagca tgaaggggac   7800
gagctgcttg ccgaaggacc ccatccaggt gtaggtttcc acatcgtagg tgaggaagag   7860
cctttcggtg cgaggatgcg agccgatggg gaagaactgg atctcctgcc accagttgga   7920
ggaatggctg ttgatgtgat ggaagtagaa atgccgacgg cgcgccgagc actcgtgctt   7980
gtgtttatac aagcgtccgc agtgctcgca acgctgcacg ggatgcacgt gctgcacgag   8040
ctgtacctgg gttcctttga cgaggaattt cagtgggcag tggagcgctg gcggctgcat   8100
ctggtgctgt actacgtcct ggccatcggc gtggccatcg tctgcctcga tggtggtcat   8160
gctgacgagc ccgcgcggga ggcaggtcca gacttcggct cggacgggtc ggagagcgag   8220
gacgagggcg cgcaggccgg agctgtccag ggtcctgaga cgctgcggag tcaggtcagt   8280
gggcagcggc ggcgcgcggt tgacttgcag gagcttttcc agggcgcgcg ggaggtccag   8340
atggtacttg atctccacgg cgccgttggt ggcgacgtcc acggcttgca gggtcccgtg   8400 ccctgggcg gccaccaccg tgccccgttt cttcttgggc gctgcttcca tgccggtcag   8460
aagcggcggc gaggacgcgc gccgggcggc aggggcggct cgggacccgg aggcaggggc   8520
ggcaggggca cgtcggcgcc gcgcgcggc aggttctggt actgcgcccg gagaagactg   8580
gcgtgagcga cgacgcgacg gttgacgtcc tggatctgac gcctctgggt gaaggccacg   8640
ggacccgtga gtttgaacct gaaagagagt tcgacagaat caatctcggt atcgttgacg   8700
gcggcctgcc gcaggatctc ttgcacgtcg cccgagttgt cctggtaggc gatctcggtc   8760
atgaactgct cgatctcctc ctcctgaagg tctccgcggc cggcgcgctc gacggtggcc   8820
gcgaggtcgt tggagatgcg gcccatgagc tgcgagaagg cgttcatgcc ggcctcgttc   8880
cagacgcggc tgtagaccac ggctccgtcg ggtcgcgcg cgcgcatgac cacctgggcg   8940
aggttgagct cgacgtggcg cgtgaagacc gcgtagttgc agaggcgctg gtagaggtag   9000
ttgagcgtgg tggcgatgtg ctcggtgacg aagaagtaca tgatccagcg gcggagcggc   9060
atctcgctga cgtcgcccag ggcttccaag cgctccatgg cctcgtagaa gtccacggcg   9120
aagttgaaaa actgggagtt gcgcgccgag acggtcaact cctcctccag aagacggatg   9180
agctcagcga tggtggcgcg cacctcgcgc tcgaaggccc cgggggctc ctcttcttcc    9240 atctcttcct cctccactaa catctcttct acttcctcct caggaggcgg cggcggggga   9300 gggcctgc gtcgccggcg gcgcacgggc agacggtcga tgaagcgctc gatggtctcc     9360
ccgcgccggc gacgcatggt ctcggtgacg gcgcgcccgt cctcgcgggg ccgcagcgtg   9420
aagacgccgc cgcgcatctc caggtggccg ccgggggggt ctccgttggg cagggagagg   9480
gcgctgacga tgcatcttat caattggccc gtagggactc cgcgcaagga cctgagcgtc   9540
tcgagatcca cgggatccga aaaccgctga acgaaggctt cgagccagtc gcagtcgcaa   9600
ggtaggctga gccggttttc ttgttcttcg gggatttcgg gaggcgggcg ggcgatgctg   9660
ctggtgatga agttgaagta ggcggtcctg agacggcgga tggtggcgag gagcaccagg   9720
tccttgggcc cggcttgctg gatgcgcaga cggtcggcca tgccccaggc gtggtcctga   9780
```

```
cacctggcga ggtccttgta gtagtcctgc atgagccgct ccacgggcac ctcctcctcg    9840
cccgcgcggc cgtgcatgcg cgtgagcccg aacccgcgct ggggctggac gagcgccagg    9900
tcggcgacga cgcgctcggc gaggatggcc tgctgtatct gggtgagggt ggtctggaag    9960
tcgtcgaagt cgacgaagcg gtggtaggct ccggtgttga tggtatagga gcagttggcc   10020
atgacggacc agttgacggt ctggtggccg ggtcgcacga gctcgtggta cttgaggcgc   10080
gagtaggcgc gcgtgtcgaa gatgtagtcg ttgcaggtgc gcacgaggta ctggtatccg   10140
acgaggaagt gcggcggcgg ctggcggtag agcggccatc gctcggtggc ggggcgccg    10200
ggcgcgaggt cctcgagcat gaggcggtgg tagccgtaga tgtacctgga catccaggtg   10260
atgccgcgg cggtggtgga ggcgcgcggg aactcgcgga cgcggttcca gatgttgcgc    10320
agcggcagga agtagttcat ggtggccgcg gtctggcccg tgaggcgcgc gcagtcgtgg   10380
atgctctaga catacgggca aaaacgaaag cggtcagcgg ctcgactccg tggcctggag   10440
gctaagcgaa cgggttgggc tgcgcgtgta ccccggttcg aatctcgaat caggctggag   10500
ccgcagctaa cgtggtactg gcactcccgt ctcgacccaa gcctgctaac gaaacctcca   10560
ggatacgag gcgggtcgtt ttttggcctt ggtcgctggt catgaaaaac tagtaagcgc    10620
ggaaagcgac cgcccgcgat ggctcgctgc cgtagtctgg agaaagaatc gccagggttg   10680
cgttgcggtg tgccccggtt cgagcctcag cgctcggcgc cggccggatt ccgcggctaa   10740
cgtgggcgtg gctgccccgt cgtttccaag accccttagc cagccgactt ctccagttac   10800
ggagcgagcc cctctttttc ttgtgttttt gccagatgca tcccgtactg cggcagatgc   10860
gcccccaccc tccacctcaa ccgcccctac cgccgcagca gcagcaacag ccggcgcttc   10920
tgccccgcc ccagcagcag ccagccacta ccgcggcggc cgccgtgagc ggagccggcg    10980
ttcagtatga cctggccttg aagagggcg aggggctggc gcggctgggg gcgtcgtcgc     11040
cggagcggca cccgcgcgtg cagatgaaaa gggacgctcg cgaggcctac gtgcccaagc   11100
agaacctgtt cagagacagg agcggcgagg agcccgagga gatgcgcgcc tcccgcttcc   11160
acgcggggcg ggagctgcgg cgcggcctgg accgaaagcg ggtgctgagg gacgaggatt   11220
tcgaggcgga cgagctgacg gggatcagcc ccgcgcgcgc gcacgtggcc gcggccaacc   11280
tggtcacggc gtacgagcag accgtgaagg aggagagcaa cttccaaaaa tccttcaaca   11340
accacgtgcg cacgctgatc gcgcgcgagg aggtgaccct gggcctgatg cacctgtggg   11400
acctgctgga ggccatcgtg cagaacccca cgagcaagcc gctgacggcg cagctgtttc   11460
tggtggtgca gcacagtcgg gacaacgaga cgttcaggga ggcgctgctg aatatcaccg   11520
agcccgaggg ccgctggctc ctggacctgg tgaacattct gcagagcatc gtggtgcagg   11580
agcgcgggct gccgctgtcc gagaagctgg cggctatcaa cttctcggtg ctgagcctgg   11640
gcaagtacta cgctaggaag atctacaaga ccccgtacgt gcccatagac aaggaggtga   11700
agatcgacgg gttttacatg cgcatgaccc tgaaagtgct gaccctgagc gacgatctgg   11760
gggtgtaccg caacgacagg atgcaccgcg cggtgagcgc cagccgccgg cgcgagctga   11820
gcgaccagga gctgatgcac agcctgcagc gggccctgac cggggccggg accgagggg     11880
agagctactt tgacatgggc gcggacctgc gctggcagcc cagccgccgg gccttggaag   11940
ctgccggcgg ttcccctac gtggaggagg tggacgatga ggaggaggag ggcgagtacc    12000
tggaagactg atggcgcgac cgtattttg ctagatgcag caacagccac cgcctcctga    12060
tcccgcgatg cgggcggcgc tgcagagcca gccgtccggc attaactcct cggacgattg   12120
gacccaggcc atgcaacgca tcatggcgct gacgacccgc aatcccgaag cctttagaca   12180
```

```
gcagcctcag gccaaccggc tctcggccat cctggaggcc gtggtgccct cgcgctcgaa   12240
ccccacgcac gagaaggtgc tggccatcgt gaacgcgctg gtggagaaca aggccatccg   12300
cggcgacgag gccgggctgg tgtacaacgc gctgctggag cgcgtggccc gctacaacag   12360
caccaacgtg cagacgaacc tggaccgcat ggtgaccgac gtgcgcgagg cggtgtcgca   12420
gcgcgagcgg ttccaccgcg agtcgaacct gggctccatg gtggcgctga acgccttcct   12480
gagcacgcag cccgccaacg tgccccgggg ccaggaggac tacaccaact tcatcagcgc   12540
gctgcggctg atggtggccg aggtgcccca gagcgaggtg taccagtcgg ggccggacta   12600
cttcttccag accagtcgcc agggcttgca gaccgtgaac ctgagccagg ctttcaagaa   12660
cttgcaggga ctgtggggcg tgcaggcccc ggtcggggac cgcgcgacgg tgtcgagcct   12720
gctgacgccg aactcgcgcc tgctgctgct gctggtggcg cccttcacgg acagcggcag   12780
cgtgagccgc gactcgtacc tgggctacct gcttaacctg taccgcgagg ccatcgggca   12840
ggcgcacgtg gacgagcaga cctaccagga gatcacccac gtgagccgcg cgctgggcca   12900
ggaggacccg ggcaacctgg aggccaccct gaacttcctg ctgaccaacc ggtcgcagaa   12960
gatcccgccc cagtacgcgc tgagcaccga ggaggagcgc atcctgcgct acgtgcagca   13020
gagcgtgggg ctgttcctga tgcaggaggg ggccacgccc agcgccgcgc tcgacatgac   13080
cgcgcgcaac atggagccca gcatgtacgc tcgcaaccgc ccgttcatca ataagctgat   13140
ggactacttg catcgggcgg ccgccatgaa ctcggactac tttaccaacg ccatcttgaa   13200
cccgcactgg ctcccgccgc ccgggttcta cacgggcgag tacgacatgc ccgaccccaa   13260
cgacgggttc ctgtgggacg acgtggacag cagcgtgttc tcgccgcgcc ccgccaccac   13320
cgtgtggaag aaagagggcg gggaccggcg gccgtcctcg gcgctgtccg gtcgcgcggg   13380
tgctgccgcg gcggtgcctg aggccgccag ccccttcccg agcctgccct tttcgctgaa   13440
cagcgtgcgc agcagcgagc tgggtcggct gacgcggccg cgcctgctgg gcgaggagga   13500
gtacctgaac gactccttgt tgaggcccga gcgcgagaag aacttcccca ataacgggat   13560
agagagcctg gtggacaaga tgagccgctg gaagacgtac gcgcacgagc acagggcgga   13620
gccccgagct agcagcagcg caggcacccg tagacgccag cgacacgaca ggcagcgggg   13680
tctggtgtgg gacgatgagg attccgccga cgacagcagc gtgttggact ggggtgggag   13740
tggtggtggt aacccgttcg ctcacttgcg cccccgtatc gggcgcctga tgtaagaatc   13800
tgaaaaaata aaaacggta ctcaccaagg ccatggcgac cagcgtgcgt tcttctctgt   13860
tgtttgtagt agt atg atg agg cgc gtg tac ccg gag ggt cct cct ccc       13909
            Met Met Arg Arg Val Tyr Pro Glu Gly Pro Pro Pro
              1               5                  10 tcg tac gag agc gtg atg cag cag gcg gtg gcg gcg gcg atg cag ccc       13957
Ser Tyr Glu Ser Val Met Gln Gln Ala Val Ala Ala Ala Met Gln Pro
          15                  20                  25 ccg ctg gag gcg cct tac gtg ccc ccg cgg tac ctg gcg cct acg gag       14005
Pro Leu Glu Ala Pro Tyr Val Pro Pro Arg Tyr Leu Ala Pro Thr Glu
    30                  35                  40 ggg cgg aac agc att cgt tac tcg gag ctg gca ccc ttg tac gat acc       14053
Gly Arg Asn Ser Ile Arg Tyr Ser Glu Leu Ala Pro Leu Tyr Asp Thr
45                  50                  55                  60 acc cgg ttg tac ctg gtg gac aac aag tcg gcg gac atc gcc tcg ctg       14101
Thr Arg Leu Tyr Leu Val Asp Asn Lys Ser Ala Asp Ile Ala Ser Leu
                65                  70                  75 aac tac cag aac gac cac agc aac ttc ctg acc acc gtg gtg cag aac       14149
Asn Tyr Gln Asn Asp His Ser Asn Phe Leu Thr Thr Val Val Gln Asn
        80                  85                  90
```

```
aac gat ttc acc ccc acg gag gcc agc acc cag acc atc aac ttt gac     14197
Asn Asp Phe Thr Pro Thr Glu Ala Ser Thr Gln Thr Ile Asn Phe Asp
         95                 100                 105 gag cgc tcg cgg tgg ggc ggc cag ctg aaa acc atc atg cac acc aac     14245
Glu Arg Ser Arg Trp Gly Gly Gln Leu Lys Thr Ile Met His Thr Asn
110                 115                 120 atg ccc aac gtg aac gag ttc atg tac agc aac aag ttc aag gcg cgg     14293
Met Pro Asn Val Asn Glu Phe Met Tyr Ser Asn Lys Phe Lys Ala Arg
125                 130                 135                 140 gtg atg gtc tcg cgc aag acc ccc aat ggg gtc gcg gtg gat gag aat     14341
Val Met Val Ser Arg Lys Thr Pro Asn Gly Val Ala Val Asp Glu Asn
                145                 150                 155 tat gat ggt agt cag gac gag ctg act tac gag tgg gtg gag ttt gag     14389
Tyr Asp Gly Ser Gln Asp Glu Leu Thr Tyr Glu Trp Val Glu Phe Glu
            160                 165                 170 ctg ccc gag ggc aac ttc tcg gtg acc atg acc atc gat ctg atg aac     14437
Leu Pro Glu Gly Asn Phe Ser Val Thr Met Thr Ile Asp Leu Met Asn
        175                 180                 185 aac gcc atc atc gac aac tac ttg gcg gtg ggg cgt cag aac ggg gtg     14485
Asn Ala Ile Ile Asp Asn Tyr Leu Ala Val Gly Arg Gln Asn Gly Val
    190                 195                 200 ctg gag agc gac atc ggc gtg aag ttc gac acg cgc aac ttc cgg ctg     14533
Leu Glu Ser Asp Ile Gly Val Lys Phe Asp Thr Arg Asn Phe Arg Leu
205                 210                 215                 220 ggc tgg gac ccc gtg acc gag ctg gtg atg ccg ggc gtg tac acc aac     14581
Gly Trp Asp Pro Val Thr Glu Leu Val Met Pro Gly Val Tyr Thr Asn
                225                 230                 235 gag gcc ttc cac ccc gac atc gtc ctg ctg ccc ggc tgc ggc gtg gac     14629
Glu Ala Phe His Pro Asp Ile Val Leu Leu Pro Gly Cys Gly Val Asp
            240                 245                 250 ttc acc gag agc cgc ctc agc aac ctg ctg ggc atc cgc aag cgg cag     14677
Phe Thr Glu Ser Arg Leu Ser Asn Leu Leu Gly Ile Arg Lys Arg Gln
        255                 260                 265 ccc ttc cag gag ggc ttc cag atc ctg tac gag gac ctg gag ggg ggc     14725
Pro Phe Gln Glu Gly Phe Gln Ile Leu Tyr Glu Asp Leu Glu Gly Gly
    270                 275                 280 aac atc ccc gcg ctc ttg gat gtc gaa gcc tat gag aaa agc aag gag     14773
Asn Ile Pro Ala Leu Leu Asp Val Glu Ala Tyr Glu Lys Ser Lys Glu
285                 290                 295                 300 gag gcc gcc gca gcg gcg acc gca gcc gtg gcc acc gcc tct acc gag     14821
Glu Ala Ala Ala Ala Thr Ala Ala Val Ala Thr Ala Ser Thr Glu
                305                 310                 315 gtg cgg ggc gat aat ttt gct agc gcc gcg gca gtg gcc gag gcg gct     14869
Val Arg Gly Asp Asn Phe Ala Ser Ala Ala Ala Val Ala Glu Ala Ala
            320                 325                 330 gaa acc gaa agt aag ata gtc atc cag ccg gtg gag aag gac agc aag     14917
Glu Thr Glu Ser Lys Ile Val Ile Gln Pro Val Glu Lys Asp Ser Lys
        335                 340                 345 gac agg agc tac aac gtg ctc gcg gac aag aaa aac acc gcc tac cgc     14965
Asp Arg Ser Tyr Asn Val Leu Ala Asp Lys Lys Asn Thr Ala Tyr Arg
    350                 355                 360 agc tgg tac ctg gcc tac aac tac ggc gac ccc gag aag ggc gtg cgc     15013
Ser Trp Tyr Leu Ala Tyr Asn Tyr Gly Asp Pro Glu Lys Gly Val Arg
365                 370                 375                 380 tcc tgg acg ctg ctc acc acc tcg gac gtc acc tgc ggc gtg gag caa     15061
Ser Trp Thr Leu Leu Thr Thr Ser Asp Val Thr Cys Gly Val Glu Gln
                385                 390                 395 gtc tac tgg tcg ctg ccc gac atg atg caa gac ccg gtc acc ttc cgc     15109
Val Tyr Trp Ser Leu Pro Asp Met Met Gln Asp Pro Val Thr Phe Arg
            400                 405                 410
```

| | | | | | | | | | | | | | | | |
|---|---|---|---|---|---|---|---|---|---|---|---|---|---|---|---|
| tcc | acg | cgt | caa | gtt | agc | aac | tac | ccg | gtg | gtg | ggc | gcc | gag | ctc | ctg | 15157 |
| Ser | Thr | Arg | Gln | Val | Ser | Asn | Tyr | Pro | Val | Val | Gly | Ala | Glu | Leu | Leu | |
| | 415 | | | | | 420 | | | | | 425 | | | | | |

| ccc | gtc | tac | tcc | aag | agc | ttc | ttc | aac | gag | cag | gcc | gtc | tac | tcg | cag | 15205 |
|---|---|---|---|---|---|---|---|---|---|---|---|---|---|---|---|---|
| Pro | Val | Tyr | Ser | Lys | Ser | Phe | Phe | Asn | Glu | Gln | Ala | Val | Tyr | Ser | Gln | |
| 430 | | | | | 435 | | | | | 440 | | | | | | |

| cag | ctg | cgc | gcc | ttc | acc | tcg | ctc | acg | cac | gtc | ttc | aac | cgc | ttc | ccc | 15253 |
|---|---|---|---|---|---|---|---|---|---|---|---|---|---|---|---|---|
| Gln | Leu | Arg | Ala | Phe | Thr | Ser | Leu | Thr | His | Val | Phe | Asn | Arg | Phe | Pro | |
| 445 | | | | 450 | | | | | 455 | | | | | 460 | | |

| gag | aac | cag | atc | ctc | gtc | cgc | ccg | ccc | gcg | ccc | acc | att | acc | acc | gtc | 15301 |
|---|---|---|---|---|---|---|---|---|---|---|---|---|---|---|---|---|
| Glu | Asn | Gln | Ile | Leu | Val | Arg | Pro | Pro | Ala | Pro | Thr | Ile | Thr | Thr | Val | |
| | | | 465 | | | | | 470 | | | | | 475 | | | |

| agt | gaa | aac | gtt | cct | gct | ctc | aca | gat | cac | ggg | acc | ctg | ccg | ctg | cgc | 15349 |
|---|---|---|---|---|---|---|---|---|---|---|---|---|---|---|---|---|
| Ser | Glu | Asn | Val | Pro | Ala | Leu | Thr | Asp | His | Gly | Thr | Leu | Pro | Leu | Arg | |
| | | 480 | | | | | 485 | | | | | 490 | | | | |

| agc | agt | atc | cgg | gga | gtc | cag | cgc | gtg | acc | gtc | act | gac | gcc | aga | cgc | 15397 |
|---|---|---|---|---|---|---|---|---|---|---|---|---|---|---|---|---|
| Ser | Ser | Ile | Arg | Gly | Val | Gln | Arg | Val | Thr | Val | Thr | Asp | Ala | Arg | Arg | |
| | | 495 | | | | 500 | | | | | 505 | | | | | |

| cgc | acc | tgc | ccc | tac | gtc | tac | aag | gcc | ctg | ggc | gta | gtc | gcg | ccg | cgc | 15445 |
|---|---|---|---|---|---|---|---|---|---|---|---|---|---|---|---|---|
| Arg | Thr | Cys | Pro | Tyr | Val | Tyr | Lys | Ala | Leu | Gly | Val | Val | Ala | Pro | Arg | |
| 510 | | | | | 515 | | | | | 520 | | | | | | |

| gtc | ctc | tcg | agc | cgc | acc | ttc | taa | aaaatgtcca | ttctcatctc | gcccagtaat | 15499 |
|---|---|---|---|---|---|---|---|---|---|---|---|
| Val | Leu | Ser | Ser | Arg | Thr | Phe | | | | | |
| 525 | | | | 530 | | | | | | | |

| | |
|---|---|
| aacaccggtt ggggcctgcg cgcgcccagc aagatgtacg gaggcgctcg ccaacgctcc | 15559 |
| acgcaacacc ccgtgcgcgt gcgcgggcac ttccgcgctc cctggggcgc cctcaagggc | 15619 |
| cgcgtgcgct cgcgcaccac cgtcgacgac gtgatcgacc aggtggtggc cgacgcgcgc | 15679 |
| aactacacgc ccgccgccgc gcccgcctcc accgtggacg ccgtcatcga cagcgtggtg | 15739 |
| gccgatgcgc gccggtacgc ccgcgccaag agccggcggc ggcgcatcgc ccggcggcac | 15799 |
| cggagcaccc ccgccatgcg cgcggcgcga gccttgctgc gcagggccag cgcacgggac | 15859 |
| cgcagggcca tgctcagggc ggccagacgc gcggcctccg gcagcagcag cgccggcagg | 15919 |
| acccgcagac gcgcggccac ggcggcgcg gcggccatcg ccagcatgtc ccgcccgcgg | 15979 |
| cgcggcaacg tgtactgggt gcgcgacgcc gccaccggtg tgcgcgtgcc cgtgcgcacc | 16039 |
| cgccccctc gcacttgaag atgctgactt cgcgatgttg atgtgtccca gcggcgagga | 16099 |
| ggatgtccaa gcgcaaatac aaggaagaga tgctccaggt catcgcgcct gagatctacg | 16159 |
| gccccgcgt gaaggaggaa agaaagcccc gcaaactgaa gcgggtcaaa aggacaaaa | 16219 |
| aggaggagga agatgtggac ggactggtgg agtttgtgcg cgagttcgcc ccccggcggc | 16279 |
| gcgtgcagtg gcgcgggcgg aaagtgaaac cggtgctgcg gcccggcacc acggtggtct | 16339 |
| tcacgcccgg cgagcgttcc ggctccgcct ccaagcgctc ctacgacgag gtgtacgggg | 16399 |
| acgaggacat cctcgagcag gcggtcgagc gtctgggcga gtttgcttac ggcaagcgca | 16459 |
| gccgccccgc gcccttgaaa gaggaggcgg tgtccatccc gctggaccac ggcaacccca | 16519 |
| cgccgagcct gaagccggtg accctgcagc aggtgctgcc gagcgcggcg ccgcgccggg | 16579 |
| gcttcaagcg cgagggcggc gaggatctgt acccgaccat gcagctgatg gtgcccaagc | 16639 |
| gccagaagct ggaggacgtg ctggagcaca tgaaggtgga ccccgaggtg cagcccgagg | 16699 |
| tcaaggtgcg gcccatcaag caggtggccc cgggcctggg cgtgcagacc gtggacatca | 16759 |
| agatccccac ggagcccatg gaaacgcaga ccgagcccgt gaagcccagc accagcacca | 16819 |
| tggaggtgca gacggatccc tggatgccgg cgccggcttc caccactcgc cgaagacgca | 16879 |
| agtacggcgc ggccagcctg ctgatgccca actacgcgct gcatccttcc atcatcccca | 16939 |

```
cgccgggcta ccgcggcacg cgcttctacc gcggctacac cagcagccgc cgcaagacca    16999
ccaccccgccg ccgccgtcgt cgcacccgcc gcagcagcac cgcgacttcc gccgccgccc    17059
tggtgcggag agtgtaccgc agcgggcgcg agcctctgac cctgccgcgc gcgcgctacc    17119
acccgagcat cgccatttaa ctctgccgtc gcctcctact tgcagatatg gccctcacat    17179
gccgcctccg cgtccccatt acgggctacc gaggaagaaa gccgcgccgt agaaggctga    17239
cggggaacgg gctgcgtcgc catcaccacc ggcggcggcg cgccatcagc aagcggttgg    17299
ggggaggctt cctgcccgcg ctgatcccca tcatcgccgc ggcgatcggg gcgatccccg    17359
gcatagcttc cgtggcggtg caggcctctc agcgccactg agacacagct tggaaaattt    17419
gtaataaaaa aatggactga cgctcctggt cctgtgatgt gtgtttttag atggaagaca    17479
tcaattttc gtccctggca ccgcgacacg gcacgcggcc gtttatgggc acctggagcg    17539
acatcggcaa cagccaactg aacggggggcg ccttcaattg gagcagtctc tggagcgggc    17599
ttaagaattt cgggtccacg ctcaaaacct atggcaacaa ggcgtggaac agcagcacag    17659
ggcaggcgct gagggaaaag ctgaaagagc agaacttcca gcagaaggtg gtcgatggcc    17719
tggcctcggg catcaacggg gtggtggacc tggccaacca ggccgtgcag aaacagatca    17779
acagccgcct ggacgcggtc ccgcccgcgg ggtccgtgga gatgccccag gtggaggagg    17839
agctgcctcc cctggacaag cgcggcgaca agcgaccgcg tcccgacgcg gaggagacgc    17899
tgctgacgca cacggacgag ccgcccccgt acgaggaggc ggtgaaactg ggtctgccca    17959
ccacgcggcc cgtggcgcct ctggccaccg gggtgctgaa acccagcagc agcagccagc    18019
ccgcgaccct ggacttgcct ccgcctgctt cccgcccctc cacagtggct aagcccctgc    18079
cgccggtggc cgtcgcgtcg cgcgcccccc gaggccgccc ccaggcgaac tggcagagca    18139
ctctgaacag catcgtgggt ctgggagtgc agagtgtgaa gcgccgccgc tgctattaaa    18199
agacactgta gcgcttaact tgcttgtctg tgtgtatatg tatgtccgcc gaccagaagg    18259
aggaagaggc gcgtcgccga gttgcaag atg gcc acc cca tcg atg ctg ccc       18311
                                Met Ala Thr Pro Ser Met Leu Pro
                                                535 cag tgg gcg tac atg cac atc gcc gga cag gac gct tcg gag tac ctg     18359
Gln Trp Ala Tyr Met His Ile Ala Gly Gln Asp Ala Ser Glu Tyr Leu
540             545                 550                 555 agt ccg ggt ctg gtg cag ttc gcc cgc gcc aca gac acc tac ttc agt     18407
Ser Pro Gly Leu Val Gln Phe Ala Arg Ala Thr Asp Thr Tyr Phe Ser
                560                 565                 570 ctg ggg aac aag ttt agg aac ccc acg gtg gcg ccc acg cac gat gtg     18455
Leu Gly Asn Lys Phe Arg Asn Pro Thr Val Ala Pro Thr His Asp Val
            575                 580                 585 acc acc gac cgc agc cag cgg ctg acg ctg cgc ttc gtg ccc gtg gac     18503
Thr Thr Asp Arg Ser Gln Arg Leu Thr Leu Arg Phe Val Pro Val Asp
        590                 595                 600 cgc gag gac aac acc tac tcg tac aaa gtg cgc tac acg ctg gcc gtg     18551
Arg Glu Asp Asn Thr Tyr Ser Tyr Lys Val Arg Tyr Thr Leu Ala Val
605                 610                 615 ggc gac aac cgc gtg ctg gac atg gcc agc acc tac ttt gac atc cgc     18599
Gly Asp Asn Arg Val Leu Asp Met Ala Ser Thr Tyr Phe Asp Ile Arg
620                 625                 630                 635 ggc gtg ctg gat cgg ggg ccc agc ttc aaa ccc tac tcc ggc acc gcc     18647
Gly Val Leu Asp Arg Gly Pro Ser Phe Lys Pro Tyr Ser Gly Thr Ala
                640                 645                 650 tac aac agc ctg gct ccc aag gga gcg ccc aac act tgc cag tgg aca     18695
Tyr Asn Ser Leu Ala Pro Lys Gly Ala Pro Asn Thr Cys Gln Trp Thr
            655                 660                 665
```

| | |
|---|---|
| tat aaa gct ggt gat act gat aca gaa aaa acc tat aca tat gga aat<br>Tyr Lys Ala Gly Asp Thr Asp Thr Glu Lys Thr Tyr Thr Tyr Gly Asn<br>670 675 680 | 18743 |
| gca cct gtg caa ggc att agc att aca aag gat ggt att caa ctt gga<br>Ala Pro Val Gln Gly Ile Ser Ile Thr Lys Asp Gly Ile Gln Leu Gly<br>685 690 695 | 18791 |
| act gac agc gat ggt cag gca atc tat gca gac gaa act tat caa cca<br>Thr Asp Ser Asp Gly Gln Ala Ile Tyr Ala Asp Glu Thr Tyr Gln Pro<br>700 705 710 715 | 18839 |
| gag cct caa gtg ggt gat gct gaa tgg cat gac atc act ggt act gat<br>Glu Pro Gln Val Gly Asp Ala Glu Trp His Asp Ile Thr Gly Thr Asp<br>720 725 730 | 18887 |
| gaa aaa tat gga ggc aga gct ctt aag cct gac acc aaa atg aag cct<br>Glu Lys Tyr Gly Gly Arg Ala Leu Lys Pro Asp Thr Lys Met Lys Pro<br>735 740 745 | 18935 |
| tgc tat ggt tct ttt gcc aag cct acc aat aaa gaa gga ggc cag gca<br>Cys Tyr Gly Ser Phe Ala Lys Pro Thr Asn Lys Glu Gly Gly Gln Ala<br>750 755 760 | 18983 |
| aat gtg aaa acc gaa aca ggc ggt acc aaa gaa tat gac att gac atg<br>Asn Val Lys Thr Glu Thr Gly Gly Thr Lys Glu Tyr Asp Ile Asp Met<br>765 770 775 | 19031 |
| gca ttc ttc gat aat cga agt gca gct gcc gcc ggc cta gcc cca gaa<br>Ala Phe Phe Asp Asn Arg Ser Ala Ala Ala Ala Gly Leu Ala Pro Glu<br>780 785 790 795 | 19079 |
| att gtt ttg tat act gag aat gtg gat ctg gaa act cca gat acc cat<br>Ile Val Leu Tyr Thr Glu Asn Val Asp Leu Glu Thr Pro Asp Thr His<br>800 805 810 | 19127 |
| att gta tac aag gca ggt aca gat gac agt agc tct tct atc aat ttg<br>Ile Val Tyr Lys Ala Gly Thr Asp Asp Ser Ser Ser Ser Ile Asn Leu<br>815 820 825 | 19175 |
| ggt cag cag tcc atg ccc aac aga ccc aac tac att ggc ttc aga gac<br>Gly Gln Gln Ser Met Pro Asn Arg Pro Asn Tyr Ile Gly Phe Arg Asp<br>830 835 840 | 19223 |
| aac ttt atc ggt ctg atg tac tac aac agc act ggc aat atg ggt gta<br>Asn Phe Ile Gly Leu Met Tyr Tyr Asn Ser Thr Gly Asn Met Gly Val<br>845 850 855 | 19271 |
| ctg gct gga cag gcc tcc cag ctg aat gct gtg gtg gac ttg cag gac<br>Leu Ala Gly Gln Ala Ser Gln Leu Asn Ala Val Val Asp Leu Gln Asp<br>860 865 870 875 | 19319 |
| aga aac acc gaa ctg tcc tac cag ctc ttg ctt gac tct ctg ggt gac<br>Arg Asn Thr Glu Leu Ser Tyr Gln Leu Leu Leu Asp Ser Leu Gly Asp<br>880 885 890 | 19367 |
| aga acc agg tat ttc agt atg tgg aat cag gcg gtg gac agt tat gac<br>Arg Thr Arg Tyr Phe Ser Met Trp Asn Gln Ala Val Asp Ser Tyr Asp<br>895 900 905 | 19415 |
| ccc gat gtg cgc att att gaa aat cac ggt gtg gag gat gaa ctt cct<br>Pro Asp Val Arg Ile Ile Glu Asn His Gly Val Glu Asp Glu Leu Pro<br>910 915 920 | 19463 |
| aac tat tgc ttc ccc ctg gat gct gtg ggt aga act gat act tac cag<br>Asn Tyr Cys Phe Pro Leu Asp Ala Val Gly Arg Thr Asp Thr Tyr Gln<br>925 930 935 | 19511 |
| gga att aag gcc aat ggt gat aat caa acc acc tgg acc aaa gat gat<br>Gly Ile Lys Ala Asn Gly Asp Asn Gln Thr Thr Trp Thr Lys Asp Asp<br>940 945 950 955 | 19559 |
| act gtt aat gat gct aat gaa ttg ggc aag ggc aat cct ttc gcc atg<br>Thr Val Asn Asp Ala Asn Glu Leu Gly Lys Gly Asn Pro Phe Ala Met<br>960 965 970 | 19607 |
| gag atc aac atc cag gcc aac ctg tgg cgg aac ttc ctc tac gcg aac<br>Glu Ile Asn Ile Gln Ala Asn Leu Trp Arg Asn Phe Leu Tyr Ala Asn<br>975 980 985 | 19655 |

```
                                             -continued gtg gcg ctg tac ctg ccc gac tcc tac aag tac acg ccg gcc aac atc     19703
Val Ala Leu Tyr Leu Pro Asp Ser Tyr Lys Tyr Thr Pro Ala Asn Ile
        990                 995                 1000 acg ctg ccc acc aac acc aac acc tac gat tac atg aac ggc cgc         19748
Thr Leu Pro Thr Asn Thr Asn Thr Tyr Asp Tyr Met Asn Gly Arg
    1005                1010                1015 gtg gtg gcg ccc tcg ctg gtg gac gcc tac atc aac atc ggg gcg         19793
Val Val Ala Pro Ser Leu Val Asp Ala Tyr Ile Asn Ile Gly Ala
1020                1025                1030 cgc tgg tcg ctg gac ccc atg gac aac gtc aac ccc ttc aac cac         19838
Arg Trp Ser Leu Asp Pro Met Asp Asn Val Asn Pro Phe Asn His
    1035                1040                1045 cac cgc aac gcg ggc ctg cga tac cgc tcc atg ctc ctg ggc aac         19883
His Arg Asn Ala Gly Leu Arg Tyr Arg Ser Met Leu Leu Gly Asn
1050                1055                1060 ggg cgc tac gtg ccc ttc cac atc cag gtg ccc caa aag ttt ttc         19928
Gly Arg Tyr Val Pro Phe His Ile Gln Val Pro Gln Lys Phe Phe
    1065                1070                1075 gcc atc aag agc ctc ctg ctc ctg ccc ggg tcc tac acc tac gag         19973
Ala Ile Lys Ser Leu Leu Leu Leu Pro Gly Ser Tyr Thr Tyr Glu
1080                1085                1090 tgg aac ttc cgc aag gac gtc aac atg atc ctg cag agc tcc ctc         20018
Trp Asn Phe Arg Lys Asp Val Asn Met Ile Leu Gln Ser Ser Leu
    1095                1100                1105 ggc aac gac ctg cgc acg gac ggg gcc tcc atc gcc ttc acc agc         20063
Gly Asn Asp Leu Arg Thr Asp Gly Ala Ser Ile Ala Phe Thr Ser
1110                1115                1120 atc aac ctc tac gcc acc ttc ttc ccc atg gcg cac aac acc gcc         20108
Ile Asn Leu Tyr Ala Thr Phe Phe Pro Met Ala His Asn Thr Ala
    1125                1130                1135 tcc acg ctc gag gcc atg ctg cgc aac gac acc aac gac cag tcc         20153
Ser Thr Leu Glu Ala Met Leu Arg Asn Asp Thr Asn Asp Gln Ser
1140                1145                1150 ttc aac gac tac ctc tcg gcg gcc aac atg ctc tac ccc atc ccg         20198
Phe Asn Asp Tyr Leu Ser Ala Ala Asn Met Leu Tyr Pro Ile Pro
    1155                1160                1165 gcc aac gcc acc aac gtg ccc atc tcc atc ccc tcg cgc aac tgg         20243
Ala Asn Ala Thr Asn Val Pro Ile Ser Ile Pro Ser Arg Asn Trp
1170                1175                1180 gcc gcc ttc cgc ggc tgg tcc ttc acg cgc ctc aag acc cgc gag         20288
Ala Ala Phe Arg Gly Trp Ser Phe Thr Arg Leu Lys Thr Arg Glu
    1185                1190                1195 acg ccc tcg ctc ggc tcc ggg ttc gac ccc tac ttc gtc tac tcg         20333
Thr Pro Ser Leu Gly Ser Gly Phe Asp Pro Tyr Phe Val Tyr Ser
1200                1205                1210 ggc tcc atc ccc tac ctc gac ggc acc ttc tac ctc aac cac acc         20378
Gly Ser Ile Pro Tyr Leu Asp Gly Thr Phe Tyr Leu Asn His Thr
    1215                1220                1225 ttc aag aag gtc tcc atc acc ttc gac tcc tcc gtc agc tgg ccc         20423
Phe Lys Lys Val Ser Ile Thr Phe Asp Ser Ser Val Ser Trp Pro
1230                1235                1240 ggc aac gac cgc ctc ctg acg ccc aac gag ttc gaa atc aag cgc         20468
Gly Asn Asp Arg Leu Leu Thr Pro Asn Glu Phe Glu Ile Lys Arg
    1245                1250                1255 acc gtc gac gga gag ggg tac aac gtg gcc cag tgc aac atg acc         20513
Thr Val Asp Gly Glu Gly Tyr Asn Val Ala Gln Cys Asn Met Thr
1260                1265                1270 aag gac tgg ttc ctg gtc cag atg ctg gcc cac tac aac atc ggc         20558
Lys Asp Trp Phe Leu Val Gln Met Leu Ala His Tyr Asn Ile Gly
    1275                1280                1285
```

-continued

| | | |
|---|---|---|
| tac cag ggc ttc tac gtg ccc gag ggc tac aag gac cgc atg tac<br>Tyr Gln Gly Phe Tyr Val Pro Glu Gly Tyr Lys Asp Arg Met Tyr<br>1290                       1295                    1300 | | 20603 |
| tcc ttc ttc cgc aac ttc cag ccc atg agc cgc cag gtc gtg gac<br>Ser Phe Phe Arg Asn Phe Gln Pro Met Ser Arg Gln Val Val Asp<br>1305                       1310                    1315 | | 20648 |
| gag gtc aac tac aag gac tac cag gcc gtc acc ctg gcc tac cag<br>Glu Val Asn Tyr Lys Asp Tyr Gln Ala Val Thr Leu Ala Tyr Gln<br>1320                       1325                    1330 | | 20693 |
| cac aac aac tcg ggc ttc gtc ggc tac ctc gcg ccc acc atg cgc<br>His Asn Asn Ser Gly Phe Val Gly Tyr Leu Ala Pro Thr Met Arg<br>1335                       1340                    1345 | | 20738 |
| cag ggc cag ccc tac ccc gcc aac tac ccc tac ccg ctc atc ggc<br>Gln Gly Gln Pro Tyr Pro Ala Asn Tyr Pro Tyr Pro Leu Ile Gly<br>1350                       1355                    1360 | | 20783 |
| aag agc gcc gtc gcc agc gtc acc cag aaa aag ttc ctc tgc gac<br>Lys Ser Ala Val Ala Ser Val Thr Gln Lys Lys Phe Leu Cys Asp<br>1365                       1370                    1375 | | 20828 |
| cgg gtc atg tgg cgc atc ccc ttc tcc agc aac ttc atg tcc atg<br>Arg Val Met Trp Arg Ile Pro Phe Ser Ser Asn Phe Met Ser Met<br>1380                       1385                    1390 | | 20873 |
| ggc gcg ctc acc gac ctc ggc cag aac atg ctc tac gcc aac tcc<br>Gly Ala Leu Thr Asp Leu Gly Gln Asn Met Leu Tyr Ala Asn Ser<br>1395                       1400                    1405 | | 20918 |
| gcc cac gcg cta gac atg aat ttc gaa gtc gac ccc atg gat gag<br>Ala His Ala Leu Asp Met Asn Phe Glu Val Asp Pro Met Asp Glu<br>1410                       1415                    1420 | | 20963 |
| tcc acc ctt ctc tat gtt gtc ttc gaa gtc ttc gac gtc gtc cga<br>Ser Thr Leu Leu Tyr Val Val Phe Glu Val Phe Asp Val Val Arg<br>1425                       1430                    1435 | | 21008 |
| gtg cac cag ccc cac cgc ggc gtc atc gag gcc gtc tac ctg cgc<br>Val His Gln Pro His Arg Gly Val Ile Glu Ala Val Tyr Leu Arg<br>1440                       1445                    1450 | | 21053 |
| acg ccc ttc tcg gcc ggc aac gcc acc acc taa gcctcttgct<br>Thr Pro Phe Ser Ala Gly Asn Ala Thr Thr<br>1455                       1460 | | 21096 | tcttgcaaga tgacggcctg cgcgggctcc ggcgagcagg agctcagggc catcctccgc  21156 gacctgggct gcgggccctg cttcctgggc accttcgaca gcgcttccc gggattcatg  21216 gccccgcaca agctggcctg cgccatcgtc aacacggccg gccgcgagac cggggggcgag  21276 cactggctgg ccttcgcctg gaacccgcgc tcccacacct gctacctctt cgacccttc  21336 gggttctcgg acgagcgcct caagcagatc taccagttcg agtacgaggg cctgctgcgt  21396 cgcagcgccc tggccaccga ggaccgctgc gtcaccctgg aaaagtccac ccagaccgtg  21456 cagggtccgc gctcggccgc ctgcgggctc ttctgctgca tgttcctgca cgccttcgtg  21516 cactggcccg accgcccat ggacaagaac cccaccatga acttgctgac gggggtgccc  21576 aacggcatgc tccagtcgcc ccaggtggaa cccaccctgc cccgcaacca ggaggcgctc  21636 taccgcttcc tcaacgccca ctccgcctac tttcgctccc accgcgcgcg catcgagaag  21696 gccaccgcct tcgaccgcat gaatcaagac atgtaatccg gtgtgtgtat gtgaatgctt  21756 tattcatcat aataaacagc acatgtttat gccaccttct ctgaggctct gactttattt  21816 agaaatcgaa ggggttctgc cggctctcgg catggcccgc gggcagggat acgttgcgga  21876 actggtactt gggcagccac ttgaactcgg ggatcagcag cttcggcacg gggaggtcgg  21936 ggaacgagtc gctccacagc ttgcgcgtga gttcagggc gccagcagg tcgggcgcgg  21996 agatcttgaa atcgcagttg ggacccgcgt tctgcgcgcg agagttacgg tacacggggt  22056

```
tgcagcactg gaacaccatc agggccgggt gcttcacgct cgccagcacc gtcgcgtcgg   22116
tgatgccctc cacgtccaga tcctcggcgt tggccatccc gaaggggtc atcttgcagg    22176 tctgccgccc catgctgggc acgcagccgg gcttgtggtt gcaatcgcag tgcagggga    22236 tcagcatcat ctgggcctgc tcggagctca tgcccgggta catggccttc atgaaagcct   22296
ccagctggcg gaaggcctgc tgcgccttgc cgccctcggt gaagaagacc ccgcaggact   22356
tgctagagaa ctggttggtg gcgcagccag cgtcgtgcac gcagcagcgc gcgtcgttgt   22416
tggccagctg caccacgctg cgcccccagc ggttctgggt gatcttggcc cggtcggggt   22476
tctccttcag cgcgcgctgc ccgttctcgc tcgccacatc catctcgatc gtgtgctcct   22536
tctggatcat cacggtcccg tgcaggcacc gcagcttgcc ctcggcctcg gtgcacccgt   22596
gcagccacag cgcgcagccg gtgctctccc agttcttgtg ggcgatctgg gagtgcgagt   22656
gcacgaagcc ctgcaggaag cggcccatca tcgtggtcag ggtcttgttg ctggtgaagg   22716
tcagcggaat gccgcggtgc tcctcgttca catacaggtg gcagatacgg cggtacacct   22776
cgccctgctc gggcatcagc tggaaggcgg acttcaggtc gctctccacg cggtaccggt   22836
ccatcagcag cgtcatcact tccatgccct tctcccaggc cgaaacgatc ggcaggctca   22896
gggggttctt caccgttgtc atcttagtcg ccgccgccga agtcagggggg tcgttctcgt   22956 ccagggtctc aaacactcgc ttgccgtcct tctcggtgat gcgcacgggg ggaaagctga   23016
agcccacggc cgccagctcc tcctcggcct gcctttcgtc ctcgctgtcc tggctgatgt   23076
cttgcaaagg cacatgcttg gtcttgcggg gttttctttt gggcggcaga ggcggcggcg   23136
gagacgtgct gggcgagcgc gagttctcgc tcaccacgac tatttcttct ccttggccgt   23196
cgtccgagac cacgcggcgg taggcatgcc tcttctgggg cagaggcgga ggcgacgggc   23256
tctcgcggtt cggcgggcgg ctggcagagc cccttccgcg ttcgggggtg cgctcctggc   23316
ggcgctgctc tgactgactt cctccgcggc cggccattgt gttctcctag ggagcaagca   23376
tggagactca gccatcgtcg ccaacatcgc catctgcccc cgccgccgcc gacgagaacc   23436
agcagcagca gaatgaaagc ttaaccgccc cgccgcccag ccccacctcc gacgccgcag   23496
ccccagacat gcaagagatg gaggaatcca tcgagattga cctgggctac gtgacgcccg   23556
cggagcacga ggaggagctg gcagcgcgct tttcagcccc ggaagagaac caccaagagc   23616
agccagagca ggaagcagag agcgagcaga accaggctgg gctcgagcat ggcgactacc   23676
tgagcggggc agaggacgtg ctcatcaagc atctggcccg ccaatgcatc atcgtcaagg   23736
acgcgctgct cgaccgcgcc gaggtgcccc tcagcgtggc ggagctcagc cgcgcctacg   23796
agcgcaacct cttctcgccg cgcgtgcccc caagcgcca gcccaacggc acctgcgagc    23856
ccaacccgcg cctcaacttc taccggtct tcgcggtgcc cgaggccctg gccacctacc    23916
acctcttttt caagaaccaa aggatccccg tctcctgccg cgccaacgc acccgcgccg    23976 acgccctgct caacctgggc cccggcgccc gcctacctga tatcgcctcc ttggaagagg   24036
ttcccaagat cttcgagggt ctgggcagcg acgagactcg ggccgcgaac gctctgcaag   24096
gaagcggaga ggagcatgag caccacgcg ccctggtgga gttggaaggc gacaacgcgc    24156
gcctggcggt cctcaagcgc acggtcgagc tgacccactt cgcctacccg gcgctcaacc   24216 tgcccccaa ggtcatgagc gccgtcatgg accaggtgct catcaagcgc gcctcgcccc    24276
tctcggagga ggagatgcag gaccccgaga gctcggacga gggcaagccc gtggtcagcg   24336
acgagcagct ggcgcgctgg ctgggagcga gtagcacccc ccagagcctg gaagagcggc   24396
gcaagctcat gatggccgtg gtcctggtga ccgtggagct ggagtgtctg cgccgcttct   24456
```

```
tcgccgacgc ggagaccctg cgcaaggtcg aggagaacct gcactacctc ttcagacacg   24516
ggttcgtgcg ccaggcctgc aagatctcca acgtggagct gaccaacctg gtctcctaca   24576
tgggcatcct gcacgagaac cgcctggggc agaacgtgct gcacaccacc ctgcgcgggg   24636
aggcccgccg cgactacatc cgcgactgcg tctacctgta cctctgccac acctggcaga   24696
cgggcatggg cgtgtggcag cagtgcctgg aggagcagaa cctgaaagag ctctgcaagc   24756
tcctgcagaa gaacctcaag gccctgtgga ccgggttcga cgagcgcacc accgccgcgg   24816
acctggccga cctcatcttc cccgagcgcc tgcggctgac gctgcgcaac gggctgcccg   24876
actttatgag ccaaagcatg ttgcaaaact ttcgctcttt catcctcgaa cgctccggga   24936
tcctgcccgc cacctgctcc gcgctgccct cggacttcgt gccgctgacc ttccgcgagt   24996 gcccccccgcc gctctggagc cactgctacc tgctgcgcct ggccaactac ctggcctacc   25056
actcggacgt gatcgaggac gtcagcggcg agggcctgct cgagtgccac tgccgctgca   25116
acctctgcac gccgcaccgc tccctggcct gcaaccccca gctgctgagc gagacccaga   25176
tcatcggcac cttcgagttg caaggcccccg gcgagggcaa ggggggtctg aaactcaccc   25236
cggggctgtg gacctcggcc tacttgcgca agttcgtgcc cgaggactac catcccttcg   25296
agatcaggtt ctacgaggac caatcccagc cgcccaaggc cgagctgtcg gcctgcgtca   25356
tcacccaggg ggccatcctg gcccaattgc aagccatcca gaaatcccgc caagaatttc   25416
tgctgaaaaa gggccacggg gtctacttgg accccagac cggagaggag ctcaacccca   25476
gcttccccca ggatgccccg aggaagcagc aagaagctga agtggagct gccgccgccg   25536 ccggaggatt tggaggaaga ctgggagagc agtcaggcag aggaggagga gatggaagac   25596
tgggacagca ctcaggcaga ggaggacagc ctgcaagaca gtctggagga ggaagacgag   25656
gtggaggagg cagaggaaga agcagccgcc gccagaccgt cgtcctcggc ggaggaggag   25716
aaagcaagca gcacggatac catctccgct ccgggtcggg gtcgcggcgg ccgggcccac   25776
agtagatggg acgagaccgg gcgcttcccg aaccccacca cccagaccgg taagaaggag   25836
cggcagggat acaagtcctg gcggggggcac aaaaacgcca tcgtctcctg cttgcaagcc   25896
tgcgggggca acatctcctt caccccggcgc tacctgctct tccaccgcgg ggtgaacttc   25956
ccccgcaaca tcttgcatta ctaccgtcac ctccacagcc cctactactg tttccaagaa   26016
gaggcagaaa cccagcagca gcagcagcag cagaaaacca gcggcagcag ctagaaaatc   26076
cacagcggcg gcaggtggac tgaggatcgc ggcgaacgag ccggcgcaga cccgggagct   26136
gaggaaccgg atctttccca ccctctatgc catcttccag cagagtcggg ggcaagagca   26196
ggaactgaaa gtcaagaacc gttctctgcg ctcgctcacc cgcagttgtc tgtatcacaa   26256
gagcgaagac caacttcagc gcactctcga ggacgccgag gctctcttca acaagtactg   26316
cgcgctcact cttaaagagt agcccgcgcc cgcccacaca cggaaaaagg cgggaattac   26376
gtcaccacct gcgcccttcg cccgaccatc atcatgagca aagagattcc cacgccttac   26436
atgtggagct accagcccca gatgggcctg gccgccggcg ccgcccagga ctactccacc   26496
cgcatgaact ggctcagtgc cgggcccgcg atgatctcac gggtgaatga catccgcgcc   26556
caccgaaacc agatactcct agaacagtca gcgatcaccg ccacgccccg ccatcacctt   26616
aatccgcgta attggcccgc cgccctggtg taccaggaaa ttccccagcc cacgaccgta   26676
ctacttccgc gagacgccca ggccgaagtc cagctgacta actcaggtgt ccagctggcc   26736
ggcggcgccg ccctgtgtcg tcaccgcccc gctcagggta taaagcggct ggtgatccga   26796
ggcagaggca cacagctcaa cgacgaggtg gtgagctctt cgctgggtct gcgacctgac   26856
```

```
ggagtcttcc aactcgccgg atcggggaga tcttccttca cgcctcgtca ggccgtcctg   26916
actttggaga gttcgtcctc gcagcccgc tcgggtggca tcggcactct ccagttcgtg    26976
gaggagttca ctccctcggt ctacttcaac cccttctccg gctcccccgg ccactacccg   27036
gacgagttca tcccgaactt cgacgccatc agcgagtcgg tggacggcta cgattgaatg   27096
tcccatggtg gcgcggctga cctagctcgg cttcgacacc tggaccactg ccgccgcttc   27156
cgctgcttcg ctcgggatct cgccgagttt gcctactttg agctgcccga ggagcaccct   27216
cagggcccgg cccacggagt gcggatcgtc gtcgaagggg gtctcgactc ccacctgctt   27276
cggatcttca gccagcgtcc gatcctggcc gagcgcgagc aaggacagac ccttctgacc   27336
ctgtactgca tctgcaacca ccccggcctg catgaaagtc tttgttgtct gctgtgtact   27396
gagtataata aaagctgaga tcagcgacta ctccggactt ccgtgtgttc ctgctatcaa   27456
ccagtccctg ttcttcaccg ggaacgagac cgagctccag ctccagtgta agccccacaa   27516
gaagtacctc acctggctgt tccagggctc tccgatcgcc gttgtcaacc actgcgacaa   27576
cgacggagtc ctgctgagcg gccctgccaa ccttactttt tccacccgca gaagcaagct   27636
ccagctcttc caacccttcc tccccgggac ctatcagtgc gtctcgggac cctgccatca   27696
caccttccac ctgatcccga ataccacagc gtcgctcccc gctactaaca accaaactac   27756
ccaccaacgc caccgtcgcg acctttcctc tgggtctaat accactaccg gaggtgagct   27816
ccgaggtcga ccaacctctg ggatttacta cggcccctgg gaggtggtag ggttaatagc   27876
gctaggccta gttgcgggtg ggcttttggc tctctgctac ctatacctcc cttgctgttc   27936
gtacttagtg gtgctgtgtt gctggtttaa gaaatgggga agatcaccct agtgagctgc   27996
ggtgtgctgg tggcggtggt gctttcgatt gtgggactgg gcggcgcggc tgtagtgaag   28056
gagaaggccg atccctgctt gcatttcaat cccgacaaat gccagctgag ttttcagccc   28116
gatggcaatc ggtgcgcggt gctgatcaag tgcggatggg aatgcgagaa cgtgagaatc   28176
gagtacaata acaagactcg gaacaatact ctcgcgtccg tgtggcagcc cggggacccc   28236
gagtggtaca ccgtctctgt ccccggtgct gacggctccc cgcgcaccgt gaataatact   28296 ttcattttg cgcacatgtg cgacacggtc atgtggatga gcaagcagta cgatatgtgg   28356 cccccacga aggagaacat cgtggtcttc tccatcgctt acagcgtgtg cacggcgcta   28416
atcaccgcta tcgtgtgcct gagcattcac atgctcatcg ctattcgccc cagaaataat   28476
gccgaaaaag aaaaacagcc ataacacgtt ttttcacaca cctttttcag accatggcct   28536
ctgttaaatt tttgctttta tttgccagtc tcattgccgt cattcatgga atgagtaatg   28596
agaaaattac tatttacact ggcactaatc acacattgaa aggtccagaa aaagccacag   28656
aagtttcatg gtattgttat tttaatgaat cagatgtatc tactgaactc tgtggaaaca   28716
ataacaaaaa aaatgagagc attactctca tcaagtttca atgtggatct gacttaaccc   28776
taattaacat cactagagac tatgtaggta tgtattatgg aactacagca ggcatttcgg   28836
acatggaatt ttatcaagtt tctgtgtctg aacccaccac gcctagaatg accacaacca   28896
caaaaactac acctgttacc actatacagc tcactaccaa tggctttctt gccatgcttc   28956
aagtggctga aaatagcacc agcattcaac ccaccccacc cagtgaggaa attcccagat   29016
ccatgattgg cattattgtt gctgtagtgg tgtgcatgtt gatcatcgcc ttgtgcatgg   29076
tgtactatgc cttctgctac agaaagcaca gactgaacga caagctggaa cacttactaa   29136
gtgttgaatt taattttttt agaaccatga agatcctagg ccttttagtt ttttctatca   29196
ttacctctgc tctatgcaat tctgacaatg aggacgttac tgtcgttgtc ggatcaaatt   29256
```

```
atacactaaa aggtccagca aaaggtatgc tttcgtggta ttgttggttc ggaactgacg  29316
agcaacagac agaactttgc aatgctcaaa aaggcaaaac ctcaaattct aaaatctcta  29376
attatcaatg caatggcact gacttagtat tgctcaatgt cacgaaagca tatgctggca  29436
gttacacctg ccctggagat gatgccgaca atatgatttt ttacaaagtg gaagtggttg  29496
atcccactac tccaccgccc accaccacaa ctactcatac cacacacaca gaacaaacac  29556
cagaggcagc agaagcagag ttggccttcc aggttcacgg agattccttt gctgtcaata  29616
cccctacacc cgatcagcgg tgtccggggc tgctcgtcag cggcattgtc ggtgtgcttt  29676
cgggattagc agtcataatc atctgcatgt tcattttttgc ttgctgctat agaaggcttt  29736
accgacaaaa atcagaccca ctgctgaacc tctatgttta atttttttcca gagccatgaa  29796
ggcagttagc gctctagttt tttgttcttt gattggcatt gttttttagtg ctgggttttt  29856
gaaaaatctt accatttatg aaggtgagaa tgccactcta gtgggcatca gtggtcaaaa  29916
tgtcagctgg ctaaaatacc atctagatgg gtggaaagac atttgcgatt ggaatgtcac  29976
tgtgtataca tgtaatggag ttaacctcac cattactaat gccacccaag atcagaatgg  30036
taggtttaag ggccagagtt tcactagaaa taatgggtat gaatcccata acatgtttat  30096
ctatgacgtc actgtcatca gaaatgagac tgccaccacc acacagatgc ccactacaca  30156
cagttctacc actactacca tgcaaaccac acagacaacc actacatcaa ctcagcatat  30216
gaccaccact acagcagcaa agccaagtag tgcagcgcct cagccccagg ctttggcttt  30276
gaaagctgca caacctagta caactactag gaccaatgag cagactactg aattttttgtc  30336
cactgtcgag agccacacca cagctacctc cagtgccttc tctagcaccg ccaatctctc  30396
ctcgcttttcc tctacaccaa tcagtcccgc tactactccc accccagctc ttctccccac  30456
tcccctgaag caaactgagg acagcggcat gcaatggcag atcaccctgc tcattgtgat  30516
cgggttggtc atcctggccg tgttgctcta ctacatcttc tgccgccgca ttcccaacgc  30576
gcaccgcaaa ccggcctaca agcccatcgt tatcgggcag ccggagccgc ttcaggtgga  30636
aggggggtcta aggaatcttc tcttctcttt tacagtatgg tgattgaact atgattccta  30696
gacaattctt gatcactatt cttatctgcc tcctccaagt ctgtgccacc ctcgctctgg  30756
tggccaacgc cagtccagac tgtattgggc ccttcgcctc ctacgtgctc tttgccttca  30816
tcacctgcat ctgctgctgt agcatagtct gcctgcttat caccttcttc cagttcattg  30876
actggatctt tgtgcgcatc gcctacctgc gccaccaccc ccagtaccgc gaccagcgag  30936
tggcgcggct gctcaggctc ctctgataag catgcgggct ctgctacttc tcgcgcttct  30996
gctgttagtg ctccccgcc ccgtcgaccc ccggtccccc actcagtccc ccgaagaggt  31056
ccgcaaatgc aaattccaag aaccctggaa attcctcaaa tgctaccgcc aaaaatcaga  31116
catgcttccc agctggatca tgatcattgg gatcgtgaac attctggcct gcaccctcat  31176
ctcctttgtg atttacccct gctttgactt tggttggaac tcgccagagg cgctctatct  31236
cccgcctgaa cctgacacac caccacagca acctcaggca cacgcactac caccaccaca  31296
gcctaggcca caatacatgc ccatattaga ctatgaggcc gagccacagc gacccatgct  31356
ccccgctatt agttacttca atctaaccgg cggagatgac tgacccactg gccaacaaca  31416
acgtcaacga ccttctcctg gacatggacg gccgcgcctc ggagcagcga ctcgcccaac  31476
ttcgcattcg ccagcagcag gagagagccg tcaaggagct gcaggacggc atagccatcc  31536
accagtgcaa gaaaggcatc ttctgcctgg tgaaacaggc caagatctcc tacgaggtca  31596
ccccgaccga ccatcgcctc tcctacgagc tcctgcagca gcgccagaag ttcacctgcc  31656
```

```
tggtcggagt caaccccatc gtcatcaccc agcagtcggg cgataccaag gggtgcatcc    31716
actgctcctg cgactccccc gactgcgtcc acactctgat caagaccctc tgcggcctcc    31776
gcgacctcct ccccatgaac taatcacccc cttatccagt gaaataaata tcatattgat    31836
gatgatttaa ataaaaaata atcatttgat ttgaaataaa gatacaatca tattgatgat    31896
ttgagtttta aaaataaag aatcacttac ttgaaatctg ataccaggtc tctgtccatg     31956
ttttctgcca acaccacctc actcccctct tcccagctct ggtactgcag accccggcgg    32016
gctgcaaact tcctcacac gctgaagggg atgtcaaatt cctcctgtcc ctcaatcttc     32076
attttatctt ctatcag atg tcc aaa aag cgc gtc cgg gtg gat gat gac      32126
                    Met Ser Lys Lys Arg Val Arg Val Asp Asp Asp
                        1465              1470 ttc gac ccc gtc tac ccc tac gat gca gac aac gca ccg acc gtg          32171
Phe Asp Pro Val Tyr Pro Tyr Asp Ala Asp Asn Ala Pro Thr Val
1475            1480                1485 ccc ttc atc aac ccc ccc ttc gtc tct tca gat gga ttc caa gag          32216
Pro Phe Ile Asn Pro Pro Phe Val Ser Ser Asp Gly Phe Gln Glu
1490            1495                1500 aag ccc ctg ggg gtg ctg tcc ctg cga ctg gct gac ccc gtc acc          32261
Lys Pro Leu Gly Val Leu Ser Leu Arg Leu Ala Asp Pro Val Thr
1505            1510                1515 acc aag aac ggg gaa atc acc ctc aag ctg gga gag ggg gtg gac          32306
Thr Lys Asn Gly Glu Ile Thr Leu Lys Leu Gly Glu Gly Val Asp
1520            1525                1530 ctc gac tcc tcg gga aaa ctc atc tcc aac acg gcc acc aag gcc          32351
Leu Asp Ser Ser Gly Lys Leu Ile Ser Asn Thr Ala Thr Lys Ala
1535            1540                1545 gcc gcc cct ctc agt ttt tcc aac aac acc att tcc ctt aac atg          32396
Ala Ala Pro Leu Ser Phe Ser Asn Asn Thr Ile Ser Leu Asn Met
1550            1555                1560 gat acc cct ctt tat acc aaa gat gga aaa tta tcc tta caa gtt          32441
Asp Thr Pro Leu Tyr Thr Lys Asp Gly Lys Leu Ser Leu Gln Val
1565            1570                1575 tct cca ccg tta aac ata tta aaa tca acc att ctg aac aca tta          32486
Ser Pro Pro Leu Asn Ile Leu Lys Ser Thr Ile Leu Asn Thr Leu
1580            1585                1590 gct gta gct tat gga tca ggt tta gga ctg agt ggt ggc act gct          32531
Ala Val Ala Tyr Gly Ser Gly Leu Gly Leu Ser Gly Gly Thr Ala
1595            1600                1605 ctt gca gta cag ttg gcc tct cca ctc act ttt gat gaa aaa gga          32576
Leu Ala Val Gln Leu Ala Ser Pro Leu Thr Phe Asp Glu Lys Gly
1610            1615                1620 aat att aaa att aac cta gcc agt ggt cca tta aca gtt gat gca          32621
Asn Ile Lys Ile Asn Leu Ala Ser Gly Pro Leu Thr Val Asp Ala
1625            1630                1635 agt cga ctt agt atc aac tgc aaa aga ggg gtc act gtc act acc          32666
Ser Arg Leu Ser Ile Asn Cys Lys Arg Gly Val Thr Val Thr Thr
1640            1645                1650 tca gga gat gca att gaa agc aac ata agc tgg cct aaa ggt ata          32711
Ser Gly Asp Ala Ile Glu Ser Asn Ile Ser Trp Pro Lys Gly Ile
1655            1660                1665 aga ttt gaa ggt aat ggc ata gct gca aac att ggc aga gga ttg          32756
Arg Phe Glu Gly Asn Gly Ile Ala Ala Asn Ile Gly Arg Gly Leu
1670            1675                1680 gaa ttt gga acc act agt aca gag act gat gtc aca gat gca tac          32801
Glu Phe Gly Thr Thr Ser Thr Glu Thr Asp Val Thr Asp Ala Tyr
1685            1690                1695 cca att caa gtt aaa ttg ggt act ggc ctt acc ttt gac agt aca          32846
```

```
              Pro  Ile  Gln  Val  Lys  Leu  Gly  Thr  Gly  Leu  Thr  Phe  Asp  Ser  Thr
              1700                1705                     1710 ggc  gcc  att  gtt  gct  tgg  aac  aaa  gag  gat  gat  aaa  ctt  aca  tta         32891
Gly  Ala  Ile  Val  Ala  Trp  Asn  Lys  Glu  Asp  Asp  Lys  Leu  Thr  Leu
1715                1720                     1725 tgg  acc  aca  gcc  gac  ccc  tcg  cca  aat  tgc  aaa  ata  tac  tct  gaa         32936
Trp  Thr  Thr  Ala  Asp  Pro  Ser  Pro  Asn  Cys  Lys  Ile  Tyr  Ser  Glu
1730                1735                     1740 aaa  gat  gcc  aaa  ctc  aca  ctt  tgc  ttg  aca  aag  tgt  gga  agt  caa         32981
Lys  Asp  Ala  Lys  Leu  Thr  Leu  Cys  Leu  Thr  Lys  Cys  Gly  Ser  Gln
1745                1750                     1755 att  ctg  ggt  act  gtg  act  gta  ttg  gca  gtg  aat  aat  gga  agt  ctc         33026
Ile  Leu  Gly  Thr  Val  Thr  Val  Leu  Ala  Val  Asn  Asn  Gly  Ser  Leu
1760                1765                     1770 aac  cca  atc  aca  aac  aca  gta  agc  act  gca  ctc  gtc  tcc  ctc  aag         33071
Asn  Pro  Ile  Thr  Asn  Thr  Val  Ser  Thr  Ala  Leu  Val  Ser  Leu  Lys
1775                1780                     1785 ttt  gat  gca  agt  gga  gtt  ttg  cta  agc  agc  tcc  aca  tta  gac  aaa         33116
Phe  Asp  Ala  Ser  Gly  Val  Leu  Leu  Ser  Ser  Ser  Thr  Leu  Asp  Lys
1790                1795                     1800 gaa  tat  tgg  aac  ttc  aga  aag  gga  gat  gtt  aca  cct  gct  gag  ccc         33161
Glu  Tyr  Trp  Asn  Phe  Arg  Lys  Gly  Asp  Val  Thr  Pro  Ala  Glu  Pro
1805                1810                     1815 tat  act  aat  gct  ata  ggt  ttt  atg  cct  aac  ata  aag  gcc  tat  cct         33206
Tyr  Thr  Asn  Ala  Ile  Gly  Phe  Met  Pro  Asn  Ile  Lys  Ala  Tyr  Pro
1820                1825                     1830 aaa  aac  aca  tct  gca  gct  tca  aaa  agc  cat  att  gtc  agt  caa  gtt         33251
Lys  Asn  Thr  Ser  Ala  Ala  Ser  Lys  Ser  His  Ile  Val  Ser  Gln  Val
1835                1840                     1845 tat  ctc  aat  ggg  gat  gag  gcc  aaa  cca  ctg  atg  ctg  att  att  act         33296
Tyr  Leu  Asn  Gly  Asp  Glu  Ala  Lys  Pro  Leu  Met  Leu  Ile  Ile  Thr
1850                1855                     1860 ttt  aat  gaa  act  gag  gat  gca  act  tgc  acc  tac  agt  atc  act  ttt         33341
Phe  Asn  Glu  Thr  Glu  Asp  Ala  Thr  Cys  Thr  Tyr  Ser  Ile  Thr  Phe
1865                1870                     1875 caa  tgg  aaa  tgg  gat  agt  act  aag  tac  aca  ggt  gaa  aca  ctt  gct         33386
Gln  Trp  Lys  Trp  Asp  Ser  Thr  Lys  Tyr  Thr  Gly  Glu  Thr  Leu  Ala
1880                1885                     1890 acc  agc  tcc  ttc  acc  ttc  tcc  tac  atc  gcc  caa  gaa  tga  acactgtatc     33435
Thr  Ser  Ser  Phe  Thr  Phe  Ser  Tyr  Ile  Ala  Gln  Glu
1895                1900                     1905 ccacccctgca tgccaaccct tcccacccca ctctgtctat ggaaaaaact ctgaagcaca              33495
aaataaaata aagttcaagt gttttattga ttcaacagtt ttacaggatt cgagcagtta              33555 ttttcctcc accctcccag gacatggaat acaccaccct ctcccccgc acagccttga                 33615 acatctgaat gccattggtg atggacatgc ttttggtctc cacgttccac acagtttcag              33675
agcgagccag tctcgggtcg gtcagggaga tgaaaccctc cgggcactcc cgcatctgca              33735
cctcacagct caacagctga ggattgtcct cggtggtcgg gatcacggtt atctggaaga              33795
agcagaagag cggcggtggg aatcatagtc cgcgaacggg atcggccggt ggtgtcgcat              33855
caggccccgc agcagtcgct gccgccgccg ctccgtcaag ctgctgctca gggggtccgg              33915
gtccagggac tccctcagca tgatgcccac ggccctcagc atcagtcgtc tggtgcggcg              33975
ggcgcagcag cgcatgcgga tctcgctcag gtcgctgcaa tacgtgcaac acaggaccac              34035
caggttgttc aacagtccat agttcaacac gctccagccg aaactcatcg cgggaaggat              34095
gctacccacg tggccgtcgt accagatcct caggtaaatc aagtggcgct ccctccagaa              34155
cacgctgccc acgtacatga tctccttggg catgtggcgg ttcaccacct cccggtacca              34215
```

-continued

```
catcaccctc tggttgaaca tgcagccccg gatgatcctg cggaaccaca gggccagcac    34275
cgccccgccc gccatgcagc gaagagaccc cgggtcccgg caatggcaat ggaggaccca    34335
ccgctcgtac ccgtggatca tctgggagct gaacaagtct atgttggcac agcacaggca    34395
tatgctcatg catctcttca gcactctcag ctcctcgggg gtcaaaacca tatcccaggg    34455
cacggggaac tcttgcagga cagcgaaccc cgcagaacag ggcaatcctc gcacataact    34515
tacattgtgc atggacaggg tatcgcaatc aggcagcacc gggtgatcct ccaccagaga    34575
agcgcgggtc tcggtctcct cacagcgtgg taagggggcc ggccgatacg ggtgatggcg    34635
ggacgcggct gatcgtgttc gcgaccgtgt catgatgcag ttgctttcgg acattttcgt    34695
acttgctgta gcagaacctg gtccggcgcg tgcacaccga tcgccggcgg cggtcccggc    34755
gcttggaacg ctcggtgttg aaattgtaaa acagccactc tctcagaccg tgcagcagat    34815
ctagggcctc aggagtgatg aagatcccat catgcctgat agctctgatc acatcgacca    34875
ccgtggaatg ggccagaccc agccagatga tgcaattttg ttgggtttcg gtgacggcgg    34935
gggagggaag aacaggaaga accatgatta acttttaatc caaacggtct cggagcactt    34995
caaaatgaag gtcgcggaga tggcacctct cgccccgct gtgttggtgg aaaataacag    35055
ccaggtcaaa ggtgatacgg ttctcgagat gttccacggt ggcttccagc aaagcctcca    35115
cgcgcacatc cagaaacaag acaatagcga aagcgggagg gttctctaat tcctcaatca    35175
tcatgttaca ctcctgcacc atccccagat aattttcatt tttccagcct tgaatgattc    35235
gaactagttc ctgaggtaaa tccaagccag ccatgataaa gagctcgcgc agagcgccct    35295
ccaccggcat tcttaagcac accctcataa ttccaagata ttctgctcct ggttcacctg    35355
cagcagatta acaagcggaa tatcaaaatc tctgccgcga tccctaagct cctccctcag    35415
caataactgt aagtactctt tcatatcctc tccgaaattt ttagccatag gaccaccagg    35475
aataagatta gggcaagcca cagtacagat aaaccgaagt cctccccagt gagcattgcc    35535
aaatgcaaga ctgctataag catgctggct agacccggtg atatcttcca gataactgga    35595
cagaaaatca cccaggcaat ttttaagaaa atcaacaaaa gaaaaatcct ccaggtgcac    35655
gtttagagcc tcgggaacaa cgatgaagta aatgcaagcg gtgcgttcca gcatggttag    35715
ttagctgatc tgtaaaaaac aaaaaataaa acattaaacc atgctagcct ggcgaacagg    35775
tgggtaaatc gttctctcca gcaccaggca ggccacgggg tctccggcgc gaccctcgta    35835
aaaattgtcg ctatgattga aaaccatcac agagagacgt tcccggtggc cggcgtgaat    35895
gattcgacaa gatgaataca cccccggaac attggcgtcc gcgagtgaaa aaaagcgccc    35955
gaggaagcaa taaggcacta caatgctcag tctcaagtcc agcaaagcga tgccatgcgg    36015
atgaagcaca aaatcctcag gtgcgtacaa aatgtaatta ctcccctcct gcacaggcag    36075
cgaagccccc gatccctcca gatacacata caaagcctca gcgtccatag cttaccgagc    36135
agcagcacac aacaggcgca agagtcagag aaaggctgag ctctaacctg tccacccgct    36195
ctctgctcaa tatatagccc agatctacac tgacgtaaag gccaaagtct aaaaatacc    36255 gccaaataat cacacacgcc cagcacacgc ccagaaaccg gtgacacact caaaaaaata    36315
cgcgcacttc ctcaaacgcc caaactgccg tcatttccgg gttccacgc tacgtcatcg    36375 gaattcgact ttcaaattcc gtcgaccgtt aaaaacgtca cccgcccgc ccctaacggt    36435 cgcccgtctc tcggccaatc accttcctcc ctccccaaat tcaaacagct catttgcata    36495
ttaacgcgca ccaaaagttt gaggtatatt attgatgatg                         36535
```

<210> SEQ ID NO 10
<211> LENGTH: 531
<212> TYPE: PRT
<213> ORGANISM: chimpanzee adenovirus serotype Pan7

<400> SEQUENCE: 10

```
Met Met Arg Arg Val Tyr Pro Glu Gly Pro Pro Ser Tyr Glu Ser
1               5                   10                  15

Val Met Gln Gln Ala Val Ala Ala Met Gln Pro Leu Glu Ala
            20                  25                  30

Pro Tyr Val Pro Pro Arg Tyr Leu Ala Pro Thr Glu Gly Arg Asn Ser
                35                  40                  45

Ile Arg Tyr Ser Glu Leu Ala Pro Leu Tyr Asp Thr Thr Arg Leu Tyr
        50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
                100                 105                 110

Trp Gly Gly Gln Leu Lys Thr Ile Met His Thr Asn Met Pro Asn Val
            115                 120                 125

Asn Glu Phe Met Tyr Ser Asn Lys Phe Lys Ala Arg Val Met Val Ser
130                 135                 140

Arg Lys Thr Pro Asn Gly Val Ala Val Asp Glu Asn Tyr Asp Gly Ser
145                 150                 155                 160

Gln Asp Glu Leu Thr Tyr Glu Trp Val Glu Phe Glu Leu Pro Glu Gly
                165                 170                 175

Asn Phe Ser Val Thr Met Thr Ile Asp Leu Met Asn Asn Ala Ile Ile
            180                 185                 190

Asp Asn Tyr Leu Ala Val Gly Arg Gln Asn Gly Val Leu Glu Ser Asp
        195                 200                 205

Ile Gly Val Lys Phe Asp Thr Arg Asn Phe Arg Leu Gly Trp Asp Pro
    210                 215                 220

Val Thr Glu Leu Val Met Pro Gly Val Tyr Thr Asn Glu Ala Phe His
225                 230                 235                 240

Pro Asp Ile Val Leu Leu Pro Gly Cys Gly Val Asp Phe Thr Glu Ser
                245                 250                 255

Arg Leu Ser Asn Leu Leu Gly Ile Arg Lys Arg Gln Pro Phe Gln Glu
            260                 265                 270

Gly Phe Gln Ile Leu Tyr Glu Asp Leu Glu Gly Gly Asn Ile Pro Ala
        275                 280                 285

Leu Leu Asp Val Glu Ala Tyr Glu Lys Ser Lys Glu Glu Ala Ala Ala
    290                 295                 300

Ala Ala Thr Ala Ala Val Ala Thr Ala Ser Thr Glu Val Arg Gly Asp
305                 310                 315                 320

Asn Phe Ala Ser Ala Ala Val Ala Glu Ala Glu Thr Glu Ser
                325                 330                 335

Lys Ile Val Ile Gln Pro Val Glu Lys Asp Ser Lys Asp Arg Ser Tyr
            340                 345                 350

Asn Val Leu Ala Asp Lys Lys Asn Thr Ala Tyr Arg Ser Trp Tyr Leu
        355                 360                 365

Ala Tyr Asn Tyr Gly Asp Pro Glu Lys Gly Val Arg Ser Trp Thr Leu
    370                 375                 380

Leu Thr Thr Ser Asp Val Thr Cys Gly Val Glu Gln Val Tyr Trp Ser
```

```
                385                 390                 395                 400

Leu Pro Asp Met Met Gln Asp Pro Val Thr Phe Arg Ser Thr Arg Gln
                    405                 410                 415

Val Ser Asn Tyr Pro Val Val Gly Ala Glu Leu Leu Pro Val Tyr Ser
                420                 425                 430

Lys Ser Phe Phe Asn Glu Gln Ala Val Tyr Ser Gln Gln Leu Arg Ala
            435                 440                 445

Phe Thr Ser Leu Thr His Val Phe Asn Arg Phe Pro Glu Asn Gln Ile
        450                 455                 460

Leu Val Arg Pro Pro Ala Pro Thr Ile Thr Thr Val Ser Glu Asn Val
465                 470                 475                 480

Pro Ala Leu Thr Asp His Gly Thr Leu Pro Leu Arg Ser Ser Ile Arg
                485                 490                 495

Gly Val Gln Arg Val Thr Val Thr Asp Ala Arg Arg Arg Thr Cys Pro
                500                 505                 510

Tyr Val Tyr Lys Ala Leu Gly Val Val Ala Pro Arg Val Leu Ser Ser
            515                 520                 525

Arg Thr Phe
    530

<210> SEQ ID NO 11
<211> LENGTH: 932
<212> TYPE: PRT
<213> ORGANISM: chimpanzee adenovirus serotype Pan7

<400> SEQUENCE: 11

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
                20                  25                  30

Arg Ala Thr Asp Thr Tyr Phe Ser Leu Gly Asn Lys Phe Arg Asn Pro
            35                  40                  45

Thr Val Ala Pro Thr His Asp Val Thr Thr Asp Arg Ser Gln Arg Leu
        50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
                100                 105                 110

Phe Lys Pro Tyr Ser Gly Thr Ala Tyr Asn Ser Leu Ala Pro Lys Gly
            115                 120                 125

Ala Pro Asn Thr Cys Gln Trp Thr Tyr Lys Ala Gly Asp Thr Asp Thr
        130                 135                 140

Glu Lys Thr Tyr Thr Tyr Gly Asn Ala Pro Val Gln Gly Ile Ser Ile
145                 150                 155                 160

Thr Lys Asp Gly Ile Gln Leu Gly Thr Asp Ser Asp Gly Gln Ala Ile
                165                 170                 175

Tyr Ala Asp Glu Thr Tyr Gln Pro Glu Pro Gln Val Gly Asp Ala Glu
            180                 185                 190

Trp His Asp Ile Thr Gly Thr Asp Glu Lys Tyr Gly Gly Arg Ala Leu
        195                 200                 205

Lys Pro Asp Thr Lys Met Lys Pro Cys Tyr Gly Ser Phe Ala Lys Pro
    210                 215                 220

Thr Asn Lys Glu Gly Gly Gln Ala Asn Val Lys Thr Glu Thr Gly Gly
```

```
              225                 230                 235                 240
Thr Lys Glu Tyr Asp Ile Asp Met Ala Phe Phe Asp Asn Arg Ser Ala
              245                 250                 255
Ala Ala Ala Gly Leu Ala Pro Glu Ile Val Leu Tyr Thr Glu Asn Val
              260                 265                 270
Asp Leu Glu Thr Pro Asp Thr His Ile Val Tyr Lys Ala Gly Thr Asp
              275                 280                 285
Asp Ser Ser Ser Ile Asn Leu Gly Gln Gln Ser Met Pro Asn Arg
    290                 295                 300
Pro Asn Tyr Ile Gly Phe Arg Asp Asn Phe Ile Gly Leu Met Tyr Tyr
305                 310                 315                 320
Asn Ser Thr Gly Asn Met Gly Val Leu Ala Gly Gln Ala Ser Gln Leu
              325                 330                 335
Asn Ala Val Val Asp Leu Gln Asp Arg Asn Thr Glu Leu Ser Tyr Gln
              340                 345                 350
Leu Leu Leu Asp Ser Leu Gly Asp Arg Thr Arg Tyr Phe Ser Met Trp
              355                 360                 365
Asn Gln Ala Val Asp Ser Tyr Asp Pro Asp Val Arg Ile Ile Glu Asn
    370                 375                 380
His Gly Val Glu Asp Glu Leu Pro Asn Tyr Cys Phe Pro Leu Asp Ala
385                 390                 395                 400
Val Gly Arg Thr Asp Thr Tyr Gln Gly Ile Lys Ala Asn Gly Asp Asn
              405                 410                 415
Gln Thr Thr Trp Thr Lys Asp Asp Thr Val Asn Asp Ala Asn Glu Leu
              420                 425                 430
Gly Lys Gly Asn Pro Phe Ala Met Glu Ile Asn Ile Gln Ala Asn Leu
              435                 440                 445
Trp Arg Asn Phe Leu Tyr Ala Asn Val Ala Leu Tyr Leu Pro Asp Ser
    450                 455                 460
Tyr Lys Tyr Thr Pro Ala Asn Ile Thr Leu Pro Thr Asn Thr Asn Thr
465                 470                 475                 480
Tyr Asp Tyr Met Asn Gly Arg Val Val Ala Pro Ser Leu Val Asp Ala
              485                 490                 495
Tyr Ile Asn Ile Gly Ala Arg Trp Ser Leu Asp Pro Met Asp Asn Val
              500                 505                 510
Asn Pro Phe Asn His His Arg Asn Ala Gly Leu Arg Tyr Arg Ser Met
              515                 520                 525
Leu Leu Gly Asn Gly Arg Tyr Val Pro Phe His Ile Gln Val Pro Gln
              530                 535                 540
Lys Phe Phe Ala Ile Lys Ser Leu Leu Leu Pro Gly Ser Tyr Thr
545                 550                 555                 560
Tyr Glu Trp Asn Phe Arg Lys Asp Val Asn Met Ile Leu Gln Ser Ser
              565                 570                 575
Leu Gly Asn Asp Leu Arg Thr Asp Gly Ala Ser Ile Ala Phe Thr Ser
              580                 585                 590
Ile Asn Leu Tyr Ala Thr Phe Phe Pro Met Ala His Asn Thr Ala Ser
              595                 600                 605
Thr Leu Glu Ala Met Leu Arg Asn Asp Thr Asn Asp Gln Ser Phe Asn
              610                 615                 620
Asp Tyr Leu Ser Ala Ala Asn Met Leu Tyr Pro Ile Pro Ala Asn Ala
625                 630                 635                 640
Thr Asn Val Pro Ile Ser Ile Pro Ser Arg Asn Trp Ala Ala Phe Arg
              645                 650                 655
```

```
Gly Trp Ser Phe Thr Arg Leu Lys Thr Arg Glu Thr Pro Ser Leu Gly
            660                 665                 670

Ser Gly Phe Asp Pro Tyr Phe Val Tyr Ser Gly Ser Ile Pro Tyr Leu
        675                 680                 685

Asp Gly Thr Phe Tyr Leu Asn His Thr Phe Lys Lys Val Ser Ile Thr
    690                 695                 700

Phe Asp Ser Ser Val Ser Trp Pro Gly Asn Asp Arg Leu Leu Thr Pro
705                 710                 715                 720

Asn Glu Phe Glu Ile Lys Arg Thr Val Asp Gly Glu Gly Tyr Asn Val
                725                 730                 735

Ala Gln Cys Asn Met Thr Lys Asp Trp Phe Leu Val Gln Met Leu Ala
            740                 745                 750

His Tyr Asn Ile Gly Tyr Gln Gly Phe Tyr Val Pro Glu Gly Tyr Lys
        755                 760                 765

Asp Arg Met Tyr Ser Phe Phe Arg Asn Phe Gln Pro Met Ser Arg Gln
    770                 775                 780

Val Val Asp Glu Val Asn Tyr Lys Asp Tyr Gln Ala Val Thr Leu Ala
785                 790                 795                 800

Tyr Gln His Asn Asn Ser Gly Phe Val Gly Tyr Leu Ala Pro Thr Met
                805                 810                 815

Arg Gln Gly Gln Pro Tyr Pro Ala Asn Tyr Pro Tyr Pro Leu Ile Gly
            820                 825                 830

Lys Ser Ala Val Ala Ser Val Thr Gln Lys Lys Phe Leu Cys Asp Arg
        835                 840                 845

Val Met Trp Arg Ile Pro Phe Ser Ser Asn Phe Met Ser Met Gly Ala
    850                 855                 860

Leu Thr Asp Leu Gly Gln Asn Met Leu Tyr Ala Asn Ser Ala His Ala
865                 870                 875                 880

Leu Asp Met Asn Phe Glu Val Asp Pro Met Asp Glu Ser Thr Leu Leu
                885                 890                 895

Tyr Val Val Phe Glu Val Phe Asp Val Val Arg Val His Gln Pro His
            900                 905                 910

Arg Gly Val Ile Glu Ala Val Tyr Leu Arg Thr Pro Phe Ser Ala Gly
        915                 920                 925

Asn Ala Thr Thr
    930

<210> SEQ ID NO 12
<211> LENGTH: 443
<212> TYPE: PRT
<213> ORGANISM: chimpanzee adenovirus serotype Pan7

<400> SEQUENCE: 12

Met Ser Lys Lys Arg Val Arg Val Asp Asp Phe Asp Pro Val Tyr
1               5                   10                  15

Pro Tyr Asp Ala Asp Asn Ala Pro Thr Val Pro Phe Ile Asn Pro Pro
                20                  25                  30

Phe Val Ser Ser Asp Gly Phe Gln Glu Lys Pro Leu Gly Val Leu Ser
            35                  40                  45

Leu Arg Leu Ala Asp Pro Val Thr Thr Lys Asn Gly Glu Ile Thr Leu
        50                  55                  60

Lys Leu Gly Glu Gly Val Asp Leu Asp Ser Ser Gly Lys Leu Ile Ser
65                  70                  75                  80

Asn Thr Ala Thr Lys Ala Ala Pro Leu Ser Phe Ser Asn Asn Thr
                85                  90                  95
```

```
Ile Ser Leu Asn Met Asp Thr Pro Leu Tyr Thr Lys Asp Gly Lys Leu
                100                 105                 110

Ser Leu Gln Val Ser Pro Pro Leu Asn Ile Leu Lys Ser Thr Ile Leu
            115                 120                 125

Asn Thr Leu Ala Val Ala Tyr Gly Ser Gly Leu Gly Leu Ser Gly Gly
130                 135                 140

Thr Ala Leu Ala Val Gln Leu Ala Ser Pro Leu Thr Phe Asp Glu Lys
145                 150                 155                 160

Gly Asn Ile Lys Ile Asn Leu Ala Ser Gly Pro Leu Thr Val Asp Ala
                165                 170                 175

Ser Arg Leu Ser Ile Asn Cys Lys Arg Gly Val Thr Val Thr Thr Ser
            180                 185                 190

Gly Asp Ala Ile Glu Ser Asn Ile Ser Trp Pro Lys Gly Ile Arg Phe
        195                 200                 205

Glu Gly Asn Gly Ile Ala Ala Asn Ile Gly Arg Gly Leu Glu Phe Gly
            210                 215                 220

Thr Thr Ser Thr Glu Thr Asp Val Thr Asp Ala Tyr Pro Ile Gln Val
225                 230                 235                 240

Lys Leu Gly Thr Gly Leu Thr Phe Asp Ser Thr Gly Ala Ile Val Ala
                245                 250                 255

Trp Asn Lys Glu Asp Asp Lys Leu Thr Leu Trp Thr Thr Ala Asp Pro
            260                 265                 270

Ser Pro Asn Cys Lys Ile Tyr Ser Glu Lys Asp Ala Lys Leu Thr Leu
        275                 280                 285

Cys Leu Thr Lys Cys Gly Ser Gln Ile Leu Gly Thr Val Thr Val Leu
        290                 295                 300

Ala Val Asn Asn Gly Ser Leu Asn Pro Ile Thr Asn Thr Val Ser Thr
305                 310                 315                 320

Ala Leu Val Ser Leu Lys Phe Asp Ala Ser Gly Val Leu Leu Ser Ser
                325                 330                 335

Ser Thr Leu Asp Lys Glu Tyr Trp Asn Phe Arg Lys Gly Asp Val Thr
            340                 345                 350

Pro Ala Glu Pro Tyr Thr Asn Ala Ile Gly Phe Met Pro Asn Ile Lys
        355                 360                 365

Ala Tyr Pro Lys Asn Thr Ser Ala Ala Ser Lys Ser His Ile Val Ser
        370                 375                 380

Gln Val Tyr Leu Asn Gly Asp Glu Ala Lys Pro Leu Met Leu Ile Ile
385                 390                 395                 400

Thr Phe Asn Glu Thr Glu Asp Ala Thr Cys Thr Tyr Ser Ile Thr Phe
                405                 410                 415

Gln Trp Lys Trp Asp Ser Thr Lys Tyr Thr Gly Glu Thr Leu Ala Thr
            420                 425                 430

Ser Ser Phe Thr Phe Ser Tyr Ile Ala Gln Glu
            435                 440

<210> SEQ ID NO 13
<211> LENGTH: 338
<212> TYPE: PRT
<213> ORGANISM: simian serotype C1

<400> SEQUENCE: 13

Ala Pro Lys Gly Ala Pro Asn Thr Ser Gln Trp Leu Asp Lys Gly Val
1               5                   10                  15

Thr Thr Thr Asp Asn Asn Thr Glu Asn Gly Asp Glu Glu Asp Glu Val
            20                  25                  30
```

```
Ala Glu Glu Gly Glu Glu Lys Gln Ala Thr Tyr Thr Phe Gly Asn
         35                  40                  45

Ala Pro Val Lys Ala Glu Ala Glu Ile Thr Lys Glu Gly Leu Pro Ile
 50                  55                  60

Gly Leu Glu Val Pro Ser Glu Gly Asp Pro Lys Pro Ile Tyr Ala Asp
 65                  70                  75                  80

Lys Leu Tyr Gln Pro Glu Pro Gln Val Gly Glu Ser Trp Thr Asp
             85                  90                  95

Thr Asp Gly Thr Asp Glu Lys Tyr Gly Gly Arg Ala Leu Lys Pro Glu
            100                 105                 110

Thr Lys Met Lys Pro Cys Tyr Gly Ser Phe Ala Lys Pro Thr Asn Val
            115                 120                 125

Lys Gly Gly Gln Ala Lys Val Lys Lys Val Glu Glu Gly Lys Val Glu
130                 135                 140

Tyr Asp Ile Asp Met Asn Phe Phe Asp Leu Arg Ser Gln Lys Thr Gly
145                 150                 155                 160

Leu Lys Pro Lys Ile Val Met Tyr Ala Glu Asn Val Asp Leu Glu Thr
                165                 170                 175

Pro Asp Thr His Val Val Tyr Lys Pro Gly Ala Ser Ala Ser Ser
                180                 185                 190

His Ala Asn Leu Gly Gln Gln Ser Met Pro Asn Arg Pro Asn Tyr Ile
            195                 200                 205

Gly Phe Arg Asp Asn Phe Ile Gly Leu Met Tyr Tyr Asn Ser Thr Gly
210                 215                 220

Asn Met Gly Val Leu Ala Gly Gln Ala Ser Gln Leu Asn Ala Val Val
225                 230                 235                 240

Asp Leu Gln Asp Arg Asn Thr Glu Leu Ser Tyr Gln Leu Leu Leu Asp
                245                 250                 255

Ser Leu Gly Asp Arg Thr Arg Tyr Phe Ser Met Trp Asn Gln Ala Val
            260                 265                 270

Asp Ser Tyr Asp Pro Asp Val Arg Val Ile Glu Asn His Gly Val Glu
        275                 280                 285

Asp Glu Leu Pro Asn Tyr Cys Phe Pro Leu Asp Gly Val Gly Pro Arg
    290                 295                 300

Thr Asp Ser Tyr Lys Gly Ile Glu Thr Asn Gly Asp Glu Asn Thr Thr
305                 310                 315                 320

Trp Lys Asp Leu Asp Pro Asn Gly Ile Ser Glu Leu Ala Lys Gly Asn
            325                 330                 335

Pro Phe

<210> SEQ ID NO 14
<211> LENGTH: 315
<212> TYPE: PRT
<213> ORGANISM: chimpanzee adenovirus Pan-9

<400> SEQUENCE: 14

Ala Pro Lys Gly Ala Pro Asn Thr Cys Gln Trp Thr Tyr Lys Ala Asp
 1               5                  10                  15

Gly Glu Thr Ala Thr Glu Lys Thr Tyr Thr Tyr Gly Asn Ala Pro Val
                 20                  25                  30

Gln Gly Ile Asn Ile Thr Lys Asp Gly Ile Gln Leu Gly Thr Asp Thr
             35                  40                  45

Asp Asp Gln Pro Ile Tyr Ala Asp Lys Thr Tyr Gln Pro Glu Pro Gln
 50                  55                  60

Val Gly Asp Ala Glu Trp His Asp Ile Thr Gly Thr Asp Glu Lys Tyr
```

```
                65                  70                  75                  80
Gly Gly Arg Ala Leu Lys Pro Asp Thr Lys Met Lys Pro Cys Tyr Gly
                    85                  90                  95

Ser Phe Ala Lys Pro Thr Asn Lys Glu Gly Gln Ala Asn Val Lys
                100                 105                 110

Thr Gly Thr Gly Thr Thr Lys Glu Tyr Asp Ile Asp Met Ala Phe Phe
            115                 120                 125

Asp Asn Arg Ser Ala Ala Ala Ala Gly Leu Ala Pro Glu Ile Val Leu
        130                 135                 140

Tyr Thr Glu Asn Val Asp Leu Glu Thr Pro Asp Thr His Ile Val Tyr
145                 150                 155                 160

Lys Ala Gly Thr Asp Asp Ser Ser Ser Ile Asn Leu Gly Gln Gln
                165                 170                 175

Ala Met Pro Asn Arg Pro Asn Tyr Ile Gly Phe Arg Asp Asn Phe Ile
                180                 185                 190

Gly Leu Met Tyr Tyr Asn Ser Thr Gly Asn Met Gly Val Leu Ala Gly
            195                 200                 205

Gln Ala Ser Gln Leu Asn Ala Val Val Asp Leu Gln Asp Arg Asn Thr
        210                 215                 220

Glu Leu Ser Tyr Gln Leu Leu Asp Ser Leu Gly Asp Arg Thr Arg
225                 230                 235                 240

Tyr Phe Ser Met Trp Asn Gln Ala Val Asp Ser Tyr Asp Pro Asp Val
                245                 250                 255

Arg Ile Ile Glu Asn His Gly Val Glu Asp Glu Leu Pro Asn Tyr Cys
                260                 265                 270

Phe Pro Leu Asp Ala Val Gly Arg Thr Asp Thr Tyr Gln Gly Ile Lys
            275                 280                 285

Ala Asn Gly Thr Asp Gln Thr Thr Trp Thr Lys Asp Asp Ser Val Asn
        290                 295                 300

Asp Ala Asn Glu Ile Gly Lys Gly Asn Pro Phe
305                 310                 315

<210> SEQ ID NO 15
<211> LENGTH: 315
<212> TYPE: PRT
<213> ORGANISM: chimpanzee adenovirus Pan-5

<400> SEQUENCE: 15

Ala Pro Lys Gly Ala Pro Asn Thr Cys Gln Trp Thr Tyr Lys Ala Asp
1               5                   10                  15

Gly Asp Thr Gly Thr Glu Lys Thr Tyr Thr Tyr Gly Asn Ala Pro Val
                20                  25                  30

Gln Gly Ile Ser Ile Thr Lys Asp Gly Ile Gln Leu Gly Thr Asp Thr
            35                  40                  45

Asp Asp Gln Pro Ile Tyr Ala Asp Lys Thr Tyr Gln Pro Glu Pro Gln
        50                  55                  60

Val Gly Asp Ala Glu Trp His Asp Ile Thr Gly Thr Asp Glu Lys Tyr
65                  70                  75                  80

Gly Gly Arg Ala Leu Lys Pro Asp Thr Lys Met Lys Pro Cys Tyr Gly
                85                  90                  95

Ser Phe Ala Lys Pro Thr Asn Lys Glu Gly Gln Ala Asn Val Lys
                100                 105                 110

Thr Glu Thr Gly Gly Thr Lys Glu Tyr Asp Ile Asp Met Ala Phe Phe
            115                 120                 125

Asp Asn Arg Ser Ala Ala Ala Ala Gly Leu Ala Pro Glu Ile Val Leu
```

```
            130                 135                 140
Tyr Thr Glu Asn Val Asp Leu Glu Thr Pro Asp Thr His Ile Val Tyr
145                 150                 155                 160

Lys Ala Gly Thr Asp Ser Ser Ser Ile Asn Leu Gly Gln Gln
                165                 170                 175

Ser Met Pro Asn Arg Pro Asn Tyr Ile Gly Phe Arg Asp Asn Phe Ile
                180                 185                 190

Gly Leu Met Tyr Tyr Asn Ser Thr Gly Asn Met Gly Val Leu Ala Gly
                195                 200                 205

Gln Ala Ser Gln Leu Asn Ala Val Val Asp Leu Gln Asp Arg Asn Thr
                210                 215                 220

Glu Leu Ser Tyr Gln Leu Leu Asp Ser Leu Gly Asp Arg Thr Arg
225                 230                 235                 240

Tyr Phe Ser Met Trp Asn Gln Ala Val Asp Ser Tyr Asp Pro Asp Val
                245                 250                 255

Arg Ile Ile Glu Asn His Gly Val Glu Asp Glu Leu Pro Asn Tyr Cys
                260                 265                 270

Phe Pro Leu Asp Ala Val Gly Arg Thr Asp Thr Tyr Gln Gly Ile Lys
                275                 280                 285

Ala Asn Gly Ala Asp Gln Thr Thr Trp Thr Lys Asp Asp Thr Val Asn
                290                 295                 300

Asp Ala Asn Glu Leu Gly Lys Gly Asn Pro Phe
305                 310                 315

<210> SEQ ID NO 16
<211> LENGTH: 324
<212> TYPE: PRT
<213> ORGANISM: chimpanzee adenovirus Pan-6

<400> SEQUENCE: 16

Ala Pro Lys Gly Ala Pro Asn Ser Ser Gln Trp Glu Gln Ala Lys Thr
1               5                   10                  15

Gly Asn Gly Gly Thr Met Glu Thr His Thr Tyr Gly Val Ala Pro Met
                20                  25                  30

Gly Gly Glu Asn Ile Thr Lys Asp Gly Leu Gln Ile Gly Thr Asp Val
                35                  40                  45

Thr Ala Asn Gln Asn Lys Pro Ile Tyr Ala Asp Lys Thr Phe Gln Pro
50                  55                  60

Glu Pro Gln Val Gly Glu Asn Trp Gln Thr Glu Asn Phe Tyr
65                  70                  75                  80

Gly Gly Arg Ala Leu Lys Lys Asp Thr Lys Met Lys Pro Cys Tyr Gly
                85                  90                  95

Ser Tyr Ala Arg Pro Thr Asn Glu Lys Gly Gly Gln Ala Lys Leu Lys
                100                 105                 110

Val Gly Asp Asp Gly Val Pro Thr Lys Glu Phe Asp Ile Asp Leu Ala
                115                 120                 125

Phe Phe Asp Thr Pro Gly Gly Thr Val Asn Gly Gln Asp Glu Tyr Lys
                130                 135                 140

Ala Asp Ile Val Met Tyr Thr Glu Asn Thr Tyr Leu Glu Thr Pro Asp
145                 150                 155                 160

Thr His Val Val Tyr Lys Pro Gly Lys Asp Asp Ala Ser Ser Glu Ile
                165                 170                 175

Asn Leu Val Gln Gln Ser Met Pro Asn Arg Pro Asn Tyr Ile Gly Phe
                180                 185                 190

Arg Asp Asn Phe Ile Gly Leu Met Tyr Tyr Asn Ser Thr Gly Asn Met
```

```
                    195                 200                 205
Gly Val Leu Ala Gly Gln Ala Ser Gln Leu Asn Ala Val Val Asp Leu
            210                 215                 220

Gln Asp Arg Asn Thr Glu Leu Ser Tyr Gln Leu Leu Leu Asp Ser Leu
225                 230                 235                 240

Gly Asp Arg Thr Arg Tyr Phe Ser Met Trp Asn Gln Ala Val Asp Ser
            245                 250                 255

Tyr Asp Pro Asp Val Arg Ile Ile Glu Asn His Gly Val Glu Asp Glu
            260                 265                 270

Leu Pro Asn Tyr Cys Phe Pro Leu Asp Gly Ser Gly Thr Asn Ala Ala
            275                 280                 285

Tyr Gln Gly Val Lys Val Lys Asp Gly Gln Asp Gly Asp Val Glu Ser
            290                 295                 300

Glu Trp Glu Asn Asp Asp Thr Val Ala Ala Arg Asn Gln Leu Cys Lys
305                 310                 315                 320

Gly Asn Ile Phe

<210> SEQ ID NO 17
<211> LENGTH: 314
<212> TYPE: PRT
<213> ORGANISM: chimpanzee adenovirus Pan-7

<400> SEQUENCE: 17

Ala Pro Lys Gly Ala Pro Asn Thr Cys Gln Trp Thr Tyr Lys Ala Gly
1               5                   10                  15

Asp Thr Asp Thr Glu Lys Thr Tyr Thr Tyr Gly Asn Ala Pro Val Gln
                20                  25                  30

Gly Ile Ser Ile Thr Lys Asp Gly Ile Gln Leu Gly Thr Asp Ser Asp
            35                  40                  45

Gly Gln Ala Ile Tyr Ala Asp Glu Thr Tyr Gln Pro Glu Pro Gln Val
        50                  55                  60

Gly Asp Ala Glu Trp His Asp Ile Thr Gly Thr Asp Glu Lys Tyr Gly
65                  70                  75                  80

Gly Arg Ala Leu Lys Pro Asp Thr Lys Met Lys Pro Cys Tyr Gly Ser
                85                  90                  95

Phe Ala Lys Pro Thr Asn Lys Glu Gly Gly Gln Ala Asn Val Lys Thr
            100                 105                 110

Glu Thr Gly Gly Thr Lys Glu Tyr Asp Ile Asp Met Ala Phe Phe Asp
        115                 120                 125

Asn Arg Ser Ala Ala Ala Gly Leu Ala Pro Glu Ile Val Leu Tyr
130                 135                 140

Thr Glu Asn Val Asp Leu Glu Thr Pro Asp Thr His Ile Val Tyr Lys
145                 150                 155                 160

Ala Gly Thr Asp Asp Ser Ser Ser Ile Asn Leu Gly Gln Gln Ser
                165                 170                 175

Met Pro Asn Arg Pro Asn Tyr Ile Gly Phe Arg Asp Asn Phe Ile Gly
            180                 185                 190

Leu Met Tyr Tyr Asn Ser Thr Gly Asn Met Gly Val Leu Ala Gly Gln
        195                 200                 205

Ala Ser Gln Leu Asn Ala Val Val Asp Leu Gln Asp Arg Asn Thr Glu
    210                 215                 220

Leu Ser Tyr Gln Leu Leu Leu Asp Ser Leu Gly Asp Arg Thr Arg Tyr
225                 230                 235                 240

Phe Ser Met Trp Asn Gln Ala Val Asp Ser Tyr Asp Pro Asp Val Arg
                245                 250                 255
```

```
Ile Ile Glu Asn His Gly Val Glu Asp Glu Leu Pro Asn Tyr Cys Phe
            260                 265                 270

Pro Leu Asp Ala Val Gly Arg Thr Asp Thr Tyr Gln Gly Ile Lys Ala
            275                 280                 285

Asn Gly Asp Asn Gln Thr Thr Trp Thr Lys Asp Thr Val Asn Asp
            290                 295                 300

Ala Asn Glu Leu Gly Lys Gly Asn Pro Phe
305                 310

<210> SEQ ID NO 18
<211> LENGTH: 179
<212> TYPE: PRT
<213> ORGANISM: chimpanzee adenovirus Pan9

<400> SEQUENCE: 18

Thr Leu Trp Thr Thr Pro Asp Pro Ser Pro Asn Cys Gln Ile Leu Ala
1               5                   10                  15

Glu Asn Asp Ala Lys Leu Thr Leu Cys Leu Thr Lys Cys Gly Ser Gln
            20                  25                  30

Ile Leu Ala Thr Val Ser Val Leu Val Val Gly Ser Gly Asn Leu Asn
            35                  40                  45

Pro Ile Thr Gly Thr Val Ser Ser Ala Gln Val Phe Leu Arg Phe Asp
        50                  55                  60

Ala Asn Gly Val Leu Leu Thr Glu His Ser Thr Leu Lys Lys Tyr Trp
65                  70                  75                  80

Gly Tyr Arg Gln Gly Asp Ser Ile Asp Gly Thr Pro Tyr Thr Asn Ala
                85                  90                  95

Val Gly Phe Met Pro Asn Leu Lys Ala Tyr Pro Lys Ser Gln Ser Ser
            100                 105                 110

Thr Thr Lys Asn Asn Ile Val Gly Gln Val Tyr Met Asn Gly Asp Val
            115                 120                 125

Ser Lys Pro Met Leu Leu Thr Ile Thr Leu Asn Gly Thr Asp Asp Ser
        130                 135                 140

Asn Ser Thr Tyr Ser Met Ser Phe Ser Tyr Thr Trp Thr Asn Gly Ser
145                 150                 155                 160

Tyr Val Gly Ala Thr Phe Gly Ala Asn Ser Tyr Thr Phe Ser Tyr Ile
                165                 170                 175

Ala Gln Glu

<210> SEQ ID NO 19
<211> LENGTH: 185
<212> TYPE: PRT
<213> ORGANISM: chimpanzee adenovirus Pan6

<400> SEQUENCE: 19

Thr Leu Trp Thr Thr Pro Asp Pro Ser Pro Asn Cys Gln Leu Leu Ser
1               5                   10                  15

Asp Arg Asp Ala Lys Phe Thr Leu Cys Leu Thr Lys Cys Gly Ser Gln
            20                  25                  30

Ile Leu Gly Thr Val Ala Val Ala Ala Val Thr Val Gly Ser Ala Leu
            35                  40                  45

Asn Pro Ile Asn Asp Thr Val Lys Ser Ala Ile Val Phe Leu Arg Phe
        50                  55                  60

Asp Ser Asp Gly Val Leu Met Ser Asn Ser Ser Met Val Gly Asp Tyr
65                  70                  75                  80

Trp Asn Phe Arg Glu Gly Gln Thr Thr Gln Ser Val Ala Tyr Thr Asn
```

```
                    85                  90                  95
Ala Val Gly Phe Met Pro Asn Ile Gly Ala Tyr Pro Lys Thr Gln Ser
            100                 105                 110

Lys Thr Pro Lys Asn Ser Ile Val Ser Gln Val Tyr Leu Thr Gly Glu
        115                 120                 125

Thr Thr Met Pro Met Thr Leu Thr Ile Thr Phe Asn Gly Thr Asp Glu
    130                 135                 140

Lys Asp Thr Thr Pro Val Ser Thr Tyr Ser Met Thr Phe Thr Trp Gln
145                 150                 155                 160

Trp Thr Gly Asp Tyr Lys Asp Lys Asn Ile Thr Phe Ala Thr Asn Ser
                165                 170                 175

Phe Ser Phe Ser Tyr Ile Ala Gln Glu
            180                 185

<210> SEQ ID NO 20
<211> LENGTH: 179
<212> TYPE: PRT
<213> ORGANISM: chimpanzee adenovirus Pan7

<400> SEQUENCE: 20

Thr Leu Trp Thr Thr Ala Asp Pro Ser Pro Asn Cys Lys Ile Tyr Ser
1               5                   10                  15

Glu Lys Asp Ala Lys Leu Thr Leu Cys Leu Thr Lys Cys Gly Ser Gln
            20                  25                  30

Ile Leu Gly Thr Val Thr Val Leu Ala Val Asn Asn Gly Ser Leu Asn
        35                  40                  45

Pro Ile Thr Asn Thr Val Ser Thr Ala Leu Val Ser Leu Lys Phe Asp
    50                  55                  60

Ala Ser Gly Val Leu Leu Ser Ser Thr Leu Asp Lys Glu Tyr Trp
65                  70                  75                  80

Asn Phe Arg Lys Gly Asp Val Thr Pro Ala Glu Pro Tyr Thr Asn Ala
                85                  90                  95

Ile Gly Phe Met Pro Asn Ile Lys Ala Tyr Pro Lys Asn Thr Ser Ala
            100                 105                 110

Ala Ser Lys Ser His Ile Val Ser Gln Val Tyr Leu Asn Gly Asp Glu
        115                 120                 125

Ala Lys Pro Leu Met Leu Ile Ile Thr Phe Asn Glu Thr Glu Asp Ala
    130                 135                 140

Thr Cys Thr Tyr Ser Ile Thr Phe Gln Trp Lys Trp Asp Ser Thr Lys
145                 150                 155                 160

Tyr Thr Gly Glu Thr Leu Ala Thr Ser Ser Phe Thr Phe Ser Tyr Ile
                165                 170                 175

Ala Gln Glu

<210> SEQ ID NO 21
<211> LENGTH: 179
<212> TYPE: PRT
<213> ORGANISM: chimpanzee adenovirus Pan5

<400> SEQUENCE: 21

Thr Leu Trp Thr Thr Ala Asp Pro Ser Pro Asn Cys His Ile Tyr Ser
1               5                   10                  15

Glu Lys Asp Ala Lys Leu Thr Leu Cys Leu Thr Lys Cys Gly Ser Gln
            20                  25                  30

Ile Leu Gly Thr Val Ser Leu Ile Ala Val Asp Thr Gly Ser Leu Asn
        35                  40                  45
```

```
Pro Ile Thr Gly Thr Val Thr Ala Leu Val Ser Leu Lys Phe Asp
    50              55                  60

Ala Asn Gly Val Leu Gln Ser Ser Ser Thr Leu Asp Ser Asp Tyr Trp
65              70                  75                  80

Asn Phe Arg Gln Gly Asp Val Thr Pro Ala Glu Ala Tyr Thr Asn Ala
                85                  90                  95

Ile Gly Phe Met Pro Asn Leu Lys Ala Tyr Pro Lys Asn Thr Ser Gly
                100                 105                 110

Ala Ala Lys Ser His Ile Val Gly Lys Val Tyr Leu His Gly Asp Thr
                115                 120                 125

Gly Lys Pro Leu Asp Leu Ile Ile Thr Phe Asn Glu Thr Ser Asp Glu
                130                 135                 140

Ser Cys Thr Tyr Cys Ile Asn Phe Gln Trp Gln Trp Gly Ala Asp Gln
145                 150                 155                 160

Tyr Lys Asn Glu Thr Leu Ala Val Ser Ser Phe Thr Phe Ser Tyr Ile
                165                 170                 175

Ala Lys Glu

<210> SEQ ID NO 22
<211> LENGTH: 183
<212> TYPE: PRT
<213> ORGANISM: human adenovirus Ad 2

<400> SEQUENCE: 22

Thr Leu Trp Thr Thr Pro Asp Pro Ser Pro Asn Cys Arg Ile His Ser
1               5                   10                  15

Asp Asn Asp Cys Lys Phe Thr Leu Val Leu Thr Lys Cys Gly Ser Gln
                20                  25                  30

Val Leu Ala Thr Val Ala Ala Leu Ala Val Ser Gly Asp Leu Ser Ser
                35                  40                  45

Met Thr Gly Thr Val Ala Ser Val Ser Ile Phe Leu Arg Phe Asp Gln
                50                  55                  60

Asn Gly Val Leu Met Glu Asn Ser Ser Leu Lys Lys His Tyr Trp Asn
65              70                  75                  80

Phe Arg Asn Gly Asn Ser Thr Asn Ala Asn Pro Tyr Thr Asn Ala Val
                85                  90                  95

Gly Phe Met Pro Asn Leu Leu Ala Tyr Pro Lys Thr Gln Ser Gln Thr
                100                 105                 110

Ala Lys Asn Asn Ile Val Ser Gln Val Tyr Leu His Gly Asp Lys Thr
                115                 120                 125

Lys Pro Met Ile Leu Thr Ile Thr Leu Asn Gly Thr Ser Glu Ser Thr
                130                 135                 140

Glu Thr Ser Glu Val Ser Thr Tyr Ser Met Ser Phe Thr Trp Ser Trp
145                 150                 155                 160

Glu Ser Gly Lys Tyr Thr Thr Glu Thr Phe Ala Thr Asn Ser Tyr Thr
                165                 170                 175

Phe Ser Tyr Ile Ala Gln Glu
                180

<210> SEQ ID NO 23
<211> LENGTH: 182
<212> TYPE: PRT
<213> ORGANISM: human adenovirus Ad 5

<400> SEQUENCE: 23

Thr Leu Trp Thr Thr Pro Ala Pro Ser Pro Asn Cys Arg Leu Asn Ala
1               5                   10                  15
```

```
Glu Lys Asp Ala Lys Leu Thr Leu Val Leu Thr Lys Cys Gly Ser Gln
            20                  25                  30

Ile Leu Ala Thr Val Ser Val Leu Ala Val Lys Gly Ser Leu Ala Pro
        35                  40                  45

Ile Ser Gly Thr Val Gln Ser Ala His Leu Ile Ile Arg Phe Asp Glu
    50                  55                  60

Asn Gly Val Leu Ile Asn Asn Ser Phe Leu Asp Pro Glu Tyr Trp Asn
65                  70                  75                  80

Phe Arg Asn Gly Asp Leu Thr Glu Gly Thr Ala Tyr Thr Asn Ala Val
                85                  90                  95

Gly Phe Met Pro Asn Leu Ser Ala Tyr Pro Lys Ser His Gly Lys Thr
            100                 105                 110

Ala Lys Ser Asn Ile Val Ser Gln Val Tyr Leu Asn Gly Asp Lys Thr
        115                 120                 125

Lys Pro Val Thr Leu Thr Ile Thr Leu Asn Gly Thr Gln Glu Thr Gly
    130                 135                 140

Asp Thr Thr Pro Ser Ala Tyr Ser Met Ser Phe Ser Trp Asp Trp Ser
145                 150                 155                 160

Gly His Asn Tyr Ile Asn Glu Ile Phe Ala Thr Ser Ser Tyr Thr Glu
                165                 170                 175

Ser Tyr Ile Ala Gln Glu
            180
```

```
<210> SEQ ID NO 24
<211> LENGTH: 34264
<212> TYPE: DNA
<213> ORGANISM: simian adenovirus SV-1
<220> FEATURE:
<221> NAME/KEY: CDS
<222> LOCATION: (12454)..(13965)
<223> OTHER INFORMATION: L2 Penton
<220> FEATURE:
<221> NAME/KEY: CDS
<222> LOCATION: (16841)..(19636)
<223> OTHER INFORMATION: L3 Hexon
<220> FEATURE:
<221> NAME/KEY: CDS
<222> LOCATION: (28059)..(29150)
<223> OTHER INFORMATION: L5 Fiber #2
<220> FEATURE:
<221> NAME/KEY: CDS
<222> LOCATION: (29183)..(30865)
<223> OTHER INFORMATION: L5 Fiber #1

<400> SEQUENCE: 24
tccttattct ggaaacgtgc caatatgata atgagcgggg aggagcgagg cggggccggg      60
gtgacgtgcg gtgacgtggg gtgacgcggg gtggcgcgag ggcggggcgg gagtggggag     120
gcgcttagtt tttacgtatg cggaaggagg tttttataccg gaagttgggt aatttgggcg    180
tatacttgta agttttgtgt aatttggcgc gaaaaccggg taatgaggaa gttgaggtta    240
atatgtactt tttatgactg ggcggaattt ctgctgatca gcagtgaact ttgggcgctg    300
acggggaggt ttcgctacgt ggcagtacca cgagaaggct caaaggtccc atttattgta    360
ctcctcagcg tttttcgctgg gtatttaaac gctgtcagat catcaagagg ccactcttga    420
gtgccggcga gtagagtttt ctcctccgcg ctgccgcgat gaggctggtt cccgagatgt    480
acggtgtttt ctgcagcgag acggcccgga actcagatga gctgcttaat acagatctgc    540
tggatgttcc caactcgcct gtggcttcgc ctccgtcgct tcatgatctt ttcgatgtgg    600
aagtggatcc accgcaagat cccaacgagg acgcggtaaa cagtatgttc cctgaatgtc    660
```

```
tgtttgaggc ggctgaggag ggttctcaca gcagtgaaga gagcagacgg ggagaggaac    720
tggacttgaa atgctacgag gaatgtctgc cttctagcga ttctgaaacg gaacagacag    780
ggggagacgg ctgtgagtcg gcaatgaaaa atgaacttgt attagactgt ccagaacatc    840
ctggtcatgg ctgccgtgcc tgtgcttttc atagaaatgc cagcggaaat cctgagactc    900
tatgtgctct gtgttatctg cgccttacca gcgattttgt atacagtaag taaagtgttt    960
tcattggcgt acggtagggg attcgttgaa gtgctttgtg acttattatg tgtcattatt   1020
tctaggtgac gtgtccgacg tggaagggga aggagataga tcaggggctg ctaattctcc   1080
ttgcactttg ggggctgtgg ttccagttgg catttttaaa ccgagtggtg gaggagaacg   1140
agccggagga gaccgagaat ctgagagccg gcctggaccc tccagtggaa gactaggtgc   1200
tgaggatgat cctgaagagg ggactagtgg gggtgctagg aaaaagcaaa aaactgagcc   1260
tgaacctaga aacttttttga atgagttgac tgtaagccta atgaatcggc agcgtcctga   1320
gacggtgttt tggactgagt tggaggatga gttcaagaag ggggaattaa acctcttgta   1380
caagtatggg tttgagcagt tgaaaactca ctggttggag ccgtgggagg atatggaaat   1440
ggctctagac acctttgcta aagtggctct gcggccggat aaagtttaca ctattcgccg   1500
cactgttaat ataaaaaaga gtgtttatgt tatcggccat ggagctctgg tgcaggtgca   1560
gaccccagac cgggtggctt tcaattgcgg catgcagagt ttgggccccg gggtgatagg   1620
tttgaatgga gttacatttc aaaatgtcag gtttactggt gatgatttta atggctctgt   1680
gtttgtgact agcacccagc taaccctcca cggtgtttac ttttttaact ttaacaatac   1740
atgtgtggag tcatggggta gggtgtctct gaggggctgc agttttcatg gttgctggaa   1800
ggcggtggtg ggaagaatta aaagtgtcat gtctgtgaag aaatgcatat ttgaacgctg   1860
tgtgatagct ctagcagtag aggggtacgg acgatcagg aataacgccg catctgagaa   1920
tggatgtttt cttttgctga aaggtacggc cagcgttaag cataatatga tttgcggcag   1980
cggcctgtgc ccctcgcagc tcttaacttg cgcagatgga aactgtcaca ccttgcgcac   2040
cgtgcacata gtgtcccact cgcgccgcac ctggccaaca tttgagcaca atatgctcat   2100
gcgttgcgcc gttcacctag gtgctagacg cggcgtgttt atgccttatc aatgtaactt   2160
tagtcatact aagattttgc tggaaactga ttccttccct cgagtatgtt tcaatggggt   2220
gtttgacatg tcaatggaac ttttttaaagt gataagatat gatgaaacca agtctcgttg   2280
tcgctcatgt gaatgcggag ctaatcattt gaggttgtat cctgtaaccc tgaacgttac   2340
cgaggagctg aggacggacc accacatgct gtcttgcctg cgtaccgact atgaatccag   2400
cgatgaggag tgaggtgagg ggcggagcca caaagggtat aaaggggcat gagggggtggg   2460 cgcggtgttt caaaatgagc gggacgacgg acggcaatgc gtttgagggg ggagtgttca   2520
gcccatatct gacatctcgt cttccttcct gggcaggagt tcgtcagaat gtagtgggct   2580
ccaccgtgga cggacggccg gtcgcccctg caaattccgc caccctcacc tatgccaccg   2640
tgggatcatc gttggacact gccgcggcag ctgccgcttc tgctgccgct tctactgctc   2700
gcggcatggc ggctgatttt ggactatata ccaactggc cactgcagct gtggcgtctc   2760
ggtctctggt tcaagaagat gccctgaatg tgatcttgac tcgcctggag atcatgtcac   2820
gtcgcctgga cgaactggct gcgcagatat cccaagctaa ccccgatacc gcttcagaat   2880
cttaaaataa agacaaacaa atttgttgaa aagtaaaatg gctttatttg tttttttttgg   2940 ctcggtaggc tcgggtccac ctgtctcggt cgttaaggac tttgtgtatg ttttccaaaa   3000
cacggtacag atgggcttgg atgttcaagt acatgggcat gaggccatct ttggggtgga   3060
```

-continued

```
gataggacca ctgaagagcg tcatgttccg ggtggtatt gtaaatcacc cagtcgtagc      3120 agggttttg agcgtggaac tggaatatgt ccttcaggag caggctaatg ccaagggta       3180 gacccttagt gtaggtgttt acaaagcggt tgagctggga gggatgcatg cggggggaga     3240
tgatatgcat cttggcttgg attttgaggt tagctatgtt accacccagg tctctgcggg     3300
ggttcatgtt atgaaggacc accagcacgg tatagccagt gcatttgggg aacttgtcat     3360
gcagtttgga ggggaaggcg tggaagaatt tagataccccc cttgtgcccc ctaggtttt     3420 ccatgcactc atccataata atggcaatgg gaccctggc ggccgcttta gcaaacacgt      3480
tttgggggtt ggaaacatca tagttttgct ctagagtgag ctcatcatag gccatcttta    3540
caaagcgggg taggagggtg cccgactggg ggatgatagt tccatctggg cctggagcgt     3600
agttgccctc acagatctgc atctcccagg ccttaatttc cgaggggggg atcatgtcca     3660 cctgggggc gataaaaaac acggtttctg gcggggggtt aatgagctgg gtggaaagca      3720
agttacgcaa cagctgggat ttgccgcaac cggtgggacc gtagatgacc ccgatgacgg     3780
gttgcagctg gtagttcaga gaggaacagc tgccgtcggg gcgcaggagg ggagctacct    3840
cattcatcat gcttctgaca tgtttatttt cactcactaa gttttgcaag agcctctccc    3900
cacccaggga taagagttct tccaggctgt tgaagtgttt cagcggtttc aggccgtcgg    3960
ccatgggcat cttttcaagc gactgacgaa gcaagtacag tcggtcccag agctcggtga    4020
cgtgctctat ggaatctcga tccagcagac ttcttggttt cggggttgg gccgactttc     4080 gctgtagggc accagccggt gggcgtccag ggccgcgagg gttctgtcct tccagggtct    4140
cagcgttcgg gtgagggtgg tctcggtgac ggtgaaggga tgagccccgg gctgggcgct    4200
tgcgagggtg cgcttcaggc tcatcctgct ggtgctgaag cgggcgtcgt ctccctgtga    4260
gtcggccaga tagcaacgaa gcatgaggtc gtagctgagg gactcggccg cgtgtccctt    4320
ggcgcgcagc tttcccttgg aaacgtgctg acatttggtg cagtgcagac acttgagggc    4380
gtagagtttt ggggccagga agaccgactc gggcgagtag gcgtcggctc cgcactgagc    4440
gcagacggtc tcgcactcca ccagccacgt gagctcgggt ttagcgggat caaaaaccaa    4500
gttgcctcca tttttttga tgcgtttctt accttgcgtc tccatgagtc tgtgtcccgc     4560
ttccgtgaca aaaaggctgt cggtatcccc gtagaccgac ttgaggggc gatcttccaa     4620 aggtgttccg aggtcttccg cgtacaggaa ctgggaccac tccgagacaa aggctcgggt    4680
ccaggctaac acgaaggagg cgatctgcga ggggtatctg tcgttttcaa tgaggggtc     4740 cacctttttcc agggtgtgca gacacaggtc gtcctcctcc gcgtccacga aggtgattgg    4800
cttgtaagtg taggtcacgt gacccgcacc cccccaaggg gtataaaagg gggcgtgccc    4860
actctccccg tcactttctt ccgcatcgct gtggaccaga gccagctgtt cgggtgagta    4920
ggccctctca aaagccggca tgatttcggc gctcaagttg tcagtttcta caaacgaggt    4980
ggatttgata ttcacgtgcc ccgcggcgat gcttttgatg gtggagggt ccatctgatc     5040 agaaaacacg atcttttat tgtcaagttt ggtggcgaaa gacccgtaga gggcgttgga     5100
aagcaacttg gcgatggagc gcagggtctg atttttctcc cgatcggccc tctccttggc    5160
ggcgatgttg agttgcacgt actcgcgggc cacgcaccgc cactcgggga acacggcggt    5220
gcgctcgtcg ggcaggatgc gcacgcgcca gccgcggttg tgcagggtga tgaggtccac    5280
gctggtggcc acctccccgc ggaggggctc gttggtccaa cacaatcgcc cccctttttct   5340 ggagcagaac ggaggcaggg gatctagcaa gttggcgggc gggggtcgg cgtcgatggt     5400 aaatatgccg ggtagcagaa ttttattaaa ataatcgatt tcggtgtccg tgtcttgcaa    5460
```

```
cgcgtcttcc cacttcttca ccgccagggc cctttcgtag ggattcaggg gcggtcccca   5520
gggcatgggg tgggtcaggg ccgaggcgta catgccgcag atgtcgtaca cgtacagggg   5580
ctccctcaac accccgatgt aagtgggta acagcgcccc ccgcggatgc tggctcgcac   5640
gtagtcgtac atctcgtgag agggagccat gagcccgtct cccaagtggg tcttgtgggg   5700
tttttcggcc cggtagagga tctgcctgaa gatggcgtgg gagttggaag agatagtggg   5760
gcgttggaag acgttaaagt tggctccggg cagtcccacg gagtcttgga tgaactgggc   5820
gtaggattcc cggagcttgt ccaccagggc tgcggttacc agcacgtcga gagcgcagta   5880
gtccaacgtc tcgcggacca ggttgtaggc cgtctcttgt ttttctccc acagttcgcg   5940 attgaggagg tattcctcgc ggtctttcca gtactcttcg gcgggaaatc cttttcgtc    6000 cgctcggtaa gaacctaaca tgtaaaattc gttcacggct ttgtatggac aacagccttt   6060
ttctaccggc agggcgtacg cttgagcggc ctttctgaga gaggtgtggg tgagggcgaa   6120
ggtgtcccgc accatcactt tcaggtactg atgtttgaag tccgtgtcgt cgcaggcgcc   6180
ctgttcccac agcgtgaagt cggtgcgctt tttctgcctg ggattgggga gggcgaatgt   6240
gacgtcgtta agaggatttt ccggcgcg gggcatgaag ttgcgagaga tcctgaaggg   6300
tccgggcacg tccgagcggt tgttgatgac ttgcgccgcc aggacgatct cgtcgaagcc   6360
gttgatgttg tggcccacga tgtaaagttc gataaagcgc ggctgtccct tgagggccgg   6420 cgctttttc aactcctcgt aggtgagaca gtccggcgag gagagaccca gctccgcccg   6480
ggcccagtcg gagagctgag ggttagccgc gaggaaagag ctccacaggt caagggctag   6540
cagagtttgc aagcggtcgc ggaactcgcg aaacttttc cccacggcca ttttctccgg   6600
cgtcaccacg tagaaagtgc aggggcggtc gttccagacg tcccatcgga gctctagggc   6660
cagctcgcag gcttgacgaa cgagggtctc ctcgcccgag acgtgcatga ccagcatgaa   6720
gggtaccaac tgtttcccga acgagcccat ccatgtgtag gtttctacgt cgtaggtgac   6780
aaagagccgc tgggtgcgcg cgtgggagcc gatcggaag aagctgatct cctgccacca   6840
gttggaggaa tgggtgttga tgtggtgaaa gtagaagtcc cgccggcgca cagagcattc   6900
gtgctgatgt ttgtaaaagc gaccgcagta gtcgcagcgc tgcacgctct gtatctcctg   6960
aatgagatgc gcttttcgcc cgcgcaccag aaaccggagg gggaagttga cacggggct    7020 tggtggggcg gcatcccctt cgccttggcg gtgggagtct gcgtctgcgc cctccttctc   7080
tgggtggacg acggtgggga cgacgacgcc ccgggtgccg caagtccaga tctccgccac   7140
ggaggggcgc aggcgttgca ggagggacg cagctgcccg ctgtccaggg agtcgagggc   7200
ggccgcgctg aggtcggcgg gaagcgtttg caagttcact ttcagaagac cggtaagagc   7260
gtgagccagg tgcacatggt acttgatttc cagggggtg ttggaagagg cgtccacggc   7320
gtagaggagg ccgtgtccgc gcggggccac caccgtgccc cgaggaggtt ttatctcact   7380
cgtcgagggc gagcgccggg gggtagaggc ggctctgcgc cgggggcag cggaggcagt   7440 ggcacgtttt cgtgaggatt cggcagcggt tgatgacgag cccggagact gctggcgtgg   7500
gcgacgacgc ggcggttgag gtcctggatg tgccgtctct gcgtgaagac caccggcccc   7560
cgggtcctga acctgaaaga gagttccaca gaatcaatgt ctgcatcgtt aacggcggcc   7620
tgcctgagga tctcctgtac gtcgcccgag ttgtcttgat aggcgatctc ggccatgaac   7680
tgctccactt cttcctcgcg gaggtcgccg tggcccgctc gctccacggt ggcggccagg   7740
tcgttggaga tgcgacgcat gagttgagag aaggcgttga ggccgttctc gttccacacg   7800
cggctgtaca ccacgtttcc gaaggagtcg cgcgctcgca tgaccacctg gccacgttg    7860
```

```
agttccacgt ggcgggcgaa gacggcgtag tttctgaggc gctggaagag gtagttgagc    7920
gtggtggcga tgtgctcgca gacgaagaag tacatgatcc agcgccgcag ggtcatctcg    7980
ttgatgtctc cgatggcttc gagacgctcc atggcctcgt agaagtcgac ggcgaagttg    8040
aaaaattggg agttgcgggc ggccaccgtg agttcttctt gcaggaggcg gatgagatcg    8100
gcgaccgtgt cgcgcacctc ctgctcgaaa gcgccccgag gcgcctctgc ttcttcctcc    8160
ggctcctcct cttccagggg cacgggttcc tccggcagct ctgcgacggg gacggggcgg    8220
cgacgtcgtc gtctgaccgg caggcggtcc acgaagcgct cgatcatttc gccgcgccgg    8280
cgacgcatgg tctcggtgac ggcgcgtccg ttttcgcgag gtcgcagttc gaagacgccg    8340
ccgcgcagag cgccccgtg cagggagggt aagtggttag ggccgtcggg cagggacacg     8400
gcgctgacga tgcattttat caattgctgc gtaggcactc cgtgcaggga tctgagaacg    8460
tcgaggtcga cgggatccga gaacttctct aggaaagcgt ctatccaatc gcagtcgcaa    8520
ggtaagctga gacggtggg ccgctggggg gcgtccgcgg gcagttggga ggtgatgctg     8580
ctgatgatgt aattaaagta ggcggtcttc aggcggcgga tggtggcgag gaggaccacg    8640
tctttgggcc cggcctgttg aatgcgcagg cgctcggcca tgcccaggc ctcgctctga     8700
cagcgacgca ggtctttgta gtagtcttgc atcagtctct ccaccggaac ctctgcttct    8760
cccctgtctg ccatgcgagt cgagccgaac ccccgcaggg gctgcagcaa cgctaggtcg    8820
gccacgaccc tctcggccag cacggcctgt tggatctgcg tgagggtggt ctggaagtcg    8880
tccaggtcca cgaagcggtg ataggccccc gtgttgatgg tgtaggtgca gttggccatg    8940
acggaccagt tgacgacttg catgccgggt tgggtgatct ccgtgtactt gaggcgcgag    9000
taggcgcggg actcgaacac gtagtcgttg catgtgcgta ccagatactg gtagccaacc    9060
aggaagtggg gaggcggttc tcggtacagg ggccagccga ctgtggcggg ggcgccgggg    9120
gacaggtcgt ccagcatgag gcgatggtag tggtagatgt agcgggagag ccaggtgatg    9180
ccggccgagg tggtcgcggc cctggtgaat tcgcggacgc ggttccagat gttgcgcagg    9240
gggcgaaagc gctccatggt gggcacgctc tgccccgtga ggcgggcgca atcttgtacg    9300
ctctagatgg aaaaaagaca gggcggtcat cgactcccft ccgtagctcg gggggtaaag    9360
tcgcaagggt gcggcggcgg ggaaccccgg ttcgagaccg gccggatccg ccgctcccga    9420
tgcgcctggc cccgcatcca cgacgtccgc gtcgagaccc agccgcgacg ctccgcccca    9480
atacggaggg gagtcttttg gtgtttttc gtagatgcat ccggtgctgc ggcagatgcg     9540
acctcagacg cccaccacca ccgccgcggc ggcagtaaac ctgagcggag gcggtgacag    9600
ggaggaggag gagctggctt tagacctgga agagggagag gggctggccc ggctgggagc    9660
gccgtcccca gagagacacc ctaggggttca gctcgtgagg gacgccaggc aggcttttgt   9720
gccgaagcag aacctgttta gggaccgcag cggtcaggag gcggaggaga tgcgcgattg    9780
caggtttcgg gcgggtagag agctgagggc gggcttcgat cgggagcggc tcctgagggc    9840
ggaggatttc gagcccgacg agcgttctgg ggtgagcccg gcccgcgctc acgtctcggc    9900
ggccaacctg gtgagcgcgt acgagcagac ggtgaacgag gagcgcaact tccaaaagag    9960
ctttaacaat cacgtgagga ccctgatcgc gagggaggag gtgaccatcg ggctgatgca    10020
tctgtggac ttcgtggagg cctacgtgca gaacccggcc agcaaacctc tgacggccca     10080
gctgttcctg atcgtgcagc acagccgcga caacgagacg ttccgcgacg ccatgttgaa    10140
catcgcggag cccgagggtc gctggctctt ggatctgatt aacatcctgc agagcatcgt    10200
ggtgcaggag aggggcctca gcttagcgga caaggtggcg gccattaact attcgatgca    10260
```

```
gagcctgggg aagttctacg ctcgcaagat ctacaagagc ccttacgtgc ccatagacaa    10320
ggaggtgaag atagacagct tttacatgcg catggcgctg aaggtgctga cgctgagcga    10380
cgacctcggc gtgtaccgta acgacaagat ccacaaggcg gtgagcgcca gccgccggcg    10440
ggagctgagc gacagggagc tgatgcacag cctgcagagg gcgctggcgg cgccggggca    10500
cgaggagcgc gaggcttact tcgacatggg agccgatctg cagtggcgtc ccagcgcgcg    10560
cgccttggag gcggcgggct accccgacga ggaggatcgg gacgatttgg aggaggcagg    10620
cgagtacgag gacgaagcct gaccgggcag gtgttgtttt agatgcagcg gccggcggac    10680
ggggccaccg cggatcccgc acttttggca tccatgcaga gtcaaccttc gggcgtgacc    10740
gcctccgatg actgggcggc ggccatggac cgcattatgg cgctgactac ccgcaacccc    10800
gaggctttta gacagcaacc ccaggccaac cgttttccgg ccatcttgga agcggtggtg    10860
ccctcccgca ccaaccccac acacgagaaa gtcctgacta tcgtgaacgc cctggtagac    10920
agcaaggcca tccgccgcga cgaggcgggc ttgatttaca acgctctgct ggaacgggtg    10980
gcgcgctaca acagcactaa cgttcagacc aatctggatc gcctcaccac cgacgtgaag    11040
gaggcgctgg ctcagaagga gcggtttctg agggacagca atctgggctc tctggtggca    11100
ctcaacgcct tcctgagcac gcagccggcc aacgtgcccc gcgggcagga ggactacgtg    11160
agcttcatca gcgctctgag gctgctggtg tccgaggtgc cccagagcga ggtgtatcag    11220
tctgggccgg attacttctt ccagacgtcc cgacagggct gcaaacggt gaacctgact     11280
caggccttta aaaacttgca aggcatgtgg ggcgttaagg ccccggtggg cgatcgagcc    11340
accatctcca gtctgctgac ccccaacact cgcctgctgc tgctcttgat cgcgccgttc    11400
accaacagta gcactatcag ccgtgactcg tacctgggtc atctcatcac tttgtaccgc    11460
gaggccatcg gtcaggctca gatcgacgag cacacatatc aggagatcac taacgtgagc    11520
cgggccctgg gtcaggaaga taccggcagc ctggaagcca cgttgaactt tttgctaacc    11580
aaccggaggc aaaaaatacc ctcccagttt acgttaagcg ccgaggagga gaggattctg    11640
cgatacgtgc agcagtccgt gagtctgtac ttgatgcggg agggcgccac cgcttccacg    11700
gctttagaca tgacgctcg gaacatggaa ccgtccttt actccgccca ccggccgttc     11760
attaaccgtc tgatggacta cttccatcgc gcggccgcca tgaacgggga gtacttcacc    11820
aatgccatcc tgaatccgca ttggatgccc ccgtccggct tctacaccgg cgagtttgac    11880
ctgcccgaag ccgacgacgg ctttctttgg gacgacgtgt ccgacagcat ttccacgccg    11940
ggcaatcgcc gattccagaa gaaggagggc ggagacgagc tcccctctc cagcgtggag     12000
gcggcctcta ggggagagag tccctttccc agtctgtctt ccgccagcag tggtcgggta    12060
acgcgcccgc ggttgccggg ggagagcgac tacctgaacg accccttgct gcggccggct    12120
aggaagaaaa atttccccaa caacggggtg aaagcttgg tggataaaat gaatcgttgg      12180
aagacctacg cccaggagca gcgggagtgg gaggacagtc agccgcgacc gctggttccg    12240
ccgcactggc gtcgtcagag agaagacccg gacgactccg cagacgatag tagcgtgttg    12300
gacctgggag ggagcggagc caaccccttt gctcacttgc aacccaaggg gcgttccagt    12360
cgcctctact aataaaaaag acgcggaaac ttaccagagc catggccaca gcgtgtgtcc    12420
tttcttcctc tctttcttcc tcggcgcggc aga atg aga aga gcg gtg aga gtc    12474
                                    Met Arg Arg Ala Val Arg Val
                                     1               5 acg ccg gcg gcg tat gag ggt ccg ccc cct tct tac gaa agc gtg atg    12522
Thr Pro Ala Ala Tyr Glu Gly Pro Pro Pro Ser Tyr Glu Ser Val Met
        10              15                  20
```

| | | |
|---|---|---|
| gga tca gcg aac gtg ccg gcc acg ctg gag gcg cct tac gtt cct ccc<br>Gly Ser Ala Asn Val Pro Ala Thr Leu Glu Ala Pro Tyr Val Pro Pro<br>25                       30                       35 | | 12570 |
| aga tac ctg gga cct acg gag ggc aga aac agc atc cgt tac tcc gag<br>Arg Tyr Leu Gly Pro Thr Glu Gly Arg Asn Ser Ile Arg Tyr Ser Glu<br>40                       45                       50                       55 | | 12618 |
| ctg gca ccc ctg tac gat acc acc aag gtg tac ctg gtg gac aac aag<br>Leu Ala Pro Leu Tyr Asp Thr Thr Lys Val Tyr Leu Val Asp Asn Lys<br>                   60                       65                       70 | | 12666 |
| tcg gcg gac atc gcc tcc ctg aat tat caa aac gat cac agc aat ttt<br>Ser Ala Asp Ile Ala Ser Leu Asn Tyr Gln Asn Asp His Ser Asn Phe<br>75                       80                       85 | | 12714 |
| ctg act acc gtg gtg cag aac aat gac ttc acc ccg acg gag gcg ggc<br>Leu Thr Thr Val Val Gln Asn Asn Asp Phe Thr Pro Thr Glu Ala Gly<br>       90                       95                      100 | | 12762 |
| acg cag acc att aac ttt gac gag cgt tcc cgc tgg ggc ggt cag ctg<br>Thr Gln Thr Ile Asn Phe Asp Glu Arg Ser Arg Trp Gly Gly Gln Leu<br>105                      110                     115 | | 12810 |
| aaa acc atc ctg cac acc aac atg ccc aac atc aac gag ttc atg tcc<br>Lys Thr Ile Leu His Thr Asn Met Pro Asn Ile Asn Glu Phe Met Ser<br>120                         125                     130                     135 | | 12858 |
| acc aac aag ttc agg gcc agg ctg atg gtt aaa aag gct gaa aac cag<br>Thr Asn Lys Phe Arg Ala Arg Leu Met Val Lys Lys Ala Glu Asn Gln<br>                   140                     145                     150 | | 12906 |
| cct ccc gag tac gaa tgg ttt gag ttc acc att ccc gag ggc aac tat<br>Pro Pro Glu Tyr Glu Trp Phe Glu Phe Thr Ile Pro Glu Gly Asn Tyr<br>155                      160                     165 | | 12954 |
| tcc gag acc atg act atc gat ctg atg aac aat gcg atc gtg gac aat<br>Ser Glu Thr Met Thr Ile Asp Leu Met Asn Asn Ala Ile Val Asp Asn<br>170                         175                     180 | | 13002 |
| tac ctg caa gtg ggg agg cag aac ggg gta ttg gaa agc gat atc ggc<br>Tyr Leu Gln Val Gly Arg Gln Asn Gly Val Leu Glu Ser Asp Ile Gly<br>185                      190                     195 | | 13050 |
| gta aaa ttt gat acc aga aac ttc cga ctg ggg tgg gat ccc gtg acc<br>Val Lys Phe Asp Thr Arg Asn Phe Arg Leu Gly Trp Asp Pro Val Thr<br>200                         205                     210                     215 | | 13098 |
| aag ctg gtg atg cca ggc gtg tac acc aac gag gct ttt cac ccc gac<br>Lys Leu Val Met Pro Gly Val Tyr Thr Asn Glu Ala Phe His Pro Asp<br>                   220                     225                     230 | | 13146 |
| atc gtg ctg ctg ccg ggg tgc ggt gtg gac ttc act cag agc cgt ttg<br>Ile Val Leu Leu Pro Gly Cys Gly Val Asp Phe Thr Gln Ser Arg Leu<br>                   235                     240                     245 | | 13194 |
| agt aac ctg tta ggg atc aga aag cgc cgc ccc ttc caa gag ggc ttt<br>Ser Asn Leu Leu Gly Ile Arg Lys Arg Arg Pro Phe Gln Glu Gly Phe<br>250                      255                     260 | | 13242 |
| cag atc atg tat gag gac ctg gaa gga ggt aac att cca ggt ttg cta<br>Gln Ile Met Tyr Glu Asp Leu Glu Gly Gly Asn Ile Pro Gly Leu Leu<br>265                      270                     275 | | 13290 |
| gac gtg ccg gcg tat gaa gag agt gtt aaa cag gcg gag gcg cag gga<br>Asp Val Pro Ala Tyr Glu Glu Ser Val Lys Gln Ala Glu Ala Gln Gly<br>280                      285                     290                     295 | | 13338 |
| cga gag att cga ggc gac acc ttt gcc acg gaa cct cac gaa ctg gta<br>Arg Glu Ile Arg Gly Asp Thr Phe Ala Thr Glu Pro His Glu Leu Val<br>                   300                     305                     310 | | 13386 |
| ata aaa cct ctg gaa caa gac agt aaa aaa cgg agt tac aac att ata<br>Ile Lys Pro Leu Glu Gln Asp Ser Lys Lys Arg Ser Tyr Asn Ile Ile<br>315                      320                     325 | | 13434 |
| tcc ggc act atg aat acc ttg tac cgg agc tgg ttt ctg gct tac aac<br>Ser Gly Thr Met Asn Thr Leu Tyr Arg Ser Trp Phe Leu Ala Tyr Asn<br>330                      335                     340 | | 13482 |

| | | | | | | | | | | | | | | | | |
|---|---|---|---|---|---|---|---|---|---|---|---|---|---|---|---|---|
| tac | ggg | gat | ccc | gaa | aag | gga | gtg | aga | tca | tgg | acc | ata | ctc | acc | acc | 13530 |
| Tyr | Gly | Asp | Pro | Glu | Lys | Gly | Val | Arg | Ser | Trp | Thr | Ile | Leu | Thr | Thr | |
| | 345 | | | | 350 | | | | | 355 | | | | | | |
| acg | gac | gtg | acc | tgc | ggc | tcg | cag | caa | gtg | tac | tgg | tcc | ctg | ccg | gat | 13578 |
| Thr | Asp | Val | Thr | Cys | Gly | Ser | Gln | Gln | Val | Tyr | Trp | Ser | Leu | Pro | Asp | |
| 360 | | | | | 365 | | | | | 370 | | | | | 375 | |
| atg | atg | caa | gac | ccg | gtc | acc | ttc | cgc | ccc | tcc | acc | caa | gtc | agc | aac | 13626 |
| Met | Met | Gln | Asp | Pro | Val | Thr | Phe | Arg | Pro | Ser | Thr | Gln | Val | Ser | Asn | |
| | | | 380 | | | | | 385 | | | | | 390 | | | |
| ttc | ccg | gtg | gtg | ggc | acc | gag | ctg | ctg | ccc | gtc | cat | gcc | aag | agc | ttc | 13674 |
| Phe | Pro | Val | Val | Gly | Thr | Glu | Leu | Leu | Pro | Val | His | Ala | Lys | Ser | Phe | |
| | | | 395 | | | | | 400 | | | | | 405 | | | |
| tac | aac | gaa | cag | gcc | gtc | tac | tcg | caa | ctc | att | cgc | cag | tcc | acc | gcg | 13722 |
| Tyr | Asn | Glu | Gln | Ala | Val | Tyr | Ser | Gln | Leu | Ile | Arg | Gln | Ser | Thr | Ala | |
| | | 410 | | | | | 415 | | | | | 420 | | | | |
| ctt | acc | cac | gtg | ttc | aat | cgc | ttt | ccc | gag | aac | cag | att | ctg | gtg | cgc | 13770 |
| Leu | Thr | His | Val | Phe | Asn | Arg | Phe | Pro | Glu | Asn | Gln | Ile | Leu | Val | Arg | |
| | 425 | | | | | 430 | | | | | 435 | | | | | |
| cct | ccc | gct | cct | acc | att | acc | acc | gtc | agt | gaa | aac | gtt | ccc | gcc | ctc | 13818 |
| Pro | Pro | Ala | Pro | Thr | Ile | Thr | Thr | Val | Ser | Glu | Asn | Val | Pro | Ala | Leu | |
| 440 | | | | | 445 | | | | | 450 | | | | | 455 | |
| aca | gat | cac | gga | acc | ctg | ccg | ctg | cgc | agc | agt | atc | agt | gga | gtt | cag | 13866 |
| Thr | Asp | His | Gly | Thr | Leu | Pro | Leu | Arg | Ser | Ser | Ile | Ser | Gly | Val | Gln | |
| | | | | 460 | | | | | 465 | | | | | 470 | | |
| cgc | gtg | acc | atc | acc | gac | gcc | aga | cgt | cga | acc | tgt | ccc | tac | gtt | tac | 13914 |
| Arg | Val | Thr | Ile | Thr | Asp | Ala | Arg | Arg | Arg | Thr | Cys | Pro | Tyr | Val | Tyr | |
| | | | 475 | | | | | 480 | | | | | 485 | | | |
| aaa | gct | ctt | ggc | gta | gtg | gct | cct | aaa | gtg | ctc | tct | agt | cgc | acc | ttc | 13962 |
| Lys | Ala | Leu | Gly | Val | Val | Ala | Pro | Lys | Val | Leu | Ser | Ser | Arg | Thr | Phe | |
| | | 490 | | | | | 495 | | | | | 500 | | | | |

| | |
|---|---|
| taa acatgtccat cctcatctct cccgataaca acaccggctg ggactgggc | 14015 |
| tccggcaaga tgtacggcgg agccaaaagg cgctccagtc agcacccagt tcgagttcgg | 14075 |
| ggccacttcc gtgctccctg gggagcttac aagcgaggac tctcgggccg aacggcggta | 14135 |
| gacgatacca tagatgccgt gattgccgac gcccgccggt acaacccggg accggtcgct | 14195 |
| agcgccgcct ccaccgtgga ttccgtgatc gacagcgtgg tagctggcgc tcgggcctat | 14255 |
| gctcgccgca agaggcggct gcatcggaga cgtcgcccca ccgccgccat gctggcagcc | 14315 |
| agggccgtgc tgaggcgggc ccggagggta ggcagaaggg ctatgcgccg cgctgccgcc | 14375 |
| aacgccgccg ccgggagggc ccgccgacag gctgcccgcc aggctgctgc cgccatcgct | 14435 |
| agcatggcca gacccaggag agggaacgtg tactgggtgc gcgattctgt gacgggagtc | 14495 |
| cgagtgccgg tgcgcagccg acctccccga agttagaaga tccaagctgc gaagacggcg | 14555 |
| gtactgagtc tccctgttgt tatcagccca acatgagcaa gcgcaagttt aaagaagaac | 14615 |
| tgctgcagac gctggtgcct gagatctatg gccctccgga cgtgaagcct gacattaagc | 14675 |
| cccgcgatat caagcgtgtt aaaaagcggg aaaagaaaga ggaactcgcg gtggtagacg | 14735 |
| atggcggagt ggaatttatt aggagtttcg ccccgcgacg cagggttcaa tggaaagggc | 14795 |
| ggcgggtaca acgcgttttg aggccgggca ccgcggtagt ttttacccc ggagagcggt | 14855 |
| cggccgttag gggtttcaaa aggcagtacg acgaggtgta cggcgacgag gacatattgg | 14915 |
| aacaggcggc tcaacagatc ggagaatttg cctacgaaaa gcgttcgcgt cgcgaagacc | 14975 |
| tggccatcgc tttagacagc ggcaacccca cgcccagcct caaacctgtg acgctgcagc | 15035 |
| aggtgctccc cgtgagcgcc agcacggaca gcaagagggg aataaaaaga gaaatgaag | 15095 |
| atctgcagcc caccatccag ctcatggtcc ctaaacggca gaggctggaa gaggtcctgg | 15155 |

-continued

```
agaaaatgaa agtggaccca agcatagagc cggacgtcaa agtcaggccg atcaaagaag    15215
tggcccctgg tctcggggtg cagacggtgg atatccagat ccccgtcacg tcagcttcga    15275
ccgccgtgga agccatggaa acgcaaacgg aaaccctgc cgcgatcggt accagggaag     15335
tggcgttgca aaccgacccc tggtacgaat acgccgcccc tcggcgtcag aggcgacccg    15395
ctcgttacgg ccccgccaac gccatcatgc cagaatatgc gctgcatccg tctatcctgc    15455
ccaccccgg ctaccgggga gtgacgtatc gcccgtcagg aacccgccgc cgaacccgtc     15515
gccgccgccg ctcccgtcgt gctctggccc ccgtgtcggt gcgccgcgta acacgccggg    15575
gaaagacagt taccattccc aacccgcgct accaccctag catcctttaa tgactctgcc    15635
gttttgcaga tggctctgac ttgccgcgtg cgccttcccg ttccgcacta tcgaggaaga    15695
tctcgtcgta ggagaggcat ggcgggtagt ggtcgccggc gggctttgcg caggcgcatg    15755
aaaggcggaa ttttacccgc tctgataccc ataatcgccg ccgccatcgg tgccataccc    15815
ggcgtcgctt cagtggcctt gcaagcagct cgtaataaat aaacgaaggc ttttgcactt    15875
atgtcctggt cctgactatt ttatgcagaa agagcatgga agacatcaat tttacgtcgc    15935
tggctccgcg gcacggctcg cggccgctca tgggcacctg aacgacatc ggcaccagtc     15995
agctcaacgg gggcgctttc aattggggga gcctttggag cggcattaaa aactttggct    16055
ccacgattaa atcctacggc agcaaagcct ggaacagtag tgctggtcag atgctccgag    16115
ataaactgaa ggacaccaac ttccaagaaa aagtggtcaa tggggtggtg accggcatcc    16175
acggcgcggt agatctcgcc aaccaagcgg tgcagaaaga gattgacagg cgtttggaaa    16235
gctcgcgggt gccgccgcag agaggggatg aggtggaggt cgaggaagta gaagtagagg    16295
aaaagctgcc cccgctggag aaagttcccg gtgcgcctcc gagaccgcag aagcgaccca    16355
ggccagaact agaagaaact ctggtgacgg agagcaagga gcctccctcg tacgagcaag    16415
ccttgaaaga gggcgcctct ccaccctacc caatgacaaa accgatcgcg cctatggctc    16475
ggccggtgta cgggaaggac tacaagcctg tcacgctaga gctcccccg ccgccaccgc     16535
cgcccccac gcgccgacc gttccccccc ccctgccggc tccgtcggcg ggacccgtgt      16595
ccgcacccgt cgccgtgcct ctgccagccg cccgcccagt ggccgtggcc actgccagaa    16655
accccagagg ccagagagga gccaactggc aaagcacgct gaacagcatc gtgggcctgg    16715
gagtgaaaag cctgaaacgc cgccgttgct attattaaaa gtgtagctaa aaaatttccc    16775
gttgtatacg cctcctatgt taccgccaga gacgcgtgac tgtcgccgcg agcgccgctt    16835
tcaag atg gcc acc cca tcg atg atg ccg cag tgg tct tac atg cac atc     16885
      Met Ala Thr Pro Ser Met Met Pro Gln Trp Ser Tyr Met His Ile
          505                 510                 515
gcc ggg cag gac gcc tcg gag tac ctg agc ccc ggt ctc gtg cag ttc       16933
Ala Gly Gln Asp Ala Ser Glu Tyr Leu Ser Pro Gly Leu Val Gln Phe
    520                 525                 530
gcc cgc gcc acc gac acc tac ttc agc ttg gga aac aag ttt aga aac       16981
Ala Arg Ala Thr Asp Thr Tyr Phe Ser Leu Gly Asn Lys Phe Arg Asn
535                 540                 545                 550
ccc acc gtg gcc ccc acc cac gat gta acc acg gac cgc tcg caa agg       17029
Pro Thr Val Ala Pro Thr His Asp Val Thr Thr Asp Arg Ser Gln Arg
                555                 560                 565
ctg acc ctg cgt ttt gtg ccc gta gac cgg gag gac acc gcg tac tct       17077
Leu Thr Leu Arg Phe Val Pro Val Asp Arg Glu Asp Thr Ala Tyr Ser
            570                 575                 580
tac aaa gtg cgc tac acg ctg gcc gta ggg gac aac cga gtg ctg gac       17125
Tyr Lys Val Arg Tyr Thr Leu Ala Val Gly Asp Asn Arg Val Leu Asp
        585                 590                 595
```

```
atg gcc agc acc tac ttt gac atc cgg gga gtg ctg gat cgc ggt ccc      17173
Met Ala Ser Thr Tyr Phe Asp Ile Arg Gly Val Leu Asp Arg Gly Pro
    600             605                 610 agt ttt aag ccc tac tcg ggt acc gcg tac aat tcc ctg gct ccc aag      17221
Ser Phe Lys Pro Tyr Ser Gly Thr Ala Tyr Asn Ser Leu Ala Pro Lys
615             620                 625                 630 ggc gct ccc aac cct gca gaa tgg acg aat tca gac agc aaa gtt aaa      17269
Gly Ala Pro Asn Pro Ala Glu Trp Thr Asn Ser Asp Ser Lys Val Lys
                635                 640                 645 gtg agg gca cag gcg cct ttt gtt agc tcg tat ggt gct aca gcg att      17317
Val Arg Ala Gln Ala Pro Phe Val Ser Ser Tyr Gly Ala Thr Ala Ile
        650                 655                 660 aca aaa gag ggt att cag gtg gga gta acc tta aca gac tcc gga tca      17365
Thr Lys Glu Gly Ile Gln Val Gly Val Thr Leu Thr Asp Ser Gly Ser
            665                 670                 675 aca cca cag tat gca gat aaa acg tat cag cct gag ccg caa att gga      17413
Thr Pro Gln Tyr Ala Asp Lys Thr Tyr Gln Pro Glu Pro Gln Ile Gly
    680                 685                 690 gaa cta cag tgg aac agc gat gtt gga acc gat gac aaa ata gca gga      17461
Glu Leu Gln Trp Asn Ser Asp Val Gly Thr Asp Asp Lys Ile Ala Gly
695             700                 705                 710 aga gtg cta aag aaa aca acg ccc atg ttc cct tgt tac ggc tca tat      17509
Arg Val Leu Lys Lys Thr Thr Pro Met Phe Pro Cys Tyr Gly Ser Tyr
                715                 720                 725 gcc agg ccc act aat gaa aaa gga gga cag gca aca ccg tcc gct agt      17557
Ala Arg Pro Thr Asn Glu Lys Gly Gly Gln Ala Thr Pro Ser Ala Ser
        730                 735                 740 caa gac gtg caa aat ccc gaa tta caa ttt ttt gcc tct act aat gtc      17605
Gln Asp Val Gln Asn Pro Glu Leu Gln Phe Phe Ala Ser Thr Asn Val
            745                 750                 755 gcc aat aca cca aaa gca gtt cta tat gcg gag gac gtg tca att gaa      17653
Ala Asn Thr Pro Lys Ala Val Leu Tyr Ala Glu Asp Val Ser Ile Glu
    760                 765                 770 gcg cca gac act cac ttg gtg ttc aaa cca aca gtc act gaa ggc att      17701
Ala Pro Asp Thr His Leu Val Phe Lys Pro Thr Val Thr Glu Gly Ile
775             780                 785                 790 aca agt tca gag gct cta ctg acc caa caa gct gct ccc aac cgt cca      17749
Thr Ser Ser Glu Ala Leu Leu Thr Gln Gln Ala Ala Pro Asn Arg Pro
                795                 800                 805 aac tac ata gcc ttt aga gat aat ttt att ggt ctc atg tac tac aat      17797
Asn Tyr Ile Ala Phe Arg Asp Asn Phe Ile Gly Leu Met Tyr Tyr Asn
        810                 815                 820 agc aca ggt aac atg gga gta ctg gca ggc cag gct tct cag cta aat      17845
Ser Thr Gly Asn Met Gly Val Leu Ala Gly Gln Ala Ser Gln Leu Asn
            825                 830                 835 gca gtt gtt gac ctg caa gac aga aat act gag ctg tcc tac caa ctc      17893
Ala Val Val Asp Leu Gln Asp Arg Asn Thr Glu Leu Ser Tyr Gln Leu
    840                 845                 850 atg ttg gac gcc ctc gga gac cgc agt cgg tac ttt tct atg tgg aac      17941
Met Leu Asp Ala Leu Gly Asp Arg Ser Arg Tyr Phe Ser Met Trp Asn
855             860                 865                 870 caa gct gtg gat agt tac gat cct gat gta aga atc ata gaa aac cat      17989
Gln Ala Val Asp Ser Tyr Asp Pro Asp Val Arg Ile Ile Glu Asn His
                875                 880                 885 ggc gta gaa gat gaa ttg cct aat tat tgc ttt cct ttg gga ggc atg      18037
Gly Val Glu Asp Glu Leu Pro Asn Tyr Cys Phe Pro Leu Gly Gly Met
        890                 895                 900 gca gta acc gac acc tac tcg cct ata aag gtt aat gga gga ggc aat      18085
Ala Val Thr Asp Thr Tyr Ser Pro Ile Lys Val Asn Gly Gly Gly Asn
            905                 910                 915
```

```
gga tgg gaa gcc aat aac ggc gtt ttc acc gaa aga gga gtg gaa ata    18133
Gly Trp Glu Ala Asn Asn Gly Val Phe Thr Glu Arg Gly Val Glu Ile
    920                 925                 930 ggt tca ggg aac atg ttt gcc atg gag att aac ctg caa gcc aac cta    18181
Gly Ser Gly Asn Met Phe Ala Met Glu Ile Asn Leu Gln Ala Asn Leu
935                 940                 945                 950 tgg cgt agc ttt ctg tac tcc aat att ggg ctg tac ctg cca gac tct    18229
Trp Arg Ser Phe Leu Tyr Ser Asn Ile Gly Leu Tyr Leu Pro Asp Ser
                955                 960                 965 ctc aaa atc act cct gac aac atc aca ctc cca gag aac aaa aac acc    18277
Leu Lys Ile Thr Pro Asp Asn Ile Thr Leu Pro Glu Asn Lys Asn Thr
        970                 975                 980 tat cag tat atg aac ggt cgc gtg acg cca ccc ggg ctg gtt gac acc    18325
Tyr Gln Tyr Met Asn Gly Arg Val Thr Pro Pro Gly Leu Val Asp Thr
            985                 990                 995 tac gtt aac gtg ggc gcg cgc tgg tcc ccc gat gtc atg gac agt        18370
Tyr Val Asn Val Gly Ala Arg Trp Ser Pro Asp Val Met Asp Ser
1000                1005                1010 att aac cct ttt aat cac cac cgc aac gcc gga ctc cgc tac cgt        18415
Ile Asn Pro Phe Asn His His Arg Asn Ala Gly Leu Arg Tyr Arg
        1015                1020                1025 tcc atg ctc ctg gga aac gga cgc tac gtg ccc ttc cac atc cag        18460
Ser Met Leu Leu Gly Asn Gly Arg Tyr Val Pro Phe His Ile Gln
    1030                1035                1040 gtg ccc cag aaa ttc ttt gca att aaa aac ctg ctg ctc ctc ccc        18505
Val Pro Gln Lys Phe Phe Ala Ile Lys Asn Leu Leu Leu Leu Pro
1045                1050                1055 ggt tcc tac acc tac gag tgg aac ttc cgc aag gac gtg aac atg        18550
Gly Ser Tyr Thr Tyr Glu Trp Asn Phe Arg Lys Asp Val Asn Met
    1060                1065                1070 atc ttg cag agc tcg ctg ggc aat gac ctg cga gtg gac ggg gcc        18595
Ile Leu Gln Ser Ser Leu Gly Asn Asp Leu Arg Val Asp Gly Ala
1075                1080                1085 agc atc cgc ttc gac agc atc aac ctg tac gcc aac ttt ttc ccc        18640
Ser Ile Arg Phe Asp Ser Ile Asn Leu Tyr Ala Asn Phe Phe Pro
        1090                1095                1100 atg gcc cac aac acg gcc tcc acc ctg gaa gcc atg ctg cgc aac        18685
Met Ala His Asn Thr Ala Ser Thr Leu Glu Ala Met Leu Arg Asn
    1105                1110                1115 gac acc aac gac caa tct ttc aac gac tac ctg tgc gcg gcc aac        18730
Asp Thr Asn Asp Gln Ser Phe Asn Asp Tyr Leu Cys Ala Ala Asn
1120                1125                1130 atg ctg tac ccc atc ccc gcc aac gcc acc agc gtg ccc atc tcc        18775
Met Leu Tyr Pro Ile Pro Ala Asn Ala Thr Ser Val Pro Ile Ser
        1135                1140                1145 att ccc tct cgc aac tgg gca gcc ttc agg ggc tgg agt ttc acc        18820
Ile Pro Ser Arg Asn Trp Ala Ala Phe Arg Gly Trp Ser Phe Thr
    1150                1155                1160 cgc ctc aaa acc aag gag acc ccc tcg ctg ggc tcc ggg ttc gac        18865
Arg Leu Lys Thr Lys Glu Thr Pro Ser Leu Gly Ser Gly Phe Asp
1165                1170                1175 ccc tac ttc gtc tac tcc ggc tcc atc ccc tac ctg gac ggc acc        18910
Pro Tyr Phe Val Tyr Ser Gly Ser Ile Pro Tyr Leu Asp Gly Thr
        1180                1185                1190 ttc tac ctc aac cat act ttc aaa aag gtg tca atc atg ttc gac        18955
Phe Tyr Leu Asn His Thr Phe Lys Lys Val Ser Ile Met Phe Asp
    1195                1200                1205 tcc tcc gtc agc tgg ccc ggc aac gac cgt ctg ctg acg ccc aac        19000
Ser Ser Val Ser Trp Pro Gly Asn Asp Arg Leu Leu Thr Pro Asn
1210                1215                1220
```

```
gag ttc gaa atc aag cgt tcg gtg gac ggt gaa ggg tac aac gtg      19045
Glu Phe Glu Ile Lys Arg Ser Val Asp Gly Glu Gly Tyr Asn Val
    1225            1230                1235 gct cag agc aac atg acc aag gac tgg ttc ctg att cag atg ctc      19090
Ala Gln Ser Asn Met Thr Lys Asp Trp Phe Leu Ile Gln Met Leu
1240            1245                1250 agc cac tac aac atc ggc tac cag ggc ttc tac gtg ccc gaa aat      19135
Ser His Tyr Asn Ile Gly Tyr Gln Gly Phe Tyr Val Pro Glu Asn
    1255            1260                1265 tac aag gac cgc atg tac tct ttc ttc aga aac ttc caa ccc atg      19180
Tyr Lys Asp Arg Met Tyr Ser Phe Phe Arg Asn Phe Gln Pro Met
1270            1275                1280 agc cgc caa att gta gat tca acg gct tac act aat tat cag gat      19225
Ser Arg Gln Ile Val Asp Ser Thr Ala Tyr Thr Asn Tyr Gln Asp
    1285            1290                1295 gtg aaa ctg cca tac cag cat aac aac tca ggg ttc gtg ggc tac      19270
Val Lys Leu Pro Tyr Gln His Asn Asn Ser Gly Phe Val Gly Tyr
1300            1305                1310 atg gga ccc acc atg cga gag ggg cag gcc tac ccg gcc aac tat      19315
Met Gly Pro Thr Met Arg Glu Gly Gln Ala Tyr Pro Ala Asn Tyr
    1315            1320                1325 ccc tat ccc ctg att ggg gcc acc gcc gtg ccc agc ctc acg cag      19360
Pro Tyr Pro Leu Ile Gly Ala Thr Ala Val Pro Ser Leu Thr Gln
1330            1335                1340 aaa aag ttc ctc tgc gac cgg gtg atg tgg agg atc ccc ttc tct      19405
Lys Lys Phe Leu Cys Asp Arg Val Met Trp Arg Ile Pro Phe Ser
    1345            1350                1355 agc aac ttc atg tct atg ggc tcc ctc acc gac ctg ggg cag aac      19450
Ser Asn Phe Met Ser Met Gly Ser Leu Thr Asp Leu Gly Gln Asn
1360            1365                1370 atg ctg tac gcc aac tcc gct cac gcc ttg gat atg acc ttt gag      19495
Met Leu Tyr Ala Asn Ser Ala His Ala Leu Asp Met Thr Phe Glu
    1375            1380                1385 gtg gat ccc atg gat gag ccc acg ctt ctc tat gtt ctg ttt gaa      19540
Val Asp Pro Met Asp Glu Pro Thr Leu Leu Tyr Val Leu Phe Glu
1390            1395                1400 gtc ttc gac gtg gtg cgc atc cac cag ccg cac cgc ggc gtc atc      19585
Val Phe Asp Val Val Arg Ile His Gln Pro His Arg Gly Val Ile
    1405            1410                1415 gag gcc gtc tac ctg cgc aca cct ttc tct gcc ggt aac gcc acc      19630
Glu Ala Val Tyr Leu Arg Thr Pro Phe Ser Ala Gly Asn Ala Thr
1420            1425                1430 acc taa agaagccgat gggctccagc gaacaggagc tgcaggccat tgttcgcgac   19686
Thr ctgggctgcg ggccctactt tttgggcacc ttcgacaagc gttttcccgg cttcatgtcc 19746 ccccacaagc cggcctgtgc catcgttaac acggccggac gggagaccgg gggggtccac 19806 tggctcgcct tcgcctggaa cccgcgtaac cgcacctgct acctgttcga ccctttggt  19866 ttctccgacg aaaggctgaa gcagatctac cagttcgagt acgaggggct cctcaagcgc 19926 agcgctctgg cctccacgcc cgaccactgc gtcaccctgg aaaagtccac ccaaacggtc 19986 caggggcccc tctcggccgc ctgcgggctc ttctgttgca tgttttttgca cgccttcgtg 20046 cactggcctc acaccccat ggatcacaac cccaccatgg atctgctcac cggagtgccc  20106
aacagcatgc ttcacagccc ccaggtcgcc cccaccctgc gccgtaacca ggaacacctg  20166
tatcgctttc tggggaaaca ctctgcctat tttcgccgcc accggcagcg catcgaacgg  20226
gccacggcct tcgaaagcat gagccaaaga gtgtaatcaa taaaaaacat ttttatttga  20286
catgatacgc gcttctggcg ttttattaaa aatcgaaggg ttcgagggag gggtcctcgt  20346
```

```
gcccgctggg gagggacacg ttgcgatact ggaaacgggc gctccaacga aactcgggga   20406
tcaccagccg cggcaggggc acgtcttcta ggttctgctt ccaaaactgc cgcaccagct   20466
gcagggctcc catgacgtcg ggcgccgata tcttgaagtc gcagttaggg ccggagctcc   20526
cgcggctgtt gcggaacacg gggttggcac actggaacac cagcacgccg gggttgtgga   20586
tactggccag ggccgtcggg tcggtcacct ccgacgcatc cagatcctcg gcgttgctca   20646
gggcaaacgg ggtcagcttg cacatctgcc gcccaatctg gggtactagg tcgcgcttgt   20706
tgaggcagtc gcagcgcaga gggatcagga tgcgtcgctg cccgcgttgc atgatagggt   20766
aactcgccgc caggaactcc tccatttgac ggaaggccat ctgggctttg ccgccctcgg   20826
tgtagaatag cccgcaggac ttgctagaga atacgttatg accgcagttg acgtcctccg   20886
cgcagcagcg ggcgtcttcg ttcttcagct gaaccacgtt gcggcyccaa cggttctgga   20946
ccaccttggc tctagtgggg tgctccttca gcgcccgctg tccgttctcg ctggttacat   21006
ccatttccaa cacgtgctcc ttgcagacca tctccactcc gtggaagcaa aacaggacgc   21066
cctcctgctg ggtactgcga tgctcccata cggcgcatcc ggtgggctcc cagctcttgt   21126
gttttacccc cgcgtaggct tccatgtaag ccataaggaa tctgcccatc agctcggtga   21186
aggtcttctg gttggtgaag gttagcggca ggccgcggtg ctcctcgttc aaccaagttt   21246
gacagatctt gcgtacacc gctccctggt cgggcagaaa cttaaaagcc gctctgctgt   21306
cgttgtctac gtggaacttc tccattaaca tcatcatggt ttccatatccc ttctcccacg   21366 ctgtcaccag tggtttgctg tcggggttct tcaccaacac ggcggtagag gggccctcgc   21426
cggccccgac gtccttcatg gtcattcttt gaaactccac ggagccgtcc gcgcgacgta   21486
ctctgcgcac cggagggtag ctgaagccca cctccaccac ggtgccttcg ccctcgctgt   21546
cggagacaat ctccggggat ggcggcggcg cgggtgtcgc cttgcgagcc ttcttcttgg   21606
gagggagctg aggcgcctcc tgctcgcgct cggggctcat ctcccgcaag tagggggtaa   21666
tggagctgcc tgcttggttc tgacggttgg ccattgtatc ctaggcagaa agacatggag   21726
cttatgcgcg aggaaacttt aaccgccccg tccccgtca gcgacgaaga tgtcatcgtc   21786
gaacaggacc cgggctacgt tacgccgccc gaggatctgg aggggcctga ccggcgcgac   21846
gctagtgagc ggcaggaaaa tgagaaagag gaggcctgct acctcctgga aggcgacgtt   21906
ttgctaaagc atttcgccag gcagagcacc atagttaagg aggccttgca agaccgctcc   21966
gaggtgccct tggacgtcgc cgcgctctcc caggcctacg aggcgaacct tttctcgcct   22026
cgagtgcctc cgaagagaca gcccaacggc acctgcgagc ccaacccgcg actcaacttc   22086
taccccgtgt tcgccgtacc agaggcgctg gccacctatc acatttttt caaaaaccaa   22146 cgcatccccc tatcgtgccg ggccaaccgc accgcggccg ataggaatct caggcttaaa   22206
aacggagcca acatacctga tatcacgtcg ctggaggaag tgcccaagat tttcgagggt   22266
ctgggtcgag atgagaagcg ggcggcgaac gctctgcaga aagaacagaa agagagtcag   22326
aacgtgctgg tggagctgga gggggacaac gcgcgtctgg ccgtcctcaa cgctgcata   22386 gaagtctccc acttcgccta ccccgccctc aacttgccac ccaaagttat gaaatcggtc   22446
atggatcagc tgctcatcaa gagagctgag cccctggatc ccgaccaccc cgaggcggaa   22506
aactcagagg acgaaagcc cgtcgtcagc gacgaggagc tcgagcggtg gctggaaacc   22566 agggacccc aacagttgca agagaggcgc aagatgatga tggcggccgt gctggtcacc   22626
gtggagctgg aatgcctgca acggtttttc agcgacgtgg agacgctacg caaaatcggg   22686
gaatccctgc actacacctt ccgccagggc tacgtccgcc aggcctgcaa gatctccaac   22746
```

```
gtggagctca gcaacctggt ctcctacatg ggcatcctcc acgagaaccg gctggggcag    22806
agcgtgctgc actgcaccttg gcaaggcgag gcgcggcggg actacgtgcg agactgcatc    22866
tacctcttcc tcaccctcac ctggcagacc gccatgggcg tctggcagca gtgcttggaa    22926
gagagaaacc tcaaagagct agacaaactc ctctgccgcc agcggcgcgc cctgtggtcc    22986
ggtttcagcg agcgcacggt cgccagcgct ctggcggaca tcatcttccc ggagcgcctg    23046
atgaaaacct tgcaaaacgg cctgccggat ttcatcagtc aaagcatttt gcaaaacttc    23106
cgctcttttg tcctggaacg ctccgggatc ttgcccgcca tgagctgcgc gctaccttct    23166
gactttgtcc ccctctccta ccgcgagtgc cctcccccac tgtggagcca ctgctacctc    23226
ttccaactgg ccaactttct ggcctaccac tccgacctca tggaagacgt aagcggagag    23286
ggtttactgg agtgccactg ccgctgcaac ctgtgcaccc ccacagatc gctggcctgc    23346
aacaccgagc tactcagcga aacccaggtc ataggtacct tcgagatcca ggggccccag    23406
cagcaagagg gtgcttccgg cttgaagctc actccggcgc tgtggacctc ggcttactta    23466
cgcaaatttg tagccgagga ctaccacgcc cacaaaattc agttttacga agaccaatct    23526
cgaccaccga aagcccccct cacggcctgc gtcatcaccc agagcaagat cctggcccaa    23586
ttgcaatcca tcaaccaagc gcgccgcgat ttccttttga aaagggtcg ggggggtgtac   23646
ctggaccccc agaccggcga ggaactcaac ccgtccacac tctccgtcga agcagccccc    23706
ccgagacatg ccgcccaagg gaaccgccaa gcagctgatc gctcggcaga gagcgaagaa    23766
gcaagagctg ctccagcagc aggtggagga cgaggaagag atgtgggaca gccaggcaga    23826
ggaggtgtca gaggacgagg aggagatgga agctgggac agcctagacg aggaggagga    23886
cgagctttca gaggaagagg cgaccgaaga aaaaccacct gcatccagcg cgccttctct    23946
gagccgacag ccgaagcccc ggccccgac gccccggcc ggctcactca aagccagccg    24006
taggtgggac gccaccgaat ctccagcggc agcggcaacg gcagcgggta aggccaaacg    24066
cgagcggcgg gggtattgct cctggcgggc ccacaaaagc agtattgtga actgcttgca    24126
acactgcggg ggaaacatct cctttgcccg acgctacctc ctcttccatc acggtgtggc    24186
cttccctcgc aacgttctct attattaccg tcatctctac agccctacg aaacgctcgg    24246
agaaaaaagc taaggcctcc tccgccgcga ggaaaaactc cgccgccgct gccgccgcca    24306
aggatccacc ggccaccgaa gagctgagaa agcgcatctt tcccactctg tatgctatct    24366
ttcagcaaag ccgcgggcag caccctcagc gcgaactgaa aataaaaaac cgctccttcc    24426
gctcgctcac ccgcagctgt ctgtaccaca agagagaaga ccagctgcag cgcaccctgg    24486
acgacgccga agcactgttc agcaaatact gctcagcgtc tcttaaagac taaaagaccc    24546
gcgcttttc cccctcggcc gccaaaaccc acgtcatcgc cagcatgagc aaggagattc    24606
ccacccccta catgtggagc tatcagcccc agatgggcct ggccgcgggg gccgcccagg    24666
actactccag caagatgaac tggctcagcg ccggccccca catgatctca cgagttaacg    24726
gcatccgagc ccaccgaaac cagattctct tagaacaggc ggcaatcacc gccacacccc    24786
ggcgccaact caacccgcct agttggcccg ccgcccaggt gtatcaggaa atccccgcc    24846
cgaccacagt cctcctgcca cgcgacgcgg aggccgaagt cctcatgact aactctgggg    24906
tacaattagc gggcgggtcc aggtacgcca ggtacagagg tcgggccgct ccttactctc    24966
ccgggagtat aaagagggtg atcattcgag gccgaggtat ccagctcaac gacgagacgg    25026
tgagctcctc aacggtctc agacctgacg gagtcttcca gctcggagga gcgggccgct    25086
cttccttcac cactcgccag gcctacctga ccctgcagag ctcttcctcg cagccgcgct    25146
```

```
ccgggggaat cggcactctc cagttcgtgg aagagttcgt tccctccgtc tacttcaacc   25206
ccttctccgg ctcgcctgga cgctacccgg acgccttcat tcccaacttt gacgcagtga   25266
gtgaatccgt ggacggctac gactgatgac agatggtgcg gccgtgagag ctcggctgcg   25326
acatctgcat cactgccgtc agcctcgctg ctacgctcgg gaggcgatcg tcttcagcta   25386
ctttgagctg ccggacgagc accctcaggg tccggctcac gggttgaaac tcgagatcga   25446
gaacgcgctc gagtctcgcc tcatcgacac cttcaccgcc cgacctctcc tggtagaaat   25506
ccaacggggg atcactacca tcaccctgtt ctgcatctgc cccacgcccg gattacatga   25566
agatctgtgt tgtcatcttt gcgctcagtt taataaaaac tgaactttt gccgcacctt    25626
caacgccatc tgtgatttct acaacaaaaa gttcttctgg caaaggtaca caaactgtat   25686
tttattctaa ttctacctca tctatcgtgc tgaactgcgc ctgcactaac gaacttatcc   25746
agtggattgc aaacggtagt gtgtgcaagt acttttgggg gaacgatata gttagtagaa   25806
ataacagcct ttgcgagcac tgcaactcct ccacactaat cctttatccc ccatttgtta   25866
ctggatggta tatgtgcgtt ggctccggtt taaatcctag ttgctttcat aagtggtttc   25926
tacaaaaaga gacccttccc aacaattctg tttcttttt cgccctatcc tactgctgtt     25986
ctccctctgg ttactctttc aaacctctaa ttggtatttt agctttgata ctcataatct   26046
ttattaactt tataataatt aacaacttac agtaaacatg cttgttctac tgctcgccac   26106
atctttcgct ctctctcacg ccagaacaag tattgttggc gcaggttaca atgcaactct   26166
tcaatctgct tacatgccag attccgacca gatacccat attacgtggt acttacaaac    26226
ctccaaacct aattcttcat tttatgaagg aaacaaactc tgcgatgact ccgacaacag   26286
aacgcacaca tttccccacc cttcactaca attcgaatgc gtaaacaaaa gcttgaagct   26346
ttacaactta aagccttcag attctggctt gtaccatgct gtagttgaaa aaagtaattt   26406
agaagtccac agtgattaca ttgaattgac ggttgtggac ctgccacctc caaaatgtga   26466
ggtttcctcc tcttaccttg aagttcaagg cgtggatgcc tactgcctca tacacattaa   26526
ctgcagcaac tctaaatatc cagctagaat ttactataat ggacaggaaa gtaatctttt   26586
ttattattta acaacaagcg ctggtaacgg taaacagtta cctgactatt ttactgctgt   26646
tgttgaattt tccacctaca gagaaacgta tgccaagcgg ccttacaatt tctcatacc    26706
gtttaacgac ctttgcaatg aaatacaagc gctcgaaact ggaactgatt ttactccaat   26766
tttcattgct gccattgttg taagcttaat taccattatt gtcagcctag cattttactg   26826
cttttacaag cccaaaaacc ctaagtttga aaaacttaaa ctaaaacctg tcattcaaca   26886
agtgtgattt tgttttccag catggtagct gcatttctac ttctcctctg tctacccatc   26946
attttcgtct cttcaacttt cgccgcagtt tcccacctgg aaccagagtg cctaccgcct   27006
tttgacgtgt atctgattct caccttgtt tgttgtatat ccatttgcag tatagcctgc    27066
tttttataa caatctttca agccgccgac tatttttacg tgcgaattgc ttactttaga   27126
caccatcctg aatacagaaa tcaaaacgtt gcctccttac tttgtttggc atgattaagt   27186
tattgctgat acttaattat ttacccctaa tcaactgtaa ttgtccattc accaaacct    27246
ggtcattcta cacctgttat gataaaatcc ccgacactcc tgttgcttgg ctttacgcag   27306
ccaccgccgc tttggtattt atatctactt gccttggagt aaaattgtat tttattttac   27366
acactgggtg gctacatccc agagaagatt tacctagata tcctcttgta aacgcttttc   27426
aattacagcc tctgcctcct cctgatcttc ttcctcgagc tccctctatt gtgagctact   27486
ttcaactcac cggtggagat gactgactct caggacatta atattagtgt ggaaagaata   27546
```

```
gctgctcagc gtcagcgaga aacgcgagtg ttggaatacc tggaactaca gcaacttaaa    27606
gagtcccact ggtgtgagaa aggagtgctg tgccatgtta agcaggcagc cctttcctac    27666
gatgtcagcg ttcagggaca tgaactgtct tacactttgc ctttgcagaa acaaaccttc    27726
tgcaccatga tgggctctac ctccatcaca atcacccaac aagccgggcc tgtagagggg    27786
gctatcctct gtcactgtca cgcacctgat tgcatgtcca aactaatcaa aactctctgt    27846
gctttaggtg atatttttaa ggtgtaaatc aataataaac ttaccttaaa tttgacaaca    27906
aatttctggt gacatcattc agcagcacca ctttaccctc ttcccagctc tcgtatggga    27966
tgcgatagtg ggtggcaaac ttcctccaaa ccctaaaaga aatattggta tccacttcct    28026
tgtcctcacc cacaatttc  atcttttcat ag atg aaa aga acc aga gtt gat       28079
                                    Met Lys Arg Thr Arg Val Asp
                                    1435                1440 gaa gac ttc aac ccc gtc tac ccc tat gac acc aca acc act cct            28124
Glu Asp Phe Asn Pro Val Tyr Pro Tyr Asp Thr Thr Thr Thr Pro
        1445                1450                1455 gca gtt ccc ttt ata tca ccc ccc ttt gta aac agc gat ggt ctt            28169
Ala Val Pro Phe Ile Ser Pro Pro Phe Val Asn Ser Asp Gly Leu
        1460                1465                1470 cag gaa aac ccc cca ggt gtt tta agt ctg cga ata gct aaa ccc            28214
Gln Glu Asn Pro Pro Gly Val Leu Ser Leu Arg Ile Ala Lys Pro
        1475                1480                1485 cta tat ttc gac atg gag aga aaa cta gcc ctt tca ctt gga aga            28259
Leu Tyr Phe Asp Met Glu Arg Lys Leu Ala Leu Ser Leu Gly Arg
        1490                1495                1500 ggg ttg aca att acc gcc gcc gga caa tta gaa agt acg cag agc            28304
Gly Leu Thr Ile Thr Ala Ala Gly Gln Leu Glu Ser Thr Gln Ser
        1505                1510                1515 gta caa acc aac cca ccg ttg ata att acc aac aac aac aca ctg            28349
Val Gln Thr Asn Pro Pro Leu Ile Ile Thr Asn Asn Asn Thr Leu
        1520                1525                1530 acc cta cgt cat tct ccc ccc tta aac cta act gac aat agc tta            28394
Thr Leu Arg His Ser Pro Pro Leu Asn Leu Thr Asp Asn Ser Leu
        1535                1540                1545 gtg cta ggc tac tcg agt cct ctc cgc gtc aca gac aac aaa ctt            28439
Val Leu Gly Tyr Ser Ser Pro Leu Arg Val Thr Asp Asn Lys Leu
        1550                1555                1560 aca ttt aac ttc aca tca cca ctc cgt tat gaa aat gaa aac ctt            28484
Thr Phe Asn Phe Thr Ser Pro Leu Arg Tyr Glu Asn Glu Asn Leu
        1565                1570                1575 act ttt aac tat aca gag cct ctt aaa ctt ata aat aac agc ctt            28529
Thr Phe Asn Tyr Thr Glu Pro Leu Lys Leu Ile Asn Asn Ser Leu
        1580                1585                1590 gcc att gac atc aat tcc tca aaa ggc ctt agt agc gtc gga ggc            28574
Ala Ile Asp Ile Asn Ser Ser Lys Gly Leu Ser Ser Val Gly Gly
        1595                1600                1605 tca cta gct gta aac ctg agt tca gac tta aag ttt gac agc aac            28619
Ser Leu Ala Val Asn Leu Ser Ser Asp Leu Lys Phe Asp Ser Asn
        1610                1615                1620 gga tcc ata gct ttt ggc ata caa acc ctg tgg acc gct ccg acc            28664
Gly Ser Ile Ala Phe Gly Ile Gln Thr Leu Trp Thr Ala Pro Thr
        1625                1630                1635 tcg act ggc aac tgc acc gtc tac agc gag ggc gat tcc cta ctt            28709
Ser Thr Gly Asn Cys Thr Val Tyr Ser Glu Gly Asp Ser Leu Leu
        1640                1645                1650 agt ctc tgt tta acc aaa tgc gga gct cac gtc tta gga agt gta            28754
Ser Leu Cys Leu Thr Lys Cys Gly Ala His Val Leu Gly Ser Val
        1655                1660                1665
```

```
agt tta acc ggt tta aca gga acc ata acc caa atg act gat att      28799
Ser Leu Thr Gly Leu Thr Gly Thr Ile Thr Gln Met Thr Asp Ile
        1670            1675                1680 tct gtc acc att caa ttt aca ttt gac aac aat ggt aag cta cta      28844
Ser Val Thr Ile Gln Phe Thr Phe Asp Asn Asn Gly Lys Leu Leu
        1685            1690                1695 agc tct cca ctt ata aac aac gcc ttt agt att cga cag aat gac      28889
Ser Ser Pro Leu Ile Asn Asn Ala Phe Ser Ile Arg Gln Asn Asp
        1700            1705                1710 agt acg gcc tca aac cct acc tac aac gcc ctg gcg ttt atg cct      28934
Ser Thr Ala Ser Asn Pro Thr Tyr Asn Ala Leu Ala Phe Met Pro
        1715            1720                1725 aac agt acc ata tat gca aga ggg gga ggt ggt gaa cca cga aac      28979
Asn Ser Thr Ile Tyr Ala Arg Gly Gly Gly Gly Glu Pro Arg Asn
        1730            1735                1740 aac tac tac gtc caa acg tat ctt agg gga aat gtt caa aaa cca      29024
Asn Tyr Tyr Val Gln Thr Tyr Leu Arg Gly Asn Val Gln Lys Pro
        1745            1750                1755 atc att ctt act gta acc tac aac tca gtc gcc aca gga tat tcc      29069
Ile Ile Leu Thr Val Thr Tyr Asn Ser Val Ala Thr Gly Tyr Ser
        1760            1765                1770 tta tct ttt aag tgg act gct ctt gca cgt gaa aag ttt gca acc      29114
Leu Ser Phe Lys Trp Thr Ala Leu Ala Arg Glu Lys Phe Ala Thr
        1775            1780                1785 cca aca acc tcg ttt tgc tac att aca gaa caa taa aaccgtgtac      29160
Pro Thr Thr Ser Phe Cys Tyr Ile Thr Glu Gln
        1790            1795 cccaccgttt cgttttttc ag atg aaa cgg gcg aga gtt gat gaa gac      29209
                        Met Lys Arg Ala Arg Val Asp Glu Asp
                              1800            1805 ttc aac cca gtg tac cct tat gac ccc cca cat gct cct gtt atg      29254
Phe Asn Pro Val Tyr Pro Tyr Asp Pro Pro His Ala Pro Val Met
        1810            1815                1820 ccc ttc att act cca cct ttt acc tcc tcg gat ggg ttg cag gaa      29299
Pro Phe Ile Thr Pro Pro Phe Thr Ser Ser Asp Gly Leu Gln Glu
        1825            1830                1835 aaa cca ctt gga gtg tta agt tta aac tac aga gat ccc att act      29344
Lys Pro Leu Gly Val Leu Ser Leu Asn Tyr Arg Asp Pro Ile Thr
        1840            1845                1850 acg caa aat gag tct ctt aca att aaa cta gga aac ggc ctc act      29389
Thr Gln Asn Glu Ser Leu Thr Ile Lys Leu Gly Asn Gly Leu Thr
        1855            1860                1865 cta gac aac cag gga caa cta aca tca acc gct ggc gaa gta gaa      29434
Leu Asp Asn Gln Gly Gln Leu Thr Ser Thr Ala Gly Glu Val Glu
        1870            1875                1880 cct cca ctc act aac gct aac aac aaa ctt gca ctg gtc tat agc      29479
Pro Pro Leu Thr Asn Ala Asn Asn Lys Leu Ala Leu Val Tyr Ser
        1885            1890                1895 gat cct tta gca gta aag cgc aac agc cta acc tta tcg cac acc      29524
Asp Pro Leu Ala Val Lys Arg Asn Ser Leu Thr Leu Ser His Thr
        1900            1905                1910 gct ccc ctt gtt att gct gat aac tct tta gca ttg caa gtt tca      29569
Ala Pro Leu Val Ile Ala Asp Asn Ser Leu Ala Leu Gln Val Ser
        1915            1920                1925 gag cct att ttt ata aat gac aag gac aaa cta gcc ctg caa aca      29614
Glu Pro Ile Phe Ile Asn Asp Lys Asp Lys Leu Ala Leu Gln Thr
        1930            1935                1940 gcc gcg ccc ctt gta act aac gct ggc acc ctt cgc tta caa agc      29659
Ala Ala Pro Leu Val Thr Asn Ala Gly Thr Leu Arg Leu Gln Ser
        1945            1950                1955
```

| | | | | | | | | | | | | |
|---|---|---|---|---|---|---|---|---|---|---|---|---|
| gcc<br>Ala | gcc<br>Ala | cct<br>Pro | tta<br>Leu<br>1960 | ggc<br>Gly | att<br>Ile | gca<br>Ala | gac<br>Asp | caa<br>Gln<br>1965 | acc<br>Thr | cta<br>Leu | aaa<br>Lys | ctc<br>Leu | ctg<br>Leu<br>1970 | ttt<br>Phe | 29704 |
| acc<br>Thr | aac<br>Asn | cct<br>Pro | ttg<br>Leu<br>1975 | tac<br>Tyr | ttg<br>Leu | cag<br>Gln | aat<br>Asn | aac<br>Asn<br>1980 | ttt<br>Phe | ctc<br>Leu | acg<br>Thr | tta<br>Leu | gcc<br>Ala<br>1985 | att<br>Ile | 29749 |
| gaa<br>Glu | cga<br>Arg | ccc<br>Pro | ctt<br>Leu<br>1990 | gcc<br>Ala | att<br>Ile | acc<br>Thr | aat<br>Asn | act<br>Thr<br>1995 | gga<br>Gly | aag<br>Lys | ctg<br>Leu | gct<br>Ala | cta<br>Leu<br>2000 | cag<br>Gln | 29794 |
| ctc<br>Leu | tcc<br>Ser | cca<br>Pro | ccg<br>Pro<br>2005 | cta<br>Leu | caa<br>Gln | aca<br>Thr | gca<br>Ala | gac<br>Asp<br>2010 | aca<br>Thr | ggc<br>Gly | ttg<br>Leu | act<br>Thr | ttg<br>Leu<br>2015 | caa<br>Gln | 29839 |
| acc<br>Thr | aac<br>Asn | gtg<br>Val | cca<br>Pro<br>2020 | tta<br>Leu | act<br>Thr | gta<br>Val | agc<br>Ser | aac<br>Asn<br>2025 | ggg<br>Gly | acc<br>Thr | cta<br>Leu | ggc<br>Gly | tta<br>Leu<br>2030 | gcc<br>Ala | 29884 |
| ata<br>Ile | aag<br>Lys | cgc<br>Arg | cca<br>Pro<br>2035 | ctt<br>Leu | att<br>Ile | att<br>Ile | cag<br>Gln | gac<br>Asp<br>2040 | aac<br>Asn | aac<br>Asn | ttg<br>Leu | ttt<br>Phe | ttg<br>Leu<br>2045 | gac<br>Asp | 29929 |
| ttc<br>Phe | aga<br>Arg | gct<br>Ala | ccc<br>Pro<br>2050 | ctg<br>Leu | cgt<br>Arg | ctt<br>Leu | ttc<br>Phe | aac<br>Asn<br>2055 | agc<br>Ser | gac<br>Asp | cca<br>Pro | gta<br>Val | cta<br>Leu<br>2060 | ggg<br>Gly | 29974 |
| ctt<br>Leu | aac<br>Asn | ttt<br>Phe | tac<br>Tyr<br>2065 | acc<br>Thr | cct<br>Pro | ctt<br>Leu | gcg<br>Ala | gta<br>Val<br>2070 | cgc<br>Arg | gat<br>Asp | gag<br>Glu | gcg<br>Ala | ctc<br>Leu<br>2075 | act<br>Thr | 30019 |
| gtt<br>Val | aac<br>Asn | aca<br>Thr | ggc<br>Gly<br>2080 | cgc<br>Arg | ggc<br>Gly | ctc<br>Leu | aca<br>Thr | gtg<br>Val<br>2085 | agt<br>Ser | tac<br>Tyr | gat<br>Asp | ggt<br>Gly | tta<br>Leu<br>2090 | att<br>Ile | 30064 |
| tta<br>Leu | aat<br>Asn | ctt<br>Leu | ggt<br>Gly<br>2095 | aag<br>Lys | gat<br>Asp | ctt<br>Leu | cgc<br>Arg | ttt<br>Phe<br>2100 | gac<br>Asp | aac<br>Asn | aac<br>Asn | acc<br>Thr | gtt<br>Val<br>2105 | tct<br>Ser | 30109 |
| gtc<br>Val | gct<br>Ala | ctt<br>Leu | agt<br>Ser<br>2110 | gct<br>Ala | gct<br>Ala | ttg<br>Leu | cct<br>Pro | tta<br>Leu<br>2115 | caa<br>Gln | tac<br>Tyr | act<br>Thr | gat<br>Asp | cag<br>Gln<br>2120 | ctt<br>Leu | 30154 |
| cgc<br>Arg | ctt<br>Leu | aac<br>Asn | gtg<br>Val<br>2125 | ggc<br>Gly | gct<br>Ala | ggg<br>Gly | ctg<br>Leu | cgt<br>Arg<br>2130 | tac<br>Tyr | aat<br>Asn | cca<br>Pro | gtg<br>Val | agt<br>Ser<br>2135 | aag<br>Lys | 30199 |
| aaa<br>Lys | ttg<br>Leu | gac<br>Asp | gtg<br>Val<br>2140 | aac<br>Asn | ccc<br>Pro | aat<br>Asn | caa<br>Gln | aac<br>Asn<br>2145 | aag<br>Lys | ggt<br>Gly | tta<br>Leu | acc<br>Thr | tgg<br>Trp<br>2150 | gaa<br>Glu | 30244 |
| aat<br>Asn | gac<br>Asp | tac<br>Tyr | ctc<br>Leu<br>2155 | att<br>Ile | gta<br>Val | aag<br>Lys | cta<br>Leu | gga<br>Gly<br>2160 | aat<br>Asn | gga<br>Gly | tta<br>Leu | ggt<br>Gly | ttt<br>Phe<br>2165 | gat<br>Asp | 30289 |
| ggc<br>Gly | gat<br>Asp | gga<br>Gly | aac<br>Asn<br>2170 | ata<br>Ile | gct<br>Ala | gtt<br>Val | tct<br>Ser | cct<br>Pro<br>2175 | caa<br>Gln | gtt<br>Val | aca<br>Thr | tcg<br>Ser | cct<br>Pro<br>2180 | gac<br>Asp | 30334 |
| acc<br>Thr | tta<br>Leu | tgg<br>Trp | acc<br>Thr<br>2185 | act<br>Thr | gcc<br>Ala | gac<br>Asp | cca<br>Pro | tcc<br>Ser<br>2190 | ccc<br>Pro | aat<br>Asn | tgt<br>Cys | tcc<br>Ser | atc<br>Ile<br>2195 | tac<br>Tyr | 30379 |
| act<br>Thr | gat<br>Asp | tta<br>Leu | gat<br>Asp<br>2200 | gcc<br>Ala | aaa<br>Lys | atg<br>Met | tgg<br>Trp | ctc<br>Leu<br>2205 | tcg<br>Ser | ttg<br>Leu | gta<br>Val | aaa<br>Lys | caa<br>Gln<br>2210 | ggg<br>Gly | 30424 |
| ggt<br>Gly | gtg<br>Val | gtt<br>Val | cac<br>His<br>2215 | ggt<br>Gly | tct<br>Ser | gtt<br>Val | gct<br>Ala | tta<br>Leu<br>2220 | aaa<br>Lys | gca<br>Ala | ttg<br>Leu | aaa<br>Lys | gga<br>Gly<br>2225 | acc<br>Thr | 30469 |
| cta<br>Leu | ttg<br>Leu | agt<br>Ser | cct<br>Pro<br>2230 | acg<br>Thr | gaa<br>Glu | agc<br>Ser | gcc<br>Ala | att<br>Ile<br>2235 | gtt<br>Val | att<br>Ile | ata<br>Ile | cta<br>Leu | cat<br>His<br>2240 | ttt<br>Phe | 30514 |
| gac<br>Asp | aat<br>Asn | tat<br>Tyr | gga<br>Gly<br>2245 | gtg<br>Val | cga<br>Arg | att<br>Ile | ctc<br>Leu | aat<br>Asn<br>2250 | tat<br>Tyr | ccc<br>Pro | act<br>Thr | ttg<br>Leu | ggc<br>Gly<br>2255 | act<br>Thr | 30559 |

| | | | | | | | | | | | | |
|---|---|---|---|---|---|---|---|---|---|---|---|---|
| caa | ggc | acg | ttg | gga | aat | aat | gca | act | tgg | ggt | tat | agg | cag | gga | 30604 |
| Gln | Gly | Thr | Leu 2260 | Gly | Asn | Asn | Ala | Thr 2265 | Trp | Gly | Tyr | Arg | Gln 2270 | Gly | |
| gaa | tct | gca | gac | act | aat | gta | ctc | aat | gca | cta | gca | ttt | atg | ccc | 30649 |
| Glu | Ser | Ala | Asp 2275 | Thr | Asn | Val | Leu | Asn 2280 | Ala | Leu | Ala | Phe | Met 2285 | Pro | |
| agt | tca | aaa | agg | tac | cca | aga | ggg | cgt | gga | agc | gaa | gtt | cag | aat | 30694 |
| Ser | Ser | Lys | Arg 2290 | Tyr | Pro | Arg | Gly | Arg 2295 | Gly | Ser | Glu | Val | Gln 2300 | Asn | |
| caa | act | gtg | ggc | tac | act | tgt | ata | cag | ggt | gac | ttt | tct | atg | ccc | 30739 |
| Gln | Thr | Val | Gly 2305 | Tyr | Thr | Cys | Ile | Gln 2310 | Gly | Asp | Phe | Ser | Met 2315 | Pro | |
| gta | ccg | tac | caa | ata | cag | tac | aac | tat | gga | cca | act | ggc | tac | tcc | 30784 |
| Val | Pro | Tyr | Gln 2320 | Ile | Gln | Tyr | Asn | Tyr 2325 | Gly | Pro | Thr | Gly | Tyr 2330 | Ser | |
| ttt | aaa | ttt | att | tgg | aga | act | gtt | tca | aga | caa | cca | ttt | gac | atc | 30829 |
| Phe | Lys | Phe | Ile 2335 | Trp | Arg | Thr | Val | Ser 2340 | Arg | Gln | Pro | Phe | Asp 2345 | Ile | |
| cca | tgc | tgt | ttt | ttc | tct | tac | att | acg | gaa | gaa | taa | acaactttt | | | 30875 |
| Pro | Cys | Cys | Phe 2350 | Phe | Ser | Tyr | Ile | Thr 2355 | Glu | Glu | | | | | |

| | | |
|---|---|---|
| tcttttatt ttcttttat tttacacgca cagtaaggct tcctccaccc ttccatctca | | 30935 |
| cagcatacac cagcctctcc cccttcatgg cagtaaactg ttgtgagtca gtccggtatt | | 30995 |
| tgggagttaa gatccaaaca gtctctttgg tgatgaaaca tggatccgtg atggacacaa | | 31055 |
| atccctggga caggttctcc aacgtttcgg taaaaactg catgccgccc tacaaaacaa | | 31115 |
| acaggttcag gctctccacg ggttatctcc ccgatcaaac tcagacagag taaaggtgcg | | 31175 |
| atgatgttcc actaaaccac gcaggtggcg ctgtctgaac ctctcggtgc gactcctgtg | | 31235 |
| aggctggtaa gaagttagat tgtccagcag cctcacagca tggatcatca gtctacgagt | | 31295 |
| gcgtctggcg cagcagcgca tctgaatctc actgagattc cggcaagaat cgcacaccat | | 31355 |
| cacaatcagg ttgttcatga tcccatagct gaacacgctc cagccaaagc tcattcgctc | | 31415 |
| caacagcgcc accgcgtgtc cgtccaacct tactttaaca taaatcaggt gtctgccgcg | | 31475 |
| tacaaacatg ctaccgcat acagaacctc ccggggcaaa cccctgttca ccacctgcct | | 31535 |
| gtaccaggga aacctcacat ttatcaggga gccatagata gccatttaa accaattagc | | 31595 |
| taacaccgcc ccaccagctc tacactgaag agaaccggga gagttacaat gacagtgaat | | 31655 |
| aatccatctc tcataacccc taatggtctg atggaaatcc agatctaacg tggcacagca | | 31715 |
| gatacacact ttcatataca ttttcatcac atgttttcc caggccgtta aaatacaatc | | 31775 |
| ccaatacacg ggccactcct gcagtacaat aaagctaata caagatggta tactcctcac | | 31835 |
| ctcactaaca ttgtgcatgt tcatattttc acattctaag taccgagagt tctcctctac | | 31895 |
| aacagcactg ccgcggtcct cacaaggtgg tagctggtga cgattgtaag gagccagtct | | 31955 |
| gcagcgatac cgtctgtcgc gttgcatcgt agaccaggga ccgacgcact tcctcgtact | | 32015 |
| tgtagtagca gaaccacgtc cgctgccagc acgtctccaa gtaacgccgg tccctgcgtc | | 32075 |
| gctcacgctc cctcctcaac gcaaagtgca accactcttg taatccacac agatccctct | | 32135 |
| cggcctccgg ggcgatgcac acctcaaacc tacagatgtc tcggtacagt tccaaacacg | | 32195 |
| tagtgagggc gagttccaac caagacagac agcctgatct atcccgacac actggaggtg | | 32255 |
| gaggaagaca cggaagaggc atgttattcc aagcgattca ccaacgggtc gaaatgaaga | | 32315 |
| tcccgaagat gacaacggtc gcctccggag ccctgatgga atttaacagc cagatcaaac | | 32375 |
| attatgcgat tttccaggct atcaatcgcg gcctccaaaa gagcctggac ccgcacttcc | | 32435 |

-continued

```
acaaacacca gcaaagcaaa agcgttatta tcaaactctt cgatcatcaa gctgcaggac    32495
tgtacaatgc ccaagtaatt ttcatttctc cactcgcgaa tgatgtcgcg gcaaatagtc    32555
tgaaggttca tgccgtgcat attaaaaagc tccgaaaggg cgccctctat agccatgcgt    32615
agacacacca tcatgactgc aagatatcgg gctcctgaga cacctgcagc agatttaaca    32675
gacccaggtc aggttgctct ccgcgatcgc gaatctccat ccgcaaagtc atttgcaaat    32735
aattaaatag atctgcgccg actaaatctg ttaactccgc gctaggaact aaatcaggtg    32795
tggctacgca gcacaaaagt tccagggatg gcgccaaact cactagaacc gctcccgagt    32855
agcaaaactg atgaatggga gtaacacagt gtaaaatgtt cagccaaaaa tcactaagct    32915
gctcctttaa aaagtccagt acttctatat tcagttcgtg caagtactga agcaactgtg    32975
cgggaatatg cacagcaaaa aaaatagggc ggctcagata catgttgacc taaaataaaa    33035
agaatcatta aactaaagaa gcctggcgaa cggtgggata tatgacacgc tccagcagca    33095
ggcaagcaac cggctgtccc cgggaaccgc ggtaaaattc atccgaatga ttaaaaagaa    33155
caacagagac ttcccaccat gtactcggtt ggatctcctg agcacagagc aatacccccc    33215
tcacattcat atccgctaca gaaaaaaaac gtcccagata cccagcggga atatccaacg    33275
acagctgcaa agacagcaaa acaatccctc tgggagcaat cacaaaatcc tccggtgaaa    33335
aaagcacata catattagaa taaccctgtt gctggggcaa aaaggcccgt cgtcccagca    33395
aatgcacata aatatgttca tcagccattg ccccgtctta ccgcgtaaac agccacgaaa    33455 aaaatcgagct aaaatccacc caacagccta tagctatata tacactccac ccaatgacgc    33515
taataccgca ccacccacga ccaaagttca cccacaccca caaaacccgc gaaaatccag    33575
cgccgtcagc acttccgcaa tttcagtctc acaacgtcac ttccgcgcgc cttttcactt    33635
tcccacacac gcccttcgcc cgcccgccct cgcgccaccc cgcgtcaccc cacgtcaccg    33695
cacgtcaccc cggccccgcc tcgctcctcc ccgctcatta tcatattggc acgttttccag    33755 aataaggtat attattgatg cagcaaaaca atccctctgg gagcaatcac aaaatcctcc    33815
ggtgaaaaaa gcacatacat attagaataa ccctgttgct ggggcaaaaa ggcccgtcgt    33875
cccagcaaat gcacataaat atgttcatca gccattgccc cgtcttaccg cgtaaacagc    33935
cacgaaaaaa tcgagctaaa atccacccaa cagcctatag ctatatatac actccaccca    33995
atgacgctaa taccgcacca cccacgacca aagttcaccc acacccacaa aacccgcgaa    34055 aatcagcgc cgtcagcact tccgcaattt cagtctcaca acgtcacttc cgcgcgcctt    34115
ttcactttcc cacacacgcc cttcgcccgc ccgcctcgc gccacccgc gtcacccac    34175 gtcaccgcac gtcaccccgg ccccgcctcg ctcctcccg ctcattatca tattggcacg    34235
tttccagaat aaggtatatt attgatgca                                    34264
```

<210> SEQ ID NO 25
<211> LENGTH: 503
<212> TYPE: PRT
<213> ORGANISM: simian adenovirus SV-1

<400> SEQUENCE: 25

```
Met Arg Arg Ala Val Arg Val Thr Pro Ala Ala Tyr Glu Gly Pro Pro
1               5                   10                  15

Pro Ser Tyr Glu Ser Val Met Gly Ser Ala Asn Val Pro Ala Thr Leu
            20                  25                  30

Glu Ala Pro Tyr Val Pro Pro Arg Tyr Leu Gly Pro Thr Glu Gly Arg
        35                  40                  45
```

```
Asn Ser Ile Arg Tyr Ser Glu Leu Ala Pro Leu Tyr Asp Thr Thr Lys
 50                  55                  60

Val Tyr Leu Val Asp Asn Lys Ser Ala Asp Ile Ala Ser Leu Asn Tyr
 65                  70                  75                  80

Gln Asn Asp His Ser Asn Phe Leu Thr Thr Val Val Gln Asn Asn Asp
                 85                  90                  95

Phe Thr Pro Thr Glu Ala Gly Thr Gln Thr Ile Asn Phe Asp Glu Arg
            100                 105                 110

Ser Arg Trp Gly Gly Gln Leu Lys Thr Ile Leu His Thr Asn Met Pro
            115                 120                 125

Asn Ile Asn Glu Phe Met Ser Thr Asn Lys Phe Arg Ala Arg Leu Met
130                 135                 140

Val Lys Lys Ala Glu Asn Gln Pro Pro Glu Tyr Glu Trp Phe Glu Phe
145                 150                 155                 160

Thr Ile Pro Glu Gly Asn Tyr Ser Glu Thr Met Thr Ile Asp Leu Met
                165                 170                 175

Asn Asn Ala Ile Val Asp Asn Tyr Leu Gln Val Gly Arg Gln Asn Gly
                180                 185                 190

Val Leu Glu Ser Asp Ile Gly Val Lys Phe Asp Thr Arg Asn Phe Arg
            195                 200                 205

Leu Gly Trp Asp Pro Val Thr Lys Leu Val Met Pro Gly Val Tyr Thr
            210                 215                 220

Asn Glu Ala Phe His Pro Asp Ile Val Leu Leu Pro Gly Cys Gly Val
225                 230                 235                 240

Asp Phe Thr Gln Ser Arg Leu Ser Asn Leu Leu Gly Ile Arg Lys Arg
                245                 250                 255

Arg Pro Phe Gln Glu Gly Phe Gln Ile Met Tyr Glu Asp Leu Glu Gly
            260                 265                 270

Gly Asn Ile Pro Gly Leu Leu Asp Val Pro Ala Tyr Glu Glu Ser Val
            275                 280                 285

Lys Gln Ala Glu Ala Gln Gly Arg Glu Ile Arg Gly Asp Thr Phe Ala
290                 295                 300

Thr Glu Pro His Glu Leu Val Ile Lys Pro Leu Glu Gln Asp Ser Lys
305                 310                 315                 320

Lys Arg Ser Tyr Asn Ile Ile Ser Gly Thr Met Asn Thr Leu Tyr Arg
                325                 330                 335

Ser Trp Phe Leu Ala Tyr Asn Tyr Gly Asp Pro Glu Lys Gly Val Arg
            340                 345                 350

Ser Trp Thr Ile Leu Thr Thr Thr Asp Val Thr Cys Gly Ser Gln Gln
            355                 360                 365

Val Tyr Trp Ser Leu Pro Asp Met Met Gln Asp Pro Val Thr Phe Arg
            370                 375                 380

Pro Ser Thr Gln Val Ser Asn Phe Pro Val Val Gly Thr Glu Leu Leu
385                 390                 395                 400

Pro Val His Ala Lys Ser Phe Tyr Asn Glu Gln Ala Val Tyr Ser Gln
                405                 410                 415

Leu Ile Arg Gln Ser Thr Ala Leu Thr His Val Phe Asn Arg Phe Pro
            420                 425                 430

Glu Asn Gln Ile Leu Val Arg Pro Pro Ala Pro Thr Ile Thr Thr Val
            435                 440                 445

Ser Glu Asn Val Pro Ala Leu Thr Asp His Gly Thr Leu Pro Leu Arg
450                 455                 460

Ser Ser Ile Ser Gly Val Gln Arg Val Thr Ile Thr Asp Ala Arg Arg
465                 470                 475                 480
```

```
Arg Thr Cys Pro Tyr Val Tyr Lys Ala Leu Gly Val Val Ala Pro Lys
                485                 490                 495

Val Leu Ser Ser Arg Thr Phe
            500
```

<210> SEQ ID NO 26
<211> LENGTH: 931
<212> TYPE: PRT
<213> ORGANISM: simian adenovirus SV-1

<400> SEQUENCE: 26

```
Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Thr Ala Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Pro Ala Glu Trp Thr Asn Ser Asp Ser Lys Val Lys Val
    130                 135                 140

Arg Ala Gln Ala Pro Phe Val Ser Ser Tyr Gly Ala Thr Ala Ile Thr
145                 150                 155                 160

Lys Glu Gly Ile Gln Val Gly Val Thr Leu Thr Asp Ser Gly Ser Thr
                165                 170                 175

Pro Gln Tyr Ala Asp Lys Thr Tyr Gln Pro Glu Pro Gln Ile Gly Glu
            180                 185                 190

Leu Gln Trp Asn Ser Asp Val Gly Thr Asp Asp Lys Ile Ala Gly Arg
        195                 200                 205

Val Leu Lys Lys Thr Thr Pro Met Phe Pro Cys Tyr Gly Ser Tyr Ala
    210                 215                 220

Arg Pro Thr Asn Glu Lys Gly Gly Gln Ala Thr Pro Ser Ala Ser Gln
225                 230                 235                 240

Asp Val Gln Asn Pro Glu Leu Gln Phe Phe Ala Ser Thr Asn Val Ala
                245                 250                 255

Asn Thr Pro Lys Ala Val Leu Tyr Ala Glu Asp Val Ser Ile Glu Ala
            260                 265                 270

Pro Asp Thr His Leu Val Phe Lys Pro Thr Val Thr Glu Gly Ile Thr
        275                 280                 285

Ser Ser Glu Ala Leu Leu Thr Gln Gln Ala Ala Pro Asn Arg Pro Asn
    290                 295                 300

Tyr Ile Ala Phe Arg Asp Asn Phe Ile Gly Leu Met Tyr Tyr Asn Ser
305                 310                 315                 320

Thr Gly Asn Met Gly Val Leu Ala Gly Gln Ala Ser Gln Leu Asn Ala
                325                 330                 335

Val Val Asp Leu Gln Asp Arg Asn Thr Glu Leu Ser Tyr Gln Leu Met
            340                 345                 350
```

```
Leu Asp Ala Leu Gly Asp Arg Ser Arg Tyr Phe Ser Met Trp Asn Gln
        355                 360                 365

Ala Val Asp Ser Tyr Asp Pro Asp Val Arg Ile Ile Glu Asn His Gly
        370                 375                 380

Val Glu Asp Glu Leu Pro Asn Tyr Cys Phe Pro Leu Gly Gly Met Ala
385                 390                 395                 400

Val Thr Asp Thr Tyr Ser Pro Ile Lys Val Asn Gly Gly Asn Gly
                    405                 410                 415

Trp Glu Ala Asn Asn Gly Val Phe Thr Glu Arg Gly Val Glu Ile Gly
                420                 425                 430

Ser Gly Asn Met Phe Ala Met Glu Ile Asn Leu Gln Ala Asn Leu Trp
            435                 440                 445

Arg Ser Phe Leu Tyr Ser Asn Ile Gly Leu Tyr Leu Pro Asp Ser Leu
        450                 455                 460

Lys Ile Thr Pro Asp Asn Ile Thr Leu Pro Glu Asn Lys Asn Thr Tyr
465                 470                 475                 480

Gln Tyr Met Asn Gly Arg Val Thr Pro Pro Gly Leu Val Asp Thr Tyr
                    485                 490                 495

Val Asn Val Gly Ala Arg Trp Ser Pro Asp Val Met Asp Ser Ile Asn
                500                 505                 510

Pro Phe Asn His His Arg Asn Ala Gly Leu Arg Tyr Arg Ser Met Leu
            515                 520                 525

Leu Gly Asn Gly Arg Tyr Val Pro Phe His Ile Gln Val Pro Gln Lys
        530                 535                 540

Phe Phe Ala Ile Lys Asn Leu Leu Leu Pro Gly Ser Tyr Thr Tyr
545                 550                 555                 560

Glu Trp Asn Phe Arg Lys Asp Val Asn Met Ile Leu Gln Ser Ser Leu
                    565                 570                 575

Gly Asn Asp Leu Arg Val Asp Gly Ala Ser Ile Arg Phe Asp Ser Ile
                580                 585                 590

Asn Leu Tyr Ala Asn Phe Phe Pro Met Ala His Asn Thr Ala Ser Thr
            595                 600                 605

Leu Glu Ala Met Leu Arg Asn Asp Thr Asn Asp Gln Ser Phe Asn Asp
        610                 615                 620

Tyr Leu Cys Ala Ala Asn Met Leu Tyr Pro Ile Pro Ala Asn Ala Thr
625                 630                 635                 640

Ser Val Pro Ile Ser Ile Pro Ser Arg Asn Trp Ala Ala Phe Arg Gly
                    645                 650                 655

Trp Ser Phe Thr Arg Leu Lys Thr Lys Glu Thr Pro Ser Leu Gly Ser
                660                 665                 670

Gly Phe Asp Pro Tyr Phe Val Tyr Ser Gly Ser Ile Pro Tyr Leu Asp
            675                 680                 685

Gly Thr Phe Tyr Leu Asn His Thr Phe Lys Lys Val Ser Ile Met Phe
        690                 695                 700

Asp Ser Ser Val Ser Trp Pro Gly Asn Asp Arg Leu Leu Thr Pro Asn
705                 710                 715                 720

Glu Phe Glu Ile Lys Arg Ser Val Asp Gly Glu Gly Tyr Asn Val Ala
                    725                 730                 735

Gln Ser Asn Met Thr Lys Asp Trp Phe Leu Ile Gln Met Leu Ser His
                740                 745                 750

Tyr Asn Ile Gly Tyr Gln Gly Phe Tyr Val Pro Glu Asn Tyr Lys Asp
            755                 760                 765

Arg Met Tyr Ser Phe Phe Arg Asn Phe Gln Pro Met Ser Arg Gln Ile
```

```
               770             775             780
Val Asp Ser Thr Ala Tyr Thr Asn Tyr Gln Asp Val Lys Leu Pro Tyr
785                 790                 795                 800

Gln His Asn Asn Ser Gly Phe Val Gly Tyr Met Gly Pro Thr Met Arg
                805                 810                 815

Glu Gly Gln Ala Tyr Pro Ala Asn Tyr Pro Tyr Pro Leu Ile Gly Ala
            820                 825                 830

Thr Ala Val Pro Ser Leu Thr Gln Lys Lys Phe Leu Cys Asp Arg Val
                835                 840                 845

Met Trp Arg Ile Pro Phe Ser Ser Asn Phe Met Ser Met Gly Ser Leu
850                 855                 860

Thr Asp Leu Gly Gln Asn Met Leu Tyr Ala Asn Ser Ala His Ala Leu
865                 870                 875                 880

Asp Met Thr Phe Glu Val Asp Pro Met Asp Glu Pro Thr Leu Leu Tyr
                885                 890                 895

Val Leu Phe Glu Val Phe Asp Val Val Arg Ile His Gln Pro His Arg
            900                 905                 910

Gly Val Ile Glu Ala Val Tyr Leu Arg Thr Pro Phe Ser Ala Gly Asn
                915                 920                 925

Ala Thr Thr
    930

<210> SEQ ID NO 27
<211> LENGTH: 363
<212> TYPE: PRT
<213> ORGANISM: simian adenovirus SV-1

<400> SEQUENCE: 27

Met Lys Arg Thr Arg Val Asp Glu Asp Phe Asn Pro Val Tyr Pro Tyr
1               5                   10                  15

Asp Thr Thr Thr Thr Pro Ala Val Pro Phe Ile Ser Pro Pro Phe Val
                20                  25                  30

Asn Ser Asp Gly Leu Gln Glu Asn Pro Pro Gly Val Leu Ser Leu Arg
            35                  40                  45

Ile Ala Lys Pro Leu Tyr Phe Asp Met Glu Arg Lys Leu Ala Leu Ser
50                  55                  60

Leu Gly Arg Gly Leu Thr Ile Thr Ala Ala Gly Gln Leu Glu Ser Thr
65                  70                  75                  80

Gln Ser Val Gln Thr Asn Pro Pro Leu Ile Ile Thr Asn Asn Asn Thr
                85                  90                  95

Leu Thr Leu Arg His Ser Pro Pro Leu Asn Leu Thr Asp Asn Ser Leu
                100                 105                 110

Val Leu Gly Tyr Ser Ser Pro Leu Arg Val Thr Asp Asn Lys Leu Thr
            115                 120                 125

Phe Asn Phe Thr Ser Pro Leu Arg Tyr Glu Asn Glu Asn Leu Thr Phe
130                 135                 140

Asn Tyr Thr Glu Pro Leu Lys Leu Ile Asn Asn Ser Leu Ala Ile Asp
145                 150                 155                 160

Ile Asn Ser Ser Lys Gly Leu Ser Ser Val Gly Gly Ser Leu Ala Val
                165                 170                 175

Asn Leu Ser Ser Asp Leu Lys Phe Asp Ser Asn Gly Ser Ile Ala Phe
            180                 185                 190

Gly Ile Gln Thr Leu Trp Thr Ala Pro Thr Ser Thr Gly Asn Cys Thr
                195                 200                 205

Val Tyr Ser Glu Gly Asp Ser Leu Leu Ser Leu Cys Leu Thr Lys Cys
```

```
                    210                 215                 220
Gly Ala His Val Leu Gly Ser Val Ser Leu Thr Gly Leu Thr Gly Thr
225                 230                 235                 240

Ile Thr Gln Met Thr Asp Ile Ser Val Thr Ile Gln Phe Thr Phe Asp
                245                 250                 255

Asn Asn Gly Lys Leu Leu Ser Ser Pro Leu Ile Asn Asn Ala Phe Ser
                260                 265                 270

Ile Arg Gln Asn Asp Ser Thr Ala Ser Asn Pro Thr Tyr Asn Ala Leu
                275                 280                 285

Ala Phe Met Pro Asn Ser Thr Ile Tyr Ala Arg Gly Gly Gly Gly Glu
                290                 295                 300

Pro Arg Asn Asn Tyr Tyr Val Gln Thr Tyr Leu Arg Gly Asn Val Gln
305                 310                 315                 320

Lys Pro Ile Ile Leu Thr Val Thr Tyr Asn Ser Val Ala Thr Gly Tyr
                325                 330                 335

Ser Leu Ser Phe Lys Trp Thr Ala Leu Ala Arg Glu Lys Phe Ala Thr
                340                 345                 350

Pro Thr Thr Ser Phe Cys Tyr Ile Thr Glu Gln
                355                 360

<210> SEQ ID NO 28
<211> LENGTH: 560
<212> TYPE: PRT
<213> ORGANISM: simian adenovirus SV-1

<400> SEQUENCE: 28

Met Lys Arg Ala Arg Val Asp Glu Asp Phe Asn Pro Val Tyr Pro Tyr
1               5                   10                  15

Asp Pro Pro His Ala Pro Val Met Pro Phe Ile Thr Pro Pro Phe Thr
                20                  25                  30

Ser Ser Asp Gly Leu Gln Glu Lys Pro Leu Gly Val Leu Ser Leu Asn
            35                  40                  45

Tyr Arg Asp Pro Ile Thr Thr Gln Asn Glu Ser Leu Thr Ile Lys Leu
        50                  55                  60

Gly Asn Gly Leu Thr Leu Asp Asn Gln Gly Gln Leu Thr Ser Thr Ala
65                  70                  75                  80

Gly Glu Val Glu Pro Pro Leu Thr Asn Ala Asn Asn Lys Leu Ala Leu
                85                  90                  95

Val Tyr Ser Asp Pro Leu Ala Val Lys Arg Asn Ser Leu Thr Leu Ser
                100                 105                 110

His Thr Ala Pro Leu Val Ile Ala Asp Asn Ser Leu Ala Leu Gln Val
            115                 120                 125

Ser Glu Pro Ile Phe Ile Asn Asp Lys Asp Lys Leu Ala Leu Gln Thr
        130                 135                 140

Ala Ala Pro Leu Val Thr Asn Ala Gly Thr Leu Arg Leu Gln Ser Ala
145                 150                 155                 160

Ala Pro Leu Gly Ile Ala Asp Gln Thr Leu Lys Leu Leu Phe Thr Asn
                165                 170                 175

Pro Leu Tyr Leu Gln Asn Asn Phe Leu Thr Leu Ala Ile Glu Arg Pro
                180                 185                 190

Leu Ala Ile Thr Asn Thr Gly Lys Leu Ala Leu Gln Leu Ser Pro Pro
            195                 200                 205

Leu Gln Thr Ala Asp Thr Gly Leu Thr Leu Gln Thr Asn Val Pro Leu
        210                 215                 220

Thr Val Ser Asn Gly Thr Leu Gly Leu Ala Ile Lys Arg Pro Leu Ile
```

```
              225                 230                 235                 240
Ile Gln Asp Asn Asn Leu Phe Leu Asp Phe Arg Ala Pro Leu Arg Leu
            245                 250                 255

Phe Asn Ser Asp Pro Val Leu Gly Leu Asn Phe Tyr Thr Pro Leu Ala
        260                 265                 270

Val Arg Asp Glu Ala Leu Thr Val Asn Thr Gly Arg Gly Leu Thr Val
    275                 280                 285

Ser Tyr Asp Gly Leu Ile Leu Asn Leu Gly Lys Asp Leu Arg Phe Asp
290                 295                 300

Asn Asn Thr Val Ser Val Ala Leu Ser Ala Ala Leu Pro Leu Gln Tyr
305                 310                 315                 320

Thr Asp Gln Leu Arg Leu Asn Val Gly Ala Gly Leu Arg Tyr Asn Pro
                325                 330                 335

Val Ser Lys Lys Leu Asp Val Asn Pro Asn Gln Asn Lys Gly Leu Thr
            340                 345                 350

Trp Glu Asn Asp Tyr Leu Ile Val Lys Leu Gly Asn Gly Leu Gly Phe
        355                 360                 365

Asp Gly Asp Gly Asn Ile Ala Val Ser Pro Gln Val Thr Ser Pro Asp
    370                 375                 380

Thr Leu Trp Thr Thr Ala Asp Pro Ser Pro Asn Cys Ser Ile Tyr Thr
385                 390                 395                 400

Asp Leu Asp Ala Lys Met Trp Leu Ser Leu Val Lys Gln Gly Gly Val
                405                 410                 415

Val His Gly Ser Val Ala Leu Lys Ala Leu Lys Gly Thr Leu Leu Ser
            420                 425                 430

Pro Thr Glu Ser Ala Ile Val Ile Leu His Phe Asp Asn Tyr Gly
        435                 440                 445

Val Arg Ile Leu Asn Tyr Pro Thr Leu Gly Thr Gln Gly Thr Leu Gly
    450                 455                 460

Asn Asn Ala Thr Trp Gly Tyr Arg Gln Gly Glu Ser Ala Asp Thr Asn
465                 470                 475                 480

Val Leu Asn Ala Leu Ala Phe Met Pro Ser Ser Lys Arg Tyr Pro Arg
                485                 490                 495

Gly Arg Gly Ser Glu Val Gln Asn Gln Thr Val Gly Tyr Thr Cys Ile
            500                 505                 510

Gln Gly Asp Phe Ser Met Pro Val Pro Tyr Gln Ile Gln Tyr Asn Tyr
        515                 520                 525

Gly Pro Thr Gly Tyr Ser Phe Lys Phe Ile Trp Arg Thr Val Ser Arg
    530                 535                 540

Gln Pro Phe Asp Ile Pro Cys Cys Phe Phe Ser Tyr Ile Thr Glu Glu
545                 550                 555                 560

<210> SEQ ID NO 29
<211> LENGTH: 31044
<212> TYPE: DNA
<213> ORGANISM: simian adenovirus SV-25
<220> FEATURE:
<221> NAME/KEY: CDS
<222> LOCATION: (12284)..(13801)
<223> OTHER INFORMATION: Penton
<220> FEATURE:
<221> NAME/KEY: CDS
<222> LOCATION: (16681)..(19446)
<223> OTHER INFORMATION: Hexon
<220> FEATURE:
<221> NAME/KEY: CDS
<222> LOCATION: (25380)..(26423)
<223> OTHER INFORMATION: Fiber #2
<220> FEATURE:
```

```
<221> NAME/KEY: CDS
<222> LOCATION: (26457)..(28136)
<223> OTHER INFORMATION: Fiber #1

<400> SEQUENCE: 29
catcatcaat aatatacctt attctggaaa cgtgccaata tgataatgag cggggaggag      60
cgaggcgggg ccggggtgac gtgcggtgac gcggggtggc gcgagggcgg ggcgaagggc     120
gcgggtgtgt gtgtgggagg cgcttagttt ttacgtatgc ggaaggaggt tttataccgg     180
aagatgggta atttggcgt atacttgtaa gttttgtgta atttggcgcg aaaactgggt      240
aatgaggaag ttgaggttaa tatgtacttt ttatgactgg gcggaatttc tgctgatcag     300
cagtgaactt gggcgctga cggggaggtt tcgctacgtg acagtaccac gagaaggctc      360
aaaggtccca tttattgtac tcttcagcgt tttcgctggg tatttaaacg ctgtcagatc     420
atcaagaggc cactcttgag tgctggcgag aagagttttc tcctccgtgc tgccacgatg     480
aggctggtcc ccgagatgta cggtgttttt agcgacgaga cggtgcgtaa ctcagatgac     540
ctgctgaatt cagacgcgct ggaaatttcc aattcgcctg tgctttcgcc gccgtcactt     600
cacgacctgt ttgtgttttg gctcaacgct tagcaacgtg ttatataggg tcaagaagga     660
gcaggagacg cagtttgcta ggctgttggc cgatactcct ggagttttg tggctctgga      720
tctaggccat cactctcttt tccaagagaa aattatcaaa aacttaactt ttacgtctcc     780
tggtcgcacg gttgcttccg ctgcctttat taccatattt ttggatcaat ggagcaacag     840
cgacagccac ctgtcgtggg agtacatgct ggattacatg tcgatggcgc tgtgagggc      900
catgctgcgg aggagggttt gcatttactt gcgggcgcag cctccgcggc tggaccgagt     960
ggaggaggag gacgagccgg gggagaccga gaacctgagg gccgggctgg accctccaac    1020
ggaggactag gtgctgagga tgatcccgaa gaggggacta gtggggctag gaagaagcaa    1080
aagactgagt ctgaacctcg aaactttttg aatgagttga ctgtgagttt gatgaatcgt    1140
cagcgtccgg agacaatttt ctggtctgaa ttggaggagg aattcaggag gggggaactg    1200
aacctgctat acaagtatgg gttttgaacag ttaaaaactc actggttgga gccgtgggag    1260
gattttgaaa ccgccttgga cacttttgct aaagtggctc tgcggccgga taaggtttac    1320
actatccgcc gcactgttaa cataaagaag agtgtttatg ttataggcca tggagctctg    1380
gtgcaggtgc aaaccgtcga ccgggtggcc tttagttgcg gtatgcaaaa tctgggcccc    1440
ggggtgatag gcttaaatgg tgtaacattt cacaatgtaa ggtttactgg tgaaagtttt    1500
aacggctctg tgtttgcaaa taacacacag ctgacgctcc acggcgttta cttttttaac    1560
tttaataaca catgtgtgga gtcgtggggc agggtgtctt tgagggggctg ctgttttcac   1620
ggctgctgga aggcggtggt gggaagactt aaaagtgtaa catctgtaaa aaatgcgtg    1680
tttgagcggt gtgtgttggc tttaactgtg gagggctgtg gacgcattag gaataatgcg    1740
gcgtctgaga atggatgttt tcttttgcta aaaggcacgg ctagtattaa gcataacatg    1800
atatgcggca gcggtctgta cccttcacag ctgttaactt gcgcggatgg aaactgtcag    1860
accttgcgca ccgtgcacat agcgtcccac cagcgccgcg cctggccaac attcgagcac    1920
aatatgctta tgcgttgtgc cgtccacttg ggccctaggc gaggcgtgtt tgtgccttac    1980
cagtgtaact ttagccatac caagatttta ctagaacctg ataccttctc tcgagtgtgt    2040
ttcaatgggg tgtttgacat gtcaatggaa ctgtttaaag tgataagata tgatgaatcc    2100
aagtctcgtt gtcgcccatg tgaatgcgga gctaatcatc tgaggttgta tcctgtaacc    2160
ctaaacgtta ccgaggagct gaggacggat caccacatgt tgtcctgcct gcgcaccgac    2220
```

```
tatgaatcca gcgacgagga gtgaggtgag gggcggagcc acaaagggta taaaggggcg    2280
tgaggggtgg gtgtgatgat tcaaaatgag cgggacgacg gacggcaacg cgtttgaggg    2340
tggagtgttc agcccttatc tgacatctcg tcttccttcc tgggcaggag tgcgtcagaa    2400
tgtagtgggc tccaccgtgg acggacgacc ggtcgcccct gcaaattccg ccaccctcac    2460
ctatgccacc gtgggatcat cgttggacac tgccgcggca gctgccgctt ctgctgccgc    2520
ttctactgct cgcggcatgg cggctgattt tggactgtat aaccaactgg ccactgcagc    2580
tgtggcgtct cggtctctgg ttcaagaaga tgccctgaat gtgatcctga ctcgcctgga    2640
gatcatgtca cgtcgcttgg acgaactggc tgcgcagata tcccaagcta accccgatac    2700
cacttcagaa tcctaaaata aagacaaaca aatatgttga aaagtaaaat ggctttattt    2760 gtttttttg gctcggtagg ctcgggtcca cctgtctcgg tcgttaagaa ctttgtgtat    2820
gttttccaaa acacggtaca gatgggcttg gatgttcaag tacatgggca tgaggccatc    2880
tttggggtga agataggacc attgaagagc gtcatgctcc ggggtggtgt tgtaaattac    2940
ccagtcgtag cagggtttct gggcgtggaa ctggaagatg tcctttagga gtaggctgat    3000
ggccaagggc aggcccttag tgtaggtgtt tacaaagcgg ttaagctggg agggatgcat    3060
gcggggggag atgatatgca tcttggcttg gatcttgagg ttagctatgt taccacccag    3120
gtctctgcgg gggttcatgt tatgaaggac caccagcacg gtgtagccgg tgcatttggg    3180
gaacttgtca tgcagtttgg aggggaaggc gtggaagaat ttagagaccc ccttgtggcc    3240
ccctaggttt tccatgcact catccataat gatggcaatg ggaccctgg cggccgcttt     3300 ggcaaacacg ttttgggggt tggaaacatc atagttttgc tctagagtga gctcatcata    3360
ggccatctta acaaagcggg gtaggagggt gcccgactgg gggatgatag ttccatctgg    3420
gcctggggcg tagttaccct cacagatctg catctcccag gccttaattt ccgaggggg     3480 tatcatgtcc acctgggggg caataaagaa cacggtttct ggcggggat tgatgagctg     3540 ggtggaaagc aagttacgca gcagttgaga tttgccacag ccggtggggc cgtagatgac    3600
cccgatgacg ggttgcagct ggtagttgag agaggaacag ctgccgtcgg ggcgcaggag    3660
gggggctacc tcattcatca tgcttctaac atgtttattt tcactcacta agttttgcaa    3720
gagcctctcc ccacccaggg ataagagttc ttccaggctg ttgaagtgtt tcagcggttt    3780
taggccgtcg gccatgggca tcttttcgag cgactgacga agcaagtaca gtcggtccca    3840
gagctcggtg acgtgctcta tggaatctcg atccagcaga cttcttggtt gcggggttg     3900 ggtcgacttt cgctgtaggg caccagccgg tgggcgtcca gggccgcgag ggttctgtcc    3960
ttccagggtc tcagcgtccg ggtgagggtg gtctcggtga cggtgaaggg atgagccccg    4020
ggctgggcgc ttgcgagggt gcgcttcagg ctcatcctgc tggtgctgaa gcggacgtcg    4080
tctccctgtg agtcggccag atagcaacga agcatgaggt cgtagctgag ggactcggcc    4140
gcgtgtccct tggcgcgcag cttttccctt gaaacgtgct gacatttggt gcagtgcaga    4200
cattggaggg cgtagagttt gggggccagg aagaccgact cgggcgagta ggcgtcggct    4260
ccgcactgag cgcagacggt ctcgcactcc actagccacg tgagctcggg tttagcggga    4320
tcaaaaacca agttgcctcc attttttttg atgcgtttct taccttgcgt ttccatgagt    4380
ttgtggcccg cttccgtgac aaaaaggctg tcggtgtctc cgtagacaga cttgaggggg    4440
cgatcttcca aggtgttcc gaggtcttcc gcgtacagga actgggacca ctccgagacg     4500
aaggctctgg tccaggctaa cacgaaggag gcaatctgcg aggggtatct gtcgttttca    4560
atgagggggt ccacctttc cagggtgtgc agacacaggt cgtcctcctc cgcgtccacg     4620
```

```
aaggtgattg gcttgtaagt gtaggtcacg tgatctgcac cccccaaagg ggtataaaag    4680
ggggcgtgcc caccctctcc gtcactttct tccgcatcgc tgtggaccag agccagctgt    4740
tcgggtgagt aggccctctc aaaagccggc atgatctcgg cgctcaagtt gtcagtttct    4800
acaaacgagg tggatttgat attcacgtgc cccgcggcga tgcttttgat ggtggagggg    4860
tccatctgat cagaaaacac gatcttttg ttgtcaagtt tggtggcgaa agacccgtag    4920
agggcgttgg aaagcaactt ggcgatggag cgcagggtct gattttctc ccgatcggcc    4980 ctctccttgg cggcgatgtt gagttgcacg tactcccggg ccgcgcaccg ccactcgggg    5040
aacacggcgg tgcgctcgtc gggcaggatg cgcacgcgcc agccgcgatt gtgcagggtg    5100
atgaggtcca cgctggtagc cacctccccg cggaggggct cgttggtcca acacaatcgc    5160 ccccctttc tggagcagaa cggaggcagg ggatctagca agttggcggg cgggggtcg    5220 gcgtcgatgg tgaagatacc gggtagcagg atcttattaa aataatcgat ttcggtgtcc    5280
gtgtcttgca acgcgtcttc ccacttcttc accgccaggg ccctttcgta gggattcagg    5340
ggcggtcccc agggcatggg gtgggtcagg gccgaggcgt acatgccgca gatgtcatac    5400
acgtacaggg gttccctcaa cacccgatg taagtggggt aacagcgccc cccgcggatg    5460
ctggctcgca cgtagtcgta catctcgcgc gagggagcca tgaggccgtc tcccaagtgg    5520
gtcttgtggg gttttcggc ccggtagagg atctgtctga agatggcgtg ggagttggaa    5580
gagatggtgg ggcgttggaa gacgttaaag ttggccccgg gtagtcccac ggagtcttgg    5640
atgaactggg cgtaggattc ccggagtttg tccaccaggg cggcggtcac cagcacgtcg    5700
agagcgcagt agtccaacgt ctcgcggacc aggttgtagg ccgtctcttg ttttttctcc    5760
cacagttcgc ggttgaggag gtattcctcg cggtctttcc agtactcttc ggcgggaaat    5820 ccttttcgt ccgctcggta agaacctaac atgtaaaatt cgttcaccgc tttgtatgga    5880
caacagcctt tttctaccgg cagggcgtac gcttgagcgg cctttctgag agaggtgtgg    5940
gtgagggcga aggtgtcccg caccatcact ttcaggtact gatgtttgaa gtccgtgtcg    6000
tcgcaggcgc cctgttccca cagcgtgaag tcggtgcgct tttctgcct gggattgggg    6060 agggcgaagg tgacatcgtt aaagagtatt ttcccgcgc ggggcatgaa gttgcgagag    6120
atcctgaagg gcccgggcac gtccgagcgg ttgttgatga cctgcgccgc caggacgatc    6180
tcgtcgaagc cgttgatgtt gtgacccacg atgtaaagtt cgatgaagcg cggctgtccc    6240
ttgagggccg gcgcttttt caactcctcg taggtgagac agtccggcga ggagagaccc    6300
agctcagccc gggcccagtc ggagagttga ggattagccg caaggaagga gctccataga    6360
tccaaggcca ggagagtttg caagcggtcg cggaactcgc ggaacttttt ccccacggcc    6420
attttctccg gtgtcactac gtaaaagtg ttggggcggt tgttccacac gtcccatcgg    6480
agctctaggg ccagctcgca ggcttggcga acgagggtct cctcgccaga gacgtgcatg    6540
accagcataa agggtaccaa ctgtttcccg aacgagccca tccatgtgta ggtttctacg    6600
tcgtaggtga caaagagccg ctgggtgcgc gcgtgggagc cgatcggaaa gaagctgatc    6660
tcctgccacc agctggagga atgggtgtta atgtggtgga agtagaagtc ccgccggcgc    6720
acagagcatt cgtgctgatg tttgtaaaag cgaccgcagt agtcgcagcg ctgcacgctc    6780
tgtatctcct gaacgagatg cgcttttcgc ccgcgcacca gaaaccggag ggggaagttg    6840
agacgggggg ctggtggggc gacatcccct tcgccttggc ggtgggagtc tgcgtctgcg    6900
tcctccttct ctgggtggac gacgtgggg acgacgacgc cccgggtgcc gcaagtccag    6960
atctccgcca cggagggggtg caggcgctgc aggaggggac gcagctgccc gctgtccagg    7020
```

```
gagtcgaggg aagtcgcgct gaggtcggcg ggaagcgttt gcaagttcac tttcagaaga    7080
ccggtaagag cgtgagccag gtgcagatgg tacttgattt ccaggggggt gttggatgaa    7140
gcgtccacgg cgtagaggag tccgtgtccg cgcggggcca ccaccgtgcc ccgaggaggt    7200
tttatctcac tcgtcgaggg cgagcgccgg ggggtagagg cggctctgcg ccgggggca    7260 gcggaggcag aggcacgttt tcgtgaggat tcggcagcgg ttgatgacga gcccggagac    7320
tgctggcgtg ggcgacgacg cggcggttga ggtcctggat gtgccgtctc tgcgtgaaga    7380
ccaccggccc ccgggtcctg aacctaaaga gagttccaca gaatcaatgt ctgcatcgtt    7440
aacggcggcc tgcctgagga tctcctgcac gtcgcccgag ttgtcctgat aggcgatctc    7500
ggccatgaac tgttccactt cttcctcgcg gaggtcaccg tggcccgctc gctccacggt    7560
ggcggccagg tcgttggaga tgcggcgcat gagttgagag aaggcgttga ggccgttctc    7620
gttccacacg cggctgtaca ccacgtttcc gaaggagtcg cgcgctcgca tgaccacctg    7680
ggccacgttg agttccacgt ggcgggcgaa gacggcgtag tttctgaggc gctggaagag    7740
gtagttgagc gtggtggcga tgtgctcgca gacgaagaag tacataatcc agcgccgcag    7800
ggtcatctcg ttgatgtctc cgatggcttc gagacgctcc atggcctcgt agaagtcgac    7860
ggcgaagttg aaaaattggg agttgcgggc ggccaccgtg agttcttctt gcaggaggcg    7920
gatgagatcg gcgaccgtgt cgcgcacctc ctgttcgaaa gcgccccgag gcgcctctgc    7980
ttcttcctcc ggctcctcct cttccagggg ctcgggttcc tccggcagct ctgcgacggg    8040
gacggggcgg cgacgtcgtc gtctgaccgg caggcggtcc acgaagcgct cgatcatttc    8100
gccgcgccgg cgacgcatgg tctcggtgac ggcgcgtccg ttttcgcgag gtcgcagttc    8160
gaagacgccg ccgcgcagag cgcccccgtg cagggagggt aagtggttag ggccgtcggg    8220
cagggacacg gcgctgacga tgcatttat caattgctgc gtaggcactc cgtgcaggga    8280
tctgagaacg tcgaggtcga cgggatccga gaacttctct aggaaagcgt ctatccaatc    8340
gcaatcgcaa ggtaagctga gaacggtggg tcgctggggg gcgttcgcgg gcagttggga    8400
ggtgatgctg ctgatgatgt aattaaagta ggcggtcttc aggcggcgga tggtggcgag    8460
gaggaccacg tctttgggcc cggcctgttg aatgcgcagg cgctcggcca tgccccaggc    8520
ctcgctctga cagcgacgca ggtctttgta gaagtcttgc atcagtctct ccaccggaac    8580
ctctgcttct cccctgtctg ccatgcgagt cgagccgaac cccgcaggg gctgcagcaa    8640 cgctaggtcg gccacgaccc tttcggccag cacggcctgt tgaatctgcg tgagggtggc    8700
ctggaagtcg tccaggtcca cgaagcgtg ataggccccc gtgttgatgg tgtaggtgca    8760
gttggccatg acggaccagt tgacgacttg catgccgggt tgggtgatct ccgtgtactt    8820
gaggcgcgag taggccctgg actcgaacac gtagtcgttg catgtgcgca ccagatactg    8880
gtagccgacc aggaagtgag gaggcggctc tcggtacagg ggccagccaa cggtggcggg    8940
ggcgccgggg gacaggtcgt ccagcatgag gcggtggtag tggtagatgt agcgggagag    9000
ccaggtgatg ccggccgagg tggttgcggc cctggtgaat tcgcggacgc ggttccagat    9060
gttgcgcagg gaccaaagc gctccatggt gggcacgctc tgccccgtga ggcgggcgca    9120
atcttgtacg ctctagatgg aaaaaagaca gggcggtcat cgactccttt ccgtagcttg    9180
gggggtaaag tcgcaagggt gcggcggcgg ggaaccccgg ttcgagaccg gccggatccg    9240
ccgctcccga tgcgcctggc cccgcatcca cgacgtccgc gccgagaccc agccgcgacg    9300
ctccgcccca atacgagggg gagtcttttg gtgttttttc gtagatgcat ccggtgctgc    9360
ggcagatgcg accccagacg cccactacca ccgccgtggc ggcagtaaac ctgagcggag    9420
```

```
gcggtgacag ggaggaggaa gagctggctt tagacctgga agagggagag gggctggccc   9480
ggctgggagc gccatcccca gagagacacc ctagggttca gctcgtgagg gacgccaggc   9540
aggcttttgt gccgaagcag aacctgttta ggaccgcag cggtcaggag gcggaggaga   9600
tgcgcgattg caggtttcgg gcgggcagag agctcaggc gggcttcgat cgggagcggc   9660
tcctgagggc ggaggatttc gagcccgacg agcgttctgg ggtgagcccg gcccgcgctc   9720
acgtatcggc ggccaacctg gtgagcgcgt acgagcagac ggtgaacgag gagcgcaact   9780
tccaaaagag ctttaacaat cacgtgagga ccctgatcgc gagggaggag gtgaccatcg   9840
ggctgatgca tctgtgggac ttcgtggagg cctacgtgca gaacccggct agcaaacccc   9900
tgacggccca gctgttcctg atcgtgcagc acagccgcga caacgagacg ttccgcgacg   9960
ccatgttgaa catcgcggag cccgagggtc gctggctctt ggatctgatt aacatcctgc  10020
agagcatcgt ggtgcaggag aggggcctga gtttagcgga caaggtggcg gccattaact  10080
attcgatgca gagcctgggg aagttctacg ctcgcaagat ctacaagagc ccttacgtgc  10140
ccatagacaa ggaggtgaag atagacagct tttacatgcg catggcgctg aaggtgctga  10200
cgctgagcga cgacctcggc gtgtaccgta acgacaagat ccacaaggcg gtgagcgcca  10260
gccgccggcg ggagctgagc gacagggagc tgatgcacag cctgcagagg gcgctggcgg  10320
gcgccgggga cgaggagcgc gaggcttact tcgacatggg agccgatctg cagtggcgtc  10380
ccagcgcgcg cgccttggag gcggcgggtt atcccgacga ggaggatcgg gacgatttgg  10440
aggaggcagg cgagtacgag gacgaagcct gaccgggcag gtgttgtttt agatgcagcg  10500
gccggcggac gggaccaccg cggatcccgc acttttggca tccatgcaga gtcaaccttc  10560
gggcgtgacc gcctccgatg actgggcggc ggccatggac cgcatcatgg cgctgaccac  10620
ccgcaaccgc gaggcttta ggcagcaacc ccaggccaac cgttttcgg ccatcttgga  10680 agcggtggtg ccgtcgcgca ccaacccgac gcacgagaaa gtcctgacta tcgtgaacgc  10740
cctggtagac agcaaggcca tccgccgtga cgaggcgggc ttgatttaca acgctctttt  10800
ggaacgcgtg gcgcgctaca acagcactaa cgtgcagacc aatctggacc gcctcaccac  10860
cgacgtgaag gaggcgctgg cgcagaagga gcggttctg agggacagta atctgggctc  10920
tctggtggca ctgaacgcct tcctgagctc acagccggcc aacgtgcccc gcgggcagga  10980
ggattacgtg agcttcatca gcgctctgag actgctggtg tccgaggtgc cccagagcga  11040
ggtgtaccag tctgggccgg attactttt ccagacgtcc cgacagggct tgcaaacggt  11100
gaacctgact caggccttta aaaacttgca aggcatgtgg ggggtcaagg ccccggtggg  11160
cgatcgcgcc actatctcca gtctgctgac ccccaacact cgcctgctgc tgctcttgat  11220
cgcaccgttt accaacagta gcactatcag ccgtgactcg tacctgggtc atctcatcac  11280
tctgtaccgc gaggccatcg gccaggctca gatcgacgag catacgtatc aggagattac  11340
taacgtgagc cgtgccctgg gtcaggaaga taccggcagc ctggaagcca cgttgaactt  11400
tttgctaacc aaccggaggc aaaaaatacc ctcccagttc acgttaagcg ccgaggagga  11460
gaggattctg cgatacgtgc agcagtccgt gagcctgtac ttgatgcgcg agggcgccac  11520
cgcttccacg gcttttagaca tgacggctcg gaacatggaa ccgtcctttt actccgccca  11580
ccggccgttc attaaccgtc tgatggacta cttccatcgc gcggccgcca tgaacgggga  11640
gtacttcacc aatgccatcc tgaatccgca ttggatgccc ccgtccggct tctacaccgg  11700 ggagttttgac ctgcccgaag ccgacgacgg ctttctgtgg gacgcacgtgt ccgatagcat  11760 tttcacgccg gctaatcgcc gattccagaa gaaggagggc ggagacgagc tccccctctc  11820
```

```
cagcgtggaa gcggcctcaa ggggagagag tcccttccca agtctgtctt ccgccagtag   11880
cggtcgggta acgcgtccac ggttgccggg ggagagcgac tacctgaacg accccttgct   11940
gcgaccggct agaaagaaaa attttcccaa taacggggtg gaaagcttgg tggataaaat   12000
gaatcgttgg aagacgtacg cccaggagca gcggagtgg gaggacagtc agccgcggcc   12060
gctggtaccg ccgcattggc gtcgccagag agaagacccg gacgactccg cagacgatag   12120
tagcgtgttg gacctgggag ggagcggagc caaccccttt gctcacttgc aacccaaggg   12180
gcgctcgagt cgcctgtatt aataaaaaag acgcggaaac ttaccagagc catggccaca   12240
gcgtgtgtgc tttcttcctc tctttcttcc tcggcgcggc aga atg aga aga gcg      12295
                                                Met Arg Arg Ala
                                                1 gtg aga gtc acg ccg gcg gcg tat gag ggc ccg ccc cct tct tac gaa      12343
Val Arg Val Thr Pro Ala Ala Tyr Glu Gly Pro Pro Pro Ser Tyr Glu
5                   10                  15                  20 agc gtg atg gga tca gcg aac gtg ccg gcc acg ctg gag gcg cct tac      12391
Ser Val Met Gly Ser Ala Asn Val Pro Ala Thr Leu Glu Ala Pro Tyr
            25                  30                  35 gtt cct ccc aga tac ctg gga cct acg gag ggc aga aac agc atc cgt      12439
Val Pro Pro Arg Tyr Leu Gly Pro Thr Glu Gly Arg Asn Ser Ile Arg
        40                  45                  50 tac tcc gag ctg gcg ccc ctg tac gat acc acc aag gtg tac ctg gtg      12487
Tyr Ser Glu Leu Ala Pro Leu Tyr Asp Thr Thr Lys Val Tyr Leu Val
    55                  60                  65 gac aac aag tcg gcg gac atc gcc tcc ctg aat tac caa aac gat cac      12535
Asp Asn Lys Ser Ala Asp Ile Ala Ser Leu Asn Tyr Gln Asn Asp His
70                  75                  80 agt aac ttt ctg act acc gtg gtg cag aac aat gac ttc acc ccg acg      12583
Ser Asn Phe Leu Thr Thr Val Val Gln Asn Asn Asp Phe Thr Pro Thr
85                  90                  95                  100 gag gcg ggc acg cag acc att aac ttt gac gag cgt tcc cgc tgg ggc      12631
Glu Ala Gly Thr Gln Thr Ile Asn Phe Asp Glu Arg Ser Arg Trp Gly
            105                 110                 115 ggt cag ctg aaa acc atc ctg cac acc aac atg ccc aac atc aac gag      12679
Gly Gln Leu Lys Thr Ile Leu His Thr Asn Met Pro Asn Ile Asn Glu
        120                 125                 130 ttc atg tcc acc aac aag ttc agg gct aag ctg atg gta gaa aaa agt      12727
Phe Met Ser Thr Asn Lys Phe Arg Ala Lys Leu Met Val Glu Lys Ser
    135                 140                 145 aat gcg gaa act cgg cag ccc cga tac gag tgg ttc gag ttt acc att      12775
Asn Ala Glu Thr Arg Gln Pro Arg Tyr Glu Trp Phe Glu Phe Thr Ile
150                 155                 160 cca gag ggc aac tat tcc gaa act atg act atc gat ctc atg aat aac      12823
Pro Glu Gly Asn Tyr Ser Glu Thr Met Thr Ile Asp Leu Met Asn Asn
165                 170                 175                 180 gcg atc gtg gac aat tac ctg caa gtg ggg aga cag aac ggg gtg ctg      12871
Ala Ile Val Asp Asn Tyr Leu Gln Val Gly Arg Gln Asn Gly Val Leu
            185                 190                 195 gaa agc gat atc ggc gtg aaa ttc gat acc aga aac ttc cga ctg ggg      12919
Glu Ser Asp Ile Gly Val Lys Phe Asp Thr Arg Asn Phe Arg Leu Gly
        200                 205                 210 tgg gat ccc gtg acc aag ctg gtg atg cca ggc gtg tac acc aac gag      12967
Trp Asp Pro Val Thr Lys Leu Val Met Pro Gly Val Tyr Thr Asn Glu
    215                 220                 225 gct ttt cac ccg gac atc gtg ctg ctg ccg ggg tgc ggt gtg gac ttc      13015
Ala Phe His Pro Asp Ile Val Leu Leu Pro Gly Cys Gly Val Asp Phe
230                 235                 240 act cag agc cgt ttg agt aac ctg tta gga att aga aag cgc cgc ccc      13063
Thr Gln Ser Arg Leu Ser Asn Leu Leu Gly Ile Arg Lys Arg Arg Pro
```

```
                245                 250                 255                 260
ttc caa gag ggc ttt caa atc atg tat gag gac ctg gag gga ggt aat      13111
Phe Gln Glu Gly Phe Gln Ile Met Tyr Glu Asp Leu Glu Gly Gly Asn
                    265                 270                 275 ata ccc gcc tta ctg gac gtg tcg aag tac gaa gct agc ata caa cgc      13159
Ile Pro Ala Leu Leu Asp Val Ser Lys Tyr Glu Ala Ser Ile Gln Arg
                280                 285                 290 gcc aaa gcg gag ggt aga gag att cgg gga gac acc ttt gcg gta gct      13207
Ala Lys Ala Glu Gly Arg Glu Ile Arg Gly Asp Thr Phe Ala Val Ala
            295                 300                 305 ccc cag gac ctg gaa ata gtg cct tta act aaa gac agc aaa gac aga      13255
Pro Gln Asp Leu Glu Ile Val Pro Leu Thr Lys Asp Ser Lys Asp Arg
        310                 315                 320 agc tac aat att ata aac aac acg acg gac acc ctg tat cgg agc tgg      13303
Ser Tyr Asn Ile Ile Asn Asn Thr Thr Asp Thr Leu Tyr Arg Ser Trp
325                 330                 335                 340 ttt ctg gct tac aac tac gga gac ccc gag aaa gga gtg aga tca tgg      13351
Phe Leu Ala Tyr Asn Tyr Gly Asp Pro Glu Lys Gly Val Arg Ser Trp
                    345                 350                 355 acc ata ctc acc acc acg gac gtg acc tgt ggc tcg cag caa gtg tac      13399
Thr Ile Leu Thr Thr Thr Asp Val Thr Cys Gly Ser Gln Gln Val Tyr
                360                 365                 370 tgg tcc ctg ccg gat atg atg caa gac ccg gtc acc ttc cgc ccc tcc      13447
Trp Ser Leu Pro Asp Met Met Gln Asp Pro Val Thr Phe Arg Pro Ser
            375                 380                 385 acc caa gtc agc aac ttc ccg gtg gtg ggc acc gag ctg ctg ccc gtc      13495
Thr Gln Val Ser Asn Phe Pro Val Val Gly Thr Glu Leu Leu Pro Val
        390                 395                 400 cat gcc aag agc ttc tac aac gag cag gcc gtc tac tcg caa ctt att      13543
His Ala Lys Ser Phe Tyr Asn Glu Gln Ala Val Tyr Ser Gln Leu Ile
405                 410                 415                 420 cgc cag tcc acc gcg ctt acc cac gtg ttc aat cgc ttt ccc gag aac      13591
Arg Gln Ser Thr Ala Leu Thr His Val Phe Asn Arg Phe Pro Glu Asn
                    425                 430                 435 cag att ctg gtg cgc cct ccc gct cct acc att acc acc gtc agt gaa      13639
Gln Ile Leu Val Arg Pro Pro Ala Pro Thr Ile Thr Thr Val Ser Glu
                440                 445                 450 aac gtt ccc gcc ctc aca gat cac gga acc ctg ccg ctg cgc agc agt      13687
Asn Val Pro Ala Leu Thr Asp His Gly Thr Leu Pro Leu Arg Ser Ser
            455                 460                 465 atc agt gga gtt cag cgc gtg acc atc acc gac gcc aga cgt cga acc      13735
Ile Ser Gly Val Gln Arg Val Thr Ile Thr Asp Ala Arg Arg Arg Thr
        470                 475                 480 tgc ccc tac gtt tac aaa gcg ctt ggc gtg gtg gct cct aaa gtt ctt      13783
Cys Pro Tyr Val Tyr Lys Ala Leu Gly Val Val Ala Pro Lys Val Leu
485                 490                 495                 500 tct agt cgc acc ttc taa aaacatgtcc atcctcatct ctcccgataa             13831
Ser Ser Arg Thr Phe
                505 caacaccggc tggggactgg gctccggcaa gatgtacggc ggagccaaaa ggcgctccag    13891 tcagcaccca gttcgagttc ggggccactt ccgcgctcct tggggagctt acaagcgagg    13951 actctcgggt cgaacggctg tagacgatac catagatgcc gtgattgccg acgcccgccg    14011 gtacaacccc ggaccggtcg ctagcgccgc ctccaccgtg gattccgtga tcgacagcgt    14071 ggtagccggc gctcgggcct atgctcgccg caagaggcgg ctgcatcgga gacgtcgccc    14131 caccgccgcc atgctggcag ccagggccgt gctgaggcgg gcccggaggg caggcagaag    14191 ggctatgcgc cgcgctgccg ccaacgccgc cgccgggagg gcccgccgac aggctgcccg    14251
```

```
ccaggctgcc gctgccatcg ctagcatggc cagacccagg agagggaacg tgtactgggt    14311
gcgtgattct gtgacgggag tccgagtgcc ggtgcgcagc cgacctcccc gaagttagaa    14371
gatccaagct gcgaagacgg cggtactgag tctccctgtt gttatcagcc caacatgagc    14431
aagcgcaagt ttaaagaaga actgctgcag acgctggtgc ctgagatcta tggccctccg    14491
gacgtgaagc cagacattaa gccccgcgat atcaagcgtg ttaaaaagcg ggaaaagaaa    14551
gaggaactcg cggtggtaga cgatggcgga gtggaattta ttaggagttt cgccccgcga    14611
cgcagggttc aatggaaagg gcggcgggta caacgcgttt tgaggccggg caccgcggta    14671
gtttttaccc cgggagagcg gtcggccgtt aggggtttca aaaggcagta cgacgaggtg    14731
tacggcgacg aggacatatt ggaacaggcg gctcaacaga tcggagaatt tgcctacgga    14791
aagcgttcgc gtcgcgaaga cctggccatc gccttagaca gcggcaaccc cacgcccagc    14851
ctcaaacccg tgacgctgca gcaggtgctt cccgtgagcg ccagcacgga cagcaagagg    14911
gggattaaga gagaaatgga agatctgcat cccaccatcc aactcatggt ccctaaacgg    14971
cagaggctgg aagaggtcct ggagaagatg aaagtggacc ccagcataga gccggatgta    15031
aaagtcagac ctattaagga agtggccccc ggtcttgggg tgcaaacggt ggacattcaa    15091
atccccgtca ccaccgcttc aaccgccgtg gaagctatgg aaacgcaaac ggagacccct    15151
gccgcgatcg gtaccaggga agtggcgttg caaacgagc cttggtacga atacgcagcc     15211
cctcggcgtc agaggcgttc cgctcgttac ggccccgcca acgccatcat gccagaatat    15271
gcgctgcatc cgtctattct gcccactccc ggataccggg gtgtgacgta tcgcccgtct    15331
ggaacccgcc gccgaacccg tcgccgccgc cgctcccgtc gcgctctggc ccccgtgtcg    15391
gtgcggcgtg tgaccccgcc gggaaagaca gtcgtcattc ccaacccgcg ttaccaccct    15451
agcatccttt aataactctg ccgttttgca gatggctctg acttgccgcg tgcgccttcc    15511
cgttccgcac tatcgaggaa gatctcgtcg taggagaggc atgacgggca gtggtcgccg    15571
gcgggctttg cgcaggcgca tgaaaggcgg aattttaccc gccctgatac ccataattgc    15631
cgccgccatc ggtgccatac ccggcgttgc ttcagtggcg ttgcaagcag ctcgtaataa    15691
ataaacaaag gcttttgcac ttatgacctg gtcctgacta ttttatgcag aaagagcatg    15751
gaagacatca attttacgtc gctggctccg cggcacggct cgcggccgct catgggcacc    15811
tggaacgaca tcggcaccag tcagctcaac ggggcgctt tcaattgggg gagcctttgg     15871
agcggcatta aaactttggg ctccacgatt aaatcctacg gcagcaaagc ctggaacagt    15931
agtgctggtc agatgctccg agataaactg aaggacacca acttccaaga aaaagtggtc    15991
aatggggtgg tgaccggcat ccacggcgcg gtagatctcg ccaaccaagc ggtgcagaaa    16051
gagattgaca ggcgtttgga aagctcgcgg gtgccgccgc agagagggga tgaggtggag    16111
gtcgaggaag tagaagtaga ggaaaagctg ccccgctgg agaaagttcc cggtgcgcct     16171
ccgagaccgc agaagcggcc caggccagaa ctagaagaga ctctggtgac ggagagcaag    16231
gagcctccct cgtacgagca agccttgaaa gagggcgcct ctccacccte ctacccgatg    16291
actaagccga tcgcacccat ggctcgaccg gtgtacggca aggattacaa gcccgtcacg    16351
ctagagctgc ccccaccgcc cccacgcgc cgaccgtcc cccctgcc gactccgtcg         16411
gcggccgcgg cgggacccgt gtccgcacca tccgctgtgc ctctgccagc cgcccgtcca    16471
gtggccgtgg ccactgccag aaaccccaga ggccagagag gagccaactg gcaaagcacg    16531
ctgaacagca tcgtgggcct gggagtgaaa agcctgaaac gccgccgttg ctattattaa    16591
aaaagtgtag ctaaaaagtc tcccgttgta tacgcctcct atgttaccgc cagagacgag    16651
```

```
tgactgtcgc cgcgagcgcc gctttcaag atg gcc acc cca tcg atg atg ccg        16704
                                Met Ala Thr Pro Ser Met Met Pro
                                                510 cag tgg tct tac atg cac atc gcc ggc cag gac gcc tcg gag tac ctg        16752
Gln Trp Ser Tyr Met His Ile Ala Gly Gln Asp Ala Ser Glu Tyr Leu
    515                 520                 525 agt ccc ggc ctc gtg cag ttt gcc cgc gcc acc gac acc tac ttc agc        16800
Ser Pro Gly Leu Val Gln Phe Ala Arg Ala Thr Asp Thr Tyr Phe Ser
530                 535                 540                 545 ttg gga aac aag ttt aga aac ccc acc gtg gcc ccc acc cac gat gtg        16848
Leu Gly Asn Lys Phe Arg Asn Pro Thr Val Ala Pro Thr His Asp Val
                550                 555                 560 acc acg gac cgc tcg cag agg ctg acc ctg cgc ttt gtg ccc gta gac        16896
Thr Thr Asp Arg Ser Gln Arg Leu Thr Leu Arg Phe Val Pro Val Asp
            565                 570                 575 cgg gag gac acc gcg tac tct tac aaa gtg cgc tac acg ttg gcc gta        16944
Arg Glu Asp Thr Ala Tyr Ser Tyr Lys Val Arg Tyr Thr Leu Ala Val
        580                 585                 590 ggg gac aac cga gtg ctg gac atg gcc agc acc tac ttt gac atc cgg        16992
Gly Asp Asn Arg Val Leu Asp Met Ala Ser Thr Tyr Phe Asp Ile Arg
    595                 600                 605 ggg gtg ctg gat cgg ggt ccc agc ttc aag ccc tat tcc ggc acc gct        17040
Gly Val Leu Asp Arg Gly Pro Ser Phe Lys Pro Tyr Ser Gly Thr Ala
610                 615                 620                 625 tac aac tcc ctg gcc ccc aag gga gct ccc aac ccc tcg gaa tgg acg        17088
Tyr Asn Ser Leu Ala Pro Lys Gly Ala Pro Asn Pro Ser Glu Trp Thr
                630                 635                 640 gac act tcc gac aac aaa ctt aaa gca tat gct cag gct ccc tac cag        17136
Asp Thr Ser Asp Asn Lys Leu Lys Ala Tyr Ala Gln Ala Pro Tyr Gln
            645                 650                 655 agt caa gga ctt aca aag gat ggt att cag gtt ggg cta gtt gtg aca        17184
Ser Gln Gly Leu Thr Lys Asp Gly Ile Gln Val Gly Leu Val Val Thr
        660                 665                 670 gag tca gga caa aca ccc caa tat gca aac aaa gtg tac caa ccc gag        17232
Glu Ser Gly Gln Thr Pro Gln Tyr Ala Asn Lys Val Tyr Gln Pro Glu
    675                 680                 685 cca caa att ggg gaa aac caa tgg aat tta gaa caa gaa gat aaa gcg        17280
Pro Gln Ile Gly Glu Asn Gln Trp Asn Leu Glu Gln Glu Asp Lys Ala
690                 695                 700                 705 gcg gga aga gtc cta aag aaa gat acc cct atg ttt ccc tgc tat ggg        17328
Ala Gly Arg Val Leu Lys Lys Asp Thr Pro Met Phe Pro Cys Tyr Gly
                710                 715                 720 tca tat gcc agg ccc aca aac gaa caa gga ggg cag gca aaa aac caa        17376
Ser Tyr Ala Arg Pro Thr Asn Glu Gln Gly Gly Gln Ala Lys Asn Gln
            725                 730                 735 gaa gta gat tta cag ttt ttt gcc act ccg ggc gac acc cag aac acg        17424
Glu Val Asp Leu Gln Phe Phe Ala Thr Pro Gly Asp Thr Gln Asn Thr
        740                 745                 750 gct aaa gtg gta ctt tat gct gaa aat gtc aac ctg gaa act cca gat        17472
Ala Lys Val Val Leu Tyr Ala Glu Asn Val Asn Leu Glu Thr Pro Asp
    755                 760                 765 act cac tta gtg ttt aaa ccc gat gac gac agc acc agt tca aaa ctt        17520
Thr His Leu Val Phe Lys Pro Asp Asp Asp Ser Thr Ser Ser Lys Leu
770                 775                 780                 785 ctt ctt ggg cag cag gct gca cct aac aga ccc aac tac ata ggt ttt        17568
Leu Leu Gly Gln Gln Ala Ala Pro Asn Arg Pro Asn Tyr Ile Gly Phe
                790                 795                 800 aga gat aat ttt att ggt tta atg tac tac aat agc act gga aac atg        17616
Arg Asp Asn Phe Ile Gly Leu Met Tyr Tyr Asn Ser Thr Gly Asn Met
            805                 810                 815
```

| | | |
|---|---|---|
| ggc gtg ctg gcc gga cag gct tct caa ttg aat gcc gta gtc gac ttg<br>Gly Val Leu Ala Gly Gln Ala Ser Gln Leu Asn Ala Val Val Asp Leu<br>820               825               830 | 17664 | |
| cag gac aga aac acc gag ttg tcc tac cag ctg atg ctg gac gca ctg<br>Gln Asp Arg Asn Thr Glu Leu Ser Tyr Gln Leu Met Leu Asp Ala Leu<br>835               840               845 | 17712 | |
| ggg gat cgc agc cga tat ttt tca atg tgg aat cag gca gta gac agc<br>Gly Asp Arg Ser Arg Tyr Phe Ser Met Trp Asn Gln Ala Val Asp Ser<br>850               855               860               865 | 17760 | |
| tat gac cca gac gtt aga att ata gaa aac cac gga gtg gaa gac gaa<br>Tyr Asp Pro Asp Val Arg Ile Ile Glu Asn His Gly Val Glu Asp Glu<br>870               875               880 | 17808 | |
| ctg cca aac tat tgt ttt cct ctg gga gga atg gtg gtg act gac aat<br>Leu Pro Asn Tyr Cys Phe Pro Leu Gly Gly Met Val Val Thr Asp Asn<br>885               890               895 | 17856 | |
| tac aac tct gtg acg cct caa aat gga ggc agt gga aat aca tgg cag<br>Tyr Asn Ser Val Thr Pro Gln Asn Gly Gly Ser Gly Asn Thr Trp Gln<br>900             905               910 | 17904 | |
| gca gac aat act aca ttt agt caa aga gga gcg cag att ggc tcc gga<br>Ala Asp Asn Thr Thr Phe Ser Gln Arg Gly Ala Gln Ile Gly Ser Gly<br>915             920               925 | 17952 | |
| aac atg ttt gcc ctg gaa att aac cta cag gcc aac ctc tgg cgc ggc<br>Asn Met Phe Ala Leu Glu Ile Asn Leu Gln Ala Asn Leu Trp Arg Gly<br>930               935               940               945 | 18000 | |
| ttc ttg tat tcc aat att ggg ttg tat ctt cca gac tct ctg aaa atc<br>Phe Leu Tyr Ser Asn Ile Gly Leu Tyr Leu Pro Asp Ser Leu Lys Ile<br>950               955               960 | 18048 | |
| acc ccc gac aac atc acg ctg cca gaa aac aaa aac act tat cag tac<br>Thr Pro Asp Asn Ile Thr Leu Pro Glu Asn Lys Asn Thr Tyr Gln Tyr<br>965             970               975 | 18096 | |
| atg aac ggt cgc gta acg cca ccc ggg ctc ata gac acc tat gta aac<br>Met Asn Gly Arg Val Thr Pro Pro Gly Leu Ile Asp Thr Tyr Val Asn<br>980             985               990 | 18144 | |
| gtg ggc gcg cgc tgg tcc ccc gat gtc atg gac agc att aac ccc ttc<br>Val Gly Ala Arg Trp Ser Pro Asp Val Met Asp Ser Ile Asn Pro Phe<br>995            1000              1005 | 18192 | |
| aac cac cac cgt aac gcg ggc ttg cgc tac cgc tcc atg ctc ttg<br>Asn His His Arg Asn Ala Gly Leu Arg Tyr Arg Ser Met Leu Leu<br>1010             1015             1020 | 18237 | |
| ggc aac ggc cgt tat gtg cct ttt cac att cag gtg ccc caa aaa<br>Gly Asn Gly Arg Tyr Val Pro Phe His Ile Gln Val Pro Gln Lys<br>1025             1030             1035 | 18282 | |
| ttc ttt gcc att aaa aac ctg ctg ctt ctc ccc ggt tcc tat acc<br>Phe Phe Ala Ile Lys Asn Leu Leu Leu Leu Pro Gly Ser Tyr Thr<br>1040             1045             1050 | 18327 | |
| tat gag tgg aac ttc cgc aag gat gtc aac atg atc ctg cag agc<br>Tyr Glu Trp Asn Phe Arg Lys Asp Val Asn Met Ile Leu Gln Ser<br>1055             1060             1065 | 18372 | |
| tcg ctg ggt aat gac ctg cga gtg gac ggg gcc agc ata cgc ttt<br>Ser Leu Gly Asn Asp Leu Arg Val Asp Gly Ala Ser Ile Arg Phe<br>1070             1075             1080 | 18417 | |
| gac agc att aac ctg tat gcc aac ttt ttt ccc atg gcc cac aac<br>Asp Ser Ile Asn Leu Tyr Ala Asn Phe Phe Pro Met Ala His Asn<br>1085             1090             1095 | 18462 | |
| acg gcc tct acc ctg gaa gcc atg ctg cgc aac gac acc aat gac<br>Thr Ala Ser Thr Leu Glu Ala Met Leu Arg Asn Asp Thr Asn Asp<br>1100             1105             1110 | 18507 | |
| cag tcc ttc aac gac tac ctg tgc gcg gct aac atg ctg tac ccc<br>Gln Ser Phe Asn Asp Tyr Leu Cys Ala Ala Asn Met Leu Tyr Pro<br>1115             1120             1125 | 18552 | |

```
atc ccc gcc aac gcc acc agc gtg ccc att tct att cct tct cgg    18597
Ile Pro Ala Asn Ala Thr Ser Val Pro Ile Ser Ile Pro Ser Arg
1130                1135                1140 aac tgg gct gcc ttc agg ggc tgg agt ttt act cgc ctc aaa acc    18642
Asn Trp Ala Ala Phe Arg Gly Trp Ser Phe Thr Arg Leu Lys Thr
1145                1150                1155 aag gag act ccc tcg ctg ggc tcc ggt ttt gac ccc tac ttt gtt    18687
Lys Glu Thr Pro Ser Leu Gly Ser Gly Phe Asp Pro Tyr Phe Val
1160                1165                1170 tac tcc ggc tcc att ccc tac cta gat ggc acc ttt tac ctc aac    18732
Tyr Ser Gly Ser Ile Pro Tyr Leu Asp Gly Thr Phe Tyr Leu Asn
1175                1180                1185 cac act ttc aaa aag gtg tct att atg ttt gac tcc tcg gtt agc    18777
His Thr Phe Lys Lys Val Ser Ile Met Phe Asp Ser Ser Val Ser
1190                1195                1200 tgg ccc ggc aac gac cgc ctg cta acg ccc aac gag ttc gaa att    18822
Trp Pro Gly Asn Asp Arg Leu Leu Thr Pro Asn Glu Phe Glu Ile
1205                1210                1215 aag cgt tcc gtg gac ggt gaa ggg tac aac gtg gcc cag agc aac    18867
Lys Arg Ser Val Asp Gly Glu Gly Tyr Asn Val Ala Gln Ser Asn
1220                1225                1230 atg acc aag gac tgg ttt cta att caa atg ctc agt cac tat aat    18912
Met Thr Lys Asp Trp Phe Leu Ile Gln Met Leu Ser His Tyr Asn
1235                1240                1245 ata ggt tac cag ggc ttc tat gtg ccc gag aac tac aag gac cgc    18957
Ile Gly Tyr Gln Gly Phe Tyr Val Pro Glu Asn Tyr Lys Asp Arg
1250                1255                1260 atg tac tcc ttc ttc cgc aac ttc caa cca atg agc cgg cag gtg    19002
Met Tyr Ser Phe Phe Arg Asn Phe Gln Pro Met Ser Arg Gln Val
1265                1270                1275 gta gat acc gtg act tat aca gac tac aaa gat gtc aag ctc ccc    19047
Val Asp Thr Val Thr Tyr Thr Asp Tyr Lys Asp Val Lys Leu Pro
1280                1285                1290 tac caa cac aac aac tca ggg ttc gtg ggc tac atg gga ccc acc    19092
Tyr Gln His Asn Asn Ser Gly Phe Val Gly Tyr Met Gly Pro Thr
1295                1300                1305 atg cga gag gga cag gcc tac ccg gcc aac tat ccc tac ccc ctg    19137
Met Arg Glu Gly Gln Ala Tyr Pro Ala Asn Tyr Pro Tyr Pro Leu
1310                1315                1320 atc gga gag act gcc gta ccc agc ctc acg cag aaa aag ttc ctc    19182
Ile Gly Glu Thr Ala Val Pro Ser Leu Thr Gln Lys Lys Phe Leu
1325                1330                1335 tgc gac cgg gtg atg tgg agg ata ccc ttc tct agc aac ttt atg    19227
Cys Asp Arg Val Met Trp Arg Ile Pro Phe Ser Ser Asn Phe Met
1340                1345                1350 tcg atg ggc tcc ctc acc gac ctg ggg cag aac atg ctg tac gcc    19272
Ser Met Gly Ser Leu Thr Asp Leu Gly Gln Asn Met Leu Tyr Ala
1355                1360                1365 aac tcc gct cac gcc ttg gac atg act ttt gag gtg gat ccc atg    19317
Asn Ser Ala His Ala Leu Asp Met Thr Phe Glu Val Asp Pro Met
1370                1375                1380 gat gag ccc acg ctt ctc tat gtt ctg ttt gaa gtc ttc gac gtg    19362
Asp Glu Pro Thr Leu Leu Tyr Val Leu Phe Glu Val Phe Asp Val
1385                1390                1395 gtg cgc atc cac cag ccg cac cgc ggc gtc atc gag gcc gtc tac    19407
Val Arg Ile His Gln Pro His Arg Gly Val Ile Glu Ala Val Tyr
1400                1405                1410 ctg cgc aca cct ttc tct gcc ggt aac gcc acc acc taa agaagctgat 19456
Leu Arg Thr Pro Phe Ser Ala Gly Asn Ala Thr Thr
1415                1420                1425
```

-continued

```
gggttccagc gaacaggagt tgcaggccat tgttcgcgac ctgggctgcg ggccctgctt   19516
tttgggcacc ttcgacaagc gttttcccgg attcatgtcc ccccacaagc cggcctgcgc   19576
catcgttaac acggccggac gggagacagg ggggtgcac tggctcgcct tcgcctggaa    19636
cccgcgcaac cgcacctgct acctgttcga cccttttggt ttctccgacg aaaggctgaa   19696
gcagatctac caattcgagt acgaggggct cctcaagcgc agcgctctgg cctccacgcc   19756
cgaccactgc gtcaccctgg aaaagtccac ccagacggtc caggggcccc tctcggccgc   19816
ctgcgggctt ttctgttgca tgttttgca cgccttcgtg cactggcctc acaccccat     19876 ggagcgcaac cccaccatgg atctgctcac cggagtgccc aacagcatgc ttcacagtcc   19936
ccaggtcgcc cccaccctgc gtcgcaatca ggaccacctg tatcgctttc tggggaaaca   19996
ctctgcctat ttccgccgcc accggcagcg catcgaacag gccacggcct tcgaaagcat   20056
gagccaaaga gtgtaatcaa taaaaaccgt ttttatttga catgatacgc gcttctggcg   20116
tttttattaa aaatcgaagg gttcgaggga ggggtcctcg tgcccgctgg ggagggacac   20176
gttgcggtac tggaatcggg cgctccaacg aaactggggg atcaccagcc gcggcagggc   20236
cacgtcttcc atgttctgct tccaaaactg tcgcaccagc tgcagggctc ccatcacgtc   20296
gggcgctgag atcttgaagt cgcagttagg gccggagccc ccgcggctgt tgcggaacac   20356
ggggttggca cactggaaca ccaacacgct ggggttgtgg atactagcca gggccgtcgg   20416
gtcggtcacc tccgatgcat ccagatcctc ggcattgctc agggcgaacg gggtcagctt   20476
gcacatctgc cgcccgatct ggggtaccag gtcgcgcttg ttgaggcagt cgcagcgcag   20536
agggatgagg atgcgacgct gcccgcgttg catgatgggg taactcgccg ccaggaactc   20596
ctctatctga cggaaggcca tctgggcctt gacgccctcg gtgaaaaata gcccacagga   20656
cttgctggaa aacacgttat tgccacagtt gatgtcttcc gcgcagcagc gcgcatcttc   20716
gttcttcagc tgaaccacgt tgcgacccca gcggttctga accaccttgg ctttcgtggg   20776
atgctccttc agcgcccgct gtccgttctc gctggtcaca tccatttcca ccacgtgctc   20836
cttgcagacc atctccactc cgtggaaaca gaacagaatg ccctcctgtt gggtattgcg   20896
atgctcccac acggcgcacc cggtggactc ccagctcttg tgtttcaccc ccgcgtaggc   20956
ttccatgtaa gccattagaa atctgcccat cagctcagtg aaggtcttct ggttggtgaa   21016
ggttagcggc aggccgcggt gttcctcgtt caaccaagtt tgacagatct tgcggtacac   21076
ggctccctgg tcgggcagaa acttaaaagt cgttctgctc tcgttgtcca cgtggaactt   21136
ctccatcaac atcgtcatga cttccatgcc cttctcccag gcagtcacca gcggcgcgct   21196
ctcggggttc ttcaccaaca cggcggtgga ggggccctcg ccggccccga cgtccttcat   21256
ggacattttt tgaaactcca cggtgccgtc cgcgcggcgt actctgcgca tcggagggta   21316
gctgaagccc acctccatga cggtgctttc gccctcgctg tcggagacga tctccgggga   21376
gggcggcgga acggggcag acttgcgagc cttcttcttg ggaggagcg gaggcacctc    21436 ctgctcgcgc tcgggactca tctcccgcaa gtaggggtg atggagcttc ctggttggtt    21496
ctgacggttg gccattgtat cctaggcaga aagacatgga gcttatgcgc gaggaaactt   21556
taaccgcccc gtcccccgtc agcgacgaag aggtcatcgt cgaacaggac ccgggctacg   21616
ttacgccgcc cgaggatctg gaggggcct tagacgaccg gcgcgacgct agtgagcggc     21676
aggaaaatga gaaagaggag gaggagggct gctacctcct ggaaggcgac gttttgctaa   21736
agcatttcgc caggcagagc accatactca aggaggcctt gcaagaccgc tccgaggtgc   21796
ccttggacgt cgccgcgctc tcccaggcct acgaggcgaa ccttttctcg ccccgagtgc   21856
```

```
ctccgaagag acagcccaac ggcacctgcg agcccaaccc gcgactcaac ttctaccccg   21916
tgttcgccgt gcccgaggcg ctggccacct accacatctt tttcaaaaac cagcgcattc   21976 cccttttcctg ccgggccaac cgcaccgcgg ccgataggaa gctaacactc agaaacggag   22036
tcagcatacc tgtatatcacg tcactggagg aagtgcctaa gatcttcgag ggtctgggtc   22096
gagatgagaa gcgggcggcg aacgctctgc agaaagaaca gaaagagagt cagaacgtgc   22156
tggtggagct ggaggggac aacgcgcgtc tgaccgtcct caaacgttgc atagaagttt   22216
cccacttcgc ctaccgggcc ctcaacctgc cgcccaaagt tatgaaatcg gtcatggacc   22276
agctactcat caagagagct gagcccctga atcccgacca ccctgaggcg gaaaactcag   22336
aggacggaaa gcccgtcgtc agcgacgagg agctcgagcg gtggctggaa accagggacc   22396
cccagcagtt gcaagagagg cgcaagatga tgatggcggc cgtgctggtc acggtggagc   22456
tagaatgcct gcaacggttt ttcagcgacg tggagacgct acgcaaaatc ggggagtccc   22516
tgcactacac cttccgccag ggctacgttc gccaggcctg caaaatctcc aacgtagagc   22576
tcagcaacct ggtttcctac atgggcatcc tccacgagaa ccggctgggg cagagcgtgc   22636
tgcactgcac cttgcaaggc gaggcgcgaa gggactacgt ccgagactgc gtctacctct   22696
tcctcaccct cacctggcag accgccatgg gcgtgtggca gcagtgcttg aagagagaa   22756 acctcaaaga gctggacaaa ctcctctgcc gccagcggcg ggccctctgg accggcttca   22816
gcgagcgcac ggtcgcctgc gccctggcag acatcatttt cccagaacgc ctgatgaaaa   22876
ccttgcagaa cggcctgccg gatttcatca gtcagagcat cttgcaaaac ttccgctcct   22936
tcgtcctgga gcgctccggg atcttgcccg ccatgagctg cgcgctgcct tctgactttg   22996
tccccctttc ctaccgcgag tgccctcccc cactgtggag ccactgctac ctcttccaac   23056
tggccaactt tctggcctac cactccgacc tcatggaaga cgtgagcgga gaggggctgc   23116
tcgagtgcca ctgccgctgc aacctctgca ccccccacag atcgctggcc tgcaacaccg   23176
agctgctcag cgaaacccag gtcataggta ccttcgagat ccaggggccc cagcagcaag   23236
agggtgcttc cggcttgaag ctcactccgg cgctgtggac ctcggcttac ttacgcaaat   23296
ttgtagccga ggactaccac gcccacaaaa ttcagtttta cgaagaccaa tctcgaccac   23356
cgaaagcccc cctcacggcc tgcgtcatca cccagagcaa aatcctggcc caattgcaat   23416
ccatcaacca agcgcgccga gatttcctttt tgaaaaaggg tcgggggggtg tacctggacc   23476 cccagaccgg cgaggaactc aacccgtcca cactttccgt cgaagcagcc ccccgagac   23536 atgccaccca agggaaccgc caagcagctg atcgctcggc agagagcgaa gaagcaagag   23596
ctgctccagc agcaggtgga ggacgaggaa gagctgtggg acagccaggc agaggaggtg   23656
tcagaggacg aggaggagat ggaaagctgg gacagcctag acgaggagga cgagctttca   23716
gaggaagagg cgaccgaaga aaaaccacct gcatccagcg cgccttctct gagccgacag   23776
ccgaagcccc ggcccccgac gccccccgcc ggctcactca agccagccg taggtgggac   23836 gccaccggat ctccagcggc agcggcaacg gcagcgggta aggccaaacg cgagcggcgg   23896
gggtattgct cctggcggac ccacaaaagc agtatcgtga actgcttgca acactgcggg   23956
ggaaacatct ccttttgcccg acgctacctc ctcttccatc acggtgtggc cttccctcgc   24016
aacgttctct attattaccg tcatctctac agccctacg aaacgctcgg agaaaaagc   24076 taaggcctcc tctgccgcga ggaaaaactc cgccgccgct gccgccaagg atccgccggc   24136
caccgaggag ctgagaaagc gcatctttcc cactctgtat gctatctttc agcaaagcc   24196 cgggcagcac cctcagcgcg aactgaaaat aaaaaaccgc tccttccgct cactcacccg   24256
```

```
                                                      -continued cagctgtctg taccacaaga gagaagacca gctgcagcgc accctggacg acgccgaagc    24316
actgttcagc aaatactgct cagcgtctct taaagactaa aagacccgcg cttttccccc    24376
ctcgggcgcc aaaacccacg tcatcgccag catgagcaag gagattccca cccttacat    24436 gtggagctat cagccccaga tgggcctggc cgcgggggcc gcccaggact actccagcaa    24496
aatgaactgg ctcagcgccg ccccccacat gatctcacga gttaacggca tccgagccca    24556
ccgaaaccag atcctcttag aacaggcggc aataccgcc acaccccggc gccaactcaa     24616
cccgcccagt tggcccgccg cccaggtgta tcaggaaact ccccgcccga ccacagtcct    24676
cctgccacgc gacgcggagg ccgaagtcct catgactaac tctggggtac aattagcggg    24736
cgggtccagg tacgccaggt acagaggtcg ggccgctcct tactctcccg ggagtataaa    24796
gagggtgatc attcgaggcc gaggtatcca gctcaacgac gaggcggtga gctcctcaac    24856
cggtctcaga cctgacggag tcttccagct cggaggagcg ggccgctctt ccttcaccac    24916
tcgccaggcc tacctgaccc tgcagagctc ttcctcgcag ccgcgctccg ggggaatcgg    24976
cactctccag ttcgtggaag agttcgtccc ctccgtctac ttcaacccgt tttccggctc    25036
acctggacgc tacccggacg ccttcattcc aactttgac gcagtgagtg aatccgtgga     25096
cggctacgac tgatgacaga tggtgcggcc gtgagagctc ggctgcgaca tctgcatcac    25156
tgccgccagc ctcgctgcta cgctcgggag gcgatcgtgt tcagctactt tgagctgccg    25216
gacgagcacc ctcagggacc ggctcacggg ttgaaactcg agattgagaa cgcgcttgag    25276
tctcacctca tcgacgcctt caccgccggg cctctcctgg tagaaaccga acgcgggatc    25336
actaccatca ccctgttctg catctgcccc acgcccggat tac atg aag atc tgt     25391
                                                Met Lys Ile Cys
                                                         1430 gtt gtc atc ttt gcg ctc agt tta ata aaa act gaa ctt ttt gcc          25436
Val Val Ile Phe Ala Leu Ser Leu Ile Lys Thr Glu Leu Phe Ala
    1435                1440                1445 gta cct tca acg cca cgc gtt gtt tct cct tgt gaa aaa acc cca          25481
Val Pro Ser Thr Pro Arg Val Val Ser Pro Cys Glu Lys Thr Pro
    1450                1455                1460 gga gtc ctt aac tta cac ata gca aaa ccc ttg tat ttt acc ata          25526
Gly Val Leu Asn Leu His Ile Ala Lys Pro Leu Tyr Phe Thr Ile
    1465                1470                1475 gaa aaa caa cta gcc ctt tca att gga aaa ggg tta aca att tct          25571
Glu Lys Gln Leu Ala Leu Ser Ile Gly Lys Gly Leu Thr Ile Ser
    1480                1485                1490 gct aca gga cag ttg gaa agc aca gca agc gta cag gac agc gct          25616
Ala Thr Gly Gln Leu Glu Ser Thr Ala Ser Val Gln Asp Ser Ala
    1495                1500                1505 aca cca ccc cta cgt ggt att tcc cct tta aag ctg aca gac aac          25661
Thr Pro Pro Leu Arg Gly Ile Ser Pro Leu Lys Leu Thr Asp Asn
    1510                1515                1520 ggt tta aca tta agc tat tca gat ccc ctg cgt gtg gta ggt gac          25706
Gly Leu Thr Leu Ser Tyr Ser Asp Pro Leu Arg Val Val Gly Asp
    1525                1530                1535 caa ctt acg ttt aat ttt act tct cca cta cgt tac gaa aat ggc          25751
Gln Leu Thr Phe Asn Phe Thr Ser Pro Leu Arg Tyr Glu Asn Gly
    1540                1545                1550 agt ctt aca ttc aac tac act tct ccc atg aca cta ata aac aac          25796
Ser Leu Thr Phe Asn Tyr Thr Ser Pro Met Thr Leu Ile Asn Asn
    1555                1560                1565 agt ctt gct att aac gtc aat acc tcc aaa ggc ctc agt agt gac          25841
Ser Leu Ala Ile Asn Val Asn Thr Ser Lys Gly Leu Ser Ser Asp
    1570                1575                1580
```

| | |
|---|---|
| aac ggc aca ctc gct gta aat gtt act cca gat ttt aga ttt aac<br>Asn Gly Thr Leu Ala Val Asn Val Thr Pro Asp Phe Arg Phe Asn<br>               1585                             1590                        1595 | 25886 |
| agc tct ggt gcc tta act ttt ggc ata caa agt cta tgg act ttt<br>Ser Ser Gly Ala Leu Thr Phe Gly Ile Gln Ser Leu Trp Thr Phe<br>               1600                             1605                        1610 | 25931 |
| cca acc aaa act cct aac tgt acc gtg ttt acc gaa agt gac tcc<br>Pro Thr Lys Thr Pro Asn Cys Thr Val Phe Thr Glu Ser Asp Ser<br>               1615                             1620                        1625 | 25976 |
| ctg ctg agt ctt tgc ttg act aaa tgc gga gct cac gta ctt gga<br>Leu Leu Ser Leu Cys Leu Thr Lys Cys Gly Ala His Val Leu Gly<br>               1630                             1635                        1640 | 26021 |
| agc gtg agt tta agc gga gtg gca gga acc atg cta aaa atg acc<br>Ser Val Ser Leu Ser Gly Val Ala Gly Thr Met Leu Lys Met Thr<br>               1645                             1650                        1655 | 26066 |
| cac act tct gtt acc gtt cag ttt tcg ttt gat gac agt ggt aaa<br>His Thr Ser Val Thr Val Gln Phe Ser Phe Asp Asp Ser Gly Lys<br>               1660                             1665                        1670 | 26111 |
| cta ata ttc tct cca ctt gcg aac aac act tgg ggt gtt cga caa<br>Leu Ile Phe Ser Pro Leu Ala Asn Asn Thr Trp Gly Val Arg Gln<br>               1675                             1680                        1685 | 26156 |
| agc gag agt ccg ttg ccc aac cca tcc ttc aac gct ctc acg ttt<br>Ser Glu Ser Pro Leu Pro Asn Pro Ser Phe Asn Ala Leu Thr Phe<br>               1690                             1695                        1700 | 26201 |
| atg cca aac agt acc att tat tct aga gga gca agt aac gaa cct<br>Met Pro Asn Ser Thr Ile Tyr Ser Arg Gly Ala Ser Asn Glu Pro<br>               1705                             1710                        1715 | 26246 |
| caa aac aat tat tat gtc cag acg tat ctt aga ggc aac gtg cga<br>Gln Asn Asn Tyr Tyr Val Gln Thr Tyr Leu Arg Gly Asn Val Arg<br>               1720                             1725                        1730 | 26291 |
| aag cca att cta cta act gtt acc tac aac tca gtt aat tca gga<br>Lys Pro Ile Leu Leu Thr Val Thr Tyr Asn Ser Val Asn Ser Gly<br>               1735                             1740                        1745 | 26336 |
| tat tcc tta act ttt aaa tgg gat gct gtc gcc aat gaa aaa ttt<br>Tyr Ser Leu Thr Phe Lys Trp Asp Ala Val Ala Asn Glu Lys Phe<br>               1750                             1755                        1760 | 26381 |
| gcc act cct aca tct tcg ttt tgc tat gtt gca gag caa taa<br>Ala Thr Pro Thr Ser Ser Phe Cys Tyr Val Ala Glu Gln<br>               1765                             1770 | 26423 |
| aaccctgtta ccccaccgtc tcgtttttt cag atg aaa cga gcg aga gtt<br>                                                   Met Lys Arg Ala Arg Val<br>                                                         1775 | 26474 |
| gat gaa gac ttc aac cca gtg tac cct tat gac ccc cca tac gct<br>Asp Glu Asp Phe Asn Pro Val Tyr Pro Tyr Asp Pro Pro Tyr Ala<br>1780                            1785                             1790 | 26519 |
| ccc gtc atg ccc ttc att act ccg cct ttt acc tcc tcg gat ggg<br>Pro Val Met Pro Phe Ile Thr Pro Pro Phe Thr Ser Ser Asp Gly<br>1795                            1800                             1805 | 26564 |
| ttg cag gaa aaa cca ctt gga gtg tta agt tta aac tac agg gat<br>Leu Gln Glu Lys Pro Leu Gly Val Leu Ser Leu Asn Tyr Arg Asp<br>1810                            1815                             1820 | 26609 |
| ccc att act aca caa aat ggg tct ctc acg tta aaa cta gga aac<br>Pro Ile Thr Thr Gln Asn Gly Ser Leu Thr Leu Lys Leu Gly Asn<br>1825                            1830                             1835 | 26654 |
| ggc ctc act cta aac aac cag gga cag tta aca tca act gct ggc<br>Gly Leu Thr Leu Asn Asn Gln Gly Gln Leu Thr Ser Thr Ala Gly<br>1840                            1845                             1850 | 26699 |
| gaa gtg gag cct ccg ctc act aat gct aac aac aaa ctt gca cta<br>Glu Val Glu Pro Pro Leu Thr Asn Ala Asn Asn Lys Leu Ala Leu<br>1855                            1860                             1865 | 26744 |

| | | | | | | | | | | | | | |
|---|---|---|---|---|---|---|---|---|---|---|---|---|---|
| gcc | tat | agc | gaa | cca | tta | gca | gta | aaa | agc | aac | cgc | cta | act cta | 26789 |
| Ala | Tyr | Ser | Glu | Pro | Leu | Ala | Val | Lys | Ser | Asn | Arg | Leu | Thr Leu |
| 1870 | | | | 1875 | | | | | 1880 | | | | |

| tca | cac | acc | gct | ccc | ctt | gtc | atc | gct | aat | aat | tct | tta | gcg ttg | 26834 |
|---|---|---|---|---|---|---|---|---|---|---|---|---|---|---|
| Ser | His | Thr | Ala | Pro | Leu | Val | Ile | Ala | Asn | Asn | Ser | Leu | Ala Leu | |
| 1885 | | | | 1890 | | | | | 1895 | | | | | |

| caa | gtt | tca | gag | cct | att | ttt | gta | aat | gac | gat | gac | aag | cta gcc | 26879 |
|---|---|---|---|---|---|---|---|---|---|---|---|---|---|---|
| Gln | Val | Ser | Glu | Pro | Ile | Phe | Val | Asn | Asp | Asp | Asp | Lys | Leu Ala | |
| 1900 | | | | 1905 | | | | | 1910 | | | | | |

| ctg | cag | aca | gcc | gcc | ccc | ctt | gta | acc | aac | gct | ggc | acc | ctt cgc | 26924 |
|---|---|---|---|---|---|---|---|---|---|---|---|---|---|---|
| Leu | Gln | Thr | Ala | Ala | Pro | Leu | Val | Thr | Asn | Ala | Gly | Thr | Leu Arg | |
| 1915 | | | | 1920 | | | | | 1925 | | | | | |

| tta | cag | agc | gct | gcc | cct | tta | gga | ttg | gtt | gaa | aat | act | ctt aaa | 26969 |
|---|---|---|---|---|---|---|---|---|---|---|---|---|---|---|
| Leu | Gln | Ser | Ala | Ala | Pro | Leu | Gly | Leu | Val | Glu | Asn | Thr | Leu Lys | |
| 1930 | | | | 1935 | | | | | 1940 | | | | | |

| ctg | ctg | ttt | tct | aaa | ccc | ttg | tat | ttg | caa | aat | gat | ttt | ctt gca | 27014 |
|---|---|---|---|---|---|---|---|---|---|---|---|---|---|---|
| Leu | Leu | Phe | Ser | Lys | Pro | Leu | Tyr | Leu | Gln | Asn | Asp | Phe | Leu Ala | |
| 1945 | | | | 1950 | | | | | 1955 | | | | | |

| tta | gcc | att | gaa | cgc | ccc | ctg | gct | gta | gca | gcc | gca | ggt | act ctg | 27059 |
|---|---|---|---|---|---|---|---|---|---|---|---|---|---|---|
| Leu | Ala | Ile | Glu | Arg | Pro | Leu | Ala | Val | Ala | Ala | Ala | Gly | Thr Leu | |
| 1960 | | | | 1965 | | | | | 1970 | | | | | |

| acc | cta | caa | ctt | act | cct | cca | tta | aag | act | aac | gat | gac | ggg cta | 27104 |
|---|---|---|---|---|---|---|---|---|---|---|---|---|---|---|
| Thr | Leu | Gln | Leu | Thr | Pro | Pro | Leu | Lys | Thr | Asn | Asp | Asp | Gly Leu | |
| 1975 | | | | 1980 | | | | | 1985 | | | | | |

| aca | cta | tcc | aca | gtc | gag | cca | tta | act | gta | aaa | aac | gga | aac cta | 27149 |
|---|---|---|---|---|---|---|---|---|---|---|---|---|---|---|
| Thr | Leu | Ser | Thr | Val | Glu | Pro | Leu | Thr | Val | Lys | Asn | Gly | Asn Leu | |
| 1990 | | | | 1995 | | | | | 2000 | | | | | |

| ggc | ttg | caa | ata | tcg | cgc | cct | tta | gtt | gtt | caa | aac | aac | ggc ctt | 27194 |
|---|---|---|---|---|---|---|---|---|---|---|---|---|---|---|
| Gly | Leu | Gln | Ile | Ser | Arg | Pro | Leu | Val | Val | Gln | Asn | Asn | Gly Leu | |
| 2005 | | | | 2010 | | | | | 2015 | | | | | |

| tcg | ctt | gct | att | acc | ccc | ccg | ctg | cgt | ttg | ttt | aac | agc | gac ccc | 27239 |
|---|---|---|---|---|---|---|---|---|---|---|---|---|---|---|
| Ser | Leu | Ala | Ile | Thr | Pro | Pro | Leu | Arg | Leu | Phe | Asn | Ser | Asp Pro | |
| 2020 | | | | 2025 | | | | | 2030 | | | | | |

| gtt | ctt | ggt | ttg | ggc | ttc | act | ttt | ccc | cta | gct | gtc | aca | aac aac | 27284 |
|---|---|---|---|---|---|---|---|---|---|---|---|---|---|---|
| Val | Leu | Gly | Leu | Gly | Phe | Thr | Phe | Pro | Leu | Ala | Val | Thr | Asn Asn | |
| 2035 | | | | 2040 | | | | | 2045 | | | | | |

| ctc | ctc | tcc | tta | aac | atg | gga | gac | gga | gtt | aaa | ctt | acc | tat aat | 27329 |
|---|---|---|---|---|---|---|---|---|---|---|---|---|---|---|
| Leu | Leu | Ser | Leu | Asn | Met | Gly | Asp | Gly | Val | Lys | Leu | Thr | Tyr Asn | |
| 2050 | | | | 2055 | | | | | 2060 | | | | | |

| aaa | cta | aca | gcc | aat | ttg | ggt | agg | gat | tta | caa | ttt | gaa | aac ggt | 27374 |
|---|---|---|---|---|---|---|---|---|---|---|---|---|---|---|
| Lys | Leu | Thr | Ala | Asn | Leu | Gly | Arg | Asp | Leu | Gln | Phe | Glu | Asn Gly | |
| 2065 | | | | 2070 | | | | | 2075 | | | | | |

| gcg | att | gcc | gta | acg | ctt | act | gcc | gaa | tta | cct | ttg | caa | tac act | 27419 |
|---|---|---|---|---|---|---|---|---|---|---|---|---|---|---|
| Ala | Ile | Ala | Val | Thr | Leu | Thr | Ala | Glu | Leu | Pro | Leu | Gln | Tyr Thr | |
| 2080 | | | | 2085 | | | | | 2090 | | | | | |

| aac | aaa | ctt | caa | ctg | aat | att | gga | gct | ggc | ctt | cgt | tac | aat gga | 27464 |
|---|---|---|---|---|---|---|---|---|---|---|---|---|---|---|
| Asn | Lys | Leu | Gln | Leu | Asn | Ile | Gly | Ala | Gly | Leu | Arg | Tyr | Asn Gly | |
| 2095 | | | | 2100 | | | | | 2105 | | | | | |

| gcc | agc | aga | aaa | cta | gat | gta | aac | att | aac | caa | aat | aaa | ggc tta | 27509 |
|---|---|---|---|---|---|---|---|---|---|---|---|---|---|---|
| Ala | Ser | Arg | Lys | Leu | Asp | Val | Asn | Ile | Asn | Gln | Asn | Lys | Gly Leu | |
| 2110 | | | | 2115 | | | | | 2120 | | | | | |

| act | tgg | gac | aac | gat | gca | gtt | att | ccc | aaa | cta | gga | tcg | ggc tta | 27554 |
|---|---|---|---|---|---|---|---|---|---|---|---|---|---|---|
| Thr | Trp | Asp | Asn | Asp | Ala | Val | Ile | Pro | Lys | Leu | Gly | Ser | Gly Leu | |
| 2125 | | | | 2130 | | | | | 2135 | | | | | |

| caa | ttt | gac | cct | aat | ggc | aac | atc | gct | gtt | atc | cct | gaa | acc gtg | 27599 |
|---|---|---|---|---|---|---|---|---|---|---|---|---|---|---|
| Gln | Phe | Asp | Pro | Asn | Gly | Asn | Ile | Ala | Val | Ile | Pro | Glu | Thr Val | |
| 2140 | | | | 2145 | | | | | 2150 | | | | | |

| aag | ccg | caa | acg | tta | tgg | acg | act | gca | gat | ccc | tcg | cct | aac tgc | 27644 |
|---|---|---|---|---|---|---|---|---|---|---|---|---|---|---|
| Lys | Pro | Gln | Thr | Leu | Trp | Thr | Thr | Ala | Asp | Pro | Ser | Pro | Asn Cys | |
| 2155 | | | | 2160 | | | | | 2165 | | | | | |

```
tca gtg tac cag gac ttg gat gcc agg ctg tgg ctc gct ctt gtt      27689
Ser Val Tyr Gln Asp Leu Asp Ala Arg Leu Trp Leu Ala Leu Val
2170            2175                2180 aaa agt ggc gac atg gtg cat gga agc att gcc cta aaa gcc cta      27734
Lys Ser Gly Asp Met Val His Gly Ser Ile Ala Leu Lys Ala Leu
2185            2190                2195 aaa ggg acg ttg cta aat cct aca gcc agc tac att tcc att gtg      27779
Lys Gly Thr Leu Leu Asn Pro Thr Ala Ser Tyr Ile Ser Ile Val
2200            2205                2210 ata tat ttt tac agc aac gga gtc agg cgt acc aac tat cca acg      27824
Ile Tyr Phe Tyr Ser Asn Gly Val Arg Arg Thr Asn Tyr Pro Thr
2215            2220                2225 ttt gac aac gaa ggc acc tta gct aac agc gcc act tgg gga tac      27869
Phe Asp Asn Glu Gly Thr Leu Ala Asn Ser Ala Thr Trp Gly Tyr
2230            2235                2240 cga cag ggg caa tct gct aac act aat gtg acc aat gcc act gaa      27914
Arg Gln Gly Gln Ser Ala Asn Thr Asn Val Thr Asn Ala Thr Glu
2245            2250                2255 ttt atg ccc agc tca agc agg tac ccc gtg aat aaa gga gac aac      27959
Phe Met Pro Ser Ser Ser Arg Tyr Pro Val Asn Lys Gly Asp Asn
2260            2265                2270 att caa aat caa tct ttt tca tac acc tgt att aaa gga gat ttt      28004
Ile Gln Asn Gln Ser Phe Ser Tyr Thr Cys Ile Lys Gly Asp Phe
2275            2280                2285 gct atg cct gtc ccg ttc cgt gta aca tat aat cac gcc ctg gaa      28049
Ala Met Pro Val Pro Phe Arg Val Thr Tyr Asn His Ala Leu Glu
2290            2295                2300 ggg tat tcc ctt aag ttc acc tgg cgc gtt gta gcc aat cag gcc      28094
Gly Tyr Ser Leu Lys Phe Thr Trp Arg Val Val Ala Asn Gln Ala
2305            2310                2315 ttt gat att cct tgc tgt tca ttt tca tac atc aca gaa taa          28136
Phe Asp Ile Pro Cys Cys Ser Phe Ser Tyr Ile Thr Glu
2320            2325                2330 aaaaccactt tttcatttta atttcttttt attttacacg aacagtgaga cttcctccac 28196 ccttccattt gacagcatac accagcctct ccccttcat agcagtaaac tgttgtgaat  28256
cagtccggta tttgggagtt aaaatccaaa cagtctcttt ggtgatgaaa cgtcgatcag 28316 taatggacac aaatccctgg gacaggtttt ccaacgtttc ggtgaaaaac tgcacaccgc 28376 cctacaaaac aaacaggttc aggctctcca cgggttatct ccccgatcaa actcagacag 28436 ggtaaaggtg cggtggtgtt ccactaaacc acgcaggtgg cgctgtctga acctctcggt 28496 gcgactcctg tgaggctggt aagaagttag attgtccagt agcctcacag catgtatcat 28556 cagtctacga gtgcgtctgg cgcagcagcg catctgaatc tcactgagat tccggcaaga 28616 atcgcacacc atcacaatca ggttgttcat gatcccatag ctgaacacgc tccagccaaa 28676 gctcattcgc tccaacagcg ccaccgcgtg tccgtccaac cttactttaa cataaatcag 28736 gtgtctgccg cgtacaaaca tgctacccac atacagaact tcccggggca ggcccctgtt 28796 caccacctgt ctgtaccagg gaaacctcac atttatcagg gagccataga tggccatttt 28856 aaaccaatta gctaataccg ccccaccagc tctacactga agagaaccgg gagagttaca 28916 atgacagtga ataatccatc tctcataacc cctgatggtc tgatgaaaat ctagatctaa 28976 cgtggcacaa caaatacaca cttttcatata cattttcata acatgttttt cccaggccgt 29036 taaaatacaa tcccaataca cgggccactc ctgcagtaca ataaagctaa tacaagatgg 29096 tatactcctc acctcactga cactgtgcat gttcatattt tcacattcta agtaccgaga 29156 gttctcctct acagcagcac tgctgcggtc ctcacaaggt ggtagctggt gatgattgta 29216
```

```
gggggccagt ctgcagcgat accgtctgtc gcgttgcatc gtagaccagg aaccgacgca    29276
cctcctcgta cttgtggtag cagaaccacg tccgctgcca gcacgtctcc acgtaacgcc    29336
ggtccctgcg tcgctcacgc tccctcctca atgcaaagtg caaccactct tgtaatccac    29396
acagatccct ctcggcctcc ggggtgatgc acacctcaaa cctacagatg tctcggtaca    29456
gttccaaaca cgtagtgagg gcgagttcca accaagacag acagcctgat ctatcccgac    29516
acactggagg tggaggaaga cacggaagag gcatgttatt ccaagcgatt caccaacggg    29576
tcgaaatgaa gatcccgaag atgacaacgg tcgcctccgg agccctgatg gaatttaaca    29636
gccagatcaa acgttatgcg attctccaag ctatcgatcg ccgcttccaa aagagcctgg    29696
acccgcactt ccacaaacac cagcaaagca aaagcactat tatcaaactc ttcaatcatc    29756
aagctgcagg actgtacaat gcctaagtaa ttttcgtttc tccactcgcg aatgatgtcg    29816
cggcagatag tctgaaggtt catcccgtgc agggtaaaaa gctccgaaag ggcgccctct    29876
acagccatgc gtagacacac catcatgact gcaagatatc gggctcctga cacacctgca    29936
gcagatttaa cagatcaagg tcaggttgct ctccgcgatc acgaatctcc atccgcaagg    29996
tcatttgcaa aaaattaaat aaatctatgc cgactagatc tgtcaactcc gcattaggaa    30056
ccaaatcagg tgtggctacg cagcacaaaa gttccaggga tggtgccaaa ctcactagaa    30116
ccgctcccga gtaacaaaac tgatgaatgg gagtaacaca gtgtaaaatg tgcaaccaaa    30176
aatcactaag gtgctccttt aaaaagtcca gtacttctat attcagtccg tgcaagtact    30236
gaagcaactg tgcgggaata tgcacaacaa aaaaaatagg gcggctcaga tacatgttga    30296
cctaaaataa aaagaatcat taaactaaag aagcttggcg aacggtggga taaatgacac    30356
gctccagcag cagacaggca accggctgtc cccgggaacc gcggtaaaat tcatccgaat    30416
gattaaaaag aacaacagaa acttcccacc atgtactcgg ttggatctcc tgagcacaca    30476 gcaataccc cctcacattc atgtccgcca cagaaaaaaa acgtcccaga tacccagcgg    30536
ggatatccaa cgacagctgc aaagacagca aaacaatccc tctgggagcg atcacaaaat    30596
cctccggtga aaaagcaca tacatattag aataaccctg ttgctggggc aaaaaggccc    30656
ggcgtcccag caaatgcaca taaatatgtt catcagccat tgccccgtct taccgcgtaa    30716
tcagccacga aaaaatcgag ctaaaattca cccaacagcc tatagctata tatacactcc    30776
gcccaatgac gctaataccg caccacccac gaccaaagtt cacccacacc cacaaaaccc    30836
gcgaaaatcc agcgccgtca gcacttccgc aatttcagtc tcacaacgtc acttccgcgc    30896 gcctttcac attcccacac acacccgcgc ccttcgcccc gccctcgcgc caccccgcgt    30956
caccgcacgt caccccggcc ccgcctcgct cctccccgct cattatcata ttggcacgtt    31016
tccagaataa ggtatattat tgatgatg                                       31044
```

<210> SEQ ID NO 30
<211> LENGTH: 505
<212> TYPE: PRT
<213> ORGANISM: simian adenovirus SV-25

<400> SEQUENCE: 30

Met Arg Arg Ala Val Arg Val Thr Pro Ala Ala Tyr Glu Gly Pro Pro
1               5                   10                  15

Pro Ser Tyr Glu Ser Val Met Gly Ser Ala Asn Val Pro Ala Thr Leu
            20                  25                  30

Glu Ala Pro Tyr Val Pro Pro Arg Tyr Leu Gly Pro Thr Glu Gly Arg
        35                  40                  45

Asn Ser Ile Arg Tyr Ser Glu Leu Ala Pro Leu Tyr Asp Thr Thr Lys

```
              50                  55                  60
Val Tyr Leu Val Asp Asn Lys Ser Ala Asp Ile Ala Ser Leu Asn Tyr
 65                  70                  75                  80

Gln Asn Asp His Ser Asn Phe Leu Thr Thr Val Val Gln Asn Asn Asp
                 85                  90                  95

Phe Thr Pro Thr Glu Ala Gly Thr Gln Thr Ile Asn Phe Asp Glu Arg
             100                 105                 110

Ser Arg Trp Gly Gly Gln Leu Lys Thr Ile Leu His Thr Asn Met Pro
             115                 120                 125

Asn Ile Asn Glu Phe Met Ser Thr Asn Lys Phe Arg Ala Lys Leu Met
130                 135                 140

Val Glu Lys Ser Asn Ala Glu Thr Arg Gln Pro Arg Tyr Glu Trp Phe
145                 150                 155                 160

Glu Phe Thr Ile Pro Glu Gly Asn Tyr Ser Glu Thr Met Thr Ile Asp
             165                 170                 175

Leu Met Asn Asn Ala Ile Val Asp Asn Tyr Leu Gln Val Gly Arg Gln
             180                 185                 190

Asn Gly Val Leu Glu Ser Asp Ile Gly Val Lys Phe Asp Thr Arg Asn
             195                 200                 205

Phe Arg Leu Gly Trp Asp Pro Val Thr Lys Leu Val Met Pro Gly Val
210                 215                 220

Tyr Thr Asn Glu Ala Phe His Pro Asp Ile Val Leu Leu Pro Gly Cys
225                 230                 235                 240

Gly Val Asp Phe Thr Gln Ser Arg Leu Ser Asn Leu Leu Gly Ile Arg
             245                 250                 255

Lys Arg Arg Pro Phe Gln Glu Gly Phe Gln Ile Met Tyr Glu Asp Leu
             260                 265                 270

Glu Gly Gly Asn Ile Pro Ala Leu Leu Asp Val Ser Lys Tyr Glu Ala
             275                 280                 285

Ser Ile Gln Arg Ala Lys Ala Glu Gly Arg Glu Ile Arg Gly Asp Thr
             290                 295                 300

Phe Ala Val Ala Pro Gln Asp Leu Glu Ile Val Pro Leu Thr Lys Asp
305                 310                 315                 320

Ser Lys Asp Arg Ser Tyr Asn Ile Ile Asn Asn Thr Asp Thr Leu
             325                 330                 335

Tyr Arg Ser Trp Phe Leu Ala Tyr Asn Tyr Gly Asp Pro Glu Lys Gly
             340                 345                 350

Val Arg Ser Trp Thr Ile Leu Thr Thr Thr Asp Val Thr Cys Gly Ser
             355                 360                 365

Gln Gln Val Tyr Trp Ser Leu Pro Asp Met Met Gln Asp Pro Val Thr
370                 375                 380

Phe Arg Pro Ser Thr Gln Val Ser Asn Phe Pro Val Val Gly Thr Glu
385                 390                 395                 400

Leu Leu Pro Val His Ala Lys Ser Phe Tyr Asn Glu Gln Ala Val Tyr
             405                 410                 415

Ser Gln Leu Ile Arg Gln Ser Thr Ala Leu Thr His Val Phe Asn Arg
             420                 425                 430

Phe Pro Glu Asn Gln Ile Leu Val Arg Pro Pro Ala Pro Thr Ile Thr
             435                 440                 445

Thr Val Ser Glu Asn Val Pro Ala Leu Thr Asp His Gly Thr Leu Pro
             450                 455                 460

Leu Arg Ser Ser Ile Ser Gly Val Gln Arg Val Thr Ile Thr Asp Ala
465                 470                 475                 480
```

```
Arg Arg Arg Thr Cys Pro Tyr Val Tyr Lys Ala Leu Gly Val Val Ala
            485                 490                 495

Pro Lys Val Leu Ser Ser Arg Thr Phe
            500                 505

<210> SEQ ID NO 31
<211> LENGTH: 921
<212> TYPE: PRT
<213> ORGANISM: simian adenovirus SV-25

<400> SEQUENCE: 31

Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Thr Ala Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Pro Ser Glu Trp Thr Asp Thr Ser Asp Asn Lys Leu Lys
    130                 135                 140

Ala Tyr Ala Gln Ala Pro Tyr Gln Ser Gln Gly Leu Thr Lys Asp Gly
145                 150                 155                 160

Ile Gln Val Gly Leu Val Val Thr Glu Ser Gly Gln Thr Pro Gln Tyr
                165                 170                 175

Ala Asn Lys Val Tyr Gln Pro Glu Pro Gln Ile Gly Glu Asn Gln Trp
            180                 185                 190

Asn Leu Glu Gln Glu Asp Lys Ala Ala Gly Arg Val Leu Lys Lys Asp
        195                 200                 205

Thr Pro Met Phe Pro Cys Tyr Gly Ser Tyr Ala Arg Pro Thr Asn Glu
    210                 215                 220

Gln Gly Gly Gln Ala Lys Asn Gln Glu Val Asp Leu Gln Phe Phe Ala
225                 230                 235                 240

Thr Pro Gly Asp Thr Gln Asn Thr Ala Lys Val Val Leu Tyr Ala Glu
                245                 250                 255

Asn Val Asn Leu Glu Thr Pro Asp Thr His Leu Val Phe Lys Pro Asp
            260                 265                 270

Asp Asp Ser Thr Ser Ser Lys Leu Leu Leu Gly Gln Gln Ala Ala Pro
        275                 280                 285

Asn Arg Pro Asn Tyr Ile Gly Phe Arg Asp Asn Phe Ile Gly Leu Met
    290                 295                 300

Tyr Tyr Asn Ser Thr Gly Asn Met Gly Val Leu Ala Gly Gln Ala Ser
305                 310                 315                 320

Gln Leu Asn Ala Val Val Asp Leu Gln Asp Arg Asn Thr Glu Leu Ser
                325                 330                 335

Tyr Gln Leu Met Leu Asp Ala Leu Gly Asp Arg Ser Arg Tyr Phe Ser
            340                 345                 350
```

-continued

```
Met Trp Asn Gln Ala Val Asp Ser Tyr Asp Pro Asp Val Arg Ile Ile
            355                 360                 365
Glu Asn His Gly Val Glu Asp Glu Leu Pro Asn Tyr Cys Phe Pro Leu
        370                 375                 380
Gly Gly Met Val Val Thr Asp Asn Tyr Asn Ser Val Thr Pro Gln Asn
385                 390                 395                 400
Gly Gly Ser Gly Asn Thr Trp Gln Ala Asp Asn Thr Thr Phe Ser Gln
                405                 410                 415
Arg Gly Ala Gln Ile Gly Ser Gly Asn Met Phe Ala Leu Glu Ile Asn
            420                 425                 430
Leu Gln Ala Asn Leu Trp Arg Gly Phe Leu Tyr Ser Asn Ile Gly Leu
        435                 440                 445
Tyr Leu Pro Asp Ser Leu Lys Ile Thr Pro Asp Asn Ile Thr Leu Pro
    450                 455                 460
Glu Asn Lys Asn Thr Tyr Gln Tyr Met Asn Gly Arg Val Thr Pro Pro
465                 470                 475                 480
Gly Leu Ile Asp Thr Tyr Val Asn Val Gly Ala Arg Trp Ser Pro Asp
                485                 490                 495
Val Met Asp Ser Ile Asn Pro Phe Asn His His Arg Asn Ala Gly Leu
            500                 505                 510
Arg Tyr Arg Ser Met Leu Leu Gly Asn Gly Arg Tyr Val Pro Phe His
        515                 520                 525
Ile Gln Val Pro Gln Lys Phe Phe Ala Ile Lys Asn Leu Leu Leu Leu
    530                 535                 540
Pro Gly Ser Tyr Thr Tyr Glu Trp Asn Phe Arg Lys Asp Val Asn Met
545                 550                 555                 560
Ile Leu Gln Ser Ser Leu Gly Asn Asp Leu Arg Val Asp Gly Ala Ser
                565                 570                 575
Ile Arg Phe Asp Ser Ile Asn Leu Tyr Ala Asn Phe Phe Pro Met Ala
            580                 585                 590
His Asn Thr Ala Ser Thr Leu Glu Ala Met Leu Arg Asn Asp Thr Asn
        595                 600                 605
Asp Gln Ser Phe Asn Asp Tyr Leu Cys Ala Ala Asn Met Leu Tyr Pro
    610                 615                 620
Ile Pro Ala Asn Ala Thr Ser Val Pro Ile Ser Ile Pro Ser Arg Asn
625                 630                 635                 640
Trp Ala Ala Phe Arg Gly Trp Ser Phe Thr Arg Leu Lys Thr Lys Glu
                645                 650                 655
Thr Pro Ser Leu Gly Ser Gly Phe Asp Pro Tyr Phe Val Tyr Ser Gly
            660                 665                 670
Ser Ile Pro Tyr Leu Asp Gly Thr Phe Tyr Leu Asn His Thr Phe Lys
        675                 680                 685
Lys Val Ser Ile Met Phe Asp Ser Ser Val Ser Trp Pro Gly Asn Asp
    690                 695                 700
Arg Leu Leu Thr Pro Asn Glu Phe Glu Ile Lys Arg Ser Val Asp Gly
705                 710                 715                 720
Glu Gly Tyr Asn Val Ala Gln Ser Asn Met Thr Lys Asp Trp Phe Leu
                725                 730                 735
Ile Gln Met Leu Ser His Tyr Asn Ile Gly Tyr Gln Gly Phe Tyr Val
            740                 745                 750
Pro Glu Asn Tyr Lys Asp Arg Met Tyr Ser Phe Phe Arg Asn Phe Gln
        755                 760                 765
Pro Met Ser Arg Gln Val Val Asp Thr Val Thr Tyr Thr Asp Tyr Lys
    770                 775                 780
```

```
Asp Val Lys Leu Pro Tyr Gln His Asn Asn Ser Gly Phe Val Gly Tyr
785                 790                 795                 800

Met Gly Pro Thr Met Arg Glu Gly Gln Ala Tyr Pro Ala Asn Tyr Pro
                805                 810                 815

Tyr Pro Leu Ile Gly Glu Thr Ala Val Pro Ser Leu Thr Gln Lys Lys
            820                 825                 830

Phe Leu Cys Asp Arg Val Met Trp Arg Ile Pro Phe Ser Ser Asn Phe
        835                 840                 845

Met Ser Met Gly Ser Leu Thr Asp Leu Gly Gln Asn Met Leu Tyr Ala
    850                 855                 860

Asn Ser Ala His Ala Leu Asp Met Thr Phe Glu Val Asp Pro Met Asp
865                 870                 875                 880

Glu Pro Thr Leu Leu Tyr Val Leu Phe Glu Val Phe Asp Val Val Arg
                885                 890                 895

Ile His Gln Pro His Arg Gly Val Ile Glu Ala Val Tyr Leu Arg Thr
            900                 905                 910

Pro Phe Ser Ala Gly Asn Ala Thr Thr
        915                 920

<210> SEQ ID NO 32
<211> LENGTH: 347
<212> TYPE: PRT
<213> ORGANISM: simian adenovirus SV-25

<400> SEQUENCE: 32

Met Lys Ile Cys Val Val Ile Phe Ala Leu Ser Leu Ile Lys Thr Glu
1               5                   10                  15

Leu Phe Ala Val Pro Ser Thr Pro Arg Val Val Ser Pro Cys Glu Lys
            20                  25                  30

Thr Pro Gly Val Leu Asn Leu His Ile Ala Lys Pro Leu Tyr Phe Thr
        35                  40                  45

Ile Glu Lys Gln Leu Ala Leu Ser Ile Gly Lys Gly Leu Thr Ile Ser
    50                  55                  60

Ala Thr Gly Gln Leu Glu Ser Thr Ala Ser Val Gln Asp Ser Ala Thr
65                  70                  75                  80

Pro Pro Leu Arg Gly Ile Ser Pro Leu Lys Leu Thr Asp Asn Gly Leu
                85                  90                  95

Thr Leu Ser Tyr Ser Asp Pro Leu Arg Val Val Gly Asp Gln Leu Thr
            100                 105                 110

Phe Asn Phe Thr Ser Pro Leu Arg Tyr Glu Asn Gly Ser Leu Thr Phe
        115                 120                 125

Asn Tyr Thr Ser Pro Met Thr Leu Ile Asn Asn Ser Leu Ala Ile Asn
    130                 135                 140

Val Asn Thr Ser Lys Gly Leu Ser Ser Asp Asn Gly Thr Leu Ala Val
145                 150                 155                 160

Asn Val Thr Pro Asp Phe Arg Phe Asn Ser Ser Gly Ala Leu Thr Phe
                165                 170                 175

Gly Ile Gln Ser Leu Trp Thr Phe Pro Thr Lys Thr Pro Asn Cys Thr
            180                 185                 190

Val Phe Thr Glu Ser Asp Ser Leu Leu Ser Leu Cys Leu Thr Lys Cys
        195                 200                 205

Gly Ala His Val Leu Gly Ser Val Ser Leu Ser Gly Val Ala Gly Thr
    210                 215                 220

Met Leu Lys Met Thr His Thr Ser Val Thr Val Gln Phe Ser Phe Asp
225                 230                 235                 240
```

```
Asp Ser Gly Lys Leu Ile Phe Ser Pro Leu Ala Asn Asn Thr Trp Gly
                245                 250                 255

Val Arg Gln Ser Glu Ser Pro Leu Pro Asn Pro Ser Phe Asn Ala Leu
            260                 265                 270

Thr Phe Met Pro Asn Ser Thr Ile Tyr Ser Arg Gly Ala Ser Asn Glu
        275                 280                 285

Pro Gln Asn Asn Tyr Tyr Val Gln Thr Tyr Leu Arg Gly Asn Val Arg
    290                 295                 300

Lys Pro Ile Leu Leu Thr Val Thr Tyr Asn Ser Val Asn Ser Gly Tyr
305                 310                 315                 320

Ser Leu Thr Phe Lys Trp Asp Ala Val Ala Asn Glu Lys Phe Ala Thr
                325                 330                 335

Pro Thr Ser Ser Phe Cys Tyr Val Ala Glu Gln
                340                 345

<210> SEQ ID NO 33
<211> LENGTH: 559
<212> TYPE: PRT
<213> ORGANISM: simian adenovirus SV-25

<400> SEQUENCE: 33

Met Lys Arg Ala Arg Val Asp Glu Asp Phe Asn Pro Val Tyr Pro Tyr
1               5                   10                  15

Asp Pro Pro Tyr Ala Pro Val Met Pro Phe Ile Thr Pro Pro Phe Thr
            20                  25                  30

Ser Ser Asp Gly Leu Gln Glu Lys Pro Leu Gly Val Leu Ser Leu Asn
        35                  40                  45

Tyr Arg Asp Pro Ile Thr Thr Gln Asn Gly Ser Leu Thr Leu Lys Leu
    50                  55                  60

Gly Asn Gly Leu Thr Leu Asn Asn Gln Gly Gln Leu Thr Ser Thr Ala
65                  70                  75                  80

Gly Glu Val Glu Pro Pro Leu Thr Asn Ala Asn Asn Lys Leu Ala Leu
                85                  90                  95

Ala Tyr Ser Glu Pro Leu Ala Val Lys Ser Asn Arg Leu Thr Leu Ser
            100                 105                 110

His Thr Ala Pro Leu Val Ile Ala Asn Asn Ser Leu Ala Leu Gln Val
        115                 120                 125

Ser Glu Pro Ile Phe Val Asn Asp Asp Lys Leu Ala Leu Gln Thr
    130                 135                 140

Ala Ala Pro Leu Val Thr Asn Ala Gly Thr Leu Arg Leu Gln Ser Ala
145                 150                 155                 160

Ala Pro Leu Gly Leu Val Glu Asn Thr Leu Lys Leu Leu Phe Ser Lys
                165                 170                 175

Pro Leu Tyr Leu Gln Asn Asp Phe Leu Ala Leu Ala Ile Glu Arg Pro
            180                 185                 190

Leu Ala Val Ala Ala Ala Gly Thr Leu Thr Leu Gln Leu Thr Pro Pro
        195                 200                 205

Leu Lys Thr Asn Asp Asp Gly Leu Thr Leu Ser Thr Val Glu Pro Leu
    210                 215                 220

Thr Val Lys Asn Gly Asn Leu Gly Leu Gln Ile Ser Arg Pro Leu Val
225                 230                 235                 240

Val Gln Asn Asn Gly Leu Ser Leu Ala Ile Thr Pro Pro Leu Arg Leu
                245                 250                 255

Phe Asn Ser Asp Pro Val Leu Gly Leu Gly Phe Thr Phe Pro Leu Ala
            260                 265                 270
```

```
Val Thr Asn Asn Leu Leu Ser Leu Asn Met Gly Asp Gly Val Lys Leu
        275                 280                 285

Thr Tyr Asn Lys Leu Thr Ala Asn Leu Gly Arg Asp Leu Gln Phe Glu
        290                 295                 300

Asn Gly Ala Ile Ala Val Thr Leu Thr Ala Glu Leu Pro Leu Gln Tyr
305                 310                 315                 320

Thr Asn Lys Leu Gln Leu Asn Ile Gly Ala Gly Leu Arg Tyr Asn Gly
                325                 330                 335

Ala Ser Arg Lys Leu Asp Val Asn Ile Asn Gln Asn Lys Gly Leu Thr
            340                 345                 350

Trp Asp Asn Asp Ala Val Ile Pro Lys Leu Gly Ser Gly Leu Gln Phe
        355                 360                 365

Asp Pro Asn Gly Asn Ile Ala Val Ile Pro Glu Thr Val Lys Pro Gln
    370                 375                 380

Thr Leu Trp Thr Thr Ala Asp Pro Ser Pro Asn Cys Ser Val Tyr Gln
385                 390                 395                 400

Asp Leu Asp Ala Arg Leu Trp Leu Ala Leu Val Lys Ser Gly Asp Met
                405                 410                 415

Val His Gly Ser Ile Ala Leu Lys Ala Leu Lys Gly Thr Leu Leu Asn
            420                 425                 430

Pro Thr Ala Ser Tyr Ile Ser Ile Val Ile Tyr Phe Tyr Ser Asn Gly
        435                 440                 445

Val Arg Arg Thr Asn Tyr Pro Thr Phe Asp Asn Glu Gly Thr Leu Ala
    450                 455                 460

Asn Ser Ala Thr Trp Gly Tyr Arg Gln Gly Gln Ser Ala Asn Thr Asn
465                 470                 475                 480

Val Thr Asn Ala Thr Glu Phe Met Pro Ser Ser Arg Tyr Pro Val
                485                 490                 495

Asn Lys Gly Asp Asn Ile Gln Asn Gln Ser Phe Ser Tyr Thr Cys Ile
            500                 505                 510

Lys Gly Asp Phe Ala Met Pro Val Pro Phe Arg Val Thr Tyr Asn His
        515                 520                 525

Ala Leu Glu Gly Tyr Ser Leu Lys Phe Thr Trp Arg Val Val Ala Asn
    530                 535                 540

Gln Ala Phe Asp Ile Pro Cys Cys Ser Phe Ser Tyr Ile Thr Glu
545                 550                 555

<210> SEQ ID NO 34
<211> LENGTH: 34115
<212> TYPE: DNA
<213> ORGANISM: simian adenovirus SV-39
<220> FEATURE:
<221> NAME/KEY: CDS
<222> LOCATION: (13448)..(14959)
<223> OTHER INFORMATION: L2 Penton
<220> FEATURE:
<221> NAME/KEY: CDS
<222> LOCATION: (17785)..(20538)
<223> OTHER INFORMATION: L3 Hexon
<220> FEATURE:
<221> NAME/KEY: CDS
<222> LOCATION: (29515)..(31116)
<223> OTHER INFORMATION: L5 Fiber #1

<400> SEQUENCE: 34
catcatcaat ataacaccgc aagatggcga ccgagttaac atgcaaatga ggtgggcgga    60
gttacgcgac ctttgtcttg ggaacgcgga agtgggcgcg gcgggtttcg gggaggagcg   120
cggggcgggg cgggcgtgtc gcgcggcggt gacgcgccgg ggacccggaa attgagtagt   180
```

```
ttttattcat tttgcaagtt tttctgtaca ttttggcgcg aaaactgaaa cgaggaagtg      240
aaaagtgaaa aatgccgagg tagtcaccgg gtggagatct gacctttgcc gtgtggagtt      300
tacccgctga cgtgtgggtt tcggtctcta ttttttcact gtggttttcc gggtacggtc      360
aaaggtcccc atttatgac tccacgtcag ctgatcgcta gggtatttaa tgcgcctcag      420
accgtcaaga ggccactctt gagtgccggc gagaagagtt ttctcctccg cgttccgcca      480
actgtgaaaa aatgaggaac ttcttgctat ctccggggct gccagcgacc gtagccgccg      540
agctgttgga ggacattgtt accggagctc tgggagacga tcctcaggtg atttctcact      600
tttgtgaaga ttttagtctt catgatctct atgatattga tccgggtgtt gaggggcaag      660
aggatgaatg gctggagtct gtggatgggt ttttccgga cgctatgctg ctagaggctg      720
atttgccacc acctcacaac tctcacactg agcccgagtc agctgctatt cctgaattgt      780
catcaggtga acttgacttg gcttgttacg agactatgcc tccggagtcg gatgaggagg      840
acagcgggat cagcgatccc acggctttta tggtctctaa ggcgattgct atactaaaag      900
aagatgatga tggcgatgat ggatttcgac tggacgctcc ggcggtgccg gggagagact      960
gtaagtcctg tgaataccac cgggatcgta ccggagaccc gtctatgttg tgttctctgt     1020
gttatctccg tcttaacgct gcttttgtct acagtaagtg ttttgtgctt ttttaccctg     1080
tggctttgtt gagtttattt ttttctgtgt ctcatagggt gttgtttatt ataggtcctg     1140
tttcagatgt ggaggaacct gatagtacta ctggaaatga ggaggaaaag ccctccccgc     1200
cgaaactaac tcagcgctgc agacctaata ttttgagacc ctcggcccag cgtgtgtcat     1260
cccggaaacg tgctgctgtt aattgcatag aagatttatt ggaagagccc actgaacctt     1320
tggacttgtc cttaaagcga ccccgcccgc agtagggcgc ggtgccagtt ttttctctct     1380
agcttccggg tgactcagtg caataaaaat tttcttggca acaggtgtat gtgtttactt     1440
tacgggcggg aagggattag gggagtataa agctggaggg gaaaaatctg aggctgtcag     1500
atcgagtgag aagttccatg gacttgtacg agagcctaga gaatctaagt tctttgcgac     1560
gtttgctgga ggaggcctcc gacagaacct cttacatttg gaggtttctg ttcggttccc     1620
ctctgagtcg cttttttgcac cgggtgaagc gagagcacct gacggaattt gatgggcttt     1680
tagagcagct gcctggactg tttgattctt tgaatctcgg ccaccggacg ctgctagagg     1740
agaggctttt tccacaattg gacttttcct ctccaggccg tctgtgttca gcgcttgctt     1800
ttgctgtaca tctgttggac agatggaacg agcagacgca gctcagcccg ggttacactc     1860
tggacttcct gacgctatgc ctatggaagt tcggaatcag gaggggagg aagctgtacg     1920 ggcgcttggt ggagaggcat ccgtctctgc gccagcagcg tctgcaagct caagtgctgc     1980
tgaggcggga ggatctggaa gccatttcgg aggaggagag cggcatggaa gagaagaatc     2040
cgagagcggg gctggaccct ccggcggagg agtaggggg ataccggacc cttttcctga     2100
gttggctttg ggggcggtgg ggggcgcttc tgtggtacgt gaggatgaag aggggcgcca     2160
acgcggtcag aagagggagc attttgagtc ctcgactttc ttggctgatg taaccgtggc     2220
cctgatggcg aaaacaggc tggaggtggt gtggtacccg gaagtatggg aggactttga     2280 gaaggggac ttgcacctgc tggaaaaata aactttgag caggtgaaaa catactggat     2340
gaacccggat gaggactggg aggtggtttt gaaccgatac ggcaaggtag ctctgcgtcc     2400
cgactgtcgc taccaggttc gcgacaaggt ggtcctgcga cgcaacgtgt acctgttggg     2460
caacggcgcc accgtggaga tggtggaccc cagaaggggg ggttttgtgg ccaatatgca     2520
agaaatgtgc cctggggtgg tgggcttgtc tggggtgact ttcatagtg tgaggtttag     2580
```

```
cggtagcaat tttgggggtg tggttattac cgcgaacact cctgtggtcc tgcataattg    2640
ctactttttt ggcttcagca acacctgtgt ggaaatgagg gtgggaggca aagtgcgcgg    2700
gtgttccttt tacgcttgct ggaaggggt ggtgagccag ggtaaggcta aagtgtctgt     2760
tcacaagtgt atgttggaga gatgcacctt gggcatttcc agtgagggct tcctccacgc    2820
cagcgacaac gtggcttctg acaacggctg cgcctttctt atcaagggag ggggtcgcat    2880
ctgtcacaac atgatatgcg gccctgggga tgtcccccca aagccttacc agatggttac    2940
ctgcacagat ggcaaggtgc gcatgctcaa gcctgtgcac attgtgggcc accgcgcca    3000 ccgctgggcca gagtttgaac acaatgtgat gacccgctgt agcttgtacc tgggaggcag   3060
gcgaggagtt ttcttgccca gacagtgtaa cctggcccac tgcaacgtga tcatggaaca    3120
atccgccgct acccaggttt gctttggagg aatatttgat ataagcatgg tggtgtataa    3180
gatcctgcgc tacgcgact gtcgggctcg tactcgaacc tgcgactgcg gagcctctca     3240
cctgtgtaac ctgactgtga tggggatggt gactgaggag gtgcgactgg accactgtca    3300
gcactcttgc ctgcgggagg agttttcttc ctcggacgag gaggactagg taggtggttg    3360
gggcgtggcc agcgagaggg tgggctataa aggggaggtg tcggctgacg ctgtcttctg    3420
tttttcaggt accatgagcg gatcaagcag ccagaccgcg ctgagcttcg acggggccgt    3480
gtacagcccc tttctgacgg ggcgcttgcc tgcctgggcc ggagtgcgtc agaatgttac    3540
cggttcgacc gtggacggac gtcccgtgga tccatctaac gctgcttcta tgcgctacgc    3600
tactatcagc acatctactc tggacagcgc cgctgccgcc gcagccgcca cctcagccgc    3660
tctctccgcc gccaagatca tggctattaa cccaagcctt tacagccctg tatccgtgga    3720
cacctcagcc ctggagcttt accggcgaga tctagctcaa gtggtggacc aactcgcagc    3780
cgtgagccaa cagttgcagc tggtgtcgac ccgagtggag caactttccc gccctcccca    3840
gtaaccgcaa aaattcaata aacagaattt aataaacagc acttgagaaa agtttaaact    3900
tgtggttgac tttattcctg gatagctggg gggagggaac ggcgggaacg gtaagacctg    3960
gtccatcgtt cccggtcgtt gagaacacg tggatttttt ccaagacccg atagaggtgg     4020
gtctgaacgt tgagatacat gggcatgagc ccgtctcggg ggtggaggta ggcccactgc    4080
agggcctcgt tttcagggg ggtgttgtaa atgatccagt cgtaggcccc ccgctgggcg     4140
tggtgctgga agatgtcctt cagcagcaag ctgatggcaa cgggaagacc cttggtgtag    4200
gtgttgacaa agcggttgag ttgggagggg tgcatgcggg gactgatgag gtgcattttg    4260
gcctggatct tgaggttggc tatgttgccg cccagatcgc gcctgggatt catgttatgc    4320
aagaccacca gcaccgagta accggtgcag cgggggaatt tgtcgtgcag cttggaaggg    4380
aaagcgtgga agaatttgga gacccctcgg tgcccgccta ggttttccat gcactcatcc    4440
atgatgatgg cgatgggccc ccgggaggca gcctgggcaa aaacgttgcg ggggtccgtg    4500
acatcgtagt tgtggtcctg ggtgagttca tcataggaca ttttgacaaa gcgcgggcag    4560
agggtcccag actggggaat gatggttcca tccggtccgg gggcgtagtt gccctcgcag    4620
atttgcattt cccaggcttt gatttcagag ggagggatca tgtcaacctg gggggcgatg    4680
aaaaaaatgg tctctgggc gggggtgatg agctgggtgg aaagcaggtt gcgcaagagc     4740
tgtgacttgc cgcagccggt gggcccgtag atgacagcta tgacgggttg cagggtgtag    4800
tttagagagc tacaactgcc atcatccttc aaaagcgggg ccacactgtt taaaagttct    4860
ctaacatgta agttttcccg cactaagtcc tgcaggagac gtgaccctcc tagggagaga    4920
agttcaggaa gcgaagcaaa gttttttaagt ggcttgaggc catcggccaa gggcaagttc    4980
```

```
ctgagagttt gactgagcag ttccagccgg tcccagagct cggttacgtg ctctacggca    5040
tctcgatcca gcagacctcc tcgtttcggg ggttggggcg gctctggctg tagggaatga    5100
ggcggtgggc gtccagctgg gccatggtgc ggtccctcca tgggcgcagg gttctcttca    5160
gggtggtctc ggtcacggtg aatgggtggg ccccgggctg ggcgctggcc agggtgcgct    5220
tgaggctgag gcggctggtg gcgaaccgtt gcttttcgtc tccctgcaag tcagccaaat    5280
agcaacggac catgagctca tagtccaggc tctctgcggc atgtcctttg gcgcgaagct    5340
tgcctttgga aacgtgcccg cagtttgagc agagcaagca ttttagcgcg tagagttttg    5400
gcgccaagaa cacggattcc ggggaataag catccccacc gcagttggag caaacggttt    5460
cgcattccac cagccaggtc agctgaggat cttttgggtc aaaaaccaag cgcccgccgt    5520
tttttttgat gcgcttccta cctcgggtct ccatgaggcg gtgcccgcgt tcggtgacga    5580
agaggctgtc ggtgtctccg tagacggagg tcagggcgcg ctcctccagg ggggtcccgc    5640
ggtcctcggc gtagagaaac tcgcaccact ctgacataaa cgcccgggtc caggctagga    5700
cgaatgaggc gatgtgggaa gggtaccggt cgttatcgat agggggtcg gttttttcca    5760 aggtgtgcag gcacatgtcc ccctcgtccg cttccaaaaa tgtgattggc ttgtaggtgt    5820
aagtcacgtg atcctgtcct tccgcggggg tataaaggg ggcgtttccc ccctcctcgt    5880
cactctcttc cggttcgctg tcgccaaagg ccagctgttg gggtacgtaa acgcgggtga    5940
aggcgggcat gacctgtgcg ctgaggttgt cagtttctat atacgaggaa gatttgatgg    6000
cgagcgcccc cgtggagatg cccttgaggt gctcggggcc catttggtca gaaaacacaa    6060
tctgtcggtt atcaagcttg gtggcaaaag accgtagag ggcgttggag agcaacttgg    6120
cgatggagcg ctgggtttgg ttttttttccc ggtcggcttt ttccttggcc gcgatgttga    6180
gctggacgta ctccctggcc acgcacttcc agccgggaaa acggccgtg cgctcgtccg    6240 gcaccagcct cacgctccat ccgcggttgt gcagggtgat gacgtcgatg ctggtggcca    6300
cctctccgcg caggggctcg ttggtccagc agaggcgacc gcccttgcga gagcagaagg    6360
ggggcagggg gtcaagcagg cgctcgtccg ggggtcggc gtcgatggta agatggcgg    6420 gcagcaggtg tttgtcaaag taatcgatct gatgcccggg gcaacgcagg gcggtttccc    6480
agtcccgcac cgccaaggcg cgctcgtatg gactgagggg ggcgcccag ggcatgggat    6540 gcgtcagggc cgaggcgtac atgccgcaga tgtcatagac gtaaaggggc tcctccagga    6600
cgccgaggta ggtggggtag cagcgccccc cgcggatgct ggcccgtacg tagtcgtaga    6660
gctcgtgcga gggggccaga aggtggcggc tgaggtgagc gcgctggggc ttttcatctc    6720
ggaagaggat ctgcctgaag atggcgtggg agttggagga gatggtgggc cgctgaaaaa    6780
tgttgaagcg ggcgtcgggc agacccacgg cctcgccgat aaagtgggcg taggactctt    6840
gcagcttttc caccagggag gcggtgacca gcacgtccag agcgcagtag tccagggttt    6900
cccgcacgat gtcataatgc tcttccttt tttccttcca gaggtctcgg ttgaagagat    6960
actcttcgcg gtctttccag tactcttgga gaggaaaccc gttttcgtct ccacggtaag    7020
agcccaacat gtaaaactgg ttgacggcct gatagggaca gcatcccttc tccacgggca    7080
gcgagtaggc cagggcggcc ttgcgcaggg aggtgtgagt cagggcaaag gtgtcgcgga    7140
ccataacttt tacaaactgg tacttaaagt cccggtcgtc gcacatgcct cgctcccagt    7200
ctgagtagtc tgtgcgcttt ttgtgcttgg ggttaggcag ggagtaggtg acgtcgttaa    7260
agaggatttt gccacatctg ggcataaagt tgcgagagat tctgaagggg ccgggcacct    7320
ccgagcggtt gttgatgact tgggcagcca ggagaatttc gtcgaagccg ttgatgttgt    7380
```

```
gccccacgac gtagaactct atgaaacgcg gagcgccgcg cagcaggggg cacttttcaa   7440
gttgctggaa agtaagttcc cgcggctcga cgccgtgttc cgtgcggctc cagtcctcca   7500
ccgggtttcg ctccacaaaa tcctgccaga tgtggtcgac tagcaagagc tgcagtcggt   7560
cgcgaaattc gcggaatttt ctgccgatgg cttgcttctg ggggttcaag caaaaaaagg   7620
tgtctgcgtg gtcgcgccag gcgtcccagc cgagctcgcg agccagattc agggccagca   7680
gcaccagagc cggctcaccg gtgattttca tgacgaggag aaagggcacc agctgttttc   7740
cgaacgcgcc catccaggtg taggtctcca cgtcgtaggt gagaaacaga cgttcggtcc   7800
gcgggtgcga tcccaggggg aaaaacttga tgggctgcca ccattgggag ctctgggcgt   7860
ggatgtgatg gaagtaaaag tcccggcggc gcgtggaaca ttcgtgctgg tttttgtaaa   7920
agcggccgca gtggtcgcag cgcgagacgg agtgaaggct gtgaatcagg tgaatcttgc   7980
gtcgctgagg gggccccaga gccaaaaagc ggagcgggaa cgaccgcgcg gccacttcgg   8040
cgtccgcagg caagatggat gagggttcca ccgttcccg cccgcggacc gaccagactt   8100
ccgccagctg cggcttcagt tcttgcacca gctctcgcag cgtttcgtcg ctgggcgaat   8160
cgtgaatacg gaagttgtcg ggtagaggcg ggaggcggtg gacttccagg aggtgtgtga   8220
gggccggcag gagatgcagg tggtacttga tttcccacgg atgacggtcg cgggcgtcca   8280
aggcgaagag atgaccgtgg ggccgcgcg ccaccagcgt tccgcggggg gtctttatcg   8340
gcggcgggga cgggctcccg gcggcagcgg cggctcggga cccgcgggca agtcgggcag   8400
cggcacgtcg gcgtggagct cgggcagggg ctggtgctgc gcgcggagct gactggcaaa   8460
ggctatcacc cggcgattga cgtcctggat ccggcggcgc tgcgtgaaga ccaccggacc   8520
cgtggtcttg aacctgaaag agagttcgac agaatcaatc tcggcatcgt taaccgcggc   8580
ctggcgcagg atttcggcca cgtccccgga gttgtcttga tacgcgattt ctgccatgaa   8640
ctggtcgatt tcctcttcct gcaagtctcc gtgaccggcg cgttcgacgg tggccgcgag   8700
atcgttggag atgcggccca tgagctggga aaaggcattg atgccgacct cgttccacac   8760
tcggctgtac accacctctc cgtgaacgtc gcgggcgcgc atcaccacct gggcgagatt   8820
gagttccacg tggcgggcga aaaccggata gtttcggagg cgctgataca gatagttgag   8880
ggtggtggcg gcgtgctcgg ccacaaaaaa atacatgatc cagcggcgga gggtcagctc   8940
gttgatgtcg cccagcgcct ccaggcgttc catggcctcg taaaagtcca cggcaaagtt   9000
gaaaaattgg ctgttcctgg ccgagaccgt gagctcttct tccaagagcc gaatgagatc   9060
cgccacggtg gccctgactt cgcgttcgaa agccccgggt gcctcctcca cctcttcctc   9120
ctcgacttct tcgaccgctt cgggcacctc ctcttcctcg accaccacct caggcggggc   9180
tcggcggcgc cggcggcgga cgggcaggcg gtcgacgaaa cgctcgatca tttccccccct   9240 ccgtcgacgc atggtctcgg tgacggcgcg accctgttcg cgaggacgca gggtgaaggc   9300
gccgccgccg agcggaggta acaggagat cgggggggcgg tcgtggggga gactgacggc   9360
gctaactatg catctgatca atgtttgcgt agtgacctcg ggtcggagcg agctcagcgc   9420
ttgaaaatcc acgggatcgg aaaaccgttc caggaacgcg tctagccaat cacagtcgca   9480
aggtaagctg aggaccgtct cggggggcttg tctgttctgt cttcccgcgg tggtgctgct   9540
gatgaggtag ttgaagtagg cgctcttgag gcggcggatg tggacagga gaaccacgtc   9600 tttgcgccca gcttgctgta tccgcaggcg gtcggccatg ccccacactt ctccttgaca   9660
gcggcggagg tccttgtagt attcttgcat cagcctttcc acgggcacct cgtcttcttc   9720
ttccgctcgg ccggacgaga gccgcgtcag gccgtacccg cgctgcccct gtggttggag   9780
```

-continued

```
cagggccagg tcggccacga cgcgctcggc cagcacggcc tgctggatgc gggtgagggt    9840
gtcctgaaag tcgtcgagat ccacaaagcg gtggtacgcg ccagtgttga tggtgtaggt    9900
gcagttgctc atgacggacc agtttacggt ctgggtgcca tggcccacgg tttccaggta    9960
gcggagacgc gagtaggccc gcgtctcgaa gatgtagtcg ttgcaggtcc gcagcaggta   10020
ctggtagccc accagcagat gcggcggcgg ctggcggtag aggggccacc gctgggtggc   10080
gggggcgttg ggggcgagat cttccaacat gaggcggtga tagccgtaga tgtagcgcga   10140
catccaagtg atgccgctgg ccgtggtgct ggcgcgggcg tagtcgcgaa cgcggttcca   10200
gatgtttcgc agcggctgga agtactcgat ggtggggcga ctctgccccg tgaggcgggc   10260
gcagtcggcg atgctctacg gggaaaaaga agggccagtg aacaaccgcc ttccgtagcc   10320
ggaggagaac gcaagggggt caaagaccac cgaggctcgg gttcgaaacc cggtggcgg    10380
cccgaatacg gagggcggtt ttttgctttt ttctcagatg catcccgtgc tgcggcagat   10440
gcgtccgaac gcggggtccc agtccccggc ggtgcctgcg gccgtgacgg cggcttctac   10500
ggccacgtcg cgctccaccc cgcctaccac ggcccaggcg gcggtggctc tgcgcggcgc   10560
aggggaaccc gaagcagagg cggtgttgga cgtggaggag ggccagggggt tggctcggct   10620
gggggccctg agtcccgagc ggcacccgcg cgtggctctg aagcgcgacg cggcggaggc   10680
gtacgtgccg cggagcaatc tgtttcgcga ccgcagcggc gaggaggccg aggagatgcg   10740
agacttgcgt tttcgggcgg ggagggagtt gcgtcacggg ctggaccggc agagggttct   10800
gagagaggag gactttgagg cggacagacg cacgggggtg agtcccgcgc gggctcacgt   10860
ggcggccgcc aacctggtga gcgcgtacga gcagacggtc aaggaggaga tgaacttcca   10920
gaagagcttc aatcatcacg tgcgcacgct gattgcgcgc gaagaggtgg ccatcggcct   10980
catgcatctg tgggattttg tggaggcgta cgttcagaac cccagcagca agccgctgac   11040
ggctcagctg ttcctcatcg tgcaacatag tcgagacaac gaaacgttca gggaggccat   11100
gctgaacatt gcagagcctg aggggcgctg gctcttggat ctcattaaca tcttgcagag   11160
tatcgtagtg caggagcgct cgctgagcct ggccgacaag gtggctgcca tcaactacag   11220
catgctgtcg ctgggcaaat tttacgcccg caagatctac aagtctccgt tcgtccccat   11280
agacaaggag gtgaagatag acagctttta catgcgcatg gcgctcaagg tgctgactct   11340
aagcgacgac ctgggggtgt accgcaacga ccgcatacac aaggcggtga gcgccagccg   11400
ccggcgcgag ctgagcgacc gcgagctttt gcacagcctg catcgggcgt tgactggtgc   11460
cggcagcgcc gaggcggccg agtactttga cgccggagcg gacttgcgct ggcagccatc   11520
ccgacgcgcg ctgaggcgg ctggcgtcgg ggagtacggg gtcgaggacg acgatgaagc   11580
ggacgacgag ttgggcattg acttgtagcc gttttcgtt agatatgtcg gcgaacgagc   11640
cgtctgcggc cgccatggtg acggcggcgg gcgcgcccca ggaccccggcc acgcgcgcgg   11700
cgctgcagag tcagccttcc ggagtgacgc ccgcggacga ctggtccgag gccatgcgtc   11760
gcatcctggc gctgacggcg cgcaaccccg aggcttttcg gcagcagccg caggcaaacc   11820
ggtttgcggc cattttggaa gcggtggtgc cctccagacc caaccccacc cacgaaaagg   11880
tgctggccat cgtcaacgcc ctggcggaga ccaaggccat ccgcccagac gaggccgggc   11940
aggtttacaa cgcgctgcta gaaagggtgg gacgctacaa cagctccaac gtgcagacca   12000
atctggaccg cttggtgacg gacgtgaagg aggccgtagc ccagcgagag cggttttca    12060
aggaagccaa tctgggctcg ctggtggccc tcaacgcctt cctgagcacg ctgccggcga   12120
acgtgccccg cggtcaggag gactacgtga actttctgag cgccctccgc ctgatggtgg   12180
```

-continued

```
ccgaggtgcc gcagagcgag gtgtaccagt ctggccccaa ctactacttc cagacctccc   12240
ggcagggcct gcagacggta aacctgacgc aggcctttca gaacctgcag ggcctttggg   12300
gggtgcgcgc tccgctgggc gaccgcagca cggtgtccag cctgctgacc cccaatgccc   12360
ggctgctctt gcttctcatt gctccgttca ccgacagcgg ttccatcagc cgcgactctt   12420
acctgggaca cctgctcacc ctgtaccggg aggccatcgg gcaggcgcgg gtggacgagc   12480
agacgtacca ggaaatcacc agcgtgagcc gcgcgctggg gcaggaggac acgggcagct   12540
tggaggcgac tctgaacttc ctgctgacca accggcggca gcgcctacct ccccagtacg   12600
cgctgaacgc ggaggaggag cgcatcctgc gtttcgtgca gcagagcacc cgcgctgtact  12660 tgatgcggga aggcgcctct cccagcgctt cgctggacat gacggcggcc aacatggagc   12720
catcgttcta cgccgccaac cgtcccttcg tcaaccggct aatggactat ttgcatcggg   12780
cggcggccct gaacccggaa tactttacta acgtcatcct gaacgaccgt tggctgccac   12840
ctcccggctt ctacacgggg gagttcgacc tcccggaggc caacgacggt ttcatgtggg   12900
acgacgtgga cagcgtgttc ctgcccggca agaaggaggc gggtgactct cagagccacc   12960
gcgcgagcct cgcagacctg ggggcgaccg ggcccgcgtc tccgctgcct cgcctgccga   13020
gcgccagcag cgccagcgtg gggcgggtga gccgtccgcg cctcagcggt gaggaggact   13080 ggtgaacga tccgctgctc cgtccggccc gcaacaaaaa cttccccaac aacgggatag    13140
aggatttggt agacaaaatg aaccgttgga agacgtatgc ccaggagcat cgggagtggc    13200
aggcgaggca acccatgggc cctgttctgc cgccctctcg cgcccgcgc agggacgaag     13260 acgccgacga ttcagccgat gacagcagcg tgttggatct gggcgggagc gggaaccccct   13320 ttgcccacct gcaacctcgc ggcgtgggtc ggcggtggcg ctaggaaaaa aaattattaa    13380
aagcacttac cagagccatg gtaagaagag caacaaaggt gtgtcctgct ttcttcccgg    13440
```

| | | | | | | | | | | | | | |
|---|---|---|---|---|---|---|---|---|---|---|---|---|---|
| tagcaaa | atg | cgt | cgg | gcg | gtg | gca | gtt | ccc | tcc | gcg | gca | atg | gcg tta | 13489 |
| | Met | Arg | Arg | Ala | Val | Ala | Val | Pro | Ser | Ala | Ala | Met | Ala Leu | |
| | 1 | | | 5 | | | | | 10 | | | | | | ggc ccg ccc cct tct tac gaa agc gtg atg gca gcg gcc acc ctg caa    13537
Gly Pro Pro Pro Ser Tyr Glu Ser Val Met Ala Ala Ala Thr Leu Gln
15              20                  25                  30 gcg ccg ttg gag aat cct tac gtg ccg ccg cga tac ctg gag cct acg    13585
Ala Pro Leu Glu Asn Pro Tyr Val Pro Pro Arg Tyr Leu Glu Pro Thr
                35                  40                  45 ggc ggg aga aac agc att cgt tac tcg gag ctg acg ccc ctg tac gac    13633
Gly Gly Arg Asn Ser Ile Arg Tyr Ser Glu Leu Thr Pro Leu Tyr Asp
            50                  55                  60 acc acc cgc ctg tac ctg gtg gac aac aag tca gca gat atc gcc acc    13681
Thr Thr Arg Leu Tyr Leu Val Asp Asn Lys Ser Ala Asp Ile Ala Thr
        65                  70                  75 ttg aac tac cag aac gac cac agc aac ttt ctc acg tcc gtg gtg cag    13729
Leu Asn Tyr Gln Asn Asp His Ser Asn Phe Leu Thr Ser Val Val Gln
    80                  85                  90 aac agc gac tac acg ccc gcc gaa gcg agc acg cag acc att aac ttg    13777
Asn Ser Asp Tyr Thr Pro Ala Glu Ala Ser Thr Gln Thr Ile Asn Leu
95                  100                 105                 110 gac gac cgc tcg cgc tgg ggc ggg gac ttg aaa acc att ctg cac act    13825
Asp Asp Arg Ser Arg Trp Gly Gly Asp Leu Lys Thr Ile Leu His Thr
                115                 120                 125 aac atg ccc aac gtg aac gag ttc atg ttt acc aac tcg ttc agg gct    13873
Asn Met Pro Asn Val Asn Glu Phe Met Phe Thr Asn Ser Phe Arg Ala
            130                 135                 140 aaa ctt atg gtg gcg cac gag gcc gac aag gac ccg gtt tat gag tgg    13921
Lys Leu Met Val Ala His Glu Ala Asp Lys Asp Pro Val Tyr Glu Trp

```
                        -continued

Lys Leu Met Val Ala His Glu Ala Asp Lys Asp Pro Val Tyr Glu Trp
        145                 150                 155 gtg cag ctg acg ctg ccg gag ggg aac ttt tca gag att atg acc ata      13969
Val Gln Leu Thr Leu Pro Glu Gly Asn Phe Ser Glu Ile Met Thr Ile
    160                 165                 170 gac ctg atg aac aac gcc att atc gac cac tac ctg gcg gta gcc aga      14017
Asp Leu Met Asn Asn Ala Ile Ile Asp His Tyr Leu Ala Val Ala Arg
175                 180                 185                 190 cag cag ggg gtg aaa gaa agc gag atc ggc gtc aag ttt gac acg cgc      14065
Gln Gln Gly Val Lys Glu Ser Glu Ile Gly Val Lys Phe Asp Thr Arg
                195                 200                 205 aac ttt cgt ctg ggc tgg gac ccg gag acg ggg ctt gtg atg ccg ggg      14113
Asn Phe Arg Leu Gly Trp Asp Pro Glu Thr Gly Leu Val Met Pro Gly
            210                 215                 220 gtg tac acg aac gaa gct ttc cat ccc gac gtg gtc ctc ttg ccg ggc      14161
Val Tyr Thr Asn Glu Ala Phe His Pro Asp Val Val Leu Leu Pro Gly
        225                 230                 235 tgc ggg gtg gac ttt acc tac agc cgg tta aac aac ctg cta ggc ata      14209
Cys Gly Val Asp Phe Thr Tyr Ser Arg Leu Asn Asn Leu Leu Gly Ile
    240                 245                 250 cgc aag aga atg ccc ttt cag gaa ggg ttt cag atc ctg tac gag gac      14257
Arg Lys Arg Met Pro Phe Gln Glu Gly Phe Gln Ile Leu Tyr Glu Asp
255                 260                 265                 270 ctg gag ggc ggt aac atc ccg gcc ctg ctg gac gtg ccg gcg tac gag      14305
Leu Glu Gly Gly Asn Ile Pro Ala Leu Leu Asp Val Pro Ala Tyr Glu
                275                 280                 285 gag agc atc gcc aac gca agg gag gcg gcg atc agg ggc gat aat ttc      14353
Glu Ser Ile Ala Asn Ala Arg Glu Ala Ala Ile Arg Gly Asp Asn Phe
            290                 295                 300 gcg gcg cag ccc cag gcg gct cca acc ata aaa ccc gtt ttg gaa gac      14401
Ala Ala Gln Pro Gln Ala Ala Pro Thr Ile Lys Pro Val Leu Glu Asp
        305                 310                 315 tcc aaa ggg cgg agc tac aac gta ata gcc aac acc aac aac acg gct      14449
Ser Lys Gly Arg Ser Tyr Asn Val Ile Ala Asn Thr Asn Asn Thr Ala
    320                 325                 330 tac agg agc tgg tat ctg gct tat aac tac ggc gac ccg gag aag ggg      14497
Tyr Arg Ser Trp Tyr Leu Ala Tyr Asn Tyr Gly Asp Pro Glu Lys Gly
335                 340                 345                 350 gtt agg gcc tgg acc ctg ctc acc act ccg gac gtg acg tgc ggt tca      14545
Val Arg Ala Trp Thr Leu Leu Thr Thr Pro Asp Val Thr Cys Gly Ser
                355                 360                 365 gag cag gtc tac tgg tcg ctg cct gac atg tac gtg gac cct gtg acg      14593
Glu Gln Val Tyr Trp Ser Leu Pro Asp Met Tyr Val Asp Pro Val Thr
            370                 375                 380 ttt cgc tcc acg cag caa gtt agc aac tac cca gtg gtg gga gcg gag      14641
Phe Arg Ser Thr Gln Gln Val Ser Asn Tyr Pro Val Val Gly Ala Glu
        385                 390                 395 ctt atg ccg att cac agc aag agc ttt tac aac gag cag gcc gtc tac      14689
Leu Met Pro Ile His Ser Lys Ser Phe Tyr Asn Glu Gln Ala Val Tyr
    400                 405                 410 tca cag ctc att cgt cag acc acc gcc cta acg cac gtt ttc aac cgc      14737
Ser Gln Leu Ile Arg Gln Thr Thr Ala Leu Thr His Val Phe Asn Arg
415                 420                 425                 430 ttc ccc gag aac caa atc cta gtg cga cct cca gcg ccc acc atc acc      14785
Phe Pro Glu Asn Gln Ile Leu Val Arg Pro Pro Ala Pro Thr Ile Thr
                435                 440                 445 acc gtc agc gag aac gtg ccc gct cta acc gat cac ggg acg ctg cct      14833
Thr Val Ser Glu Asn Val Pro Ala Leu Thr Asp His Gly Thr Leu Pro
            450                 455                 460 ttg cag aac agc atc cgc gga gtt cag cga gtt acc atc acg gac gcc      14881
```

```
Leu Gln Asn Ser Ile Arg Gly Val Gln Arg Val Thr Ile Thr Asp Ala
        465                 470                 475 cgt cgt cgg acc tgt ccc tac gtc tac aaa gcc ttg gga atc gtg gcc    14929
Arg Arg Arg Thr Cys Pro Tyr Val Tyr Lys Ala Leu Gly Ile Val Ala
        480                 485                 490 ccg cgc gtc ctg tcg agt cgc act ttc tag atgtccatcc tcatctctcc     14979
Pro Arg Val Leu Ser Ser Arg Thr Phe
495                 500 cagcaacaat accggttggg gtctgggcgt gaccaaaatg tacggaggcg ccaaacgacg   15039
gtccccacaa catcccgtgc gagtgcgcgg gcactttaga gccccatggg ggtcgcacac   15099
gcgcgggcgc accggccgaa ccaccgtcga cgacgtgatc gatagcgtgg tggccgacgc   15159
ccgcaactac cagcccgctc gatccacggt ggacgaagtc atcgacgcg tggtggccga    15219 cgccagggcc tacgcccgca gaaagtctcg tctgcgccgc cgccgttcgc taaagcgccc   15279
cacggccgcc atgaaagccg ctcgctctct gctgcgtcgc gcacgtatcg tgggtcgccg   15339
cgccgccaga cgcgcagccg ccaacgccgc cgccggccga gtgcgccgcc gggccgccca   15399
gcaggccgcc gccgccatct ccagtctatc cgccccccga cgcgggaatg tgtactgggt   15459
cagggactcg gccaccggcg tgcgagttcc cgtgagaacc cgtcctcctc gtccctgaat   15519
aaaaagttct aagcccaatc ggtgttccgt tgtgtgttca gctcgtcatg accaaacgca   15579
agtttaaaga ggagctgctg caagcgctgg tccccgaaat ctatgcgccg cgcccggacg   15639
tgaaaccgcg tcgcgtgaaa cgcgtgaaga agcaggaaaa gctagagaca aagaggagg    15699 cggtggcgtt gggagacggg gaggtggagt ttgtgcgctc gttcgcgccg cgtcggcgag   15759
tgaattggaa ggggcgcaag gtgcaacggg tgctgcgtcc cggcacggtg gtgtctttca   15819
ccccgggtga aaaatccgcc tggaagggca taaagcgcgt gtacgatgag gtgtacgggg   15879
acgaagacat tctggagcag gcgctggata aagcggggga gtttgcttac ggcaagaggg   15939
cgaggacggg cgagatcgcc atcccgctgg acacttccaa ccccacccc agtctgaaac    15999 ccgtgacgct gcaacaggtg ttgccggtga gcgcccctc gcgacgcggc ataaacgcg     16059 agggcggcga gctgcagccc accatgcagc tcctggttcc caagaggcag aaactagagg   16119
acgtactgga catgataaaa atggagcccg acgtgcagcc cgatattaaa atccgtccca   16179
tcaaagaagt ggcgccggga atgggcgtgc agaccgtgga catccagatt cccatgacca   16239
gcgccgcaca ggcggtagag gccatgcaga ccgacgtggg gatgatgacg gacctgcccg   16299
cagctgctgc cgccgtggcc agcgccgcga cgcaaacgga agccggcatg cagaccgacc   16359
cgtggacgga ggcgcccgtg cagccggcca gaagacgcgt cagacggacg tacggccccg   16419
tttctggcat aatgccggag tacgcgctgc atccttccat catccccacc ccggctacc    16479 gggggcgcac ctaccgtccg cgacgcagca ccactcgccg ccgtcgccgc acggcacgag   16539
tcgccaccgc cagagtgaga cgcgtaacga cacgtcgcgg ccgccgcttg accctgcccg   16599 tggtcgcta ccatcccagc attctttaaa aaaccgctcc tacgttgcag atgggcaagc    16659
ttacttgtcg actccgtatg gccgtgcccg gctaccgagg aagatcccgc cgacgacgga   16719 cttgggagg cagcggtttg cgccgccgtc gggcggttca ccggcgcctc aagggaggca    16779
ttctgccggc cctgatcccc ataatcgccg cagccatcgg ggccattccc ggaatcgcca   16839
gcgtagcggt gcaggctagc cagcgccact gattttacta accctgtcgg tcgcgccgtc   16899
tctttcggca gactcaacgc ccagcatgga agacatcaat ttctcctctc tggccccgcg   16959
gcacggcacg cggccgtata tggggacgtg gagcgagatc ggcacgaacc agatgaacgg   17019
gggcgctttc aattggagcg gtgtgtggag cggcttgaaa aatttcggtt ccactctgaa   17079
```

-continued

```
aacttacggc aaccgggtgt ggaactccag cacggggcag atgctgaggg acaagctaaa     17139
ggacacgcag tttcagcaaa aggtggtgga cggcatcgct tcgggcctca acggcgccgt     17199
cgacctggcc aaccaggcca ttcaaaagga aattaacagc cgcctggagc cgcggccgca     17259
ggtggaggag aacctgcccc ctctggaggc gctgccccc  aagggagaga agcgcccgcg     17319
gcccgacatg gaggagacgc tagttactaa gagcgaggag ccgccatcat acgaggaggc     17379
ggtgggtagc tcgcagctgc cgtccctcac gctgaagccc accacctatc ccatgaccaa     17439
gcccatcgcc tccatggcgc gccccgtggg agtcgacccg cccatcgacg cggtggccac     17499
tttggacctg ccgcgccccg aacccggcaa ccgcgtgcct cccgtcccca tcgctccgcc     17559
ggtttctcgc cccgccatcc gccccgtcgc cgtggccact ccccgctatc cgagccgcaa     17619
cgccaactgg cagaccaccc tcaacagtat tgtcggactg ggggtgaagt ctctgaagcg     17679
ccgtcgctgt ttttaaagca caatttatta aacgagtagc cctgtcttaa tccatcgttg     17739
tatgtgtgcc tatatcacgc gttcagagcc tgaccgtccg tcaag atg gcc act ccg     17796
                                                Met Ala Thr Pro
                                                    505 tcg atg atg ccg cag tgg tcg tac atg cac atc gcc ggg cag gac gcc       17844
Ser Met Met Pro Gln Trp Ser Tyr Met His Ile Ala Gly Gln Asp Ala
    510                 515                 520 tcg gag tac ctg agc ccg ggt ctg gtg cag ttt gcc cgt gcg acg gaa       17892
Ser Glu Tyr Leu Ser Pro Gly Leu Val Gln Phe Ala Arg Ala Thr Glu
525                 530                 535 acc tac ttc tca ctg ggc aac aag ttc agg aac ccc acc gtg gcg ccc       17940
Thr Tyr Phe Ser Leu Gly Asn Lys Phe Arg Asn Pro Thr Val Ala Pro
540                 545                 550                 555 acc cac gac gtc acc acc gat cgg tcc cag cga ctg aca atc cgc ttc       17988
Thr His Asp Val Thr Thr Asp Arg Ser Gln Arg Leu Thr Ile Arg Phe
                560                 565                 570 gtc ccc gtg gac aag gaa gac acc gct tac tcc tac aaa acc cgc ttc       18036
Val Pro Val Asp Lys Glu Asp Thr Ala Tyr Ser Tyr Lys Thr Arg Phe
            575                 580                 585 acg ctg gcc gtg ggc gac aac cgg gtg cta gac atg gcc agt acc tac       18084
Thr Leu Ala Val Gly Asp Asn Arg Val Leu Asp Met Ala Ser Thr Tyr
        590                 595                 600 ttt gac atc cgc ggc gtg atc gac cgc gga cct agc ttc aag cct tac       18132
Phe Asp Ile Arg Gly Val Ile Asp Arg Gly Pro Ser Phe Lys Pro Tyr
    605                 610                 615 tcc ggc acg gct tac aac tca ctg gct ccc aaa ggg gcg ccc aac aac       18180
Ser Gly Thr Ala Tyr Asn Ser Leu Ala Pro Lys Gly Ala Pro Asn Asn
620                 625                 630                 635 agc caa tgg aac gcc aca gat aac ggg aac aag cca gtg tgt ttt gct       18228
Ser Gln Trp Asn Ala Thr Asp Asn Gly Asn Lys Pro Val Cys Phe Ala
                640                 645                 650 cag gca gct ttt ata ggt caa agc att aca aaa gac gga gtg caa ata       18276
Gln Ala Ala Phe Ile Gly Gln Ser Ile Thr Lys Asp Gly Val Gln Ile
            655                 660                 665 cag aac tca gaa aat caa cag gct gct gcc gac aaa act tac caa cca       18324
Gln Asn Ser Glu Asn Gln Gln Ala Ala Ala Asp Lys Thr Tyr Gln Pro
        670                 675                 680 gag cct caa att gga gtt tcc acc tgg gat acc aac gtt acc agt aac       18372
Glu Pro Gln Ile Gly Val Ser Thr Trp Asp Thr Asn Val Thr Ser Asn
    685                 690                 695 gct gcc gga cga gtg tta aaa gcc acc act ccc atg ctg cca tgt tac       18420
Ala Ala Gly Arg Val Leu Lys Ala Thr Thr Pro Met Leu Pro Cys Tyr
700                 705                 710                 715 ggt tca tat gcc aat ccc act aat cca aac ggg ggt cag gca aaa aca       18468
```

| | | |
|---|---|---|
| Gly Ser Tyr Ala Asn Pro Thr Asn Pro Asn Gly Gln Ala Lys Thr<br>720 725 730 | | |
| gaa gga gac att tcg cta aac ttt ttc aca aca act gcg gca gca gac<br>Glu Gly Asp Ile Ser Leu Asn Phe Phe Thr Thr Thr Ala Ala Ala Asp<br>735 740 745 | | 18516 |
| aat aat ccc aaa gtg gtt ctt tac agc gaa gat gta aac ctt caa gcc<br>Asn Asn Pro Lys Val Val Leu Tyr Ser Glu Asp Val Asn Leu Gln Ala<br>750 755 760 | | 18564 |
| ccc gat act cac tta gta tat aag cca acg gtg gga gaa aac gtt atc<br>Pro Asp Thr His Leu Val Tyr Lys Pro Thr Val Gly Glu Asn Val Ile<br>765 770 775 | | 18612 |
| gcc gca gaa gcc ctg cta acg cag cag gcg tgt ccc aac aga gca aac<br>Ala Ala Glu Ala Leu Leu Thr Gln Gln Ala Cys Pro Asn Arg Ala Asn<br>780 785 790 795 | | 18660 |
| tac ata ggt ttc cga gat aac ttt atc ggt tta atg tat tat aac agc<br>Tyr Ile Gly Phe Arg Asp Asn Phe Ile Gly Leu Met Tyr Tyr Asn Ser<br>800 805 810 | | 18708 |
| aca ggg aac atg gga gtt ctg gca ggt cag gcc tcg cag tta aac gca<br>Thr Gly Asn Met Gly Val Leu Ala Gly Gln Ala Ser Gln Leu Asn Ala<br>815 820 825 | | 18756 |
| gtt gta gac ctg caa gat cga aac acg gaa ctg tcc tat cag cta atg<br>Val Val Asp Leu Gln Asp Arg Asn Thr Glu Leu Ser Tyr Gln Leu Met<br>830 835 840 | | 18804 |
| cta gat gct ctg ggt gac aga act cga tat ttc tca atg tgg aat cag<br>Leu Asp Ala Leu Gly Asp Arg Thr Arg Tyr Phe Ser Met Trp Asn Gln<br>845 850 855 | | 18852 |
| gcc gtg gac agc tac gat cca gac gtt agg att atc gag aac cat ggg<br>Ala Val Asp Ser Tyr Asp Pro Asp Val Arg Ile Ile Glu Asn His Gly<br>860 865 870 875 | | 18900 |
| gtg gaa gac gag ctg ccc aat tac tgt ttt cca ctc cca ggc atg ggt<br>Val Glu Asp Glu Leu Pro Asn Tyr Cys Phe Pro Leu Pro Gly Met Gly<br>880 885 890 | | 18948 |
| att ttt aac tcc tac aag ggg gta aaa cca caa aat ggc ggt aat ggt<br>Ile Phe Asn Ser Tyr Lys Gly Val Lys Pro Gln Asn Gly Gly Asn Gly<br>895 900 905 | | 18996 |
| aac tgg gaa gca aac ggg gac cta tca aat gcc aat gag atc gct tta<br>Asn Trp Glu Ala Asn Gly Asp Leu Ser Asn Ala Asn Glu Ile Ala Leu<br>910 915 920 | | 19044 |
| gga aac att ttt gcc atg gaa att aac ctc cac gca aac ctg tgg cgc<br>Gly Asn Ile Phe Ala Met Glu Ile Asn Leu His Ala Asn Leu Trp Arg<br>925 930 935 | | 19092 |
| agc ttc ttg tac agc aat gtg gcg ctg tac ctg cca gac agc tat aaa<br>Ser Phe Leu Tyr Ser Asn Val Ala Leu Tyr Leu Pro Asp Ser Tyr Lys<br>940 945 950 955 | | 19140 |
| ttc act ccc gct aac atc act ctg ccc gcc aac caa aac acc tac gag<br>Phe Thr Pro Ala Asn Ile Thr Leu Pro Ala Asn Gln Asn Thr Tyr Glu<br>960 965 970 | | 19188 |
| tat atc aac ggg cgc gtc act tct cca acc ctg gtg gac acc ttt gtt<br>Tyr Ile Asn Gly Arg Val Thr Ser Pro Thr Leu Val Asp Thr Phe Val<br>975 980 985 | | 19236 |
| aac att gga gcc cga tgg tcg ccg gat ccc atg gac aac gtc aac ccc<br>Asn Ile Gly Ala Arg Trp Ser Pro Asp Pro Met Asp Asn Val Asn Pro<br>990 995 1000 | | 19284 |
| ttt aac cat cac cgg aac gcg ggc ctc cgt tac cgc tcc atg ctg<br>Phe Asn His His Arg Asn Ala Gly Leu Arg Tyr Arg Ser Met Leu<br>1005 1010 1015 | | 19329 |
| ctg gga aat gga cgc gtg gtg cct ttc cac ata caa gtg ccg caa<br>Leu Gly Asn Gly Arg Val Val Pro Phe His Ile Gln Val Pro Gln<br>1020 1025 1030 | | 19374 |
| aaa ttt ttc gcg att aag aac ctc ctg ctt ttg ccc ggc tcc tac<br>| | 19419 |

```
                -continued

Lys Phe Phe Ala Ile Lys Asn Leu Leu Leu Leu Pro Gly Ser Tyr
    1035                1040                1045 act tac gag tgg agc ttc aga aaa gac gtg aac atg att ctg cag        19464
Thr Tyr Glu Trp Ser Phe Arg Lys Asp Val Asn Met Ile Leu Gln
1050                1055                1060 agc acc ctg ggc aat gat ctt cga gtg gac ggg gcc agc gtc cgc        19509
Ser Thr Leu Gly Asn Asp Leu Arg Val Asp Gly Ala Ser Val Arg
    1065                1070                1075 att gac agc gtc aac ttg tac gcc aac ttt ttc ccc atg gcg cac        19554
Ile Asp Ser Val Asn Leu Tyr Ala Asn Phe Phe Pro Met Ala His
    1080                1085                1090 aac acc gct tct acc ttg gaa gcc atg ctg cga aac gac acc aac        19599
Asn Thr Ala Ser Thr Leu Glu Ala Met Leu Arg Asn Asp Thr Asn
    1095                1100                1105 gac cag tcg ttt aac gac tac ctc agc gcg gcc aac atg ctt tat        19644
Asp Gln Ser Phe Asn Asp Tyr Leu Ser Ala Ala Asn Met Leu Tyr
    1110                1115                1120 ccc att ccg gcc aac gcc acc aac gtt ccc att tcc att ccc tcc        19689
Pro Ile Pro Ala Asn Ala Thr Asn Val Pro Ile Ser Ile Pro Ser
    1125                1130                1135 cgc aac tgg gcg gcc ttc cgg gga tgg agc ttc acc cgc ctt aaa        19734
Arg Asn Trp Ala Ala Phe Arg Gly Trp Ser Phe Thr Arg Leu Lys
    1140                1145                1150 gcc aag gaa acg cct tcc ttg ggc tcc ggc ttt gac ccc tac ttt        19779
Ala Lys Glu Thr Pro Ser Leu Gly Ser Gly Phe Asp Pro Tyr Phe
    1155                1160                1165 gtg tac tca ggc acc att cct tac ctg gac ggc agc ttt tac ctc        19824
Val Tyr Ser Gly Thr Ile Pro Tyr Leu Asp Gly Ser Phe Tyr Leu
    1170                1175                1180 aac cac act ttc aaa cgt ctg tcc atc atg ttc gat tct tcc gta        19869
Asn His Thr Phe Lys Arg Leu Ser Ile Met Phe Asp Ser Ser Val
    1185                1190                1195 agt tgg ccg ggc aac gac cgc ctc ctg acg ccg aac gag ttc gaa        19914
Ser Trp Pro Gly Asn Asp Arg Leu Leu Thr Pro Asn Glu Phe Glu
    1200                1205                1210 att aag cgc att gtg gac ggg gaa ggc tac aac gtg gct caa agt        19959
Ile Lys Arg Ile Val Asp Gly Glu Gly Tyr Asn Val Ala Gln Ser
    1215                1220                1225 aac atg acc aaa gac tgg ttt tta att caa atg ctc agc cac tac        20004
Asn Met Thr Lys Asp Trp Phe Leu Ile Gln Met Leu Ser His Tyr
    1230                1235                1240 aac atc ggc tac caa ggc ttc tat gtt ccc gag ggc tac aag gat        20049
Asn Ile Gly Tyr Gln Gly Phe Tyr Val Pro Glu Gly Tyr Lys Asp
    1245                1250                1255 cgg atg tat tct ttc ttc cga aac ttt cag ccc atg agc cgc cag        20094
Arg Met Tyr Ser Phe Phe Arg Asn Phe Gln Pro Met Ser Arg Gln
    1260                1265                1270 gtg ccg gat ccc acc gct gcc ggc tat caa gcc gtt ccc ctg ccc        20139
Val Pro Asp Pro Thr Ala Ala Gly Tyr Gln Ala Val Pro Leu Pro
    1275                1280                1285 aga caa cac aac aac tcg ggc ttt gtg ggg tac atg ggc ccg acc        20184
Arg Gln His Asn Asn Ser Gly Phe Val Gly Tyr Met Gly Pro Thr
    1290                1295                1300 atg cgc gaa gga cag cca tac ccg gcc aac tac ccc tat ccc ctg        20229
Met Arg Glu Gly Gln Pro Tyr Pro Ala Asn Tyr Pro Tyr Pro Leu
    1305                1310                1315 atc ggc gct acc gcc gtc ccc gcc att acc cag aaa aag ttt ttg        20274
Ile Gly Ala Thr Ala Val Pro Ala Ile Thr Gln Lys Lys Phe Leu
    1320                1325                1330 tgc gac cgc gtc atg tgg cgc ata cct ttt tcc agc aac ttt atg        20319
```

| | | | | | | | | | | | | |
|---|---|---|---|---|---|---|---|---|---|---|---|---|
| Cys | Asp | Arg | Val | Met | Trp | Arg | Ile | Pro | Phe | Ser | Ser | Asn Phe Met |
| 1335 | | | | 1340 | | | | 1345 | | | | |

| | | | | | | | | | | | | |
|---|---|---|---|---|---|---|---|---|---|---|---|---|
| tca | atg | ggg | gcc | ctg | acc | gac | ctc | gga | cag | aac | atg | ctt tac gct | 20364 |
| Ser | Met | Gly | Ala | Leu | Thr | Asp | Leu | Gly | Gln | Asn | Met | Leu Tyr Ala |
| | 1350 | | | | | 1355 | | | | | 1360 | |

| aac | tcc | gcc | cat | gcc | ctg | gat | atg | act | ttt | gag | gtg | gac ccc atg | 20409 |
|---|---|---|---|---|---|---|---|---|---|---|---|---|---|
| Asn | Ser | Ala | His | Ala | Leu | Asp | Met | Thr | Phe | Glu | Val | Asp Pro Met |
| 1365 | | | | | 1370 | | | | | 1375 | | |

| aac | gag | ccc | acg | ttg | ctg | tac | atg | ctt | ttt | gag | gtg | ttc gac gtg | 20454 |
|---|---|---|---|---|---|---|---|---|---|---|---|---|---|
| Asn | Glu | Pro | Thr | Leu | Leu | Tyr | Met | Leu | Phe | Glu | Val | Phe Asp Val |
| 1380 | | | | | 1385 | | | | | 1390 | | |

| gtc | aga | gtg | cac | cag | ccg | cac | cgc | ggt | att | atc | gag | gcc gtg tac | 20499 |
|---|---|---|---|---|---|---|---|---|---|---|---|---|---|
| Val | Arg | Val | His | Gln | Pro | His | Arg | Gly | Ile | Ile | Glu | Ala Val Tyr |
| 1395 | | | | | 1400 | | | | | 1405 | | |

| ctg | cgc | acc | ccc | ttc | tct | gcg | ggc | aat | gcc | acc | aca | taa gccgctgaac | 20548 |
|---|---|---|---|---|---|---|---|---|---|---|---|---|---|
| Leu | Arg | Thr | Pro | Phe | Ser | Ala | Gly | Asn | Ala | Thr | Thr | |
| 1410 | | | | | 1415 | | | | | 1420 | | |

```
tagctggttt ttaccccaga tcccatgggc tccacggaag acgaactgcg ggccattgtg    20608
cgagacctgg gctgcggacc ctacttcctg ggcacctttg acaagcggtt cccgggttc     20668
gtgtctcctc gcaaactcgc gtgcgcgatc gtgaataccg ccggccgaga accggagga     20728
gagcattggc tagctctggg ctggaacccc cgctcgtcca cgttttcct gttcgacccc    20788
tttggctttt cagaccaacg cttgaagcag atctatgcat tgaatatga gggtctactc     20848
aagcgaagcg cgctggcctc ctccgccgat cactgtctaa ccctggtaaa gagcactcag    20908
acggttcagg gccctcacag cgccgcctgt ggccttttt gttgcatgtt tttgcacgcc     20968
tttgtgaact ggccggacac ccccatggaa acaaccccca ccatggaccct cctgactggc    21028
gttcccaact ccatgctcca aagcccagc gtgcagacca ccctcctcca aaaccagaaa    21088
aatctgtacg cctttctgca caagcactct ccctactttc gccgccatcg ggaacaaata   21148
gaaaatgcaa ccgcgtttaa caaaactctg taacgtttaa taatgaact ttttattgaa   21208
ctggaaaacg ggtttgtgat tttaaaaat caaaggggtt gagctggaca tccatgtggg    21268
aggccggaag ggtggtgttc ttgtactggt acttgggcag ccacttaaac tctggaatca    21328
caaacttggg cagcggtatt tctgggaagt tgtcgtgcca cagctggcgg tcagctgaa    21388
gtgcctgcag aacatcgggg gcggagatct tgaagtcgca gtttatctgg ttcacggcac   21448
gcgcgttgcg gtacatggga ttggcacact gaaacaccag caggctggga ttcttgatgc    21508
tagccagggc cacggcgtcg gtcacgtcac cggtgtcttc tatgttggac agcgaaaaag   21568
gcgtgacttt gcaaagctgg cgtcccgcgc gaggcacgca atctcccagg tagttgcact   21628
cacagcggat gggcagaaga agatgcttgt ggccgcgggt catgtaggga taggccgctg    21688
ccataaaagc ttcgatctgc ctgaaagcct gcttggcctt gtgcccttcg gtataaaaaa    21748
caccgcagga cttgttggaa aaggtattac tggcgcaagc ggcatcgtga agcaagcgc    21808
gtgcgtcttc gtttcgtaac tgcaccacgc tgcggcccca ccggttctga atcaccttgg    21868
ccctgccggg gttttccttg agagcgcgct ggccggcttc gctgcccaca tccatttcca    21928
cgacatgctc cttgttaatc atggccagac cgtggaggca gcgcagctcc tcgtcatcgt    21988
cggtgcagtg atgctcccac acgacgcagc cagtgggctc ccacttgggc ttggaggcct    22048
cggcaatgcc agaatacagg agaacgtagt ggtgcagaaa acgtcccatc atggtgccaa    22108
aggttttctg gctgctgaag gtcatcgggc agtacctcca gtcctcgtta agccaagtgt    22168
tgcagatctt cctgaagacc gtgtactgat cgggcataaa gtggaactca ttgcgctcgg    22228
tcttgtcgat cttatacttt tccatcagac tatgcataat ctccatgccc ttttcccagg    22288
```

```
cgcaaacaat cttggtgcta cacgggttag gtatggccaa agtggttggc ctctgaggcg  22348
gcgcttgttc ttcctcttga gccctctccc gactgacggg ggttgaaaga gggtgcccct  22408
tggggaacgg cttgaacacg gtctggcccg aggcgtcccg aagaatctgc atcgggggat  22468
tgctggccgt catggcgatg atctgacccc ggggctcctc cacttcgtcc tcctcgggac  22528
tttcctcgtg cttttcgggg gacggtacgg gagtaggggg aagagcgcgg cgcgccttct  22588
tcttgggcgg cagttccgga gcctgctctt gacgactggc cattgtcttc tcctaggcaa  22648
gaaaaacaag atggaagact ctttctcctc ctcctcgtca acgtcagaaa gcgagtcttc  22708
caccttaagc gccgagaact cccagcgcat agaatccgat gtgggctacg agactccccc  22768
cgcgaacttt tcgccgcccc ccataaacac taacgggtgg acggactacc tggccctagg  22828
agacgtactg ctgaagcaca tcaggcggca gagcgttatc gtgcaagatg ctctcaccga  22888
gcgactcgcg gttccgctgg aagtggcgga acttagcgcc gcctacgagc gaaccctctt  22948
ctccccaaag actccccca agaggcaggc taacggcacc tgcgagccta accctcgact  23008
caacttctac cctgccttg ccgtgccaga ggtactggct acgtaccaca tttttttcca  23068
aaaccacaaa atccctctct cgtgccgcgc caaccgcacc aaagccgatc gcgtgctgcg  23128
actggaggaa ggggctcgca tacctgagat tgcgtgtctg gaggaagtcc caaaaatctt  23188
tgaaggtctg ggccgcgacg aaaagcgagc agcaaacgct ctggaagaga acgcagagag  23248
tcacaacagc gccttggtag aactcgaggg cgacaacgcc agactggccg tcctcaaacg  23308
gtccatagaa gtcacgcact tcgcctaccc cgccgttaac ctccctccaa aagttatgac  23368
agcggtcatg gactcgctgc tcataaagcg cgctcagccc ttagacccag agcacgaaaa  23428
caacagtgac gaaggaaaac cggtggtttc tgatgaggag ttgagcaagt ggctgtcctc  23488
caacgacccc gccacgttgg aggaacgaag aaaaaccatg atggccgtgg tgctagttac  23548
cgtgcaatta gaatgtctgc agaggttctt ttcccaccca gagaccctga gaaaagtgga  23608
ggaaacgctg cactacacat ttaggcacgg ctacgtgaag caagcctgca agatttccaa  23668
cgtagaactt agcaacctca tctcctacct ggggatcttg cacgaaaacc gcctcggaca  23728
aaacgtgctg cacagcacac tgaaaggaga agcccgccga gactatgtgc gagactgcgt  23788
gttcctagcg ctagtgtaca cctggcgagg cggaatggga gtctggcagc agtgcctgga  23848
ggacgaaaac ctcaaagagc ttgaaaagct gctggtgcgc tccagaaggg cactgtggac  23908
cagttttgac gagcgcaccg ccgcgcgaga cctagctgat attatttttc ctcccaagct  23968
ggtgcagact ctccgggaag gactgccaga ttttatgagt caaagcatct tgcaaaactt  24028
ccgctctttc atcttggaac gctcgggaat cttgcccgcc actagctgcg ccctacccac  24088
agattttgtg cctctccact accgcgaatg cccaccgccg ctgtggccgt acacttactt  24148
gcttaaactg gccaactttc taatgttcca ctctgacctg gcagaagacg ttagcggcga  24208
ggggctgcta gaatgccact gccgctgcaa cctgtgcacc ccccaccgct ctctagtatg  24268
caacactccc ctgctcaatg agacccagat catcggtacc tttgaaatcc agggaccctc  24328
cgacgcggaa aacggcaagc aggggtctgg gctaaaactc acagccggac tgtggaccts  24388
cgcctacttg cgcaaatttg taccagaaga ctatcacgcc caccaaatta aattttacga  24448
aaaccaatca aaaccaccca aaagcgagtt aacggcttgc gtcattacgc agagcagcat  24508
agttgggcag ttgcaagcca ttaacaaagc gcggcaagag tttctcctaa aaaaaggaaa  24568
aggggtctac ttggaccccc agaccggcga ggaactcaac ggaccctcct cagtcgcagg  24628
ttgtgtgccc catgccgccc aaaaagaaca cctcgcagtg aacatgcca gagacggagg  24688
```

```
aagaggagtg gagcagtgtg agcaacagcg aaacggagga agagccgtgg cccgaggggt    24748 gcaacggga  agaggacacg gagggacggc gaagtcttcg ccgaagaact ctcgccgctg    24808 ccccgaagt  cccagccggc cgcctcggcc aagatcccg  cacacacccg tagatgggat    24868
agcaagacca aaaagccggg taagagaaac gctcgccccc gccagggcta ccgctcgtgg    24928
agaaagcaca aaaactgcat cttatcgtgc ttgctccagt gcggcggaga cgtttcgttc    24988
acccgtagat acttgctttt taacaaaggg gtggccgtcc cccgtaacgt cctccactac    25048
taccgtcact cttacagctc cgaagcggac ggctaagaaa acgcagcagt tgccggcggg    25108
aggactgcgt ctcagcgccc gagaaccccc agccaccagg gagctccgaa accgcatatt    25168
tcccaccctc tacgctatct ttcagcaaag ccgggggcag cagcaagaac tgaaaataaa    25228
aaaccgcacg ctgaggtcgc ttacccgaag ctgcctctat cacaagagcg aagagcagct    25288
gcagcgaacc ctggaggacg cagaagcgct gttccagaag tactgcgcga ccaccctaaa    25348
taactaaaaa agcccgcgcg cgggacttca aaccgtctga cgtcaccagc cgcgcgccaa    25408
aatgagcaaa gagattccca cgccttacat gtggagttac cagccgcaga tgggattagc    25468
cgccggcgcc gcccaggatt actccacgaa aatgaactgg ctcagcgccg ggccccacat    25528
gatttcccgc gtaaacgaca ttcgcgccca ccgcaatcag ctattgttag aacaggctgc    25588
tctgaccgca acgccccgta ataacctgaa ccctcccagc tggccagctg ccctggtgta    25648
ccaggaaacg cctccaccca ccagcgtact tttgccccgt gacgcccagg cggaagtcca    25708
gatgactaac gcgggcgcgc aattagcggg cggatcccgg tttcggtaca gagttcacgg    25768
cgccgcaccc tatagcccag gtataaagag gctgatcatt cgaggcagag gtgtccagct    25828
caacgacgag acagtgagct cttcgcttgg tctacgacca gacggagtgt tccagctcgc    25888
gggctcgggc cgctcttcgt tcacgcctcg ccaggcatac ctgactctgc agagctctgc    25948
ctctcagcct cgctcgggag gaatcggacc ccttcagttt gtggaggagt ttgtgccctc    26008
ggtctacttt cagcctttct ccggatcgcc cggccagtac ccggacgagt tcatccccaa    26068
cttcgacgcg gtgagtgact ctgtggacgg ttatgactga tgtcgagccc gcttcagtgc    26128
tagtggaaca agcgcggctc aatcacctgg ttcgttgccg ccgccgctgc tgcgtggctc    26188
gcgacttgag cttagctctc aagtttgtaa aaaacccgtc cgaaaccggg agcgctgtgc    26248
acgggttgga gctagtgggt cctgagaagg ccaccatcca cgttctcaga aactttgtgg    26308
aaaaacccat tttggttaaa cgagatcagg ggccttttgt aatcagctta ctctgcacct    26368
gtaaccatgt tgaccttcac gactattta  tggatcattt gtgcgctgaa ttcaataagt    26428
aaagcgaatt cttaccaaga ttatgatgtc catgactgtt cctcgccact atacgatgtt    26488
gtgccagtaa actctcttgt cgacatctat ctgaactgtt ccttttggtc cgcacagctt    26548
acttggtact acggtgacac cgtcctttct ggctcactgg gcagctcaca cggaataaca    26608
cttcacctct tttcgccgtt tcgatacgga aactacagct gtcgtgccgg tacctgcctc    26668
cacgttttca atcttcagcc ctgtccaccg accaaacttg tatttgtcga ctctaagcac    26728
ttacagctca actgcagcat tctaggcccc agtatcttgt ggacatacaa taaaatcagg    26788
ttggtggaat ttgtctacta cccacccagc gcccgcggtt ttggggaaat tcctttccag    26848
atctactaca actatcttgc cacacattat gcaagtcaac agcaactaaa cttgcaagca    26908
cccttcacgc caggagagta ctcctgtcac gtaggctcct gcacagaaac ttttattctc    26968
ttcaacagat cttctgccat tgaacgcttc actactaact actttagaaa ccaagttgtg    27028
cttttcactg acgaaacccc taacgtcacc ctggactgtg catgttttc  tcatgacacc    27088
```

-continued

```
gtaacttgga ctcttaacaa tactctctgg ctcgcgttcg ataaccaaag cttgattgtt    27148
aaaaattttg atttaacctt tactaaaccc tctcctcgcg aaatagttat ctttgctcct    27208
tttaatccaa aaactacctt agcctgtcag gttttgttta agccttgcca aacaaacttt    27268
aagtttgttt atttgcctcc gcaatctgtc aaactcatag aaaaatacaa caaagcgccc    27328
gtcttggctc ctaaaacctt ctaccactgg ctaacctaca cggggctgtt tgcactaatt    27388
gttttttttcc taattaacat ttttatatgt ttcttgcctt cctccttctt ttcgcgaaca    27448
ccgttgccgc agaaagacct ctccttatta ctgtagcgct tgctatacaa aaccaagagt    27508
ggtcaaccgt gctctcaatc tattttcaat ttttcatttt gtccttaata ctttctctta    27568
ttgtcgttaa caatgatctg gagcattggt ctcgcctttt tttggctgct tagtgcaaaa    27628
gccactattt ttcacaggta tgtggaagaa ggaactagca ccctctttac gatacctgaa    27688
acaattaagg cggctgatga agtttcttgg tacaaaggct cgctctcaga cggcaaccac    27748
tcattctcag gacagaccct ttgcatccaa gaaacttatt ttaaatcaga actacaatac    27808
agctgcataa aaacttttt ccatctctac aacatctcaa aaccctatga gggtatttac    27868
aatgccaagg tttcagacaa ctccagcaca cggaactttt actttaatct gacagttatt    27928
aaagcaattt ccattcctat ctgtgagttt agctcccagt ttctttctga aacctactgt    27988
ttaattacta taaactgcac taaaaatcgc cttcacacca ccataatcta caatcacaca    28048
caatcacctt gggttttaaa cctaaaattt tctccacaca tgccttcgca atttctcacg    28108
caagttaccg tctctaacat aagcaagcag tttggctttt actatccttt ccacgaactg    28168
tgcgaaataa ttgaagccga atatgaacca gactacttta cttacattgc cattggtgta    28228
atcgttgttt gccttttgctt tgttattggg gggtgtgttt atttgtacat tcagagaaaa    28288
atattgctct cgctgtgctc ctgcggttac aaagcagaag aaagaattaa aatctctaca    28348
ctttattaat gttttccaga aatggcaaaa ctaacgctcc tacttttgct tctcacgccg    28408
gtgacgcttt ttaccatcac ttttttctgcc gccgccacac tcgaacctca atgtttgcca    28468
ccggttgaag tctactttgt ctacgtgttg ctgtgctgcg ttagcgtttg cagtataaca    28528
tgttttacct ttgttttttct tcagtgcatt gactacttct gggtcagact ctactaccgc    28588
agacacgcgc ctcagtatca aaatcaacaa attgccagac tactcggtct gccatgattg    28648
tcttgtatttt taccctgatt ttttttcacc ttacttgcgc ttgtgatttt cacttcactc    28708
aattttggaa aacgcaatgc ttcgacccgc gcctctccaa cgactggatg atggctcttg    28768
caattgccac gcttggggcg tttggacttt ttagtggttt tgctttgcat tacaaattta    28828
agactccatg gacacatggc tttctttcag attttccagt tacacctact ccgccgcctc    28888
ccccggccat cgacgtgcct caggttccct caccttctcc atctgtctgc agctactttc    28948
atctgtaatg gccgacctag aatttgacgg agtgcaatct gagcaaaggg ctatacactt    29008
ccaacgccag tcggaccgcg aacgcaaaaa cagagagctg caaaccatac aaaacaccca    29068
ccaatgtaaa cgcgggatat tttgtattgt aaaacaagct aagctccact acgagcttct    29128
atctggcaac gaccacgagc tccaatacgt ggtcgatcag cagcgtcaaa cctgtgtatt    29188
cttaattgga gtttccccca ttaaagttac tcaaaccaag ggtgaaacca agggaaccat    29248
aaggtgctca tgtcacctgt cagaatgcct ttacactcta gttaaaaccc tatgtggctt    29308
acatgattct atccccttta attaaataaa cttactttaa atctgcaatc acttcttcgt    29368
ccttgttttt gtcgccatcc agcagcacca ccttcccctc ttcccaactt tcatagcata    29428
ttttccgaaa agaggcgtac tttcgccaca ccttaaaggg aacgtttact tcgctttcaa    29488
```

```
gctctcccac gattttcatt gcagat atg aaa cgc gcc aaa gtg gaa gaa gga   29541
                             Met Lys Arg Ala Lys Val Glu Glu Gly
                                                1425 ttt aac ccc gtt tat ccc tat gga tat tct act ccg act gac gtg       29586
Phe Asn Pro Val Tyr Pro Tyr Gly Tyr Ser Thr Pro Thr Asp Val
1430                1435                1440 gct cct ccc ttt gta gcc tct gac ggt ctt caa gaa aac cca cct       29631
Ala Pro Pro Phe Val Ala Ser Asp Gly Leu Gln Glu Asn Pro Pro
1445                1450                1455 ggg gtc ttg tcc cta aaa ata tcc aaa cct tta act ttt aat gcc       29676
Gly Val Leu Ser Leu Lys Ile Ser Lys Pro Leu Thr Phe Asn Ala
1460                1465                1470 tcc aag gct cta agc ctg gct att ggt cca gga tta aaa att caa       29721
Ser Lys Ala Leu Ser Leu Ala Ile Gly Pro Gly Leu Lys Ile Gln
1475                1480                1485 gat ggt aaa cta gtg ggg gag gga caa gca att ctt gca aac ctg       29766
Asp Gly Lys Leu Val Gly Glu Gly Gln Ala Ile Leu Ala Asn Leu
1490                1495                1500 ccg ctt caa atc acc aac aac aca att tca cta cgt ttt ggg aac       29811
Pro Leu Gln Ile Thr Asn Asn Thr Ile Ser Leu Arg Phe Gly Asn
1505                1510                1515 aca ctt gcc ttg aat gac aat aat gaa ctc caa acc aca cta aaa       29856
Thr Leu Ala Leu Asn Asp Asn Asn Glu Leu Gln Thr Thr Leu Lys
1520                1525                1530 tct tca tcg ccc ctt aaa atc aca gac cag act ctg tcc ctt aac       29901
Ser Ser Ser Pro Leu Lys Ile Thr Asp Gln Thr Leu Ser Leu Asn
1535                1540                1545 ata ggg gac agc ctt gca att aaa gat gac aaa cta gaa agc gct       29946
Ile Gly Asp Ser Leu Ala Ile Lys Asp Asp Lys Leu Glu Ser Ala
1550                1555                1560 ctt caa gcg acc ctc cca ctc tcc att agc aac aac acc atc agc       29991
Leu Gln Ala Thr Leu Pro Leu Ser Ile Ser Asn Asn Thr Ile Ser
1565                1570                1575 ctc aac gtg ggc acc gga ctc acc ata aat gga aac gtt tta caa       30036
Leu Asn Val Gly Thr Gly Leu Thr Ile Asn Gly Asn Val Leu Gln
1580                1585                1590 gct gtt ccc tta aat gct cta agt ccc cta act att tcc aac aat       30081
Ala Val Pro Leu Asn Ala Leu Ser Pro Leu Thr Ile Ser Asn Asn
1595                1600                1605 aac atc agc ctg cgc tat ggc agt tcc ctg acg gtg ctt aac aat       30126
Asn Ile Ser Leu Arg Tyr Gly Ser Ser Leu Thr Val Leu Asn Asn
1610                1615                1620 gaa ctg caa agc aac ctc aca gtt cac tcc cct tta aaa ctc aac       30171
Glu Leu Gln Ser Asn Leu Thr Val His Ser Pro Leu Lys Leu Asn
1625                1630                1635 tcc aac aac tca att tct ctc aac act cta tct ccg ttt aga atc       30216
Ser Asn Asn Ser Ile Ser Leu Asn Thr Leu Ser Pro Phe Arg Ile
1640                1645                1650 gag aat ggt ttc ctc acg ctc tat ttg gga aca aaa tct ggc ttg       30261
Glu Asn Gly Phe Leu Thr Leu Tyr Leu Gly Thr Lys Ser Gly Leu
1655                1660                1665 cta gtt caa aac agt ggc tta aaa gtt caa gcg ggc tac ggc ctg       30306
Leu Val Gln Asn Ser Gly Leu Lys Val Gln Ala Gly Tyr Gly Leu
1670                1675                1680 caa gta aca gac acc aat gct ctc aca tta aga tat ctc gct cca       30351
Gln Val Thr Asp Thr Asn Ala Leu Thr Leu Arg Tyr Leu Ala Pro
1685                1690                1695 ctg acc att cca gac tcg ggc tca gaa caa ggc att ctt aaa gta       30396
Leu Thr Ile Pro Asp Ser Gly Ser Glu Gln Gly Ile Leu Lys Val
1700                1705                1710
```

| | | | | | | | | | | | | | | |
|---|---|---|---|---|---|---|---|---|---|---|---|---|---|---|
| aac | act | gga | cag | ggc | cta | agt | gtg | aac | caa | gct | gga | gcg | ctt | gaa | 30441 |
| Asn | Thr | Gly | Gln | Gly | Leu | Ser | Val | Asn | Gln | Ala | Gly | Ala | Leu | Glu | |
| 1715 | | | | 1720 | | | | | 1725 | | | | | | |
| aca | tcc | cta | gga | ggt | gga | tta | aaa | tat | gct | gat | aac | aaa | ata | acc | 30486 |
| Thr | Ser | Leu | Gly | Gly | Gly | Leu | Lys | Tyr | Ala | Asp | Asn | Lys | Ile | Thr | |
| 1730 | | | | 1735 | | | | | 1740 | | | | | | |
| ttt | gat | aca | gga | aac | gga | ctg | aca | tta | tct | gaa | aat | aaa | ctt | gca | 30531 |
| Phe | Asp | Thr | Gly | Asn | Gly | Leu | Thr | Leu | Ser | Glu | Asn | Lys | Leu | Ala | |
| 1745 | | | | 1750 | | | | | 1755 | | | | | | |
| gta | gct | gca | ggt | agt | ggt | cta | act | ttt | aga | gat | ggt | gcc | ttg | gta | 30576 |
| Val | Ala | Ala | Gly | Ser | Gly | Leu | Thr | Phe | Arg | Asp | Gly | Ala | Leu | Val | |
| 1760 | | | | 1765 | | | | | 1770 | | | | | | |
| gcc | acg | gga | acc | gca | ttt | acg | caa | aca | ctg | tgg | act | acg | gct | gat | 30621 |
| Ala | Thr | Gly | Thr | Ala | Phe | Thr | Gln | Thr | Leu | Trp | Thr | Thr | Ala | Asp | |
| 1775 | | | | 1780 | | | | | 1785 | | | | | | |
| ccg | tct | ccc | aac | tgc | aca | att | ata | cag | gac | cgc | gac | aca | aaa | ttt | 30666 |
| Pro | Ser | Pro | Asn | Cys | Thr | Ile | Ile | Gln | Asp | Arg | Asp | Thr | Lys | Phe | |
| 1790 | | | | 1795 | | | | | 1800 | | | | | | |
| act | ttg | gcg | ctt | acc | att | agt | ggg | agc | caa | gtg | ctg | ggg | acg | gtt | 30711 |
| Thr | Leu | Ala | Leu | Thr | Ile | Ser | Gly | Ser | Gln | Val | Leu | Gly | Thr | Val | |
| 1805 | | | | 1810 | | | | | 1815 | | | | | | |
| tcc | att | att | gga | gta | aaa | ggc | ccc | ctt | tca | agt | agc | ata | ccg | tca | 30756 |
| Ser | Ile | Ile | Gly | Val | Lys | Gly | Pro | Leu | Ser | Ser | Ser | Ile | Pro | Ser | |
| 1820 | | | | 1825 | | | | | 1830 | | | | | | |
| gct | acc | gtt | aca | gta | caa | ctt | aac | ttt | gat | tcc | aac | gga | gcc | cta | 30801 |
| Ala | Thr | Val | Thr | Val | Gln | Leu | Asn | Phe | Asp | Ser | Asn | Gly | Ala | Leu | |
| 1835 | | | | 1840 | | | | | 1845 | | | | | | |
| ttg | agc | tcc | tct | tca | ctt | aaa | ggt | tac | tgg | ggg | tat | cgc | caa | ggt | 30846 |
| Leu | Ser | Ser | Ser | Ser | Leu | Lys | Gly | Tyr | Trp | Gly | Tyr | Arg | Gln | Gly | |
| 1850 | | | | 1855 | | | | | 1860 | | | | | | |
| ccc | tca | att | gac | cct | tac | ccc | ata | att | aat | gcc | tta | aac | ttt | atg | 30891 |
| Pro | Ser | Ile | Asp | Pro | Tyr | Pro | Ile | Ile | Asn | Ala | Leu | Asn | Phe | Met | |
| 1865 | | | | 1870 | | | | | 1875 | | | | | | |
| cca | aac | tca | ctg | gct | tat | ccc | ccg | gga | caa | gaa | atc | caa | gca | aaa | 30936 |
| Pro | Asn | Ser | Leu | Ala | Tyr | Pro | Pro | Gly | Gln | Glu | Ile | Gln | Ala | Lys | |
| 1880 | | | | 1885 | | | | | 1890 | | | | | | |
| tgt | aac | atg | tac | gtt | tct | act | ttt | tta | cga | gga | aat | cca | caa | aga | 30981 |
| Cys | Asn | Met | Tyr | Val | Ser | Thr | Phe | Leu | Arg | Gly | Asn | Pro | Gln | Arg | |
| 1895 | | | | 1900 | | | | | 1905 | | | | | | |
| cca | ata | gtt | tta | aac | atc | act | ttt | aat | aat | caa | acc | agc | ggg | ttt | 31026 |
| Pro | Ile | Val | Leu | Asn | Ile | Thr | Phe | Asn | Asn | Gln | Thr | Ser | Gly | Phe | |
| 1910 | | | | 1915 | | | | | 1920 | | | | | | |
| tcc | att | aga | ttt | aca | tgg | aca | aat | tta | acc | aca | gga | gaa | gca | ttt | 31071 |
| Ser | Ile | Arg | Phe | Thr | Trp | Thr | Asn | Leu | Thr | Thr | Gly | Glu | Ala | Phe | |
| 1925 | | | | 1930 | | | | | 1935 | | | | | | |
| gca | atg | ccc | cca | tgc | act | ttt | tcc | tac | att | gct | gaa | caa | caa | taa | 31116 |
| Ala | Met | Pro | Pro | Cys | Thr | Phe | Ser | Tyr | Ile | Ala | Glu | Gln | Gln | Gln | |
| 1940 | | | | 1945 | | | | | 1950 | | | | | | | actatgtaac cctcaccgtt aacccgcctc cgcccttcca tttattttta taaaccaccc 31176 gatccacctt ttcagcagta aacaattgca tgtcagtagg ggcagtaaaa cttttgggag 31236 ttaaaatcca cacaggttct tcacaagcta agcgaaaatc agttacactt ataaaaccat 31296 cgctaacatc ggacaaagac aagcatgagt ccaaagcttc cggttctgga tcagattttt 31356 gttcattaac agcgggagaa acagcttctg gaggattttc catctccatc tccttcatca 31416 gttccaccat gtccaccgtg gtcatctggg acgagaacga cagttgtcat acacctcata 31476 agtcaccggt cgatgacgaa cgtacagatc tcgaagaatg tcctgtcgcc gcctttcggc 31536 agcactgggc cgaaggcgaa agcgcccatg tttaacaatg ccagcaccg cccgcttcat 31596

```
caggcgccta gttcttttag cgcaacagcg catgcgcagc tcgctaagac tggcgcaaga   31656
aacacagcac agaaccacca gattgttcat gatcccataa gcgtgctgac accagcccat   31716
actaacaaat tgtttcacta ttctagcatg aatgtcatat ctgatgttca agtaaattaa   31776
atggcgcccc cttatgtaaa cacttcccac gtacaacacc tcctttggca tctgataatt   31836
aaccacctcc cgataccaaa tacatctctg attaatagtc gccccgtaca ctacccgatt   31896
aaaccaagtt gccaacataa tccccctgc catacactgc aaagaacctg gacggctaca   31956
atgacagtgc aaagtccaca cctcgttgcc atggataact gaggaacgcc ttaagtcaat   32016
agtggcacaa ctaatacaaa catgtaaata gtgtttcaac aagtgccact cgtatgaggt   32076
gagtatcatg tcccagggaa cgggccactc cataaacact gcaaaccaa cacatcctac   32136 catccccgc acggcactca catcgtgcat ggtgttcata tcacagtccg gaagctgagg   32196
acaaggaaaa gtctcgggag cattttcata gggcggtagt gggtactcct tgtaggggtt   32256
cagtcggcac cggtatctcc tcaccttctg ggccataaca cacaagttga gatctgattt   32316
caaggtactt tctgaatgaa aaccaagtgc tttcccaaca atgtatccga tgtcttcggt   32376
ccccgcgtcg gtagcgctcc ttgcagtaca cacggaacaa ccactcacgc aggcccagaa   32436
gacagttttc cgcggacggt gacaagttaa tcccctcag tctcagagcc aatatagttt   32496
cttccacagt agcataggcc aaacccaacc aggaaacaca agctggcacg tcccgttcaa   32556
cgggaggaca aggaagcaga ggcagaggca taggcaaagc aacagaattt ttattccaac   32616
tggtcacgta gcacttcaaa caccaggtca cgtaaatggc agcgatcttg ggtttcctga   32676
tggaacataa cagcaagatc aaacatgaga cgattctcaa ggtgattaac cacagctgga   32736
attaaatcct ccacgcgcac atttagaaac accagcaata caaaagcccg gttttctccg   32796
ggatctatca tagcagcaca gtcatcaatt agtcccaagt aattttcccg tttccaatct   32856
gttataattt gcagaataat gccctgtaaa tccaagccgg ccatggcgaa aagctcagat   32916
aatgcacttt ccacgtgcat tcgtaaacac accctcatct tgtcaatcca aaaagtcttc   32976
ttcttgagaa acctgtagta aattaagaat cgccaggtta ggctcgatgc ctacatcccg   33036
gagcttcatt ctcagcatgc actgcaaatg atccagcaga tcagaacagc aattagcagc   33096
cagctcatcc ccggtttcca gttccggagt tccacggca attatcactc gaaacgtggg   33156
acaaatcgaa ataacatgag ctcccacgtg agcaaaagcc gtagggccag tgcaataatc   33216
acagaaccag cggaaaaaag attgcagctc atgtttcaaa aagctctgca gatcaaaatt   33276
cagctcatgc aaataacaca gtaaagtttg cggtatagta accgaaaacc acacgggtcg   33336
acgttcaaac atctcggctt acctaaaaaa gaagcacatt tttaaaccac agtcgcttcc   33396
tgaacaggag gaaatatggt gcggcgtaaa accagacgcg ccaccggatc tccggcagag   33456
ccctgataat acagccagct gtggttaaac agcaaaacct ttaattcggc aacggttgag   33516
gtctccacat aatcagcgcc cacaaaaatc ccatctcgaa cttgctcgcg tagggagcta   33576
aaatggccag tatagcccca tggcacccga acgctaatct gcaagtatat gagagccacc   33636
ccattcggcg ggatcacaaa atcagtcgga gaaaacaacg tatacacccc ggactgcaaa   33696
agctgttcag gcaaacgccc ctgcggtccc tctcggtaca ccagcaaagc ctcgggtaaa   33756
gcagccatgc caagcgctta ccgtgccaag agcgactcag acgaaaaagt gtactgaggc   33816
gctcagagca gcggctatat actctacctg tgacgtcaag aaccgaaagt caaaagttca   33876
cccgcgcgcg ccgaaaaaac ccgcgaaaat ccacccaaaa agcccgcgaa aaacacttcc   33936
gtataaaatt tccgggttac cggcgcgtca ccgccgcgcg acacgcccgc cccgcccgc   33996
```

```
gctcctcccc gaaacccgcc gcgcccactt ccgcgttccc aagacaaagg tcgcgtaact   34056
ccgcccacct catttgcatg ttaactcggt cgccatcttg cggtgttata ttgatgatg    34115
```

<210> SEQ ID NO 35
<211> LENGTH: 503
<212> TYPE: PRT
<213> ORGANISM: simian adenovirus SV-39

<400> SEQUENCE: 35

```
Met Arg Arg Ala Val Ala Val Pro Ser Ala Met Ala Leu Gly Pro
1               5                   10                  15

Pro Pro Ser Tyr Glu Ser Val Met Ala Ala Thr Leu Gln Ala Pro
                20                  25                  30

Leu Glu Asn Pro Tyr Val Pro Pro Arg Tyr Leu Glu Pro Thr Gly Gly
            35                  40                  45

Arg Asn Ser Ile Arg Tyr Ser Glu Leu Thr Pro Leu Tyr Asp Thr Thr
50                  55                  60

Arg Leu Tyr Leu Val Asp Asn Lys Ser Ala Asp Ile Ala Thr Leu Asn
65                  70                  75                  80

Tyr Gln Asn Asp His Ser Asn Phe Leu Thr Ser Val Val Gln Asn Ser
                85                  90                  95

Asp Tyr Thr Pro Ala Glu Ala Ser Thr Gln Thr Ile Asn Leu Asp Asp
            100                 105                 110

Arg Ser Arg Trp Gly Gly Asp Leu Lys Thr Ile Leu His Thr Asn Met
        115                 120                 125

Pro Asn Val Asn Glu Phe Met Phe Thr Asn Ser Phe Arg Ala Lys Leu
130                 135                 140

Met Val Ala His Glu Ala Asp Lys Asp Pro Val Tyr Glu Trp Val Gln
145                 150                 155                 160

Leu Thr Leu Pro Glu Gly Asn Phe Ser Glu Ile Met Thr Ile Asp Leu
                165                 170                 175

Met Asn Asn Ala Ile Ile Asp His Tyr Leu Ala Val Ala Arg Gln Gln
            180                 185                 190

Gly Val Lys Glu Ser Glu Ile Gly Val Lys Phe Asp Thr Arg Asn Phe
        195                 200                 205

Arg Leu Gly Trp Asp Pro Glu Thr Gly Leu Val Met Pro Gly Val Tyr
210                 215                 220

Thr Asn Glu Ala Phe His Pro Asp Val Val Leu Leu Pro Gly Cys Gly
225                 230                 235                 240

Val Asp Phe Thr Tyr Ser Arg Leu Asn Asn Leu Leu Gly Ile Arg Lys
                245                 250                 255

Arg Met Pro Phe Gln Glu Gly Phe Gln Ile Leu Tyr Glu Asp Leu Glu
            260                 265                 270

Gly Gly Asn Ile Pro Ala Leu Leu Asp Val Pro Ala Tyr Glu Glu Ser
        275                 280                 285

Ile Ala Asn Ala Arg Glu Ala Ala Ile Arg Gly Asp Asn Phe Ala Ala
290                 295                 300

Gln Pro Gln Ala Ala Pro Thr Ile Lys Pro Val Leu Glu Asp Ser Lys
305                 310                 315                 320

Gly Arg Ser Tyr Asn Val Ile Ala Asn Thr Asn Asn Thr Ala Tyr Arg
                325                 330                 335

Ser Trp Tyr Leu Ala Tyr Asn Tyr Gly Asp Pro Glu Lys Gly Val Arg
            340                 345                 350

Ala Trp Thr Leu Leu Thr Thr Pro Asp Val Thr Cys Gly Ser Glu Gln
```

```
              355                 360                 365
Val Tyr Trp Ser Leu Pro Asp Met Tyr Val Asp Pro Val Thr Phe Arg
370                 375                 380

Ser Thr Gln Gln Val Ser Asn Tyr Pro Val Val Gly Ala Glu Leu Met
385                 390                 395                 400

Pro Ile His Ser Lys Ser Phe Tyr Asn Glu Gln Ala Val Tyr Ser Gln
                405                 410                 415

Leu Ile Arg Gln Thr Thr Ala Leu Thr His Val Phe Asn Arg Phe Pro
                420                 425                 430

Glu Asn Gln Ile Leu Val Arg Pro Ala Pro Thr Ile Thr Thr Val
                435                 440                 445

Ser Glu Asn Val Pro Ala Leu Thr Asp His Gly Thr Leu Pro Leu Gln
450                 455                 460

Asn Ser Ile Arg Gly Val Gln Arg Val Thr Ile Thr Asp Ala Arg Arg
465                 470                 475                 480

Arg Thr Cys Pro Tyr Val Tyr Lys Ala Leu Gly Ile Val Ala Pro Arg
                485                 490                 495

Val Leu Ser Ser Arg Thr Phe
                500

<210> SEQ ID NO 36
<211> LENGTH: 917
<212> TYPE: PRT
<213> ORGANISM: simian adenovirus SV-39

<400> SEQUENCE: 36

Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
                20                  25                  30

Arg Ala Thr Glu Thr Tyr Phe Ser Leu Gly Asn Lys Phe Arg Asn Pro
            35                  40                  45

Thr Val Ala Pro Thr His Asp Val Thr Thr Asp Arg Ser Gln Arg Leu
        50                  55                  60

Thr Ile Arg Phe Val Pro Val Asp Lys Glu Asp Thr Ala Tyr Ser Tyr
65                  70                  75                  80

Lys Thr Arg Phe Thr Leu Ala Val Gly Asp Asn Arg Val Leu Asp Met
                85                  90                  95

Ala Ser Thr Tyr Phe Asp Ile Arg Gly Val Ile Asp Arg Gly Pro Ser
                100                 105                 110

Phe Lys Pro Tyr Ser Gly Thr Ala Tyr Asn Ser Leu Ala Pro Lys Gly
            115                 120                 125

Ala Pro Asn Asn Ser Gln Trp Asn Ala Thr Asp Asn Gly Asn Lys Pro
        130                 135                 140

Val Cys Phe Ala Gln Ala Ala Phe Ile Gly Gln Ser Ile Thr Lys Asp
145                 150                 155                 160

Gly Val Gln Ile Gln Asn Ser Glu Asn Gln Gln Ala Ala Ala Asp Lys
                165                 170                 175

Thr Tyr Gln Pro Glu Pro Gln Ile Gly Val Ser Thr Trp Asp Thr Asn
                180                 185                 190

Val Thr Ser Asn Ala Ala Gly Arg Val Leu Lys Ala Thr Thr Pro Met
            195                 200                 205

Leu Pro Cys Tyr Gly Ser Tyr Ala Asn Pro Thr Asn Pro Asn Gly Gly
        210                 215                 220

Gln Ala Lys Thr Glu Gly Asp Ile Ser Leu Asn Phe Phe Thr Thr Thr
```

-continued

```
                 225                 230                 235                 240
Ala Ala Ala Asp Asn Asn Pro Lys Val Val Leu Tyr Ser Glu Asp Val
                 245                 250                 255

Asn Leu Gln Ala Pro Asp Thr His Leu Val Tyr Lys Pro Thr Val Gly
                 260                 265                 270

Glu Asn Val Ile Ala Ala Glu Ala Leu Leu Thr Gln Gln Ala Cys Pro
                 275                 280                 285

Asn Arg Ala Asn Tyr Ile Gly Phe Arg Asp Asn Phe Ile Gly Leu Met
                 290                 295                 300

Tyr Tyr Asn Ser Thr Gly Asn Met Gly Val Leu Ala Gly Gln Ala Ser
305                              310                 315                 320

Gln Leu Asn Ala Val Val Asp Leu Gln Asp Arg Asn Thr Glu Leu Ser
                 325                 330                 335

Tyr Gln Leu Met Leu Asp Ala Leu Gly Asp Arg Thr Arg Tyr Phe Ser
                 340                 345                 350

Met Trp Asn Gln Ala Val Asp Ser Tyr Asp Pro Asp Val Arg Ile Ile
                 355                 360                 365

Glu Asn His Gly Val Glu Asp Glu Leu Pro Asn Tyr Cys Phe Pro Leu
                 370                 375                 380

Pro Gly Met Gly Ile Phe Asn Ser Tyr Lys Gly Val Lys Pro Gln Asn
385                              390                 395                 400

Gly Gly Asn Gly Asn Trp Glu Ala Asn Gly Asp Leu Ser Asn Ala Asn
                 405                 410                 415

Glu Ile Ala Leu Gly Asn Ile Phe Ala Met Glu Ile Asn Leu His Ala
                 420                 425                 430

Asn Leu Trp Arg Ser Phe Leu Tyr Ser Asn Val Ala Leu Tyr Leu Pro
                 435                 440                 445

Asp Ser Tyr Lys Phe Thr Pro Ala Asn Ile Thr Leu Pro Ala Asn Gln
                 450                 455                 460

Asn Thr Tyr Glu Tyr Ile Asn Gly Arg Val Thr Ser Pro Thr Leu Val
465                              470                 475                 480

Asp Thr Phe Val Asn Ile Gly Ala Arg Trp Ser Pro Asp Pro Met Asp
                 485                 490                 495

Asn Val Asn Pro Phe Asn His His Arg Asn Ala Gly Leu Arg Tyr Arg
                 500                 505                 510

Ser Met Leu Leu Gly Asn Gly Arg Val Val Pro Phe His Ile Gln Val
                 515                 520                 525

Pro Gln Lys Phe Phe Ala Ile Lys Asn Leu Leu Leu Leu Pro Gly Ser
                 530                 535                 540

Tyr Thr Tyr Glu Trp Ser Phe Arg Lys Asp Val Asn Met Ile Leu Gln
545                              550                 555                 560

Ser Thr Leu Gly Asn Asp Leu Arg Val Asp Gly Ala Ser Val Arg Ile
                 565                 570                 575

Asp Ser Val Asn Leu Tyr Ala Asn Phe Phe Pro Met Ala His Asn Thr
                 580                 585                 590

Ala Ser Thr Leu Glu Ala Met Leu Arg Asn Asp Thr Asn Asp Gln Ser
                 595                 600                 605

Phe Asn Asp Tyr Leu Ser Ala Ala Asn Met Leu Tyr Pro Ile Pro Ala
                 610                 615                 620

Asn Ala Thr Asn Val Pro Ile Ser Ile Pro Ser Arg Asn Trp Ala Ala
625                              630                 635                 640

Phe Arg Gly Trp Ser Phe Thr Arg Leu Lys Ala Lys Glu Thr Pro Ser
                 645                 650                 655
```

-continued

```
Leu Gly Ser Gly Phe Asp Pro Tyr Phe Val Tyr Ser Gly Thr Ile Pro
            660                 665                 670

Tyr Leu Asp Gly Ser Phe Tyr Leu Asn His Thr Phe Lys Arg Leu Ser
    675                 680                 685

Ile Met Phe Asp Ser Ser Val Ser Trp Pro Gly Asn Asp Arg Leu Leu
690                 695                 700

Thr Pro Asn Glu Phe Glu Ile Lys Arg Ile Val Asp Gly Glu Gly Tyr
705                 710                 715                 720

Asn Val Ala Gln Ser Asn Met Thr Lys Asp Trp Phe Leu Ile Gln Met
                725                 730                 735

Leu Ser His Tyr Asn Ile Gly Tyr Gln Gly Phe Tyr Val Pro Glu Gly
            740                 745                 750

Tyr Lys Asp Arg Met Tyr Ser Phe Phe Arg Asn Phe Gln Pro Met Ser
        755                 760                 765

Arg Gln Val Pro Asp Pro Thr Ala Gly Tyr Gln Ala Val Pro Leu
    770                 775                 780

Pro Arg Gln His Asn Asn Ser Gly Phe Val Gly Tyr Met Gly Pro Thr
785                 790                 795                 800

Met Arg Glu Gly Gln Pro Tyr Pro Ala Asn Tyr Pro Tyr Pro Leu Ile
                805                 810                 815

Gly Ala Thr Ala Val Pro Ala Ile Thr Gln Lys Lys Phe Leu Cys Asp
            820                 825                 830

Arg Val Met Trp Arg Ile Pro Phe Ser Ser Asn Phe Met Ser Met Gly
        835                 840                 845

Ala Leu Thr Asp Leu Gly Gln Asn Met Leu Tyr Ala Asn Ser Ala His
    850                 855                 860

Ala Leu Asp Met Thr Phe Glu Val Asp Pro Met Asn Glu Pro Thr Leu
865                 870                 875                 880

Leu Tyr Met Leu Phe Glu Val Phe Asp Val Val Arg Val His Gln Pro
                885                 890                 895

His Arg Gly Ile Ile Glu Ala Val Tyr Leu Arg Thr Pro Phe Ser Ala
            900                 905                 910

Gly Asn Ala Thr Thr
        915

<210> SEQ ID NO 37
<211> LENGTH: 533
<212> TYPE: PRT
<213> ORGANISM: simian adenovirus SV-39

<400> SEQUENCE: 37

Met Lys Arg Ala Lys Val Glu Glu Gly Phe Asn Pro Val Tyr Pro Tyr
1               5                   10                  15

Gly Tyr Ser Thr Pro Thr Asp Val Ala Pro Pro Phe Val Ala Ser Asp
            20                  25                  30

Gly Leu Gln Glu Asn Pro Pro Gly Val Leu Ser Leu Lys Ile Ser Lys
        35                  40                  45

Pro Leu Thr Phe Asn Ala Ser Lys Ala Leu Ser Leu Ala Ile Gly Pro
    50                  55                  60

Gly Leu Lys Ile Gln Asp Gly Lys Leu Val Gly Glu Gly Gln Ala Ile
65                  70                  75                  80

Leu Ala Asn Leu Pro Leu Gln Ile Thr Asn Asn Thr Ile Ser Leu Arg
                85                  90                  95

Phe Gly Asn Thr Leu Ala Leu Asn Asp Asn Asn Glu Leu Gln Thr Thr
            100                 105                 110
```

-continued

```
Leu Lys Ser Ser Pro Leu Lys Ile Thr Asp Gln Thr Leu Ser Leu
        115                 120                 125

Asn Ile Gly Asp Ser Leu Ala Ile Lys Asp Asp Lys Leu Glu Ser Ala
130                 135                 140

Leu Gln Ala Thr Leu Pro Leu Ser Ile Ser Asn Asn Thr Ile Ser Leu
145                 150                 155                 160

Asn Val Gly Thr Gly Leu Thr Ile Asn Gly Asn Val Leu Gln Ala Val
                165                 170                 175

Pro Leu Asn Ala Leu Ser Pro Leu Thr Ile Ser Asn Asn Ile Ser
                180                 185                 190

Leu Arg Tyr Gly Ser Ser Leu Thr Val Leu Asn Glu Leu Gln Ser
        195                 200                 205

Asn Leu Thr Val His Ser Pro Leu Lys Leu Asn Ser Asn Asn Ser Ile
210                 215                 220

Ser Leu Asn Thr Leu Ser Pro Phe Arg Ile Glu Asn Gly Phe Leu Thr
225                 230                 235                 240

Leu Tyr Leu Gly Thr Lys Ser Gly Leu Leu Val Gln Asn Ser Gly Leu
                245                 250                 255

Lys Val Gln Ala Gly Tyr Gly Leu Gln Val Thr Asp Thr Asn Ala Leu
                260                 265                 270

Thr Leu Arg Tyr Leu Ala Pro Leu Thr Ile Pro Asp Ser Gly Ser Glu
        275                 280                 285

Gln Gly Ile Leu Lys Val Asn Thr Gly Gln Gly Leu Ser Val Asn Gln
        290                 295                 300

Ala Gly Ala Leu Glu Thr Ser Leu Gly Gly Gly Leu Lys Tyr Ala Asp
305                 310                 315                 320

Asn Lys Ile Thr Phe Asp Thr Gly Asn Gly Leu Thr Leu Ser Glu Asn
                325                 330                 335

Lys Leu Ala Val Ala Ala Gly Ser Gly Leu Thr Phe Arg Asp Gly Ala
                340                 345                 350

Leu Val Ala Thr Gly Thr Ala Phe Thr Gln Thr Leu Trp Thr Thr Ala
        355                 360                 365

Asp Pro Ser Pro Asn Cys Thr Ile Ile Gln Asp Arg Asp Thr Lys Phe
370                 375                 380

Thr Leu Ala Leu Thr Ile Ser Gly Ser Gln Val Leu Gly Thr Val Ser
385                 390                 395                 400

Ile Ile Gly Val Lys Gly Pro Leu Ser Ser Ile Pro Ser Ala Thr
                405                 410                 415

Val Thr Val Gln Leu Asn Phe Asp Ser Asn Gly Ala Leu Leu Ser Ser
        420                 425                 430

Ser Ser Leu Lys Gly Tyr Trp Gly Tyr Arg Gln Gly Pro Ser Ile Asp
        435                 440                 445

Pro Tyr Pro Ile Ile Asn Ala Leu Asn Phe Met Pro Asn Ser Leu Ala
450                 455                 460

Tyr Pro Pro Gly Gln Glu Ile Gln Ala Lys Cys Asn Met Tyr Val Ser
465                 470                 475                 480

Thr Phe Leu Arg Gly Asn Pro Gln Arg Pro Ile Val Leu Asn Ile Thr
                485                 490                 495

Phe Asn Asn Gln Thr Ser Gly Phe Ser Ile Arg Phe Thr Trp Thr Asn
                500                 505                 510

Leu Thr Thr Gly Glu Ala Phe Ala Met Pro Pro Cys Thr Phe Ser Tyr
        515                 520                 525

Ile Ala Glu Gln Gln
        530
```

<210> SEQ ID NO 38
<211> LENGTH: 50
<212> TYPE: DNA
<213> ORGANISM: Artificial sequence
<220> FEATURE:
<223> OTHER INFORMATION: oligomer SV25T

<400> SEQUENCE: 38
aatttaaata cgtagcgcac tagtcgcgct aagcgcggat atcatttaaa    50

<210> SEQ ID NO 39
<211> LENGTH: 49
<212> TYPE: DNA
<213> ORGANISM: Artificial sequence
<220> FEATURE:
<223> OTHER INFORMATION: oligomer SV25B

<400> SEQUENCE: 39
tatttaaatg atatccgcgc ttaagcgcga ctagtgcgct acgtattta    49

<210> SEQ ID NO 40
<211> LENGTH: 338
<212> TYPE: PRT
<213> ORGANISM: hexon protein of Hu5

<400> SEQUENCE: 40

Ala Pro Lys Gly Ala Pro Asn Pro Cys Glu Trp Asp Glu Ala Ala Thr
1               5                   10                  15

Ala Leu Glu Ile Asn Leu Glu Glu Glu Asp Asp Asp Asn Glu Asp Glu
            20                  25                  30

Val Asp Glu Gln Ala Glu Gln Gln Lys Thr His Val Phe Gly Gln Ala
        35                  40                  45

Pro Tyr Ser Gly Ile Asn Ile Thr Lys Glu Gly Ile Gln Ile Gly Val
    50                  55                  60

Glu Gly Gln Thr Pro Lys Tyr Ala Asp Lys Thr Phe Gln Pro Glu Pro
65                  70                  75                  80

Gln Ile Gly Glu Ser Gln Trp Tyr Glu Thr Glu Ile Asn His Ala Ala
                85                  90                  95

Gly Arg Val Leu Lys Lys Thr Thr Pro Met Lys Pro Cys Tyr Gly Ser
            100                 105                 110

Tyr Ala Lys Pro Thr Asn Glu Asn Gly Gly Gln Gly Ile Leu Val Lys
        115                 120                 125

Gln Gln Asn Gly Lys Leu Glu Ser Gln Val Glu Met Gln Phe Phe Ser
    130                 135                 140

Thr Thr Glu Ala Thr Ala Gly Asn Gly Asp Asn Leu Thr Pro Lys Val
145                 150                 155                 160

Val Leu Tyr Ser Glu Asp Val Asp Ile Glu Thr Pro Asp Thr His Ile
                165                 170                 175

Ser Tyr Met Pro Thr Ile Lys Glu Gly Asn Ser Arg Glu Leu Met Gly
            180                 185                 190

Gln Gln Ser Met Pro Asn Arg Pro Asn Tyr Ile Ala Phe Arg Asp Asn
        195                 200                 205

Phe Ile Gly Leu Met Tyr Tyr Asn Ser Thr Gly Asn Met Gly Val Leu
    210                 215                 220

Ala Gly Gln Ala Ser Gln Leu Asn Ala Val Val Asp Leu Gln Asp Arg
225                 230                 235                 240

Asn Thr Glu Leu Ser Tyr Gln Leu Leu Leu Asp Ser Ile Gly Asp Arg
                245                 250                 255

-continued

```
Thr Arg Tyr Phe Ser Met Trp Asn Gln Ala Val Asp Ser Tyr Asp Pro
            260                 265                 270

Asp Val Arg Ile Ile Glu Asn His Gly Thr Glu Asp Glu Leu Pro Asn
        275                 280                 285

Tyr Cys Phe Pro Leu Gly Gly Val Ile Asn Thr Glu Thr Leu Thr Lys
    290                 295                 300

Val Lys Pro Lys Thr Gly Gln Glu Asn Gly Trp Glu Lys Asp Ala Thr
305                 310                 315                 320

Glu Phe Ser Asp Lys Asn Glu Ile Arg Val Gly Asn Asn Phe Ala Met
                325                 330                 335

Glu Ile
```